(12) United States Patent
Rosenblum et al.

(10) Patent No.: US 7,868,005 B2
(45) Date of Patent: Jan. 11, 2011

(54) PYRAZINYL SUBSTITUTED PIPERAZINE-PIPERIDINES WITH CXCR3 ANTAGONIST ACTIVITY

(75) Inventors: Stuart B. Rosenblum, West Orange, NJ (US); Seong Heon Kim, Livingston, NJ (US); Qingbei Zeng, Edison, NJ (US); Michael K. C. Wong, North Brunswick, NJ (US); Gopinadhan N. Anilkumar, Edison, NJ (US); Yueheng Jiang, Whitehouse Station, NJ (US); Wensheng Yu, Edison, NJ (US); Joseph A. Kozlowski, Princeton, NJ (US); Neng-Yang Shih, Warren, NJ (US); Bandarpalle B. Shankar, Branchburg, NJ (US); Brian F. McGuinness, Plainsboro, NJ (US); Guizhen Dong, Dayton, NJ (US); Lisa Guise Zawacki, Yardley, PA (US); Douglas W. Hobbs, Yardley, PA (US); John J. Baldwin, Gwynedd Valley, PA (US); Yuefei Shao, Princeton, NJ (US)

(73) Assignee: Schering Corporation, Kenilworth, NJ (US)

(*) Notice: Subject to any disclaimer, the term of this patent is extended or adjusted under 35 U.S.C. 154(b) by 859 days.

(21) Appl. No.: 11/354,138

(22) Filed: Feb. 14, 2006

(65) Prior Publication Data
US 2007/0054919 A1    Mar. 8, 2007

Related U.S. Application Data

(60) Provisional application No. 60/653,338, filed on Feb. 16, 2005.

(51) Int. Cl.
| | |
|---|---|
| C07D 241/04 | (2006.01) |
| C07D 401/14 | (2006.01) |
| A61K 31/443 | (2006.01) |
| A61K 31/4433 | (2006.01) |
| A61K 31/4439 | (2006.01) |
| A61K 31/444 | (2006.01) |
| A61K 31/4436 | (2006.01) |
| A61K 31/695 | (2006.01) |
| C07F 7/18 | (2006.01) |
| A61P 25/28 | (2006.01) |
| A61P 35/00 | (2006.01) |
| A61P 29/00 | (2006.01) |

(52) U.S. Cl. .................. 514/252.11; 544/357; 544/229; 514/63

(58) Field of Classification Search ............ 514/252.11; 544/357
See application file for complete search history.

(56) References Cited

U.S. PATENT DOCUMENTS

| | | | |
|---|---|---|---|
| 6,124,319 | A | 9/2000 | MacCoss et al. |
| 6,525,070 | B2 * | 2/2003 | Rigby et al. ............... 514/316 |

FOREIGN PATENT DOCUMENTS

| | | |
|---|---|---|
| WO | WO93/10091 | 5/1993 |
| WO | WO93/14077 | 7/1993 |
| WO | WO99/20606 | 4/1999 |
| WO | WO00/066558 | 11/2000 |
| WO | WO02/085861 | 10/2002 |
| WO | WO03/070242 | 8/2003 |
| WO | WO03/082335 | 10/2003 |

(Continued)

OTHER PUBLICATIONS

Vippagunta et al, "Crystalline Solids" Advanced Drug Delivery Reviews, vol. 48, pp. 3-26 (2001).*

(Continued)

*Primary Examiner*—James O Wilson
(74) *Attorney, Agent, or Firm*—Eric A. Meade; Krishna G. Banerjee; Palaiyur Kalyanaraman

(57) ABSTRACT

The present application discloses a compound, or enantiomers, stereoisomers, rotamers, tautomers, racemates or prodrug of said compound, or pharmaceutically acceptable salts, solvates or esters of said compound, or of said prodrug, said compound having the general structure shown in Formula 1:

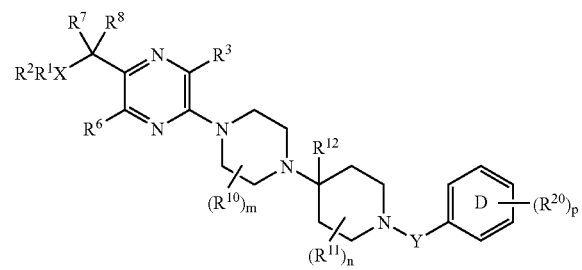

Formula 1 and the pharmaceutically acceptable salts, solvates and esters thereof. Also disclosed is a method of treating chemokine mediated diseases, such as, palliative therapy, curative therapy, prophylactic therapy of certain diseases and conditions such as inflammatory diseases (non-limiting example(s) include, psoriasis), autoimmune diseases (non-limiting example(s) include, rheumatoid arthritis, multiple sclerosis), graft rejection (non-limiting example(s) include, allograft rejection, xenograft rejection), infectious diseases (e.g, tuberculoid leprosy), fixed drug eruptions, cutaneous delayed-type hypersensitivity responses, ophthalmic inflammation, type I diabetes, viral meningitis and tumors using a compound of Formula 1.

29 Claims, No Drawings

U.S. PATENT DOCUMENTS

| | | | |
|---|---|---|---|
| 7,417,045 | B2 | 8/2008 | Anilkumar et al. |
| 7,566,718 | B2 | 7/2009 | Wong et al. |
| 2002/0018776 | A1 | 2/2002 | Hancock |
| 2003/0055054 | A1 | 3/2003 | Medina et al. |
| 2006/0276448 | A1 | 12/2006 | Zeng et al. |
| 2006/0276457 | A1 | 12/2006 | Yu et al. |
| 2006/0276479 | A1 | 12/2006 | Kim et al. |
| 2007/0021611 | A1 | 1/2007 | McGuinness et al. |
| 2007/0082913 | A1 | 4/2007 | Kim et al. |
| 2008/0039474 | A1 | 2/2008 | Rosenblum et al. |
| 2008/0058343 | A1 | 3/2008 | Rosenblum et al. |
| 2008/0292589 | A1 | 11/2008 | Anilkumar et al. |

FOREIGN PATENT DOCUMENTS

| | | |
|---|---|---|
| WO | WO03/098185 | 11/2003 |
| WO | WO03/101970 | 12/2003 |
| WO | WO2006/088921 | 8/2006 |

OTHER PUBLICATIONS

Gavezzotti, "Are Crystal Structures Predictable?" Accounts of Chemical Research, vol. 27, pp. 309-314 (1994).*

Lazzeri and Romagnani, "CXCR3-binding Chemokines: Novel Multifunctional Therapeutic Targets" Current Drug Targets—Immune, Endocrine & Metabololic Disorders, vol. 5, pp. 109-118 (2005).*

Dorwald F. A. Side Reactions in Organic Synthesis, 2005, Wiley: VCH, Weinheim p. IX of Preface.*

Angiolilo, Anne L., et al.; "Human Interferon-inducible Protein 10 is a Potent Inhibitor of Angiogenesis In Vivo"; The Journal of Experimental Medicine; 182:155-162 (1995).

Baggiolini, Marco, et al.; "Interleukin-8 and Related Chemotactic Cytokines—CXC and CC Chemokines"; Advances in Immunol.; 55:97-179 (1994).

Baggiolini, Marco, et al.; "CC chemokines in allergic inflammation"; Immunology Today; 15(3):127-133 (1994).

Clark-Lewis, Ian, et al.; "Structure-Activity Relationships of Interleukin-8 Determined Using Chemically Synthesized Analogs"; The Journal of Biological Chemistry; 266(34):23128-23134 (1991).

Clark-Lewis, Ian, et al.; "Platelet factor 4 binds to interleukin 8 receptors and activates neutrophils when its N terminus is modified with Glu-Leu-Arg"; Proc. Natl. Acad. Sci. USA; 90:3574-3577 (1993).

Cole, Katherine E., et al.; "Interferon-inducible T Cell Alpha Chemoattractant (I-TAC): A Novel Non-ELR CXC Chemokine with Potent Activity on Activated T Cells through Selective High Affinity Binding to CXCR3"; J. Exp. Med.; 187(12):2009-2021 (1998).

Farber, Joshua M.; "A macrophage mRNA selectively induced by γ—interferon encodes a member of the platelet factor 4 family of cytokines"; Proc. Natl. Acad. Sci. USA; 87:5238-5242 (1990).

Farber, Joshua M.; "HuMIG: A New Human Member of the Chemokine Family of Cytokines"; Biochemical and Biophysical Research Communications; 192(1):223-230 (1993).

Galy, Anne H. M., et al.; "IL-1, IL-4, and IFN-γ Differentially Regulate Cytokine Production and Cell Surface Molecule Expression in Cultured Human Thymic Epithelial Cells"; The Journal of Immunology; 147(11):3823-3830 (1991).

Hebert, Caroline A., et al.; "Scanning Mutagenesis of Interleukin-8 Identifies a Cluster of Residues Required for Receptor Binding"; The Journal of Biological Chemistry; 266(28):18989-18994 (1991).

Liao, Fang, et al.; "Human Mig Chemokine: Biochemical and Functional Characterization"; J. Exp. Med.; 182:1301-1314 (1995).

Loetscher, Marcel, et al.; "Chemokine Receptor Specific for IP10 and Mig: Structure, Function, and Expression in Activated T-Lymphocytes"; J. Exp. Med.; 184:963-969 (1996).

Loetscher, Pius, et al.; "Monocyte chemotactic proteins MCP-1, MCP-2, and MCP-3 are major attractants for human CD4+ and CD8+ T lymphocytes"; FASEB J.; 8:1055-1060 (1994).

Luster, Andrew D., et al.; "Ip-10, a -C-X-C- Chemokine, Elicits a Potent Thymus-dependent Antitumor Response In Vivo"; J. Exp. Med.; 178:1057-1065 (1993).

Luster, Andrew D., et al.; "The IP-10 Chemokine Binds to a Specific Cell Surface Heparan Sulfate Site Shared with Platelet Factor 4 and Inhibits Endothelial Cell Proliferation"; J. Exp. Med.; 182:219-231 (1995).

Luster, Andrew D., et al.; "γ-Interferon transcriptionally regulates an early-response gene containing homology to platelet proteins"; Nature; 315:672-676 (1985).

Qin, Shixin, et al.; "The Chemokine Receptors CXCR3 and CCR5 Mark Subsets of T Cells Associated with Certain Inflammatory Reactions"; J. Clin. Invest.; 101(4):746-754 (1998).

Schall, Thomas J., et al.; "Hemokines, leukocyte trafficking, and inflammation"; Current Opinion in Immunology; 6:865-873 (1994).

Seitz, Michael, et al.;. "Enhanced Productionof Neutrophil-activiating Peptide-1/Interleukin-8 in Rheumatoid Arthritis"; Journal Clin. Invest.; 87:463-469 (1991).

Springer, Timothy A.; "Traffic Signals on Endothelium for Lymphocyte Recirculation and Leukocyte Emigration"; Annu. Rev. Physio.; 57:827-872 (1995).

Taub, Dennis D., et al.; "Recombinant Human Interferon-inducible Protein 10 is a Chemoattractant for Human Monocytes and T Lymphocytes and Promotes T Cell Adhesion to Endothelial Cells"; The Journal of Experimental Medicine; 177:1809-1814 (1993).

Taub, Dennis D., et al.; "α and β Chemokines Induce NK Cell Migration and Enhance NK-Mediated Cytolysis"; The Journal of Immunol.; 155:3877-3888 (1995).

Uguccioni, Mariagrazia, et al.; "Actions of the chemotactic cytokines MCP-1, MCP-2, MCP-3, RANTES, MIP-1α and MIP-1β on human monocytes"; Eur. J. Immunol.; 25:64-68 (1995).

Qingbei Zeng et al., U.S. Appl. No. 12/519,970; Preliminary Amendment—Filed Jun. 18, 2009.

International Search Report for International Application No. PCT/US2006/005267 dated Jul. 18, 2006.

Notice of Allowance in U.S. Appl. No. 11/545,201 mailed Nov. 17, 2009.

Notice of Allowance in U.S. Appl. No. 11/353,697 mailed Jan. 7, 2010.

Notice of Allowance in U.S. Appl. No. 11/688,014 mailed Jan. 19, 2010.

* cited by examiner

PYRAZINYL SUBSTITUTED PIPERAZINE-PIPERIDINES WITH CXCR3 ANTAGONIST ACTIVITY

REFERENCE TO PRIORITY APPLICATIONS

This application claims the benefit of U.S. Provisional Application Ser. No. 60/653,338 filed Feb. 16, 2005, which is incorporated herein in its entirety by reference.

FIELD OF THE INVENTION

The present invention relates to novel pyrazinyl substituted piperazine-piperidines with CXCR3 antagonist activity, pharmaceutical compositions containing one or more such antagonists, one or more such antagonists in combination with other compounds with chemokine activity, one or more such antagonists in combination with known immunosuppressive agents, non-limiting example(s) include Methotrexate, interferon, cyclosporin, FK-506 and FTY720, methods of preparing such antagonists and methods of using such antagonists to modulate CXCR3 activity. This invention also discloses methods of using such CXCR3 antagonists for the treatment (non-limiting examples include palliative, curative and prophylactic therapies) of diseases and conditions where CXCR3 has been implicated. Diseases and conditions where CXCR3 has been implicated include but are not limited to inflammatory conditions (psoriasis and inflammatory bowel disease), autoimmune disease (multiple sclerosis, rheumatoid arthritis), fixed drug eruptions, cutaneous delayed-type hypersensitivity responses, type I diabetes, viral meningitis and tuberculoid leprosy. CXCR3 antagonist activity has also been indicated as a therapy for tumor growth suppression as well as graft rejection (allograft and zenograft rejections for example).

BACKGROUND OF THE INVENTION

Chemokines constitute a family of small cytokines that are produced in inflammation and regulate leukocyte recruitment (Baggiolini, M. et al., *Adv. Immunol.*, 55 : 97-179 (1994); Springer, T. A., *Annu. Rev. Physio.*, 57 : 827-872 (1995); and Schall, T. J. and K. B. Bacon, *Curr. Opin. Immunol*, 6: 865-873 (1994)). Chemokines are capable of selectively inducing chemotaxis of the formed elements of the blood (other than red blood cells), including leukocytes such as neutrophils, monocytes, macrophages, eosinophils, basophils, mast cells, and lymphocytes, such as T cells and B cells. In addition to stimulating chemotaxis, other changes can be selectively induced by chemokines in responsive cells, including changes in cell shape, transient rises in the concentration of intracellular free calcium ions ($[Ca^{2+}]_i$), granule exocytosis, integrin upregulation, formation of bioactive lipids (e.g., leukotrienes) and respiratory burst, associated with leukocyte activation. Thus, the chemokines are early triggers of the inflammatory response, causing inflammatory mediator release, chemotaxis and extravasation to sites of infection or inflammation.

The chemokines are related in primary structure and share four conserved cysteines, which form disulfide bonds. Based upon this conserved cysteine motif, the family can be divided into distinct branches, including the C—X—C chemokines (α-chemokines) in which the first two conserved cysteines are separated by an intervening residue (e.g., IL-8, IP-10, Mig, I-TAC, PF4, ENA-78, GCP-2, GROα, GROβ, GROδ, NAP-2, NAP-4), and the C—C chemokines (β-chemokines), in which the first two conserved cysteines are adjacent residues (e.g., MIP-1α, MIP-1β, RANTES, MCP-1, MCP-2, MCP-3, 1-309) (Baggiolini, M. and Dahinden, C. A., *Immunology Today*, 15 : 127-133 (1994)). Most CXC-chemokines attract neutrophil leukocytes. For example, the CXC-chemokines interleukin 8 (IL-8), GRO alpha (GROα), and neutrophil-activating peptide 2 (NAP-2) are potent chemoattractants and activators of neutrophils. The CXC-chemokines designated Mig (monokine induced by gamma interferon) and IP-10 (interferon-gamma inducible 10 kDa protein) are particularly active in inducing chemotaxis of activated peripheral blood lymphocytes. CC-chemokines are generally less selective and can attract a variety of leukocyte cell types, including monocytes, eosinophils, basophils, T lymphocytes and natural killer cells. CC-chemokines such as human monocyte chemotactic proteins 1-3 (MCP-1, MCP-2 and MCP-3), RANTES (Regulated on Activation, Normal T Expressed and Secreted), and the macrophage inflammatory proteins 1α and 1β (MIP-1α and MIP-1β) have been characterized as chemoattractants and activators of monocytes or lymphocytes, but do not appear to be chemoattractants for neutrophils.

A chemokine receptor that binds the CXC-chemokines IP-10 and Mig has been cloned and characterized (Loetscher, M. et al., *J. Exp. Med.*, 184 : 963-969 (1996)). CXCR3 is a G-protein coupled receptor with seven transmembrane-spanning domains and has been shown to be restrictively expressed in activated T cells, preferentially human Th1 cells. On binding of the appropriate ligand, chemokine receptors transduce an intracellular signal through the associated G-protein resulting in a rapid increase in intracellular calcium concentration.

The receptor mediates $Ca^{2+}$ (calcium ion) mobilization and chemotaxis in response to IP-10 and Mig. CXCR3 expressing cells show no significant response to the CXC-chemokines IL-8, GROα, NAP-2, GCP-2 (granulocyte chemotactic protein-2), ENA78 (epithelial-derived neutrophil-activating peptide 78), PF4 (platelet factor 4), or the CC-chemokines MCP-1, MCP-2, MCP-3, MCP-4, MIP-Iα, MIP-1β, RANTES, I309, eotaxin or lymphotactin. Moreover, a third ligand for CXCR3, I-TAC (Interferon-inducible T cell Alpha Chemoattractant), has also been found to bind to the receptor with high affinity and mediate functional responses (Cole, K. E. et al., *J. Exp. Med.*, 187: 2009-2021 (1998)).

The restricted expression of human CXCR3 in activated T lymphocytes and the ligand selectivity of CXCR3 are noteworthy. The human receptor is highly expressed in IL-2 activated T lymphocytes, but was not detected in resting T lymphocytes, monocytes or granulocytes (Qin, S. et al., *J. Clin. Invest.*, 101: 746-754 (1998)). Additional studies of receptor distribution indicate that it is mostly $CD3^+$ cells that express CXCR3, including cells which are $CD95^+$, $CD45RO^+$, and $CD45RA^{low}$, a phenotype consistent with previous activation, although a proportion of $CD20^+$ (B) cells and $CD56^+$ (NK) cells also express this receptor. The selective expression in activated T lymphocytes is of interest, because other receptors for chemokines which have been reported to attract lymphocytes (e.g., MCP-1, MCP-2, MCP-3, MIP-1α, MIP-1β, RANTES) are also expressed by granulocytes, such as neutrophils, eosinophils, and basophils, as well as monocytes. These results suggest that the CXCR3 receptor is involved in the selective recruitment of effector T cells.

CXCR3 recognizes unusual CXC-chemokines, designated IP-10, Mig and I-TAC. Although these belong to the CXC-subfamily, in contrast to IL-8 and other CXC-chemokines which are potent chemoattractants for neutrophils, the primary targets of IP-10, Mig and I-TAC are lymphocytes, particularly effector cells such as activated or stimulated T lymphocytes and natural killer (NK) cells (Taub, D. D. et al., *J. Exp. Med.*, 177: 18090-1814 (1993); Taub, D. D. et al., *J. Immunol.*, 155: 3877-3888 (1995); Cole, K. E. et al., *J. Exp. Med.*, 187: 2009-2021 (1998)). (NK cells are large granular lymphocytes, which lack a specific T cell receptor for antigen recognition, but possess cytolytic activity against cells such as tumor cells and virally infected cells.) Consistently, IP-10, Mig and I-TAC lack the ELR motif, an essential binding epitope in those CXC-chemokines that efficiently induce neutrophil chemotaxis (Clark-Lewis, I. et al., *J. Biol. Chem.* 266: 23128-23134 (1991); Hebert, C. A. et al., *J. Biol. Chem.*, 266 : 18989-18994 (1991); and Clark-Lewis, 1. et al., *Proc. Natl. Acad. Sci. USA*, 90: 3574-3577 (1993)). In addition, both recombinant human Mig and recombinant human IP-10 have been reported to induce calcium flux in tumor infiltrating lymphocytes (TIL) (Liao, F. et al., *J Exp. Med*, 182: 1301-1314 (1995)). While IP-10 has been reported to induce chemotaxis of monocytes in vitro (Taub, D. D. et al., *J. Exp. Med.*, 177: 1809-1814 (1993), the receptor responsible has not been identified), human Mig and I-TAC appear highly selective, and do not show such an effect (Liao, F. et al., *J. Exp. Med.*, 182: 1301-1314 (1995); Cole, K. E. et al., *J. Exp. Med.*, 187: 2009-2021 (1998)). IP-10 expression is induced in a variety of tissues in inflammatory conditions such as psoriasis, fixed drug eruptions, cutaneous delayed-type hypersensitivity responses and tuberculoid leprosy as well as tumors and in animal model studies, for example, experimental glomerulonephritis, and experimental allergic encephalomyelitis. IP-10 has a potent in vivo antitumor effect that is T cell dependent, is reported to be an inhibitor of angiogenesis in vivo and can induce chemotaxis and degranulation of NK cells in vitro, suggesting a role as a mediator of NK cell recruitment and degranulation (in tumor cell destruction, for example) (Luster, A. D. and P. Leder, *J. Exp. Med.*, 178: 1057-1065 (1993); Luster, A. D. et al., *J. Exp. Med.* 182: 219-231 (1995); Angiolillo, A. L. et al., *J. Exp. Med.*, 182: 155-162 (1995); Taub, D. D. et al., *J. Immunol.*, 155: 3877-3888 (1995)). The expression patterns of IP-10, Mig and I-TAC are also distinct from that of other CXC chemokines in that expression of each is induced by interferon-gamma (IFNδ), while the expression of IL-8 is down-regulated by IFNδ (Luster, A. D. et al., *Nature*, 315 : 672-676 (1985); Farber, J. M., *Proc. Natl. Acad. Sci. USA*, 87 : 5238-5242 (1990); Farber, J. M., *Biochem. Biophys. Res. Commun.*, 192 (1): 223-230 (1993), Liao, F. et al., *J. Exp. Med.*, 182: 1301-1314 (1995); Seitz, M. et al., *J. Clin. Invest.*, 87 : 463-469 (1991); Galy, A. H. M. and H. Spits, *J. Immunol.*, 147: 3823-3830 (1991); Cole, K. E. et al., *J. Exp. Med.*, 187 : 2009-2021 (1998)).

Chemokines are recognized as the long-sought mediators for the recruitment of lymphocytes. Several CC-chemokines were found to elicit lymphocyte chemotaxis (Loetscher, P. et al., *FASEB J.*, 8: 1055-1060 (1994)), however, they are also active on granulocytes and monocytes (Uguccioni, M. et al., *Eur. J. Immunol.*, 25 : 64-68 (1995); Baggiolini, M. and C. A. Dahinden, *Immunol. Today*, 15 : 127-133 (1994)). The situation is different for IP-10, Mig and I-TAC, which are selective in their action on lymphocytes, including activated T lymphocytes and NK cells, and which bind CXCR3, a receptor which does not recognize numerous other chemokines and which displays a selective pattern of expression.

In view of these observations, it is reasonable to conclude that the formation of the characteristic infiltrates in inflammatory lesions, such as, for example, delayed-type hypersensitivity lesions, sites of viral infection and certain tumors is a process mediated via CXCR3 and regulated by CXCR3 expression. Lymphocytes, particularly T lymphocytes, bearing a CXCR3 receptor as a result of activation can be recruited into inflammatory lesions, sites of infection and/or tumors by IP-10, Mig and/or I-TAC, which can be induced locally by interferon-gamma. Thus, CXCR3 plays a role in the selective recruitment of lymphocytes, particularly effector cells such as activated or stimulated T lymphocytes. Accordingly, activated and effector T cells have been implicated in a number of disease states such as graft-rejection, inflammation, rheumatoid arthritis, multiple sclerosis, inflammatory bowel disease (such as Crohn's disease and ulcerative colitis) and psoriasis. Thus, CXCR3 represents a promising target for the development of novel therapeutics.

Reference is made to PCT Publication No. WO 93/10091 (Applicant: Glaxo Group Limited, Published May 27, 1993) which discloses piperidine acetic acid derivatives as inhibitors of fibrinogen-dependent blood platelet aggregation having the formula:

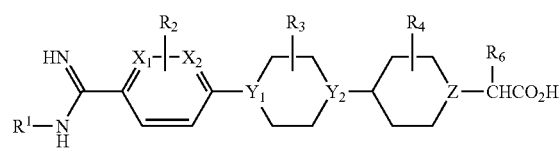

An illustrative compound of that series is:

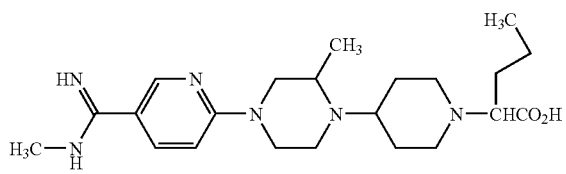

Reference is also made to PCT Publication No. WO 9/20606 (Applicant: J. Uriach & CIA. S. A., Published Apr. 29, 1999) which discloses piperazines as platelet aggregation inhibitors having the formula:

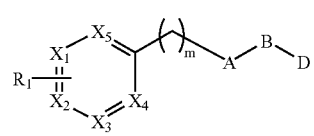

Reference is also made to US Patent Application No. US 2002/0018776 A1 (Applicant: Hancock, et al. *Published Feb.* 14, 2002) which discloses methods of treating graft rejection.

Reference is also made to PCT Publication No. WO 03/098185 A2 (Applicant: Renovar, Inc., Published Nov. 27, 2003) which discloses methods of diagnosing and predicting organ transplant rejection by detection of chemokines, for example, CXCR3 and CCL chemokines in urine.

Reference is also made to PCT Publication No. WO 03/082335 A1 (Applicant: Sumitomo Pharmaceuticals Co. Ltd., Published Oct. 9, 2003) which discloses methods of screening a CXCR3 ligand and methods of diagnosing type 2 diabetes by detecting the expression dose of a CXCR3 ligand in a biological sample.

Reference is also made to PCT Publication No. WO 02/085861 (Applicant: Millennium Pharmaceuticals, Inc.

Published Oct. 31, 2002) which discloses imidazolidine compounds and their use as CXCR3 antagonists having the formula:

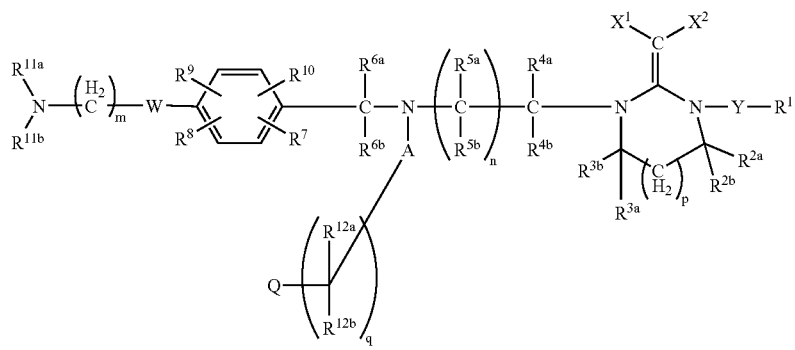

An illustrative compound of that series is:

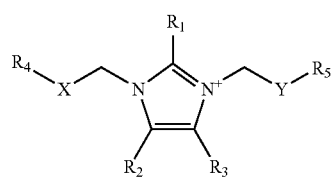

Reference is also made to PCT Publication No. WO 03/101970 (Applicant: SmithKline Beecham Corporation, Published Dec. 11, 2003) which discloses imidazolium compounds and their use as CXCR3 antagonists having the formula:

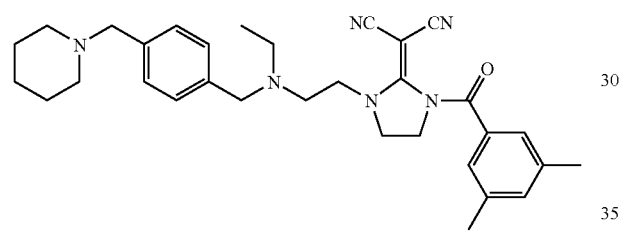

An illustrative example of that series is:

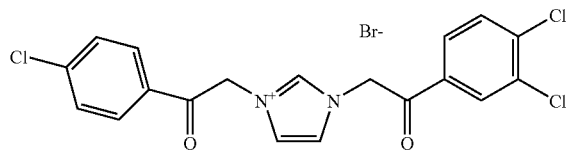

Reference is also made to US Patent Application No. US 2003/0055054 A1 (Applicant: Medina et al, Published Mar. 20, 2003) which discloses compounds having the formula:

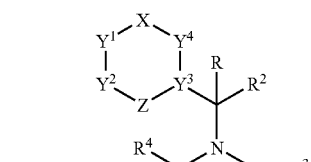

An illustrative compound of that series is:

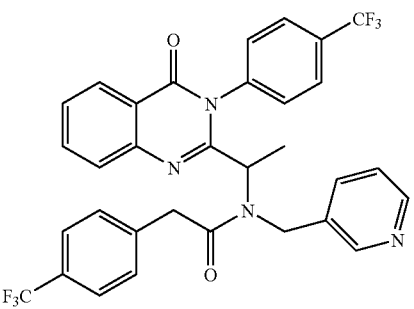

Reference is also made to U.S. Pat. No. 6,124,319 (Applicant: MacCoss et al., issued Sep. 6, 2000) which discloses compounds useful as chemokine receptor modulators having the formula:

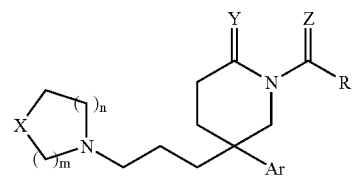

Reference is also made to PCT Publication WO 03/070242 A1 (Applicant: CELLTECH R&D limited, Published Aug. 28, 2003) which discloses compounds useful as "chemokine receptor inhibitors for the treatment of inflammatory diseases" having the formula:

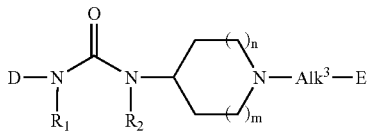

There is a need for compounds that are capable of modulating CXCR3 activity. For example, there is a need for new treatments and therapies for diseases and conditions associated with CXCR3 such as inflammatory conditions (psoriasis and inflammatory bowel disease), autoimmune disease (multiple sclerosis, rheumatoid arthritis) and graft rejection (allograft and zenograft rejections for example) as well as infectious diseases, cancers and tumors, fixed drug eruptions, cutaneous delayed-type hypersensitivity responses, type I diabetes, viral meningitis and tuberculoid leprosy.

There is a need for methods of treatment or prevention or amelioration of one or more symptoms of diseases and conditions associated with CXCR3. There is a need for methods for modulating CXCR3 activity using the compounds provided herein.

SUMMARY OF THE INVENTION

In its many embodiments, the invention provides novel compounds of the Formula 1:

Formula 1

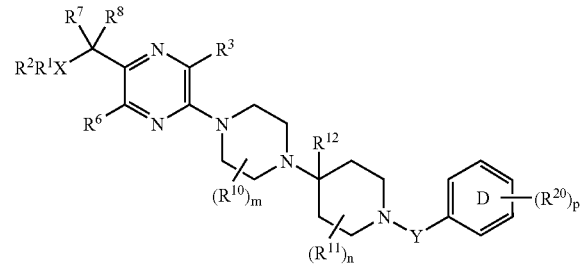

or pharmaceutically acceptable salts, solvates or esters thereof wherein:

X is N, O, alkyl, cycloalkyl, heteroaryl, heterocyclyl or heterocyclenyl;

ring D is a phenyl ring unsubstituted or optionally substituted with independently selected $R^{20}$ moieties as stated below;

$R^1$ and $R^2$ are independently absent or present, and if present each is independently selected from the group consisting of H, alkyl, alkoxy, alkenyl, carbonyl, cycloalkyl, alkyl-cycloalkyl-, cycloalkenyl, alkylaryl, arylalkyl, aryl, amino, alkylamino, amidinyl, carboxamido, cyano, hydroxyl, urea, —N≡CH, ═NCN, —$(CH_2)_q$OH, —$(CH_2)_q$OR$^{31}$, —$(CH_2)_q$NH$_2$, —$(CH_2)_q$NHR$^{31}$, —$(CH_2)_q$N(R$^{31}$)$_2$, —$(CH_2)_q$C(═O)NHR$^{31}$, —$(CH_2)_q$SO$_2$R$^{31}$, —$(CH_2)_q$NHSO$_2$R$^{31}$, —$(CH_2)_q$SO$_2$NHR$^{31}$, —C(═S)N(H)alkyl, —N(H)—S(O)$_2$-alkyl, —N(H)C(═O)N(H)-alkyl, —S(O)$_2$alkyl, —S(O)$_2$N(H)alkyl, —S(O)$_2$N(alkyl)$_2$, —S(O)$_2$aryl, —C(═S)N(H)cycloalkyl, —C(═O)N(H)NH$_2$, —C(═O)alkyl, -heteroaryl, heterocyclyl, and heterocyclenyl; or alternatively when X is N, the N taken together with the R$^1$ and R$^2$ forms a heterocyyl, heteroaryl or —N═C(NH$_2$)$_2$;

$R^3$ and $R^6$ moieties can be the same or different, each being independently selected from the group consisting of H, alkyl, alkylaryl, aralkyl, —CN, CF$_3$, haloalkyl, cycloalkyl, halogen, hydroxyalkyl, —N═CH—(R$^{31}$), —C(═O)N(R$^{30}$)$_2$, —N(R$^{30}$)$_2$, —OR$^{30}$, —SO$_2$(R$^{31}$), —N(R$^{30}$)C(═O)N(R$^{30}$)$_2$ and —N(R$^{30}$)C(═O)R$^{31}$;

$R^7$ and $R^8$ are the same or different, each being independently selected from the group consisting of H, alkyl, alkylaryl, heteroaryl, hydroxyl, —CN, alkoxy, alkylamino, —N(H)S(O)$_2$alkyl and —N(H)C(═O)N(H)alkyl; or alternatively $R^7$ and $R^8$ taken together is ═O, ═S, ═NH, ═N(alkyl), ═N(Oalkyl), ═N(OH) or cycloalkyl;

the $R^{10}$ moieties can be the same or different, each being independently selected from the group consisting of H, alkyl, cycloalkyl, aryl, heteroaryl, heterocyclenyl, heterocyclyl, alkylaryl, arylalkyl, —CO$_2$H, hydroxyalkyl, —C(═O)N(R$^{30}$)$_2$, —$(CH_2)_q$OH, —$(CH_2)_q$OR$^{31}$, —$(CH_2)_q$NHR$^{31}$, —$(CH_2)_q$N(R$^{31}$)$_2$, —OR$^{30}$, halogen, ═O, and —C(═O)R$^{31}$;

the $R^{11}$ moieties can be the same or different, each being independently selected from the group consisting of H, alkyl, cycloalkyl, aryl, heteroaryl, heterocyclyl, heterocyclenyl, alkylaryl, arylalkyl, hydroxyalkyl, carboxamide, CO$_2$H, —$(CH_2)_q$OH, —$(CH_2)_q$OR$^{31}$, —$(CH_2)_q$NHR$^{31}$, —$(CH_2)_q$N(R$^{31}$)$_2$, —OR$^{30}$, halogen, ═O, and —C(═O)R$^{31}$;

$R^{12}$ is selected from the group consisting of H, alkyl, —CN, —C(═O)N(R$^{30}$)$_2$, —$(CH_2)_q$OH, —$(CH_2)_q$OR$^{31}$, —$(CH_2)_q$NHR$^{31}$, —$(CH_2)_q$N(R$^{31}$)$_2$, and —S(O$_2$)R$^{31}$;

the $R^{20}$ moieties can be the same or different, each being independently selected from the group consisting of H, alkyl, alkenyl, alkylaryl, alkynyl, alkoxy, alkylamino, alkylthiocarboxy, alkylheteroaryl, alkylthio, alkylsulfinyl, alkylsulfonyl, alkoxycarbonyl, aminoalkyl, amidinyl, aralkyl, aralkenyl, aralkoxy, aralkoxycarbonyl, aralkylthio, aryl, aroyl, aryloxy, cyano, cycloalkyl, cycloalkenyl, formyl, guanidinyl, halogen, haloalkyl, heteroalkyl, heteroaryl, heterocyclyl, heterocyclenyl, hydroxyalkyl, haloalkoxy, hydroxamate, nitro, trifluoromethyl, trifluoromethoxy, —$(CH_2)_q$OH, —$(CH_2)_q$OR$^{31}$, —$(CH_2)_q$NH$_2$, —$(CH_2)_q$NHR$^{31}$, —$(CH_2)_q$N(R$^{31}$)$_2$, —$(CH_2)_q$C(═O)NHR$^{31}$, —$(CH_2)_q$SO$_2$R$^{31}$, —$(CH_2)_q$NHSO$_2$R$^{31}$, —$(CH_2)_q$SO$_2$NHR$^{31}$, -alkynylC(R$^{31}$)$_2$OR$^{31}$, —C(═O)R$^{30}$, —C(═O)N(R$^{30}$)$_2$, —C(═NR$^{30}$)NHR$^{30}$, —C(═NOH)N(R$^{30}$)$_2$, —C(═NOR$^{31}$)N(R$^{30}$)$_2$, —C(═O)OR$^{30}$, —N(R$^{30}$)$_2$, —N(R$^{30}$)C(═O)R$^{31}$, —NHC(═O)N(R$^{30}$)$_2$, —N(R$^{30}$)C(═O)OR$^{31}$, —N(R$^{30}$)C(═NCN)N(R$^{30}$)$_2$, —N(R$^{30}$)C(═O)N(R$^{30}$)SO$_2$(R$^{31}$), —N(R$^{30}$)C(═O)N(R$^{30}$)$_2$, —N(R$^{30}$)SO$_2$(R$^{31}$), —N(R$^{30}$)S(O)$_2$N(R$^{30}$)$_2$, —OR$^{30}$, —OC(═O)N(R$^{30}$)$_2$, —SR$^{30}$, —SO$_2$N(R$^{30}$)$_2$, —SO$_2$(R$^{31}$), —OSO$_2$(R$^{31}$), —O(CH$_2$)$_q$SO$_2$R$^{31}$, and —OSi(R$^{30}$)$_3$; or alternatively two R$^{20}$ moieties are linked together to form a five or six membered aryl, cycloalkyl, heterocyclyl, heterocyclenyl, or heteroaryl ring wherein said five or six membered aryl, cycloalkyl, heterocyclyl, heterocyclenyl, or heteroaryl ring is fused to ring D and the fused ring is optionally substituted with 0-4 R$^{21}$ moieties;

the $R^{21}$ moieties can be the same or different, each being independently selected from the group consisting of H, alkyl, alkenyl, alkylaryl, alkynyl, alkoxy, alkylamino, alkylthiocarboxy, alkylheteroaryl, alkylthio, alkylsulfinyl, alkylsulfonyl, alkoxycarbonyl, aminoalkyl, amidinyl, aralkyl, aralkenyl, aralkoxy, aralkoxycarbonyl, aralkylthio, aryl, aroyl, aryloxy, carboxamido, cyano, cycloalkyl, cycloalkenyl, formyl, guanidinyl, halogen, haloalkyl, heteroalkyl, heteroaryl, heterocyclyl, heterocyclenyl, hydroxyalkyl, hydroxamate, nitro, trifluoromethoxy, —$(CH_2)_q$OH, —$(CH_2)_q$OR$^{31}$, $(CH_2)_q$NH$_2$, —$(CH_2)_q$NHR$^{31}$, —$(CH_2)_q$N(R$^{31}$)$_2$, —$(CH_2)_q$C(═O)

NHR$^{31}$, —(CH$_2$)$_q$SO$_2$R$^{31}$, (CH$_2$)$_q$NSO$_2$R$^{31}$, —(CH$_2$)$_q$SO$_2$NHR$^{31}$, -alkynylC(R$^{31}$)$_2$OR$^{31}$, —C(=O)R$^{30}$, —C(=O)N(R$^{30}$)$_2$—C(=NR$^{30}$)NHR$^{30}$, —C(=NOH)N(R$^{30}$)$_2$, —C(=NOR$^{31}$)N(R$^{30}$)$_2$, —C(=O)OR$^{30}$, —N(R$^{30}$)$_2$, —N(R$^{30}$)C(=O)R$^{31}$, —NHC(=O)N(R$^{30}$)$_2$, —N(R$^{30}$)C(=O)OR$^{31}$, —N(R$^{30}$)C(=NCN)N(R$^{30}$)$_2$, —N(R$^{30}$)C(=O)N(R$^{30}$)SO$_2$(R$^{31}$), —N(R$^{30}$)C(=O)N(R$^{30}$)$_2$, —N(R$^{30}$)SO$_2$(R$^{31}$), —N(R$^{30}$)S(O)$_2$N(R$^{30}$)$_2$, —OR$^{30}$, —OC(=O)N(R$^{30}$)$_2$, —SR$^{30}$, —SO$_2$N(R$^{30}$)$_2$, —SO$_2$(R$^{31}$), —OSO$_2$(R$^{31}$), and —OSi(R$^{30}$)$_3$;

Y is selected from the group consisting of —(CR$^{13}$R$^{13}$)$_r$—, —CHR$^{13}$C(=O)—, —(CHR$^{13}$)$_r$O—, —(CHR$^{13}$)$_r$N(R$^{30}$)—, —C(=O)—, —C(=NR$^{30}$)—, —C(=N—OR$^{30}$)—, —CH(C(=O)NHR$^{30}$)—, CH-heteroaryl-, —C(R$^{13}$R$^{13}$)$_r$C(R$^{13}$)=C(R$^{13}$)—, —(CHR$^{13}$)$_r$C(=O)— and —(CHR$^{13}$)$_r$N(H)C(=O)—; or alternatively Y is cycloalkyl, heterocyclenyl, or heterocyclyl wherein the cycloalkyl, heterocyclenyl, or heterocyclyl is fused with the phenyl ring marked D;

the R$^{13}$ moieties can be the same or different, each being independently selected from the group consisting of H, alkyl, alkylaryl, cycloalkyl, alkoxy, aryl, heteroaryl, heterocyclenyl, heterocyclyl, spiroalkyl, —CN, —CO$_2$H, —C(=O)R$^{30}$, —C(=O)OR$^{31}$, —C(=O)N(R$^{30}$)$_2$, —(CHR$^{30}$)$_q$OH, —(CHR$^{30}$)$_q$OR$^{31}$, —(CHR$^{30}$)$_q$NH$_2$, —(CH R$^{30}$)$_q$NHR$^{31}$, —(CH$_2$)$_q$C(=O)NHR$^{31}$, —(CH$_2$)$_q$SO$_2$R$^{31}$, —(CH$_2$)$_q$NSO$_2$R$^{31}$, —(CH$_2$)$_q$SO$_2$NHR$^{31}$, —NH$_2$, —N(R$^{30}$)$_2$, —N(R$^{30}$)C(=O)N(R$^{30}$)$_2$, —N(R$^{30}$)SO$_2$(R$^{31}$), —OH, OR$^{30}$, —SO$_2$N(R$^{30}$)$_2$, and —SO$_2$(R$^{31}$);

the R$^{30}$ moieties can be the same or different, each being independently selected from the group consisting of H, alkyl, alkylaryl, aryl, aralkyl, cycloalkyl, CN, —(CH$_2$)$_q$OH, —(CH$_2$)$_q$Oalkyl, —(CH$_2$)$_q$Oalkylaryl, —(CH$_2$)$_q$Oaryl, —(CH$_2$)$_q$Oaralkyl, —(CH$_2$)$_q$Ocycloalkyl, —(CH$_2$)$_q$NH$_2$, —(CH$_2$)$_q$NHalkyl, —(CH$_2$)$_q$N(alkyl)$_2$, —(CH$_2$)$_q$NHalkylaryl, —(CH$_2$)$_q$NHaryl, —(CH$_2$)$_q$NHaralkyl, —(CH$_2$)$_q$NHcycloalkyl, —(CH$_2$)$_q$C(=O)NHalkyl, —(CH$_2$)$_q$C(=O)N(alkyl)$_2$, —(CH$_2$)$_q$C(=O)NHalkylaryl, —(CH$_2$)$_q$C(=O)NHaryl, —(CH$_2$)$_q$C(=O)NHaralkyl, —(CH$_2$)$_q$C(=O)NHcycloalkyl, —(CH$_2$)$_q$SO$_2$alkyl, —(CH$_2$)$_q$SO$_2$alkylaryl, —(CH$_2$)$_q$SO$_2$aryl, —(CH$_2$)$_q$SO$_2$aralkyl, —(CH$_2$)$_q$SO$_2$cycloalkyl, —(CH$_2$)$_q$NSO$_2$alkyl, —(CH$_2$)$_q$NSO$_2$alkylaryl, —(CH$_2$)$_q$NSO$_2$aryl, —(CH$_2$)$_q$NSO$_2$aralkyl, —(CH$_2$)$_q$NSO$_2$cycloalkyl, —(CH$_2$)$_q$SO$_2$NHalkyl, —(CH$_2$)$_q$SO$_2$NHalkylaryl, —(CH$_2$)$_q$SO$_2$NHaryl, —(CH$_2$)$_q$SO$_2$NHaralkyl, —(CH$_2$)$_q$SO$_2$NHcycloalkyl, heterocyclenyl, heterocyclyl, and heteroaryl;

the R$^{31}$ moieties can be the same or different, each being independently selected from the group consisting of alkyl, alkylaryl, aryl, aralkyl, cycloalkyl, —(CH$_2$)$_q$OH, —(CH$_2$)$_q$Oalkyl, —(CH$_2$)$_q$Oalkylaryl, —(CH$_2$)$_q$Oaryl, —(CH$_2$)$_q$Oaralkyl, —(CH$_2$)$_q$Ocycloalkyl, —(CH$_2$)$_q$NH$_2$, —(CH$_2$)$_q$NHalkyl, —(CH$_2$)$_q$N(alkyl)$_2$, —(CH$_2$)$_q$NHalkylaryl, —(CH$_2$)$_q$NHaryl, —(CH$_2$)$_q$NHaralkyl, —(CH$_2$)$_q$NHcycloalkyl, —(CH$_2$)$_q$C(=O)NHalkyl, —(CH$_2$)$_q$C(=O)N(alkyl)$_2$, —(CH$_2$)$_q$C(=O)NHalkylaryl, —(CH$_2$)$_q$C(=O)NHaryl, —(CH$_2$)$_q$C(=O)NHaralkyl, —(CH$_2$)$_q$C(=O)NHcycloalkyl, —(CH$_2$)$_q$SO$_2$alkyl, —(CH$_2$)$_q$SO$_2$alkylaryl, —(CH$_2$)$_q$SO$_2$aryl, —(CH$_2$)$_q$SO$_2$aralkyl, —(CH$_2$)$_q$SO$_2$cycloalkyl, —(CH$_2$)$_q$NSO$_2$alkyl, —(CH$_2$)$_q$NSO$_2$alkylaryl, —(CH$_2$)$_q$NSO$_2$aryl, —(CH$_2$)$_q$NSO$_2$aralkyl, —(CH$_2$)$_q$NSO$_2$cycloalkyl, —(CH$_2$)$_q$SO$_2$NHalkyl, —(CH$_2$)$_q$SO$_2$NHalkylaryl, —(CH$_2$)$_q$SO$_2$NHaryl, —(CH$_2$)$_q$SO$_2$NHaralkyl, —(CH$_2$)$_q$SO$_2$NHcycloalkyl, heterocyclenyl, heterocyclyl, and heteroaryl;

m is 0 to 4;
n is 0 to 4;
p is 0 to 5;
each q can be the same or different, each being independently selected from 1 to 5; and
r is 1 to 4;

with the proviso that there are no two adjacent double bonds in any ring, and that when a nitrogen is substituted by two alkyl groups, said two alkyl groups may be optionally joined to each other to form a ring.

The present invention also provides novel compounds of the Formula 1, or pharmaceutically acceptable salts, solvates, or esters thereof, wherein:

X is N, O, alkyl, cycloalkyl, heteroaryl, heterocyclyl or heterocyclenyl;

ring D is a phenyl ring unsubstituted or optionally substituted with independently selected R$^{20}$ moieties as stated below;

R$^1$ and R$^2$ are independently absent or present, and if present each is independently selected from the group consisting of H, alkyl, alkoxy, alkenyl, carbonyl, cycloalkyl, cycloalkenyl, alkylaryl, arylalkyl, aryl, amino, alkylamino, amidinyl, carboxamido, cyano, hydroxyl, urea, —N=CH, =NCN, —(CH$_2$)$_q$OH, —(CH$_2$)$_q$OR$^{31}$, —(CH$_2$)$_q$NH$_2$, —(CH$_2$)$_q$NHR$^{31}$, —(CH$_2$)$_q$N(R$^{31}$)$_2$, —(CH$_2$)$_q$C(=O)NHR$^{31}$, —(CH$_2$)$_q$SO$_2$R$^{31}$, —(CH$_2$)$_q$NHSO$_2$R$^{31}$, —(CH$_2$)$_q$SO$_2$NHR$^{31}$, —C(=S)N(H)alkyl, —N(H)—S(O)$_2$-alkyl, —N(H)C(=O)N(H)-alkyl, —S(O)$_2$alkyl, —S(O)$_2$N(H)alkyl, —S(O)$_2$N(alkyl)$_2$, —S(O)$_2$aryl, —C(=S)N(H)cycloalkyl, —C(=O)N(H)NH$_2$, —C(=O)alkyl, -heteroaryl, heterocyclyl, and heterocyclenyl; or alternatively when X is N, the N taken together with the R$^1$ and R$^2$ forms a heterocycyl, heteroaryl or —N=C(NH$_2$)$_2$;

R$^3$ and R$^6$ moieties can be the same or different, each being independently selected from the group consisting of H, alkyl, alkylaryl, aralkyl, —CN, CF$_3$, haloalkyl, cycloalkyl, halogen, hydroxyalkyl, —N=CH—(R$^{31}$), —C(=O)N(R$^{30}$)$_2$, —N(R$^{30}$)$_2$, —OR$^{30}$, —SO$_2$(R$^{31}$), —N(R$^{30}$)C(=O)N(R$^{30}$)$_2$ and —N(R$^{30}$)C(=O)R$^{31}$;

R$^7$ and R$^8$ are the same or different, each being independently selected from the group consisting of H, alkyl, alkylaryl, heteroaryl, hydroxyl, —CN, alkoxy, alkylamino, —N(H)S(O)$_2$alkyl and —N(H)C(=O)N(H)alkyl; or alternatively R$^7$ and R$^8$ taken together is =O, =S, =NH, =N(alkyl), =N(Oalkyl), =N(OH) or cycloalkyl;

the R$^{10}$ moieties can be the same or different, each being independently selected from the group consisting of H, alkyl, cycloalkyl, aryl, heteroaryl, heterocyclenyl, heterocyclyl, alkylaryl, arylalkyl, —CO$_2$H, hydroxyalkyl, —C(=O)N(R$^{30}$)$_2$, —(CH$_2$)$_q$OH, —(CH$_2$)$_q$OR$^{31}$—(CH$_2$)$_q$NHR$^{31}$, —(CH$_2$)$_q$N(R$^{31}$)$_2$, —OR$^{30}$, halogen, =O, and —C(=O)R$^{31}$;

the R$^{11}$ moieties can be the same or different, each being independently selected from the group consisting of H, alkyl, cycloalkyl, aryl, heteroaryl, heterocyclyl, heterocyclenyl, alkylaryl, arylalkyl, hydroxyalkyl, carboxamide, CO$_2$H, —(CH$_2$)$_q$OH, —(CH$_2$)$_q$OR$^{31}$, —(CH$_2$)$_q$NHR$^{31}$, —(CH$_2$)$_q$N(R$^{31}$)$_2$, —OR$^{30}$, halogen, =O, and —C(=O)R$^{31}$;

R$^{12}$ is selected from the group consisting of H, alkyl, —CN, —C(=O)N(R$^{30}$)$_2$, —(CH$_2$)$_q$OH, —(CH$_2$)$_q$OR$^{31}$, —(CH$_2$)$_q$NHR$^{31}$—(CH$_2$)$_q$N(R$^{31}$)$_2$, and —S(O)$_2$R$^{31}$;

the R$^{20}$ moieties can be the same or different, each being independently selected from the group consisting of H, alkyl, alkenyl, alkylaryl, alkynyl, alkoxy, alkylamino, alkylthiocarboxy, alkylheteroaryl, alkylthio, alkylsulfinyl, alkylsulfonyl, alkoxycarbonyl, aminoalkyl, amidinyl, aralkyl, aralkenyl, aralkoxy, aralkoxycarbonyl, aralkylthio, aryl, aroyl, aryloxy, cyano, cycloalkyl, cycloalkenyl, formyl, guanidinyl, halogen, haloalkyl, heteroalkyl, heteroaryl, heterocyclyl, heterocyclenyl, hydroxyalkyl, hydroxamate, nitro, trifluoromethoxy, —(CH$_2$)$_q$OH, —(CH$_2$)$_q$OR$^{31}$, —(CH$_2$)$_q$NH$_2$, —(CH$_2$)$_q$NHR$^{31}$, —(CH$_2$)$_q$N(R$^{31}$)$_2$, —(CH$_2$)$_q$C(=O)NHR$^{31}$, —(CH$_2$)$_q$SO$_2$R$^{31}$, —(CH$_2$)$_q$NHSO$_2$R$^{31}$, —(CH$_2$)$_q$SO$_2$NHR$^{31}$, -alkynylC(R$^{31}$)$_2$OR$^{31}$, —C(=O)R$^{30}$, —C(=O)N(R$^{30}$)$_2$, —C(=NR$^{30}$)NHR$^{30}$, —C(=NOH)N(R$^{30}$)$_2$, —C(=NOR$^{31}$)N(R$^{30}$)$_2$, —C(=O)OR$^{30}$, —N(R$^{30}$)$_2$, —N(R$^{30}$)C(=O)R$^{31}$, —NHC(=O)N(R$^{30}$)$_2$, —N(R$^{30}$)C(=O)OR$^{31}$, —N(R$^{30}$)C(=NCN)N(R$^{30}$)$_2$, —N(R$^{30}$)C(=O)N(R$^{30}$)SO$_2$(R$^{31}$), —N(R$^{30}$)C(=O)N(R$^{30}$)$_2$, —N(R$^{30}$)SO$_2$(R$^{31}$), —N(R$^{30}$)S(O)$_2$N(R$^{30}$)$_2$, —OR$^{30}$, —OC(=O)N(R$^{30}$)$_2$, —SR$^{30}$, —SO$_2$N(R$^{30}$)$_2$, —SO$_2$(R$^{31}$), —OSO$_2$(R$^{31}$), and —OSi(R$^{30}$)$_3$; or alternatively two R$^{20}$ moieties are linked together to form a five or six membered aryl, cycloalkyl, heterocyclyl, heterocyclenyl, or heteroaryl ring wherein said five or six membered aryl, cycloalkyl, heterocyclyl, heterocyclenyl, or heteroaryl ring is fused to ring D and the fused ring is optionally substituted with 0-4 R$^{21}$ moieties;

the R$^{21}$ moieties can be the same or different, each being independently selected from the group consisting of H, alkyl, alkenyl, alkylaryl, alkynyl, alkoxy, alkylamino, alkylthiocarboxy, alkylheteroaryl, alkylthio, alkylsulfinyl, alkylsulfonyl, alkoxycarbonyl, aminoalkyl, amidinyl, aralkyl, aralkenyl, aralkoxy, aralkoxycarbonyl, aralkylthio, aryl, aroyl, aryloxy, carboxamido, cyano, cycloalkyl, cycloalkenyl, formyl, guanidinyl, halogen, haloalkyl, heteroalkyl, heteroaryl, heterocyclyl, heterocyclenyl, hydroxyalkyl, hydroxamate, nitro, trifluoromethoxy, —(CH$_2$)$_q$OH, —(CH$_2$)$_q$OR$^{31}$, —(CH$_2$)$_q$NH$_2$, —(CH$_2$)$_q$NHR$^{31}$, —(CH$_2$)$_q$N(R$^{31}$)$_2$, —(CH$_2$)$_q$C(=O)NHR$^{31}$, —(CH$_2$)$_q$SO$_2$R$^{31}$, —(CH$_2$)$_q$NSO$_2$R$^{31}$, —(CH$_2$)$_q$SO$_2$NHR$^{31}$, -alkynylC(R$^{31}$)$_2$OR$^{31}$, —C(=O)R$^{30}$, —C(=O)N(R$^{30}$)$_2$, —C(=NR$^{30}$)NHR$^{30}$, —C(=NOH)N(R$^{30}$)$_2$, —C(=NOR$^{31}$)N(R$^{30}$)$_2$, —C(=O)OR$^{30}$, —N(R$^{30}$)$_2$, —N(R$^{30}$)C(=O)R$^{31}$, —NHC(=O)N(R$^{30}$)$_2$, —N(R$^{30}$)C(=O)OR$^{31}$, —N(R$^{30}$)C(=NCN)N(R$^{30}$)$_2$, —N(R$^{30}$)C(=O)N(R$^{30}$)SO$_2$(R$^{31}$), —N(R$^{30}$)C(=O)N(R$^{30}$)$_2$, —N(R$^{30}$)SO$_2$(R$^{31}$), —N(R$^{30}$)S(O)$_2$N(R$^{30}$)$_2$, —OR$^{30}$, —OC(=O)N(R$^{30}$)$_2$, —SR$^{30}$, —SO$_2$N(R$^{30}$)$_2$, —SO$_2$(R$^{31}$), —OSO$_2$(R$^{31}$), and —OSi(R$^{30}$)$_3$;

Y is selected from the group consisting of —(CR$^{13}$R$^{13}$)$_r$—, —CHR$^{13}$C(=O)—, —(CHR$^{13}$)$_r$O—, —(CHR$^{13}$)$_r$N(R$^{30}$)—, —C(=O)—, —C(=NR$^{30}$)—, —C(=N—OR$^{30}$)—, —CH(C(=O)NHR$^{30}$)—, CH-heteroaryl-, —C(R$^{13}$R$^{13}$)$_r$C(R$^{13}$)=C(R$^{13}$)—, —(CHR$^{13}$)$_r$C(=O)— and —(CHR$^{13}$)$_r$N(H)C(=O)—; or alternatively Y is cycloalkyl, heterocyclenyl, or heterocyclyl wherein the cycloalkyl, heterocyclenyl, or heterocyclyl is fused with the phenyl ring marked D;

the R$^{13}$ moieties can be the same or different, each being independently selected from the group consisting of H, alkyl, alkylaryl, cycloalkyl, alkoxy, aryl, heteroaryl, heterocyclenyl, heterocyclyl, spiroalkyl, —CN, —CO$_2$H, —C(=O)R$^{30}$, —C(=O)N(R$^{30}$)$_2$, —(CHR$^{30}$)$_q$OH, —(CHR$^{30}$)$_q$OR$^{31}$, —(CHR$^{30}$)$_q$NH$_2$, —(CH R$^{30}$)$_q$NHR$^{31}$, —(CH$_2$)$_q$C(=O)NHR$^{31}$, —(CH$_2$)$_q$SO$_2$R$^{31}$, —(CH$_2$)$_q$NSO$_2$R$^{31}$, —(CH$_2$)$_q$sO$_2$NHR$^{31}$, —NH$_2$, —N(R$^{30}$)$_2$, —N(R$^{30}$)C(=O)N(R$^{30}$)$_2$, —N(R$^{30}$)SO$_2$(R$^{31}$), —OH, OR$^{30}$, —SO$_2$N(R$^{30}$)$_2$, and —SO$_2$(R$^{31}$);

the R$^{30}$ moieties can be the same or different, each being independently selected from the group consisting of H, alkyl, alkylaryl, aryl, aralkyl, cycloalkyl, CN, —(CH$_2$)$_q$OH, —(CH$_2$)$_q$Oalkyl, —(CH$_2$)$_q$Oalkylaryl, —(CH$_2$)$_q$Oaryl, —(CH$_2$)$_q$Oaralkyl, —(CH$_2$)$_q$Ocycloalkyl, —(CH$_2$)$_q$NH$_2$, —(CH$_2$)$_q$NHalkyl, —(CH$_2$)$_q$N(alkyl)$_2$, —(CH$_2$)$_q$NHalkylaryl, —(CH$_2$)$_q$NHaryl, —(CH$_2$)$_q$NHaralkyl, —(CH$_2$)$_q$NHcycloalkyl, —(CH$_2$)$_q$C(=O)NHalkyl, —(CH$_2$)$_q$C(=O)N(alkyl)$_2$, —(CH$_2$)$_q$C(=O)NHalkylaryl, —(CH$_2$)$_q$C(=O)NHaryl, —(CH$_2$)$_q$C(=O)NHaralkyl, —(CH$_2$)$_q$C(=O)NHcycloalkyl, —(CH$_2$)$_q$SO$_2$alkyl, —(CH$_2$)$_q$SO$_2$alkylaryl, —(CH$_2$)$_q$SO$_2$aryl, —(CH$_2$)$_q$SO$_2$aralkyl, —(CH$_2$)$_q$SO$_2$cycloalkyl, —(CH$_2$)$_q$NSO$_2$alkyl, —(CH$_2$)$_q$NSO$_2$alkylaryl, —(CH$_2$)$_q$NSO$_2$aryl, —(CH$_2$)$_q$NSO$_2$aralkyl, —(CH$_2$)$_q$NSO$_2$cycloalkyl, —(CH$_2$)$_q$SO$_2$NHalkyl, —(CH$_2$)$_q$SO$_2$NHalkylaryl, —(CH$_2$)$_q$SO$_2$NHaryl, —(CH$_2$)$_q$SO$_2$NHaralkyl, —(CH$_2$)$_q$SO$_2$NHcycloalkyl, heterocyclenyl, heterocyclyl, and heteroaryl;

the R$^{31}$ moieties can be the same or different, each being independently selected from the group consisting of alkyl, alkylaryl, aryl, aralkyl, cycloalkyl, —(CH$_2$)$_q$OH, —(CH$_2$)$_q$Oalkyl, —(CH$_2$)$_q$Oalkylaryl, —(CH$_2$)$_q$Oaryl, —(CH$_2$)$_q$Oaralkyl, —(CH$_2$)$_q$Ocycloalkyl, —(CH$_2$)$_q$NH$_2$, —(CH$_2$)$_q$NHalkyl, —(CH$_2$)$_q$N(alkyl)$_2$, —(CH$_2$)$_q$NHalkylaryl, —(CH$_2$)$_q$NHaryl, —(CH$_2$)$_q$NHaralkyl, —(CH$_2$)$_q$NHcycloalkyl, —(CH$_2$)$_q$C(=O)NHalkyl, —(CH$_2$)$_q$C(=O)N(alkyl)$_2$, —(CH$_2$)$_q$C(=O)NHalkylaryl, —(CH$_2$)$_q$C(=O)NHaryl, —(CH$_2$)$_q$C(=O)NHaralkyl, —(CH$_2$)$_q$C(=O)NHcycloalkyl, —(CH$_2$)$_q$SO$_2$alkyl, —(CH$_2$)$_q$SO$_2$alkylaryl, —(CH$_2$)$_q$SO$_2$aryl, —(CH$_2$)$_q$SO$_2$aralkyl, —(CH$_2$)$_q$SO$_2$cycloalkyl, —(CH$_2$)$_q$NSO$_2$alkyl, —(CH$_2$)$_q$NSO$_2$alkylaryl, —(CH$_2$)$_q$NSO$_2$aryl, —(CH$_2$)$_q$NSO$_2$aralkyl, —(CH$_2$)$_q$NSO$_2$cycloalkyl, —(CH$_2$)$_q$SO$_2$NHalkyl, —(CH$_2$)$_q$SO$_2$NHalkylaryl, —(CH$_2$)$_q$SO$_2$NHaryl, —(CH$_2$)$_q$SO$_2$NHaralkyl, —(CH$_2$)$_q$SO$_2$NHcycloalkyl, heterocyclenyl, heterocyclyl, and heteroaryl;

m is 0 to 4;

n is 0 to 4;

p is 0 to 5;

each q can be the same or different, each being independently selected from 1 to 5; and r is 1 to 4;

with the proviso that there are no two adjacent double bonds in any ring, and that when a nitrogen is substituted by two alkyl groups, said two alkyl groups may be optionally joined to each other to form a ring.

A further feature of the invention is a pharmaceutical composition containing as active ingredient at least one compound of Formula 1 together with at least one pharmaceutically acceptable carrier or excipient.

The invention provides methods of preparing compounds of Formula 1, as well as methods for treating diseases, for example, treatment (e.g., palliative therapy, curative therapy, prophylactic therapy) of certain diseases and conditions e.g., inflammatory diseases (e.g., psoriasis), autoimmune diseases (e.g., rheumatoid arthritis, multiple sclerosis), graft rejection (e.g., allograft rejection, xenograft rejection), infectious diseases and tumors. The invention provides a method of treating a CXCR3 chemokine mediated disease in a patient in need of such treatment comprising administering to the patient a therapeutically effective amount of at least one compound of Formula 1, or a pharmaceutically acceptable salt, solvate or ester thereof.

The invention provides methods of treating diseases, for example, treatment (e.g., palliative therapy, curative therapy, prophylactic therapy) of certain diseases and conditions such as inflammatory diseases (e.g., psoriasis, inflammatory bowel disease), autoimmune diseases (e.g., rheumatoid arthritis, multiple sclerosis), graft rejection (e.g., allograft rejection, xenograft rejection), infectious diseases as well as cancers and tumors, fixed drug eruptions, cutaneous delayed-type hypersensitivity responses, ophthalmic inflammation or dry eye, type I diabetes, viral meningitis and tuberculoid leprosy comprising administering: (a) a therapeutically effective amount of at least one compound according to Formula 1, or a pharmaceutically acceptable salt, solvate or ester thereof concurrently or sequentially with (b) at least one medicament selected from the group consisting of: disease modifying antirheumatic drugs; nonsteroidal anti-inflammatory drugs; COX-2 selective inhibitors; COX-1 inhibitors; immunosuppressives (such as cyclosporins and methotrexate); steroids (including corticosteroids such as glucorticoids); PDE IV inhibitors, anti-TNF-α compounds, TNF-α-convertase (TACE) inhibitors, MMP inhibitors, cytokine inhibitors, glucocorticoids, other chemokine inhibitors such as CCR2 and CCR5, CB2-selective inhibitors, p38 inhibitors, biological response modifiers; anti-inflammatory agents and therapeutics.

The invention also provides a method of modulating (inhibiting or promoting) an inflammatory response in an individual in need of such therapy. The method comprises administering a therapeutically effective amount of a compound (e.g., small organic molecule) which inhibits or promotes mammalian CXCR3 function in an individual in need thereof. Also disclosed is a method of inhibiting or blocking T-cell mediated chemotaxis in a patient in need of such treatment comprising administering to the patient a therapeutically effective amount of a compound of Formula 1 or a pharmaceutically acceptable salt, solvate or ester thereof.

Also disclosed is a method of treating inflammatory bowel disease (such Crohn's disease, ulcerative colitis) in a patient in need of such treatment comprising administering to the patient a therapeutically effective amount of at least one compound of Formula 1, or a pharmaceutically acceptable salt, solvate or ester thereof.

Also disclosed is a method of treating inflammatory bowel disease in a patient in need of such treatment comprising administering to the patient a therapeutically effective amount of: (a) at least one compound of Formula 1, or a pharmaceutically acceptable salt, solvate or ester thereof concurrently or sequentially with (b) at least one compound selected from the group consisting of: sulfasalazine, 5-aminosalicylic acid, sulfapyridine, anti-TNF compounds, anti-IL-12 compounds, corticosteroids, glucocorticoids, T-cell receptor directed therapies (such as anti-CD3 antibodies), immunosuppresives, methotrexate, azathioprine, and 6-mercaptopurines.

Also disclosed is a method of treating graft rejection in a patient in need of such treatment comprising administering to the patient a therapeutically effective amount of at least one compound of Formula 1, or a pharmaceutically acceptable salt, solvate or ester thereof.

Also disclosed is a method of treating graft rejection in a patient in need of such treatment comprising administering to the patient a therapeutically effective amount of: (a) at least one compound of Formula 1, or a pharmaceutically acceptable salt, solvate or ester thereof concurrently or sequentially with (b) at least one compound selected from the group consisting of: cyclosporine A, FK-506, FTY720, beta-interferon, rapamycin, mycophenolate, prednisolone, azathioprine, cyclophosphamide and an antilymphocyte globulin.

Also disclosed is a method of treating multiple sclerosis in a patient in need of such treatment the method comprising administering to the patient a therapeutically effective amount of: (a) a therapeutically effective amount of at least one compound of Formula 1, or a pharmaceutically acceptable salt, solvate or ester thereof concurrently or sequentially with (b) at least one compound selected from the group consisting of: beta-interferon, glatiramer acetate, corticosteroids, glucocorticoids, methotrexate, azothioprine, mitoxantrone, VLA-4 inhibitors, FTY720, anti-IL-12 inhibitors, and CB2-selective inhibitors.

Also disclosed is a method of treating multiple sclerosis in a patient in need of such treatment the method comprising administering to the patient a therapeutically effective amount of: (a) a therapeutically effective amount of at least one compound of Formula 1, or a pharmaceutically acceptable salt, solvate or ester thereof concurrently or sequentially with (b) at least one compound selected from the group consisting of: methotrexate, cyclosporin, leflunomide, sulfasalazine, corticosteroids, β-methasone, β-interferon, glatiramer acetate, prednisone, etonercept, and infliximab.

Also disclosed is a method of treating rheumatoid arthritis in a patient in need of such treatment the method comprising administering to the patient a therapeutically effective amount of: (a) at least one compound of Formula 1, or a pharmaceutically acceptable salt, solvate or ester thereof concurrently or sequentially with (b) at least one compound selected from the group consisting of: non-steroidal anti-inflammatory agents, COX-2 inhibitors, COX-1 inhibitors, immunosuppressives, cyclosporine, methotrexate, steroids, PDE IV inhibitors, anti-TNF-α compounds, MMP inhibitors, corticosteroids, glucocorticoids, chemokine inhibitors, CB2-selective inhibitors, caspase (ICE) inhibitors and other classes of compounds indicated for the treatment of rheumatoid arthritis.

Also disclosed is a method of treating psoriasis in a patient in need of such treatment the method comprising administering to the patient a therapeutically effective amount of: a) at least one compound of Formula 1, or a pharmaceutically acceptable salt, solvate or ester thereof concurrently or sequentially with (b) at least one compound selected from the group consisting of: immunosuppressives, cyclosporins, methotrexate, steroids, corticosteroids, anti-TNF-α compounds, anti-IL compounds, anti-IL-23 compounds, vitamin A and D compounds and fumarates.

Also disclosed is a method of treating ophthalmic inflammation (including, for e.g., uveitis, posterior segment intraocular inflammation, Sjogren's syndrome) or dry eye in a patient in need of such treatment the method comprising administering to the patient a therapeutically effective amount of: a) at least one compound according to Formula 1, or a pharmaceutically acceptable salt, solvate or ester thereof concurrently or sequentially with (b) at least one compound selected from the group consisting of: immunosuppressives, cyclosporins, methotrexate, FK506, steroids, corticosteroids, and anti-TNF-α compounds.

Also disclosed is a method of treating a disease selected from the group consisting of: inflammatory disease, rheumatoid arthritis, multiple sclerosis, inflammatory bowel disease, graft rejection, psoriasis, fixed drug eruptions, cutaneous delayed-type hypersensitivity responses, ophthalmic inflammation (including e.g., uveitis, posterior segment intraocular inflammation, and Sjogren's syndrome), tuberculoid leprosy and cancer in a patient in need of such treatment, such method comprising administering to the patient an effective amount of at least one compound according to Formula 1, or a pharmaceutically acceptable salt, solvate or ester thereof.

The invention also provides a method of treating a disease selected from the group consisting of: inflammatory disease, rheumatoid arthritis, multiple sclerosis, inflammatory bowel disease, graft rejection, psoriasis, fixed drug eruptions, cutaneous delayed-type hypersensitivity responses and tuberculoid leprosy, ophthalmic inflammation, type I diabetes, viral meningitis and cancer in a patient in need of such treatment, such method comprising administering to the patient an effective amount of (a) at least one compound according to Formula 1, or a pharmaceutically acceptable salt, solvate or ester thereof concurrently or sequentially with (b) at least one medicament selected from the group consisting of: disease modifying antirheumatic drugs; nonsteroidal antiinflammatory drugs; COX-2 selective inhibitors; COX-1 inhibitors; immunosuppressives; steroids; PDE IV inhibitors, anti-TNF-α compounds, MMP inhibitors, corticosteroids, glucocorticoids, chemokine inhibitors, CB2-selective inhibitors, biological response modifiers; anti-inflammatory agents and therapeutics.

DETAILED DESCRIPTION OF THE INVENTION

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "alkoxy," etc.

As used above, and throughout the specification, the following terms, unless otherwise indicated, shall be understood to have the following meanings:

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. The alkenyl group may be substituted by one or more substituents which may be the same or different, each substituent being independently selected from the group consisting of alkyl, alkenyl, alkynyl, alkoxyl, aryl, aryloxy, cycloalkyl, cycloalkenyl, cyano, heteroaryl, heterocyclyl, heterocyclenyl, amino, aminosulfonyl, halo, carboxyl, carboxyalkyl (non-limiting example(s) include ester), alkoxycarbonyl, hydroxyalkyl, carbonyl (non-limiting example(s) include ketone), —C(=O)heterocyclyl, formyl (non-limiting example(s) include aldehyde), carboxamido (i.e. amido, —C(=O)NH$_2$), —C(=O)N(alkyl)$_2$, —C(=O)NH(alkyl), —C(=O)N(cycloalkyl)$_2$, —C(=O)NH(cycloalkyl), —NHC(=O)alkyl, urea (e.g. —NH(C=O)NH$_2$, —NH(C=O)NH(alkyl), —NH(C=O)NH(alkyl)$_2$, —NH(C=O)NH(heteroaryl), —NH(C=O)NH(heterocyclyl)), guanidinyl, —NHC(=NCN)NH$_2$, —NHC(=NCN)N(alkyl)$_2$, carbamoyl (i.e. —CO$_2$NH$_2$), NHC(=O)Oalkyl, —CO$_2$N(alkyl)$_2$, —NHC(=O))NH—S(O)$_2$alkyl, —NHC(=O)N(alkyl)$_2$-S(O)$_2$alkyl, —NH—S(O)$_2$alkyl, —NH—S(O)$_2$heteroaryl, —N(alkyl)-S(O)$_2$alkyl, —NH—S(O)$_2$aryl, —N(alkyl)-S(O)$_2$aryl, —NH—S(O)$_2$NH$_2$, —NH—S(O)$_2$NHalkyl, —NH—S(O)$_2$N(alkyl)$_2$, alkylthiocarboxy, —S(O)$_2$ alkyl, —S(O)$_2$aryl, —OS(O)$_2$alkyl, —OS(O)$_2$aryl, sulfonyl urea (non-limiting example(s) include NHC(=S)NHalkyl). Non-limiting examples of suitable alkenyl groups include ethenyl, propenyl, n-butenyl, 3-methylbut-2-enyl, n-pentenyl, octenyl and decenyl.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. The alkyl group may be substituted by one or more substituents which may be the same or different, each substituent being independently selected from the group consisting of alkyl, alkenyl, alkynyl, alkoxyl, aryl, aryloxy, cycloalkyl, cycloalkenyl, cyano, heteroaryl, heterocyclyl, heterocyclenyl, amino, —NH(alkyl), —N(alkyl)$_2$, —NH(cycloalkyl), —N(cycloalkyl)$_2$, —NH(aryl), —N(aryl)$_2$, —NH(heteroaryl), —N(heteroaryl)$_2$, —NH(heterocyclyl), N(heterocyclyl)$_2$, halo, hydroxy, carboxyl, carboxyalkyl (non-limiting example(s) include ester), alkoxycarbonyl, hydroxyalkyl, carbonyl (non-limiting example(s) include ketone), —C(=O)heterocyclyl, formyl, carboxamido (i.e. amido, —C(=O)NH$_2$, —C(=O)N(alkyl)$_2$, —C(=O)NH(alkyl), —C(=O)N(cycloalkyl)$_2$, —C(=O)NH(cycloalkyl)), —NHC(=O)alkyl, amidinyl, hydrazidyl, hydroxamate, —NHC(=O)H, —NHC(=O)alkyl, urea (non-limiting example(s) include —NH(C=O)NH$_2$, —NH(C=O)NH(alkyl), —NH(C=O)N(alkyl)$_2$, —NH(C=O)NH(heteroaryl), —NH(C=O)NH(heterocyclyl)), guanidinyl, —NHC(=NCN)NH$_2$, —NHC(=NCN)N(alkyl)$_2$, carbamoyl (i.e., —CO$_2$NH$_2$), —NHC(=O)Oalkyl, —CO$_2$N(alkyl)$_2$, —NHC(=O)NH—S(O)$_2$alkyl, —NHC(=O)N(alkyl)-S(O)$_2$alkyl, —NH—S(O)$_2$alkyl, —NH—S(O)$_2$heteroaryl, —N(alkyl)-S(O)$_2$alkyl, —NH—S(O)$_2$aryl, —N(alkyl)-S(O)$_2$aryl, —NH—S(O)$_2$NH$_2$, —NH—S(O)$_2$NHalkyl, —NH—S(O)$_2$N(alkyl)$_2$, thio, alkylthio, alkylthiocarboxy, —S(O)alkyl, —S(O)$_2$alkyl, —S(O)$_2$aryl, —OS(O)$_2$alkyl, —OS(O)$_2$aryl, sulfonyl urea (non-limiting example(s) include —NHC(=S)NHalkyl) and OSi(alkyl)$_3$. Non-limiting examples of suitable alkyl groups include methyl, ethyl, n-propyl, isopropyl, n-butyl, t-butyl, n-pentyl, heptyl, nonyl, decyl, fluoromethyl, trifluoromethyl and cyclopropylmethyl.

"Alkylheteroaryl" means an alkyl-heteroaryl-group wherein the alkyl is as previously described and the bond to the parent moiety is through the heteroaryl group.

"Alkylamino" means an —NH2 or —NH3+ group in which one or more of the hydrogen atoms on the nitrogen is replaced by an alkyl group as defined above. The bond to the parent is through the nitrogen.

"Alkylaryl" means an alkyl-aryl-group in which the alkyl and aryl are as described herein. Preferred alkylaryls comprise a lower alkyl group. Non-limiting examples of suitable alkylaryl groups include o-tolyl, p-tolyl and xylyl. The bond to the parent moiety is through the aryl.

"Alkylthio" means an alkyl-S— group in which the alkyl group is as described herein. Non-limiting examples of suitable alkylthio groups include methylthio, ethylthio, i-propylthio and heptylthio. The bond to the parent moiety is through the sulfur.

"Alkylthiocarboxy" means an alkyl-S—C(=O)O— group. Preferred groups are those in which the alkyl group is lower alkyl. The bond to the parent moiety is through the carboxy.

"Alkylsulfonyl" means an alkyl-S(O)$_2$— group. Preferred groups are those in which the alkyl group is lower alkyl. The bond to the parent moiety is through the sulfonyl.

"Alkylsulfinyl" means an alkyl-S(O)— group. Preferred groups are those in which the alkyl group is lower alkyl. The bond to the parent moiety is through the sulfinyl.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl, 3-methylbutynyl, n-pentynyl, and decynyl. The alkynyl group may be substituted by one or more substituents which may be the same or different, each substituent being independently selected from the group consisting of alkyl, alkoxyl, aryl, aryloxy, cycloalkyl, cycloalkenyl, cyano, heteroaryl, heterocyclyl, heterocyclenyl, —NH(alkyl), —N(alkyl)$_2$, —NH(cycloalkyl), —N(cycloalkyl)$_2$, —NH(aryl), —N(aryl)$_2$, —NH(heteroaryl), —N(heteroaryl)$_2$, —NH(heterocyclyl), N(heterocyclyl)$_2$, alkoxycarbonyl, hydroxyalkyl, carbonyl (non-limiting example(s) include ketone), —C(=O)heterocyclyl, carboxamido (i.e. amido, —C(=O)NH$_2$), —C(=O)N(alkyl)$_2$, —C(=O)NH(alkyl), —C(=O)N(cycloalkyl)$_2$, —C(=O)NH(cycloalkyl)), alkylC(=O)NH—, —NHC(=O)alkyl), urea (e.g. —NH(C=O)NH$_2$), —NH(C=O)NH(alkyl), —NH(C=O)NH(alkyl)$_2$, —NH(C=O)NH(heteroaryl), —NH(C=O)NH(heterocyclyl), —S(O)$_2$alkyl, and —S(O)$_2$aryl.

"Alkoxy" means an alkyl-O— group in which the alkyl group is as previously described. Non-limiting examples of suitable alkoxy groups include methoxy, ethoxy, n-propoxy, isopropoxy, n-butoxy, heptoxy and methylhydroxy. The bond to the parent moiety is through the ether oxygen.

"Alkoxycarbonyl" means an alkyl-O—C(=O)— group. Non-limiting examples of suitable alkoxycarbonyl groups include methoxycarbonyl and ethoxycarbonyl. The bond to the parent moiety is through the carbonyl.

"Aminoalkyl" means an amine-alkyl-group in which alkyl is as previously defined. Preferred aminoalkyls contain lower alkyl. Non-limiting examples of suitable aminoalkyl groups include aminomethyl and 2-Dimethlyamino-2-ethyl. The bond to the parent moiety is through the alkyl.

"Amidinyl" means —C(=NR)NHR group. The R groups are defined as H, alkyl, alkylaryl, heteroaryl, hydroxyl, alkoxy, amino, ester, CN, —NHSO$_2$alkyl, —NHSO$_2$Aryl, —NHC(=O)NHalkyl, and —NHalkyl. The bond to the parent moiety is through the carbon.

"Aralkyl" or "arylalkyl" means an aryl-alkyl-group in which the aryl and alkyl are as previously described. Preferred aralkyls comprise a lower alkyl group attached to the aryl group. Non-limiting examples of suitable aralkyl groups include phenylmethylene, 2-phenethyl and naphthalenylmethyl. The bond to the parent moiety is through the alkyl.

"Aralkenyl" means an aryl-alkenyl-group in which the aryl and alkenyl are as previously described. Preferred aralkenyls contain a lower alkenyl group. Non-limiting examples of suitable aralkenyl groups include 2-phenethenyl and 2-naphthylethenyl. The bond to the parent moiety is through the alkenyl.

"Aralkylthio" means an aralkyl-S— group in which the aralkyl group is as previously described. Non-limiting example of a suitable aralkylthio group is benzylthio. The bond to the parent moiety is through the sulfur.

"Aralkoxy" means an aralkyl-O— group in which the aralkyl group is as described above. The bond to the parent moiety is through the oxygen group.

"Aralkoxycarbonyl" means an aralkyl-O—C(=O)— group. Non-limiting example of a suitable aralkoxycarbonyl group is benzyloxycarbonyl. The bond to the parent moiety is through the carbonyl.

"Aroyl" means an aryl-C(=O)— group in which the aryl group is as previously described. The bond to the parent moiety is through the carbonyl. Non-limiting examples of suitable groups include benzoyl and 1- and 2-naphthoyl.

"Aryl" (sometimes abbreviated "Ar") means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Aryloxy" means an aryl-O— group in which the aryl group is as previously described. Non-limiting examples of suitable aryloxy groups include phenoxy and naphthoxy. The bond to the parent moiety is through the ether oxygen.

"Aryloxycarbonyl" means an aryl-O—C(=O)— group. Non-limiting examples of suitable aryloxycarbonyl groups include phenoxycarbonyl and naphthoxycarbonyl. The bond to the parent moiety is through the carbonyl.

"Arylsulfonyl" means an aryl-S(O)$_2$— group. The bond to the parent moiety is through the sulfonyl.

"Arylsulfinyl" means an aryl-S(O)— group. The bond to the parent moiety is through the sulfinyl.

"Arylthio" means an aryl-S— group in which the aryl group is as previously described. Non-limiting examples of suitable arylthio groups include phenylthio and naphthylthio. The bond to the parent moiety is through the sulfur.

"Carboxyalkyl" means an alkyl-C(=O)O— group. The bond to the parent moiety is through the carboxy.

"Carboxamido" means —C(=O)NRR wherein R is H, alkyl, amino, aryl, cycloalkyl, heterocyclenyl, heteroaryl and carboxamido. The bond to the parent moiety is through the carboxy.

Carbamates and urea substituents refer to groups with oxygens and nitrogens respectively adjacent an amide; representative carbamate and urea substituents include the following:

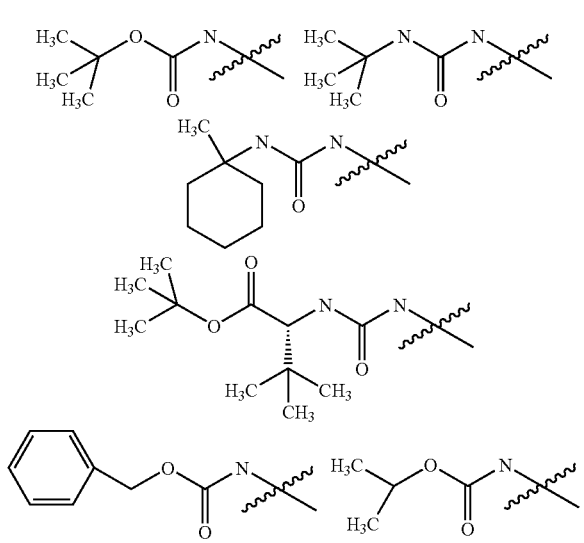

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples can include bicyclic cycloalkyls such as bicycloheptane. Non-limiting examples of suitable multicyclic cycloalkyls include 1-decalin, norbornyl, adamantyl and the like.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cycloheptenyl, and the like. Non-limiting example of a suitable multicyclic cycloalkenyl is norbornylenyl. The term "cycloalkenyl" additionally means moieties such as cyclobutenedione, cyclopentenone, cyclopentenedione and the like.

"Halogen" (or halo) means fluorine, chlorine, bromine, or iodine. Preferred are fluorine, chlorine and bromine.

"Haloalkyl" means an alkyl as defined above wherein one or more hydrogen atoms on the alkyl is replaced by a halo group defined above.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. The nitrogen or sulfur atom of the heteroaryl can be optionally oxidized to the corresponding N-oxide, S-oxide or S,S-dioxide. Non-limiting examples of suitable heteroaryls include pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like.

"Heterocyclyl" (or heterocycloalkyl) means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, oxazolidinyl, imidazolidinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like.

"Heterocyclenyl" means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable monocyclic azaheterocyclenyl groups include 1,2,3,4-tetrahydropyridine, 1,2-dihydropyridyl, 1,4-dihydropyridyl, 1,2,3,6-tetrahydropyridine, 1,4,5,6-tetrahydropyrimidine, dihydro-2-pyrrolinyl, dihydro-3-pyrrolinyl, dihydro-2-imidazolinyl, dihydro-2-pyrazolinyl, dihydro-4,5-trizolyl and the like. Non-limiting examples of suitable oxaheterocyclenyl groups include 3,4-dihydro-2H-pyran, dihydrofuranyl, fluorodihydrofuranyl, and the like. Non-limiting example of a suitable multicyclic oxaheterocyclenyl group is 7-oxabicyclo[2.2.1]heptenyl. Non-limiting examples of suitable monocyclic thiaheterocyclenyl rings include thiophenyl, dihydrothiophenyl, dihydrothiopyranyl, and the like.

"Heteroaralkyl" means a heteroaryl-alkyl-group in which the heteroaryl and alkyl are as previously described. Preferred heteroaralkyls contain a lower alkyl group. Non-limiting examples of suitable aralkyl groups include pyridylmethyl, 2-(furan-3-yl)ethyl and quinolin-(3-yl)methyl. The bond to the parent moiety is through the alkyl.

"Heteroaralkenyl" means an heteroaryl-alkenyl-group in which the heteroaryl and alkenyl are as previously described. Preferred heteroaralkenyls contain a lower alkenyl group. Non-limiting examples of suitable heteroaralkenyl groups include 2-(pyrid-3-yl)ethenyl and 2-(quinolin-3-yl)ethenyl. The bond to the parent moiety is through the alkenyl.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl. The bond to the parent moiety is through the alkyl.

"Hydroxamate" means an alkyl-C(=O)NH—O— group. The bond to the parent moiety is through the oxygen group.

"Spiroalkyl" means an alkylene group wherein two carbon atoms of an alkyl group are attached to one carbon atom of a parent molecular group thereby forming a carbocyclic or heterocyclic ring of three to eleven atoms. Representative structures include examples such as:

The spiroalkyl groups of this invention:

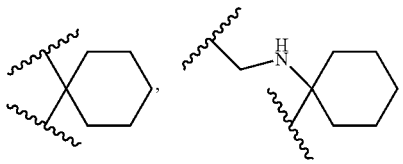

can be optionally substituted by one or more ring system substituents, wherein "ring system substituent" is as defined herein.

"Ring system substituent" means a substituent attached to an aromatic or non-aromatic ring system which, for example, replaces an available hydrogen on the ring system. Ring system substituents may be the same or different, each being independently selected from the group consisting of H, alkyl, alkenyl, alkynyl, alkoxyl, aryl, aroyl, aryloxy, cycloalkyl, cycloalkenyl, heteroaryl, heterocyclyl, heterocyclenyl, alkylaryl, alkylheteroaryl, aralkyl, aralkenyl, aralkoxy, aralkoxycarbonyl, amino, —NH(alkyl), —N(alkyl)$_2$, —NH(cycloalkyl), —N(cycloalkyl)$_2$, —NH(aryl), —N(aryl)$_2$, —NH(heteroaryl), —N(heteroaryl)$_2$, —NH(heterocyclyl), N(heterocyclyl)$_2$, halo, hydroxy, carboxyl, carboxyalkyl (non-limiting example(s) include ester), cyano, alkoxycarbonyl, hydroxyalkyl, carbonyl (non-limiting example(s) include ketone), —C(=O)heterocyclyl, formyl (non-limiting example(s) include aldehyde), carboxamido (i.e. amido, —C(=O)NH$_2$), —C(=O)N(alkyl)$_2$, —C(=O)NH(alkyl), —C(=O)N(cycloalkyl)$_2$, —C(=O)NH(cycloalkyl), alkylC(=O)NH—, -amidino, hydrazido, hydroxamate, —NHC(=O)H, —NHC(=O)alkyl, urea (e.g. —NH(C=O)NH$_2$), —NH(C=O)NH(alkyl), —NH(C=O)NH(alkyl)$_2$, —NH(C=O)NH(heteroaryl), —NH(C=O)NH(heterocyclyl), guanidinyl, —NHC(=NCN)NH$_2$, —NHC(=NCN)N(alkyl)$_2$, carbamoyl (i.e. —CO$_2$NH$_2$), NHC(=O)Oalkyl, —CO$_2$N(alkyl)$_2$, —NHC(=O))NH—S(O)$_2$alkyl, —NHC(=O)N(alkyl)$_2$-S(O)$_2$alkyl, —NH—S(O)$_2$alkyl, —NH—S(O)$_2$heteroaryl, —N(alkyl)-S(O)$_2$alkyl, —NH—S(O)$_2$aryl, —N(alkyl)-S(O)$_2$aryl, —NH—S(O)$_2$NH$_2$, —NH—S(O)$_2$NHalkyl, —NH—S(O)$_2$N(alkyl)$_2$,thio, alkylthiocarboxy, —S(O)$_2$alkyl —S(O)$_2$aryl, —OS(O)$_2$alkyl, —OS(O)$_2$aryl, sulfonyl urea (non-limiting example(s) include —NHC(=S)NHalkyl) and OSi(alkyl)$_3$.

"Ring system substituent" also means a cyclic ring of 3 to 7 ring atoms of which may contain 1 or 2 heteroatoms, attached to an aryl, heteroaryl, heterocyclyl or heterocyclenyl ring by simultaneously substituting two ring hydrogen atoms on said aryl, heteroaryl, heterocyclyl or heterocyclenyl ring. Non-limiting examples include:

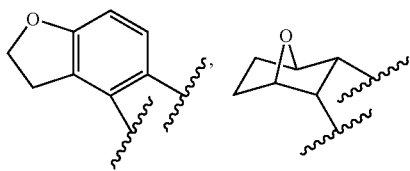

and the like.

The term "optionally substituted" means optional substitution with the specified groups, radicals or moieties, in available position or positions.

With reference to the number of moieties (non-limiting example(s) include, substituents, groups or rings) in a compound, unless otherwise defined, the phrases "one or more" and "at least one" mean that, there can be as many moieties as chemically permitted, and the determination of the maximum number of such moieties is well within the knowledge of those skilled in the art. Preferably, there are one to three substituents, or more preferably, one to two substituents, with at least one in the para position.

As used herein, the term "composition" is intended to encompass a product comprising the specified ingredients in the specified amounts, as well as any product which results, directly or indirectly, from combination of the specified ingredients in the specified amounts.

The straight line —— as a bond generally indicates a mixture of, or either of, the possible isomers, non-limiting example(s) include, containing (R)— and (S)— stereochemistry. For example,

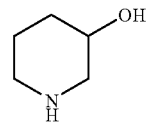

means containing both

Lines drawn into the ring systems, such as, for example:

indicate that the indicated line (bond) may be attached to any of the substitutable ring carbon atoms.

As well known in the art, a bond drawn from a particular atom wherein no moiety is depicted at the terminal end of the bond indicates a methyl group bound through that bond to the atom, unless stated otherwise. For example:

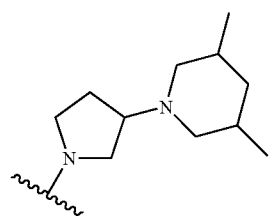

represents

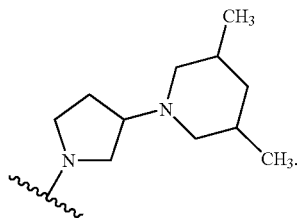

It should also be noted that any heteroatom with unsatisfied valences in the text, schemes, examples, structural formulae, and any Tables herein is assumed to have the hydrogen atom or atoms to satisfy the valences.

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of Formula 1 or a salt and/or solvate thereof. A discussion of prodrugs is provided in T. Higuchi and V. Stella, *Pro-drugs as Novel Delivery Systems* (1987) Volume 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

Metabolic conjugates, for example, glucoronides and sulfates which can under reversible conversion to compounds of Formula 1 are contemplated in this application.

"Effective amount" or "therapeutically effective amount" is meant to describe an amount of compound or a composition of the present invention effective to antagonize CXCR3 and thus produce the desired therapeutic effect in a suitable patient.

"Mammal" means humans and other mammalian animals.

"Patient" includes both human and animals.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

The compounds of Formula 1 form salts which are also within the scope of this invention. Reference to a compound of Formula 1 herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula 1 contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (non-limiting example(s) include, non-toxic, physiologically acceptable) salts are preferred, although other salts are also useful. Salts of the compounds of the Formula 1 may be formed, for example, by reacting a compound of Formula 1 with an amount of acid or base, such as an equivalent amount, in a medium such as one in which the salt precipitates or in an aqueous medium followed by lyophilization. Acids (and bases) which are generally considered suitable for the formation of pharmaceutically useful salts from basic (or acidic) pharmaceutical compounds are discussed, for example, by S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; in *The Orange Book* (Food & Drug Administration, Washington, D.C. on their website); and P. Heinrich Stahl, Camille G. Wermuth (Eds.), *Handbook of Pharmaceutical Salts: Properties, Selection, and Use*, (2002) Int'l. Union of Pure and Applied Chemistry, pp. 330-331. These disclosures are incorporated herein by reference thereto.

Exemplary acid addition salts include acetates, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, methyl sulfates, 2-naphthalenesulfonates, nicotinates, nitrates, oxalates, pamoates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates,) undecanoates, and the like.

Exemplary basic salts include ammonium salts, alkali metal salts such as sodium, lithium, and potassium salts, alkaline earth metal salts such as calcium and magnesium salts, aluminum salts, zinc salts, salts with organic bases (for example, organic amines) such as benzathines, diethylamine, dicyclohexylamines, hydrabamines (formed with N,N-bis (dehydroabietyl)ethylenediamine), N-methyl-D-glucamines, N-methyl-D-glucamides, t-butyl amines, piperazine, phenylcyclohexylamine, choline, tromethamine, and salts with amino acids such as arginine, lysine and the like. Basic nitrogen-containing groups may be quarternized with agents such as lower alkyl halides (non-limiting example(s) include methyl, ethyl, propyl, and butyl chlorides, bromides and iodides), dialkyl sulfates (non-limiting example(s) include dimethyl, diethyl, dibutyl, and diamyl sulfates), long chain halides (non-limiting example(s) include decyl, lauryl, myristyl and stearyl chlorides, bromides and iodides), aralkyl halides (non-limiting example(s) include benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$)acyl glycerol.

Compounds of Formula 1, and salts, solvates and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate" "prodrug" and the like, is intended to equally apply to the salt, solvate and prodrug of enantiomers, stereoisomers, rotamers, tautomers, racemates or prodrugs of the inventive compounds.

It should also be noted that throughout the specification and Claims appended hereto any formula, compound, moiety or chemical illustration with unsatisfied valences is assumed to have the hydrogen atom to satisfy the valences unless the context indicates a bond.

In one embodiment, the present invention discloses compounds of Formula 1, having CXCR3 antagonist activity, or a pharmaceutically acceptable derivative thereof, where the various definitions are given above. In another embodiment of the invention, wherein $R^1$ and $R^2$ are independently absent or present, and if present each is independently selected from the group consisting of H, alkyl, aryl, amino, alkoxy, halogen, hydroxy, cycloalkyl, alkyl-cycloalkyl-, cycloalkenyl, arylalkyl, amidinyl, carboxamido, heteroaryl, heterocyclyl, heterocyclenyl, urea, —S(O)$_2$alkyl, —S(O)$_2$N(H)alkyl, —S(O)$_2$ N(alkyl)$_2$, and —C(=S)N(H)cycloalkyl.

In another embodiment of the invention, $R^1$ and $R^2$ are independently absent or present, and if present each is independently selected from the group consisting of H, alkyl, aryl, amino, alkoxy, halogen, hydroxy, cycloalkyl, cycloalkenyl, arylalkyl, amidinyl, carboxamido, heteroaryl, heterocyclyl, heterocyclenyl, urea, —S(O)$_2$alkyl, —S(O)$_2$N(H)alkyl, —S(O)$_2$N(alkyl)$_2$, and —C(=S)N(H)cycloalkyl.

In another embodiment of the invention, $R^1$ and $R^2$ are independently absent or present, and if present each is independently selected from the group consisting of H, alkylaryl, alkyl-cycloalkyl-, aryl, heteroaryl, —(CH$_2$)$_q$CF$_3$, —(CH$_2$)$_q$OH, —(CH$_2$)$_q$OR$^{31}$, —(CH$_2$)$_q$NH$_2$, —(CH$_2$)$_q$NHR$^{31}$, —(CH$_2$)$_q$N(R$^{31}$)$_2$, —(CH$_2$)$_q$C(=O)NHR$^{31}$, —(CH$_2$)$_q$SO$_2$R$^{31}$, —(CH$_2$)$_q$NHSO$_2$R$^{31}$, —(CH$_2$)$_q$SO$_2$NHR$^{31}$, —(CH$_2$)$_q$-amidinyl, cyclopropyl, cyclopropylhydroxyl, cyclobutyl, cyclobutylhydroxy, cyclopentyl, and cyclopentylhydroxy; and q is an integer from 1 to 5.

In another embodiment of the invention, $R^1$ and $R^2$ are independently absent or present, and if present each is independently selected from the group consisting of H, alkylaryl, aryl, heteroaryl, —(CH$_2$)$_q$CF$_3$, —(CH$_2$)$_q$OH, —(CH$_2$)$_q$OR$^{31}$, —(CH$_2$)$_q$NH$_2$, —(CH$_2$)$_q$NHR$^{31}$, —(CH$_2$)$_q$N(R$^{31}$)$_2$, —(CH$_2$)$_q$C(=O)NHR$^{31}$, —(CH$_2$)$_q$SO$_2$R$^{31}$, —(CH$_2$)$_q$NHSO$_2$R$^{31}$, —(CH$_2$)$_q$SO$_2$NHR$^{31}$, —(CH$_2$)$_q$-amidinyl, cyclopropyl, cyclopropylhydroxyl, cyclobutyl, cyclobutylhydroxy, cyclopentyl, and cyclopentylhydroxy; and q is an integer from 1 to 5.

In another embodiment of the invention, $R^1$ and $R^2$ are independently absent or present, and if present each is independently selected from the group consisting of H, —CH$_3$, fluorophenylmethylene, trifluoromethylphenylmethylene, indanyl, cyanophenylmethylene, difluorophenylmethylene, bromophenylmethylene, chlorophenylmethylene, —CH$_2$CH$_2$O phenyl, cyclopentyl, bromochlorophenylmethylene, fluorochlorophenylmethylene, dichlorophenylmethylene, phenylmethylene, —(CH$_2$)$_3$phenyl, —CH$_2$CF$_3$, methoxyphenylmethylene, —CH(CH$_3$)$_2$, —C$_2$H$_5$, —CH$_2$-cyclopropyl, —(CH$_2$)$_2$CH$_3$, cyclohexylmethylene, cyclohexyl, —CH$_2$CH$_2$SO$_2$CH$_3$, —CH$_2$—CH$_2$—NH$_2$, —CH$_2$CH$_2$OCH$_3$, cyclopropyl, CH$_3$-cyclopropyl, isoxazolyl, —CH$_2$CH$_2$OH, —CH$_2$CH$_2$O phenyl, —CH$_2$CH$_2$CH$_3$, —NH$_2$, —(CH$_2$)$_2$NH$_2$, pyrazolyl, 5-methyl-isoxazolyl, —CH$_2$CH(OCH$_2$CH$_3$)$_2$, —OCH$_3$, —NHC(=O)NH$_2$, chloropyridyl, pyridylmethylene, —C(=O)NH-cyclopropyl, —C(=O)N(H)C$_2$H$_5$, —C(=O)N(H)CH$_2$CF$_3$, —C(=O)N(H)C(CH$_3$)$_3$, —C(=S)N(H)cyclopropyl, —C(=O)NH$_2$, —C(=O)N(H)CH$_3$, —S(O)$_2$CH$_3$, —S(O)$_2$N(CH$_3$)$_2$, —S(O)$_2$CH$_2$CH$_3$, —C(=O)CH$_3$, —S(O)$_2$(CH$_2$)$_2$CH$_3$, —C(=O)N(H)cyclohexyl, —C(=NH)NH$_2$, —C(=O)N(H)NH$_2$, —C(=O)N(H)CH(CH$_3$)$_2$, thiazolyl, —C(=O)N(CH$_3$)$_2$, —S(O)$_2$CH$_2$CF$_3$, cyclopropyl, —S(O)$_2$CF$_3$, —CH$_2$CH(OCH$_2$CH$_3$)$_2$,

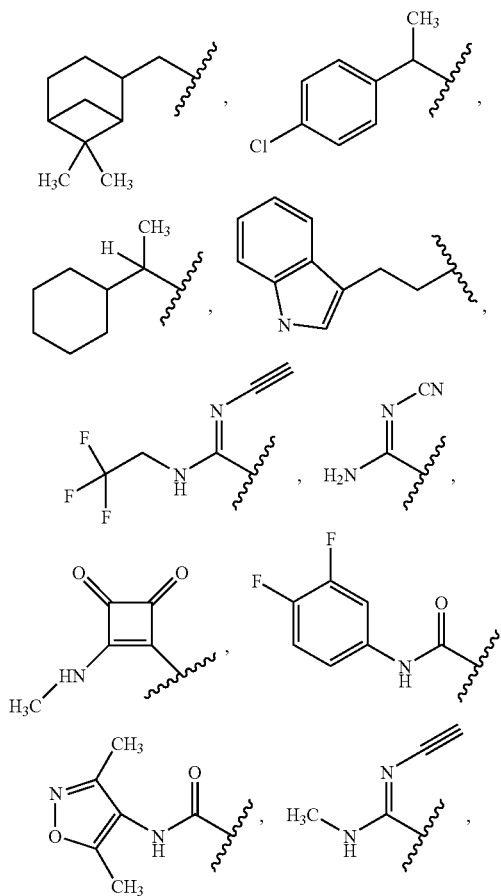

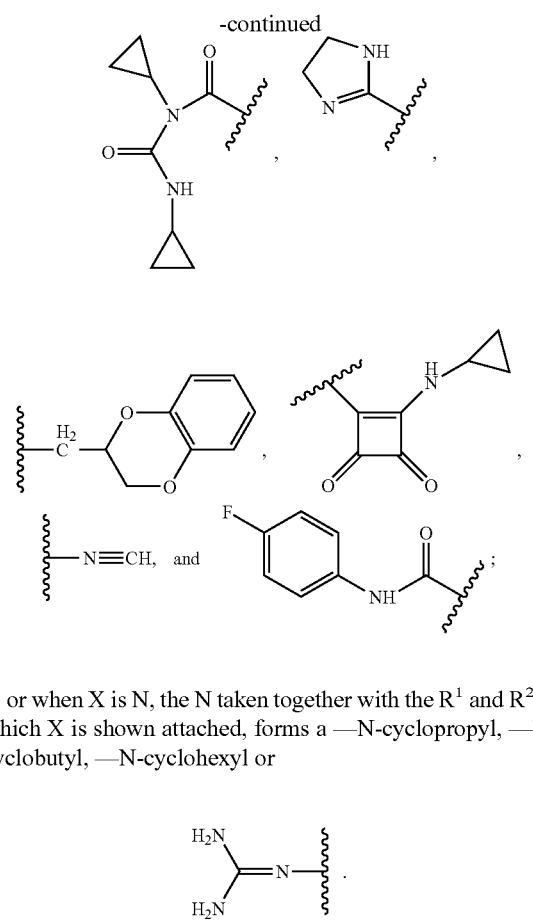

or when X is N, the N taken together with the R¹ and R² to which X is shown attached, forms a —N-cyclopropyl, —N-cyclobutyl, —N-cyclohexyl or In another embodiment of the invention, R¹ and R² are independently absent or present, and if present each is independently selected from the group consisting of H, —CH$_3$, fluorophenylmethylene, trifluoromethylphenylmethylene, indanyl, cyanophenylmethylene, difluorophenylmethylene, bromophenylmethylene, chlorophenylmethylene, —CH$_2$CH$_2$O phenyl, cyclopentyl, bromochlorophenylmethylene, fluorochlorophenylmethylene, dichlorophenylmethylene, phenylmethylene, —(CH$_2$)$_3$phenyl, —CH$_2$CF$_3$, methoxylphenylmethylene, —CH(CH$_3$)$_2$, —C$_2$H$_5$, —CH$_2$-cyclopropyl, —(CH$_2$)$_2$CH$_3$, cyclohexylmethylene, cyclohexyl, —CH$_2$CH$_2$SO$_2$CH$_3$, —CH$_2$—CH$_2$—NH$_2$, —CH$_2$CH$_2$OCH$_3$, cyclopropyl, isoxazolyl, —CH$_2$CH$_2$OH, —CH$_2$CH$_2$O phenyl, —CH$_2$CH$_2$CH$_3$, —NH$_2$, —(CH$_2$)$_2$NH$_2$, pyrazolyl, 5-methyl-isoxazolyl, —CH$_2$CH(OCH$_2$CH$_3$)$_2$, —OCH$_3$, —NHC(=O)NH$_2$, chloropyridyl, pyridylmethylene, —C(=O)NHcyclopropyl, —C(=O)N(H)C$_2$H$_5$, —C(=O)N(H)CH$_2$CF$_3$, —C(=O)N(H)C(CH$_3$)$_3$, —C(=S)N(H)cyclopropyl, —C(=O)NH$_2$, —C(=O)N(H)CH$_3$, —S(O)$_2$CH$_3$, —S(O)$_2$N(CH$_3$)$_2$, —S(O)$_2$CH$_2$CH$_3$, —C(=O)CH$_3$, —S(O)$_2$(CH$_2$)$_2$CH$_3$, —C(=O)N(H)cyclohexyl, —C(=NH)NH$_2$, —C(=O)N(H)NH$_2$, —C(=O)N(H)CH(CH$_3$)$_2$, thiazolyl, —C(=O)N(CH$_3$)$_2$, —S(O)$_2$CH$_2$CF$_3$, cyclopropyl, —S(O)$_2$CF$_3$, —CH$_2$CH(OCH$_2$CH$_3$)$_2$,

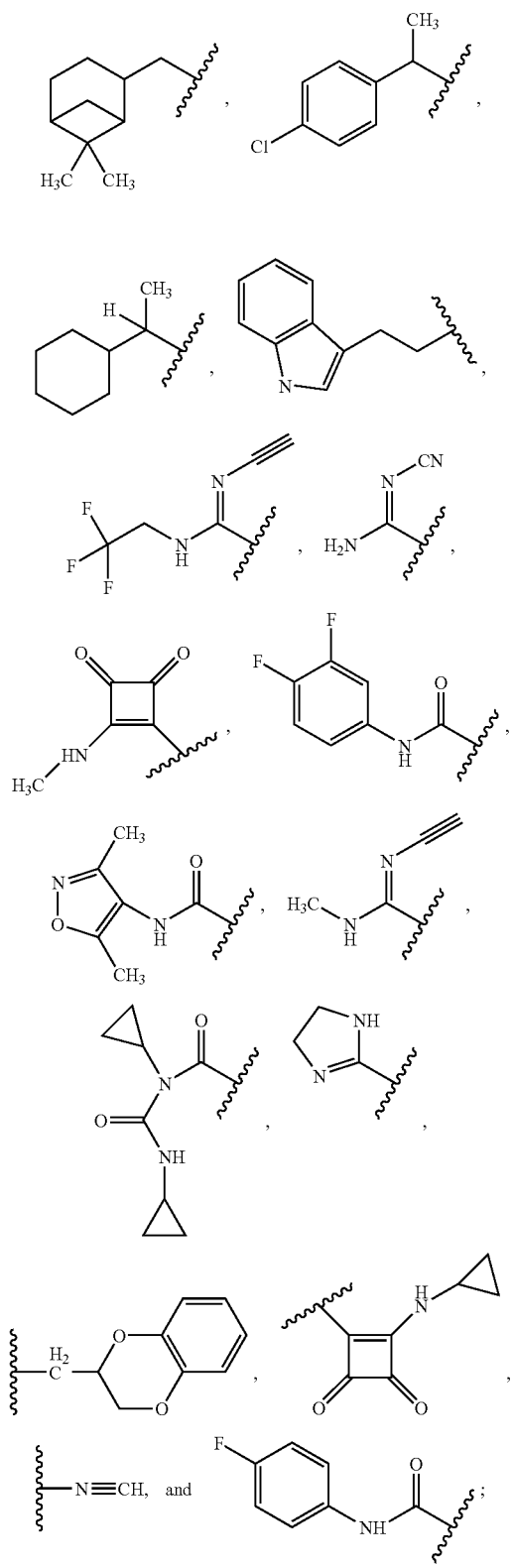

or when X is N, the N taken together with the R¹ and R² to which X is shown attached, forms a —N-cyclopropyl, —N-cyclobutyl, —N-cyclohexyl or

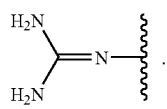

In another embodiment of the invention, $R^1$ and $R^2$ are independently absent or present, and if present each is independently selected from the group consisting of H, —CH$_3$, —C$_2$H$_5$, difluorophenylmethylene, cyclopropyl, CH$_3$-cyclopropyl-, dichlorophenylmethylene, —CH(CH$_3$)$_2$, cyclohexylmethylene, cyclohexyl, isoxazolyl, oxadizoyl, aminooxadiazoyl, substituted isooxazoyl, substituted oxadiazoyl, substituted aminooxadiazoyl, difluorophenyl, —CH$_2$CH$_2$OH, —CH$_2$CH$_2$N(CH$_3$)$_2$, —C(=O)N(H)cyclopropyl, —C(=O)N(H)C$_2$H$_5$, —C(=O)N(H)CH$_2$CF$_3$, —C(=O)N(H)CH(CH$_3$)$_2$, —C(=O)N(H)C(CH$_3$)$_3$, —C(=S)N(H)cyclopropyl, —C(=O)NH$_2$, —C(=O)N(H)CH$_3$, —S(O)$_2$CH$_3$, —S(O)$_2$N(CH$_3$)$_2$, —S(O)$_2$CH$_2$CH$_3$, —C(=O)CH$_3$, —S(O)$_2$(CH$_2$)$_2$CH$_3$, —C(=O)N(H)cyclohexyl, —C(=NH)NH$_2$, —C(=O)N(H)NH$_2$, thiazolyl,

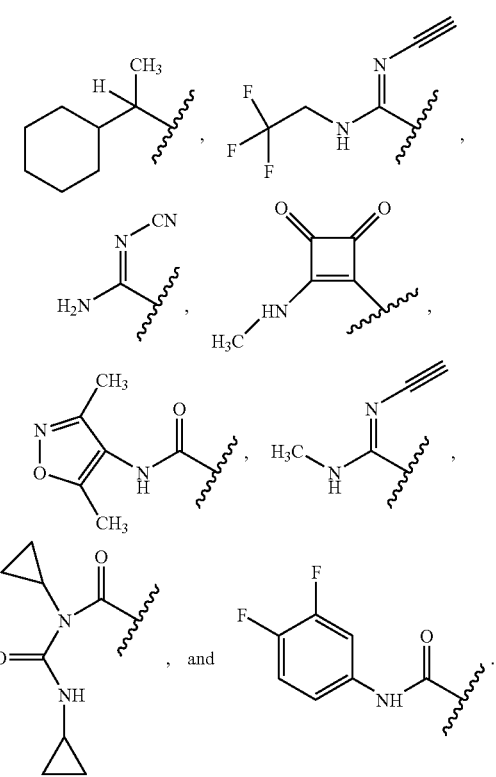

In another embodiment of the invention, $R^1$ and $R^2$ are independently absent or present, and if present each is independently selected from the group consisting of H, —CH$_3$, —C$_2$H$_5$, difluorophenylmethylene, cyclopropyl, dichlorophenylmethylene, —CH(CH$_3$)$_2$, cyclohexylmethylene, cyclohexyl, isoxazolyl, difluorophenyl, —CH$_2$CH$_2$OH, —CH$_2$—CH$_2$—N(CH$_3$))$_2$, —C(=O)N(H)cyclopropyl, —C(=O)N(H)C$_2$H$_5$, —C(=O)N(H)CH$_2$CF$_3$, —C(=O)N (H)CH(CH$_3$)$_2$, —C(=O)N(H)C(CH$_3$)$_3$, —C(=S)N(H)cyclopropyl, —C(=O)NH$_2$, —C(=O)N(H)CH$_3$, —S(O)$_2$CH$_3$, —S(O)$_2$N(CH$_3$)$_2$, —S(O)$_2$CH$_2$CH$_3$, —C(=O)CH$_3$, —S(O)$_2$(CH$_2$)$_2$CH$_3$, —C(=O)N(H)cyclohexyl, —C(=NH)NH$_2$, —C(=O)N(H)NH$_2$, thiazolyl,

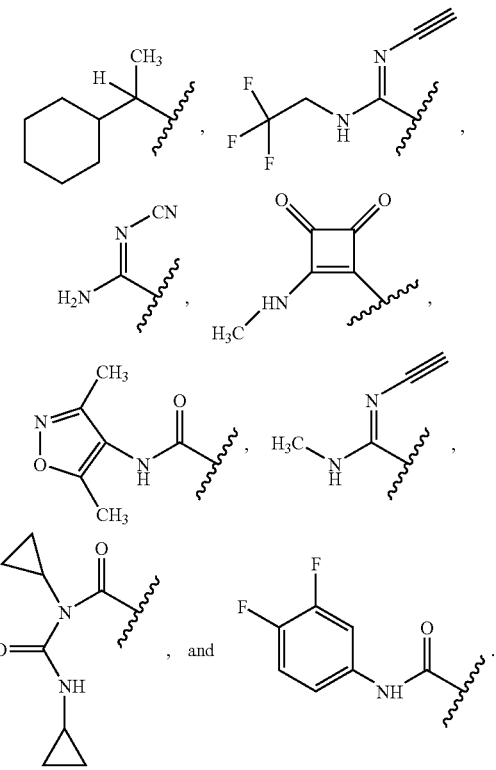

In another embodiment of the invention, X is selected from the group consisting of N, O, —CH$_3$, —CH$_2$—, —CH, —CH$_2$CH$_3$, —CH$_2$CN, —NH$_2$, cyclopropyl,

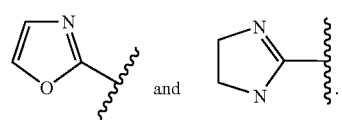

In another embodiment of the invention, X is selected from the group consisting of N, O, —CH$_3$, —CH$_2$—, —CH, —CH$_2$CH$_3$, —CH$_2$CN, —NH$_2$, cyclopropyl,

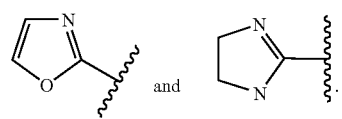

In another embodiment of the invention, $R^3$ is selected from the group consisting of H, alkyl, haloalkyl, hydroxyalkyl, halogen, —N(R$^{30}$)$_2$, —OR$^{30}$ and —CF$_3$.

In another embodiment of the invention, $R^3$ is selected from the group consisting of H, —CH$_3$, —CH$_2$CH$_3$, cyclopropyl, —F, —Cl, OCH$_3$, OCF$_3$ and CF$_3$.

In another embodiment of the invention, $R^6$ is selected from the group consisting of H, alkyl, halogen, hydroxyalkyl, —CN, —N(R$^{30}$)$_2$, —OR$^{30}$, —N=CH-alkyl, and —NR$^{30}$C (=O)alkyl.

In another embodiment of the invention, $R^6$ is selected from the group consisting of H, —$NH_2$, —$CH_3$, —CN and —F.

In another embodiment of the invention, $R^7$ and $R^8$ are the same or different, each being independently selected from the group consisting of H, —$(CH_2)_qOH$, —$(CH_2)_qOalkyl$, —$(CH_2)_qN(H)$-alkyl, —$(CH_2)_qN(H)$—$S(O)_2$alkyl, and —$(CH_2)_qN(H)$—CO—N(H)alkyl; or alternatively $R^7$ and $R^8$ taken together is =O, =N(OAlkyl), or =S.

In another embodiment of the invention, $R^7$ and $R^8$ are the same or different, each being independently selected from the group consisting of H, —$CH_3$, and —OH; or alternatively $R^7$ and $R^8$ taken together with the carbon atom to which $R^7$ and $R^8$ are shown attached, is

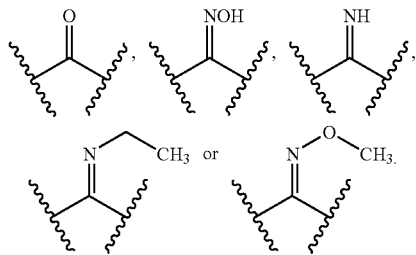

In another embodiment of the invention, $R^7$ and $R^8$ are each H; or alternatively $R^7$ and $R^8$ taken together with the carbon atom to which $R^7$ and $R^8$ are shown attached, is

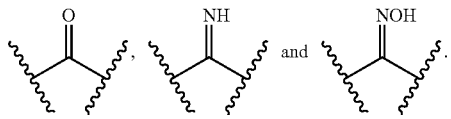

In another embodiment of the invention, $R^{10}$ is selected from the group consisting of H, alkyl, aralkyl, hydroxyalkyl, and carbonyl.

In another embodiment of the invention, $R^{10}$ is selected from the group consisting of —$CH_3$, —$CH_2CH_3$ and —$CH_2CH_2CH_3$, and m is 0-2.

In another embodiment of the invention, $R^{11}$ is selected from the group consisting of H, alkyl, hydroxyalkyl and carbonyl.

In another embodiment of the invention, $R^{11}$ is H or —$CH_3$.

In another embodiment of the invention, $R^{12}$ is selected from the group consisting of H, CN, —C(=O)N($R^{30}$)$_2$ and alkyl.

In another embodiment of the invention, $R^{12}$ is selected from the group consisting of H, —$CH_3$, CN and —$CH_2CH_3$.

In another embodiment of the invention, the phenyl ring D is substituted by independently selected 1-4 $R^{20}$ moieties.

In another embodiment of the invention, the $R^{20}$ moieties can be the same or different, each being independently selected from the group consisting of H, alkyl, alkylaryl, alkynyl, alkoxy, alkylamino, alkylheteroaryl, alkylsulfinyl, alkoxycarbonyl, aminoalkyl, amidinyl, aralkyl, aralkoxy, aryl, aryloxy, cyano, cycloalkyl, cycloalkenyl, halogen, haloalkyl, heteroalkyl, heteroaryl, heterocyclyl, hydroxyalkyl, trifluromethyl, trifluoromethoxy, —$(CH_2)_qOR^{31}$, —$(CH_2)_q NHR^{31}$, —$(CH_2)_qC(=O)NHR^{31}$, —$(CH_2)_q SO_2R^{31}$, —$(CH_2)_qNSO_2R^{31}$, —$(CH_2)_qSO_2NHR^{31}$, -alkynylC($R^{31}$)$_2$O$R^{31}$, —C(=O)$R^{30}$, —C(=O)N($R^{30}$)$_2$, —C(=O)O$R^{30}$, —N($R^{30}$)$_2$, —N($R^{30}$)C(=O)$R^{31}$, —NHC(=O)N($R^{30}$)$_2$, —N($R^{30}$)C(=O)O$R^{31}$, —N($R^{30}$)C(=NCN)N($R^{30}$)$_2$, —N($R^{30}$)C(=O)N($R^{30}$)$_2$, —N($R^{30}$)SO$_2$($R^{31}$), —N($R^{30}$)SO$_2$N($R^{30}$)$_2$, —O$R^{30}$, —OC(=O)N($R^{30}$)$_2$, —S$R^{30}$, —SO$_2$N($R^{30}$)$_2$, —SO$_2$($R^{31}$), —OSO$_2$($R^{31}$), —O($CH_2$)$_q$SO$_2R^{31}$, and —OSi($R^{30}$)$_3$.

In another embodiment of the invention, the $R^{20}$ moieties can be the same or different, each being independently selected from the group consisting of H, alkyl, alkylaryl, alkynyl, alkoxy, alkylamino, alkylheteroaryl, alkylsulfinyl, alkoxycarbonyl, aminoalkyl, amidinyl, aralkyl, aralkoxy, aryl, aryloxy, cyano, cycloalkyl, cycloalkenyl, halogen, haloalkyl, heteroalkyl, heteroaryl, heterocyclyl, hydroxyalkyl, trifluromethyl, trifluoromethoxy, —$(CH_2)_qOR^{31}$, —$(CH_2)_q NHR^{31}$, —$(CH_2)_qC(=O)NHR^{31}$, —$(CH_2)_q SO_2R^{31}$, —$(CH_2)_qNSO_2R^{31}$, —$(CH_2)_qSO_2NHR^{31}$, -alkynylC($R^{31}$)$_2$O$R^{31}$, —C(=O)$R^{30}$, —C(=O)N($R^{30}$)$_2$, —C(=O)O$R^{30}$, —N($R^{30}$)$_2$, —N($R^{30}$)C(=O)$R^{31}$, —NHC(=O)N($R^{30}$)$_2$, —N($R^{30}$)C(=O)O$R^{31}$, —N($R^{30}$)C(=NCN)N($R^{30}$)$_2$, —N($R^{30}$)C(=O)N($R^{30}$)$_2$, —N($R^{30}$)SO$_2$($R^{31}$), —N($R^{30}$)SO$_2$N($R^{30}$)$_2$, —O$R^{30}$, —OC(=O)N($R^{30}$)$_2$, —S$R^{30}$, —SO$_2$N($R^{30}$)$_2$, —SO$_2$($R^{31}$), —OSO$_2$($R^{31}$), and —OSi($R^{30}$)$_3$.

In another embodiment of the invention, the $R^{20}$ moieties can be the same or different, each being independently selected from the group consisting of H, alkyl, alkoxy, amino, halogen, CN, $CH_3$, $CF_3$, $OCH_3$, $OCF_3$, —$(CH_2)_qOR^{31}$, —$(CH_2)_qNHR^{31}$, —$(CH_2)_qC(=O)NHR^{31}$, —$(CH_2)_q SO_2R^{31}$, —$(CH_2)_qNSO_2R^{31}$, —$(CH_2)_qSO_2NHR^{31}$, -alkynylC($R^{31}$)$_2$O$R^{31}$,—C(=O)$R^{30}$, —C(=O)O$R^{30}$,—N($R^{30}$)$_2$, —N($R^{30}$)C(=O)$R^{31}$, —NHC(=O)N($R^{30}$)$_2$, —N($R^{30}$)C(=O)O$R^{31}$, —N($R^{30}$)C(=NCN)N($R^{30}$)$_2$, —N($R^{30}$)C(=O)N($R^{30}$)$_2$, —O$R^{30}$, —OC(=O)N($R^{30}$)$_2$, —O($CH_2$)$_q$SO$_2R^{31}$ and —OSO$_2$($R^{31}$).

In another embodiment of the invention, the $R^{20}$ moieties can be the same or different, each being independently selected from the group consisting of H, alkyl, amino, halogen, CN, $CH_3$, $CF_3$, $OCH_3$, $OCF_3$, —$(CH_2)_qOR^{31}$, —$(CH_2)_qNHR^{31}$, —$(CH_2)_qC(=O)NHR^{31}$, —$(CH_2)_qSO_2R^{31}$, —$(CH_2)_q NSO_2R^{31}$, —$(CH_2)_qSO_2NHR^{31}$, -alkynylC($R^{31}$)$_2$O$R^{31}$, —C(=O)$R^{30}$, —C(=O)O$R^{30}$, —N($R^{30}$)$_2$, —N($R^{30}$)C(=O)$R^{31}$, —NHC(=O)N($R^{30}$)$_2$, —N($R^{30}$)C(=O)O$R^{31}$, —N($R^{30}$)C(=NCN)N($R^{30}$)$_2$, —N($R^{30}$)C(=O)N($R^{30}$)$_2$, —O$R^{30}$, —OC(=O)N($R^{30}$)$_2$, and —OSO$_2$($R^{31}$).

In another embodiment of the invention, two $R^{20}$ moieties are linked together to form a five or six membered aryl, cycloalkyl, heterocyclenyl, heterocyclyl or heteroaryl ring wherein said five or six membered aryl, cycloalkyl, heterocyclenyl, heterocyclyl, and heteroaryl ring is fused to ring D and the fused ring is optionally substituted with 0 to 4 $R^{21}$ moieties.

In another embodiment of the invention, the $R^{20}$ moieties can be the same or different, each being independently selected from the group consisting of H, —CN, —$CH_3$, —$CF_3$, —$CH_2OH$, —$CO_2H$, —$CO_2CH_3$, —$NH_2$, —$NHCH_3$, —$OCF_3$, —OH, F, Cl, Br, —C(=NOH)$NH_2$, —$OCH_2CH_2S(O)_2CH_3$, —C(=O)$NH_2$,

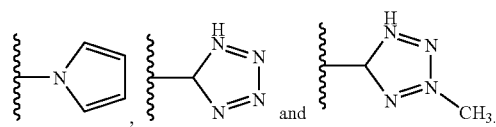

In another embodiment of the invention, Y is selected from the group consisting of: —(CHR$^{13}$)$_r$—, (CR$^{13}$R$^{13}$)$_r$—, —C(=O)— and —CHR$^{13}$C(=O)—.

In another embodiment of the invention, Y is selected from the group consisting of: —CH$_2$—, —CH(CH$_3$)—, —CH(CH$_2$OH)—, —C(=O)— and —CH(CO$_2$alkyl)-.

In another embodiment of the invention, m is 0-3.
In another embodiment of the invention, n is 0-2.
In another embodiment of the invention, q is 1, 2 or 3.
In another embodiment of the invention, p is 1, 2 or 3.
In another embodiment of the invention, r is 1 or 2.
In another embodiment of the invention, X is N;

R$^1$ and R$^2$ are independently absent or present, and if present each is independently selected from the group consisting of H, alkylaryl, aryl, heteroaryl, —(CH$_2$)$_q$CF$_3$, —(CH$_2$)$_q$OH, —(CH$_2$)$_q$OR$^{31}$, —(CH$_2$)$_q$NH$_2$, —(CH$_2$)$_q$NHR$^{31}$, —(CH$_2$)$_q$—N(R$^{31}$)$_2$, —(CH$_2$)$_q$C(=O)NHR$^{31}$, —(CH$_2$)$_q$SO$_2$R$^{31}$, —(CH$_2$)$_q$NHSO$_2$R$^{31}$, —(CH$_2$)$_q$SO$_2$NHR$^{31}$, —(CH$_2$)$_q$-amidinyl, cyclopropyl, alkyl-cyclopropyl-, cyclopropylhydroxyl, cyclobutyl, cyclobutylhydroxy, cyclopentyl, and cyclopentylhydroxy;

R$^3$ is selected from the group consisting of H, alkyl, haloalkyl, hydroxyalkyl, halogen, —N(R$^{30}$)$_2$, —OR$^{30}$ and —CF$_3$;

R$^6$ is selected from the group consisting of H, alkyl, halogen, hydroxyalkyl, —CN, —N(R$^{30}$)$_2$, —OR$^{30}$, —N=CH-alkyl, and —NR$^{30}$C(=O)alkyl;

R$^7$ and R$^8$ are independently selected from the group consisting of =O, =S, =NH, =NOH, and =N(OAlkyl);

R$^{10}$ is selected from the group consisting of H, alkyl, aralkyl, hydroxyalkyl, and carbonyl;

R$^{11}$ is selected from the group consisting of H, alkyl, hydroxyalkyl, and carbonyl;

R$^{12}$ is selected from the group consisting of H, CN, —C(=O)N(R$^{30}$)$_2$ and alkyl;

the R$^{20}$ moieties can be the same or different, each being independently selected from the group consisting of H, alkyl, alkoxy, amino, halogen, CN, CH$_3$, CF$_3$, OCH$_3$, OCF$_3$, —(CH$_2$)$_q$OR$^{31}$, —(CH$_2$)$_q$NHR$^{31}$, —(CH$_2$)$_q$C(=O)NHR$^{31}$, —(CH$_2$)$_q$SO$_2$R$^{31}$, —(CH$_2$)$_q$NSO$_2$R$^{31}$, —(CH$_2$)$_q$SO$_2$NHR$^{31}$, —alkynylC(R$^{31}$)$_2$OR$^{31}$, —C(=O)R$^{30}$, —C(=O)OR$^{30}$, —N(R$^{30}$)$_2$, —N(R$^{30}$)C(=O)R$^{31}$, —NHC(=O)N(R$^{30}$)$_2$, —N(R$^{30}$)C(=O)OR$^{31}$, —N(R$^{30}$)C(=NCN)N(R$^{30}$)$_2$, —N(R$^{30}$)C(=O)N(R$^{30}$)$_2$, —OR$^{30}$, —OC(=O)N(R$^{30}$)$_2$,

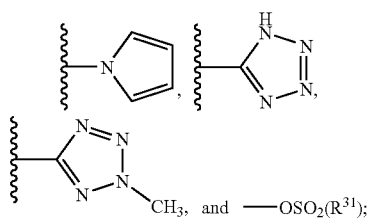

Y is selected from the group consisting of: —CH$_2$—, —CH(CH$_3$)—, —CH(CH$_2$OH)—, —C(=O)— and —CH(CO$_2$alkyl)-;
m is 0-2;
n is 0-2;
q is 1 or 2; and
r is 1 or 2.

In another embodiment of the invention,

X is N;

R$^1$ and R$^2$ are independently absent or present, and if present each is independently selected from the group consisting of H, alkylaryl, aryl, heteroaryl, —(CH$_2$)$_q$CF$_3$, —(CH$_2$)$_q$OH, —(CH$_2$)$_q$OR$^{31}$, —(CH$_2$)$_q$NH$_2$, —(CH$_2$)$_q$NHR$^{31}$, —(CH$_2$)$_q$—N(R$^{31}$)$_2$, —(CH$_2$)$_q$C(=O)NHR$^{31}$, —(CH$_2$)$_q$SO$_2$R$^{31}$, —(CH$_2$)$_q$NHSO$_2$R$^{31}$, —(CH$_2$)$_q$SO$_2$NHR$^{31}$, —(CH$_2$)$_q$-amidinyl, cyclopropyl, cyclopropylhydroxyl, cyclobutyl, cyclobutylhydroxy, cyclopentyl, and cyclopentylhydroxy;

R$^3$ is selected from the group consisting of H, alkyl, haloalkyl, hydroxyalkyl, halogen, —N(R$^{30}$)$_2$, —OR$^{30}$ and —CF$_3$;

R$^6$ is selected from the group consisting of H, alkyl, halogen, hydroxyalkyl, —CN, —N(R$^{30}$)$_2$, —OR$^{30}$, —N=CH-alkyl, and —NR$^{30}$C(=O)alkyl;

R$^7$ and R$^8$ are independently selected from the group consisting of =O, =S, =NH, =NOH, and =N(OAlkyl);

R$^{10}$ is selected from the group consisting of H, alkyl, aralkyl, hydroxyalkyl, and carbonyl;

R$^{11}$ is selected from the group consisting of H, alkyl, hydroxyalkyl, and carbonyl;

R$^{12}$ is selected from the group consisting of H, CN, —C(=O)N(R$^{30}$)$_2$ and alkyl;

the R$^{20}$ moieties can be the same or different, each being independently selected from the group consisting of H, alkyl, amino, halogen, CN, CH$_3$, CF$_3$, OCF$_3$, —(CH$_2$)$_q$OR$^{31}$, —(CH$_2$)$_q$NHR$^{31}$, —(CH$_2$)$_q$C(=O)NHR$^{31}$, —(CH$_2$)$_q$SO$_2$R$^{31}$, —(CH$_2$)$_q$NSO$_2$R$^{31}$, —(CH$_2$)$_q$SO$_2$NHR$^{31}$, -alkynylC(R$^{31}$)$_2$OR$^{31}$, —C(=O)R$^{30}$, —C(=O)OR$^{30}$, —N(R$^{30}$)$_2$, —N(R$^{30}$)C(=O)R$^{31}$, —NHC(=O)N(R$^{30}$)$_2$, —N(R$^{30}$)C(=O)OR$^{31}$, —N(R$^{30}$)C(=NCN)N(R$^{30}$)$_2$, —N(R$^{30}$)C(=O)N(R$^{30}$)$_2$, —OR$^{30}$, —OC(=O)N(R$^{30}$)$_2$,

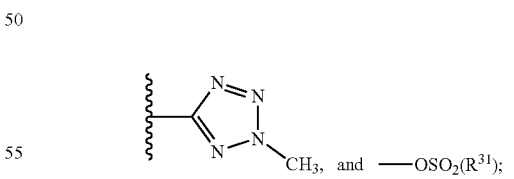

Y is selected from the group consisting of: —CH$_2$—, —CH(CH$_3$)—, —CH(CH$_2$OH)—, —C(=O)— and —CH(CO$_2$alkyl)-;
m is 0-2;
n is 0-2;
p is 0 or 1;
q is 1 or 2; and
r is 1 or 2.

In another embodiment of the invention, the compound of Formula I is represented by the following structural Formula:

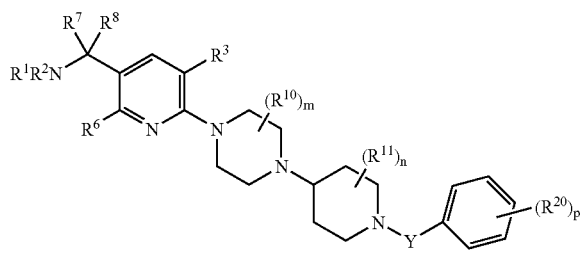

wherein the various terms are as defined earlier.

In still another embodiment of the present invention, a compound is selected from the following structures in Table 1 below (or a pharmaceutically acceptable salt, solvate or ester thereof) which are shown along with their $IC_{50}$ ratings. The $IC_{50}$ values are rated, "A" for $IC_{50}$ values less than about 25 nanomolar (nM), "B" for $IC_{50}$ values in the range of from about 25 to about 100 nM and "C" for $IC_{50}$ values greater than about 100 nM. For example, Compound No. 107 has an $IC_{50}$ of 0.2 nM.

TABLE 1

| Compound No. | Compound Structure | $IC_{50}$ |
|---|---|---|
| 1 | 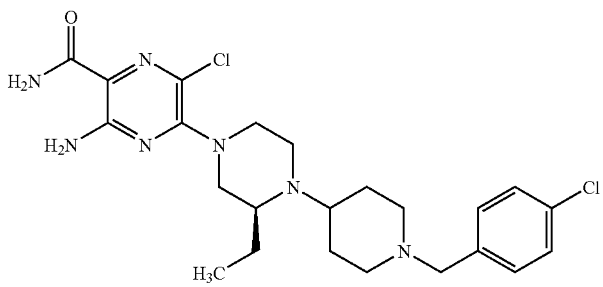 | A |
| 2 | 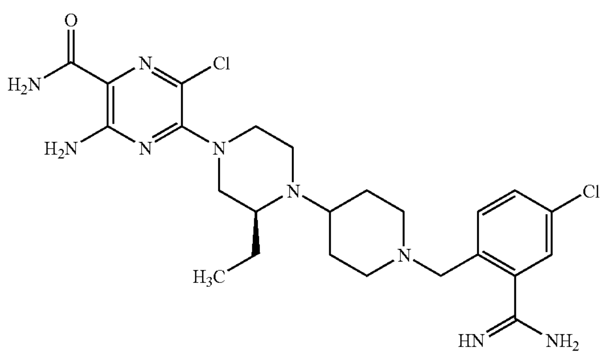 | A |
| 3 | 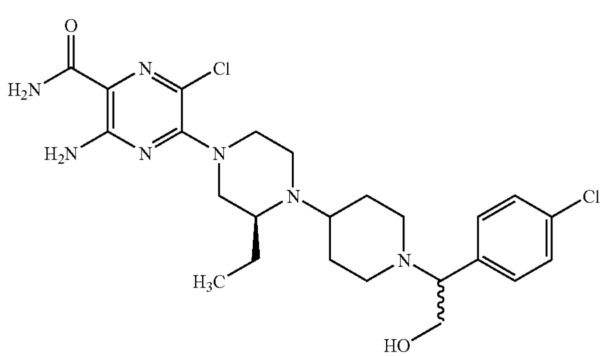 | A |

TABLE 1-continued

| Compound No. | Compound Structure | IC$_{50}$ |
|---|---|---|
| 4 | 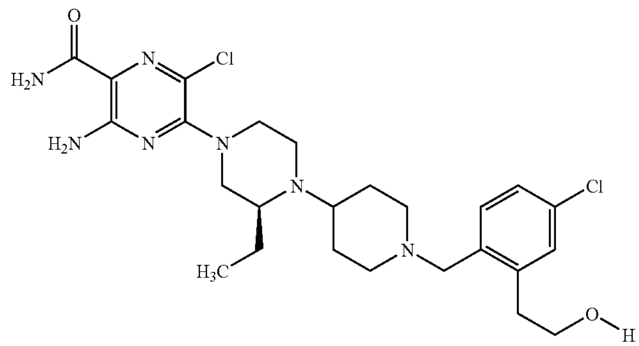 | A |
| 5 | 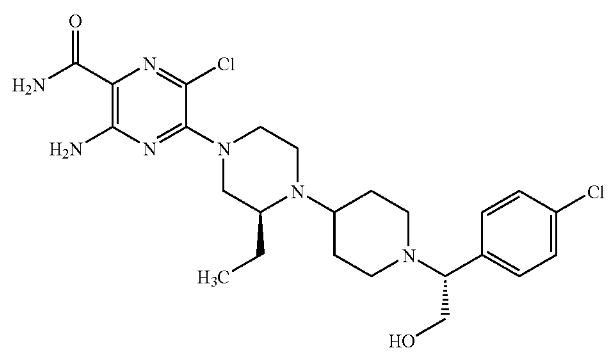 | A |
| 6 | 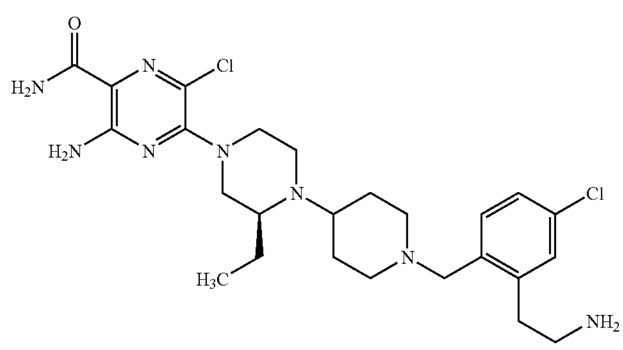 | A |
| 7 | 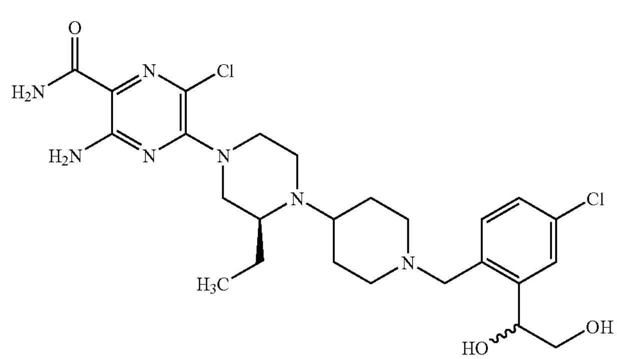 | A |

TABLE 1-continued

| Compound No. | Compound Structure | IC$_{50}$ |
|---|---|---|
| 8 | 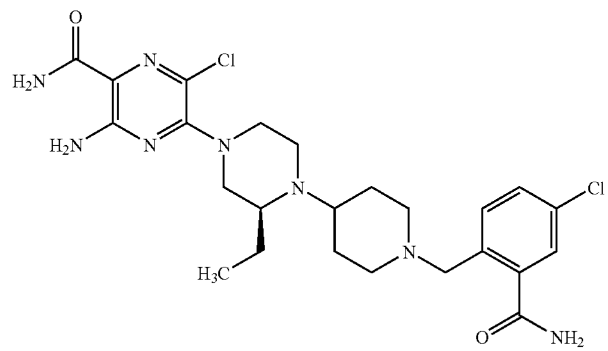 | A |
| 9 | 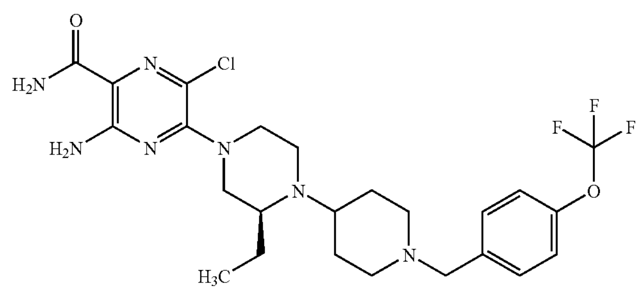 | A |
| 10 | 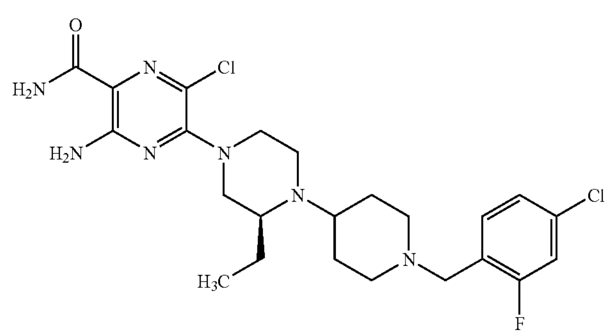 | A |
| 11 | 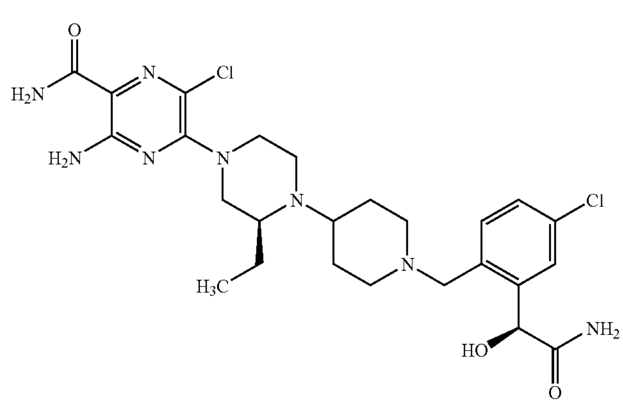 | A |

TABLE 1-continued

| Compound No. | Compound Structure | IC$_{50}$ |
|---|---|---|
| 12 | 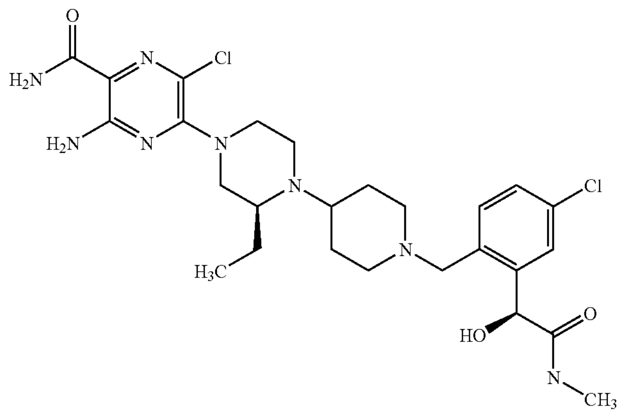 | A |
| 13 | 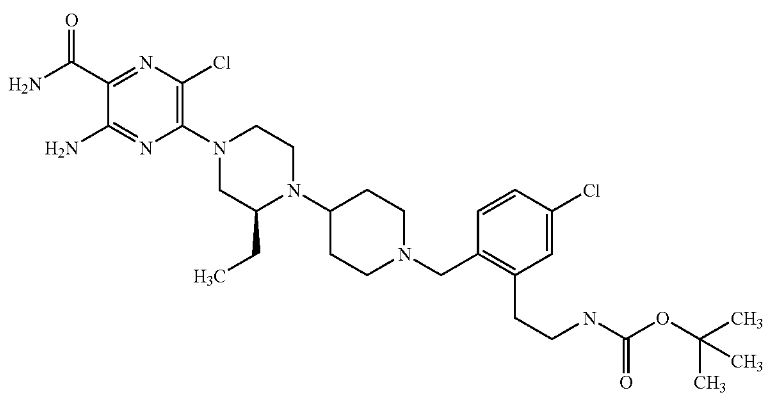 | A |
| 14 | 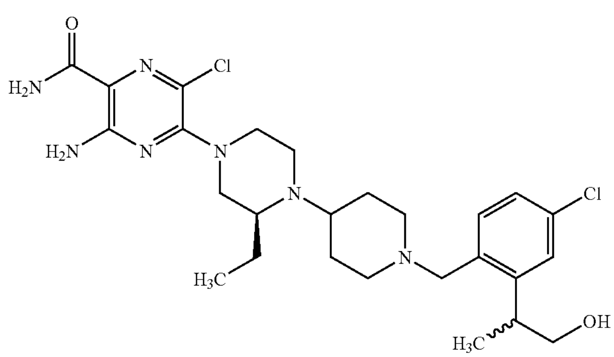 | A |
| 15 | 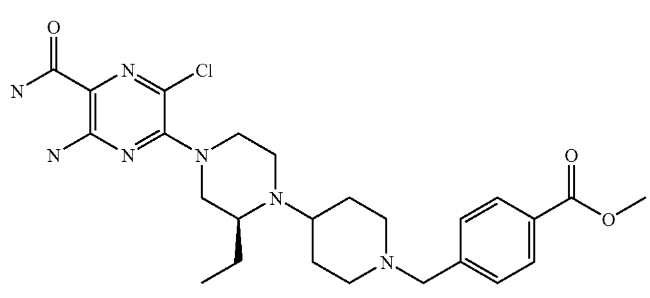 | A |

TABLE 1-continued

| Compound No. | Compound Structure | IC$_{50}$ |
|---|---|---|
| 16 | 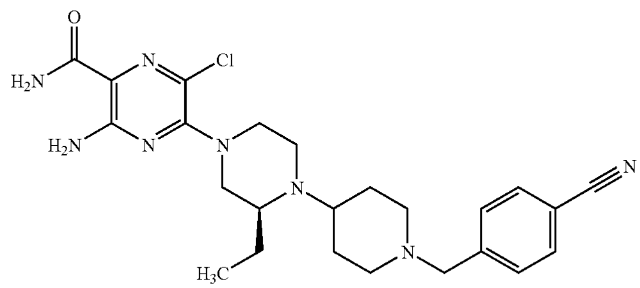 | A |
| 17 | 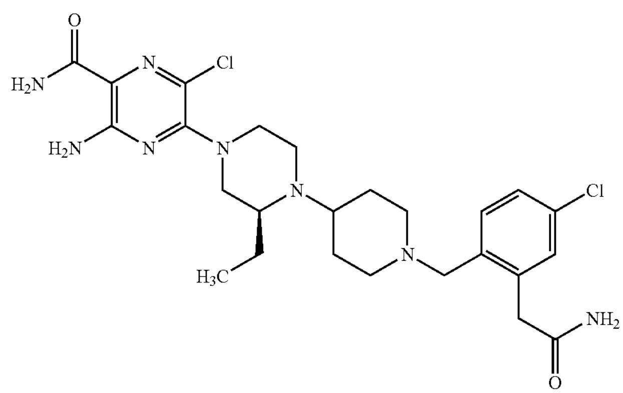 | A |
| 18 | 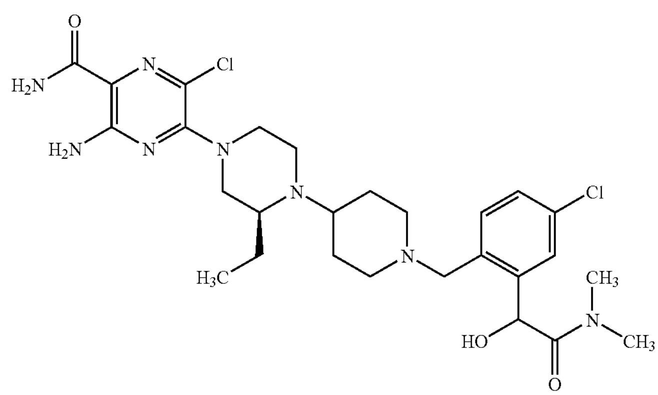 | A |
| 19 | 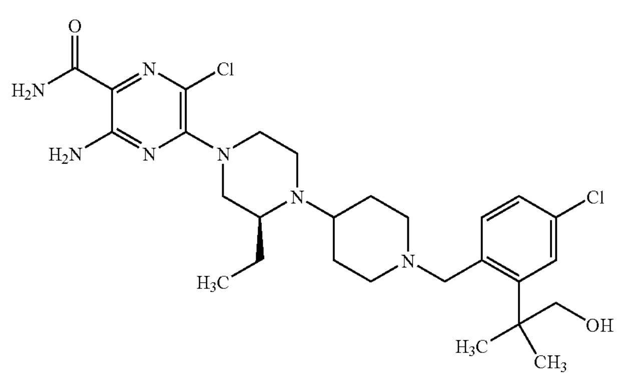 | A |

TABLE 1-continued

| Compound No. | Compound Structure | IC$_{50}$ |
| --- | --- | --- |
| 20 | 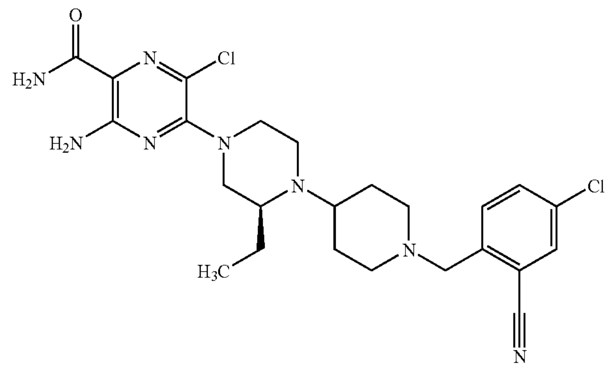 | A |
| 21 | 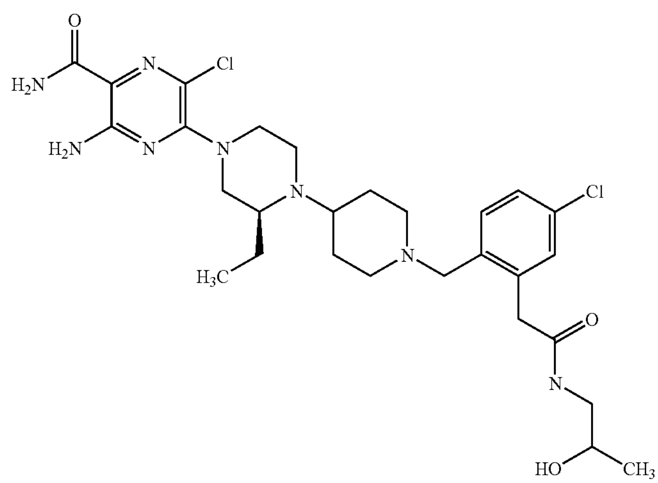 | A |
| 22 | 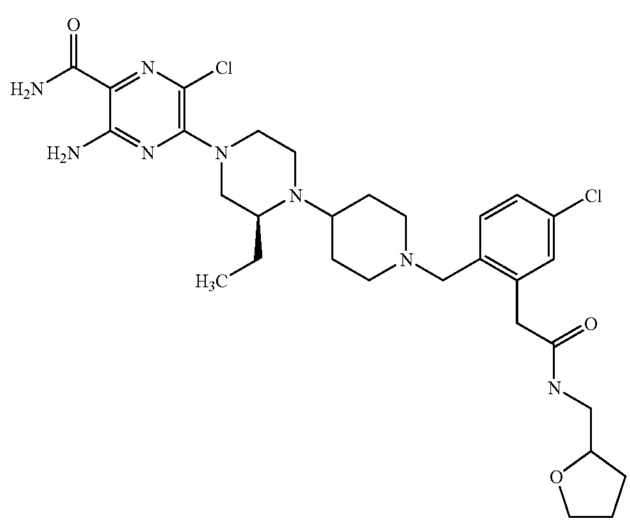 | A |

TABLE 1-continued

| Compound No. | Compound Structure | IC$_{50}$ |
|---|---|---|
| 23 | 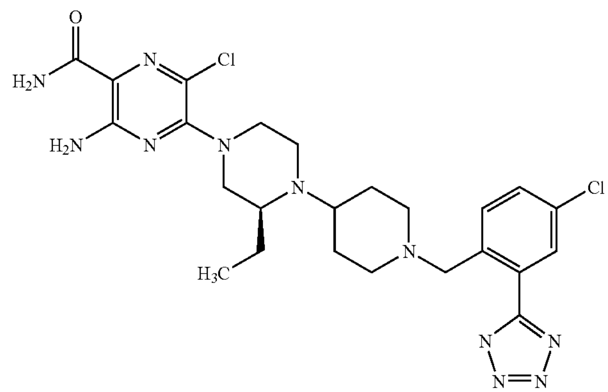 | B |
| 24 | 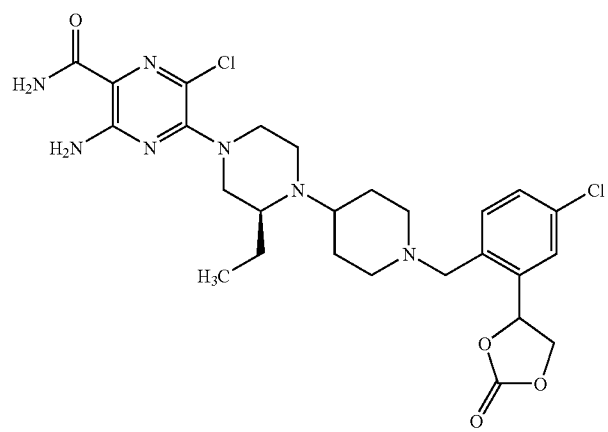 | B |
| 25 | 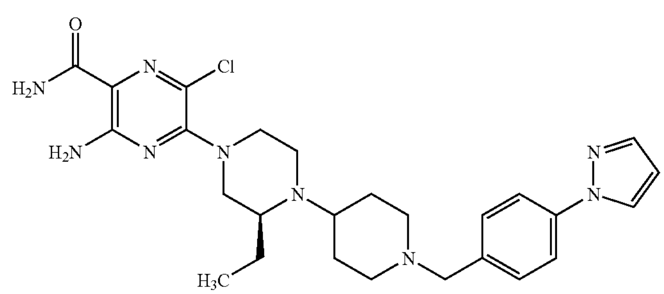 | B |
| 26 | 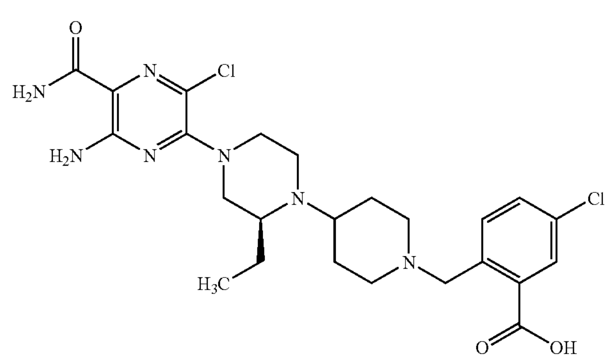 | B |

TABLE 1-continued

| Compound No. | Compound Structure | IC$_{50}$ |
|---|---|---|
| 27 | 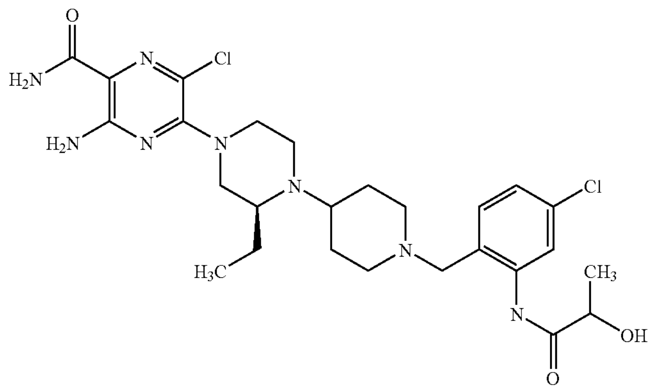 | B |
| 28 | 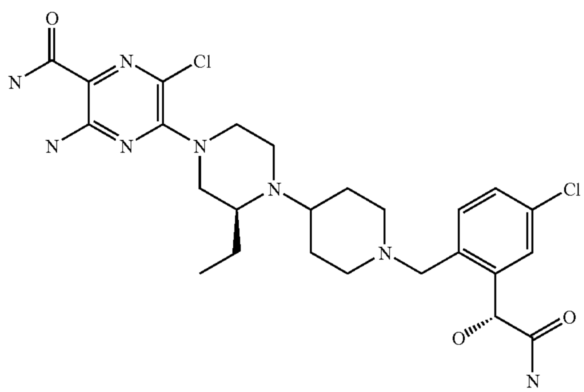 | B |
| 29 | 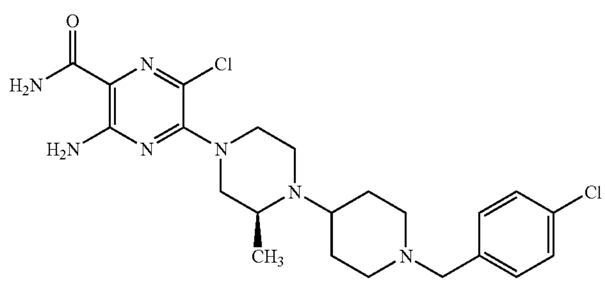 | B |
| 30 | 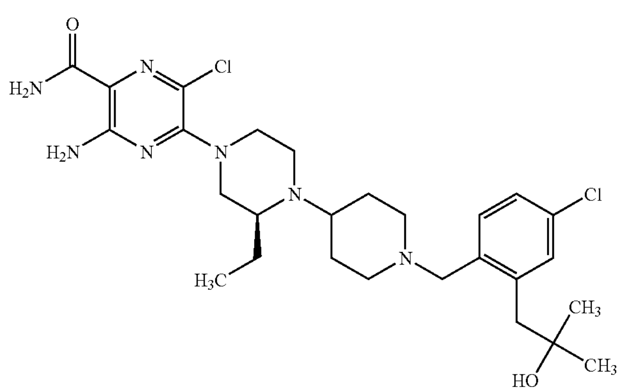 | B |

TABLE 1-continued

| Compound No. | Compound Structure | IC$_{50}$ |
| --- | --- | --- |
| 31 | (structure) | B |
| 32 | (structure) | B |
| 33 | (structure) | B |
| 34 | (structure) | B |

TABLE 1-continued

| Compound No. | Compound Structure | IC$_{50}$ |
|---|---|---|
| 35 | 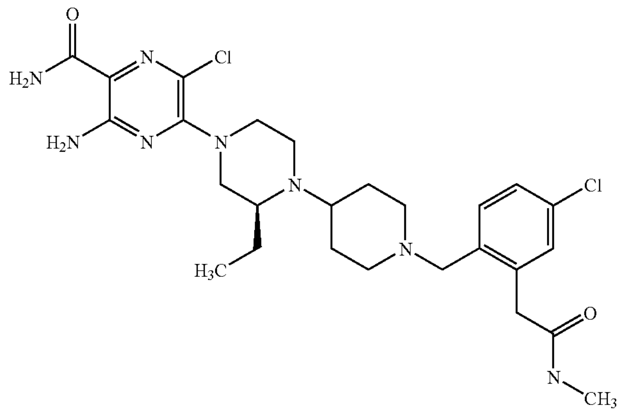 | B |
| 36 | 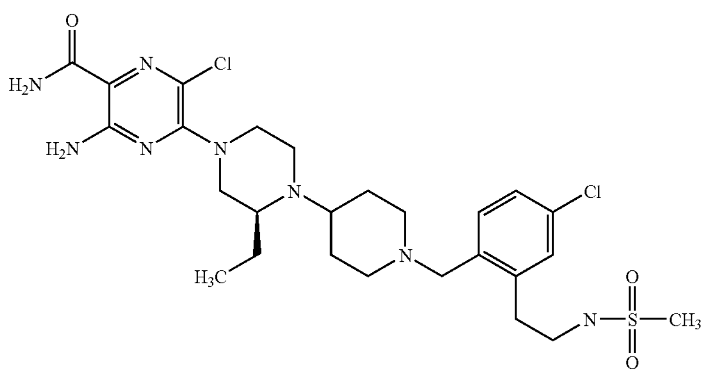 | B |
| 37 | 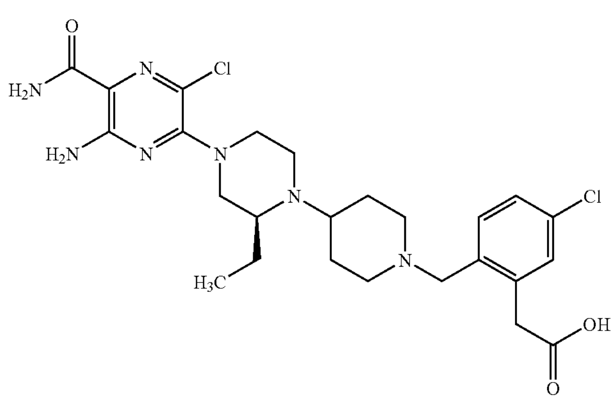 | B |

TABLE 1-continued

| Compound No. | Compound Structure | IC$_{50}$ |
|---|---|---|
| 38 | 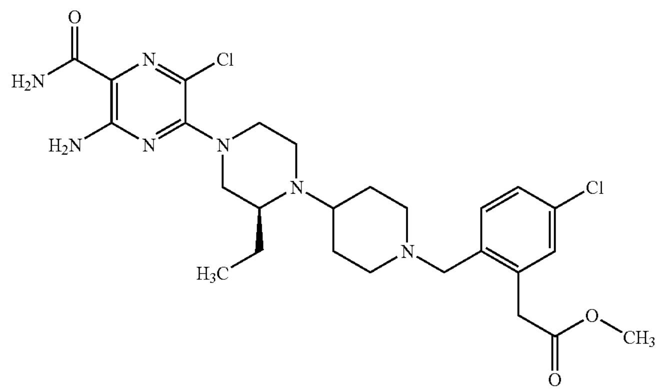 | B |
| 39 | 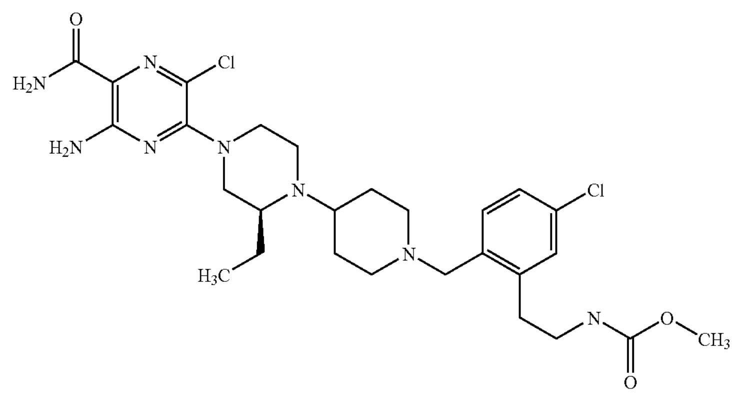 | B |
| 40 | 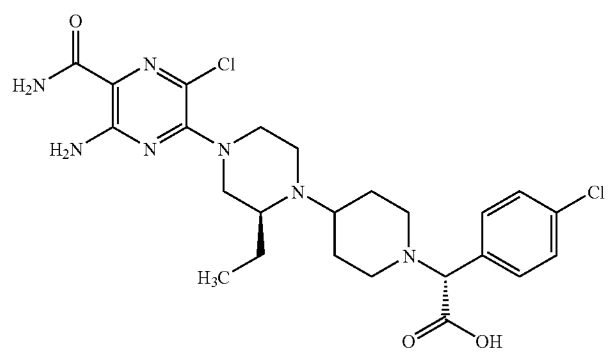 | B |
| 41 | 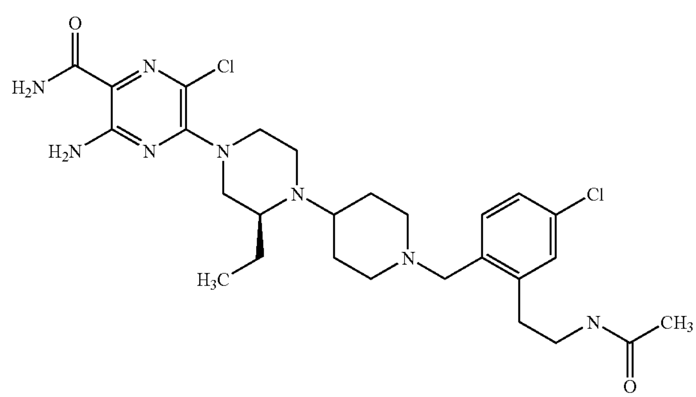 | B |

TABLE 1-continued

| Compound No. | Compound Structure | IC$_{50}$ |
|---|---|---|
| 42 | 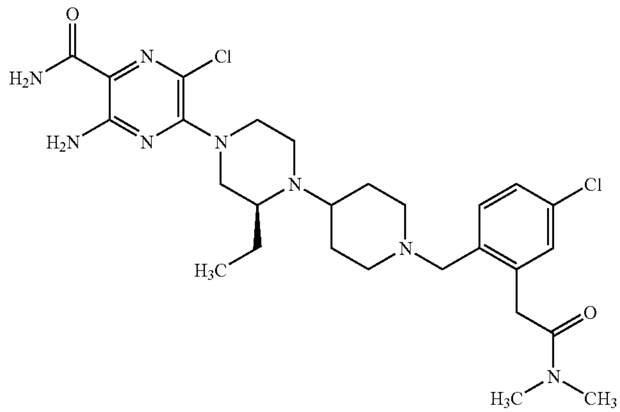 | C |
| 43 | 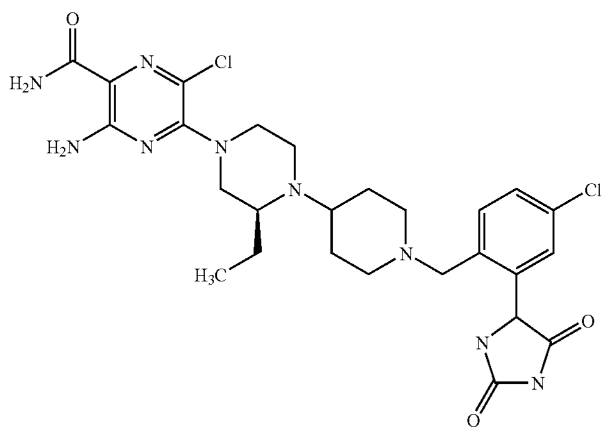 | C |
| 44 | 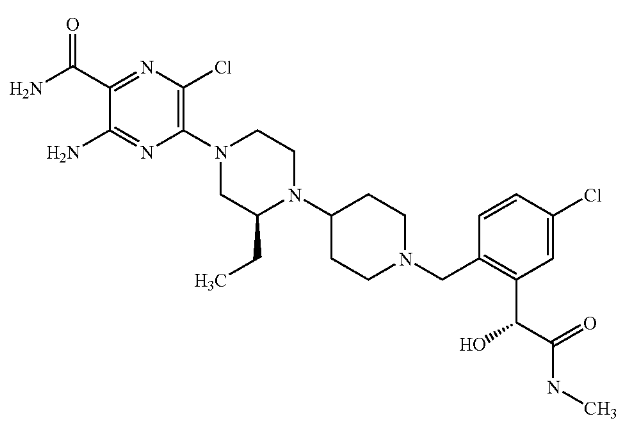 | C |

TABLE 1-continued

| Compound No. | Compound Structure | IC$_{50}$ |
|---|---|---|
| 45 | 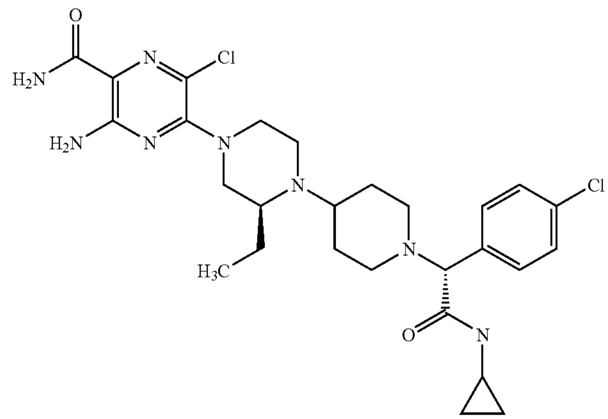 | C |
| 46 | 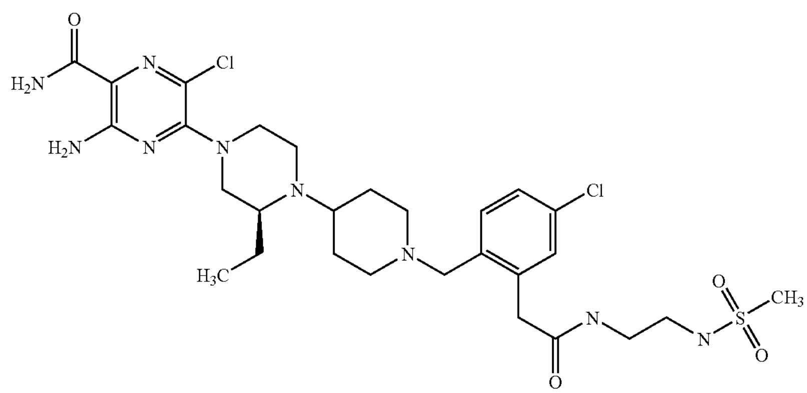 | C |
| 47 | 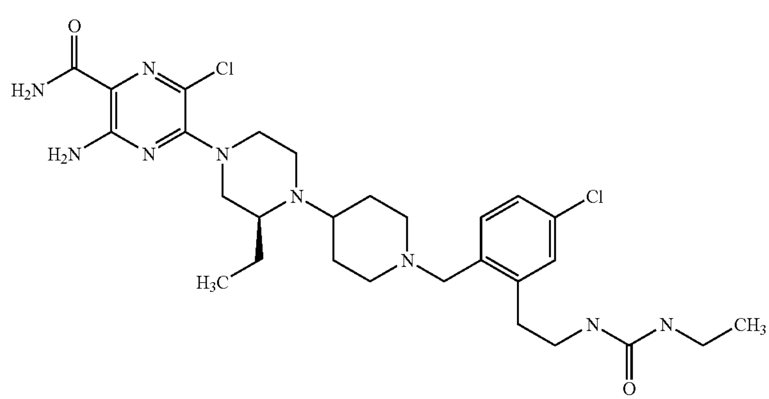 | C |

TABLE 1-continued

| Compound No. | Compound Structure | IC$_{50}$ |
|---|---|---|
| 48 | 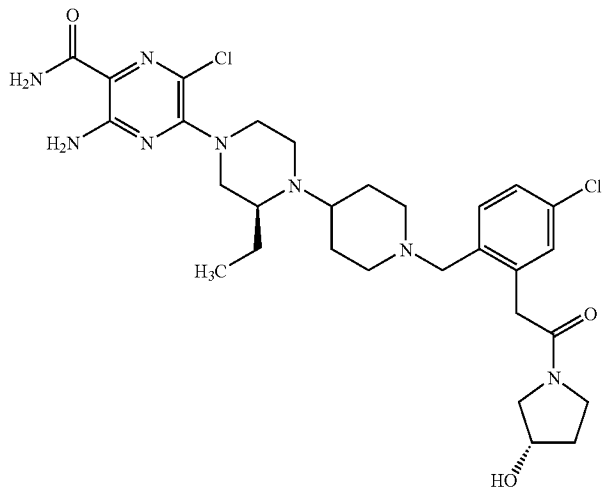 | C |
| 49 | 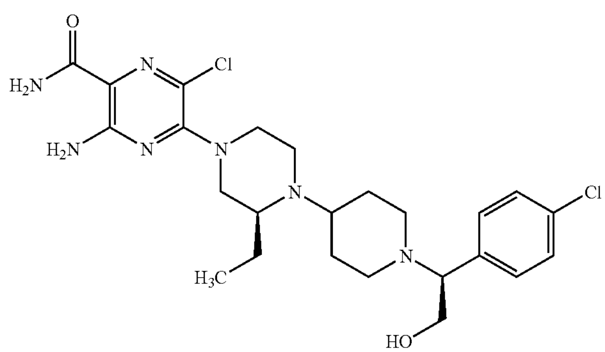 | C |
| 50 | 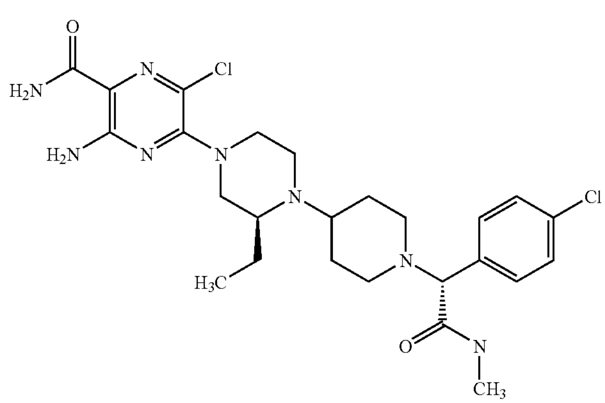 | C |

TABLE 1-continued

| Compound No. | Compound Structure | IC$_{50}$ |
|---|---|---|
| 51 | 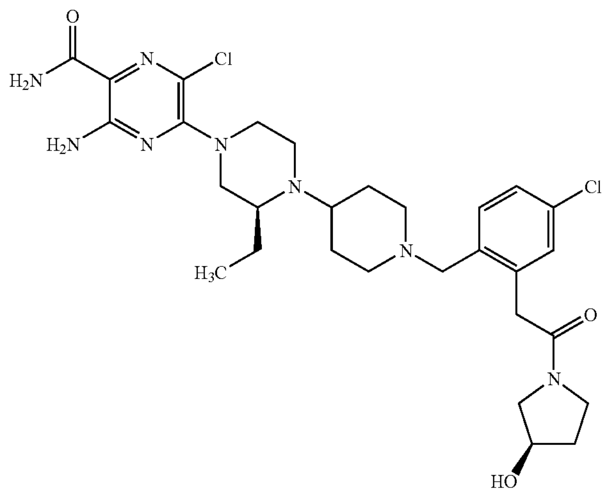 | C |
| 52 | 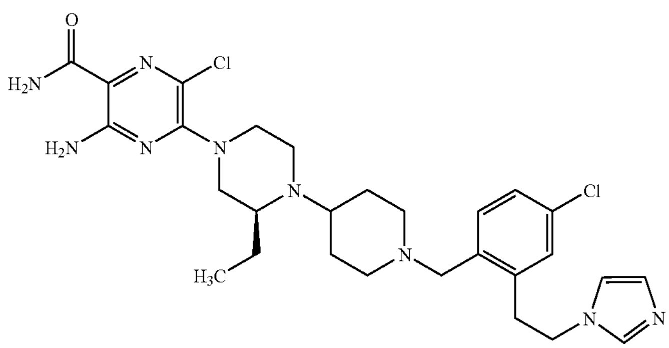 | C |
| 53 | 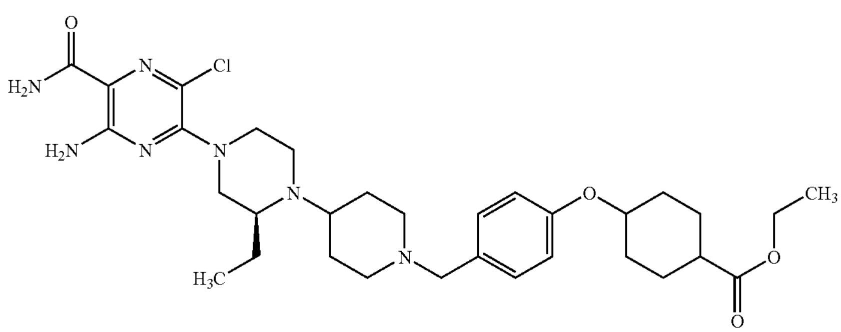 | C |
| 54 | 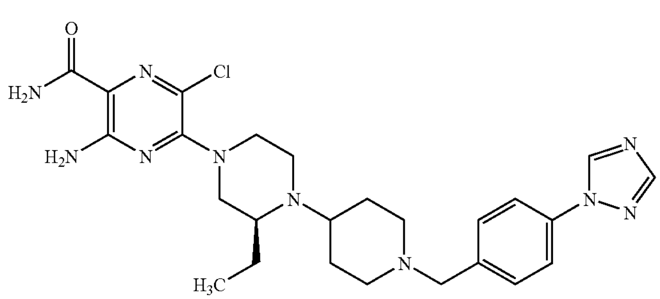 | C |

TABLE 1-continued

| Compound No. | Compound Structure | IC$_{50}$ |
|---|---|---|
| 55 | 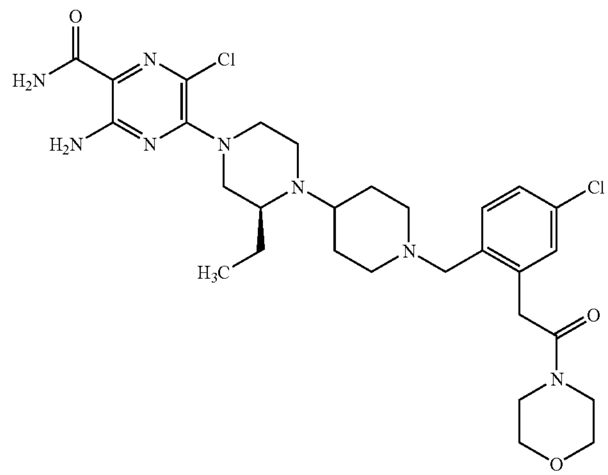 | C |
| 56 | 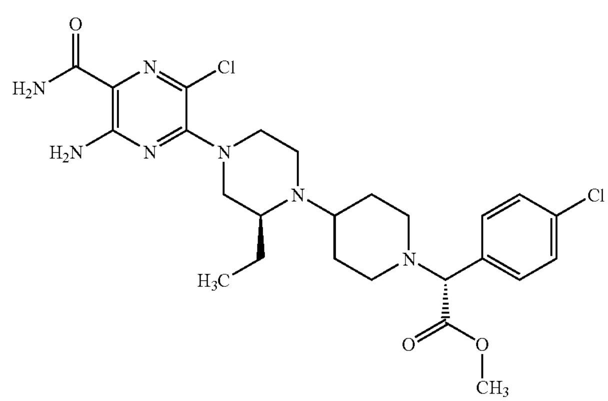 | C |
| 57 | 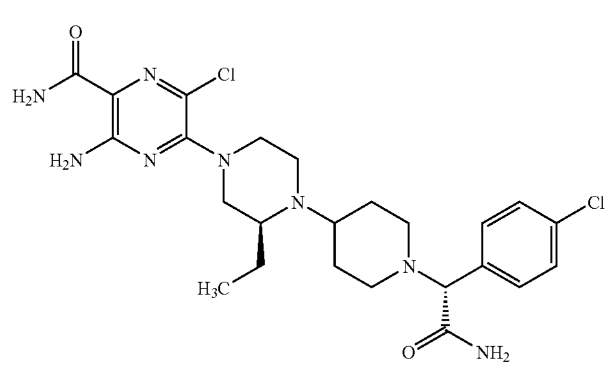 | C |

TABLE 1-continued

| Compound No. | Compound Structure | IC$_{50}$ |
|---|---|---|
| 58 | 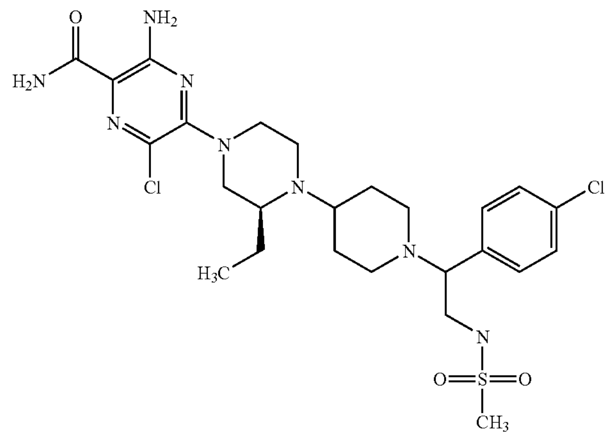 | C |
| 59 | 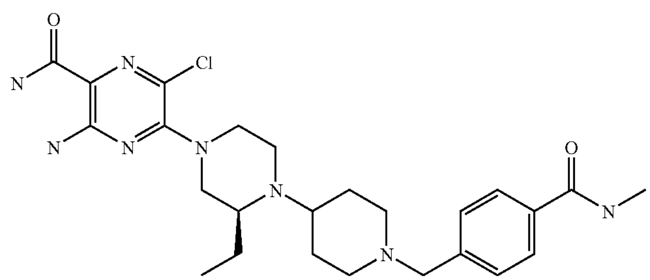 | C |
| 60 | 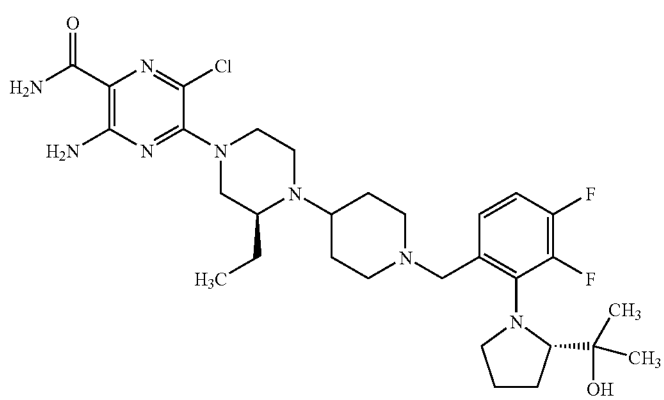 | C |
| 61 | 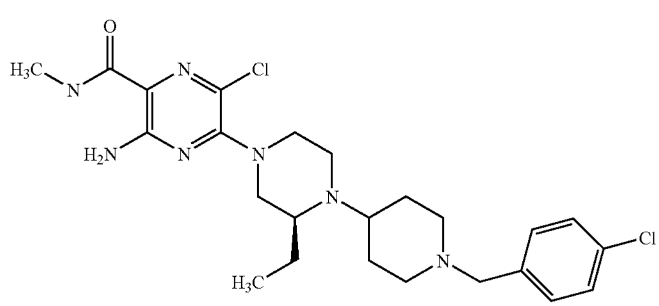 | A |

TABLE 1-continued

| Compound No. | Compound Structure | IC$_{50}$ |
|---|---|---|
| 62 | 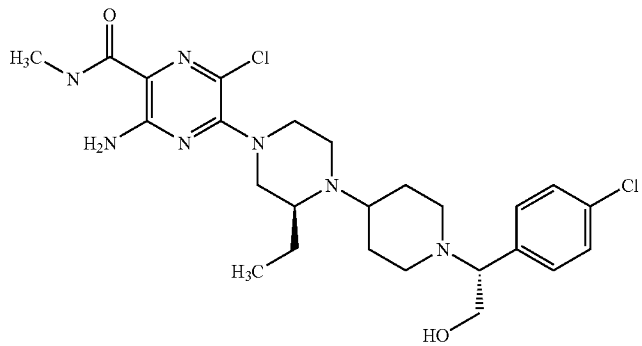 | A |
| 63 | 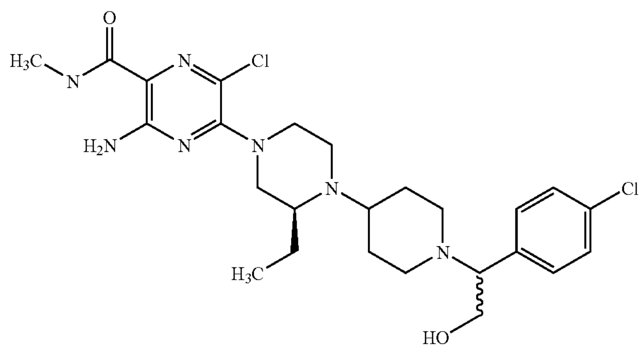 | A |
| 64 | 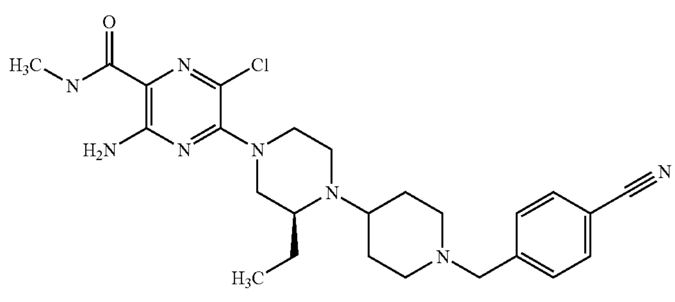 | A |
| 65 | 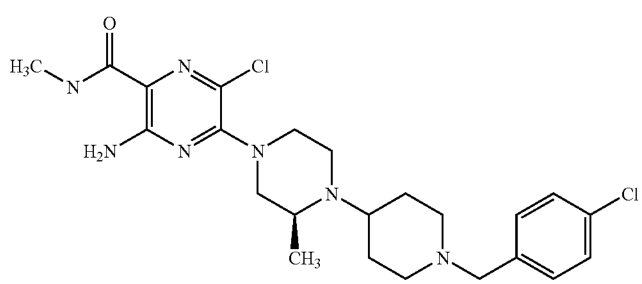 | A |

TABLE 1-continued

| Compound No. | Compound Structure | IC$_{50}$ |
|---|---|---|
| 66 | 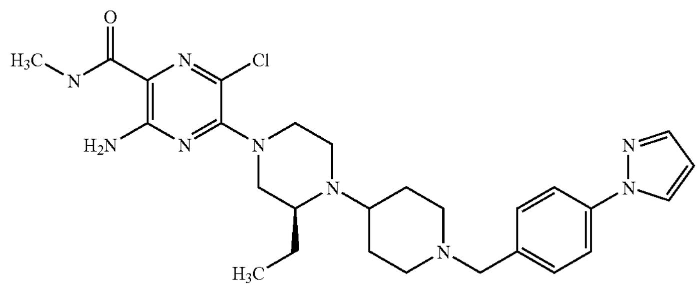 | A |
| 67 | 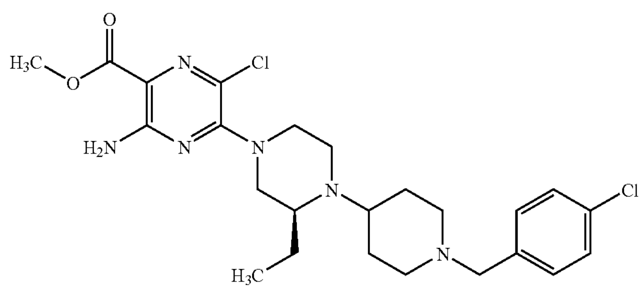 | A |
| 68 | 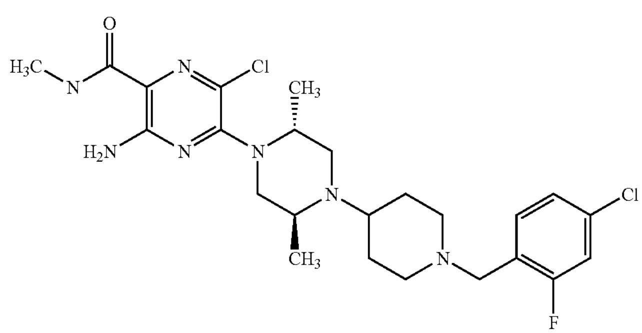 | A |
| 69 | 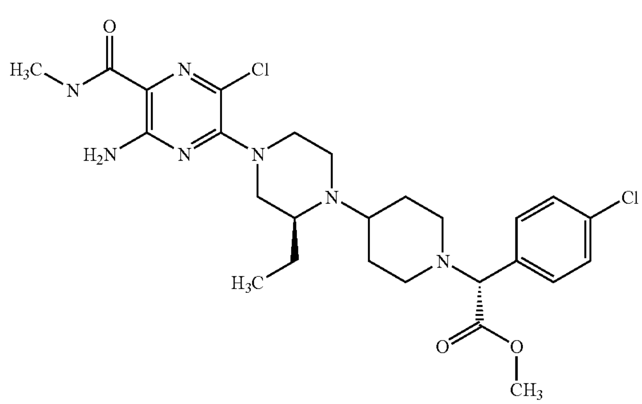 | A |

TABLE 1-continued

| Compound No. | Compound Structure | IC$_{50}$ |
|---|---|---|
| 70 | 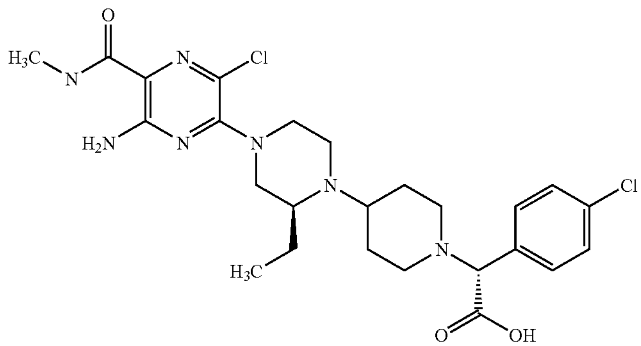 | A |
| 71 | 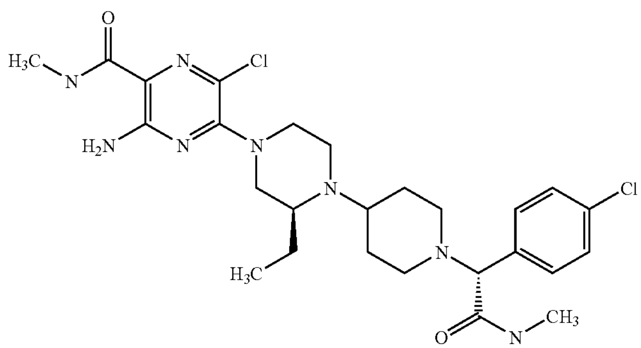 | B |
| 72 | 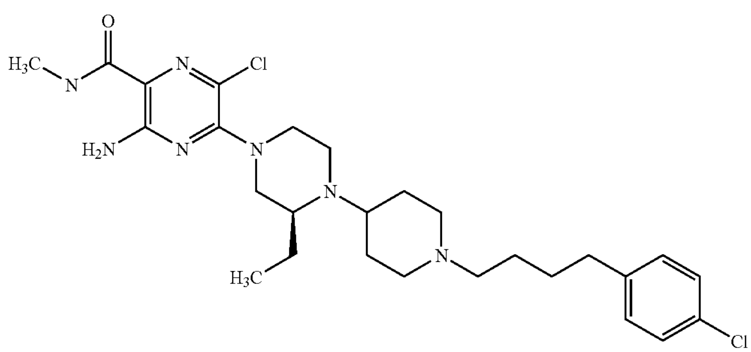 | B |
| 73 | 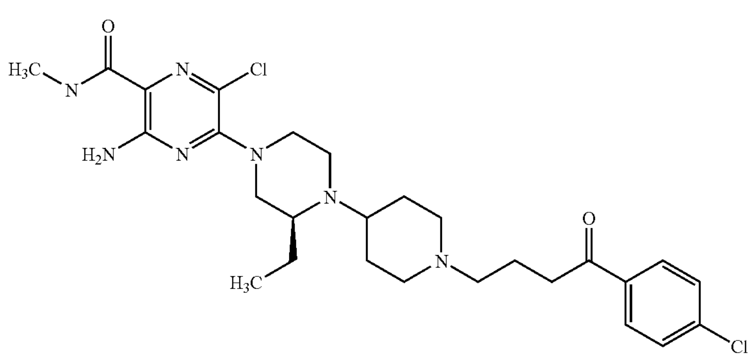 | B |

TABLE 1-continued

| Compound No. | Compound Structure | IC$_{50}$ |
|---|---|---|
| 74 | 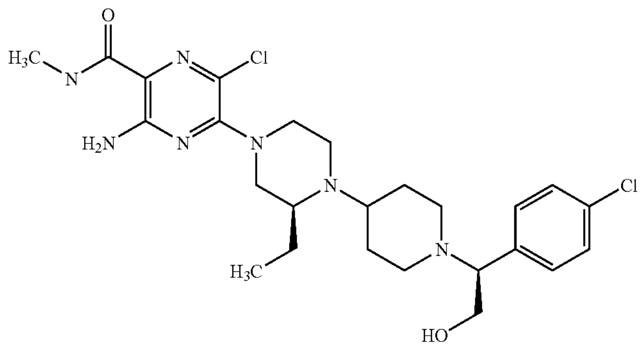 | B |
| 75 | 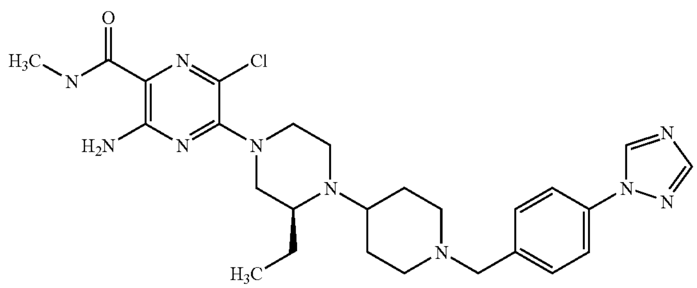 | B |
| 76 | 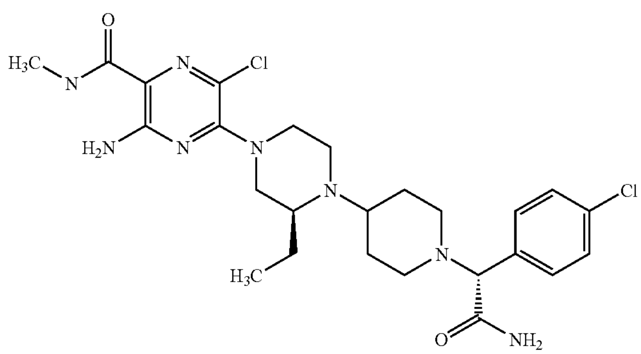 | C |
| 77 | 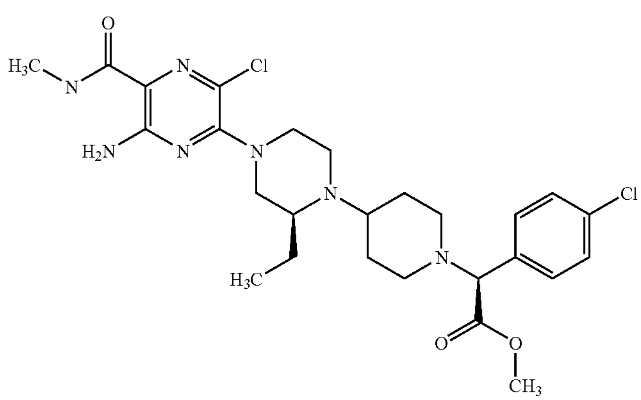 | C |

TABLE 1-continued
| Compound No. | Compound Structure | IC$_{50}$ |
|---|---|---|
| 78 | 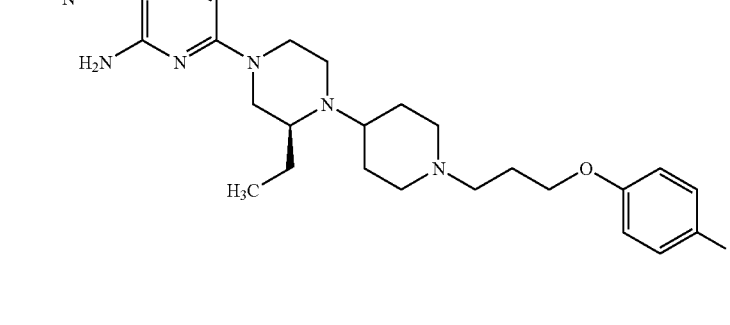 | C |
| 79 | 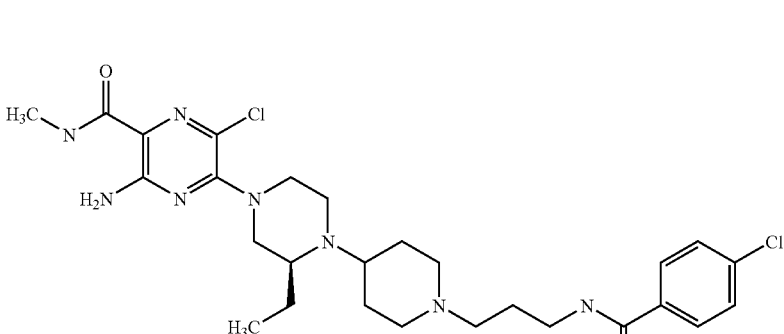 | C |
| 80 | 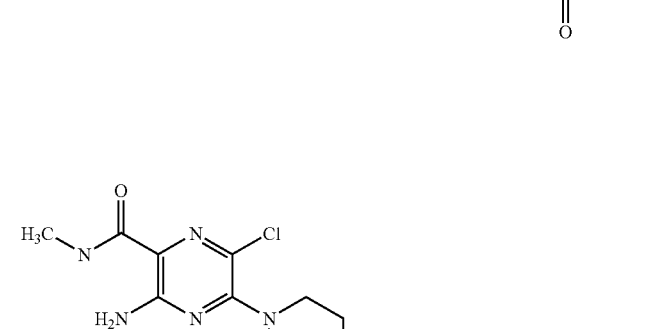 | C |
| 81 | 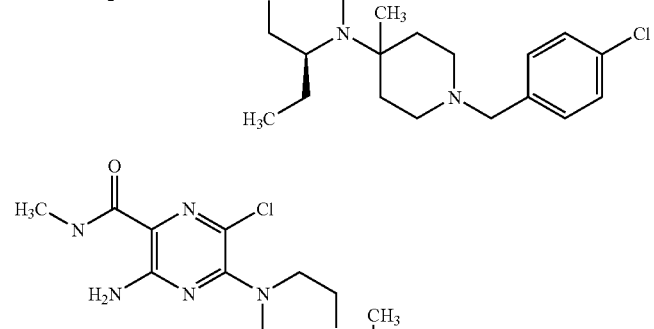 | C |

TABLE 1-continued

| Compound No. | Compound Structure | IC$_{50}$ |
|---|---|---|
| 82 | 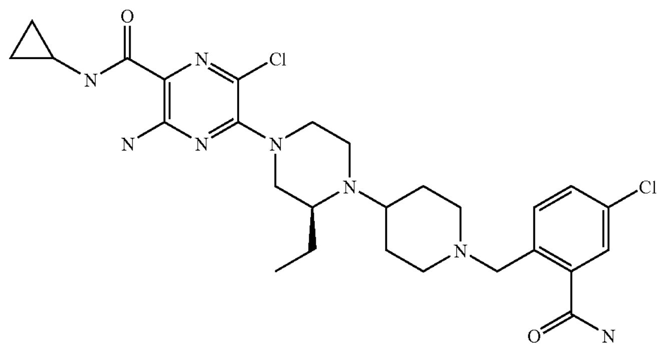 | A |
| 83 | 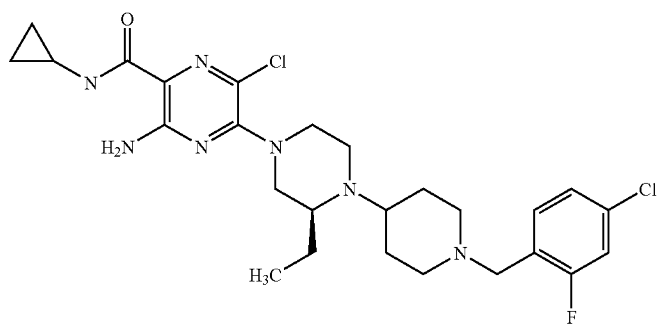 | A |
| 84 | 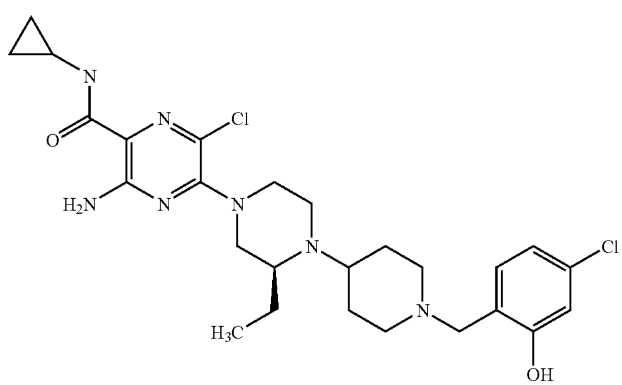 | A |
| 85 | 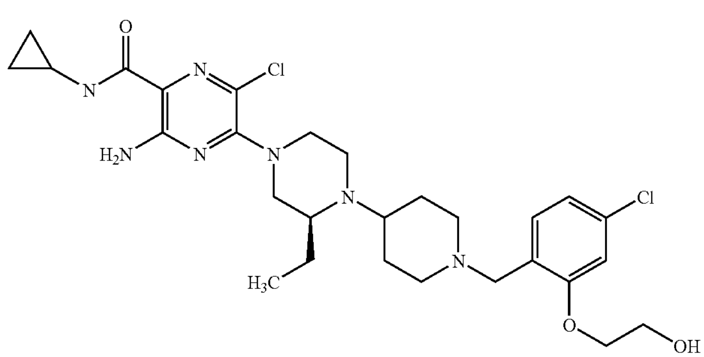 | A |

TABLE 1-continued
| Compound No. | Compound Structure | IC$_{50}$ |
|---|---|---|
| 86 | 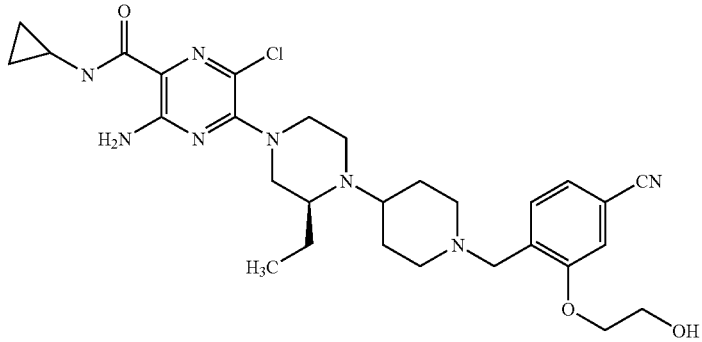 | A |
| 87 | 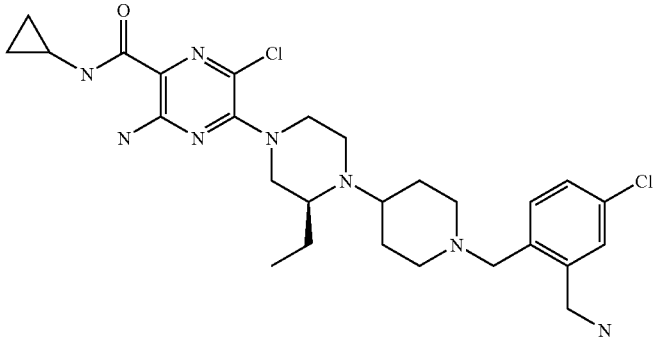 | A |
| 88 | 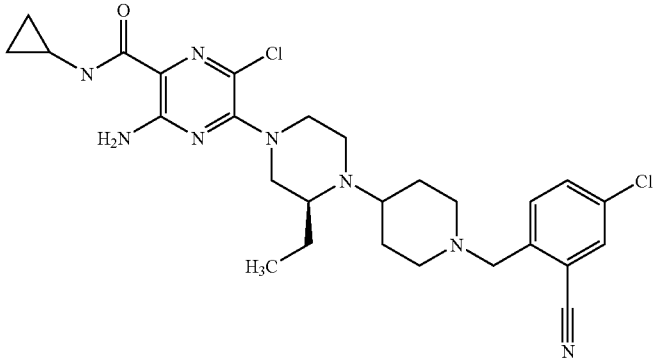 | A |
| 89 | 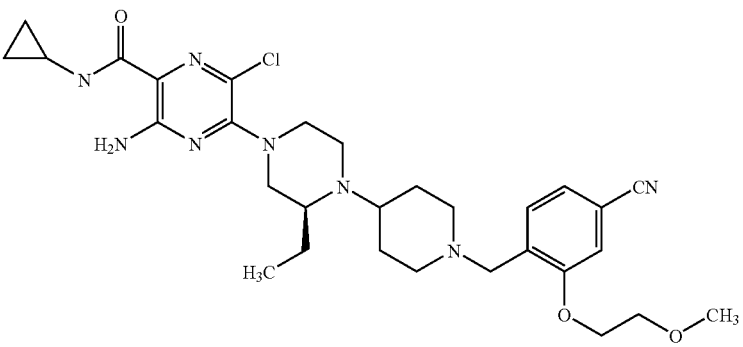 | A |

TABLE 1-continued

| Compound No. | Compound Structure | IC$_{50}$ |
|---|---|---|
| 90 | 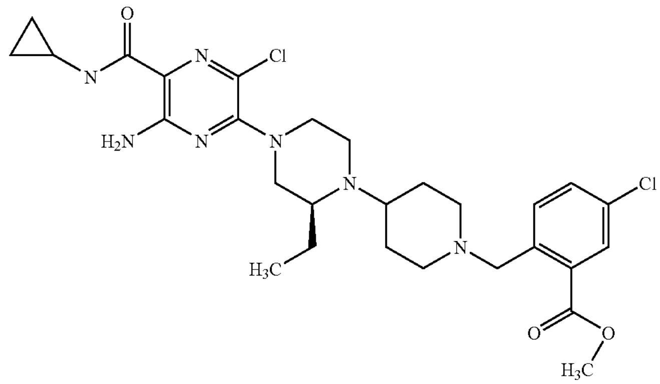 | A |
| 91 | 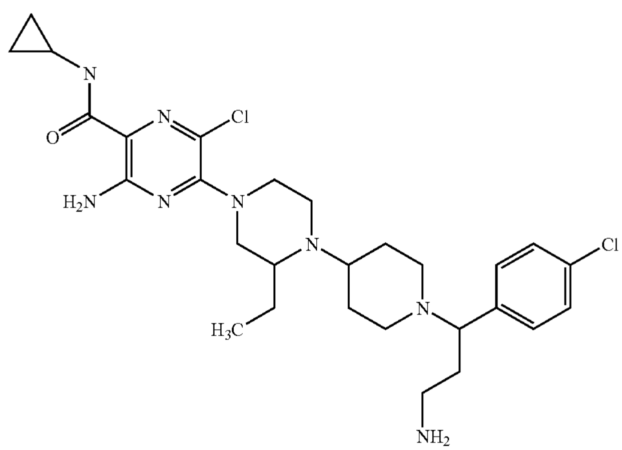 | A |
| 92 | 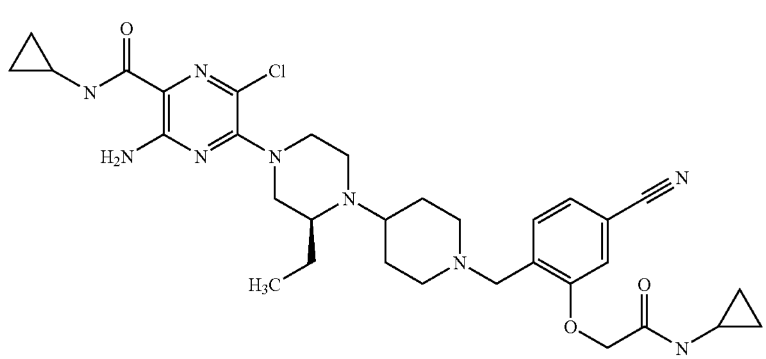 | A |

TABLE 1-continued

| Compound No. | Compound Structure | IC$_{50}$ |
|---|---|---|
| 93 | 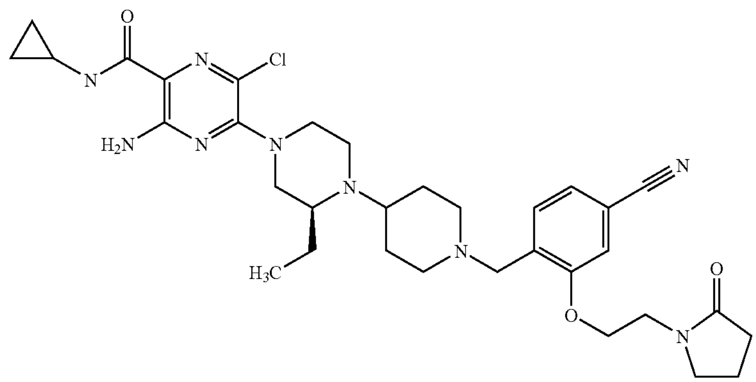 | A |
| 94 | 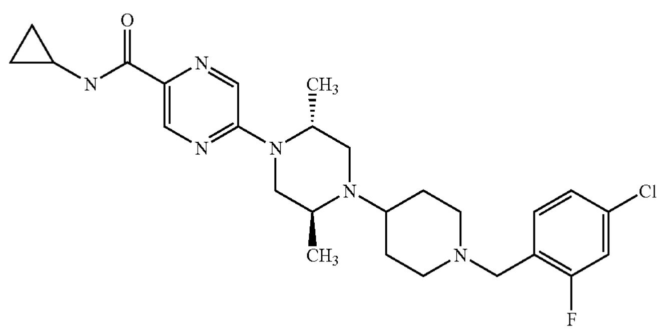 | B |
| 95 | 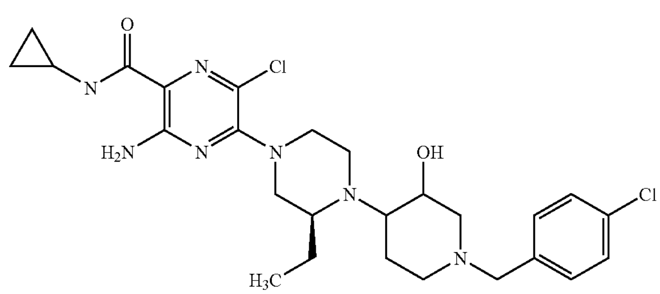 | B |
| 96 | 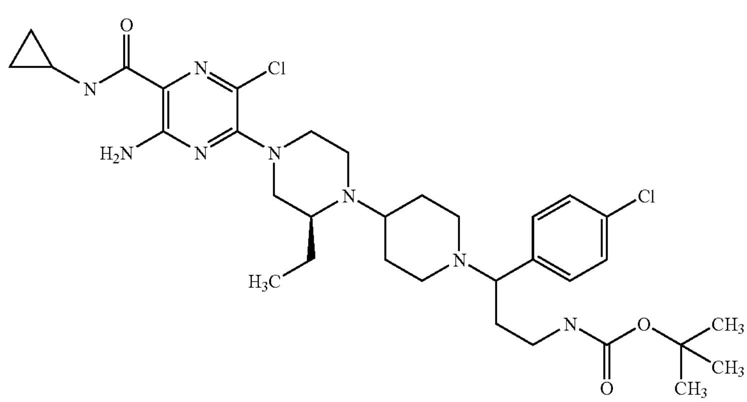 | C |

TABLE 1-continued

| Compound No. | Compound Structure | IC$_{50}$ |
|---|---|---|
| 97 | 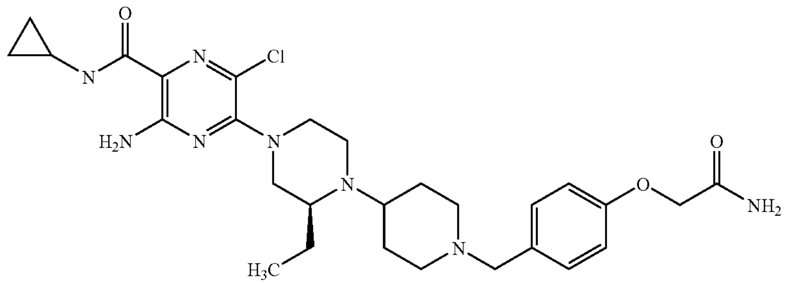 | C |
| 98 | 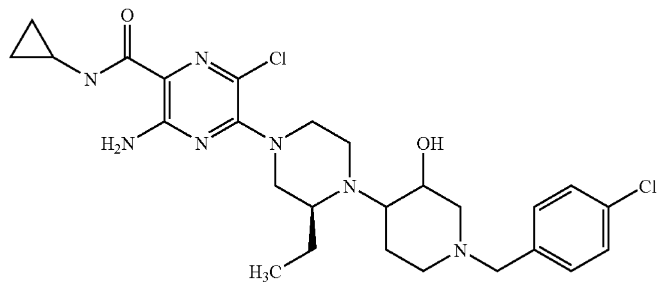 | C |
| 99 | 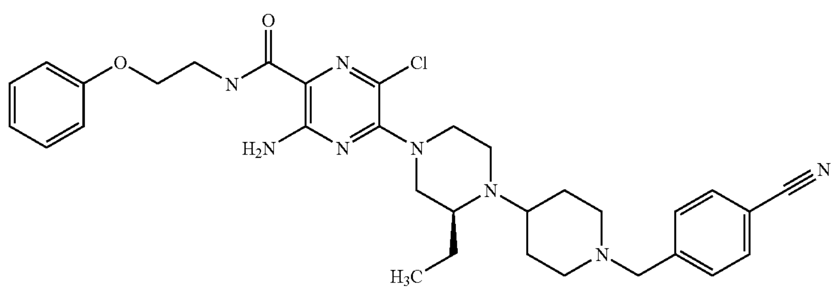 | A |
| 100 | 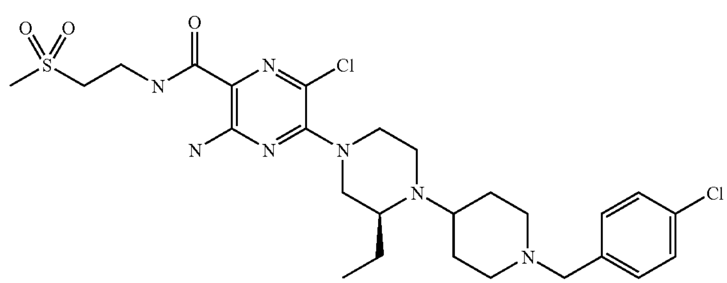 | A |
| 101 | 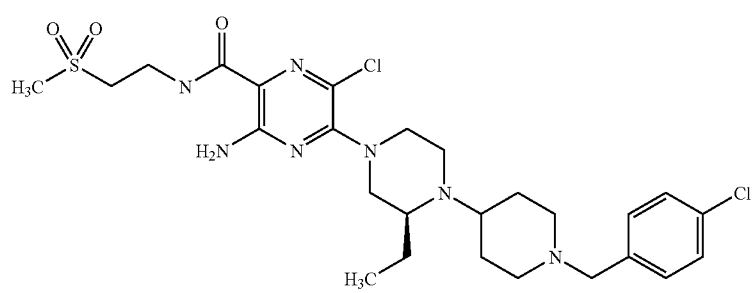 | B |

TABLE 1-continued
| Compound No. | Compound Structure | IC$_{50}$ |
|---|---|---|
| 102 | 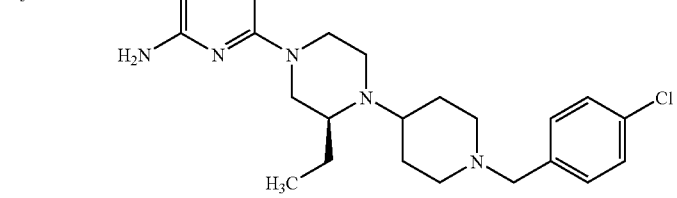 | A |
| 103 | 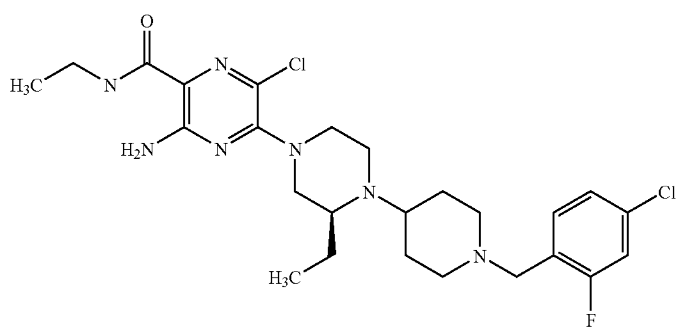 | A |
| 104 | 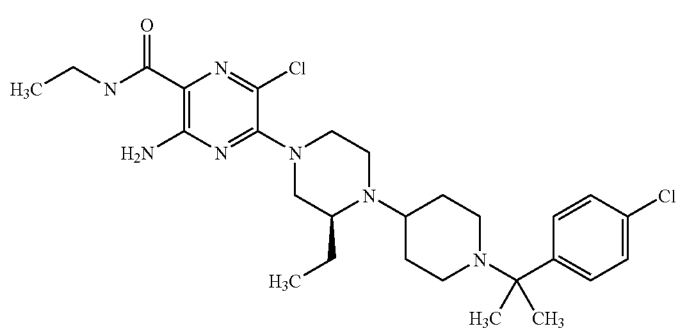 | B |
| 105 | 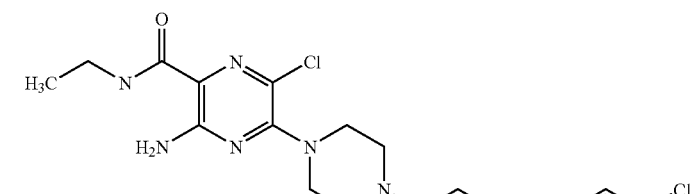 | C |

TABLE 1-continued

| Compound No. | Compound Structure | IC$_{50}$ |
|---|---|---|
| 106 | 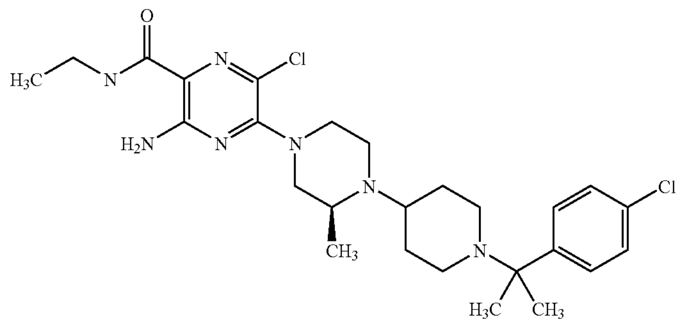 | C |
| 107 | 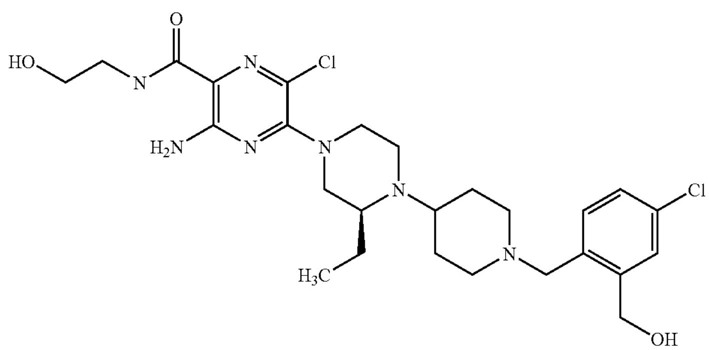 | A |
| 108 | 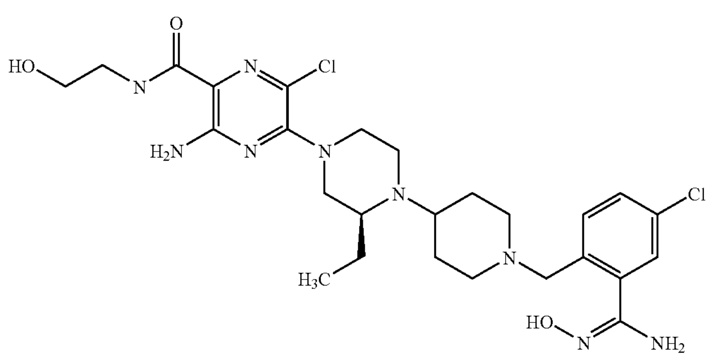 | A |
| 109 | 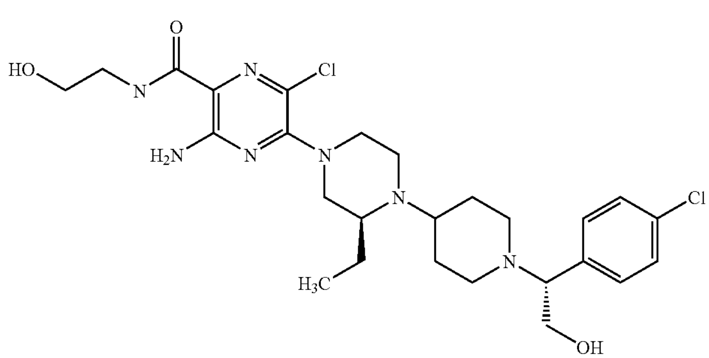 | A |

TABLE 1-continued
| Compound No. | Compound Structure | IC$_{50}$ |
|---|---|---|
| 110 | 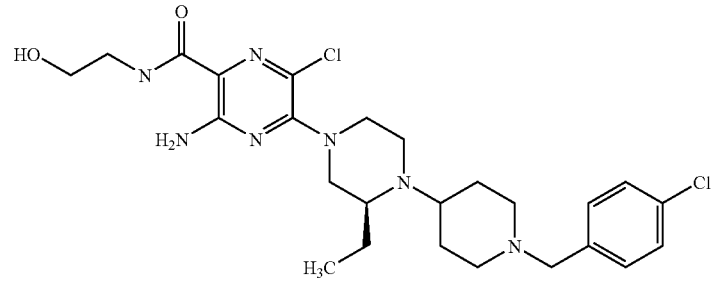 | A |
| 111 | 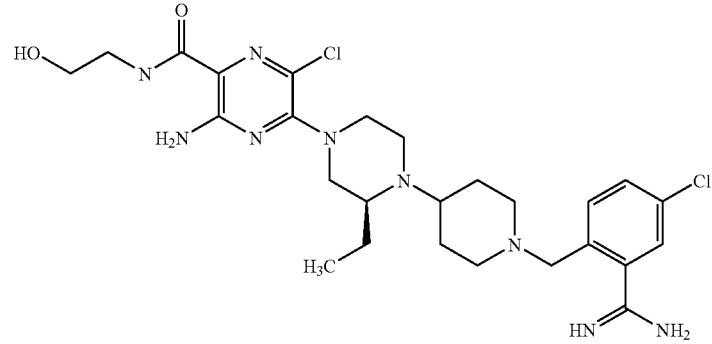 | A |
| 112 | 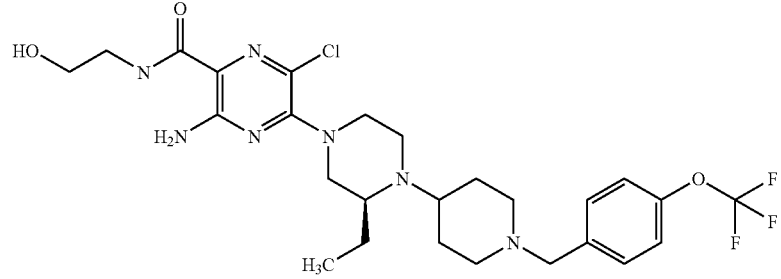 | A |
| 113 | 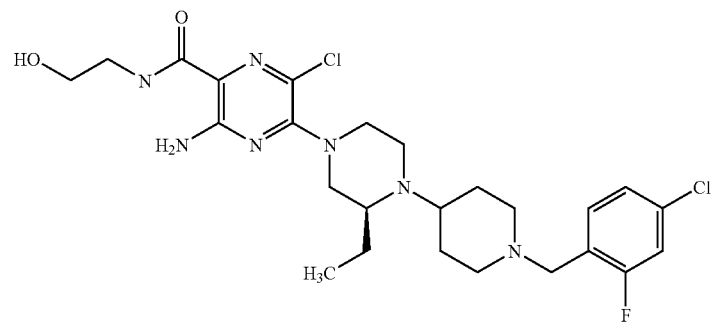 | A |

TABLE 1-continued

| Compound No. | Compound Structure | IC$_{50}$ |
|---|---|---|
| 114 | 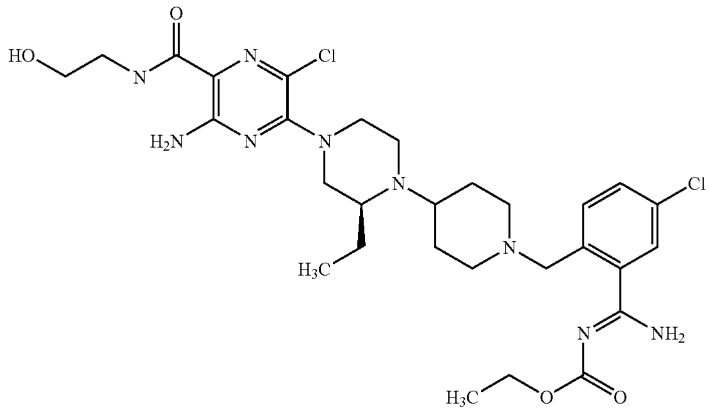 | A |
| 115 | 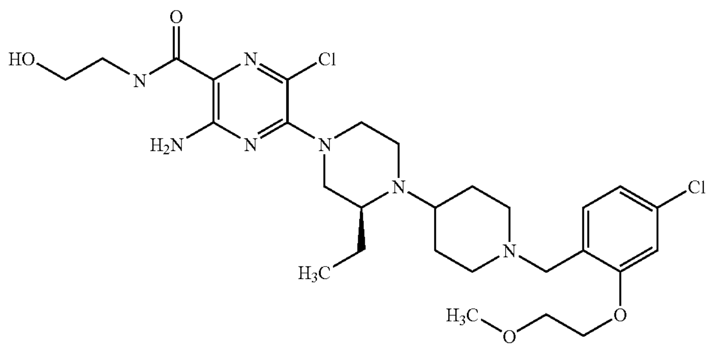 | A |
| 116 | 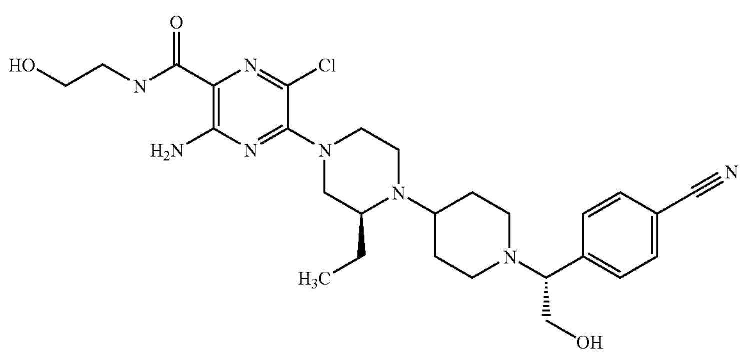 | A |
| 117 | 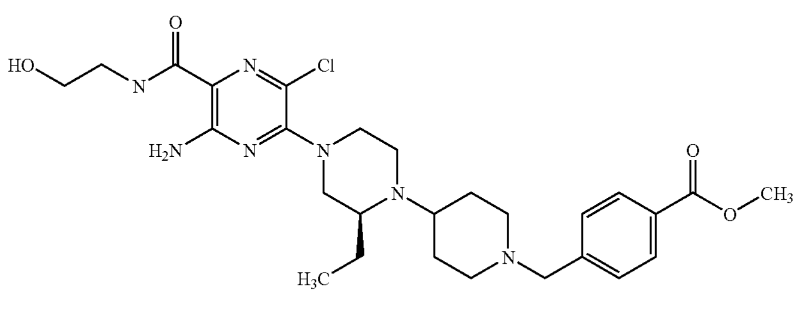 | A |

TABLE 1-continued
| Compound No. | Compound Structure | IC$_{50}$ |
|---|---|---|
| 118 | 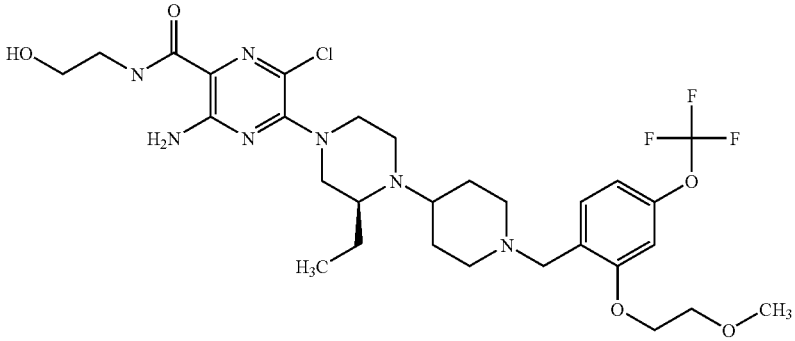 | A |
| 119 | 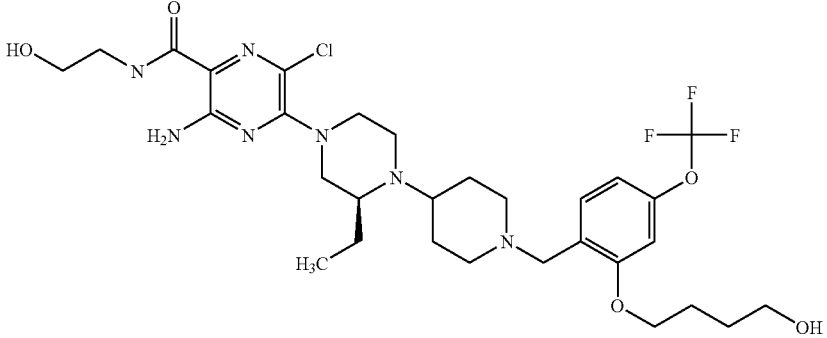 | A |
| 120 | 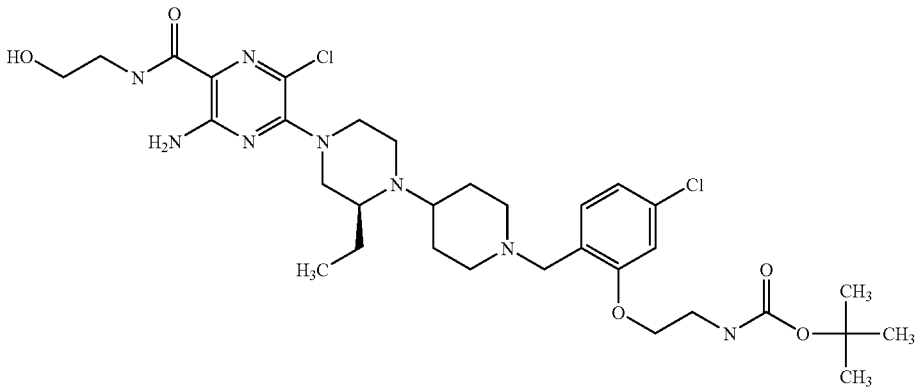 | A |
| 121 | 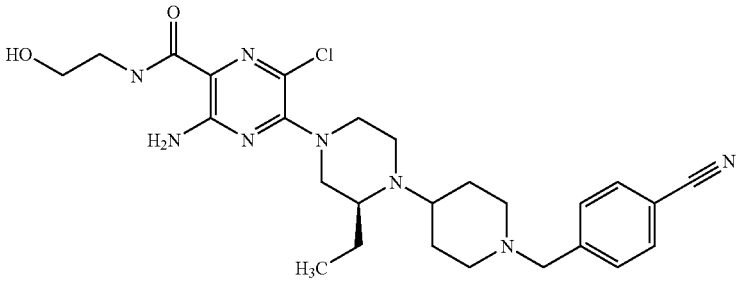 | A |

TABLE 1-continued

| Compound No. | Compound Structure | IC$_{50}$ |
|---|---|---|
| 122 | 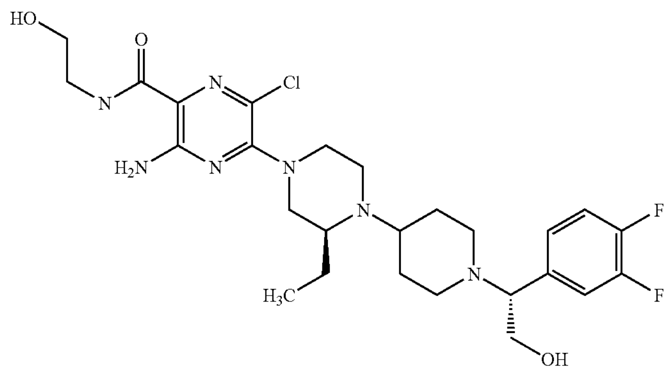 | A |
| 123 | 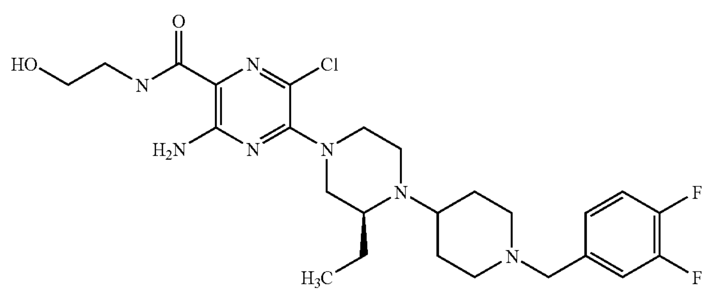 | A |
| 124 | 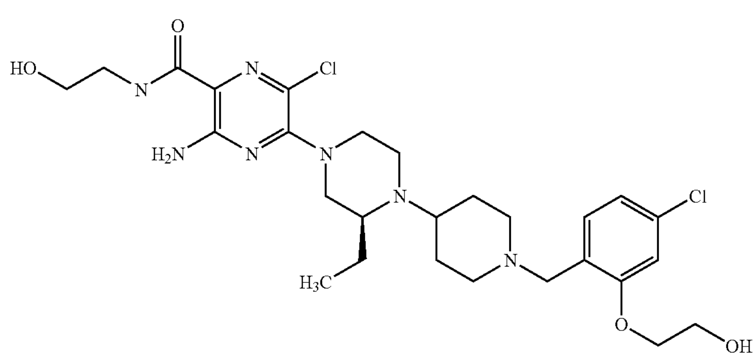 | A |
| 125 | 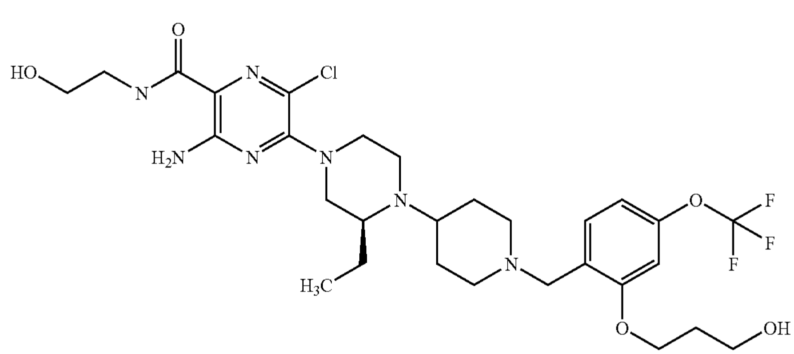 | A |

TABLE 1-continued

| Compound No. | Compound Structure | IC$_{50}$ |
|---|---|---|
| 126 | 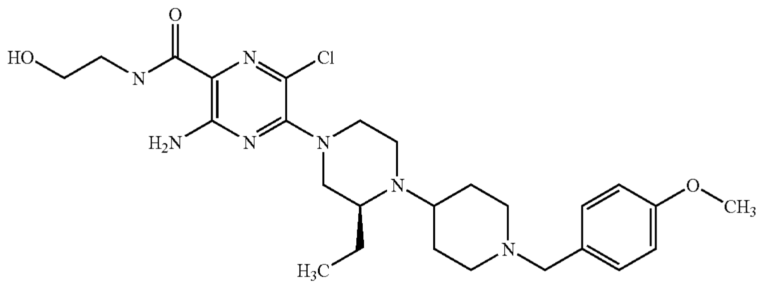 | A |
| 127 | 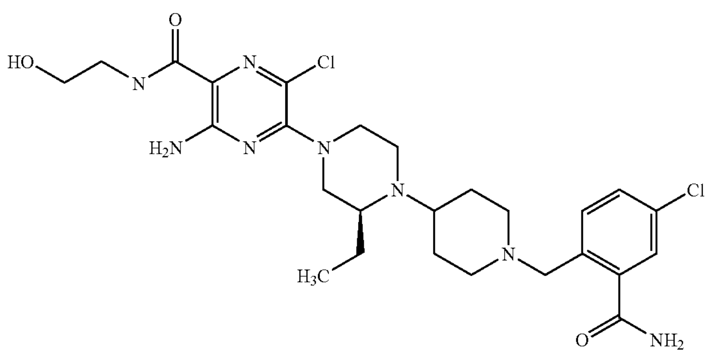 | A |
| 128 | 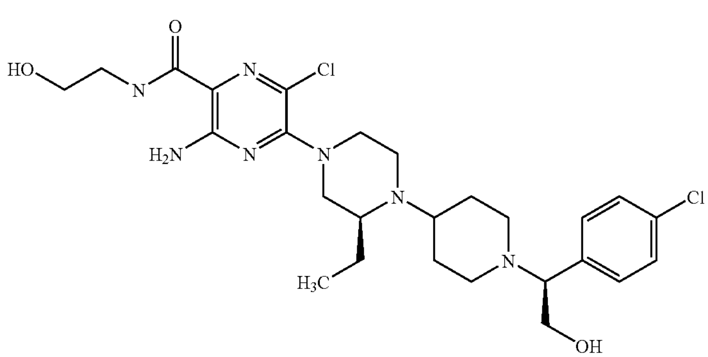 | A |

TABLE 1-continued
| Compound No. | Compound Structure | IC$_{50}$ |
|---|---|---|
| 129 | 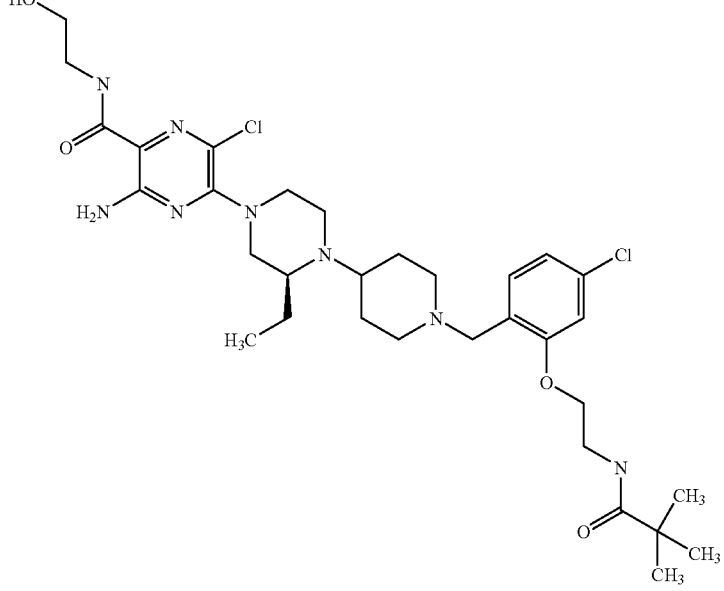 | A |
| 130 | 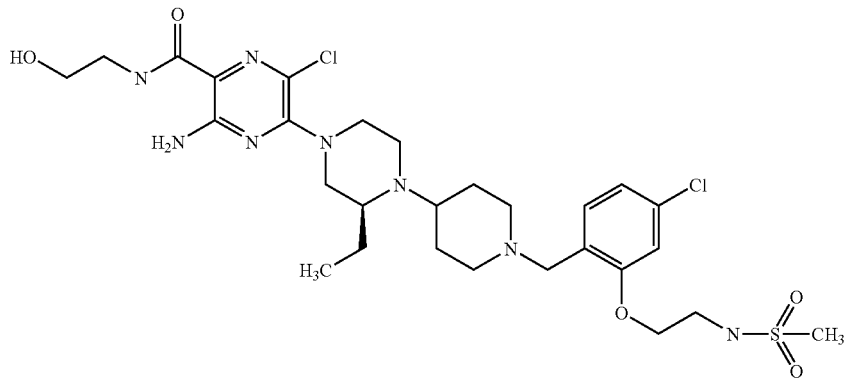 | A |

TABLE 1-continued
| Compound No. | Compound Structure | IC$_{50}$ |
|---|---|---|
| 131 | 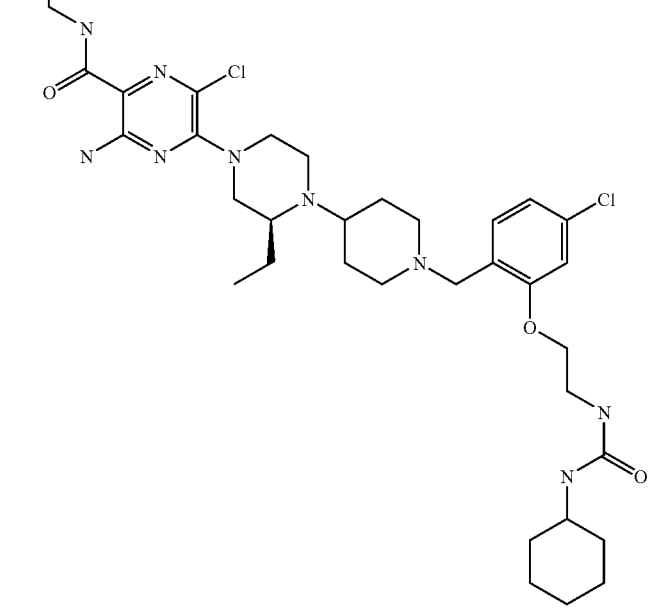 | A |
| 132 | 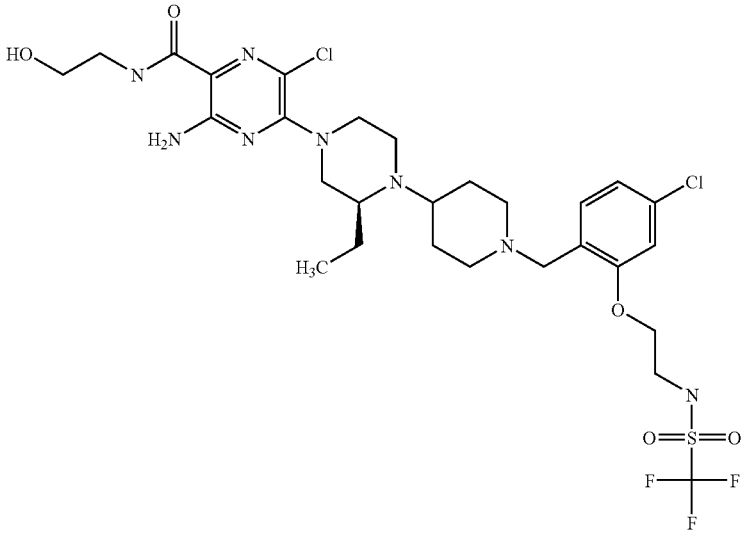 | A |
| 133 | 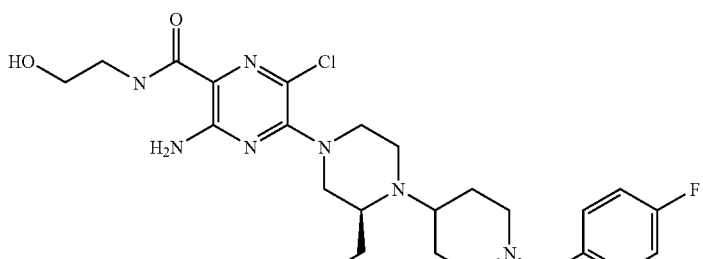 | A |

TABLE 1-continued
| Compound No. | Compound Structure | IC$_{50}$ |
|---|---|---|
| 134 | 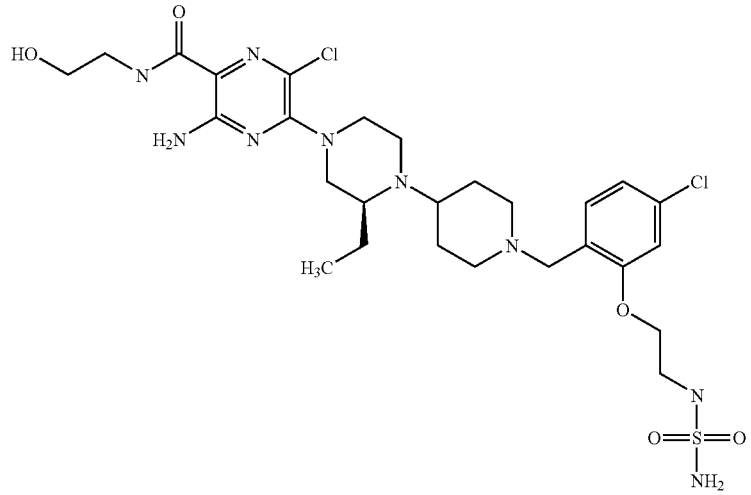 | A |
| 135 | 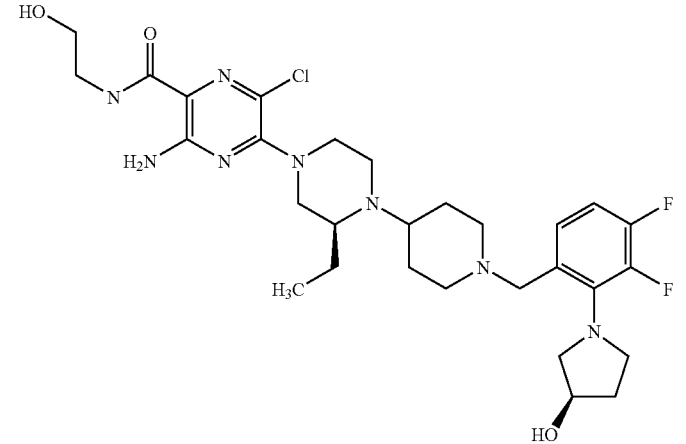 | A |
| 136 | 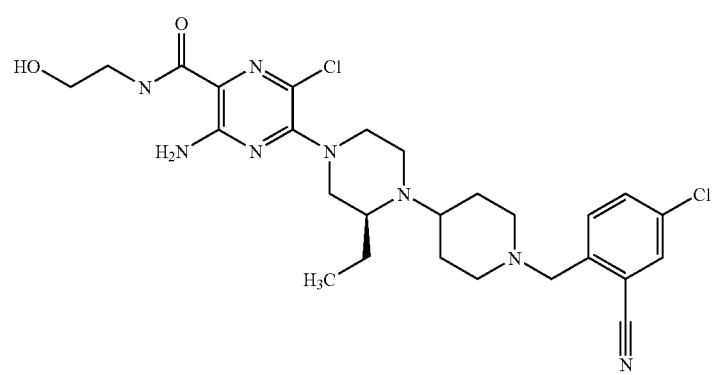 | A |

TABLE 1-continued
| Compound No. | Compound Structure | IC$_{50}$ |
|---|---|---|
| 137 | 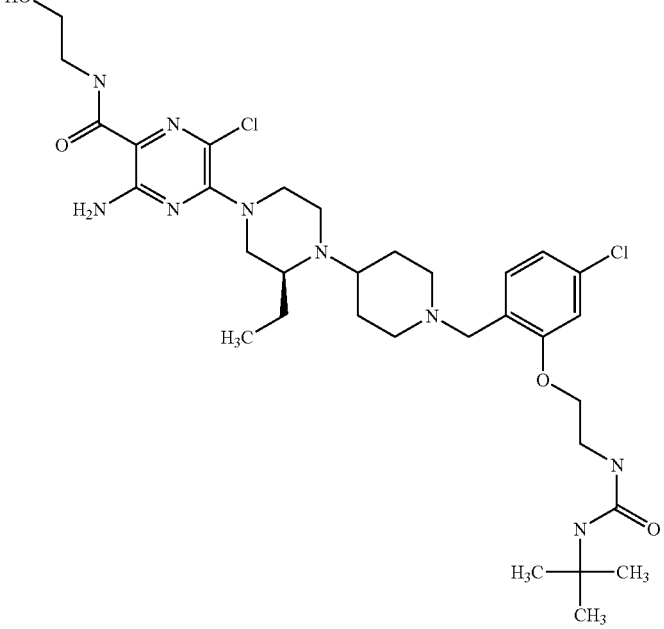 | A |
| 138 | 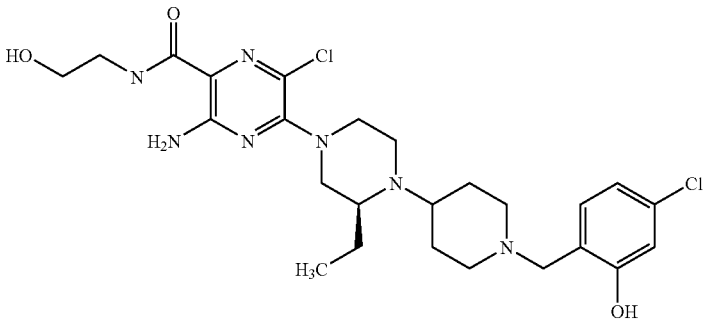 | A |
| 139 | 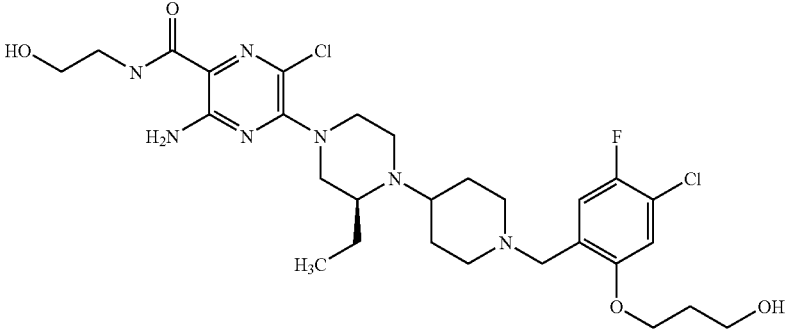 | A |

TABLE 1-continued

| Compound No. | Compound Structure | IC$_{50}$ |
|---|---|---|
| 140 | 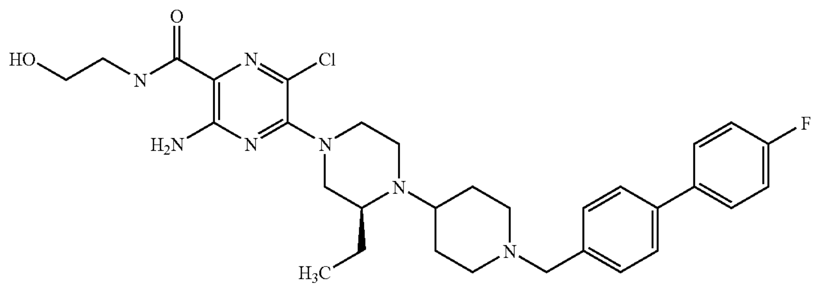 | A |
| 141 | 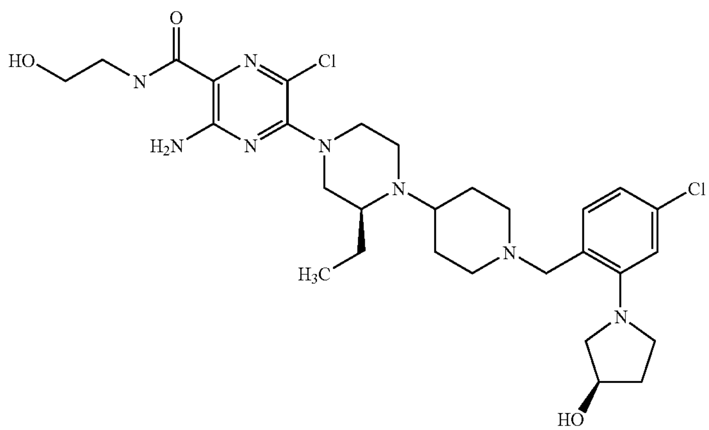 | A |
| 142 | 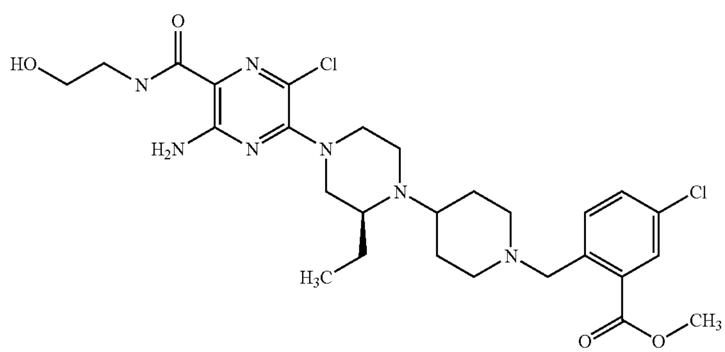 | A |
| 143 | 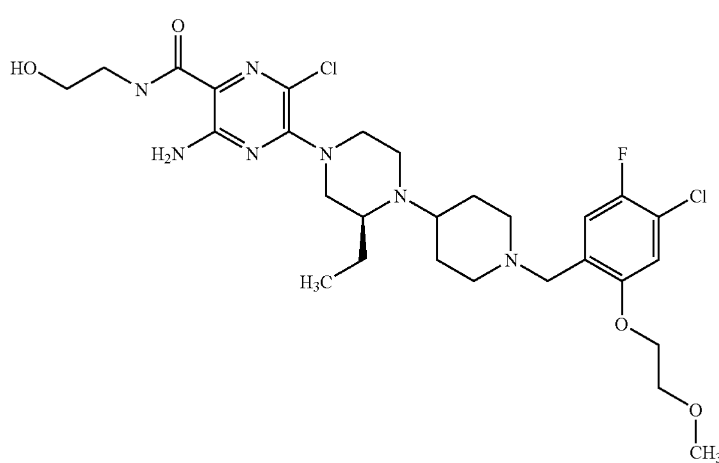 | A |

TABLE 1-continued
| Compound No. | Compound Structure | IC$_{50}$ |
|---|---|---|
| 144 | 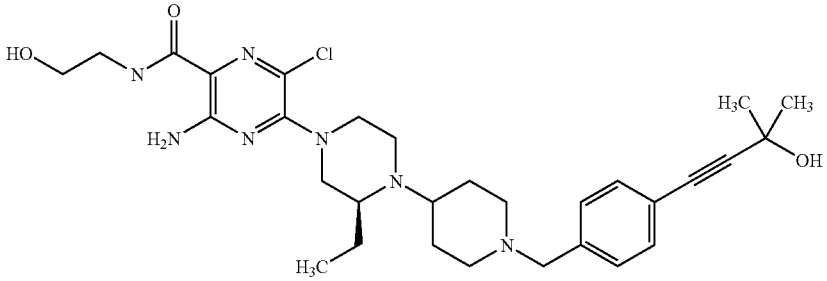 | A |
| 145 | 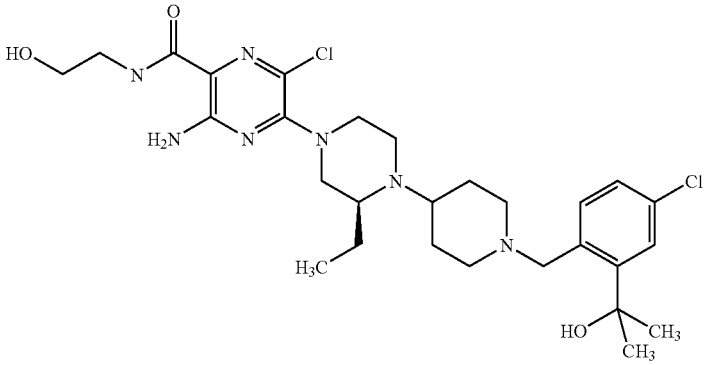 | A |
| 146 | 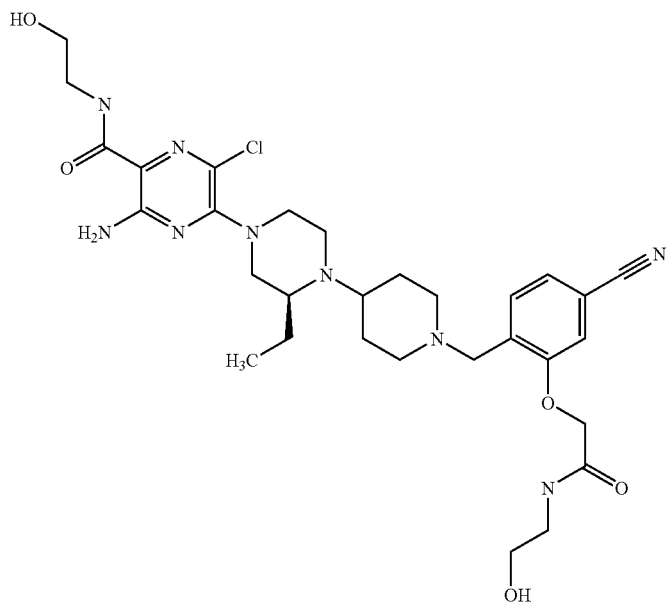 | A |

TABLE 1-continued
| Compound No. | Compound Structure | IC$_{50}$ |
|---|---|---|
| 147 | 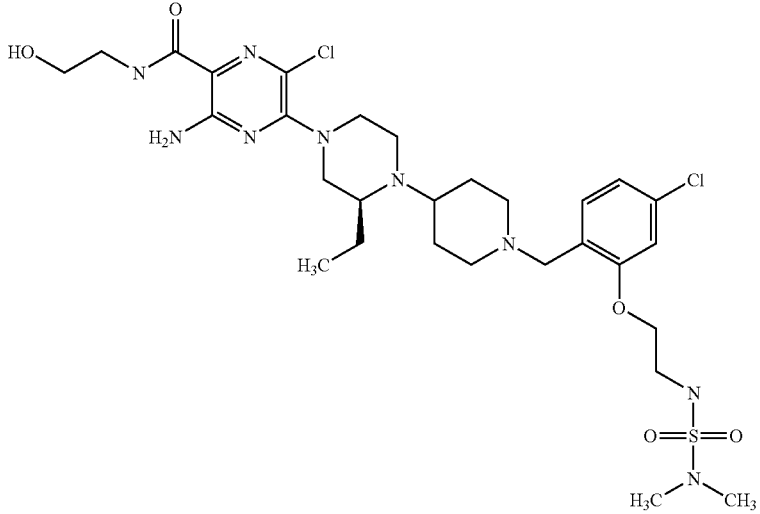 | A |
| 148 | 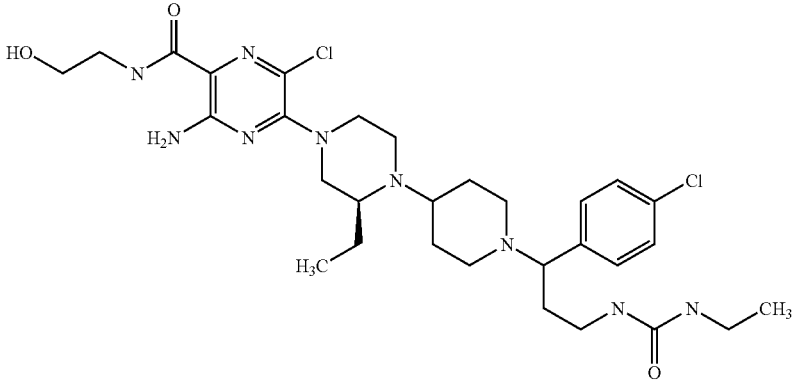 | A |
| 149 | 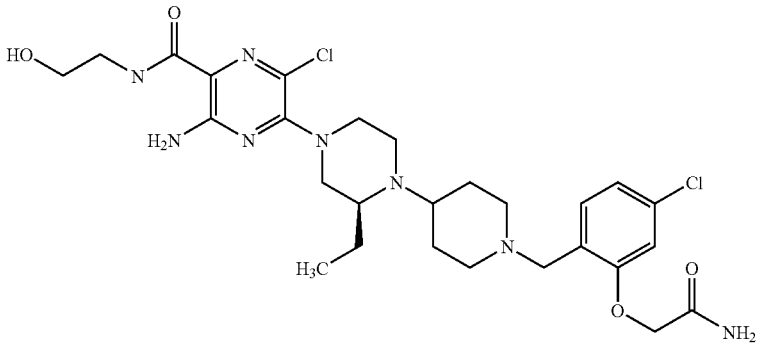 | A |

TABLE 1-continued

| Compound No. | Compound Structure | IC$_{50}$ |
|---|---|---|
| 150 | 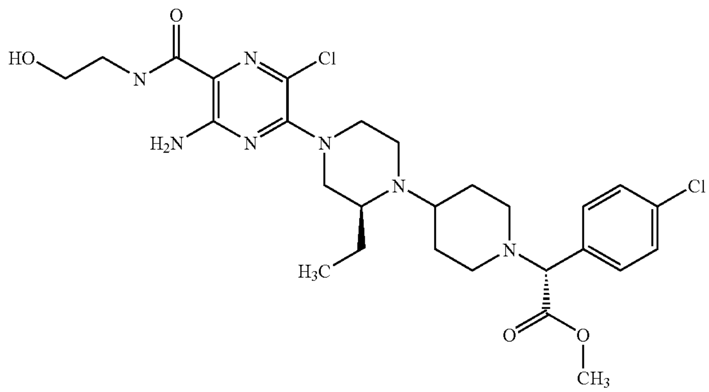 | A |
| 151 | 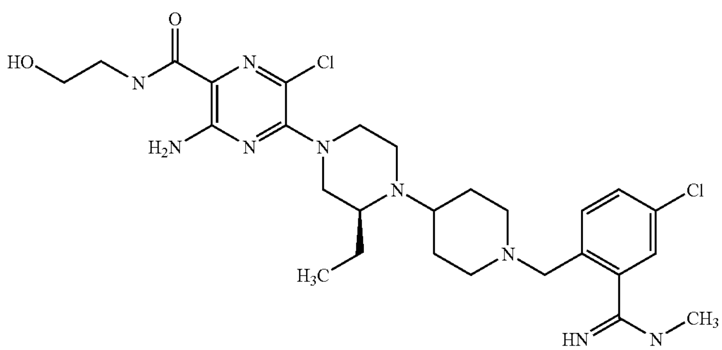 | A |
| 152 | 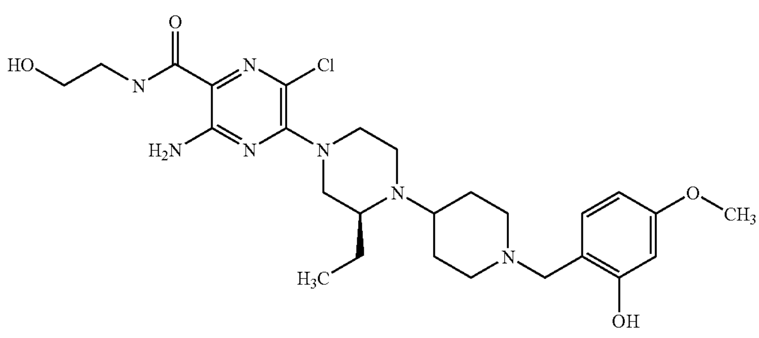 | A |
| 153 | 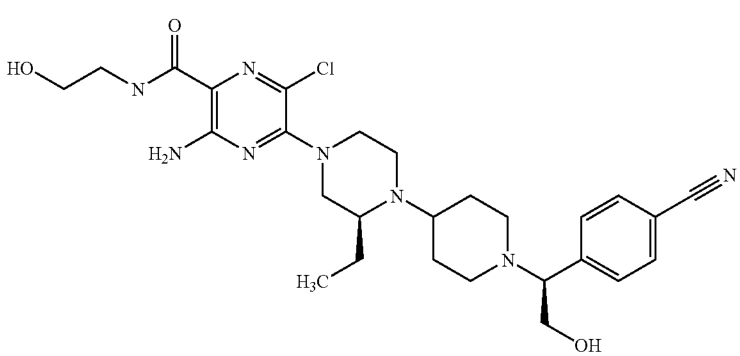 | A |

TABLE 1-continued

| Compound No. | Compound Structure | IC₅₀ |
|---|---|---|
| 154 | 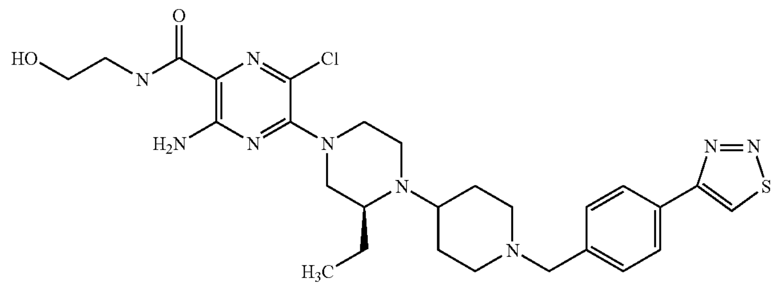 | A |
| 155 | 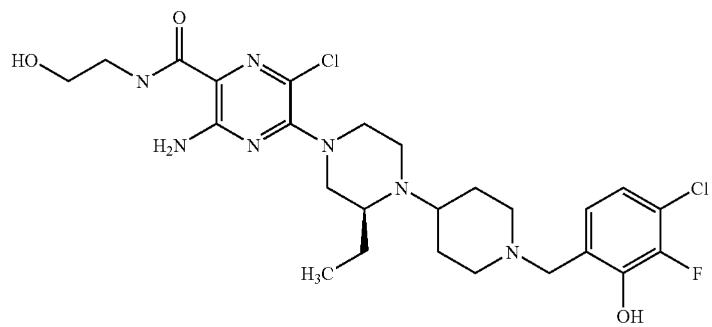 | A |
| 156 | 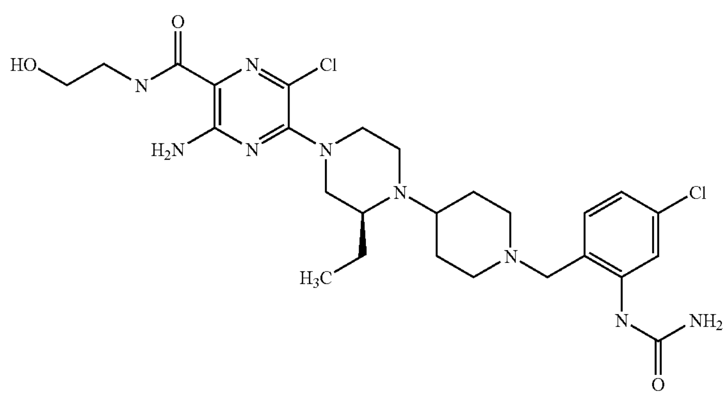 | A |
| 157 | 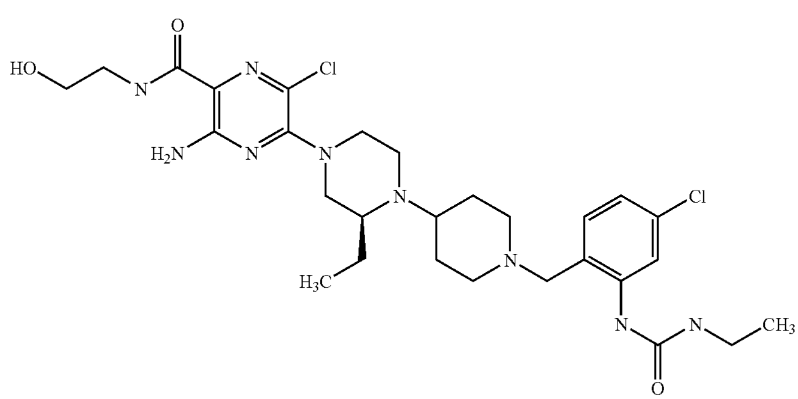 | A |

TABLE 1-continued

| Compound No. | Compound Structure | IC$_{50}$ |
|---|---|---|
| 158 | 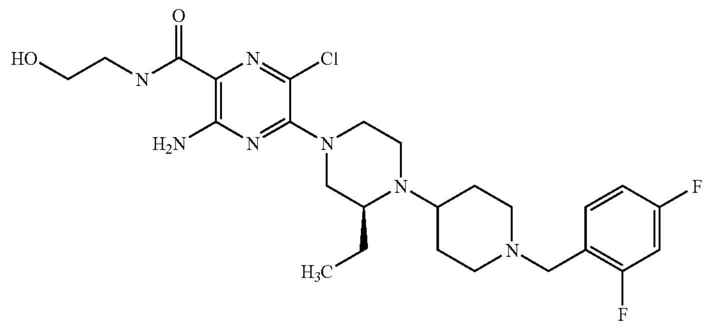 | A |
| 159 | 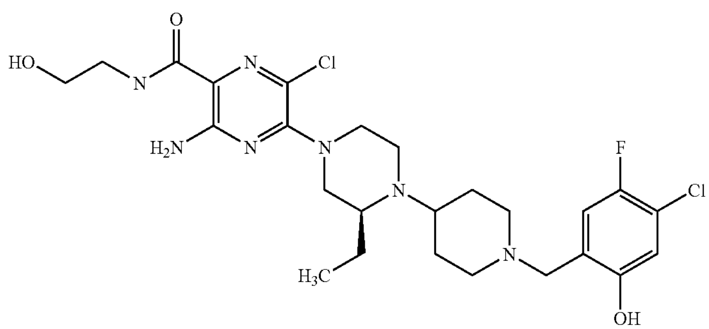 | A |
| 160 | 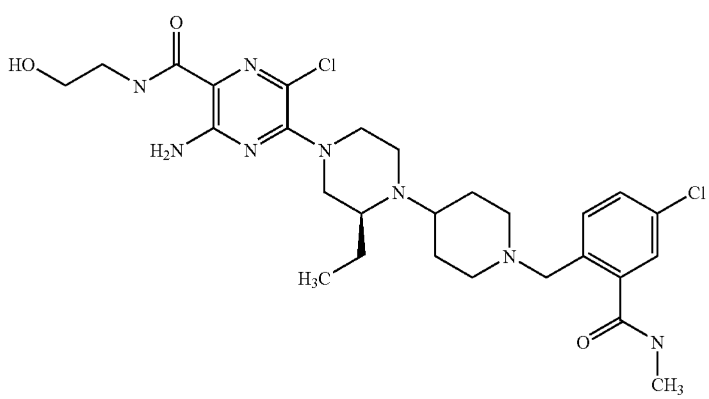 | A |
| 161 | 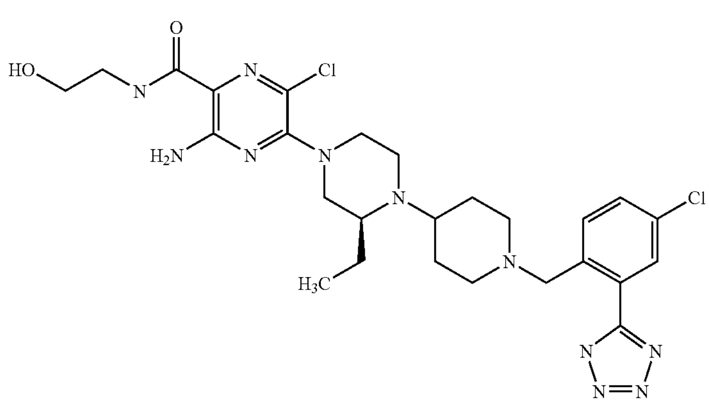 | A |

TABLE 1-continued

| Compound No. | Compound Structure | IC$_{50}$ |
|---|---|---|
| 162 | 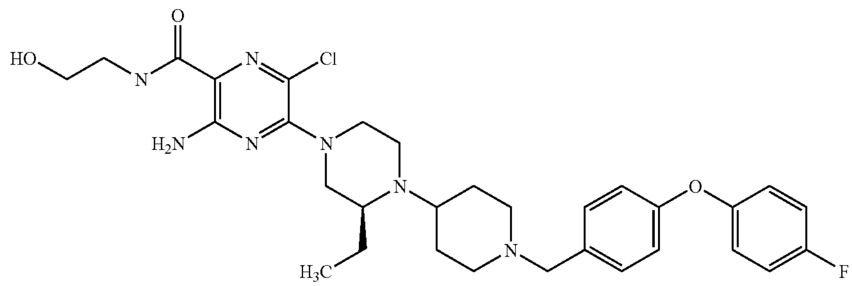 | A |
| 163 | 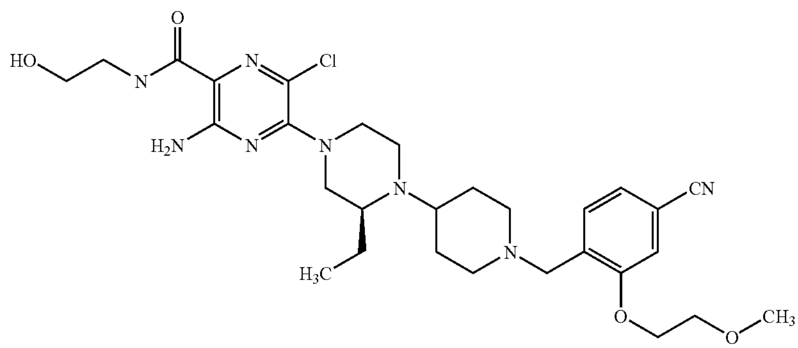 | A |
| 164 | 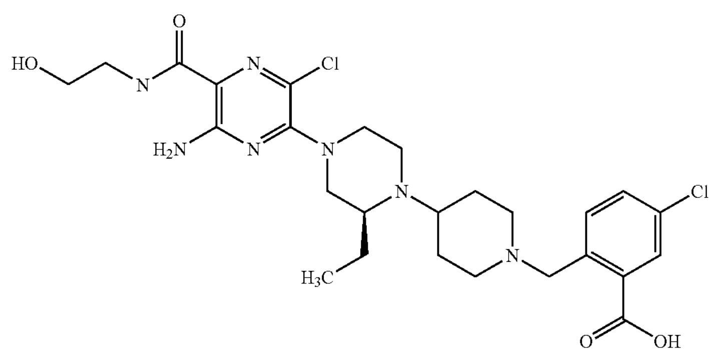 | A |
| 165 | 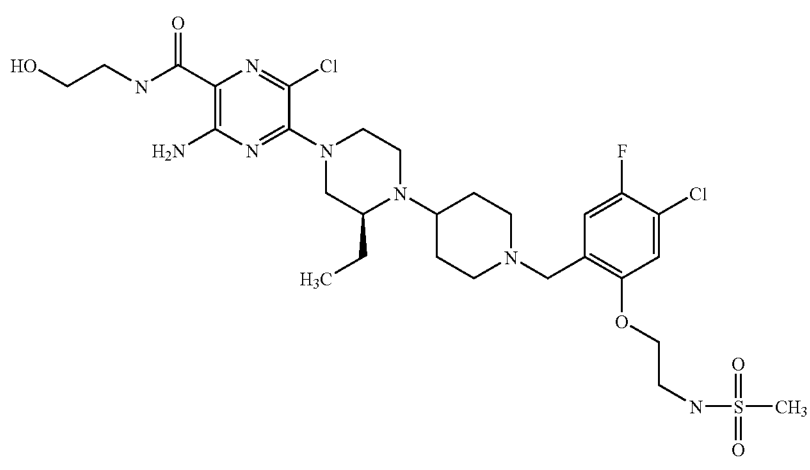 | A |

TABLE 1-continued

| Compound No. | Compound Structure | IC$_{50}$ |
|---|---|---|
| 166 | 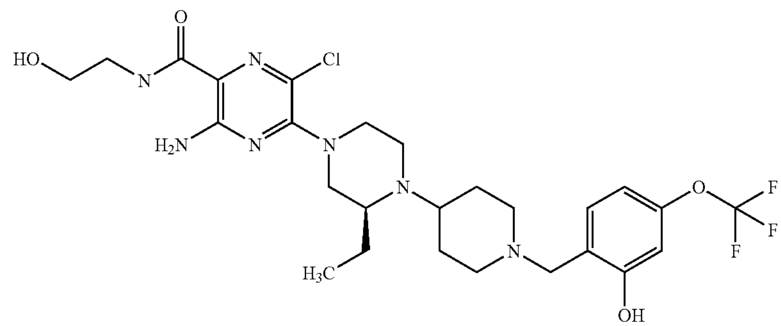 | A |
| 167 | 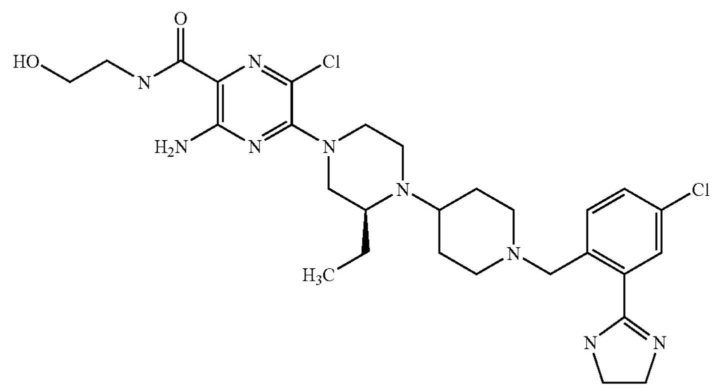 | A |
| 168 | 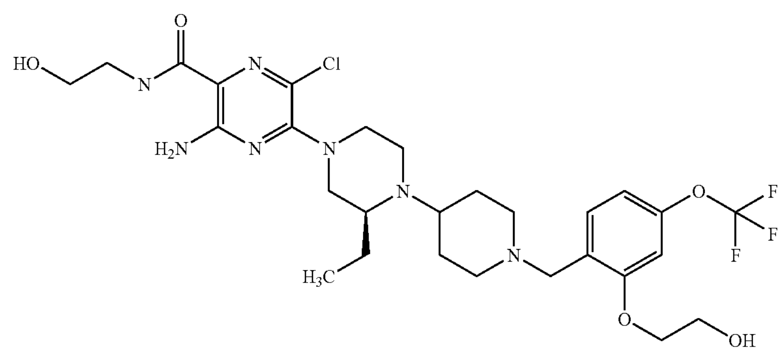 | A |
| 169 | 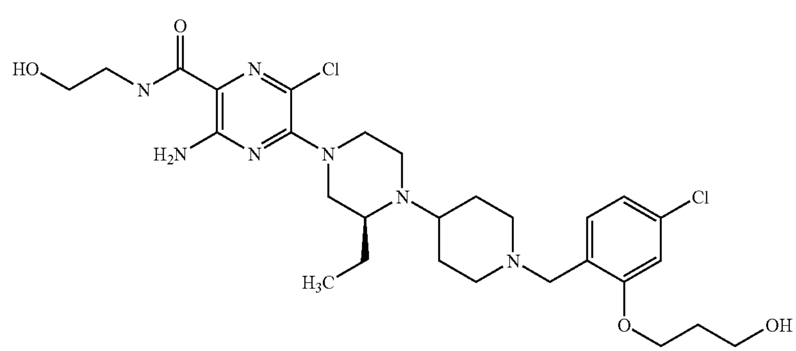 | A |

TABLE 1-continued
| Compound No. | Compound Structure | IC$_{50}$ |
|---|---|---|
| 170 | 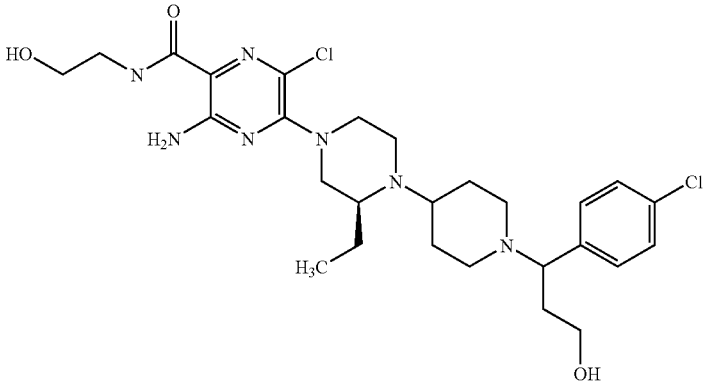 | A |
| 171 | 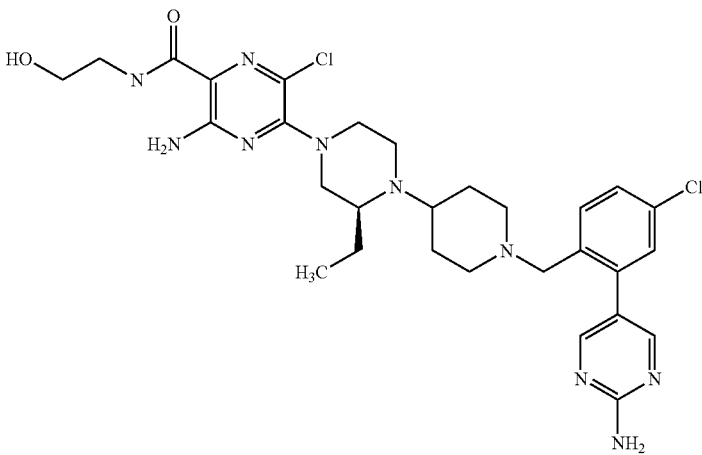 | A |
| 172 | 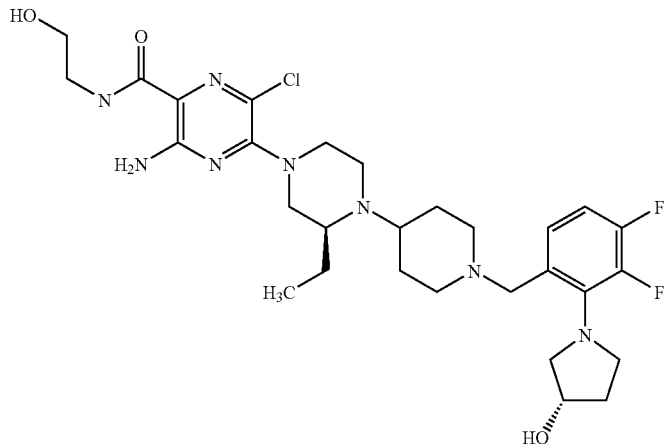 | A |

TABLE 1-continued

| Compound No. | Compound Structure | IC$_{50}$ |
|---|---|---|
| 173 | 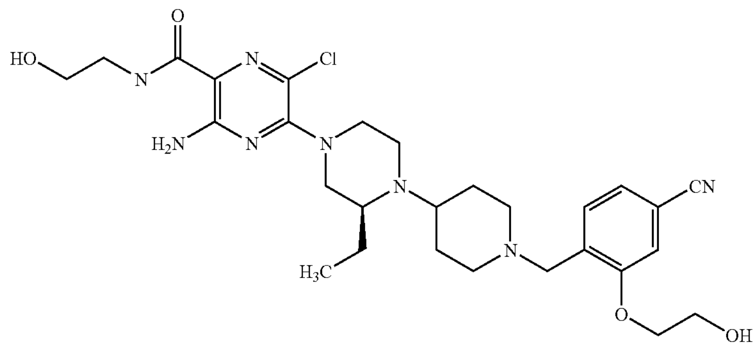 | A |
| 174 | 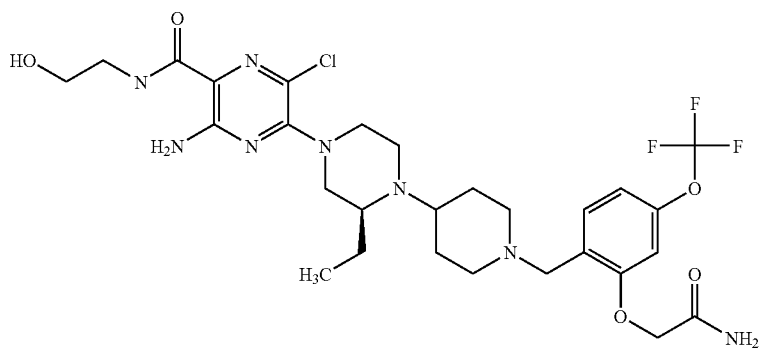 | A |
| 175 | 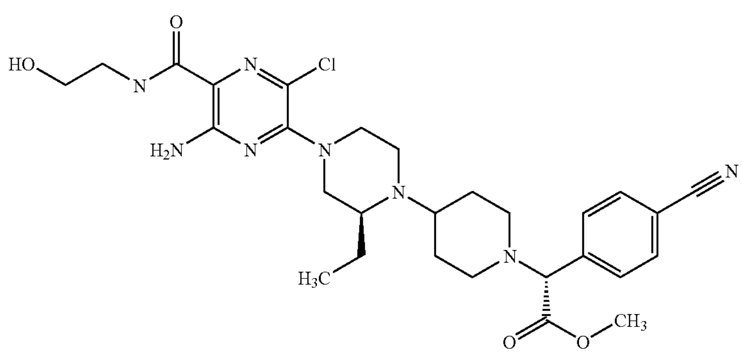 | A |
| 176 | 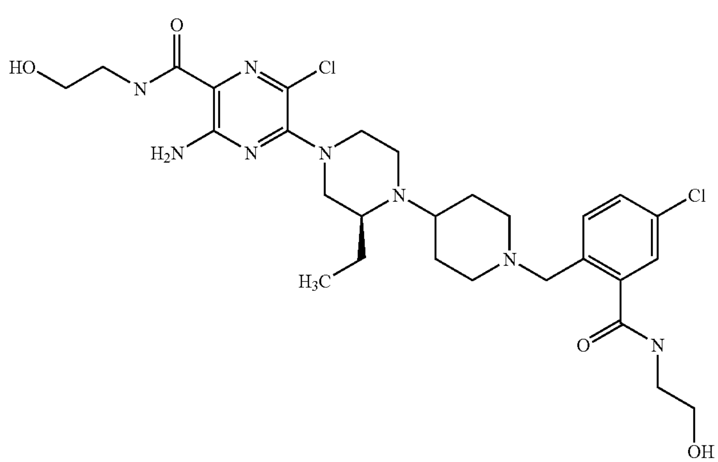 | A |

TABLE 1-continued

| Compound No. | Compound Structure | IC$_{50}$ |
|---|---|---|
| 177 | 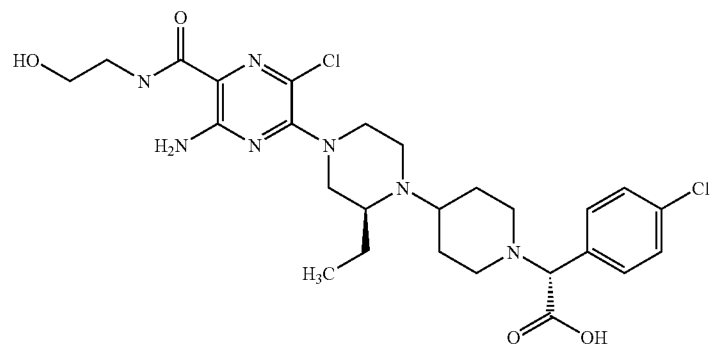 | B |
| 178 | 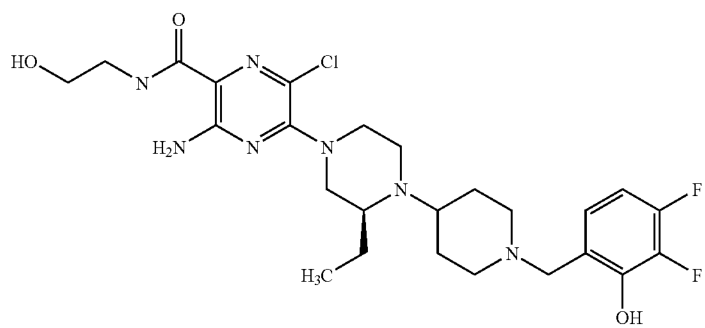 | B |
| 179 | 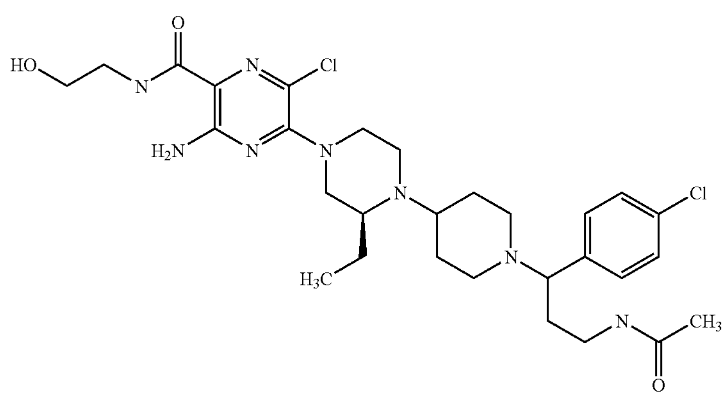 | B |
| 180 | 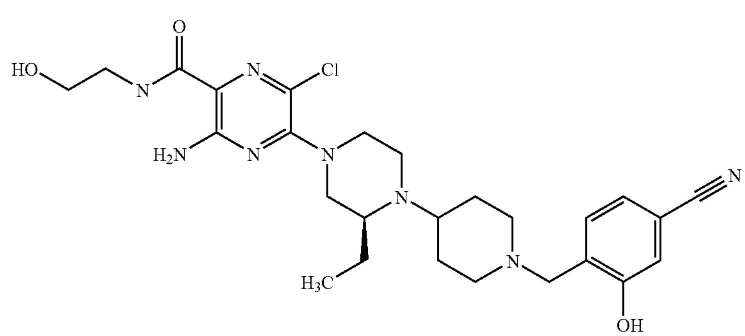 | B |

TABLE 1-continued

| Compound No. | Compound Structure | IC$_{50}$ |
|---|---|---|
| 181 | 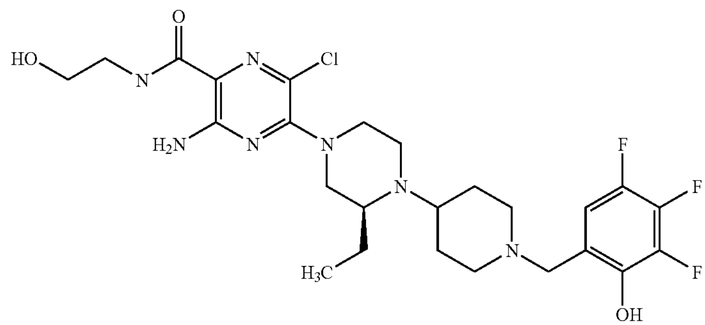 | B |
| 182 | 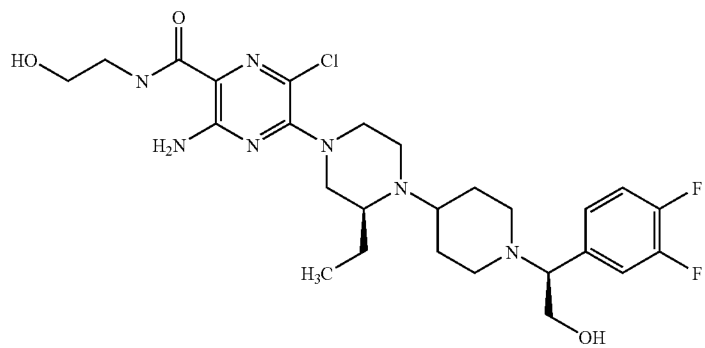 | B |
| 183 | 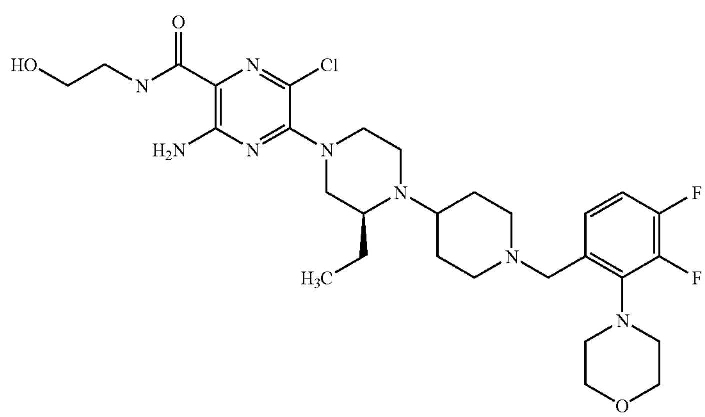 | B |
| 184 | 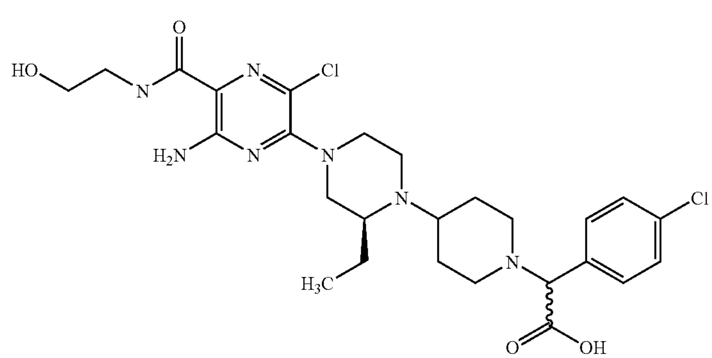 | B |

TABLE 1-continued
| Compound No. | Compound Structure | IC$_{50}$ |
|---|---|---|
| 185 | 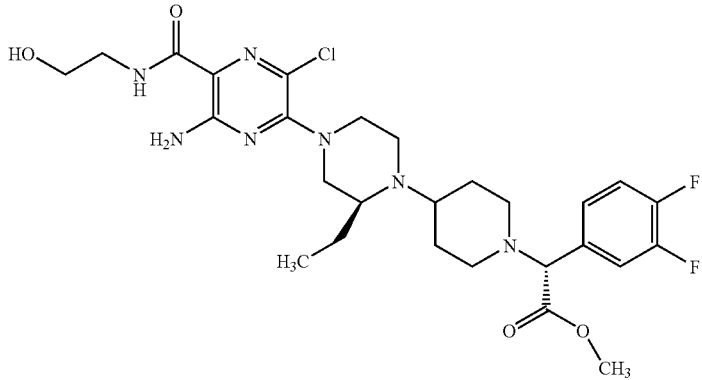 | B |
| 186 | 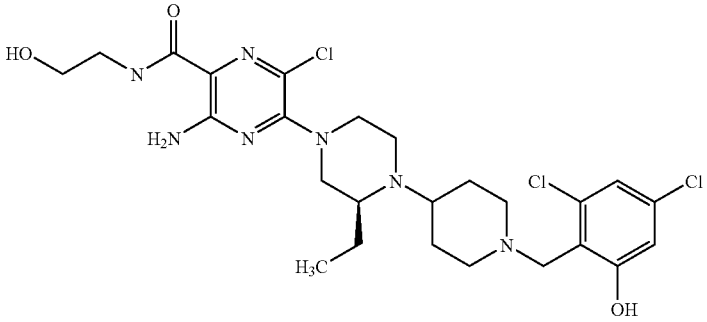 | B |
| 187 | 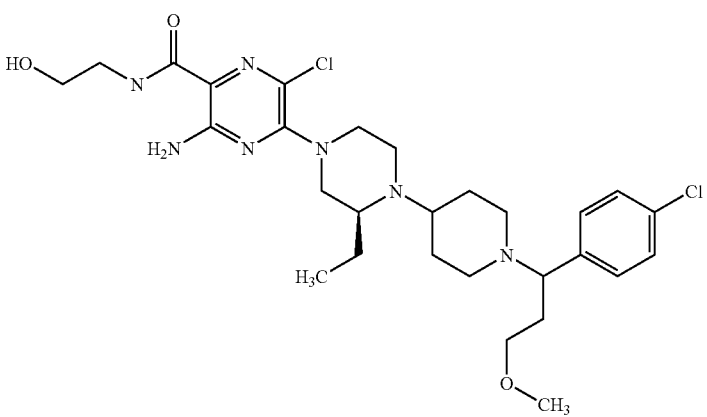 | B |

TABLE 1-continued

| Compound No. | Compound Structure | IC$_{50}$ |
|---|---|---|
| 188 | 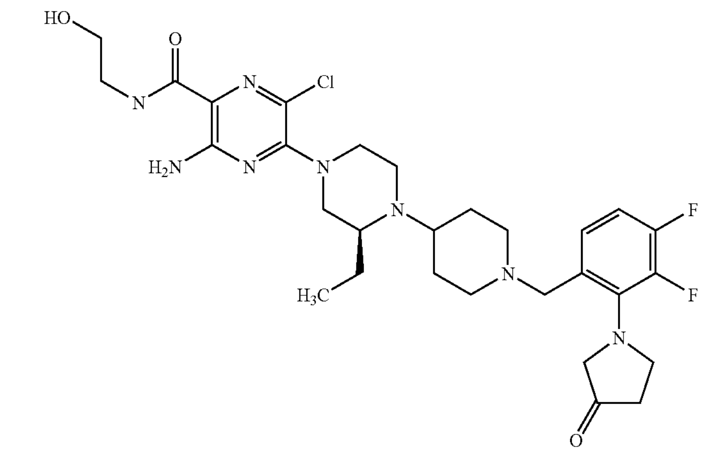 | B |
| 189 | 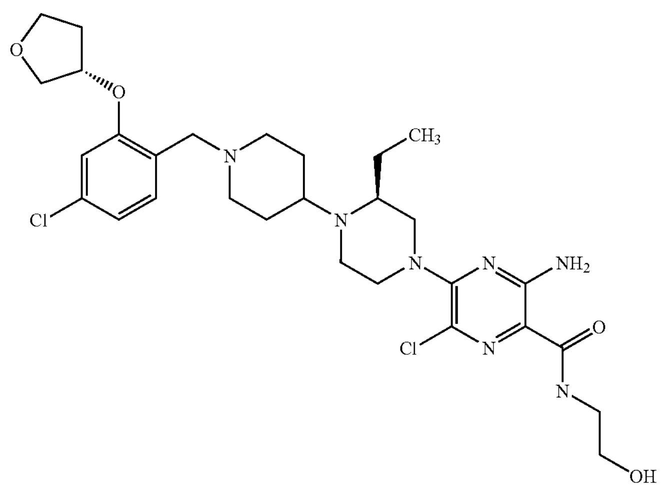 | B |
| 190 | 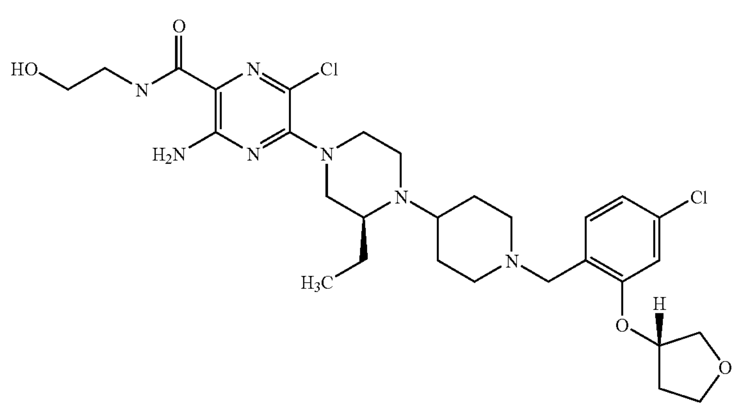 | B |

TABLE 1-continued

| Compound No. | Compound Structure | IC$_{50}$ |
|---|---|---|
| 191 | 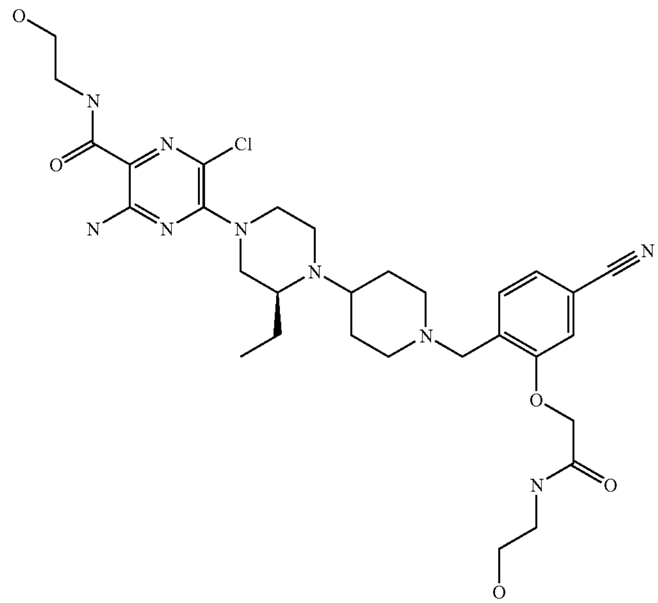 | B |
| 192 | 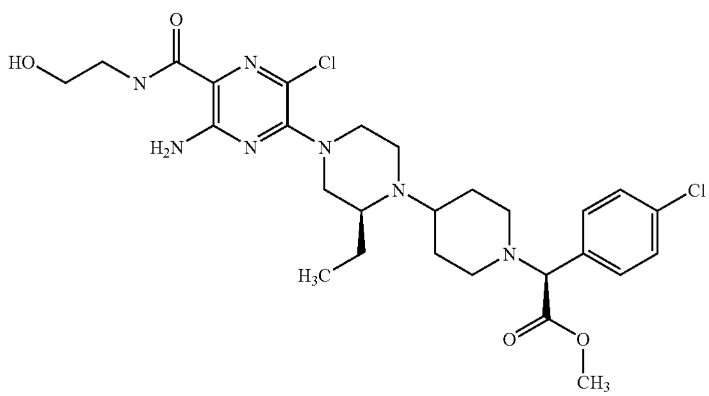 | C |
| 193 | 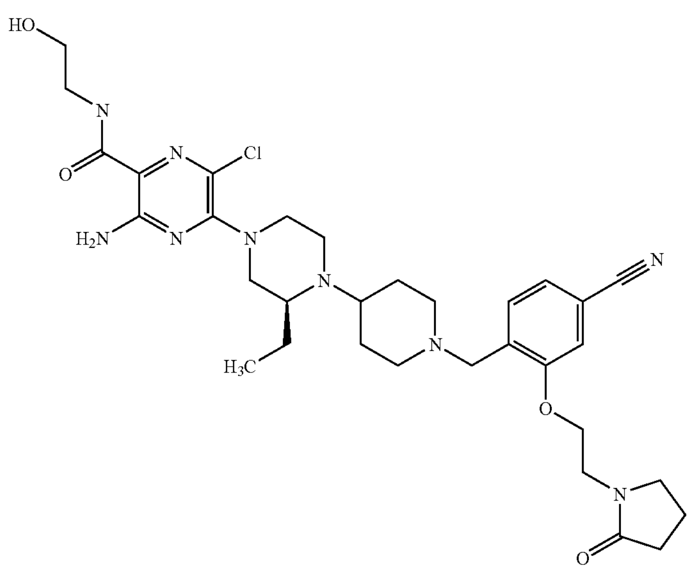 | C |

TABLE 1-continued

| Compound No. | Compound Structure | IC$_{50}$ |
|---|---|---|
| 194 | 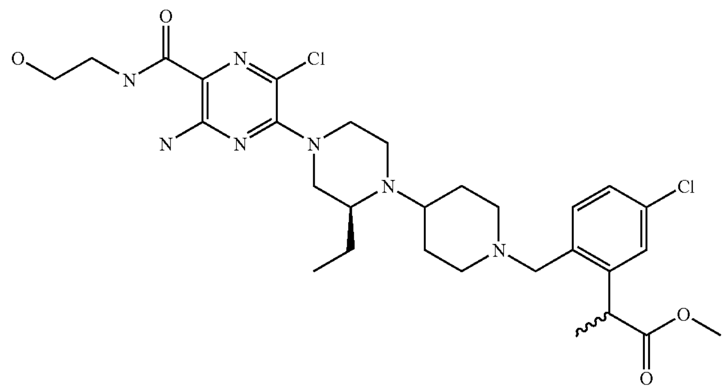 | C |
| 195 | 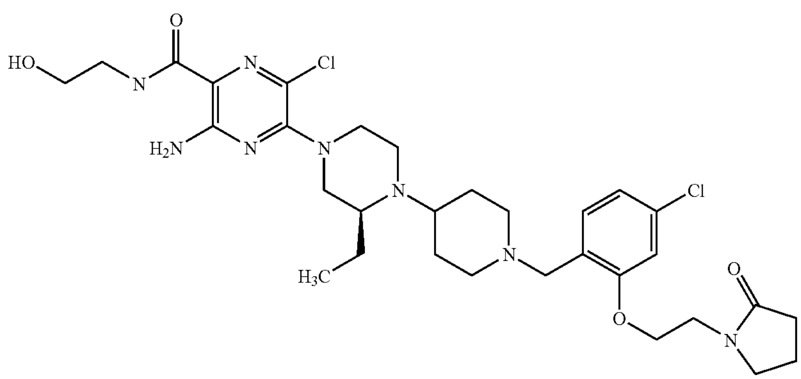 | C |
| 196 | 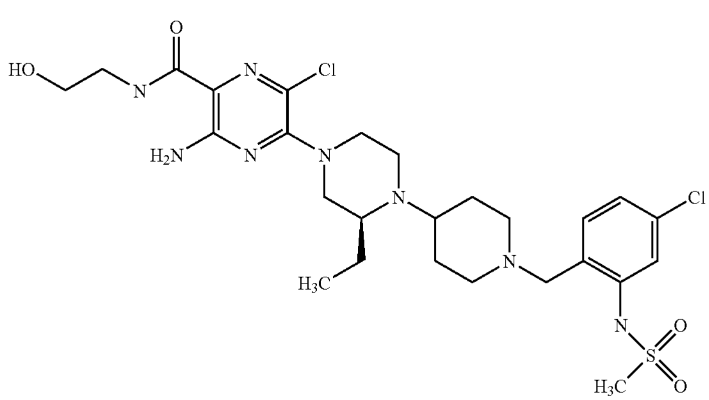 | C |

TABLE 1-continued
| Compound No. | Compound Structure | IC$_{50}$ |
|---|---|---|
| 197 | 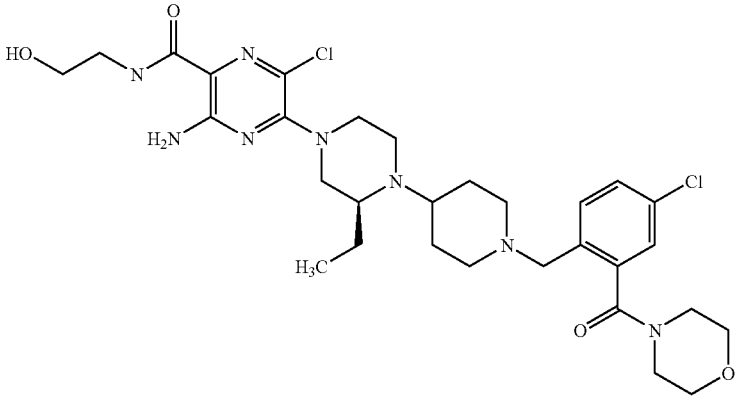 | C |
| 198 | 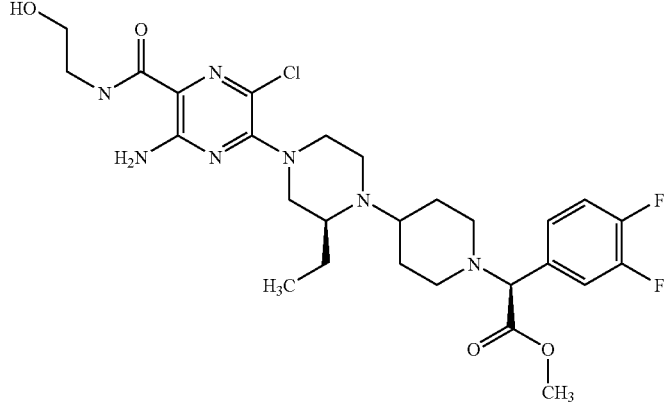 | C |
| 199 | 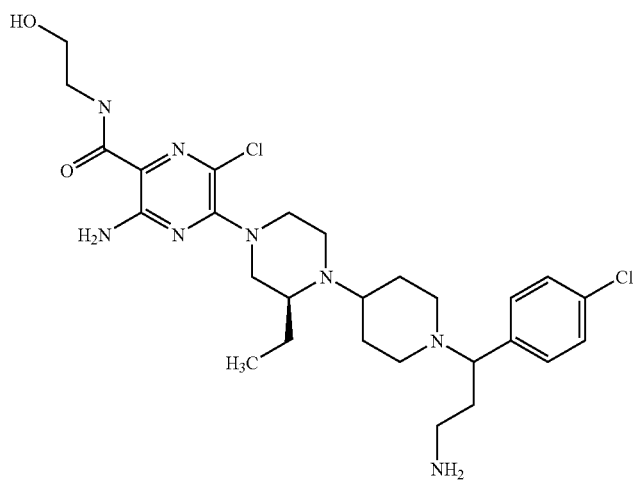 | C |

TABLE 1-continued

| Compound No. | Compound Structure | IC$_{50}$ |
|---|---|---|
| 200 | 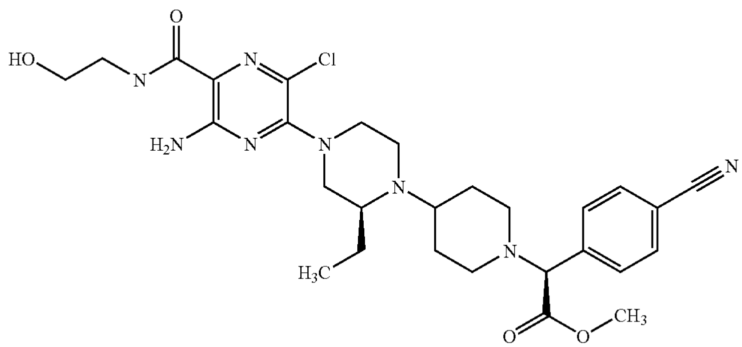 | C |
| 201 | 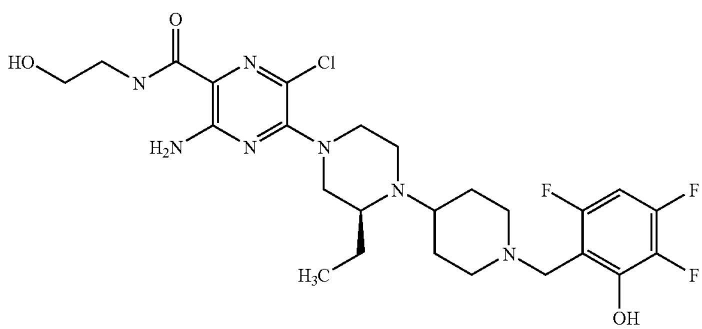 | C |
| 202 | 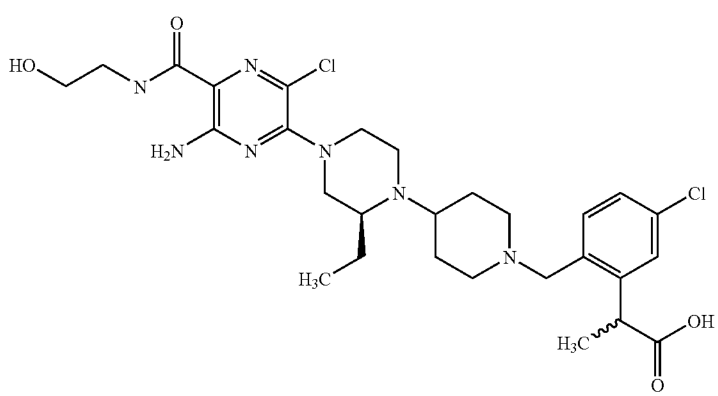 | C |
| 203 | 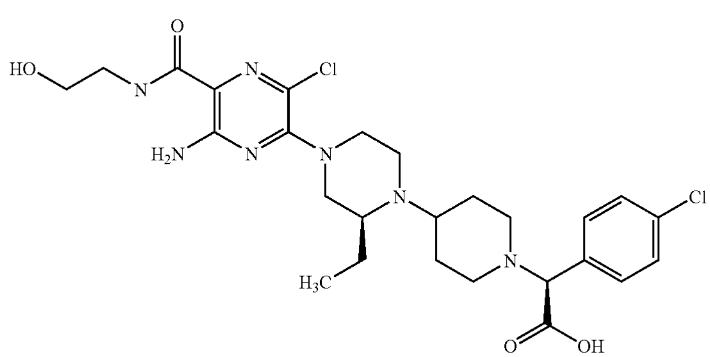 | C |

TABLE 1-continued
| Compound No. | Compound Structure | IC50 |
|---|---|---|
| 204 | 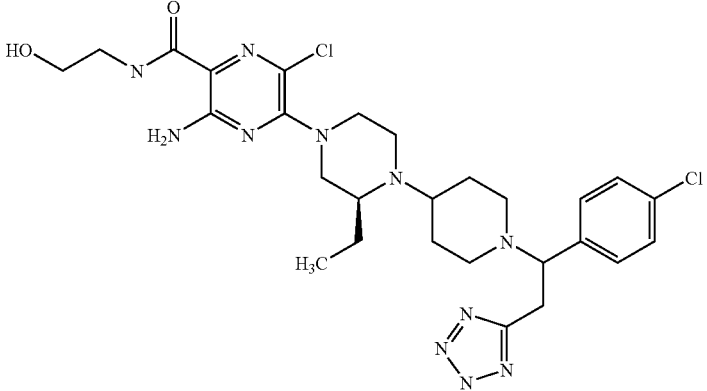 | C |
| 205 | 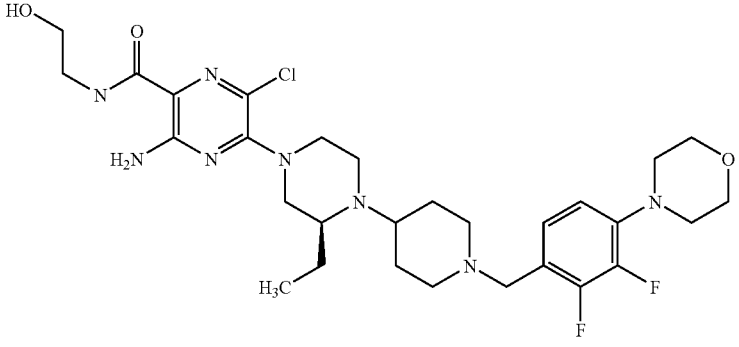 | C |
| 206 | 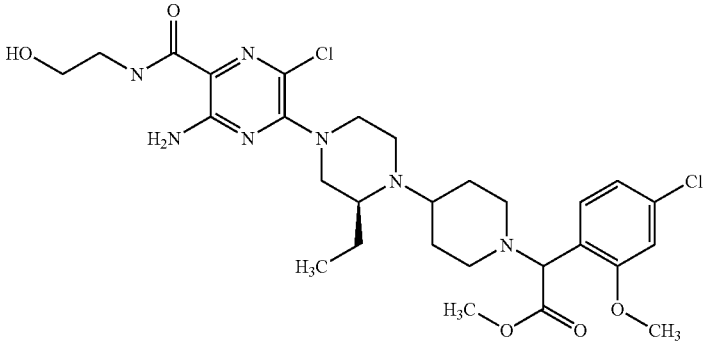 | C |
| 207 | 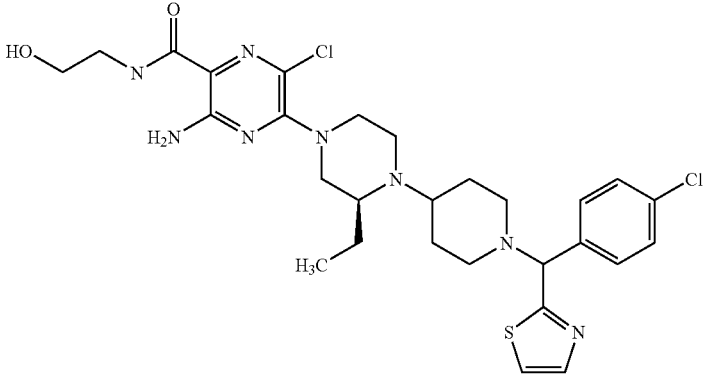 | C |

TABLE 1-continued

| Compound No. | Compound Structure | IC$_{50}$ |
|---|---|---|
| 208 | 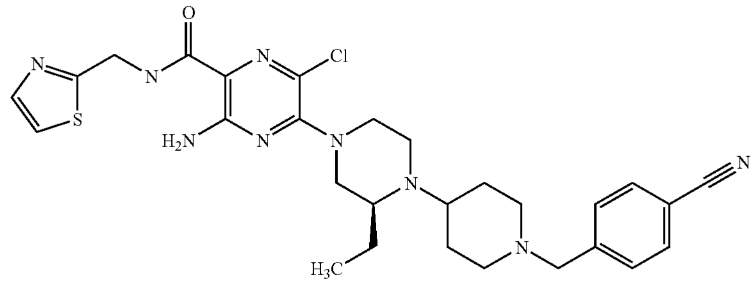 | C |
| 209 | 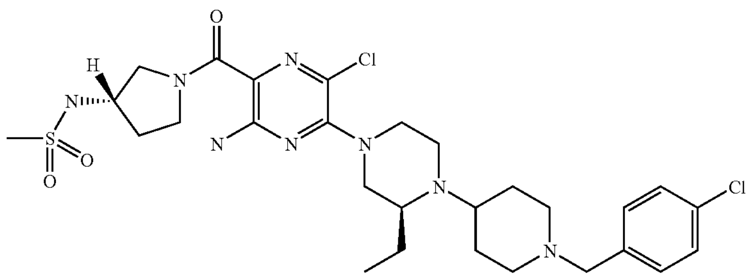 | C |
| 210 | 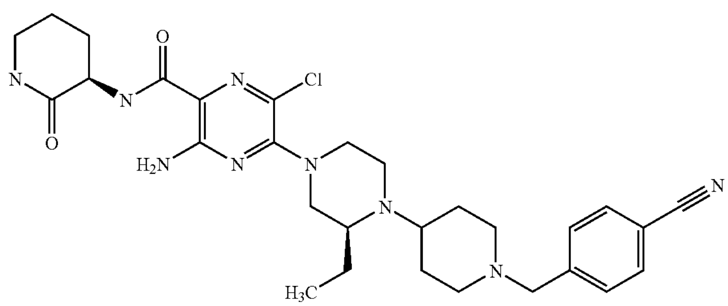 | C |
| 211 | 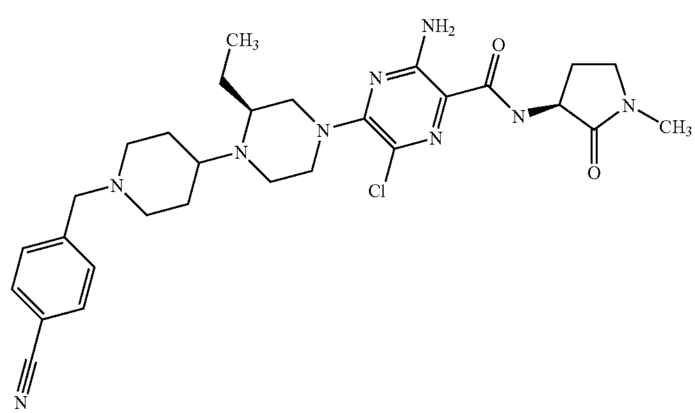 | C |

TABLE 1-continued

| Compound No. | Compound Structure | IC$_{50}$ |
|---|---|---|
| 212 | 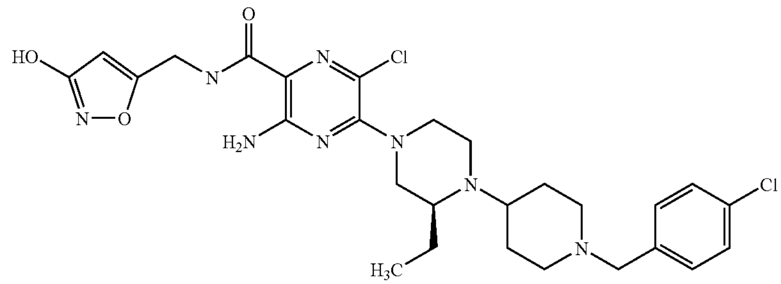 | C |
| 213 | 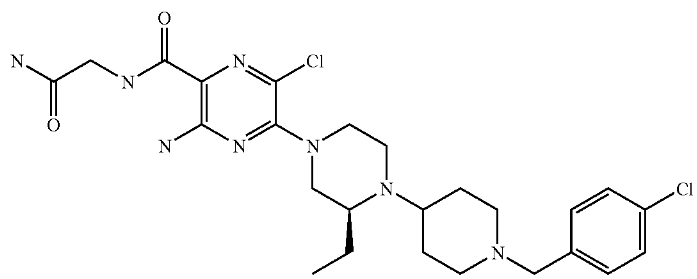 | B |
| 214 | 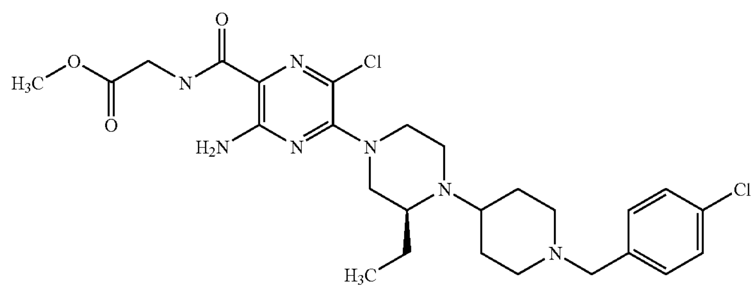 | A |
| 215 | 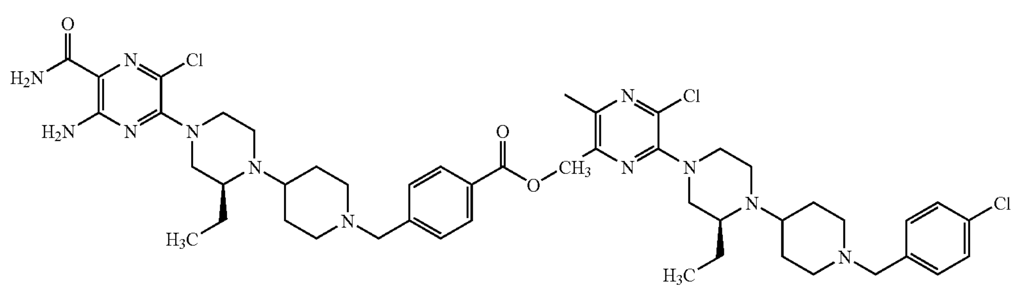 | A |
| 216 | 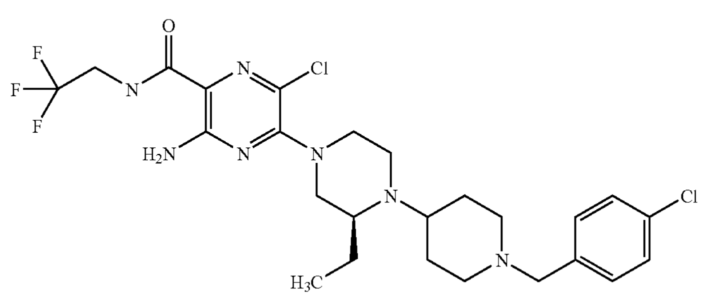 | A |

TABLE 1-continued

| Compound No. | Compound Structure | IC$_{50}$ |
|---|---|---|
| 217 | 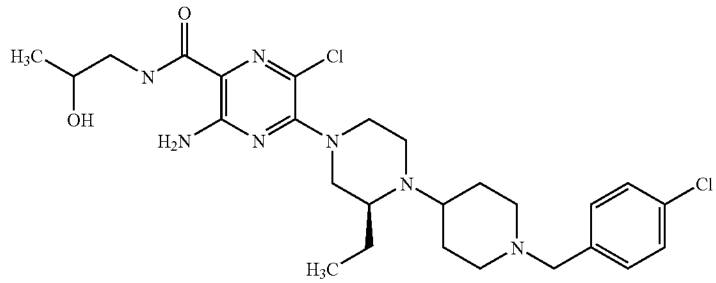 | A |
| 218 | 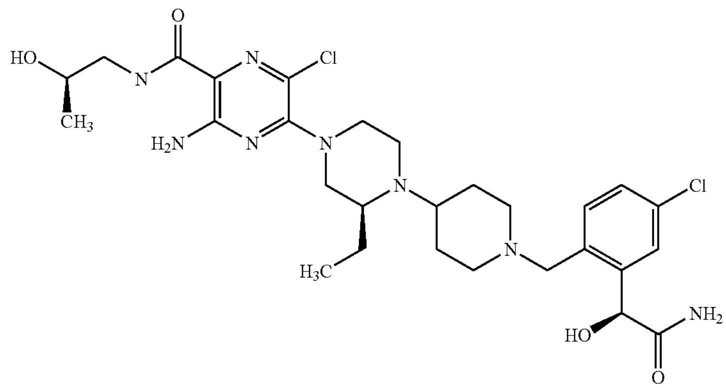 | A |
| 219 | 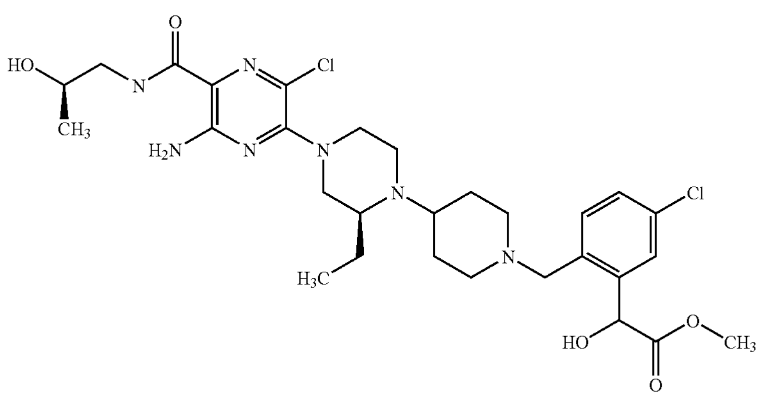 | A |
| 220 | 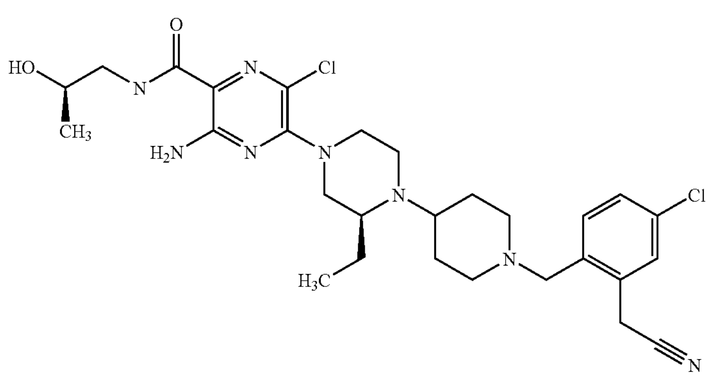 | A |

TABLE 1-continued

| Compound No. | Compound Structure | IC$_{50}$ |
|---|---|---|
| 221 | 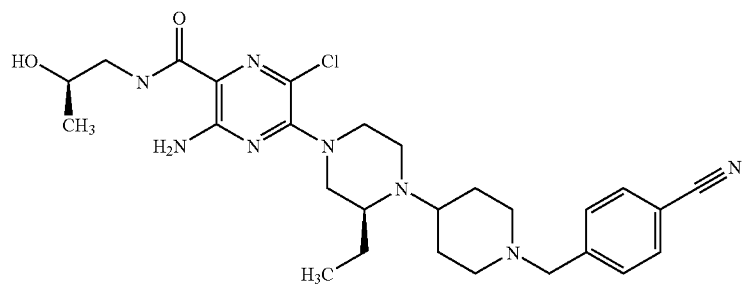 | A |
| 222 | 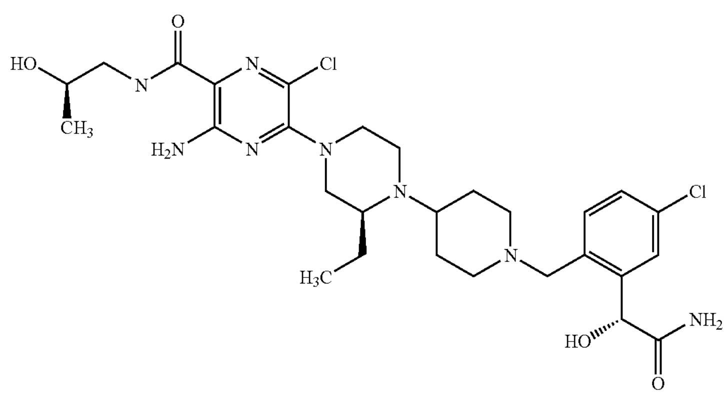 | A |
| 223 | 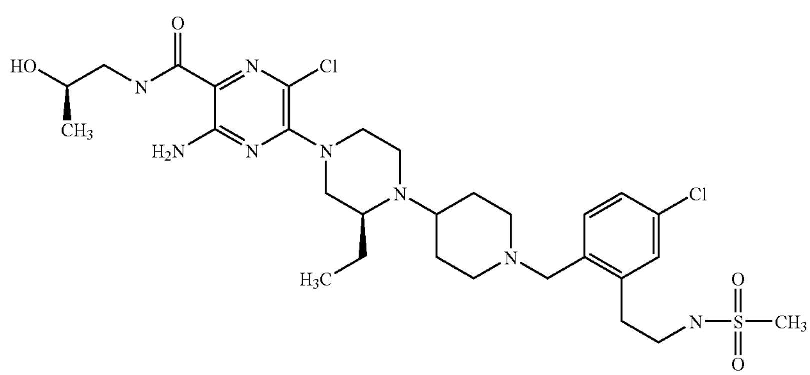 | A |
| 224 | 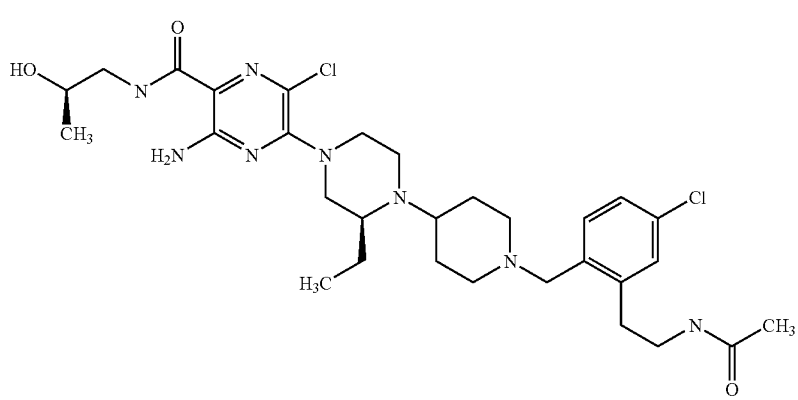 | B |

TABLE 1-continued

| Compound No. | Compound Structure | IC$_{50}$ |
|---|---|---|
| 225 | 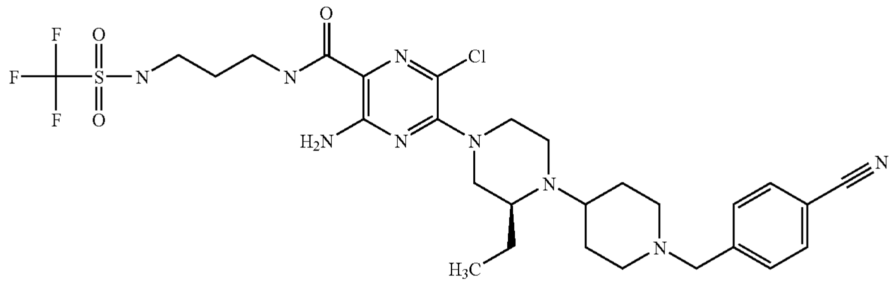 | C |
| 226 | 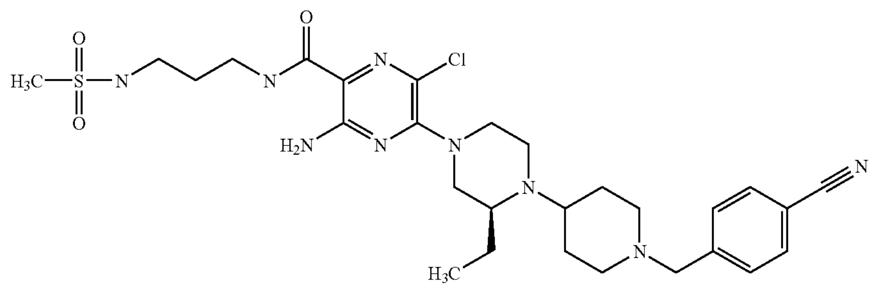 | C |
| 227 | 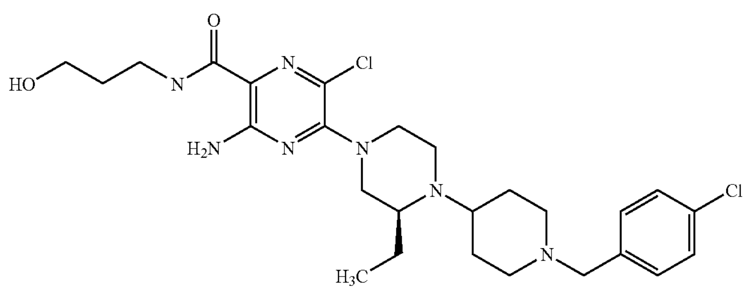 | B |
| 228 | 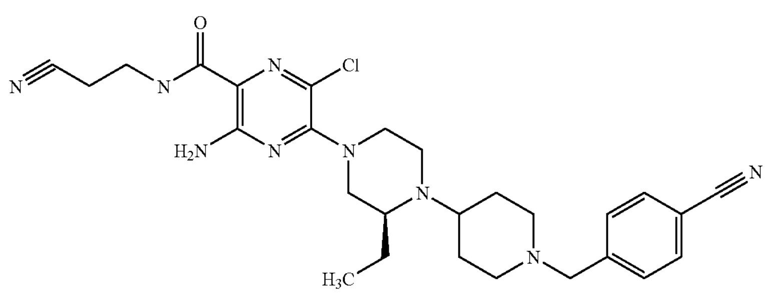 | A |
| 229 | 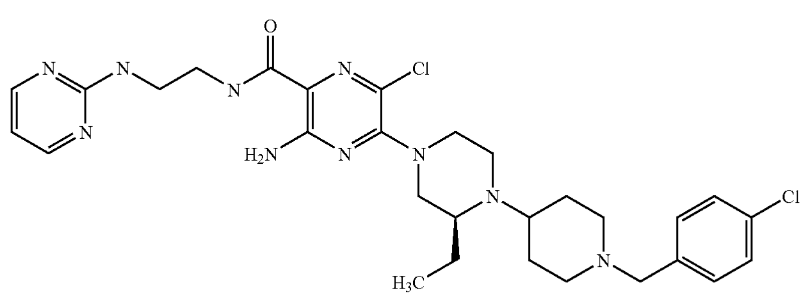 | A |

TABLE 1-continued

| Compound No. | Compound Structure | IC$_{50}$ |
|---|---|---|
| 230 | 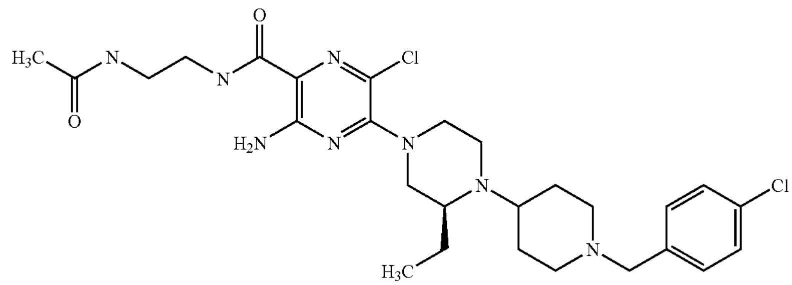 | A |
| 231 | 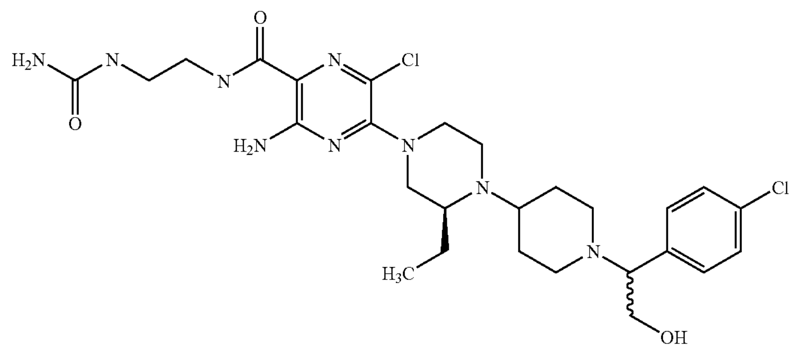 | A |
| 232 | 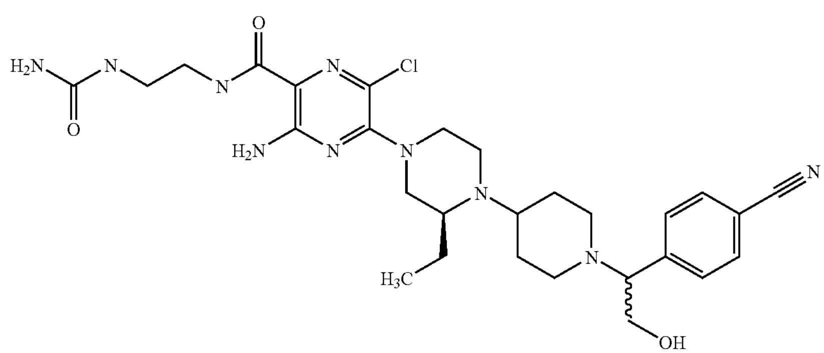 | B |
| 233 | 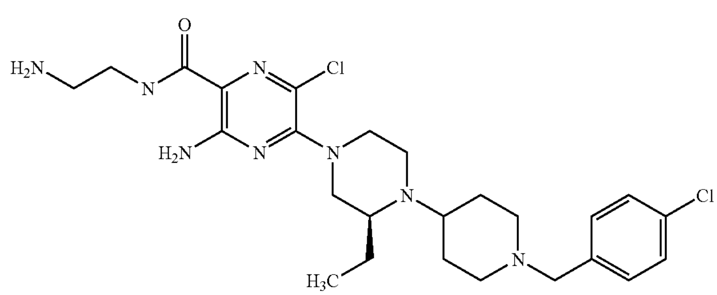 | A |

TABLE 1-continued

| Compound No. | Compound Structure | IC$_{50}$ |
|---|---|---|
| 234 | 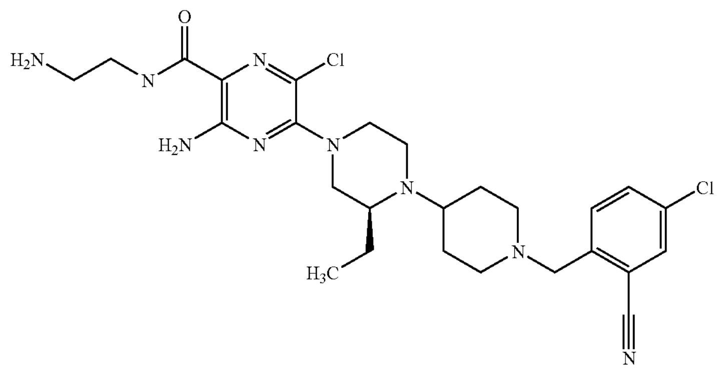 | B |
| 235 | 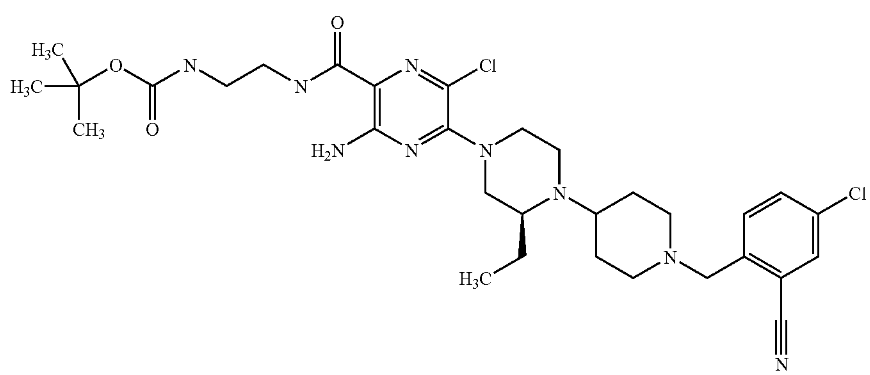 | C |
| 236 | 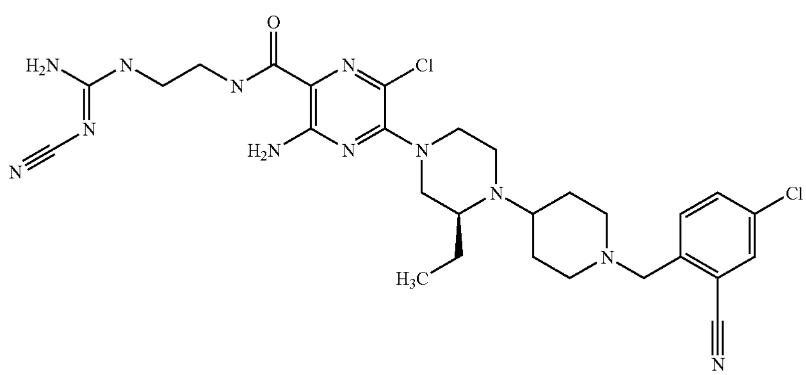 | C |
| 237 | 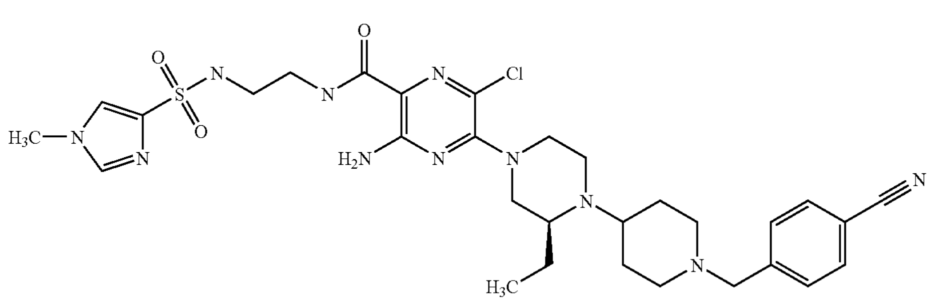 | C |

TABLE 1-continued

| Compound No. | Compound Structure | IC$_{50}$ |
|---|---|---|
| 238 | 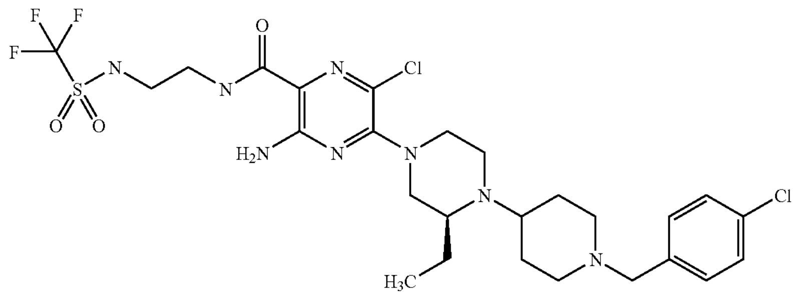 | A |
| 239 | 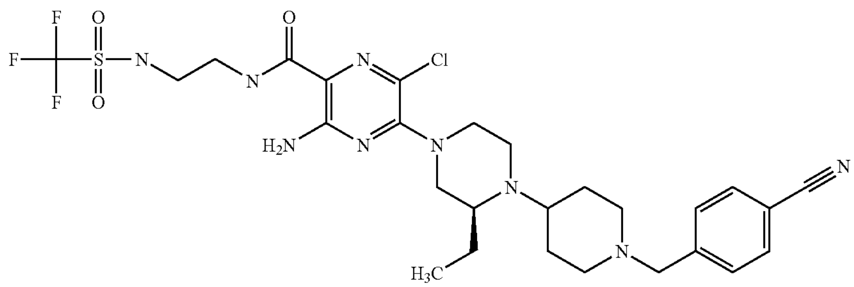 | A |
| 240 | 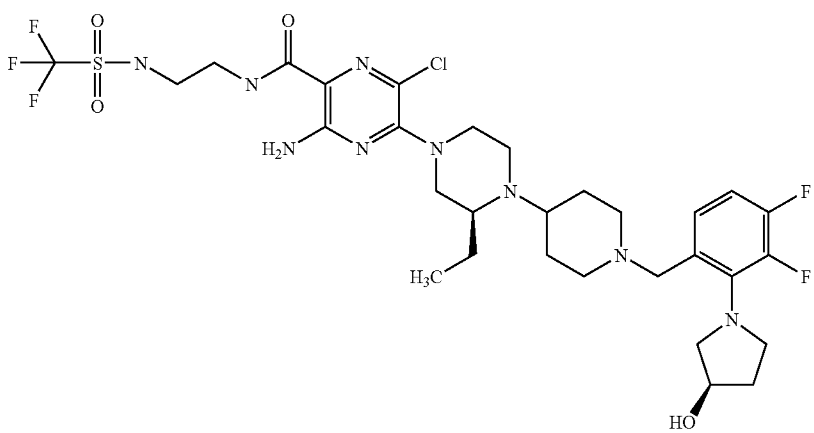 | A |
| 241 | 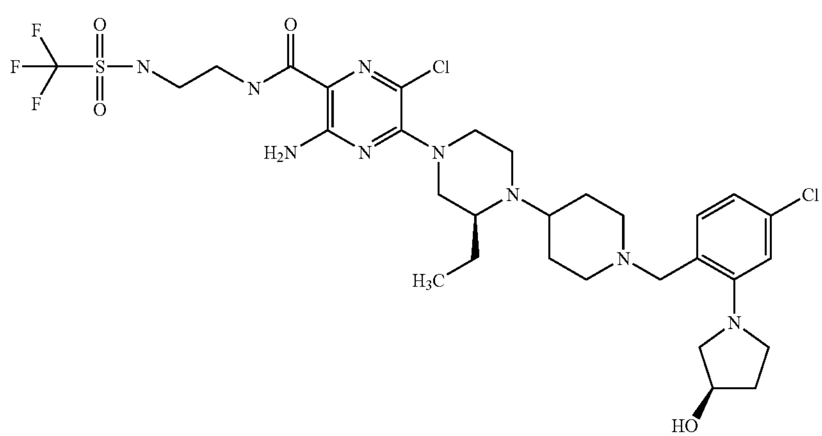 | A |

TABLE 1-continued

| Compound No. | Compound Structure | IC$_{50}$ |
|---|---|---|
| 242 | 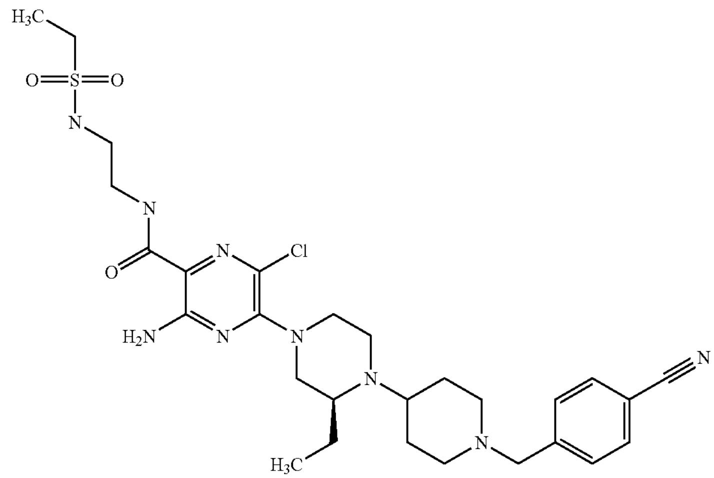 | B |
| 243 | 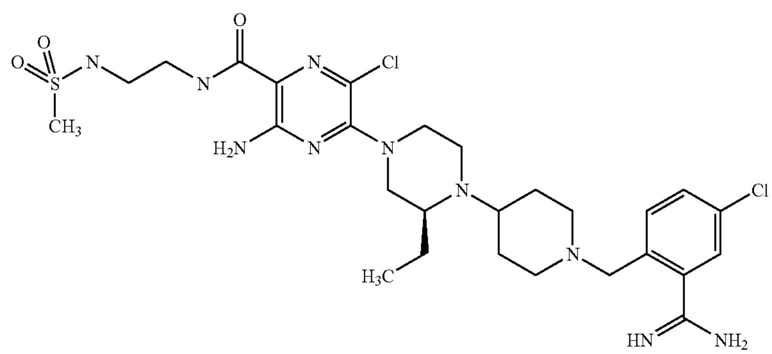 | A |
| 244 | 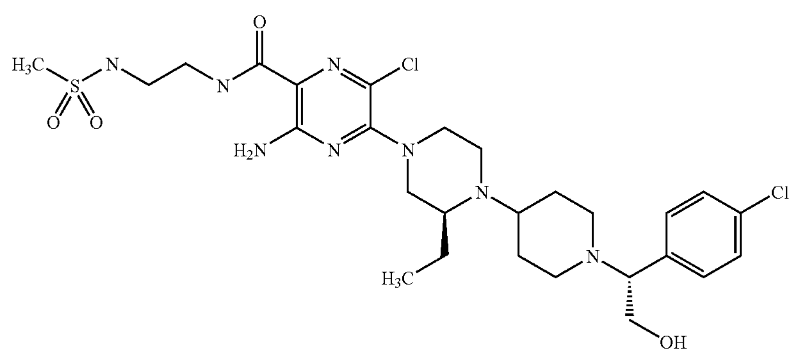 | A |
| 245 | 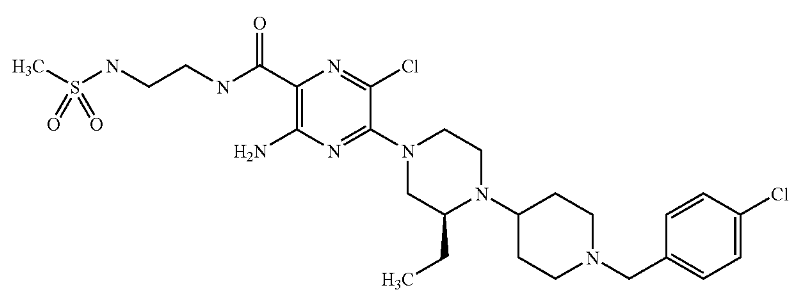 | A |

TABLE 1-continued

| Compound No. | Compound Structure | IC$_{50}$ |
|---|---|---|
| 246 | 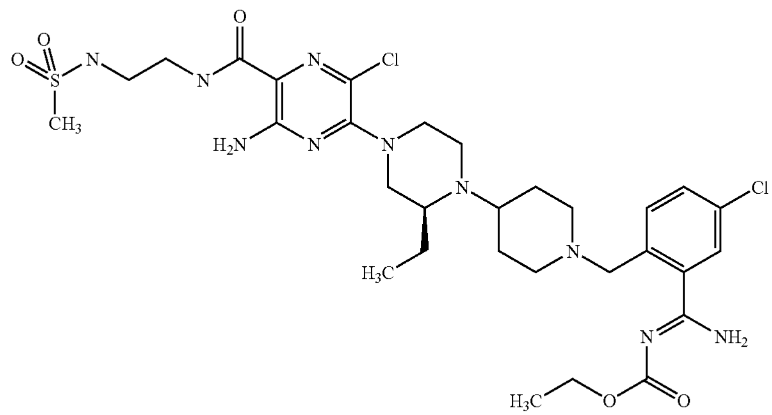 | A |
| 247 | 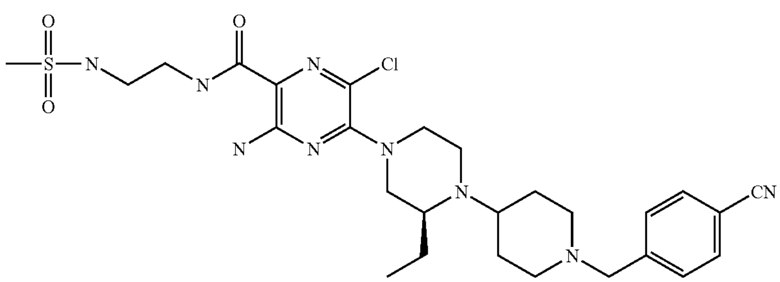 | B |
| 248 | 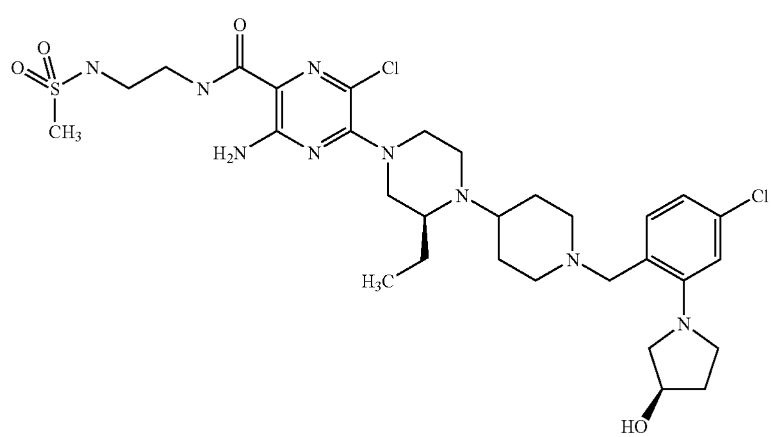 | B |
| 249 | 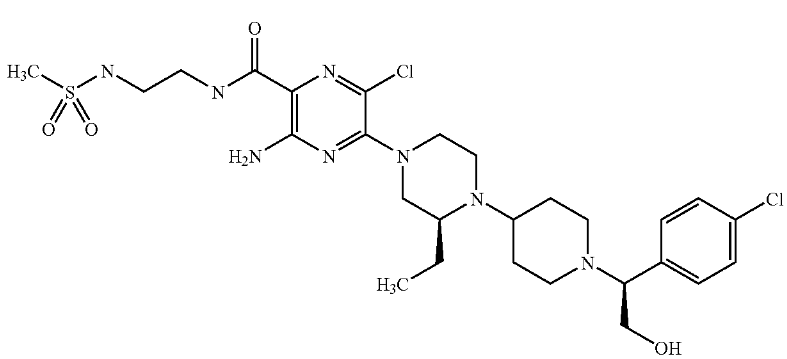 | B |

TABLE 1-continued

| Compound No. | Compound Structure | IC$_{50}$ |
|---|---|---|
| 250 | 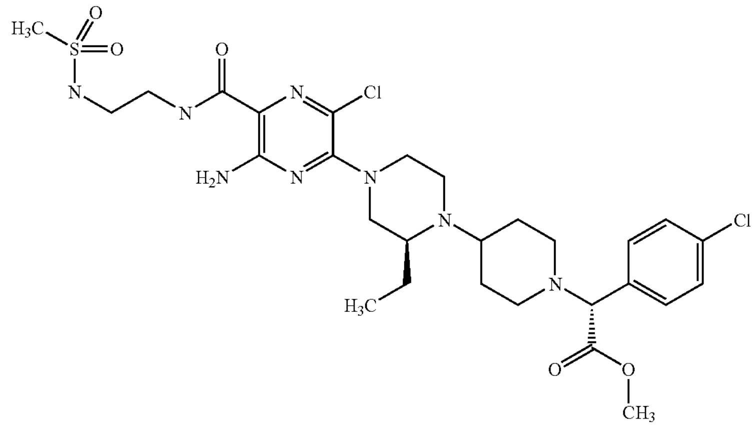 | B |
| 251 | 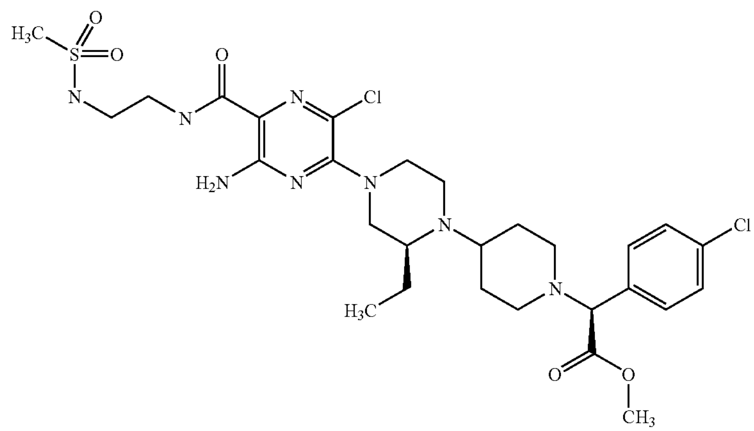 | C |
| 252 | 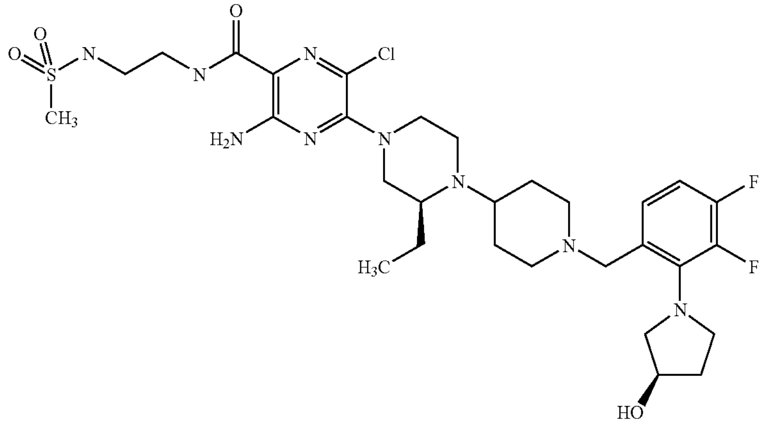 | B |

TABLE 1-continued

| Compound No. | Compound Structure | IC$_{50}$ |
| --- | --- | --- |
| 253 | 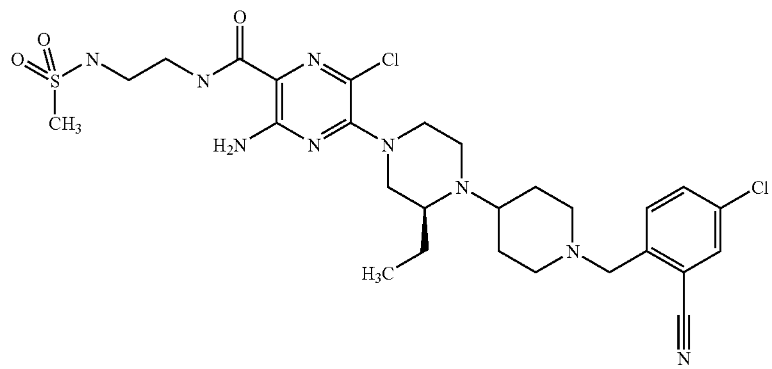 | B |
| 254 | 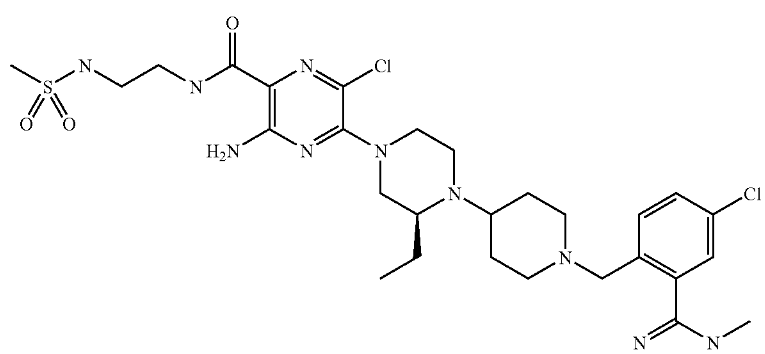 | B |
| 255 | 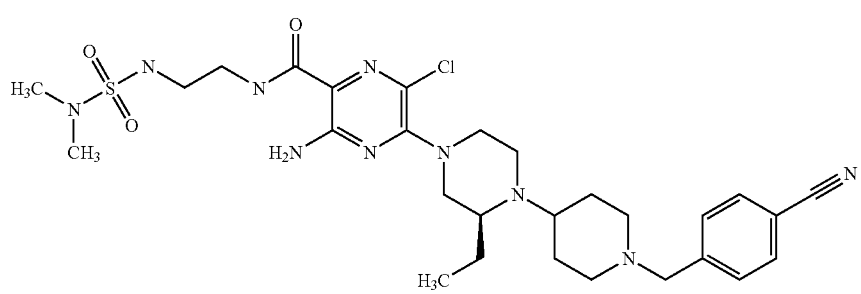 | B |
| 256 | 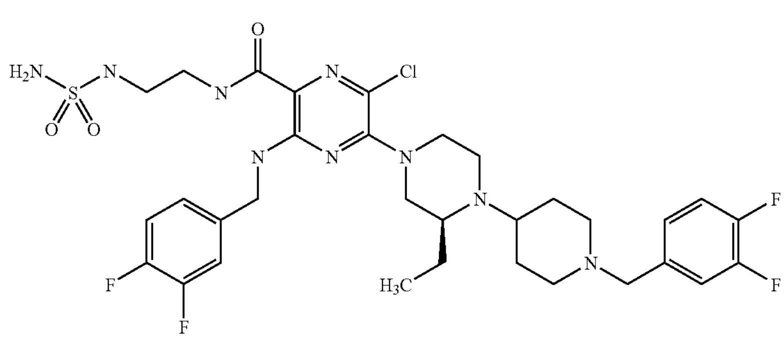 | A |

TABLE 1-continued

| Compound No. | Compound Structure | IC$_{50}$ |
|---|---|---|
| 257 | 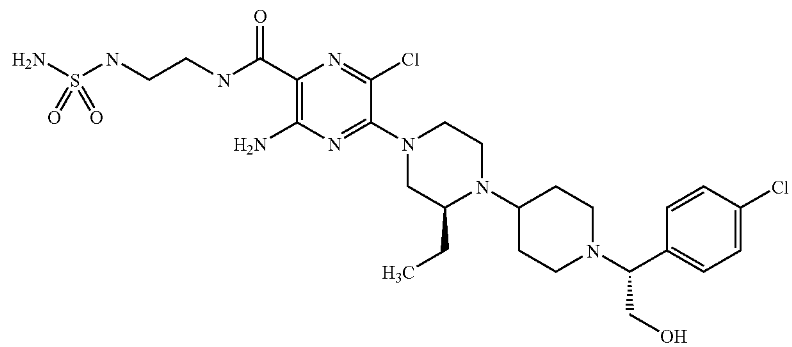 | A |
| 258 | 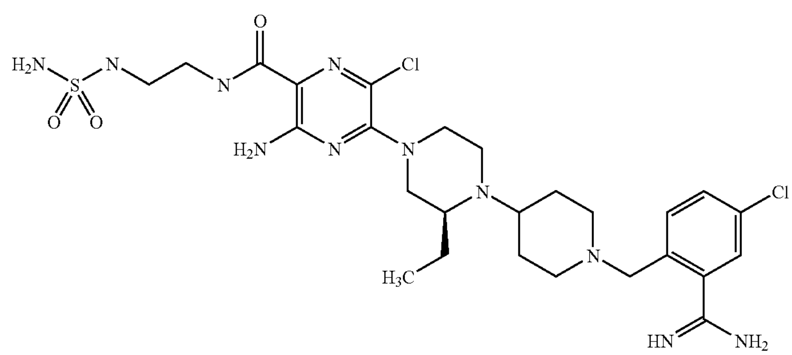 | A |
| 259 | 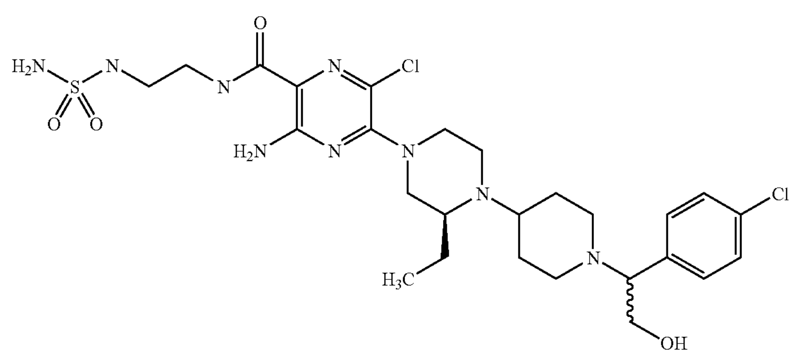 | A |
| 260 | 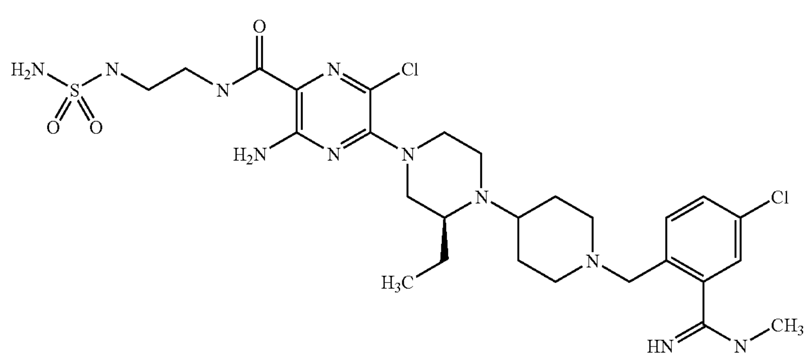 | A |

TABLE 1-continued

| Compound No. | Compound Structure | IC$_{50}$ |
|---|---|---|
| 261 | 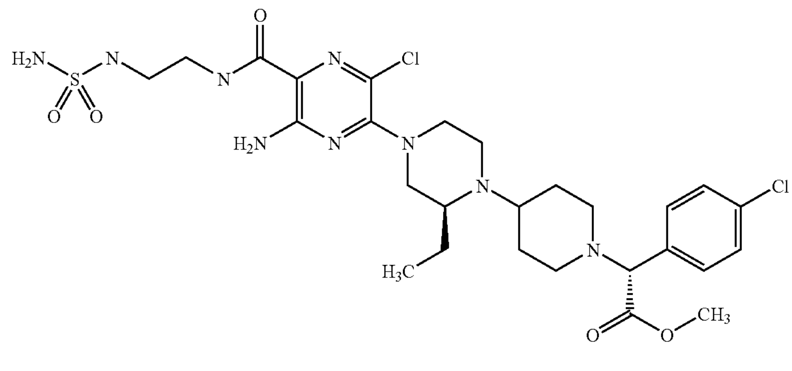 | B |
| 262 | 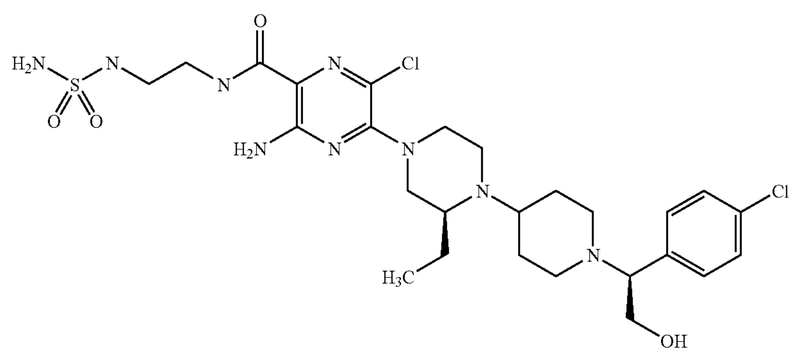 | C |
| 263 | 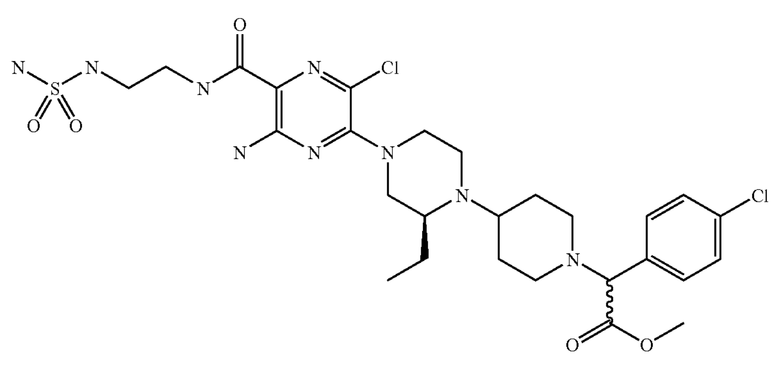 | C |
| 264 | 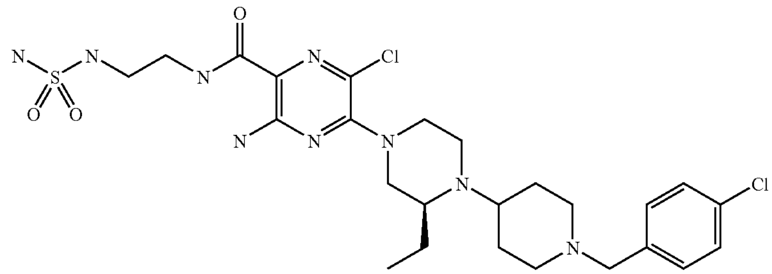 | A |

TABLE 1-continued

| Compound No. | Compound Structure | IC$_{50}$ |
|---|---|---|
| 265 | 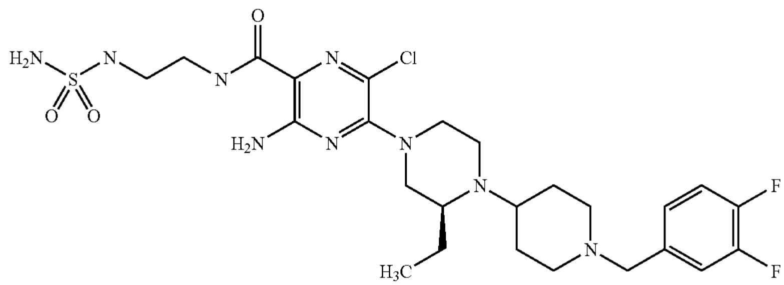 | A |
| 266 | 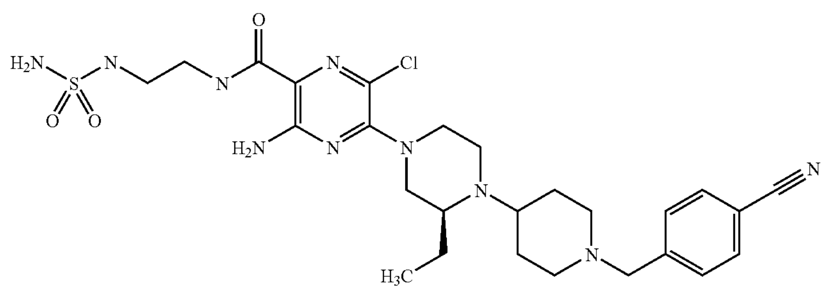 | A |
| 267 | 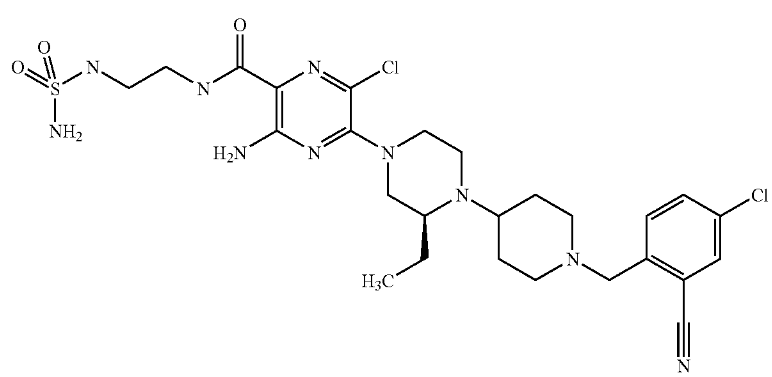 | A |
| 268 | 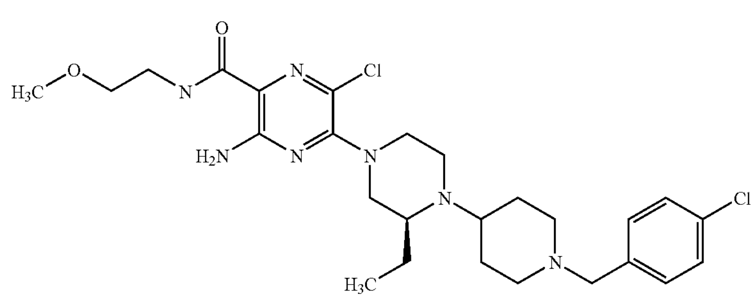 | A |

TABLE 1-continued

| Compound No. | Compound Structure | IC$_{50}$ |
|---|---|---|
| 269 | 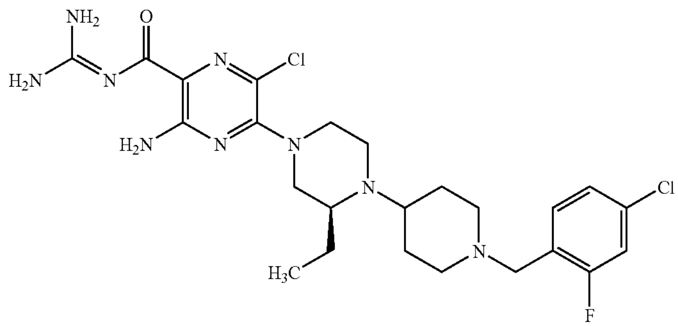 | C |
| 270 | 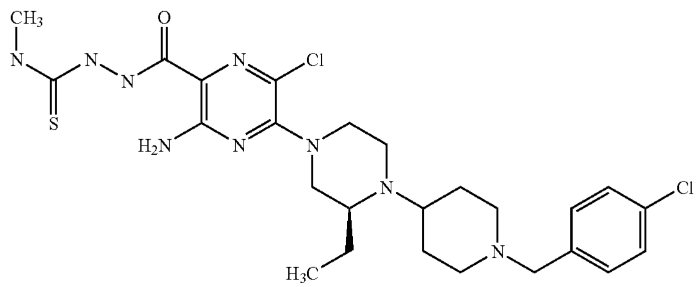 | A |
| 271 | 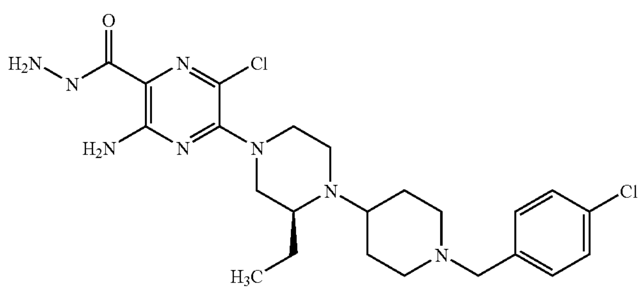 | A |
| 272 | 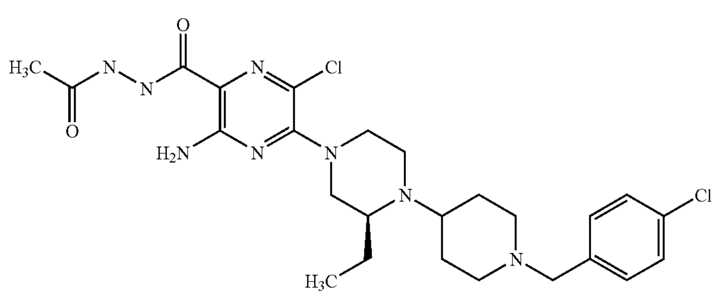 | B |
| 273 | 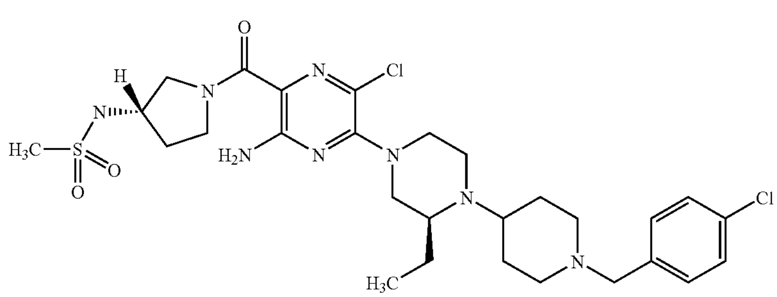 | C |

TABLE 1-continued

| Compound No. | Compound Structure | IC$_{50}$ |
|---|---|---|
| 274 | 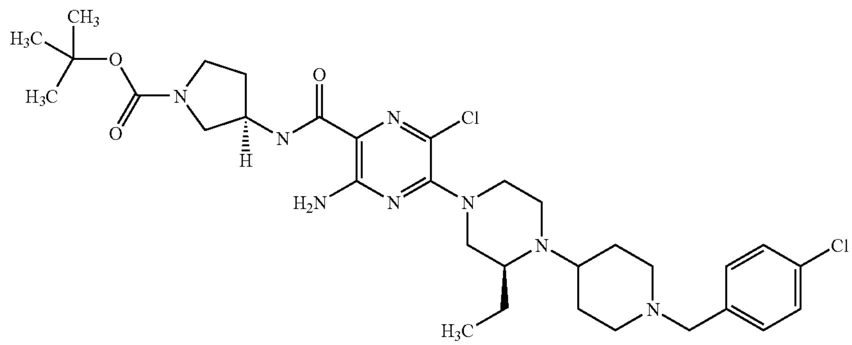 | C |
| 275 | 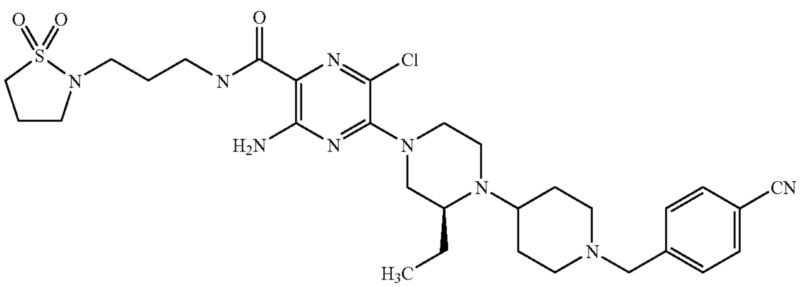 | C |
| 276 | 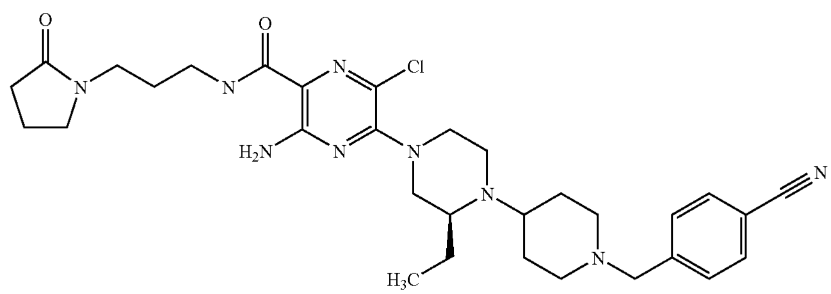 | C |
| 277 | 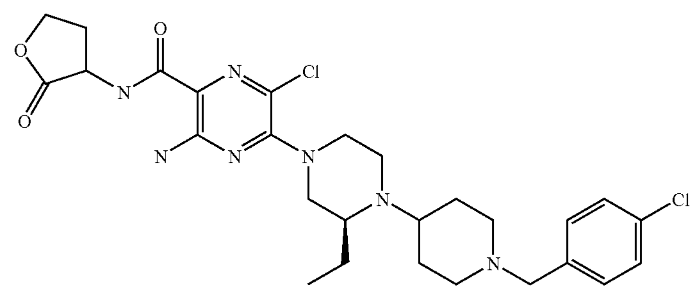 | A |
| 278 | 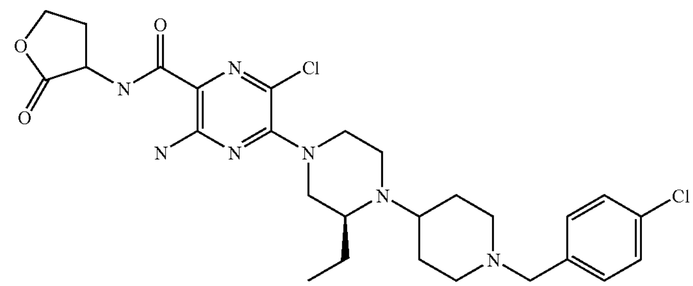 | A |

TABLE 1-continued

| Compound No. | Compound Structure | IC$_{50}$ |
|---|---|---|
| 279 | 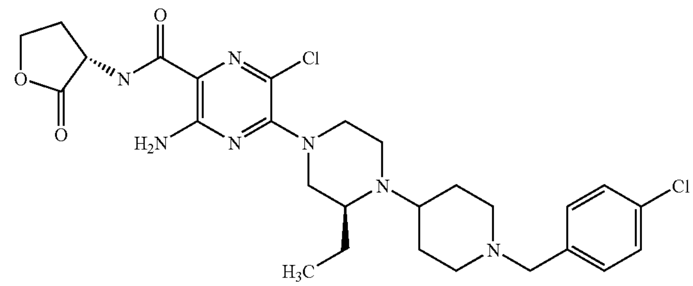 | A |
| 280 | 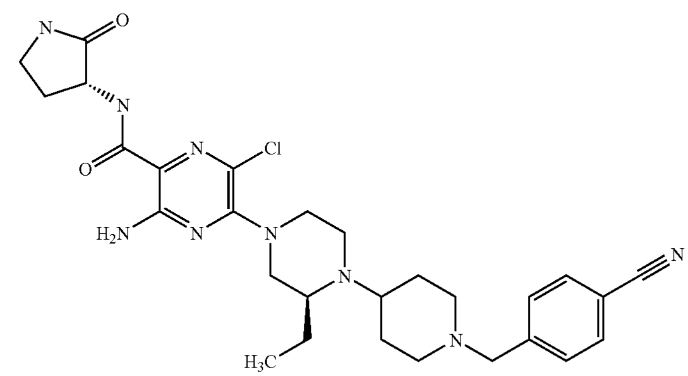 | C |
| 281 | 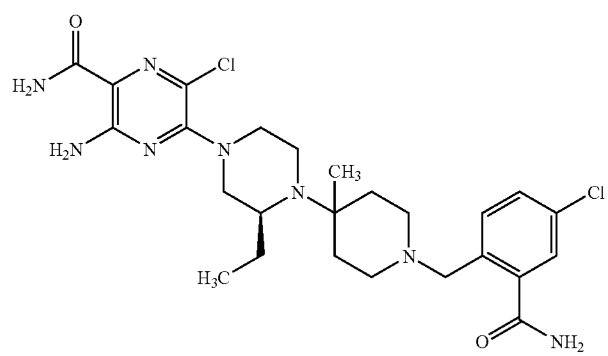 | C |
| 282 | 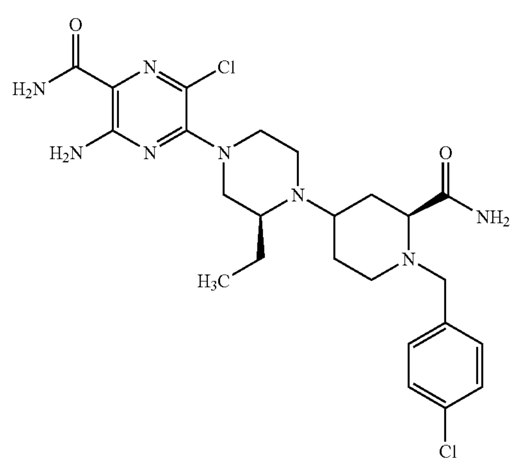 | B |

TABLE 1-continued

| Compound No. | Compound Structure | IC$_{50}$ |
|---|---|---|
| 283 | 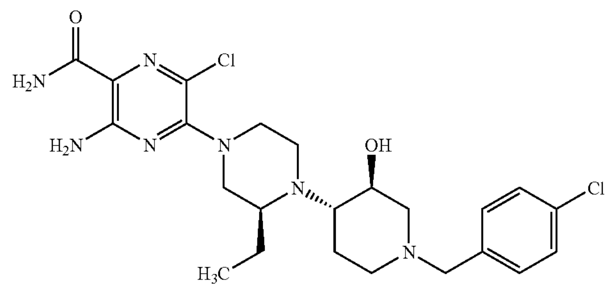 | C |
| 284 | 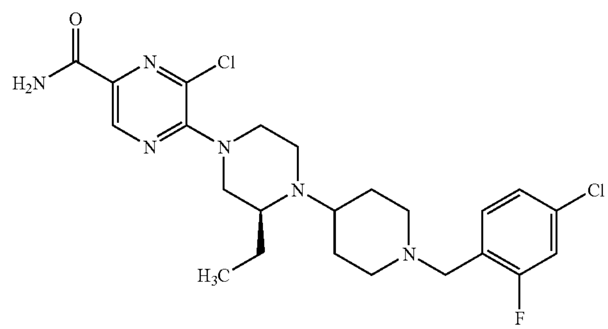 | A |
| 285 | 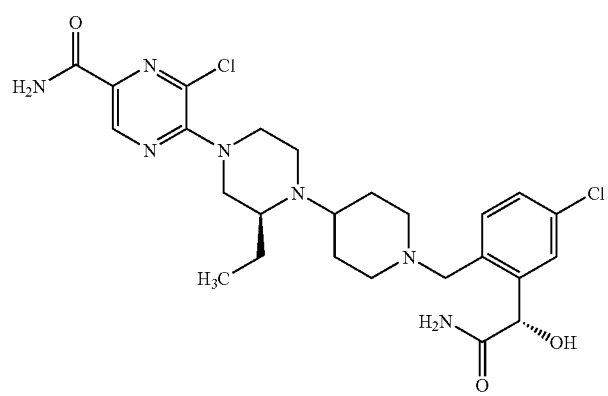 | A |
| 286 | 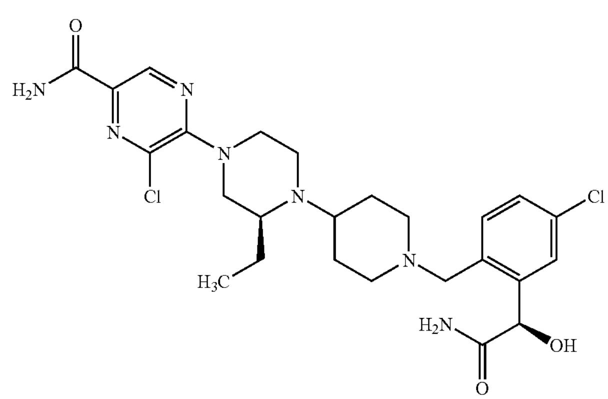 | A |

TABLE 1-continued

| Compound No. | Compound Structure | IC$_{50}$ |
|---|---|---|
| 287 | 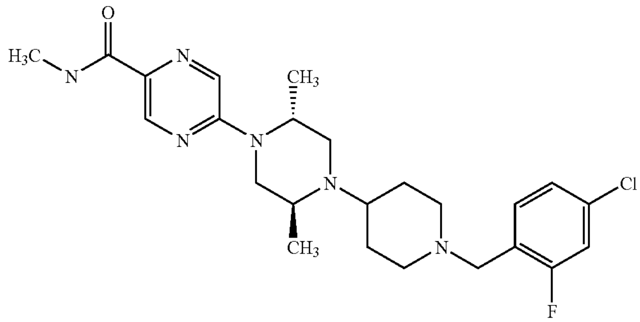 | C |
| 288 | 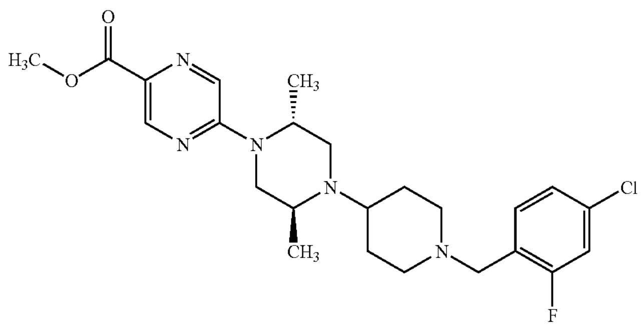 | C |
| 289 | 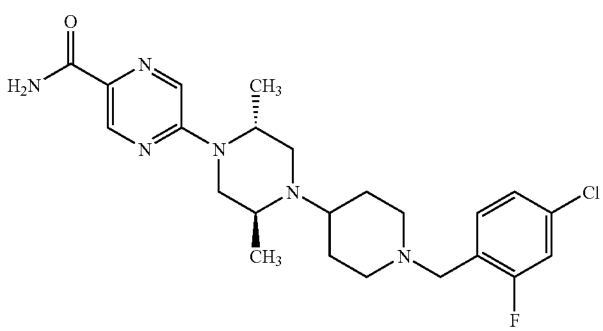 | C |
| 290 | 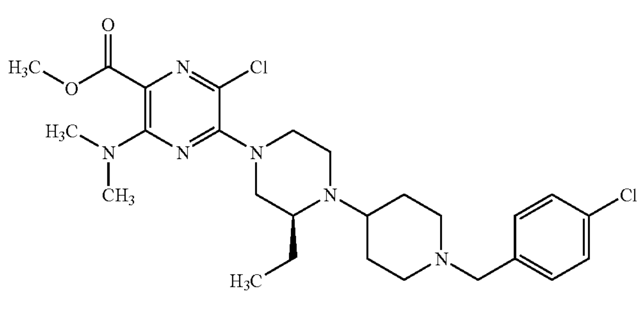 | A |

TABLE 1-continued

| Compound No. | Compound Structure | IC$_{50}$ |
|---|---|---|
| 291 | 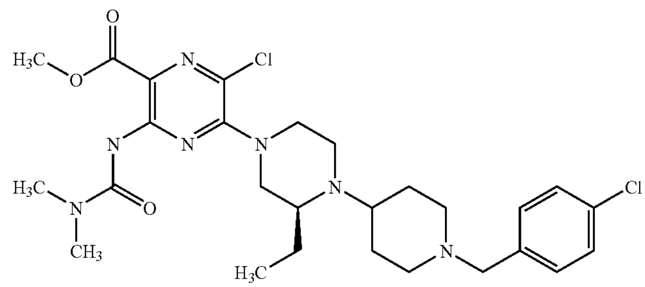 | B |
| 292 | 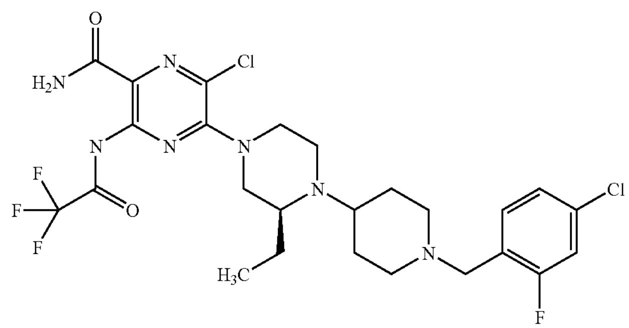 | A |
| 293 | 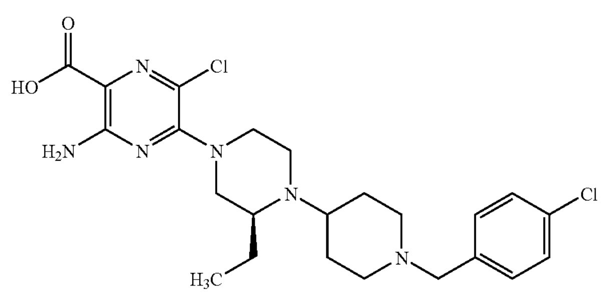 | C |
| 294 | 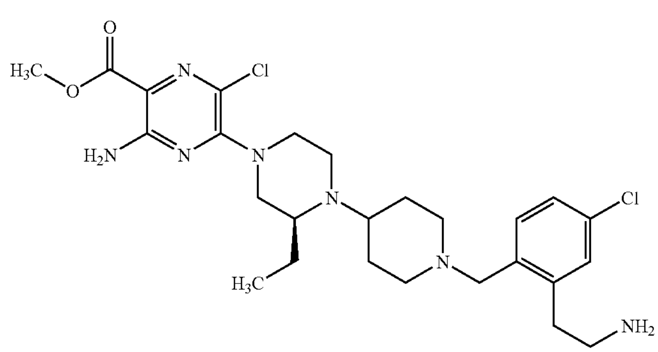 | A |

TABLE 1-continued

| Compound No. | Compound Structure | IC$_{50}$ |
|---|---|---|
| 295 | 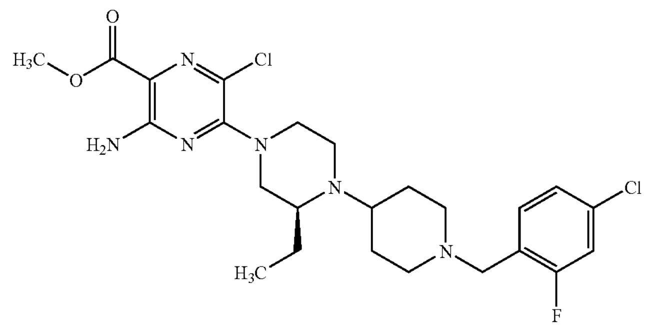 | A |
| 296 | 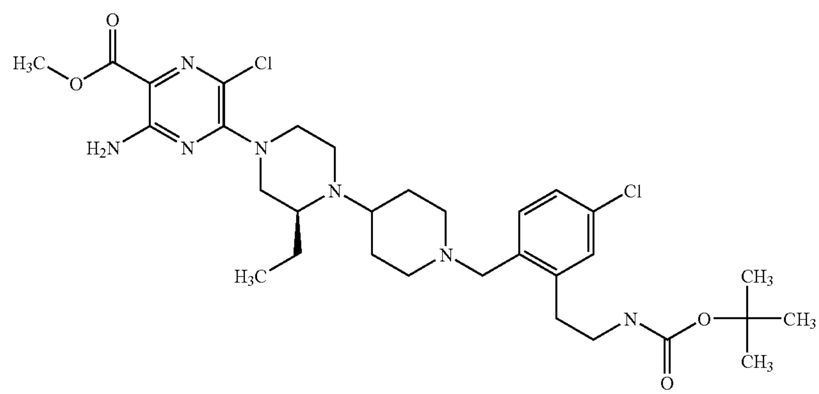 | A |
| 297 | 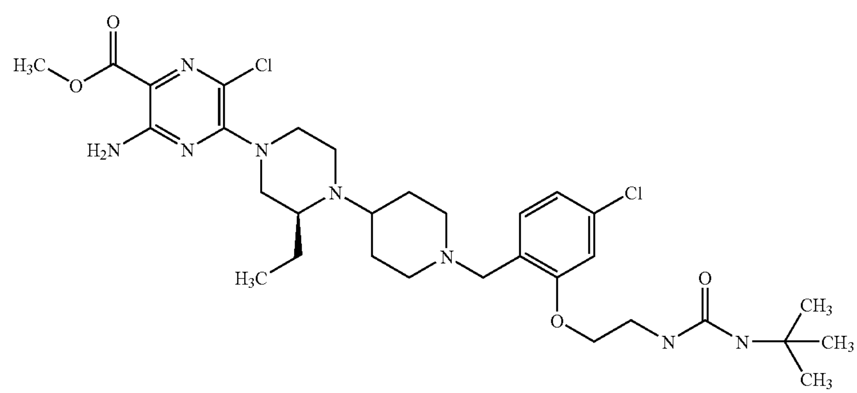 | B |
| 298 | 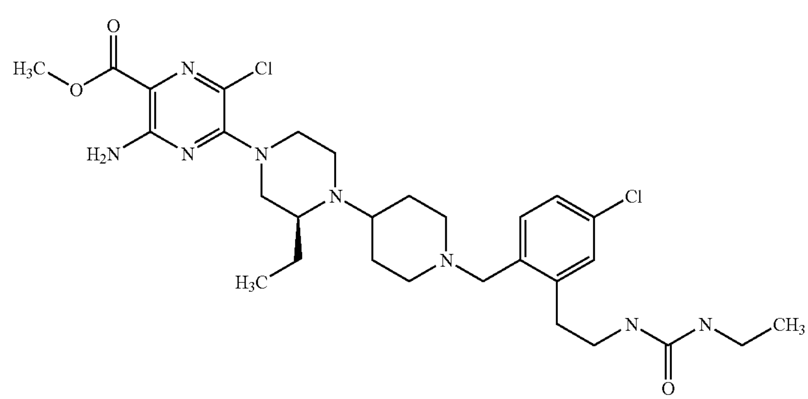 | B |

TABLE 1-continued

| Compound No. | Compound Structure | IC$_{50}$ |
|---|---|---|
| 299 | 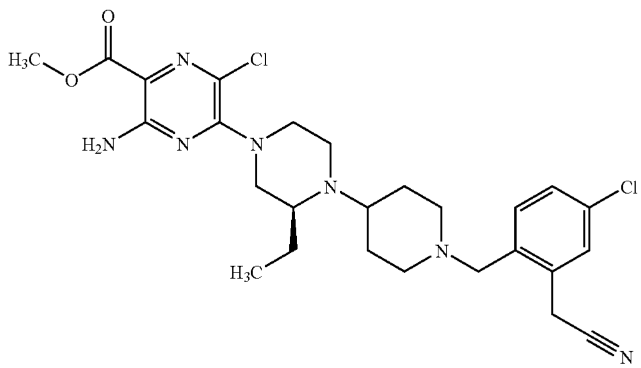 | B |
| 300 | 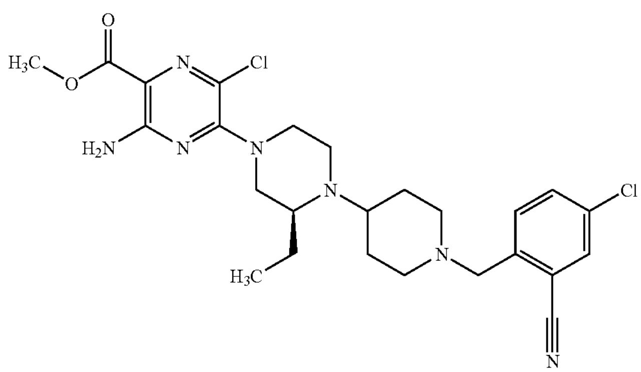 | C |
| 301 | 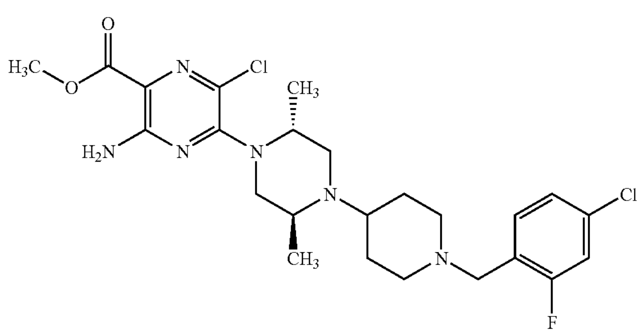 | C |
| 302 | 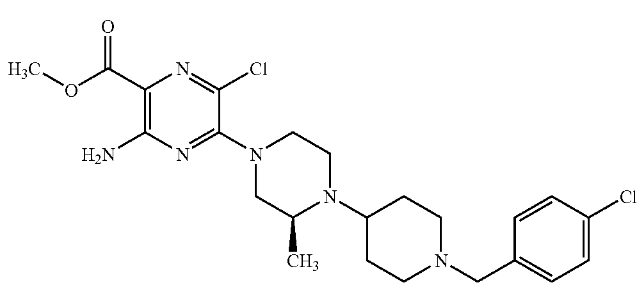 | C |

TABLE 1-continued

| Compound No. | Compound Structure | IC$_{50}$ |
|---|---|---|
| 303 | 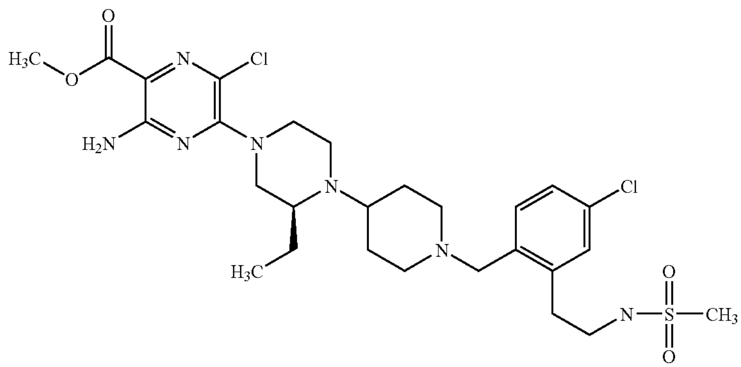 | C |
| 304 | 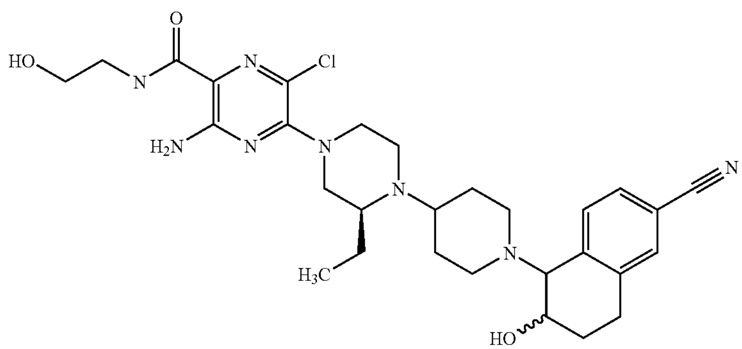 | A |
| 305 | 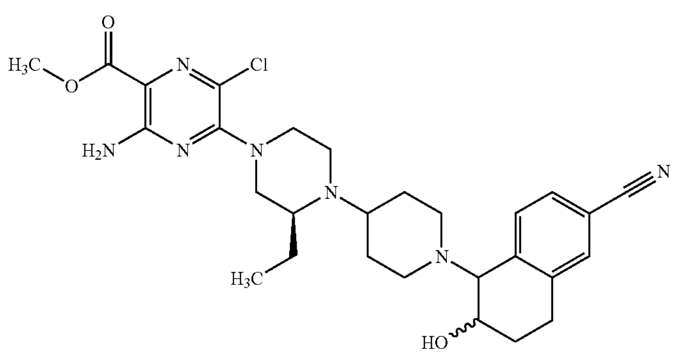 | C |
| 306 | 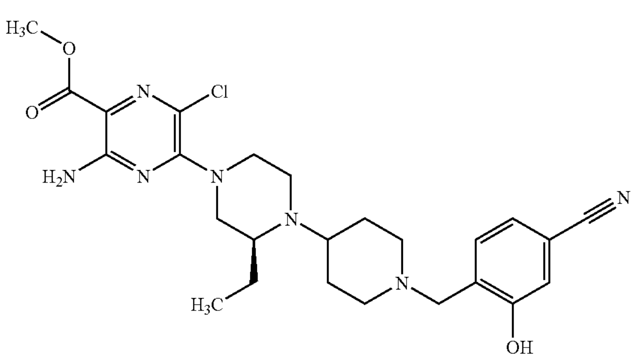 | C |

TABLE 1-continued
| Compound No. | Compound Structure | IC$_{50}$ |
|---|---|---|
| 307 | 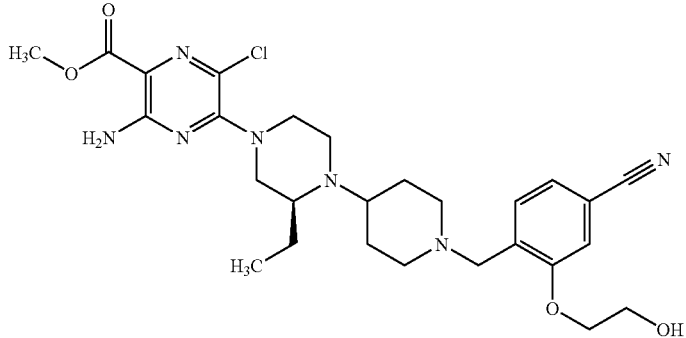 | C |
| 308 | 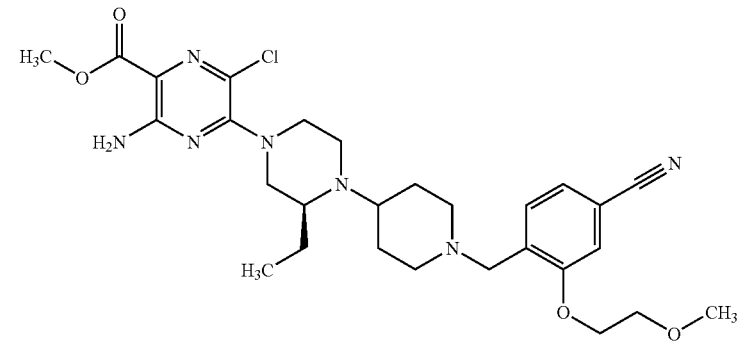 | C |
| 309 | 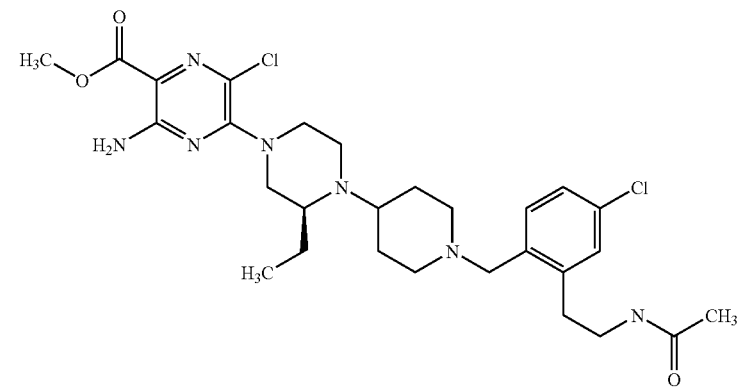 | C |
| 310 | 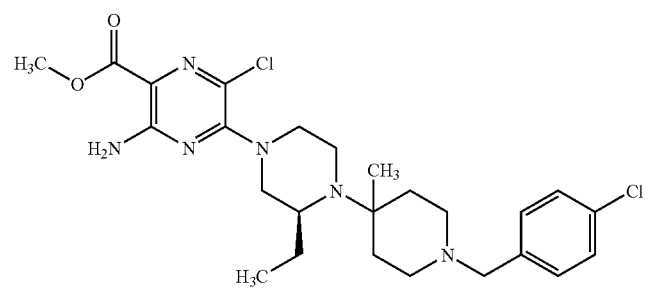 | C |

TABLE 1-continued
| Compound No. | Compound Structure | IC$_{50}$ |
|---|---|---|
| 311 | 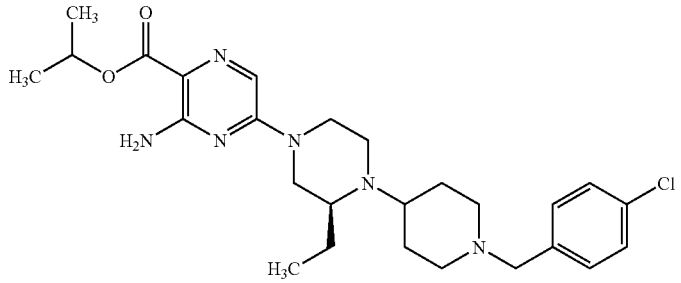 | C |
| 312 | 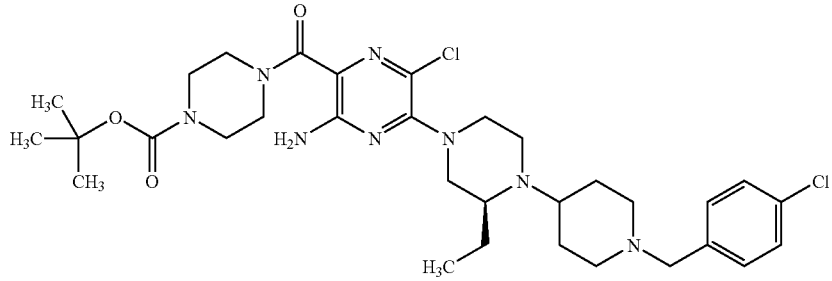 | C |
| 313 | 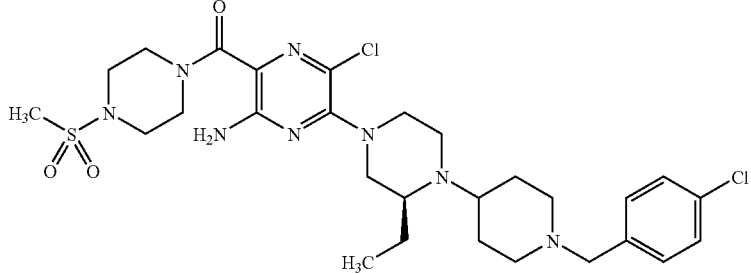 | C |
| 314 | 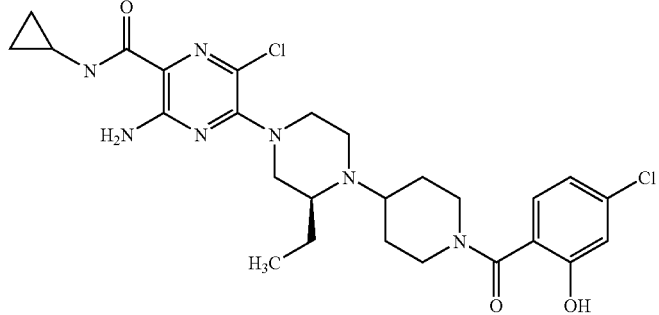 | A |

TABLE 1-continued

| Compound No. | Compound Structure | IC$_{50}$ |
|---|---|---|
| 315 | 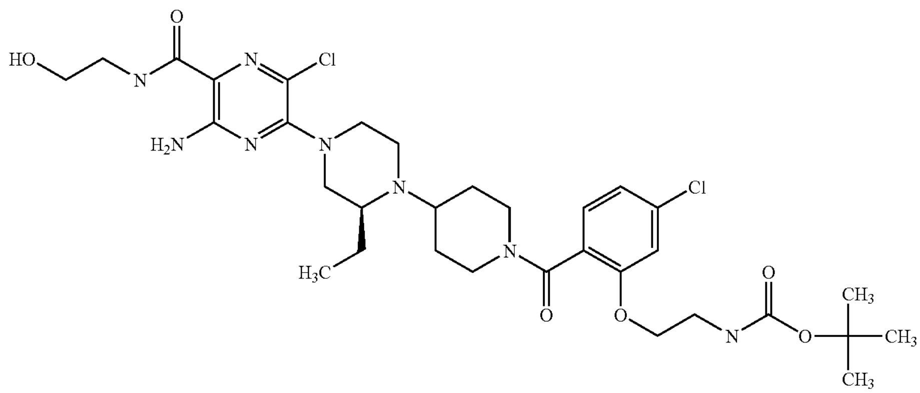 | A |
| 316 | 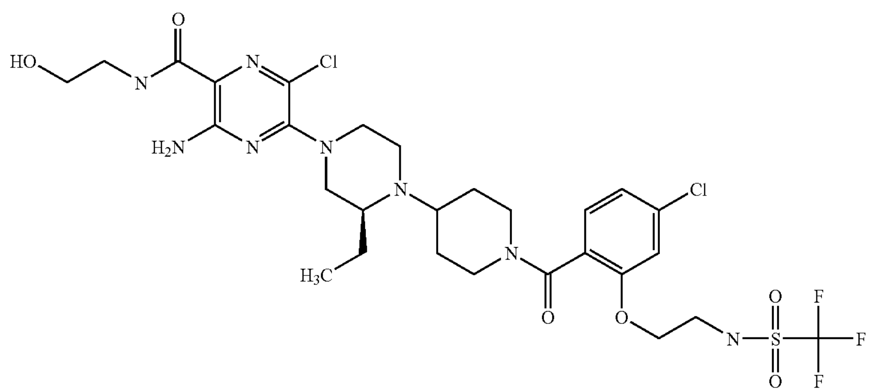 | A |
| 317 | 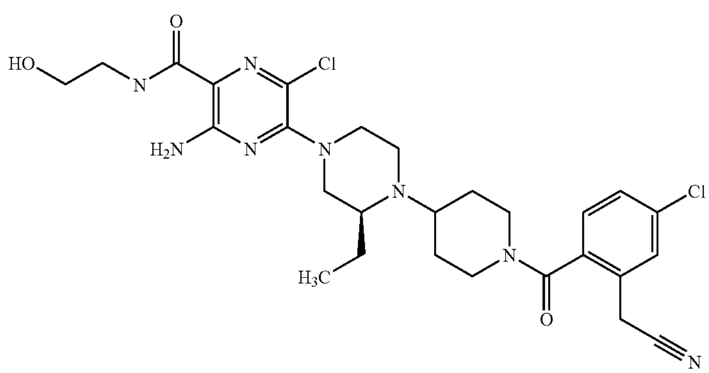 | A |
| 318 | 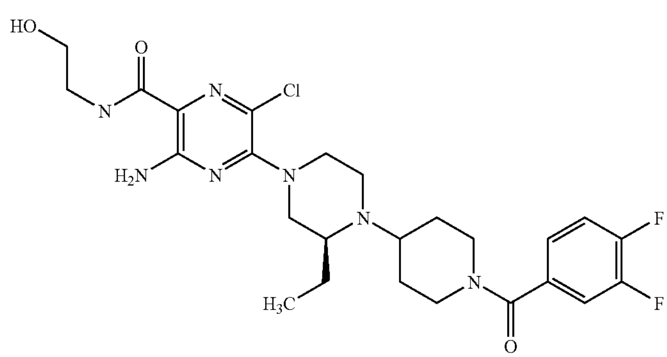 | B |

TABLE 1-continued

| Compound No. | Compound Structure | IC$_{50}$ |
| --- | --- | --- |
| 319 | 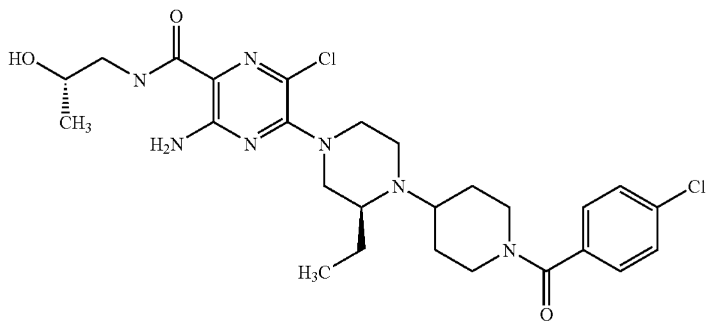 | B |
| 320 | 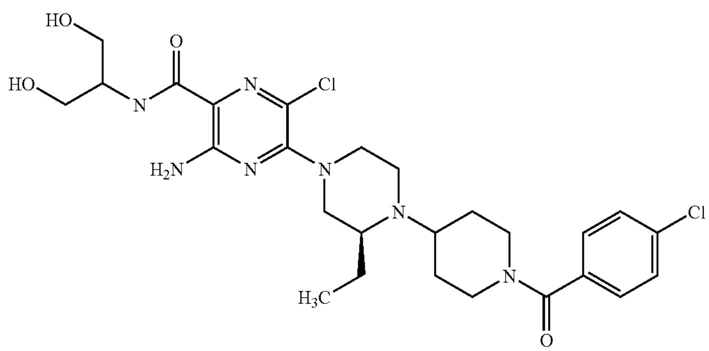 | B |
| 321 | 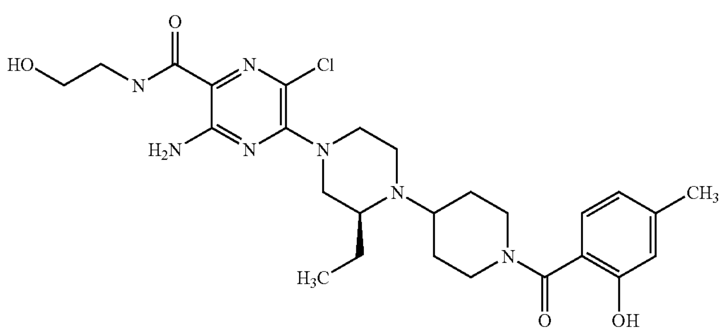 | B |
| 322 | 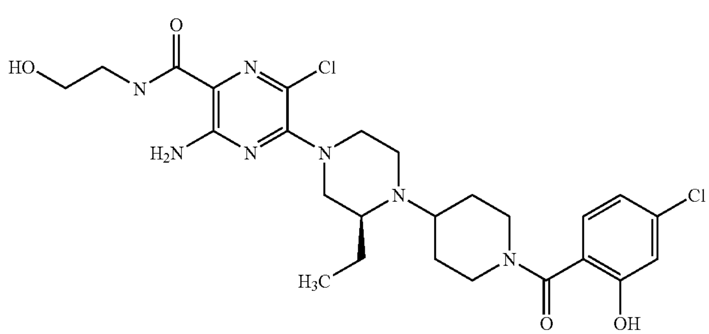 | B |

TABLE 1-continued

| Compound No. | Compound Structure | IC$_{50}$ |
| --- | --- | --- |
| 323 | 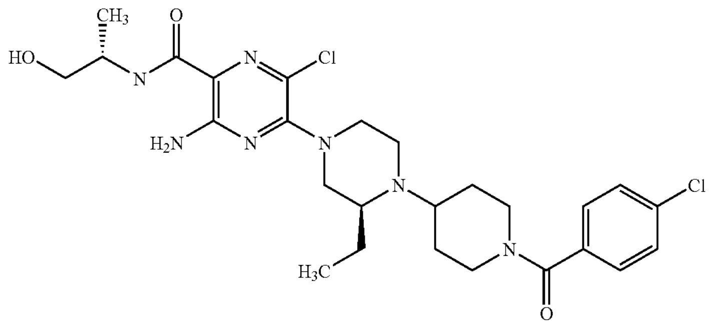 | B |
| 324 | 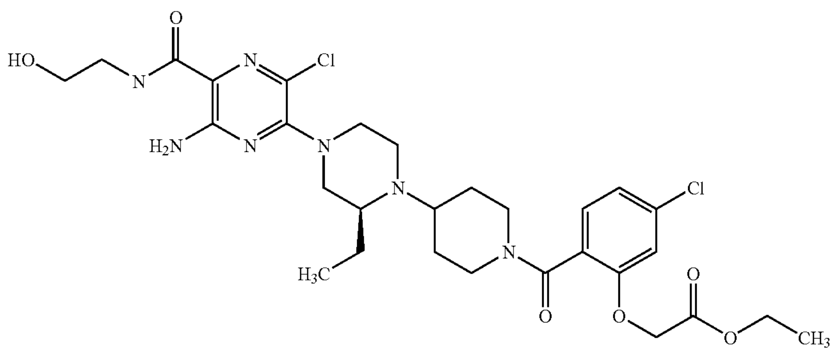 | C |
| 325 | 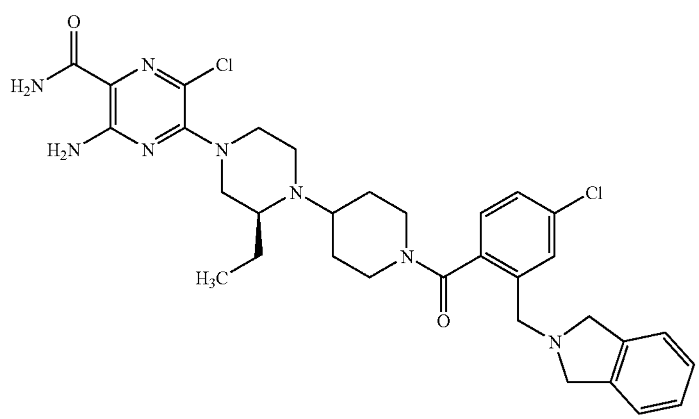 | C |
| 326 | 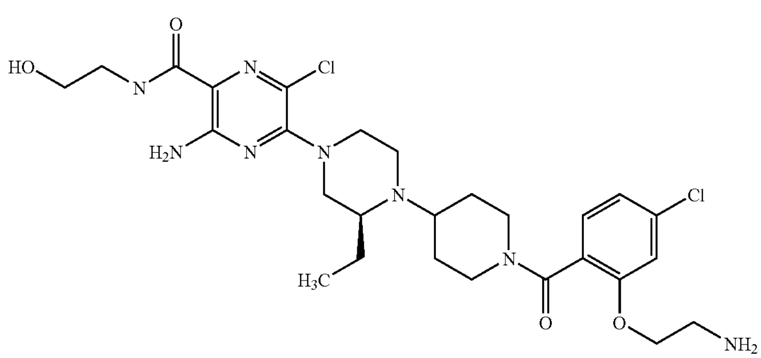 | C |

TABLE 1-continued

| Compound No. | Compound Structure | IC$_{50}$ |
|---|---|---|
| 327 | 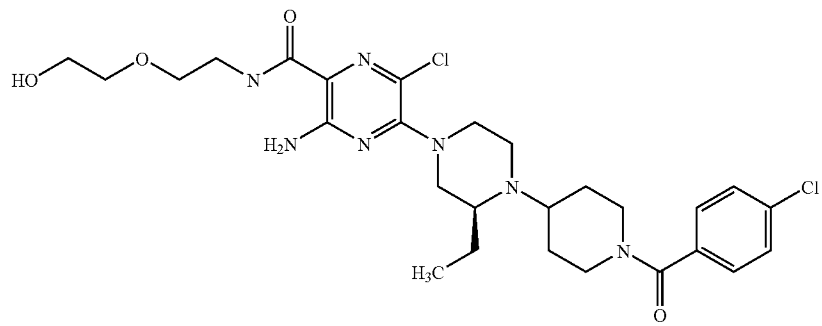 | C |
| 328 | 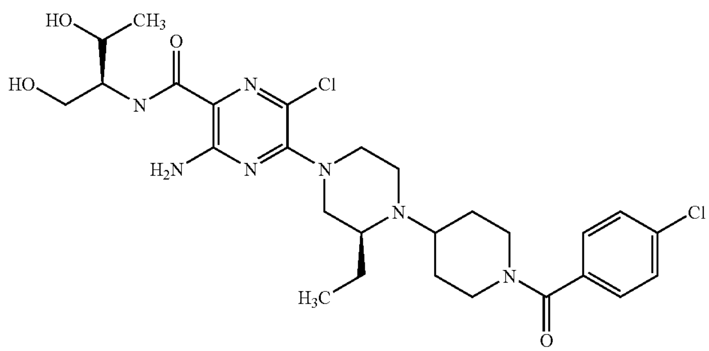 | C |
| 329 | 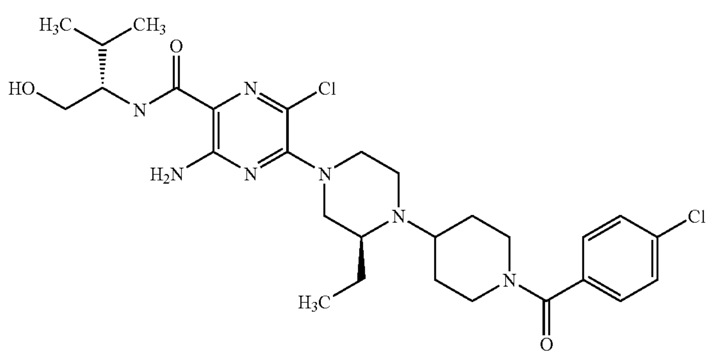 | C |
| 330 | 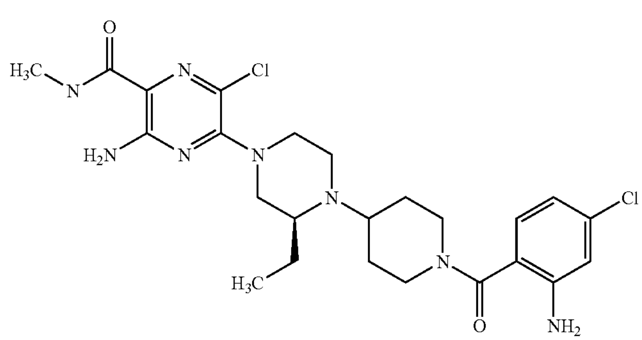 | A |

TABLE 1-continued

| Compound No. | Compound Structure | IC$_{50}$ |
|---|---|---|
| 331 | 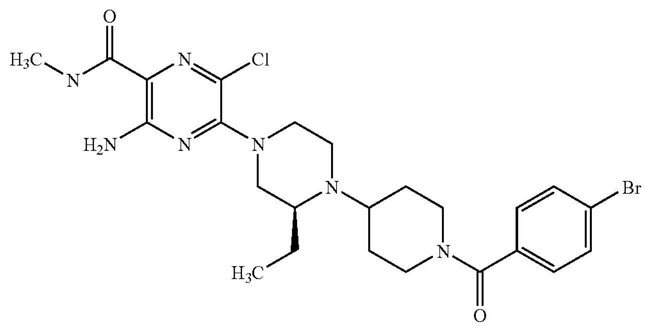 | A |
| 332 | 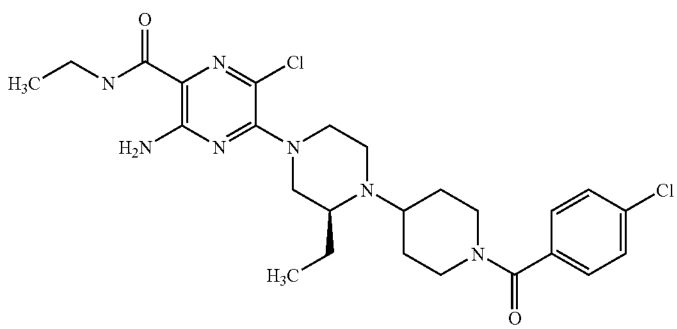 | A |
| 333 | 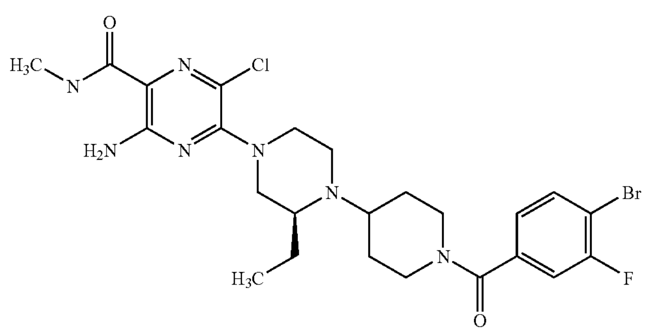 | A |
| 334 | 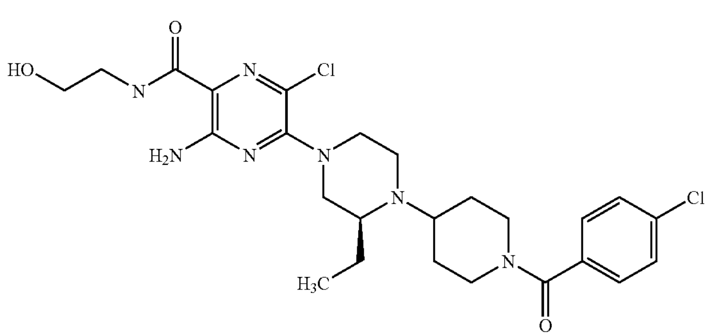 | A |

TABLE 1-continued

| Compound No. | Compound Structure | IC$_{50}$ |
|---|---|---|
| 335 | 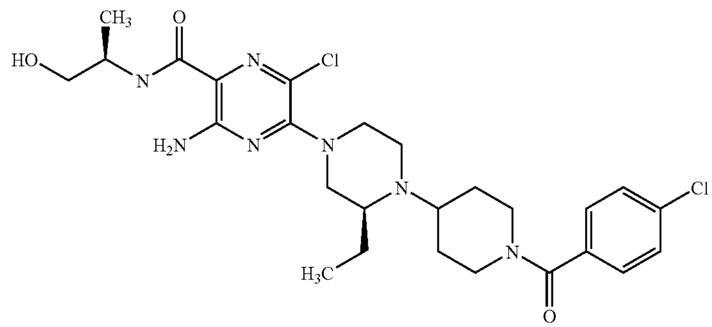 | A |
| 336 | 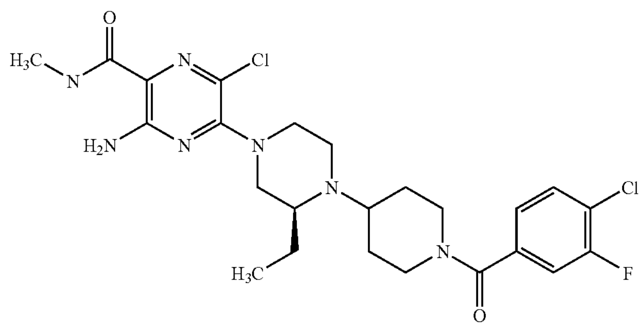 | A |
| 337 | 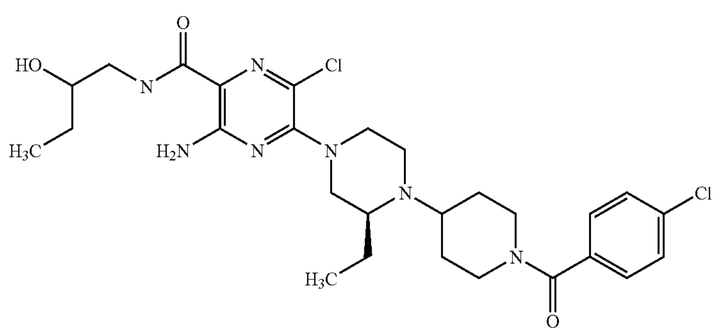 | A |
| 338 | 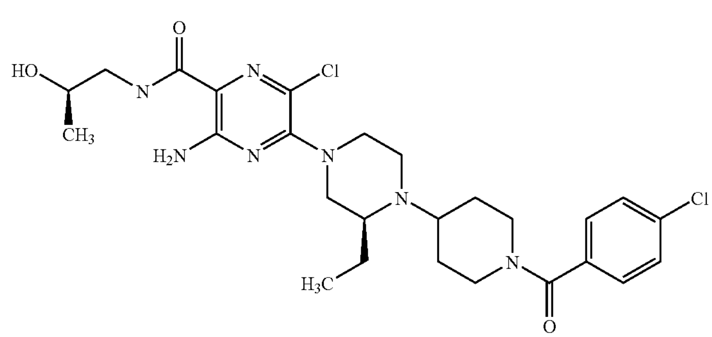 | A |

TABLE 1-continued
| Compound No. | Compound Structure | IC$_{50}$ |
|---|---|---|
| 339 | 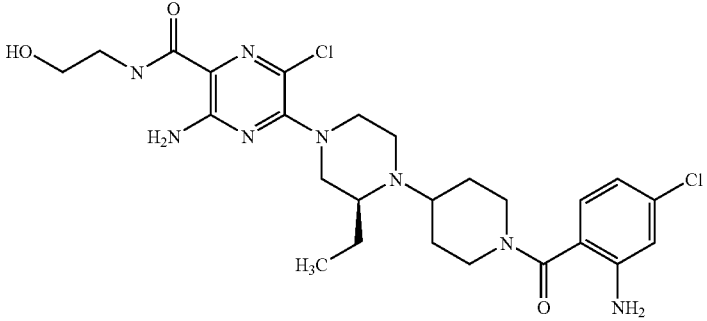 | A |
| 340 | 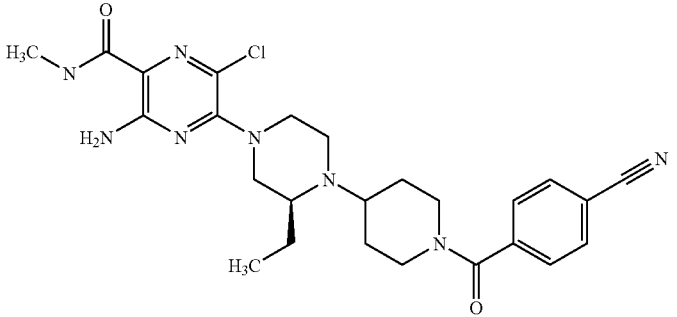 | A |
| 341 | 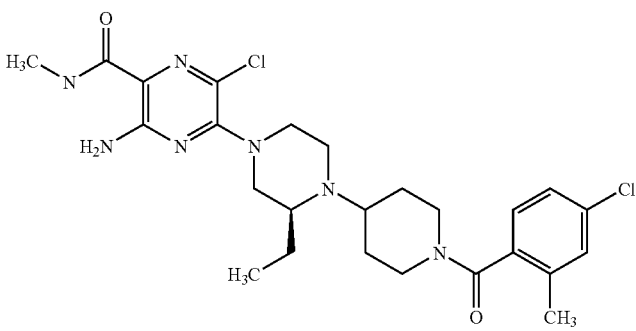 | B |
| 342 | 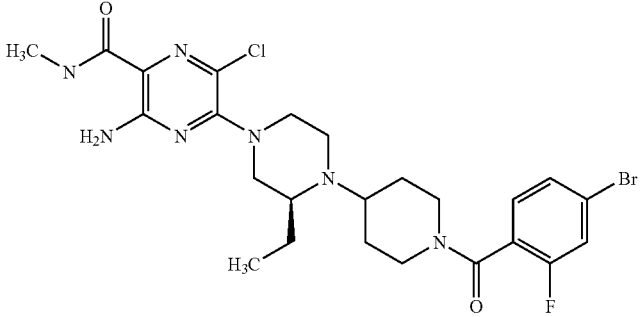 | B |

TABLE 1-continued

| Compound No. | Compound Structure | IC$_{50}$ |
|---|---|---|
| 343 | 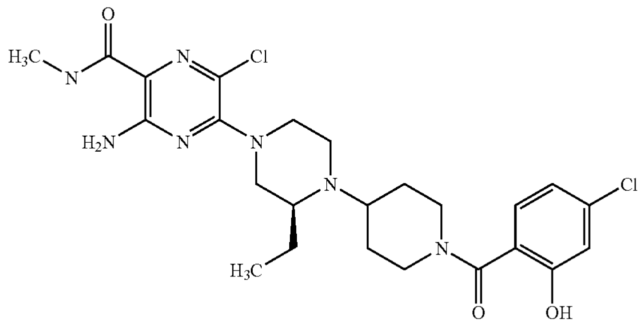 | B |
| 344 | 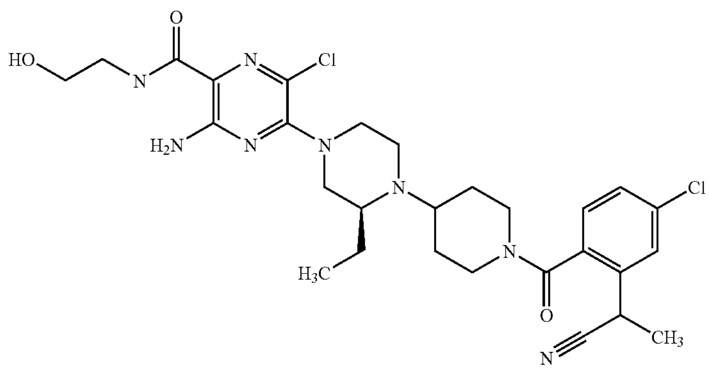 | B |
| 345 | 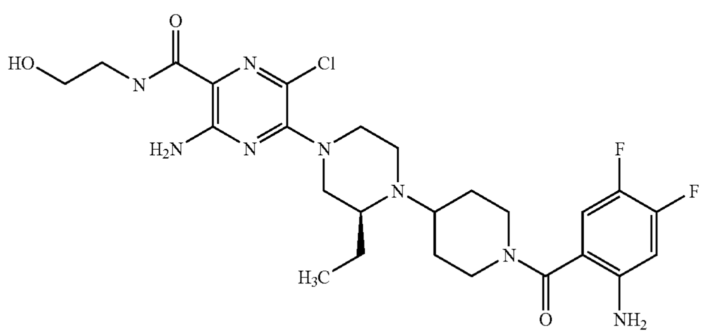 | B |
| 346 | 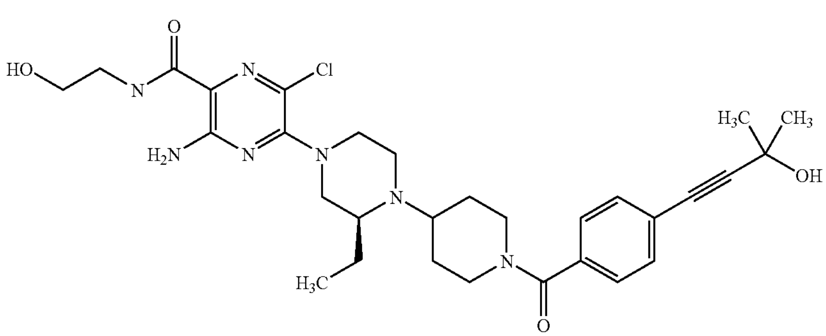 | B |

TABLE 1-continued

| Compound No. | Compound Structure | IC$_{50}$ |
|---|---|---|
| 347 | 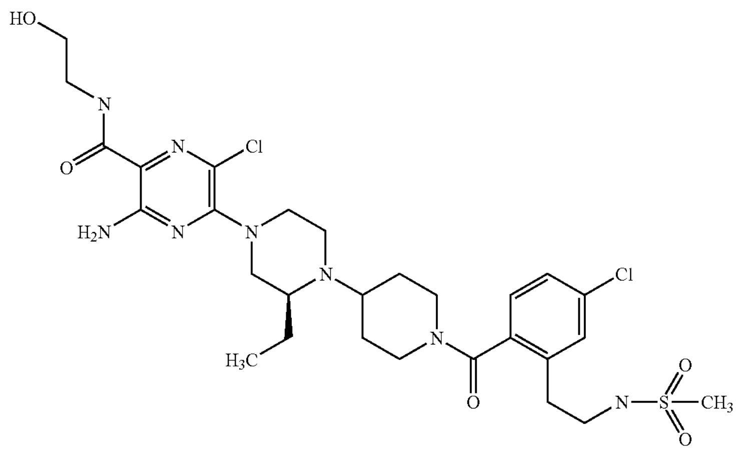 | B |
| 348 | 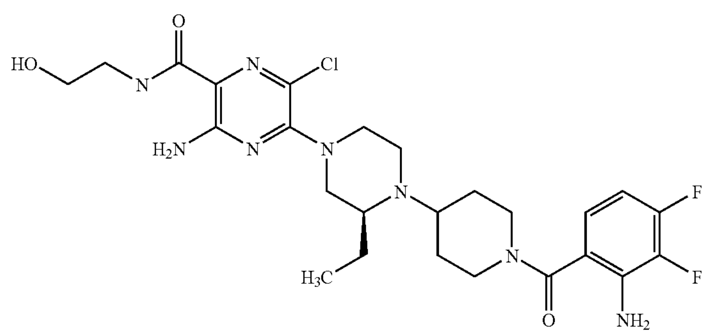 | B |
| 349 | 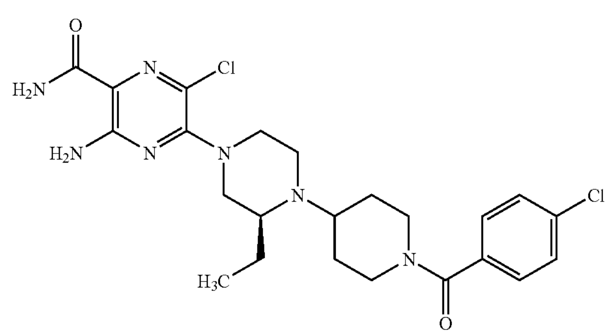 | B |
| 350 | 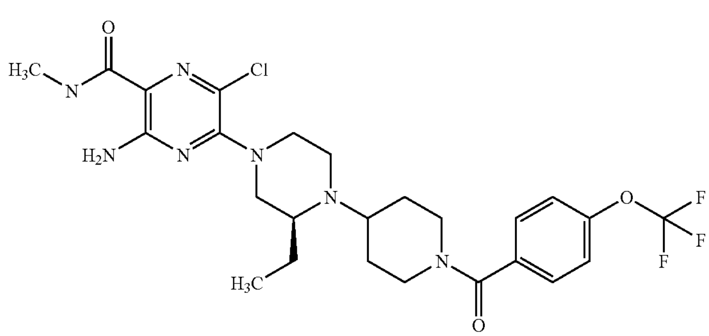 | B |

TABLE 1-continued
| Compound No. | Compound Structure | IC$_{50}$ |
|---|---|---|
| 351 | 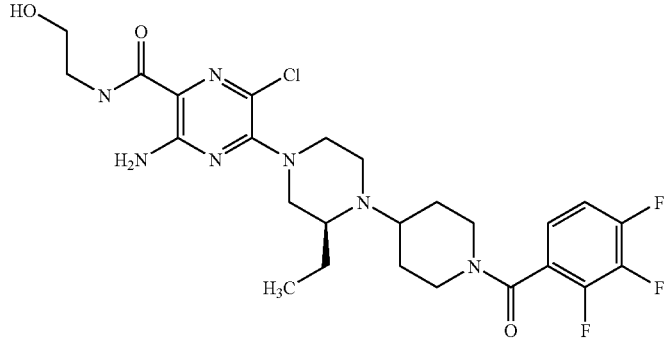 | B |
| 352 | 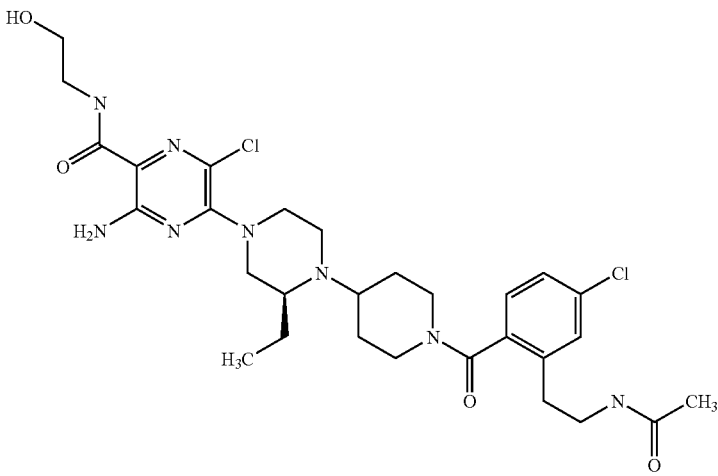 | C |
| 353 | 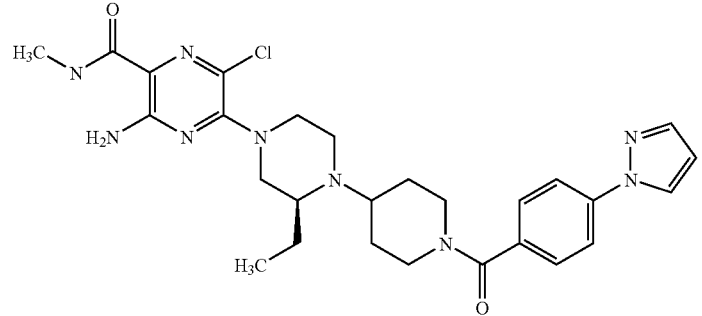 | C |
| 354 | 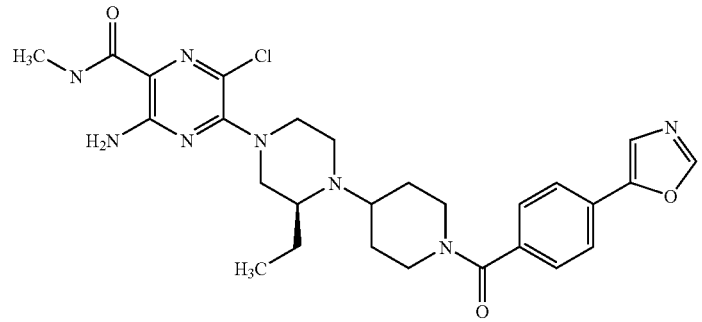 | C |

TABLE 1-continued

| Compound No. | Compound Structure | IC$_{50}$ |
|---|---|---|
| 355 | 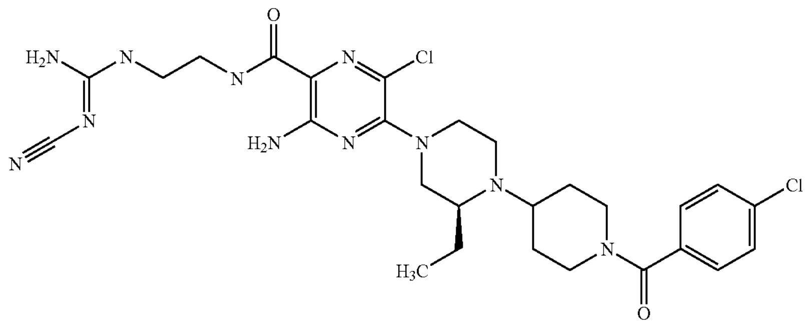 | C |
| 356 | 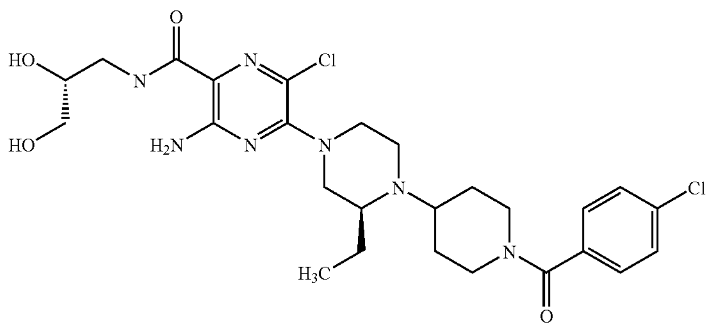 | C |
| 357 | 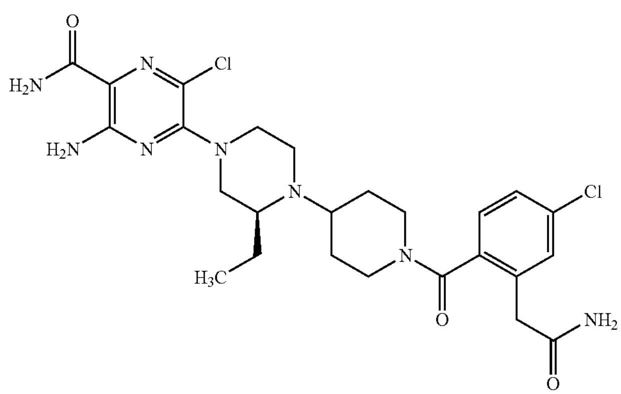 | C |
| 358 | 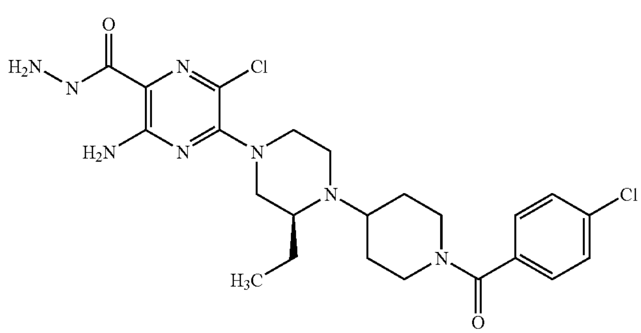 | C |

TABLE 1-continued

| Compound No. | Compound Structure | IC$_{50}$ |
|---|---|---|
| 359 | 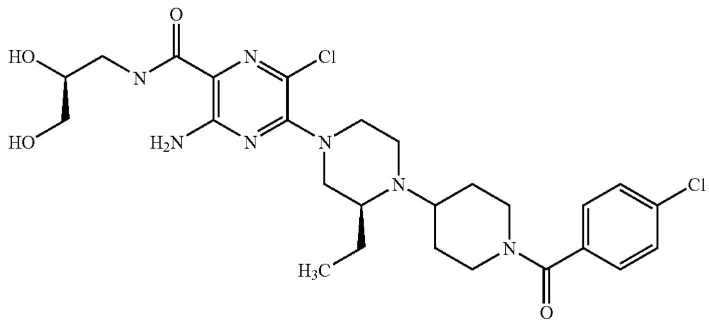 | C |
| 360 | 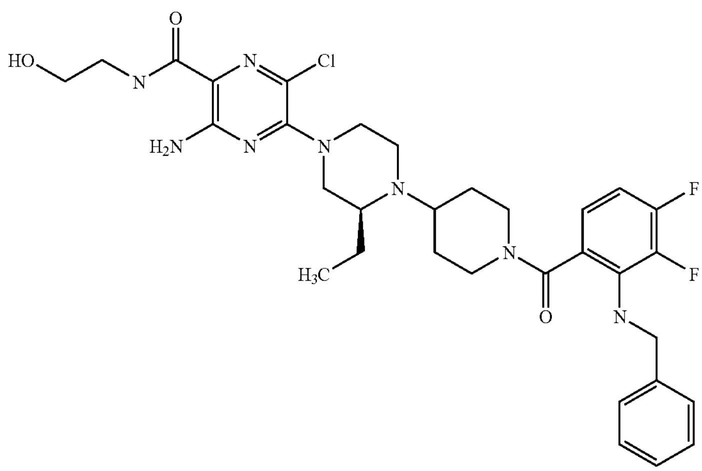 | C |
| 361 | 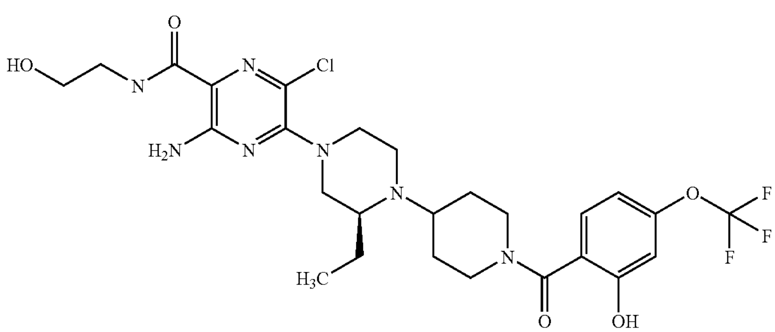 | C |
| 362 | 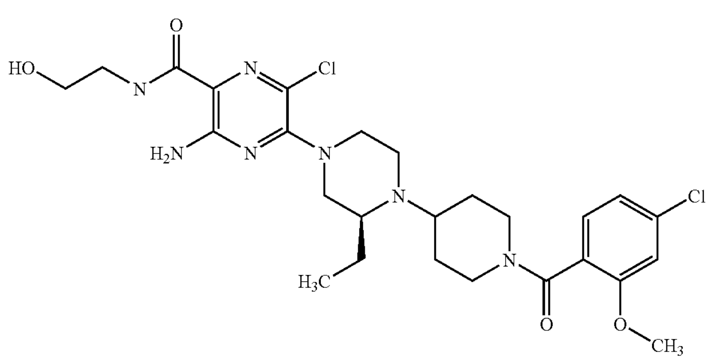 | C |

TABLE 1-continued

| Compound No. | Compound Structure | IC$_{50}$ |
|---|---|---|
| 363 | 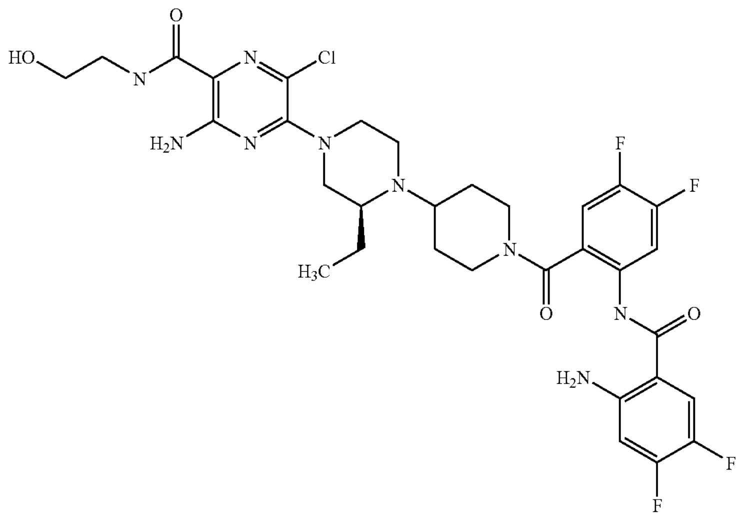 | C |
| 364 | 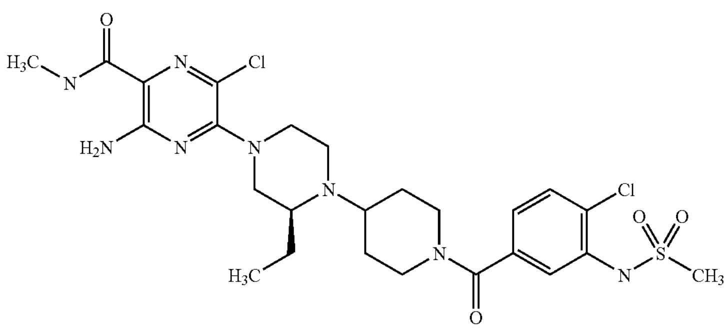 | C |
| 365 | 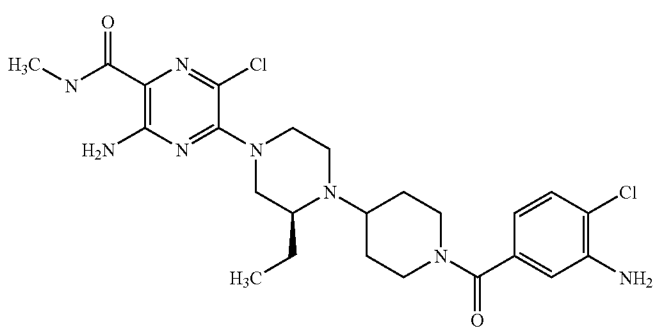 | C |
| 366 | 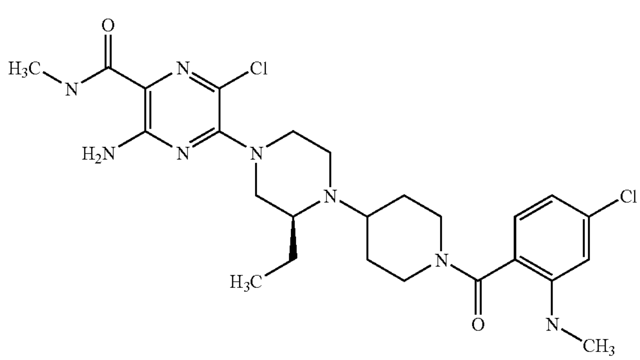 | C |

TABLE 1-continued

| Compound No. | Compound Structure | IC$_{50}$ |
| --- | --- | --- |
| 367 | 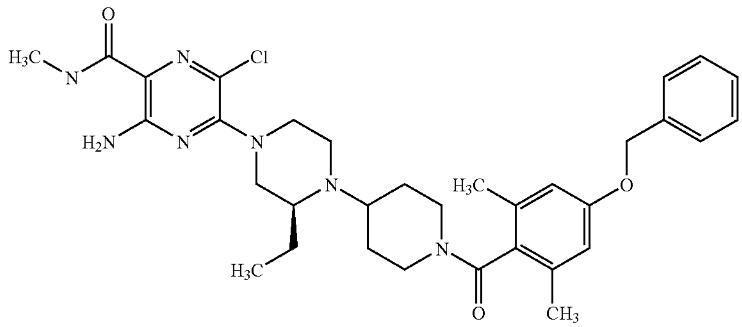 | C |
| 368 | 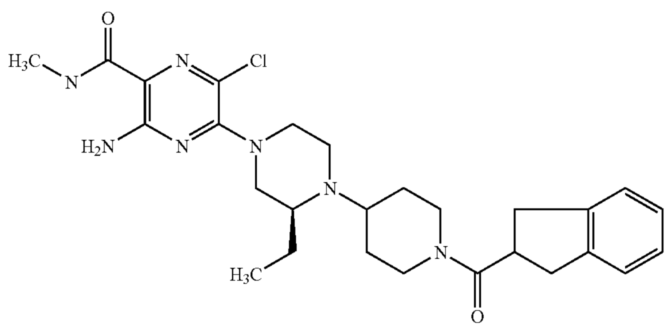 | C |
| 369 | 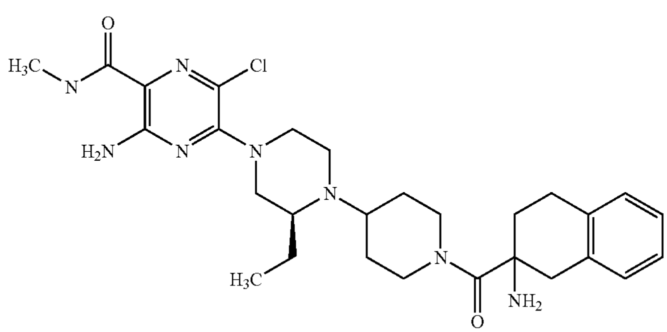 | C |
| 370 | 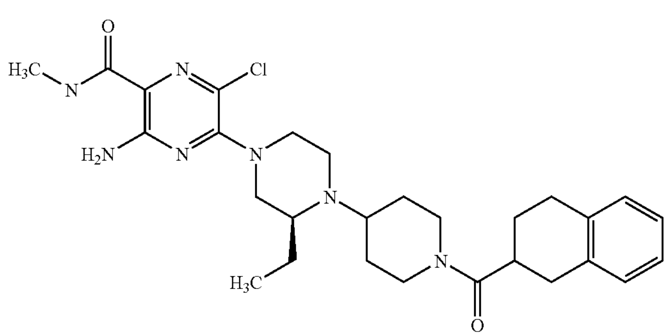 | A |

TABLE 1-continued
| Compound No. | Compound Structure | IC$_{50}$ |
|---|---|---|
| 371 | 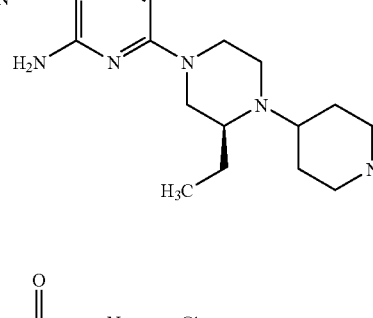 | A |
| 372 | 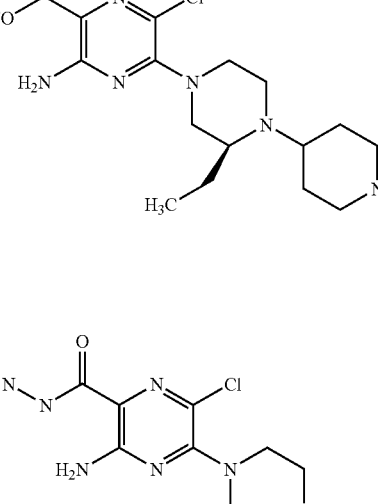 | C |
| 373 | 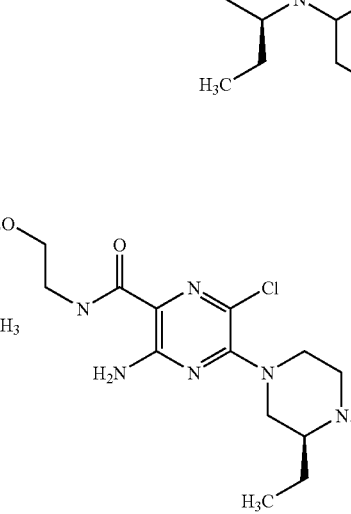 | C |
| 374 | 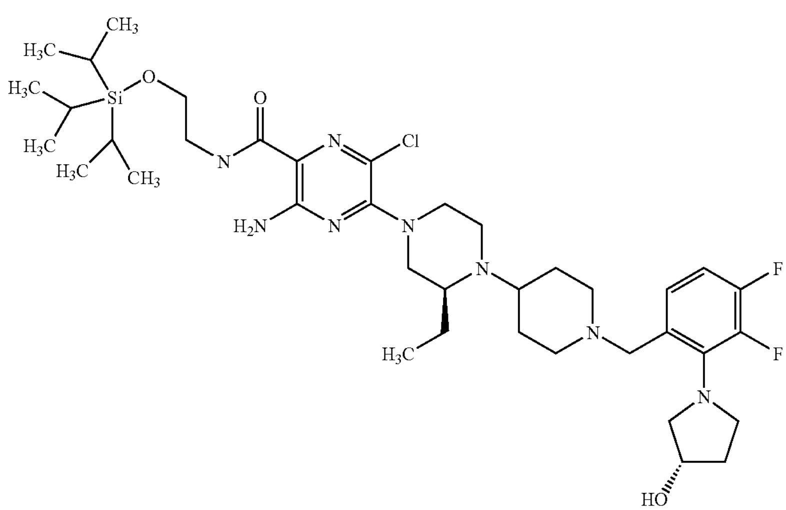 | C |

| Compound No. | Compound Structure | IC$_{50}$ |
|---|---|---|
| 375 | 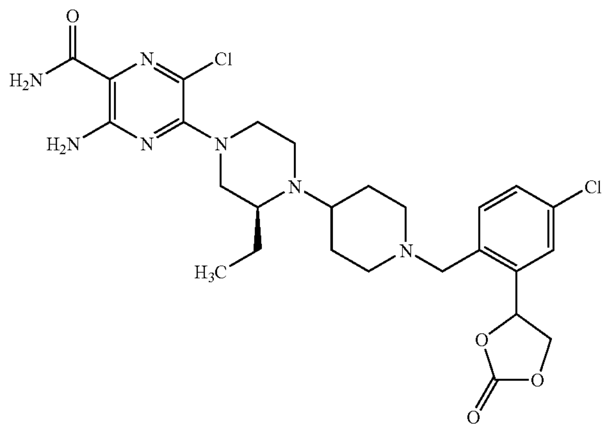 | B |
| 376 | 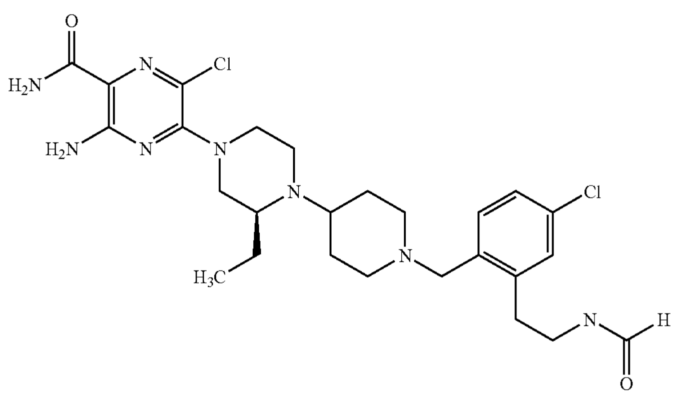 | B |
| 377 | 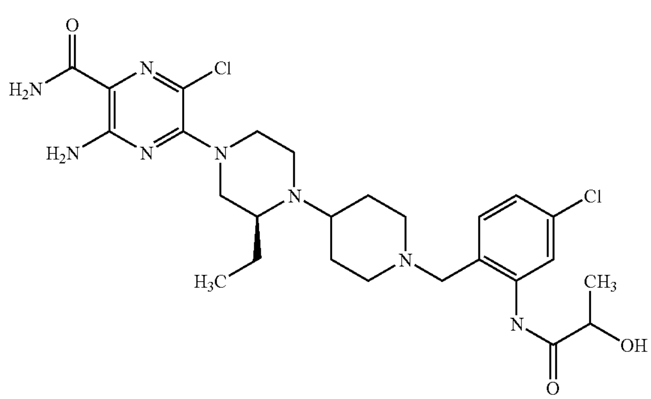 | B |

TABLE 1-continued

| Compound No. | Compound Structure | IC₅₀ |
|---|---|---|
| 378 | 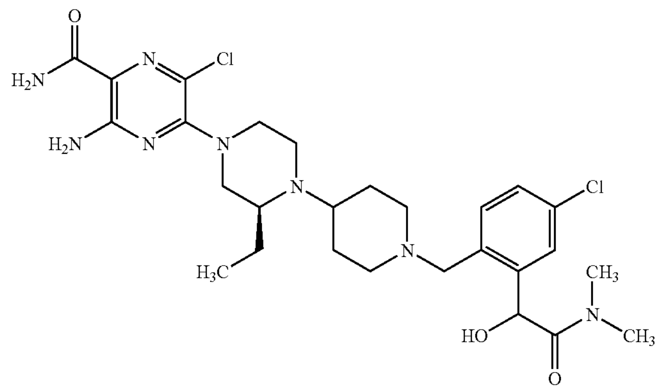 | A |
| 379 | 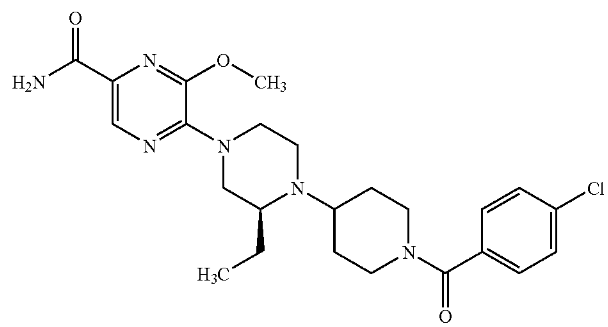 | C |
| 380 | 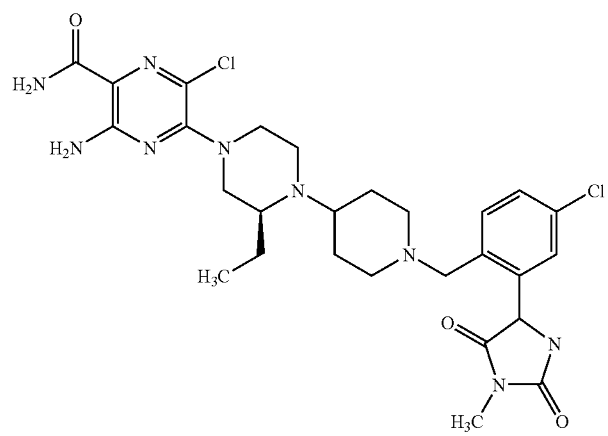 | C |
| 381 | 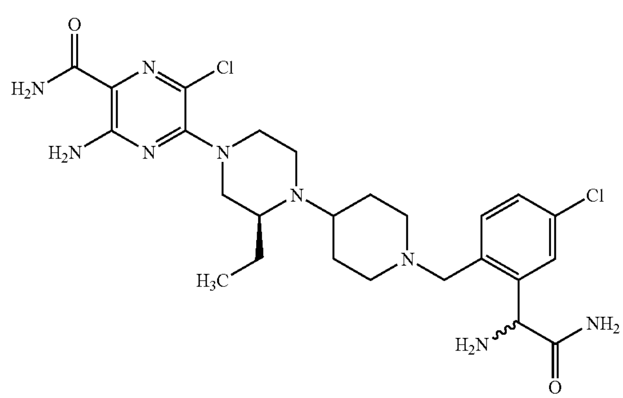 | B |

TABLE 1-continued

| Compound No. | Compound Structure | IC$_{50}$ |
|---|---|---|
| 382 | 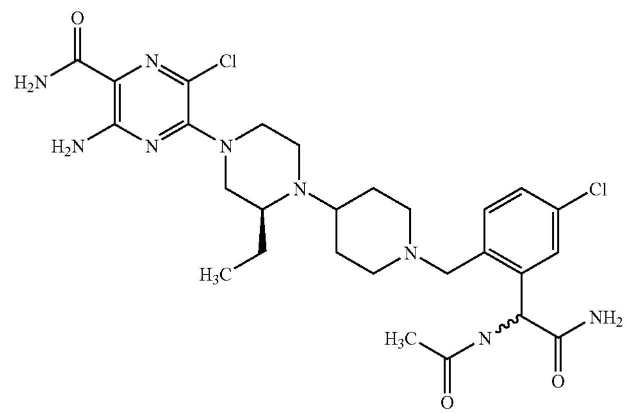 | C |
| 383 | 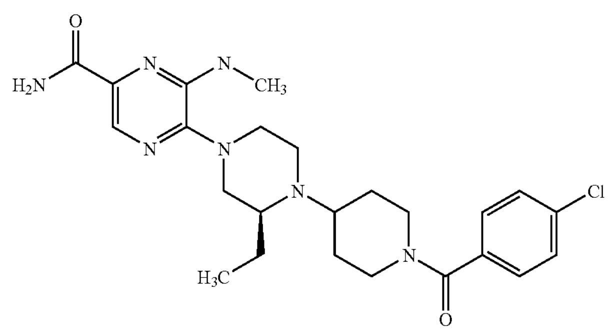 | C |
| 384 | 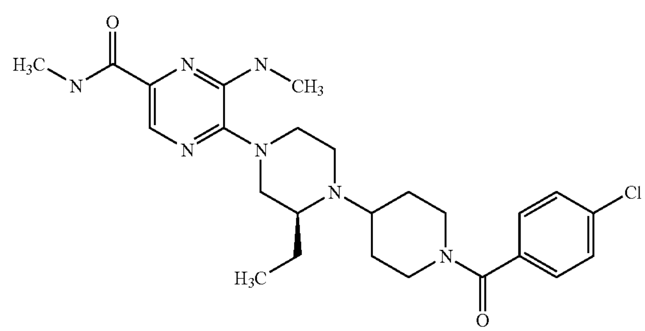 | C |
| 385 | 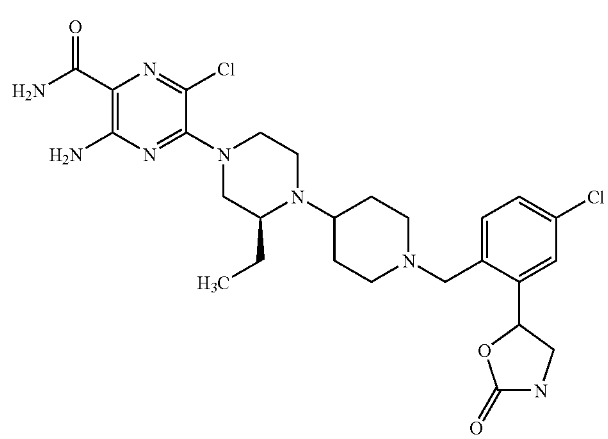 | A |

TABLE 1-continued

| Compound No. | Compound Structure | IC$_{50}$ |
|---|---|---|
| 386 | 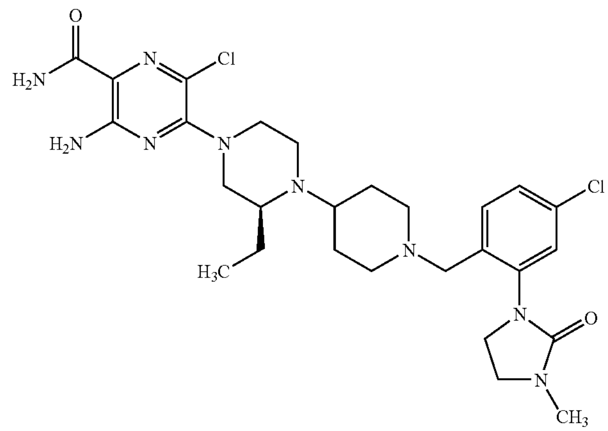 | A |
| 387 | 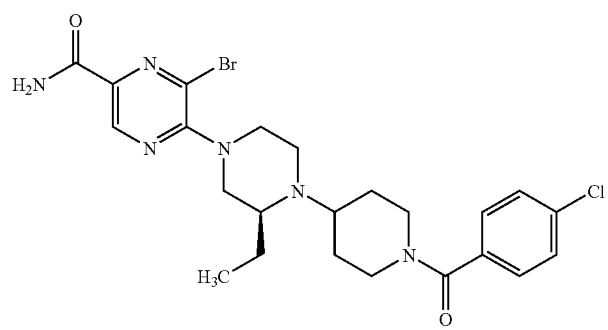 | A |
| 388 | 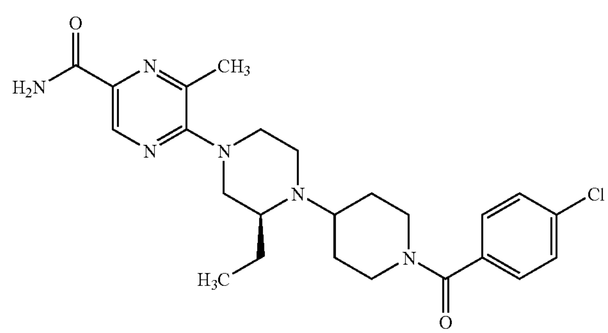 | A |
| 389 | 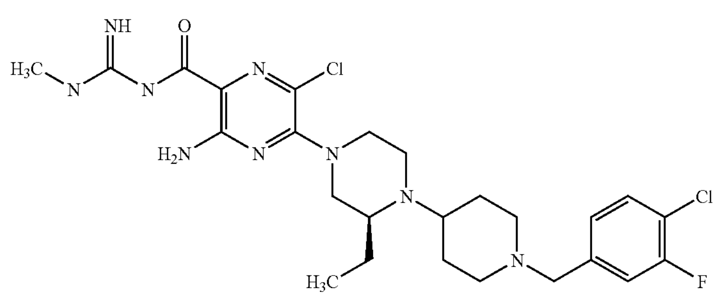 | A |

TABLE 1-continued

| Compound No. | Compound Structure | IC$_{50}$ |
| --- | --- | --- |
| 390 | 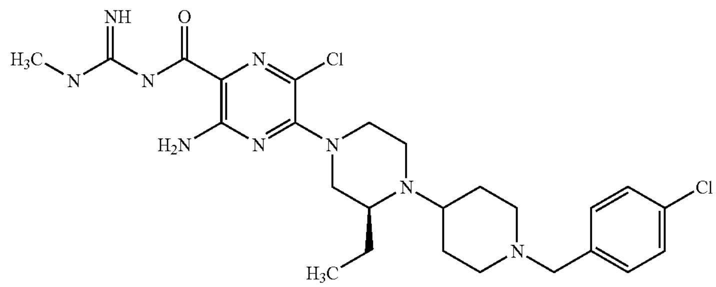 | A |
| 391 | 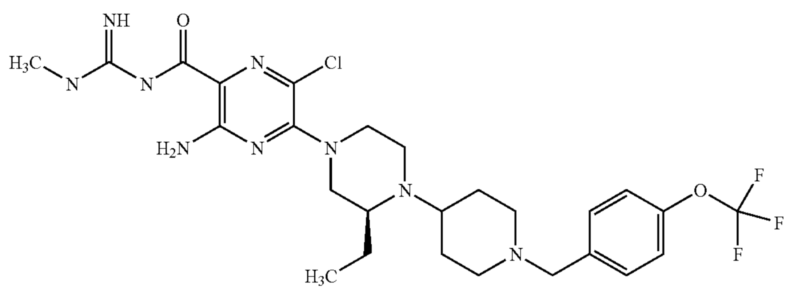 | A |
| 392 | 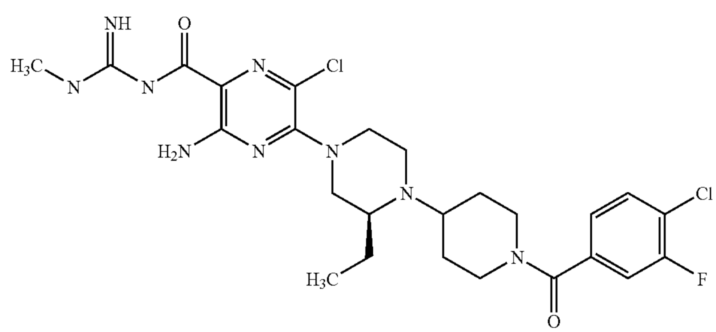 | A |
| 393 | 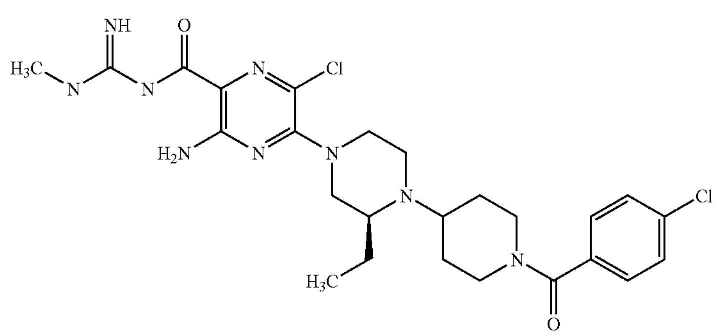 | A |

US 7,868,005 B2
TABLE 1-continued
| Compound No. | Compound Structure | IC$_{50}$ |
|---|---|---|
| 394 | 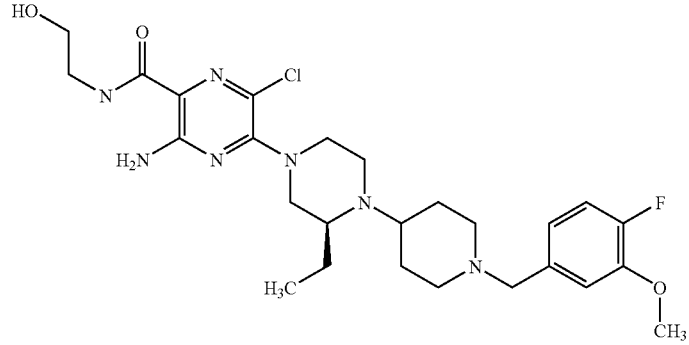 | A |
| 395 | 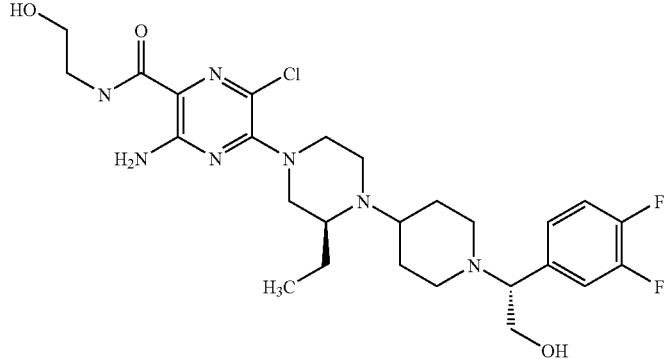 | A |
| 396 | 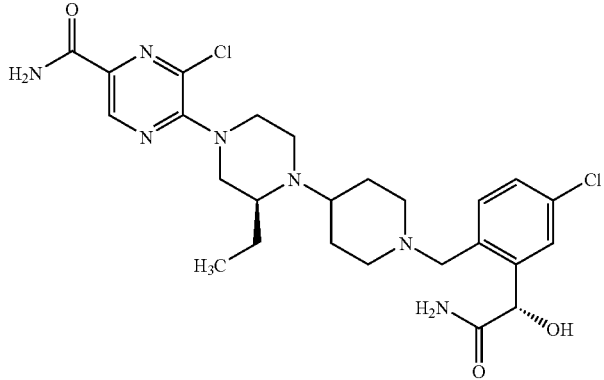 | A |
| 397 | 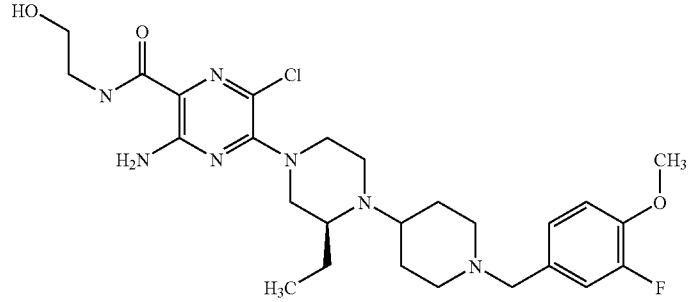 | A |

TABLE 1-continued

| Compound No. | Compound Structure | IC$_{50}$ |
|---|---|---|
| 398 | 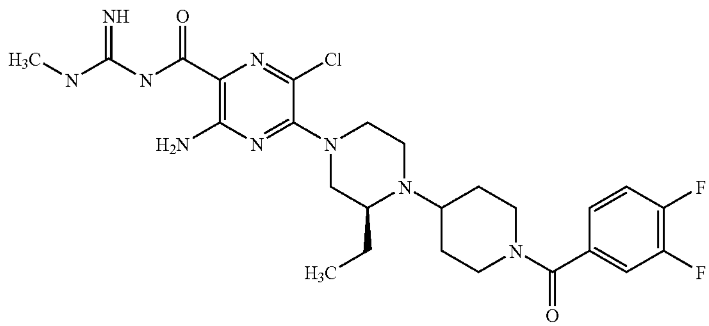 | A |
| 399 | 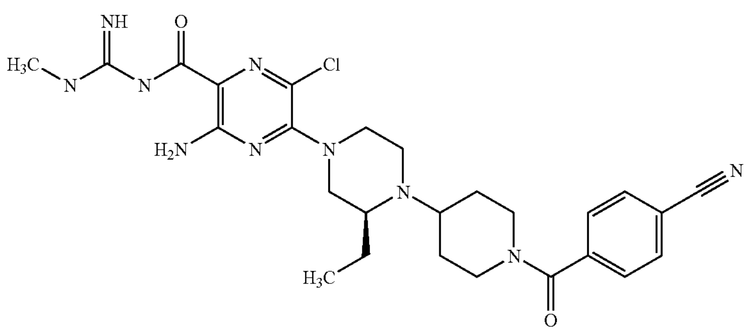 | A |
| 400 | 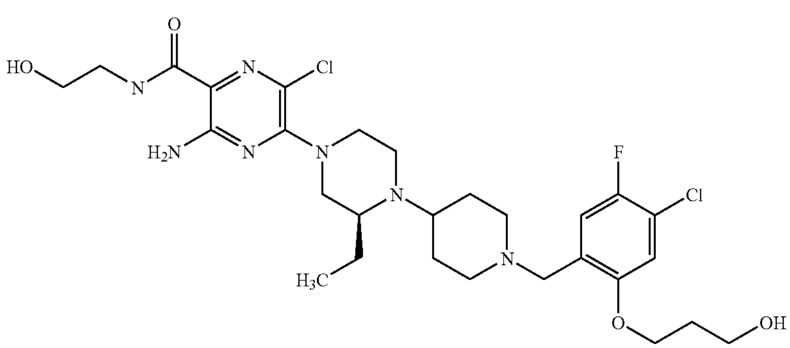 | A |
| 401 | 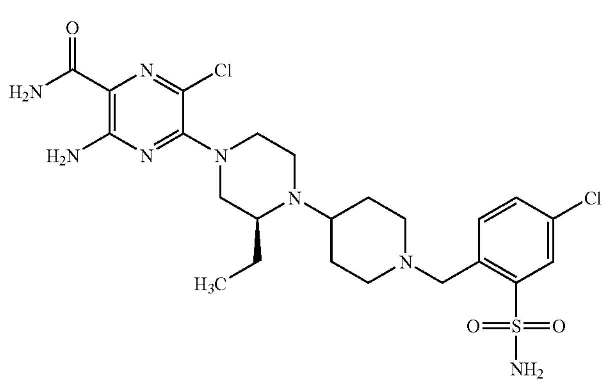 | A |

TABLE 1-continued
| Compound No. | Compound Structure | IC$_{50}$ |
|---|---|---|
| 402 | 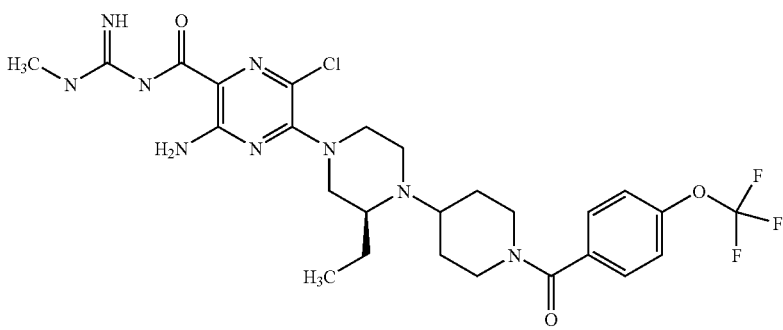 | A |
| 403 | 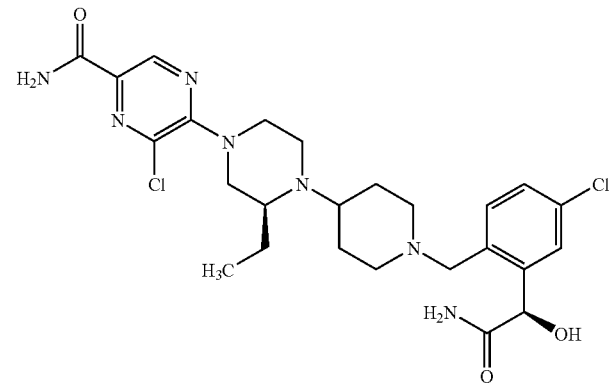 | A |
| 404 | 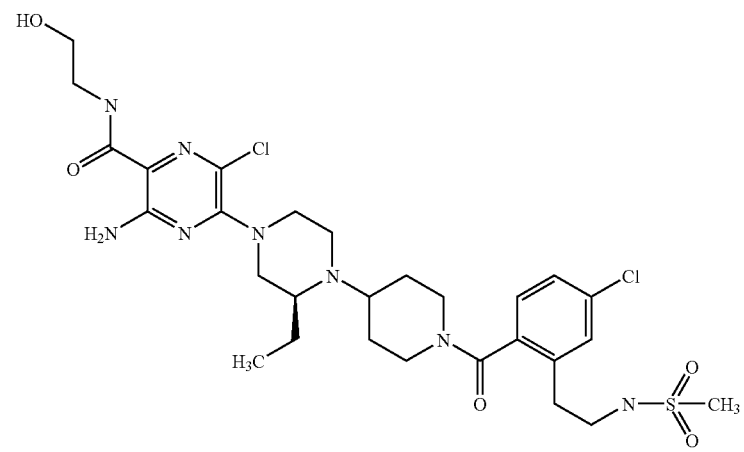 | B |

TABLE 1-continued

| Compound No. | Compound Structure | IC$_{50}$ |
|---|---|---|
| 405 | (structure) | C |
| 406 | (structure) | C |
| 407 | (structure) | C |

TABLE 1-continued
| Compound No. | Compound Structure | IC$_{50}$ |
|---|---|---|
| 408 | 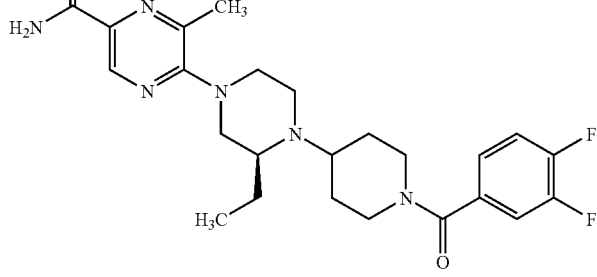 | B |
| 409 | 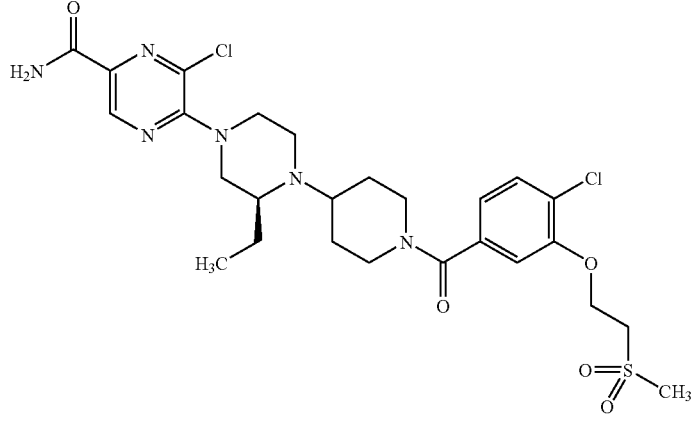 | A |
| 410 | 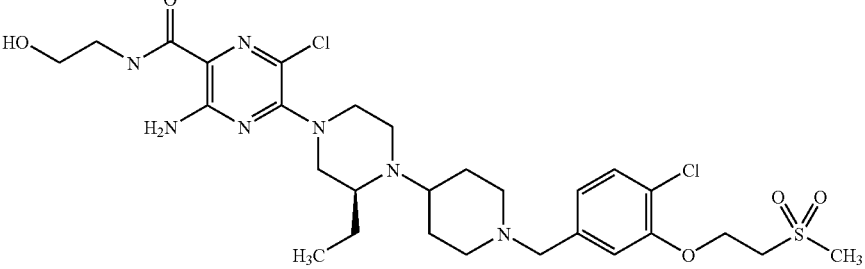 | A |
| 411 | 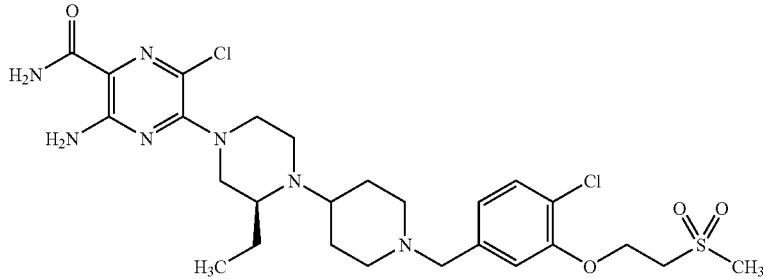 | A |

TABLE 1-continued

| Compound No. | Compound Structure | IC$_{50}$ |
|---|---|---|
| 412 | 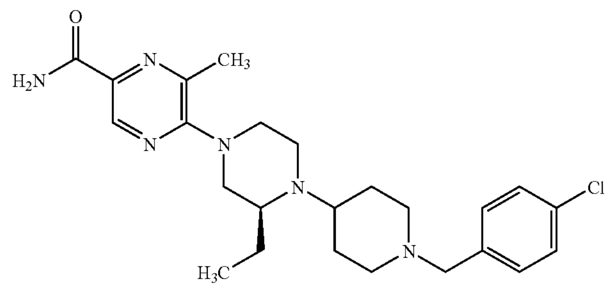 | A |
| 413 | 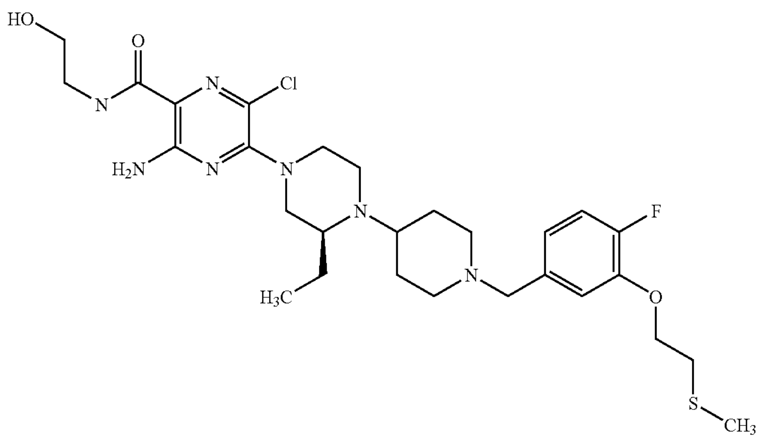 | A |
| 414 | 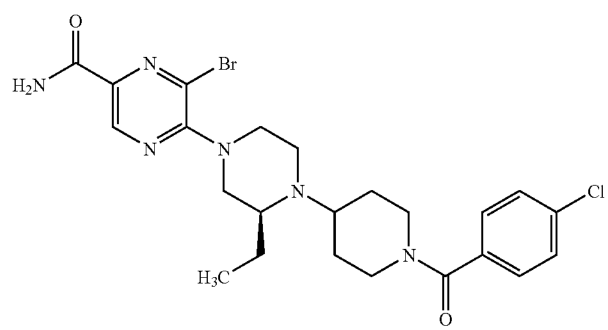 | A |
| 415 | 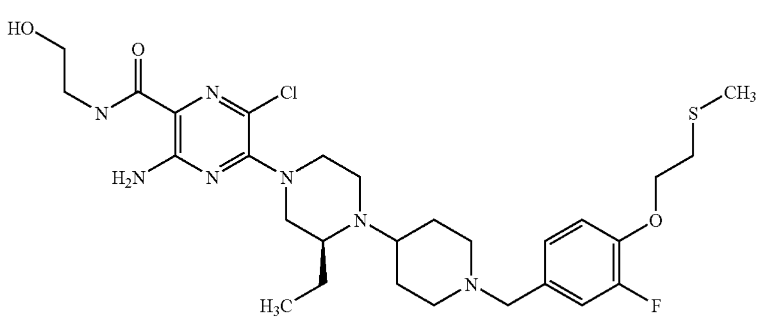 | A |

TABLE 1-continued

| Compound No. | Compound Structure | IC$_{50}$ |
|---|---|---|
| 416 | 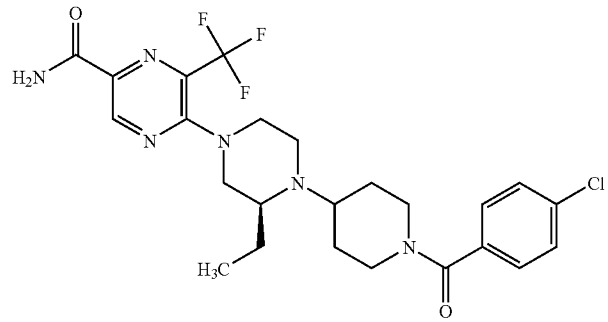 | A |
| 417 | 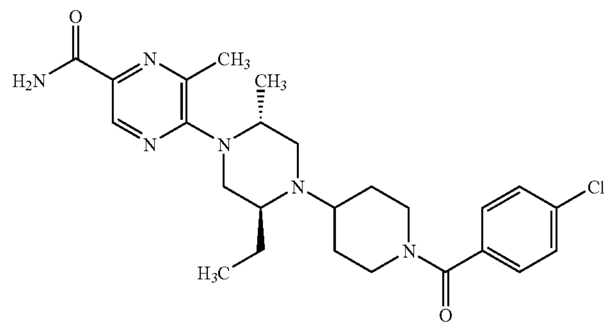 | A |
| 418 | 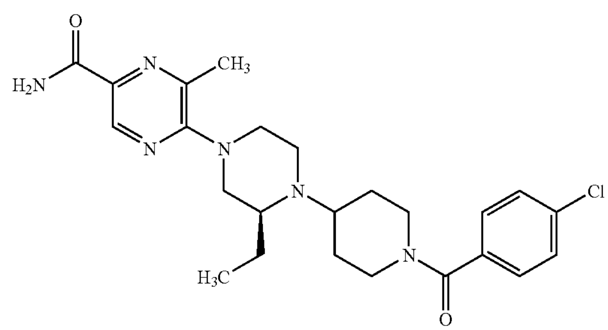 | A |
| 419 | 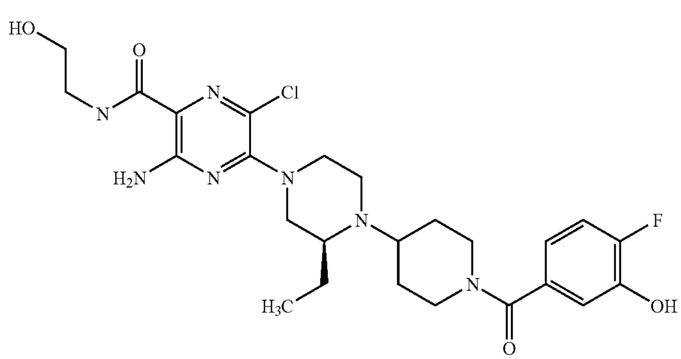 | A |

TABLE 1-continued

| Compound No. | Compound Structure | IC$_{50}$ |
|---|---|---|
| 420 | 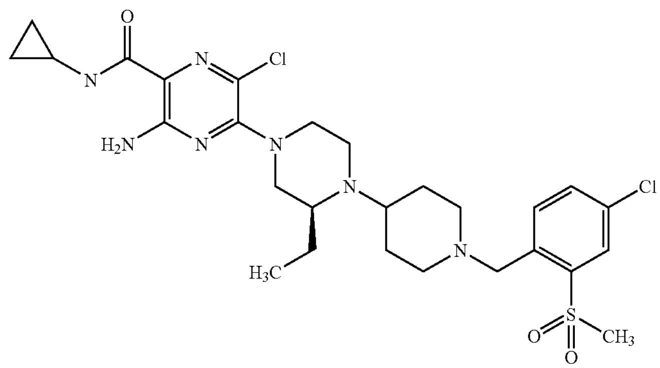 | A |
| 421 | 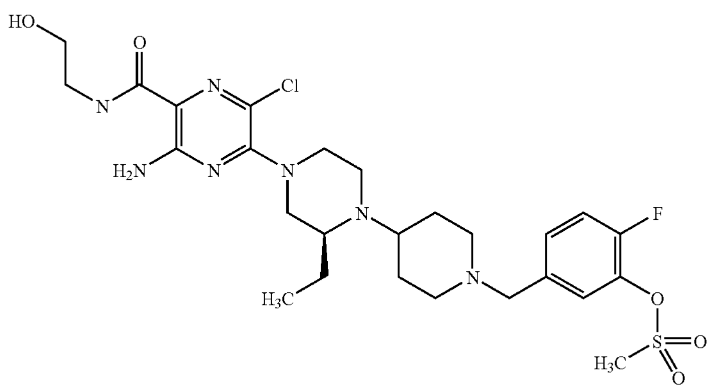 | A |
| 422 | 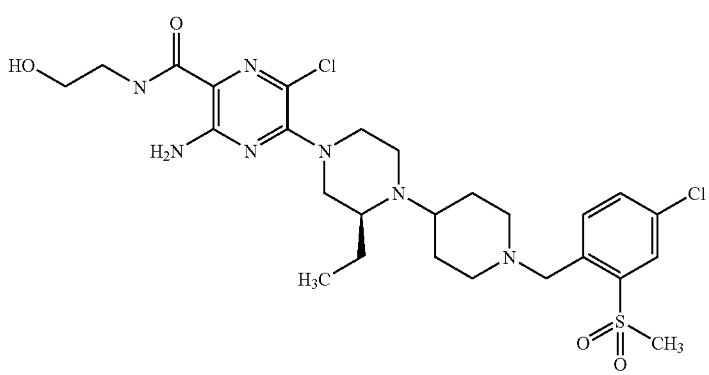 | A |
| 423 | 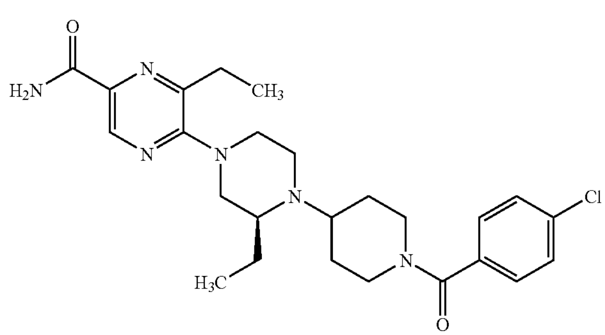 | B |

TABLE 1-continued
| Compound No. | Compound Structure | IC$_{50}$ |
|---|---|---|
| 424 | 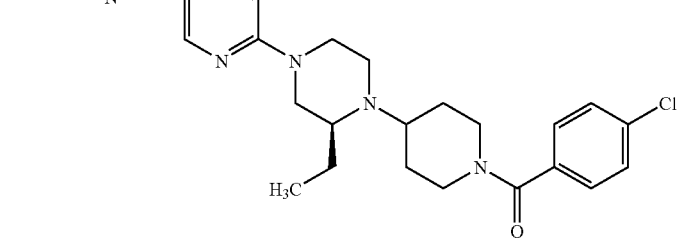 | C |
| 425 | 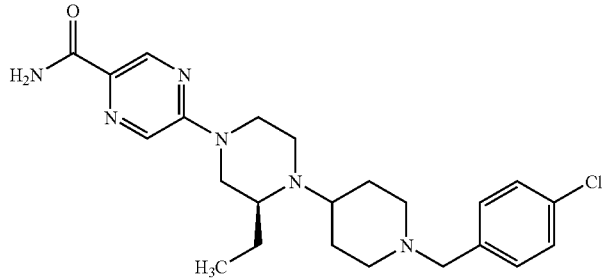 | C |
| 426 | 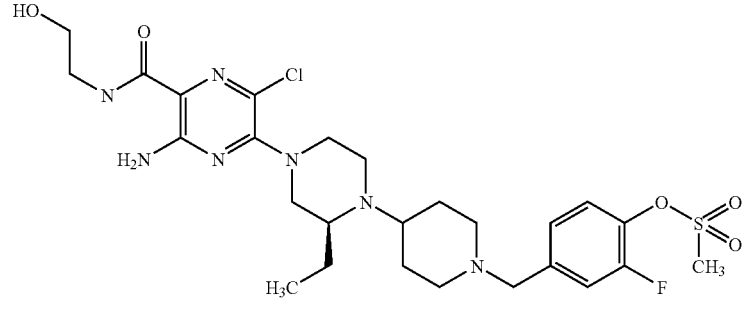 | C |
| 427 | 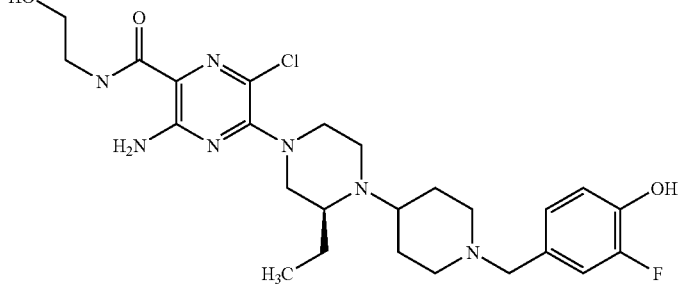 | C |
| 428 | 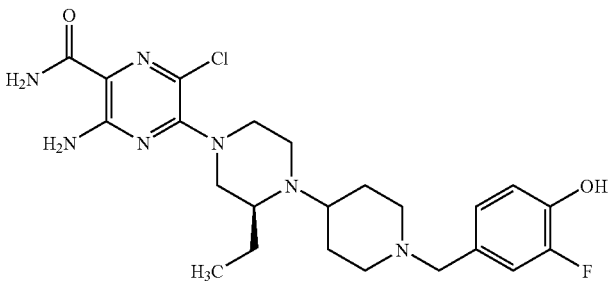 | C |

TABLE 1-continued

| Compound No. | Compound Structure | IC$_{50}$ |
|---|---|---|
| 429 | 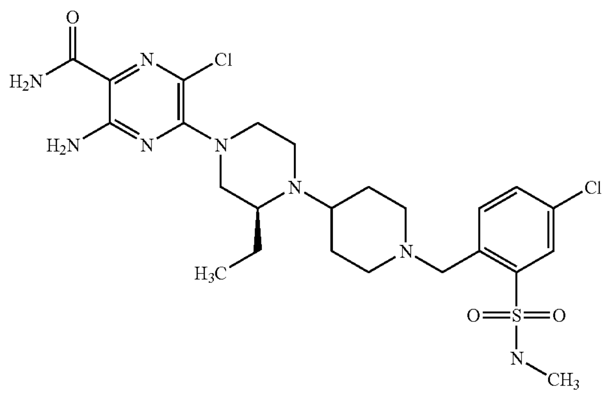 | C |
| 430 | 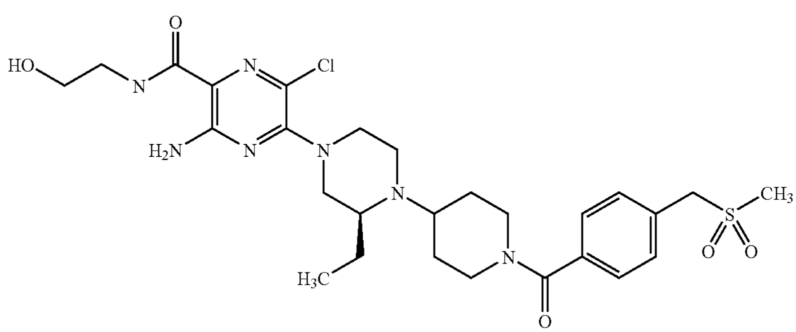 | C |
| 431 | 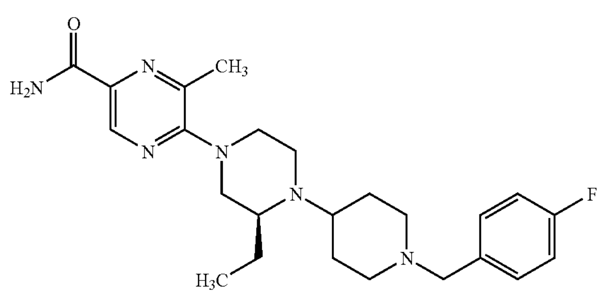 | A |
| 432 | 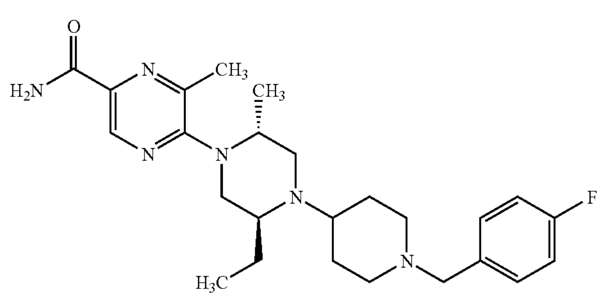 | A |

TABLE 1-continued

| Compound No. | Compound Structure | IC$_{50}$ |
|---|---|---|
| 433 | 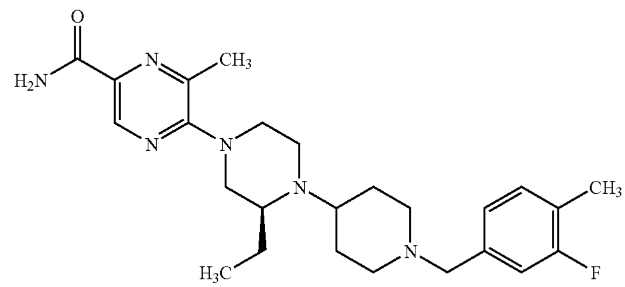 | A |
| 434 | 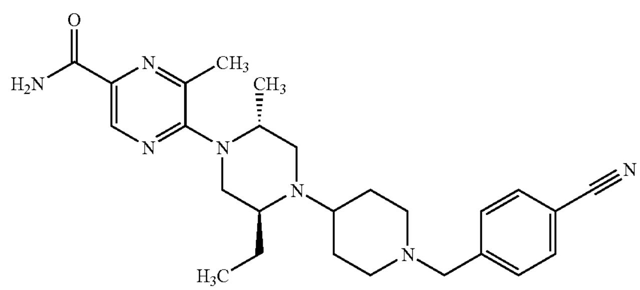 | A |
| 435 | 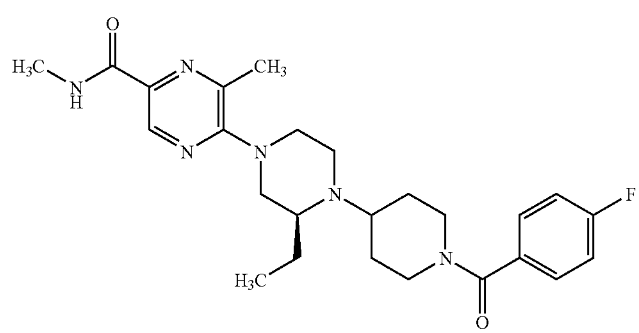 | A |
| 436 | 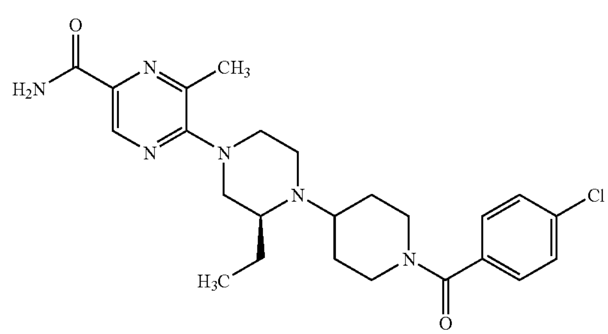 | A |

TABLE 1-continued

| Compound No. | Compound Structure | IC$_{50}$ |
|---|---|---|
| 437 | 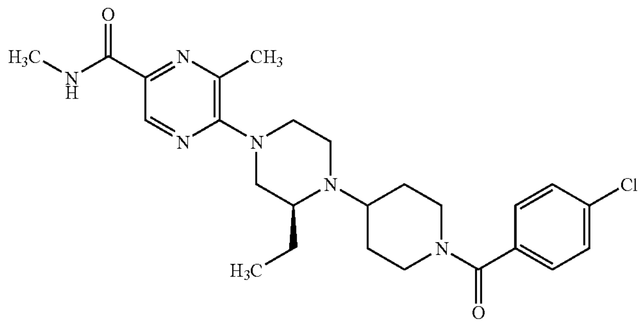 | A |
| 438 | 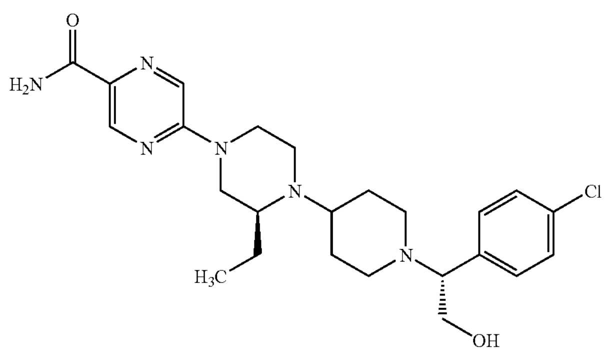 | A |
| 439 | 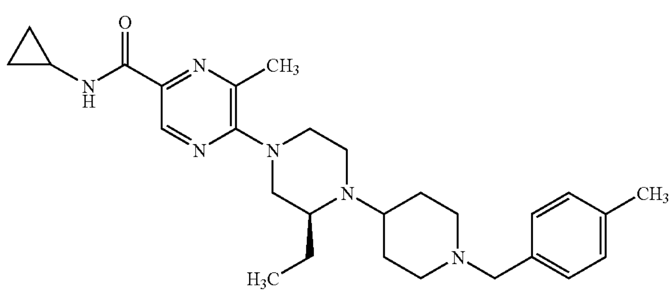 | A |
| 440 | 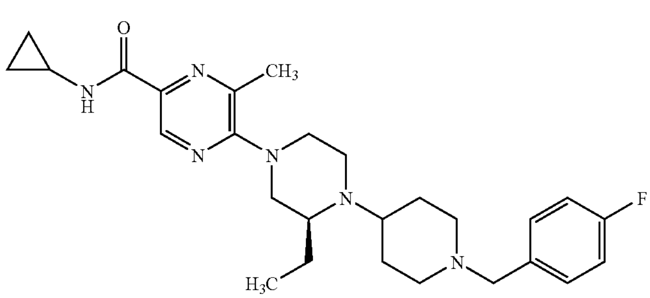 | A |

TABLE 1-continued

| Compound No. | Compound Structure | IC$_{50}$ |
|---|---|---|
| 441 | 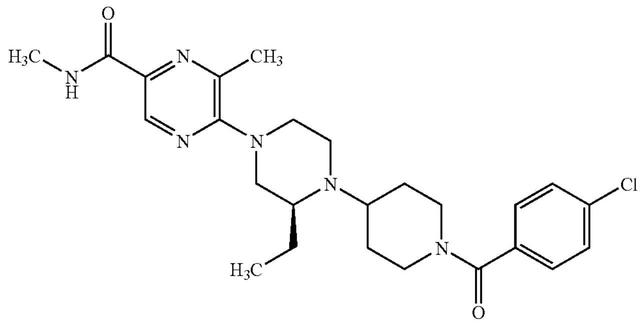 | A |
| 442 | 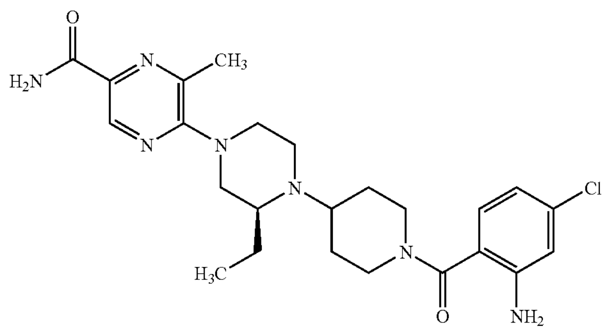 | A |
| 443 | 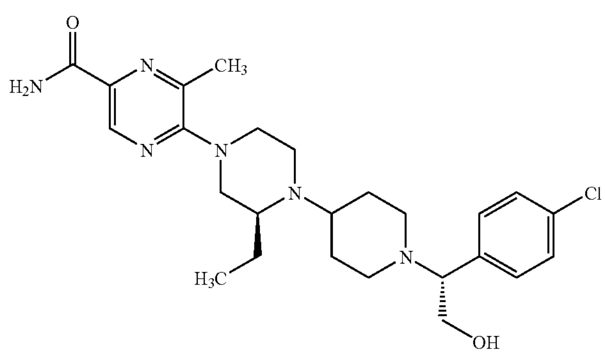 | A |
| 444 | 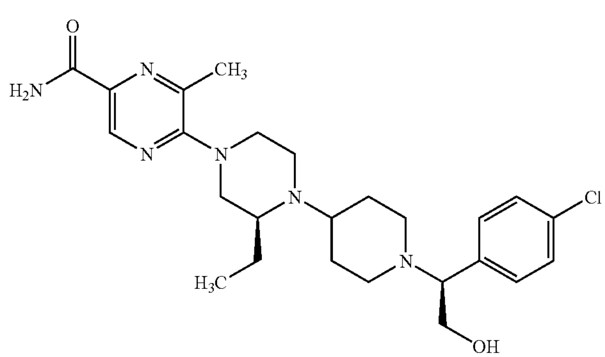 | A |

TABLE 1-continued

| Compound No. | Compound Structure | IC$_{50}$ |
|---|---|---|
| 445 | 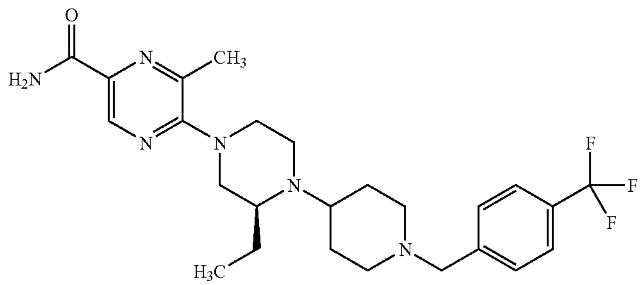 | A |
| 446 | 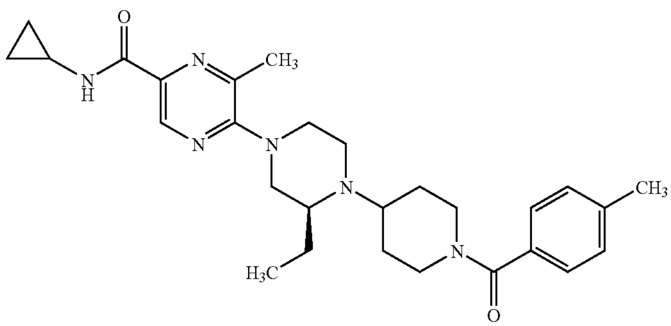 | A |
| 447 | 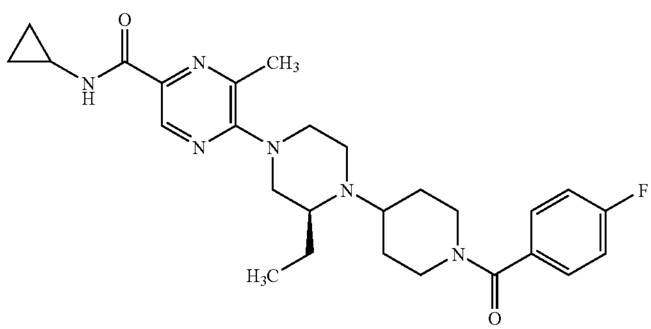 | A |
| 448 | 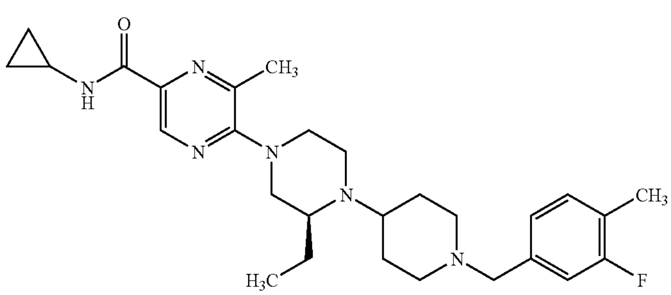 | A |
| 449 | 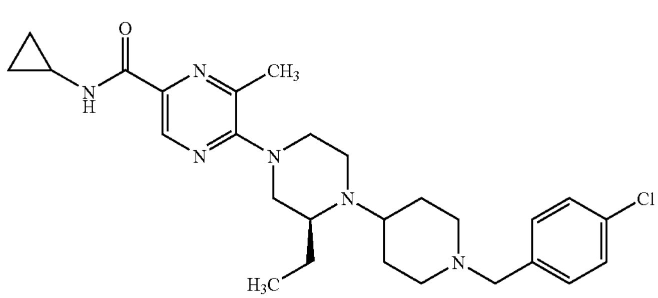 | A |

TABLE 1-continued
| Compound No. | Compound Structure | IC$_{50}$ |
|---|---|---|
| 450 | 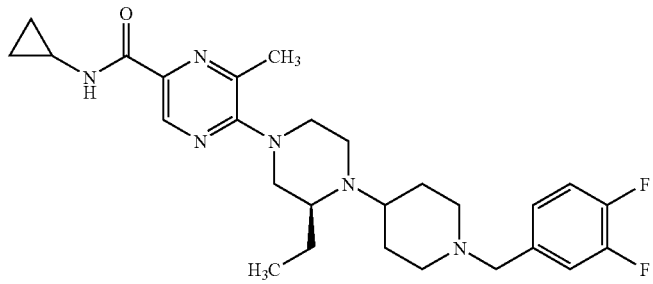 | A |
| 451 | 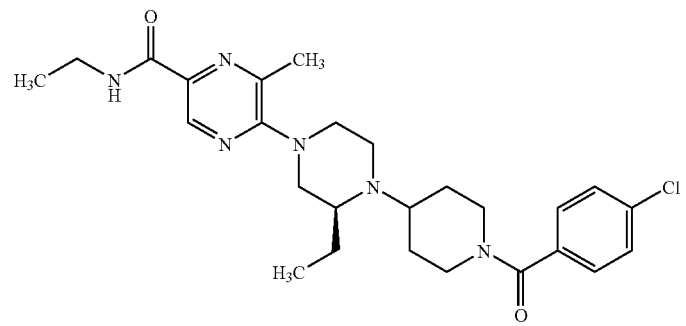 | A |
| 452 | 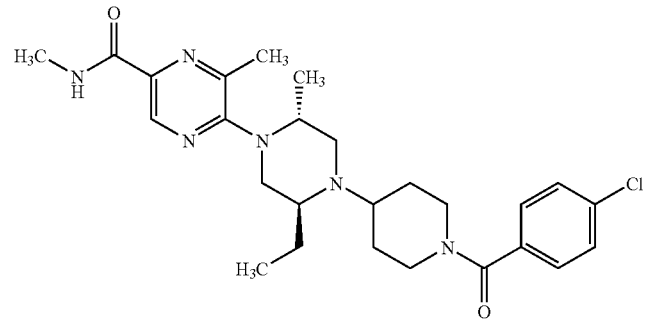 | A |
| 453 | 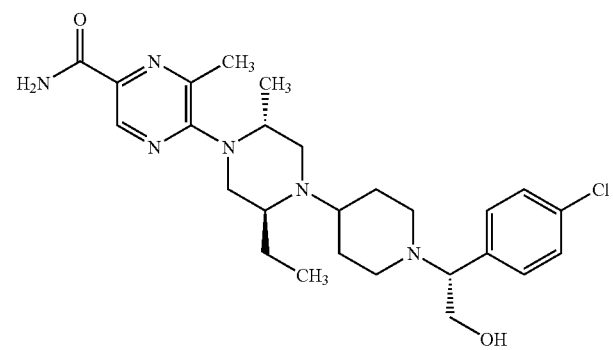 | A |

TABLE 1-continued
| Compound No. | Compound Structure | IC$_{50}$ |
|---|---|---|
| 454 | 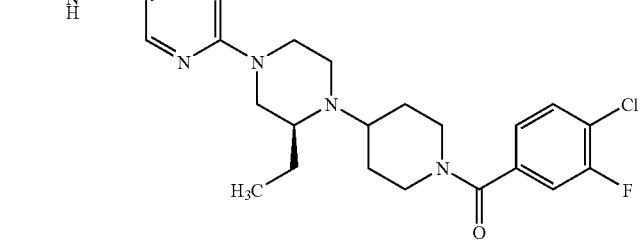 | A |
| 455 | 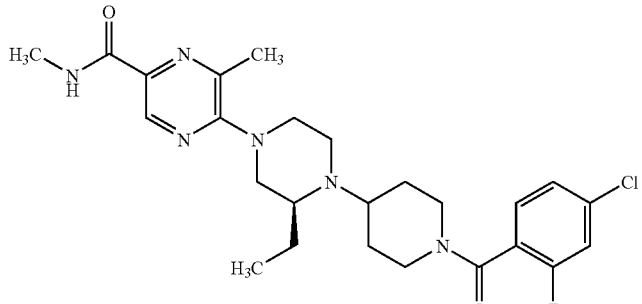 | A |
| 456 | 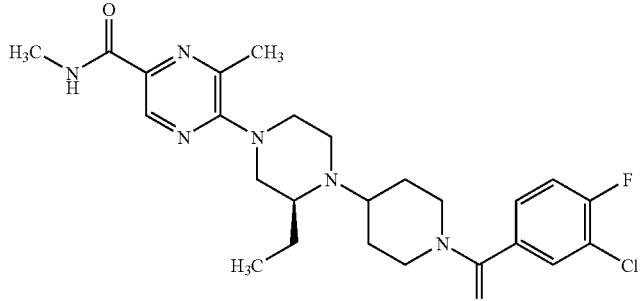 | A |
| 457 | 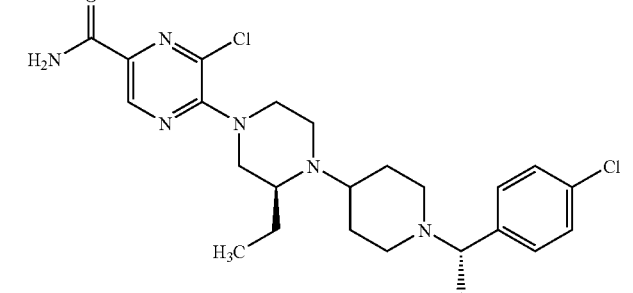 | A |

TABLE 1-continued

| Compound No. | Compound Structure | IC$_{50}$ |
|---|---|---|
| 458 | 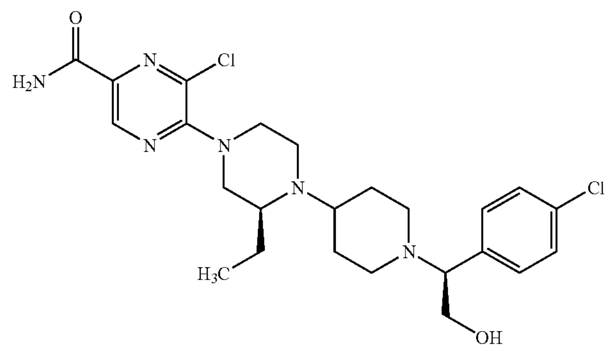 | A |
| 459 | 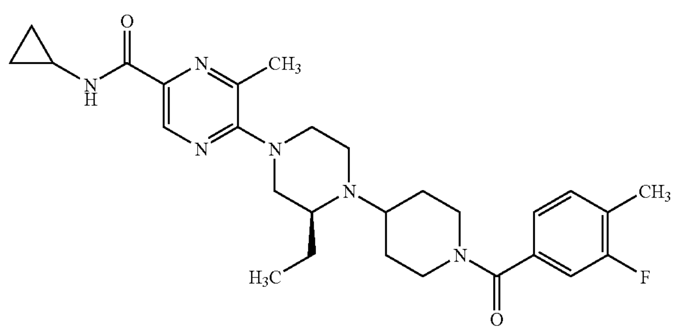 | A |
| 460 | 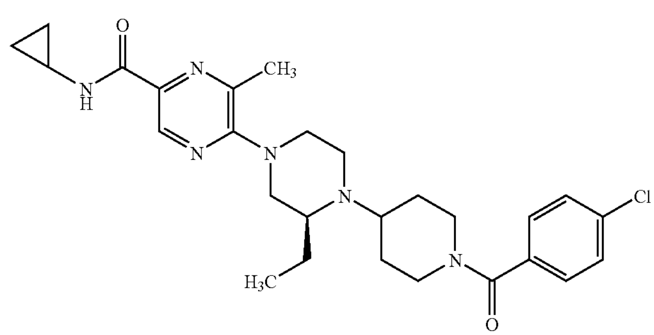 | A |
| 461 | 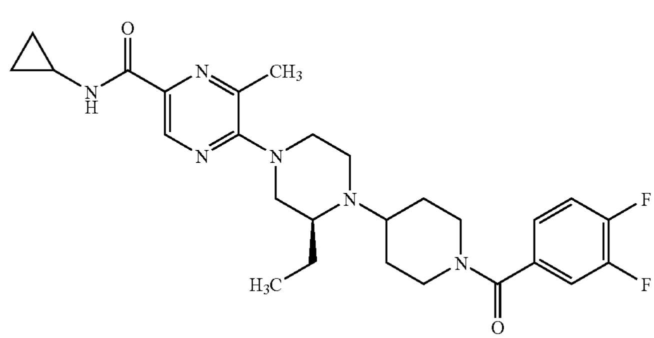 | A |

TABLE 1-continued
| Compound No. | Compound Structure | IC$_{50}$ |
|---|---|---|
| 462 | 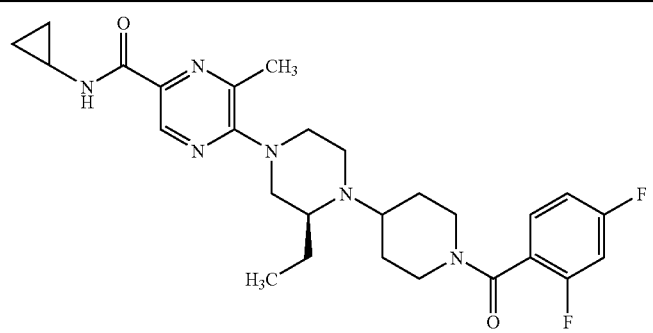 | A |
| 463 | 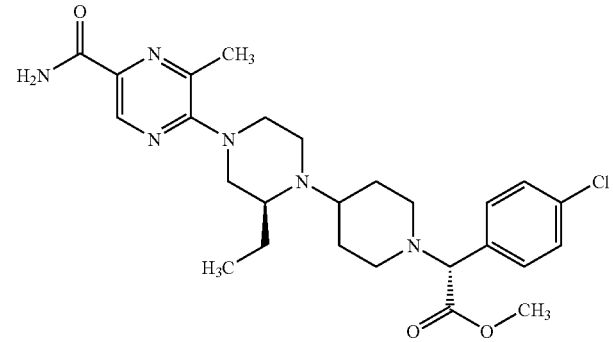 | A |
| 464 | 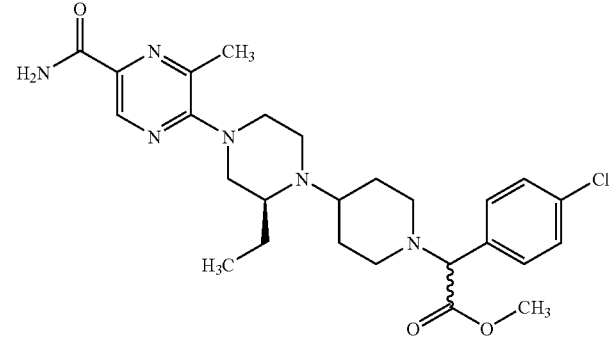 | A |
| 465 | 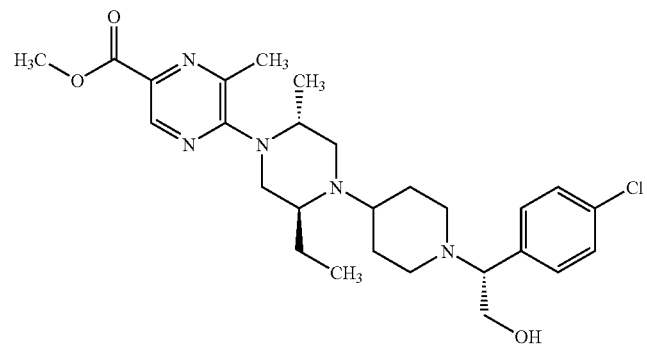 | A |

TABLE 1-continued

| Compound No. | Compound Structure | IC$_{50}$ |
|---|---|---|
| 466 | 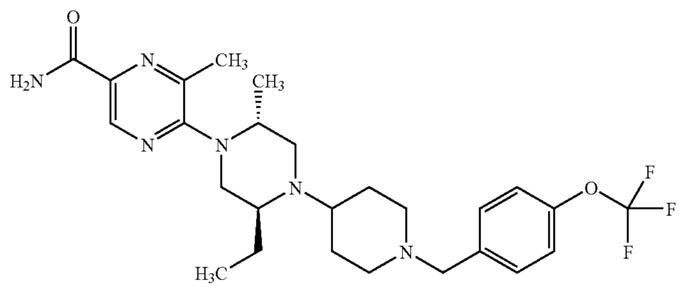 | A |
| 467 | 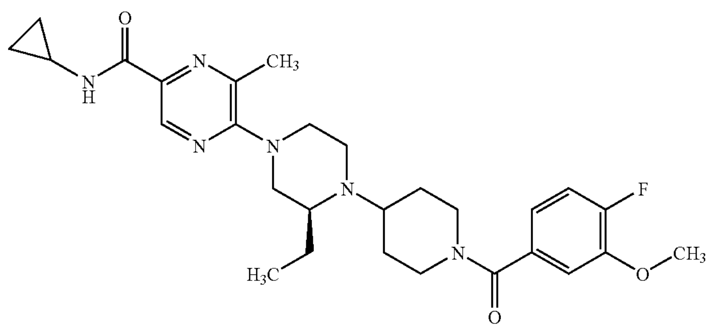 | A |
| 468 | 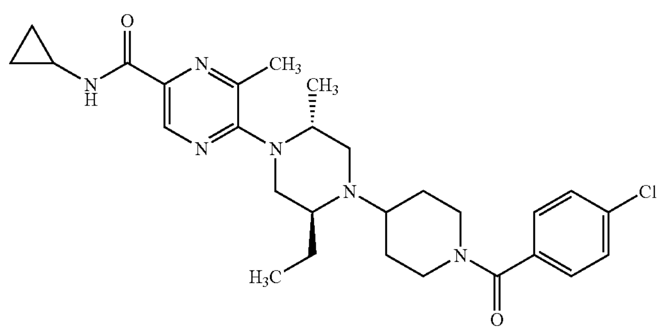 | A |
| 469 | 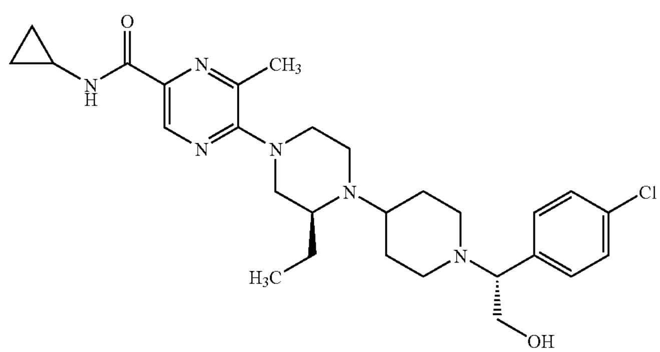 | A |

TABLE 1-continued

| Compound No. | Compound Structure | IC$_{50}$ |
|---|---|---|
| 470 | 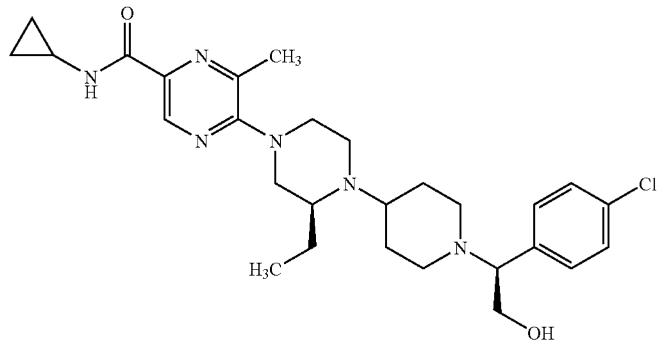 | A |
| 471 | 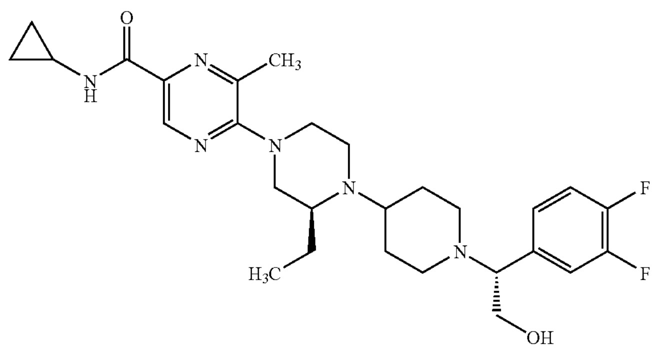 | A |
| 472 | 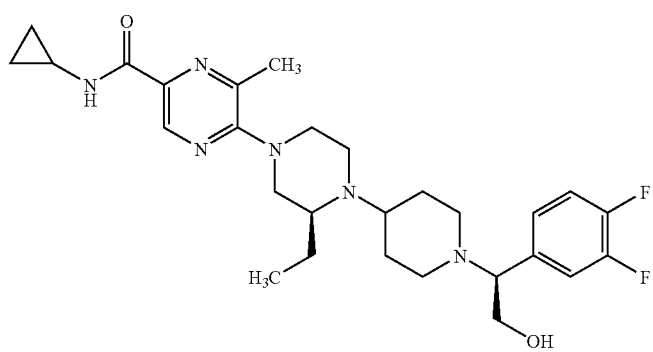 | A |
| 473 | 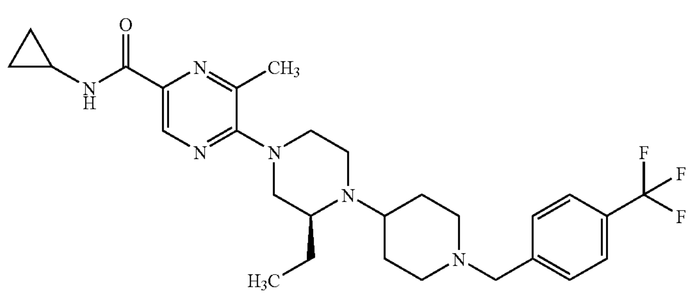 | A |

TABLE 1-continued

| Compound No. | Compound Structure | IC$_{50}$ |
|---|---|---|
| 474 | 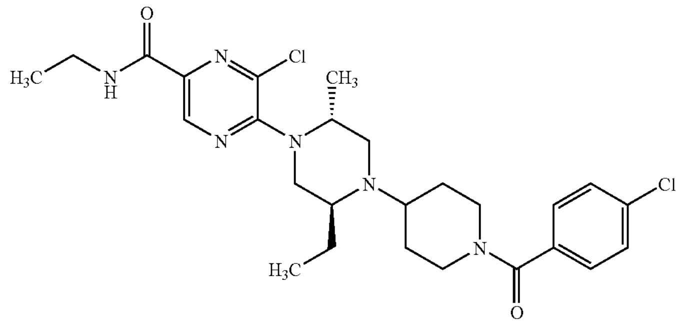 | A |
| 475 | 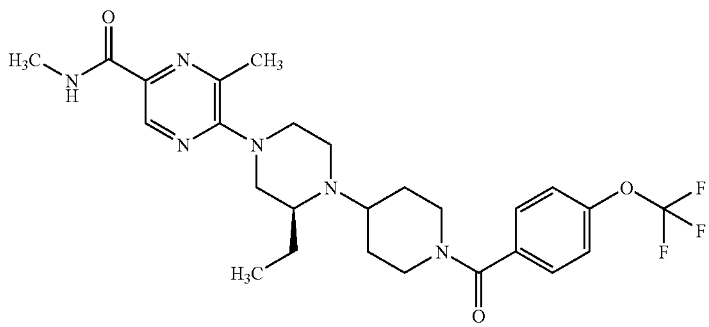 | A |
| 476 | 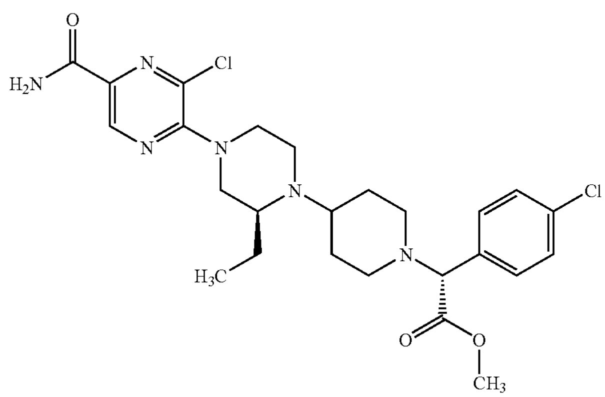 | A |
| 477 | 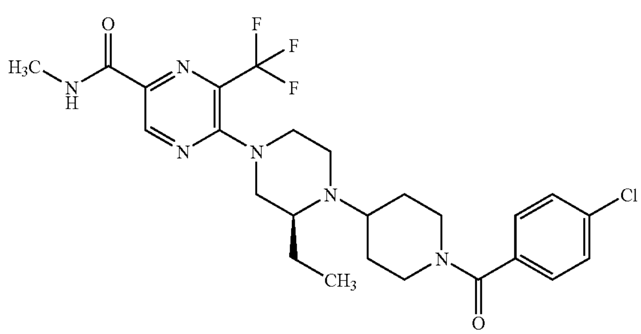 | A |

| Compound No. | Compound Structure | IC$_{50}$ |
|---|---|---|
| 478 | 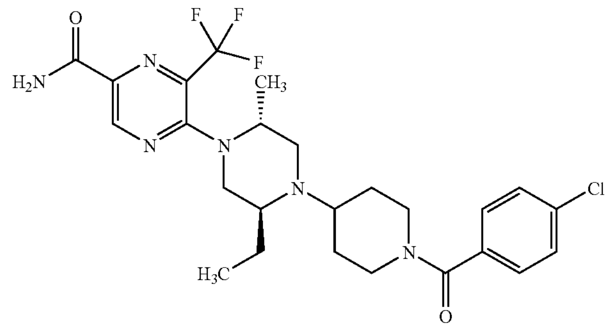 | A |
| 479 | 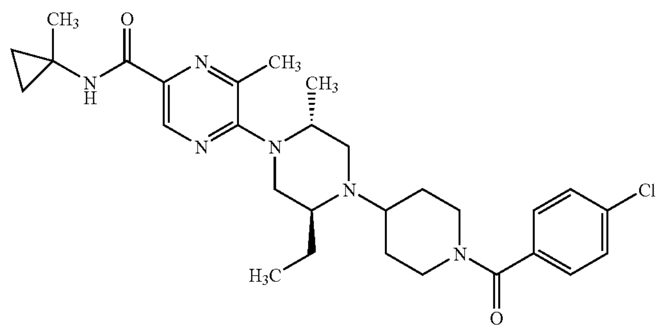 | A |
| 480 | 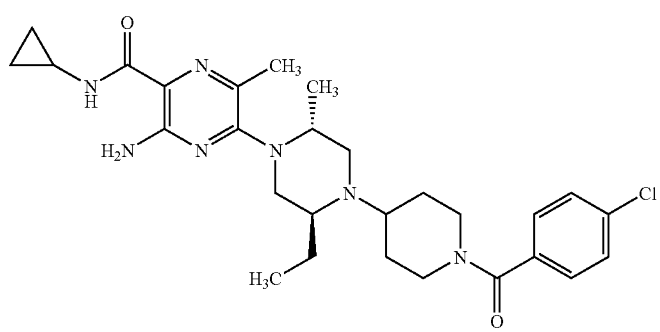 | A |
| 481 | 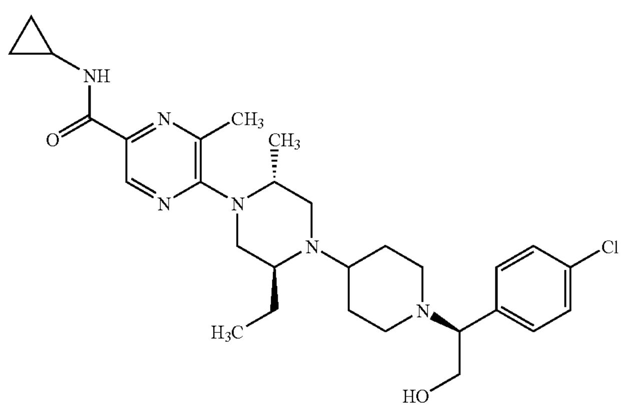 | A |

TABLE 1-continued
| Compound No. | Compound Structure | IC$_{50}$ |
|---|---|---|
| 482 | 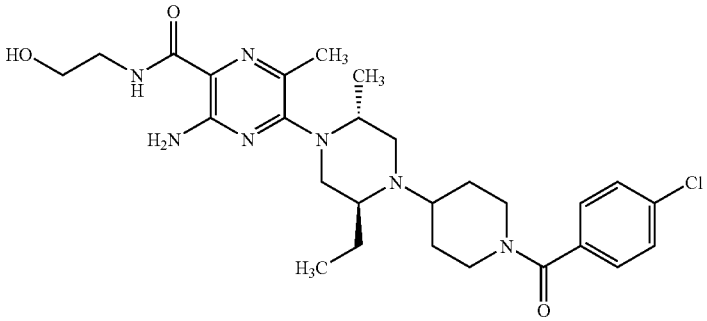 | A |
| 483 | 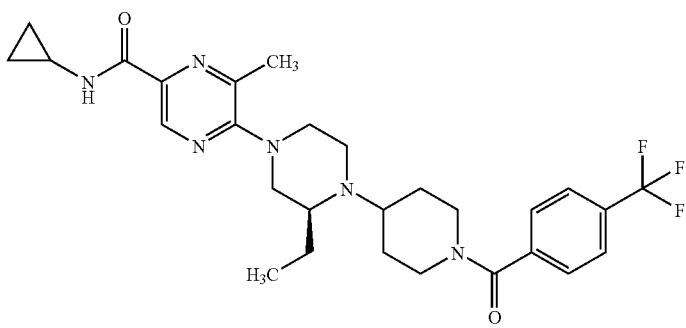 | A |
| 484 | 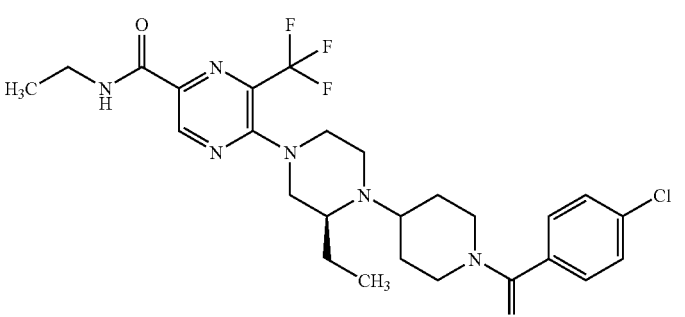 | A |
| 485 | 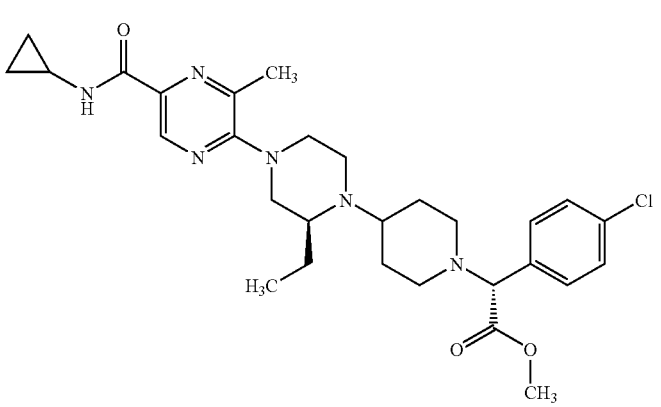 | A |

TABLE 1-continued

| Compound No. | Compound Structure | IC$_{50}$ |
|---|---|---|
| 486 | 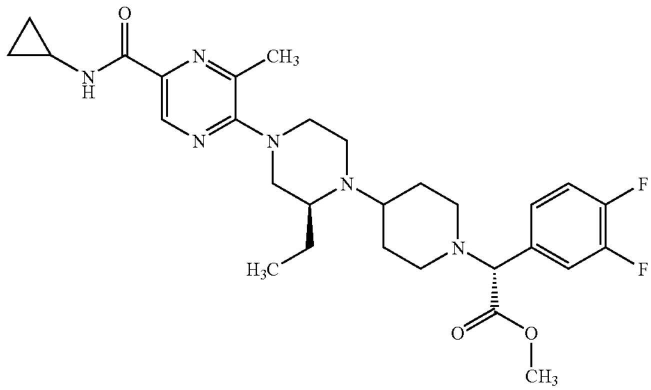 | A |
| 487 | 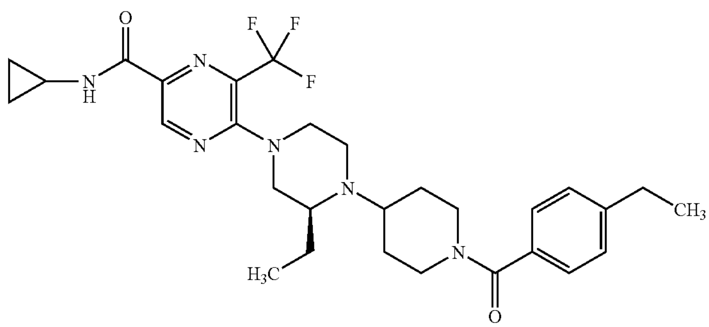 | A |
| 488 | 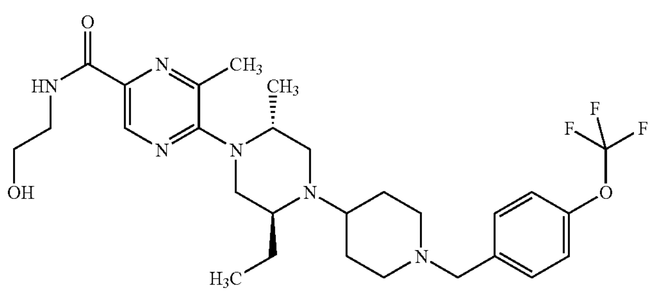 | A |
| 489 | 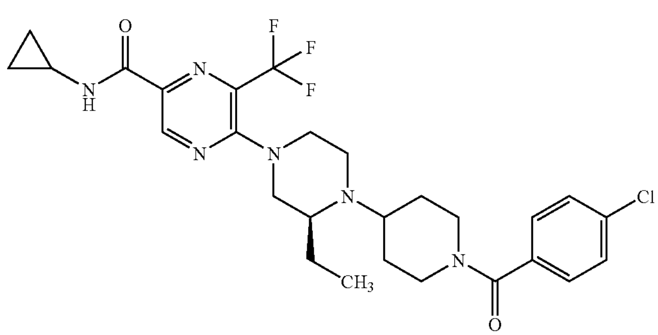 | A |

TABLE 1-continued
| Compound No. | Compound Structure | IC$_{50}$ |
|---|---|---|
| 490 | 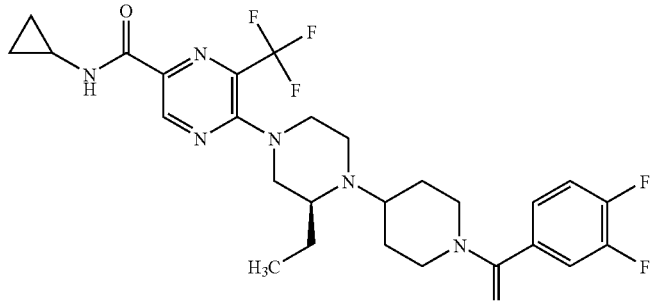 | A |
| 491 | 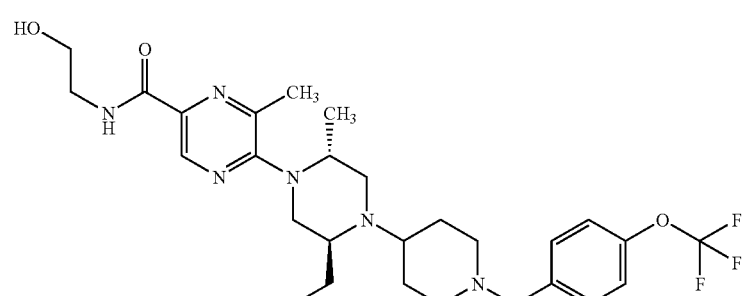 | A |
| 492 | 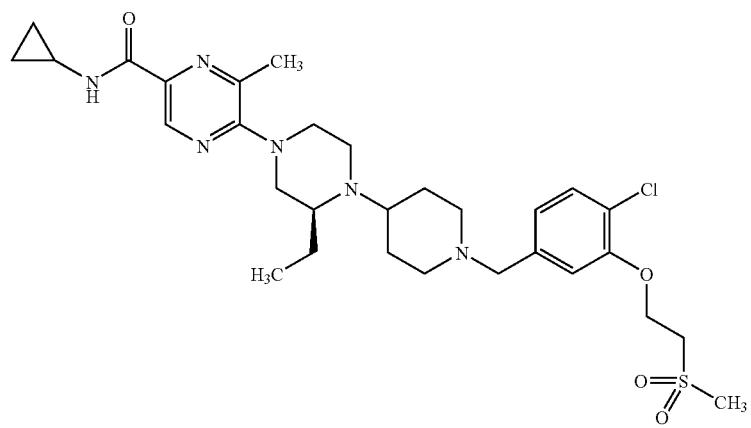 | A | or pharmaceutically acceptable salts, solvates or esters thereof.
In another aspect of the invention, the compound according to Formula 1 is selected from the group consisting of:
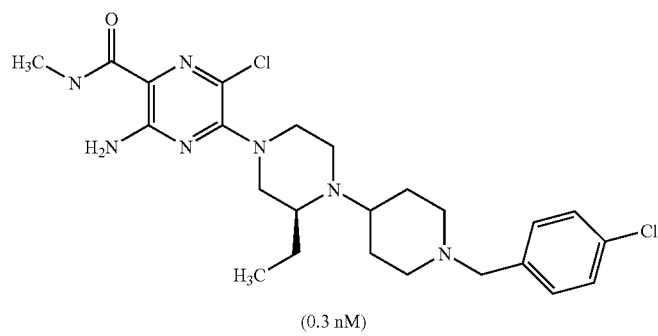
(0.3 nM)
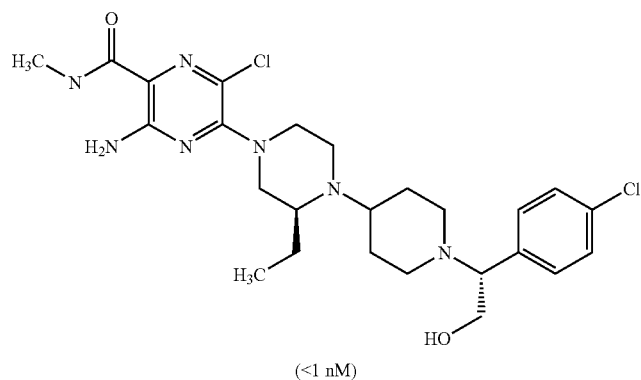
(<1 nM)
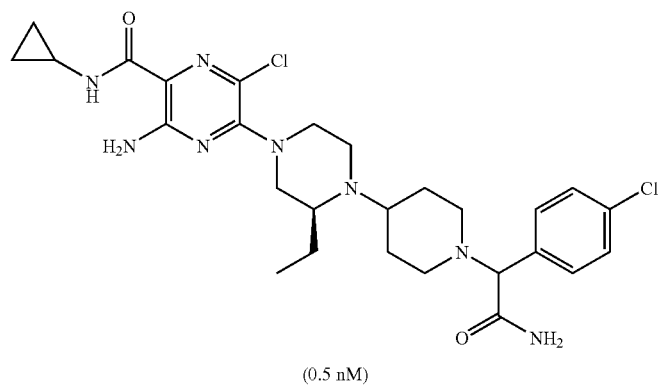
(0.5 nM)
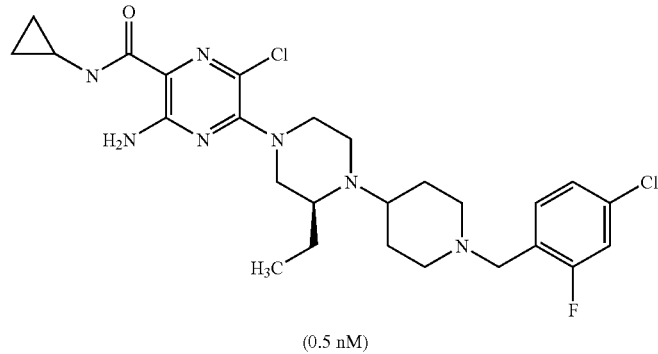
(0.5 nM)

-continued
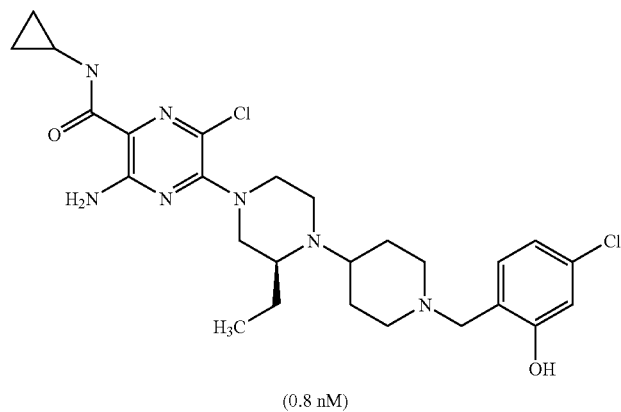
(0.8 nM)
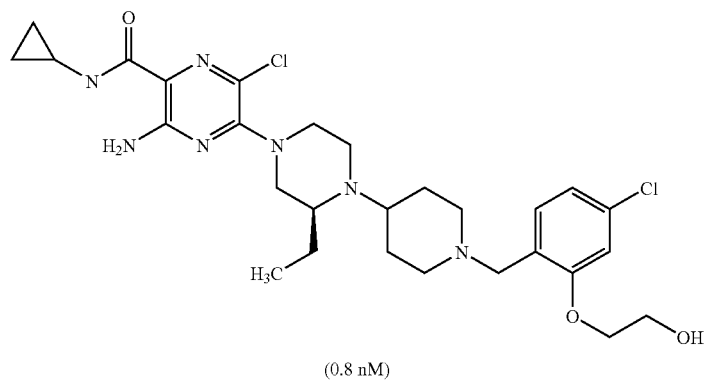
(0.8 nM)
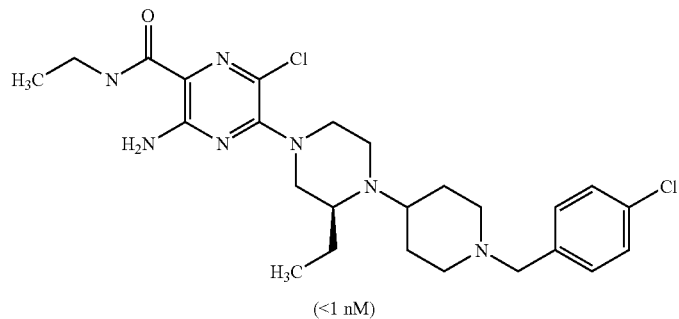
(<1 nM)
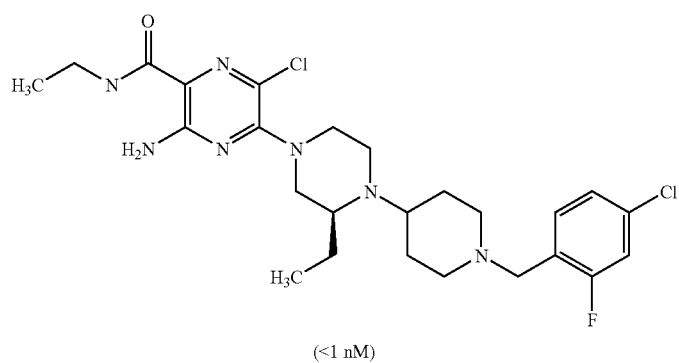
(<1 nM)

-continued
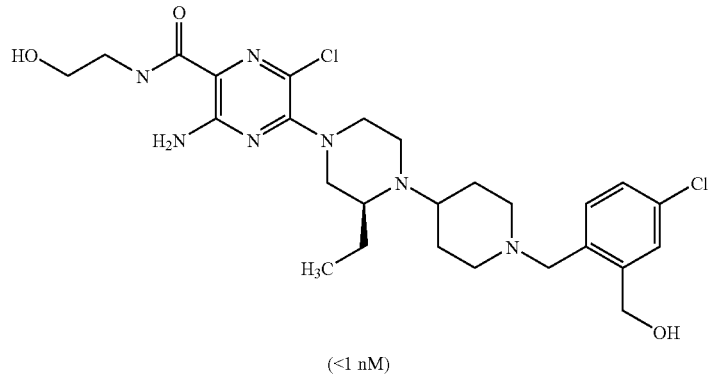
(<1 nM)
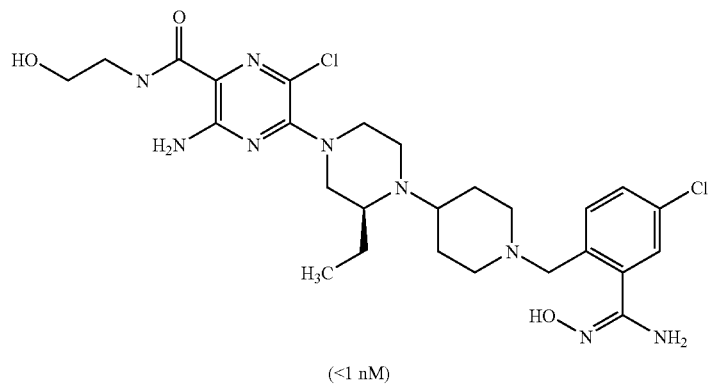
(<1 nM)
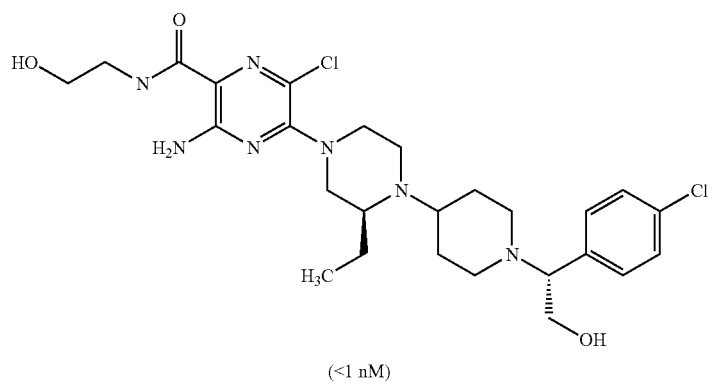
(<1 nM)
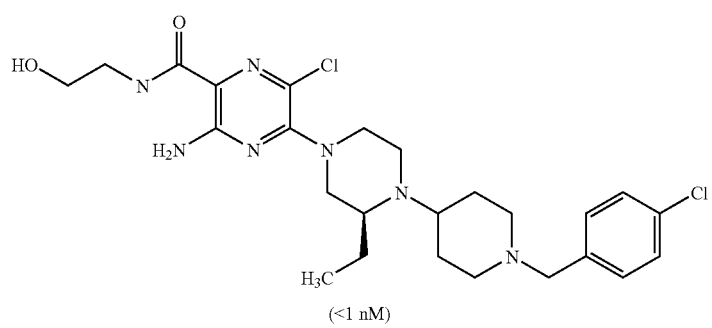
(<1 nM)

-continued
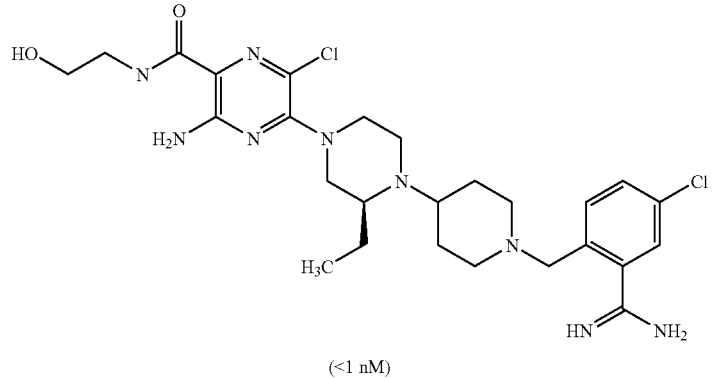
(<1 nM)
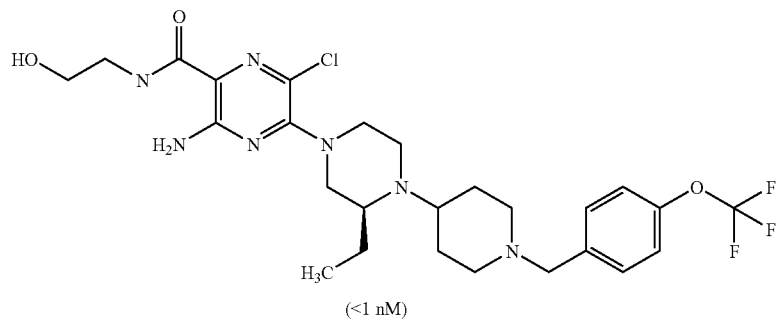
(<1 nM)
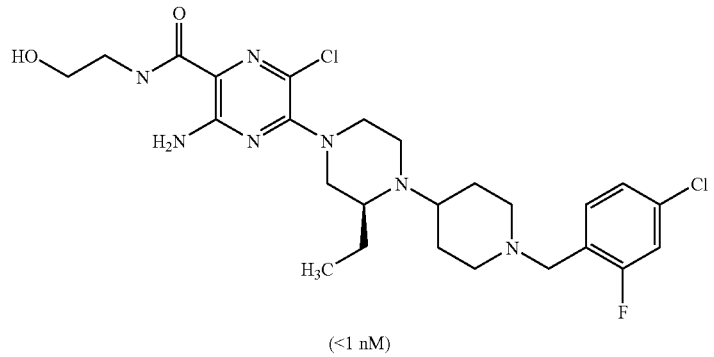
(<1 nM)
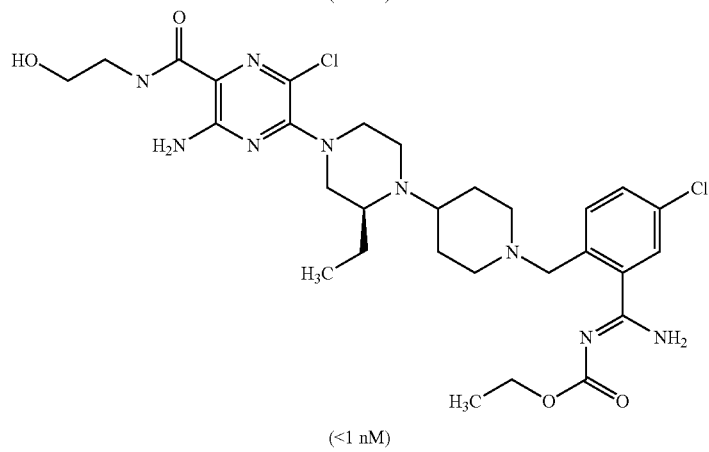
(<1 nM)

-continued
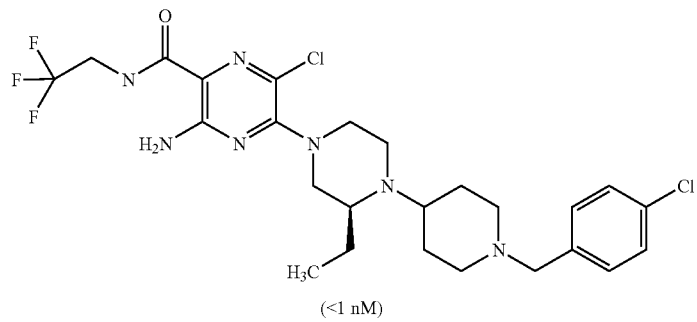
(<1 nM)
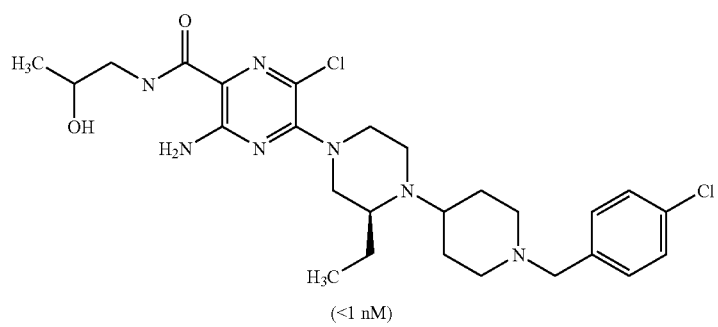
(<1 nM)
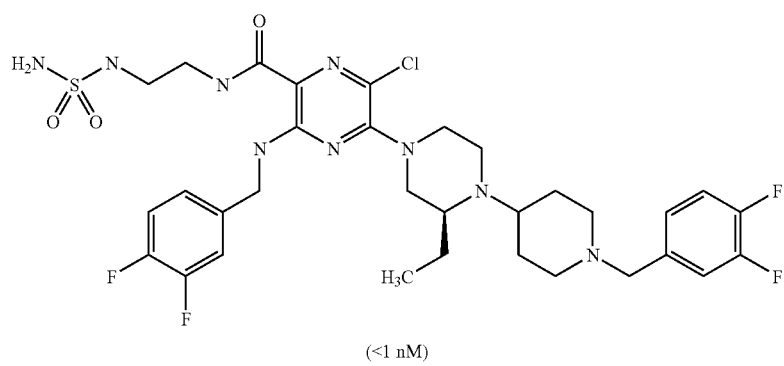
(<1 nM)
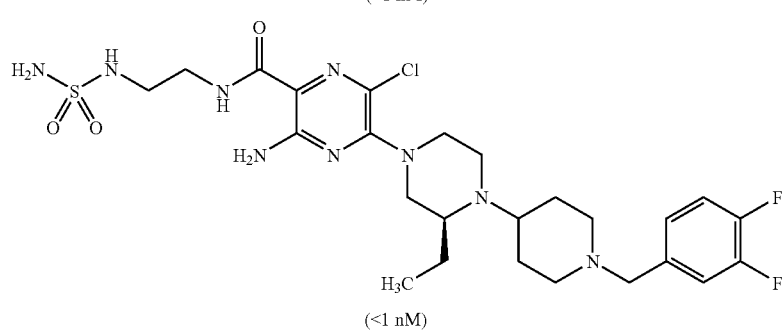
(<1 nM)
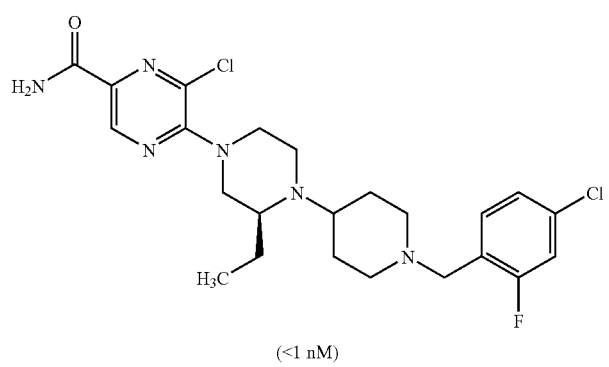
(<1 nM)

-continued
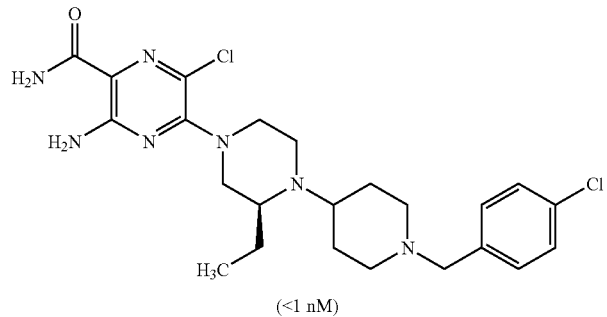
(<1 nM)
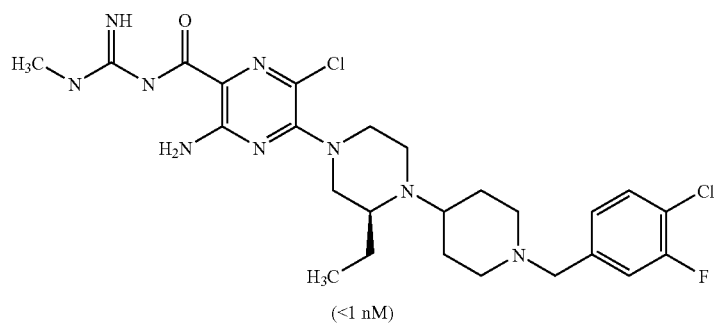
(<1 nM)
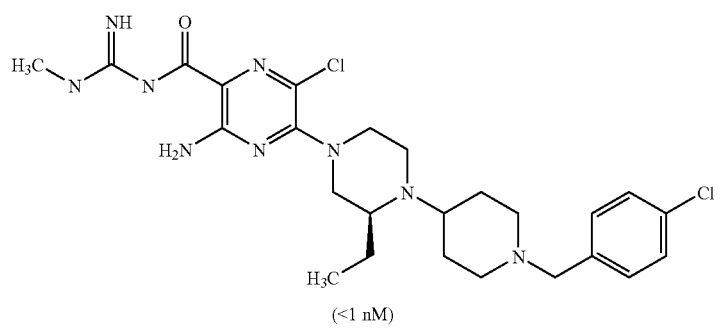
(<1 nM)
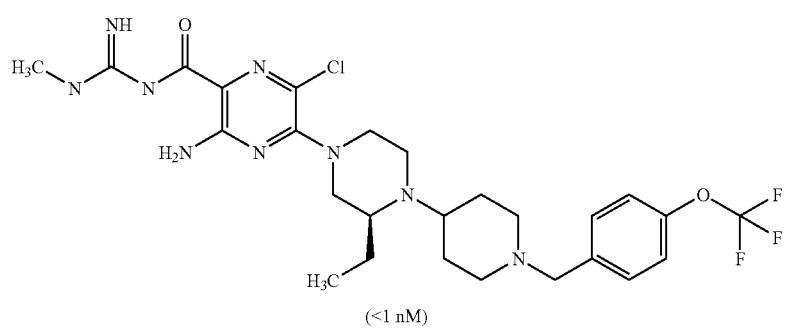
(<1 nM)
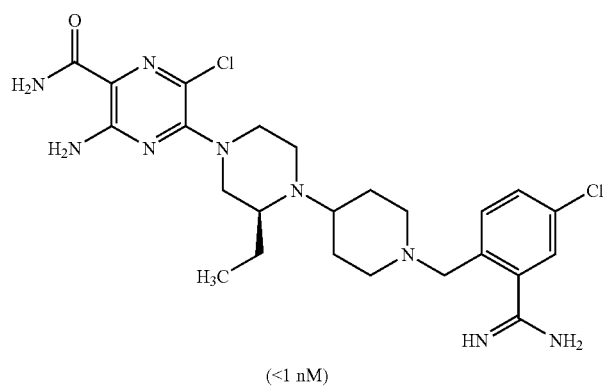
(<1 nM)

-continued
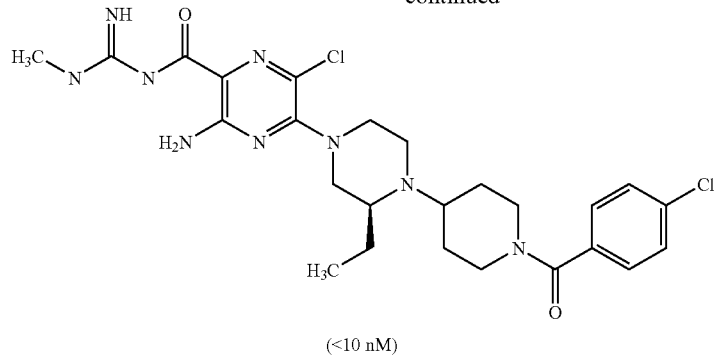
(<10 nM)
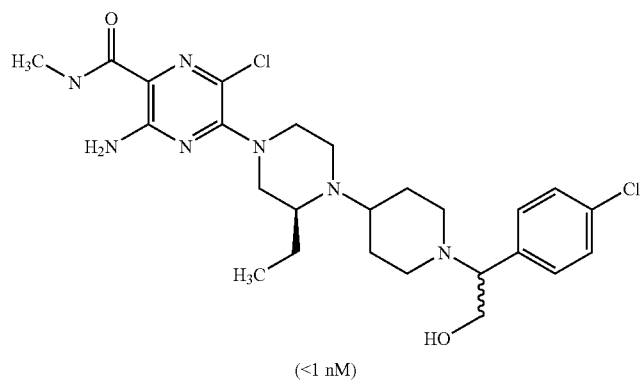
(<1 nM)
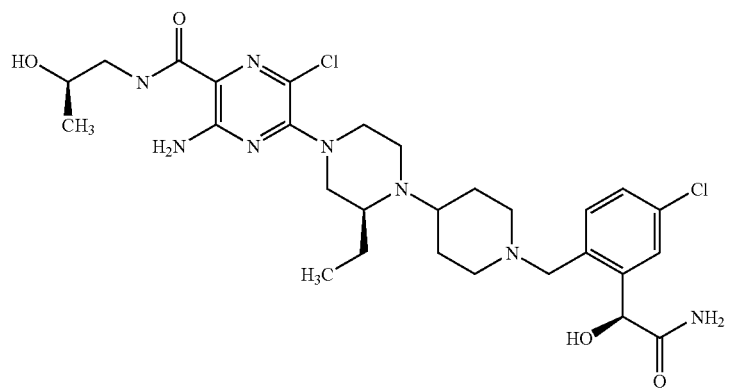
(<10 nM)
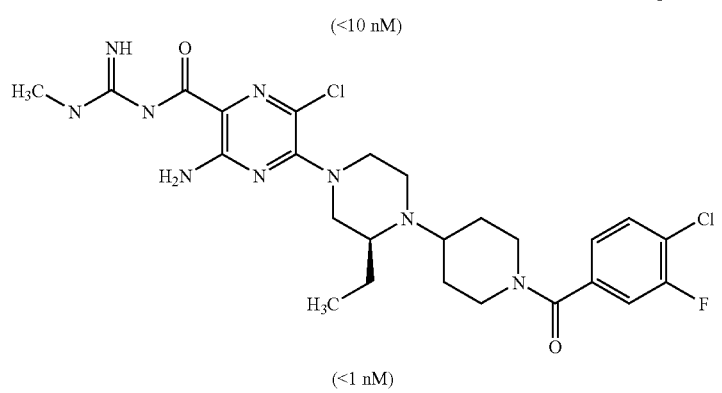
(<1 nM)

-continued
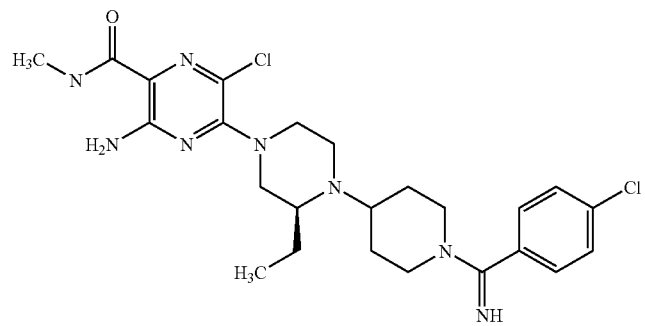
(1.5 nM)
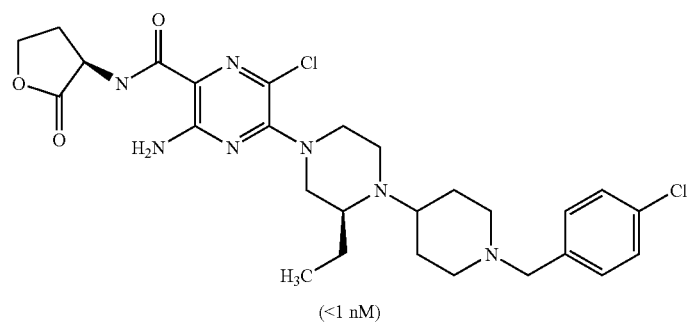
(<1 nM)
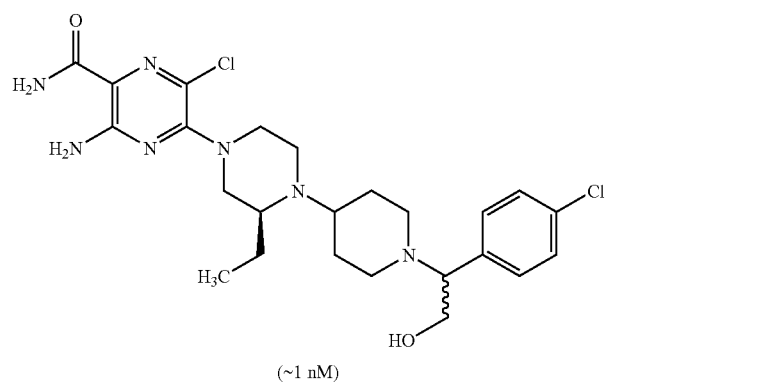
(~1 nM)
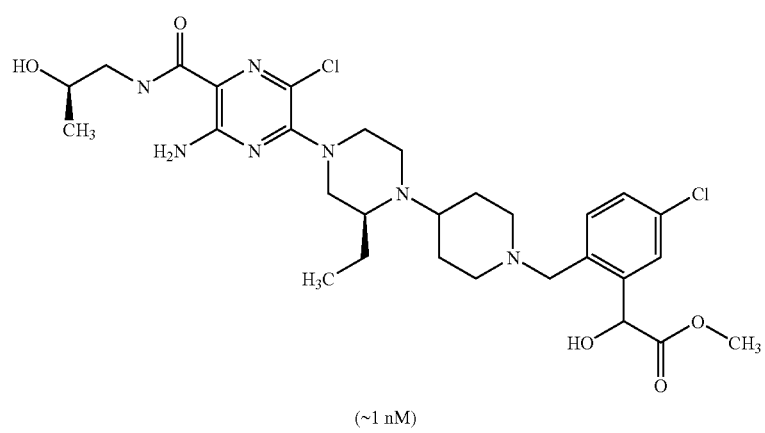
(~1 nM)

-continued
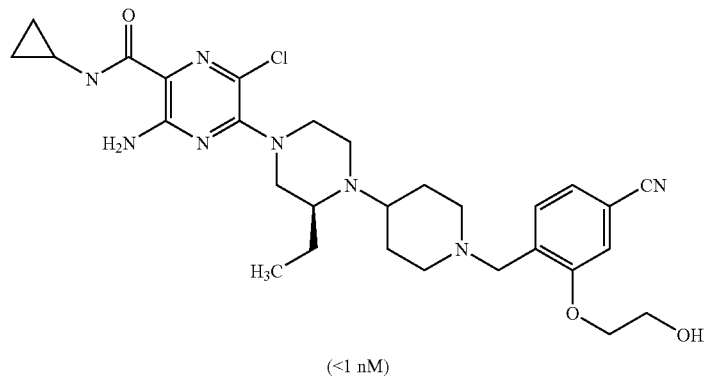
(<1 nM)
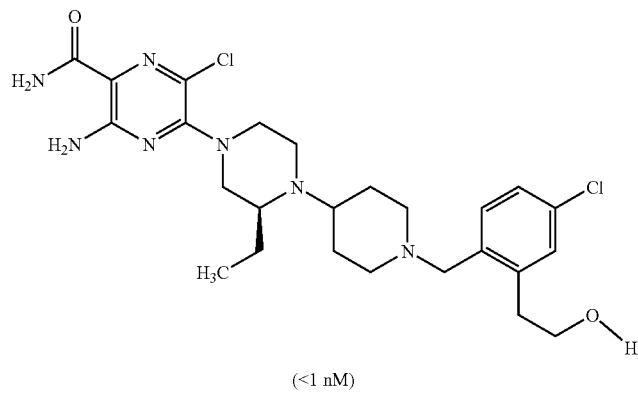
(<1 nM)
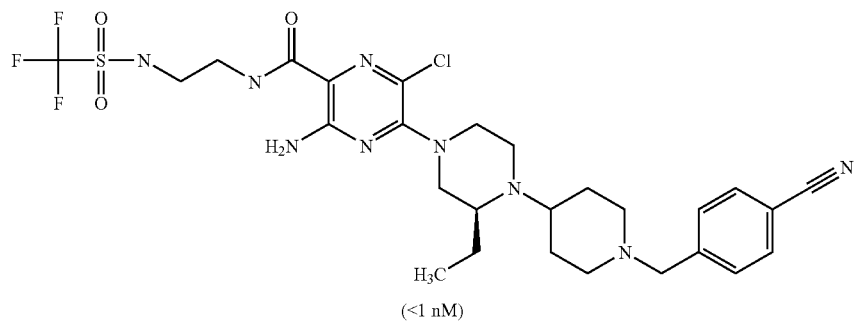
(<1 nM)
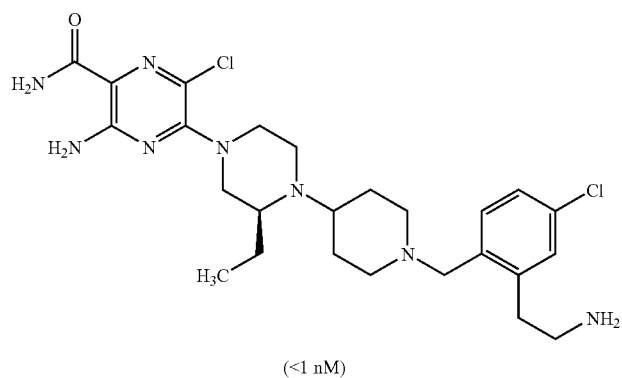
(<1 nM)

-continued
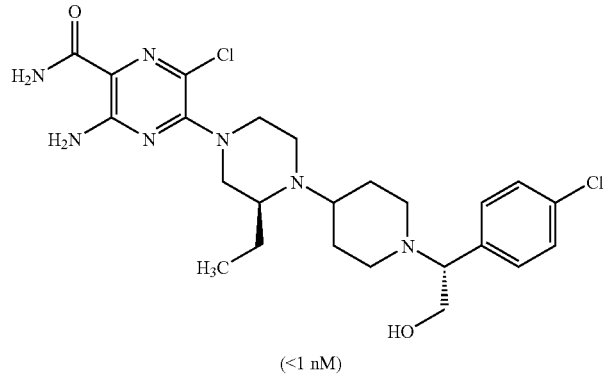
(<1 nM)
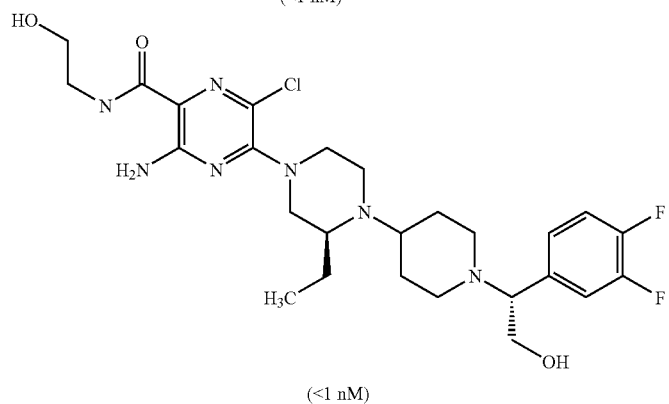
(<1 nM)
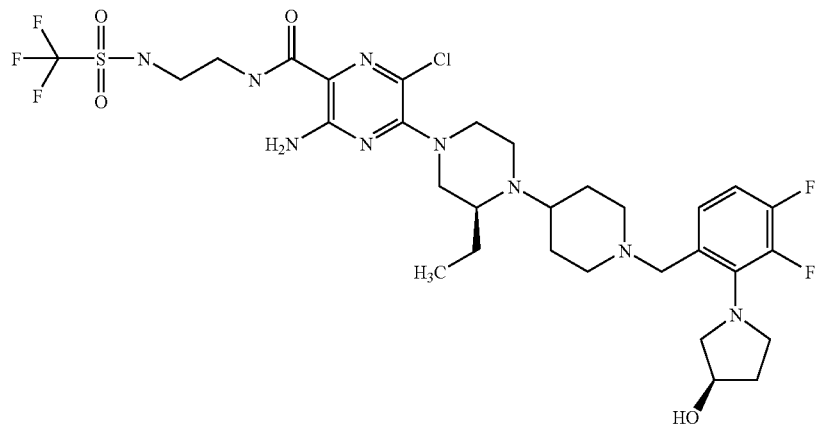
(<1 nM)
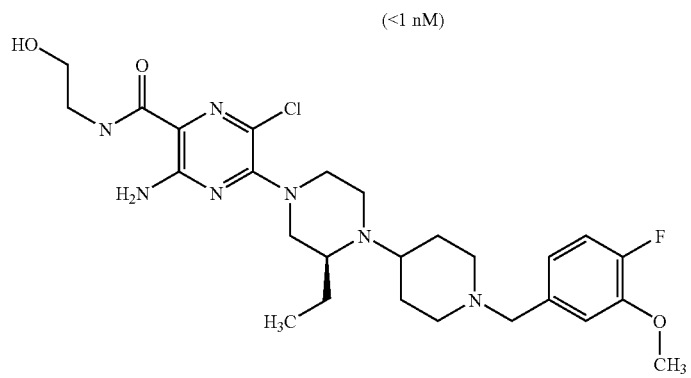
(<1 nM)

-continued
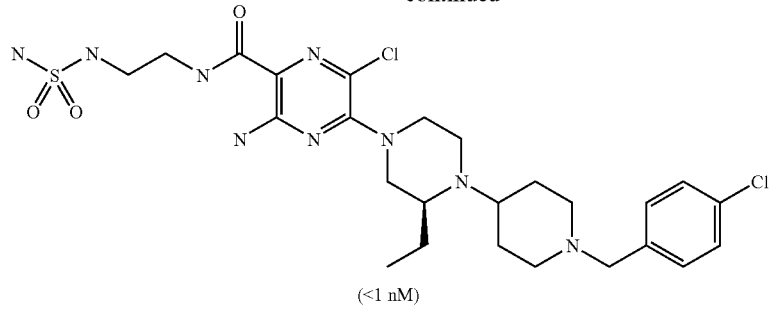
(<1 nM)
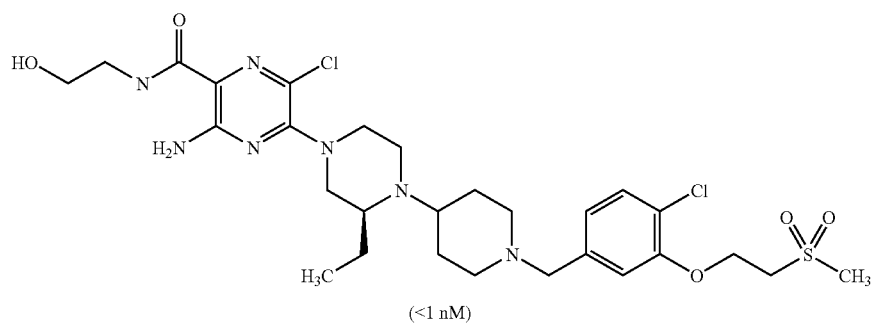
(<1 nM)
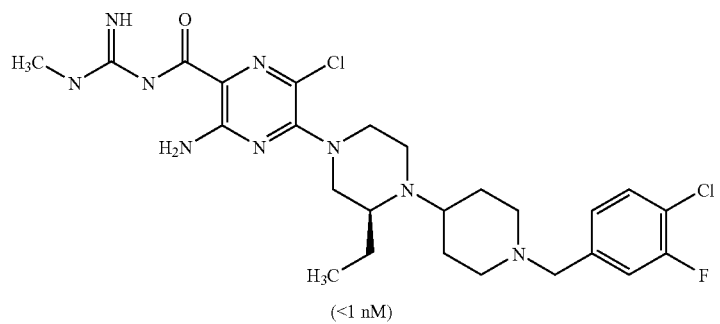
(<1 nM)
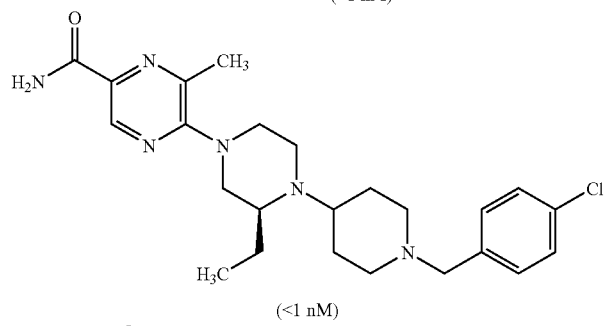
(<1 nM)
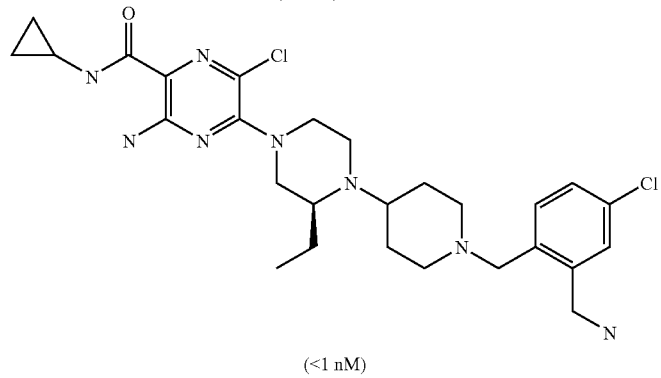
(<1 nM)

-continued
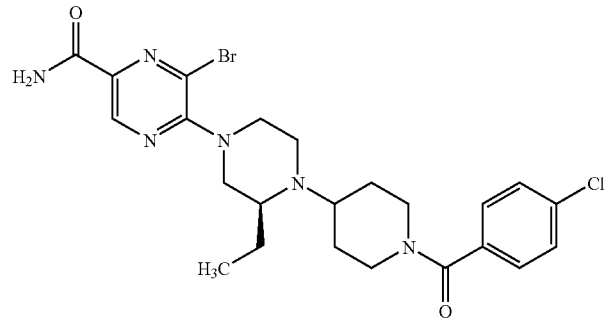
(<1 nM)
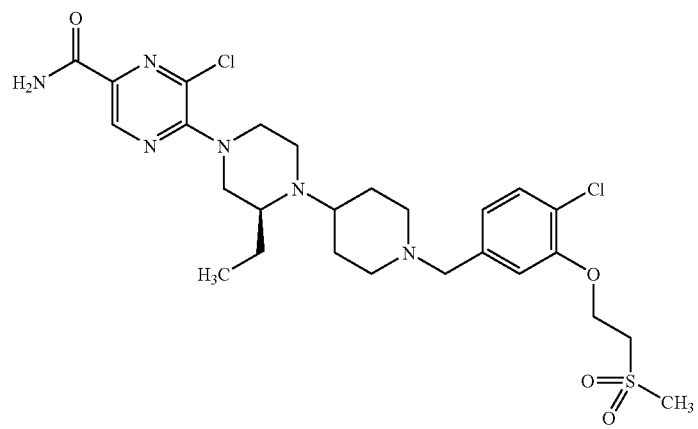
(<1 nM)
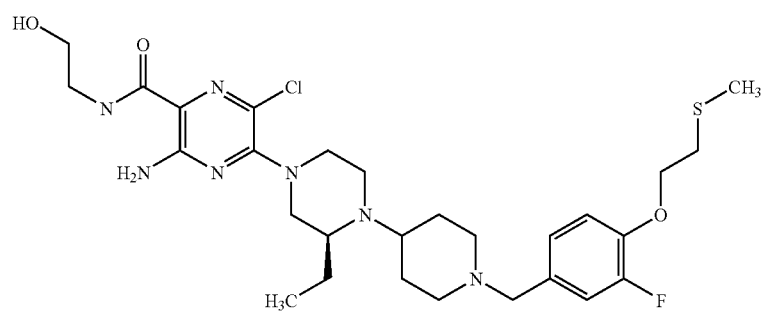
(<1 nM)
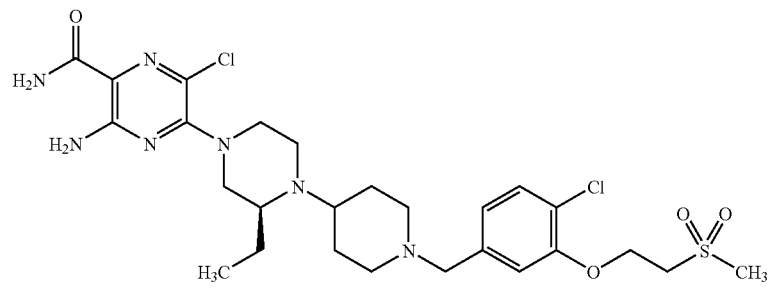
(<1 nM)

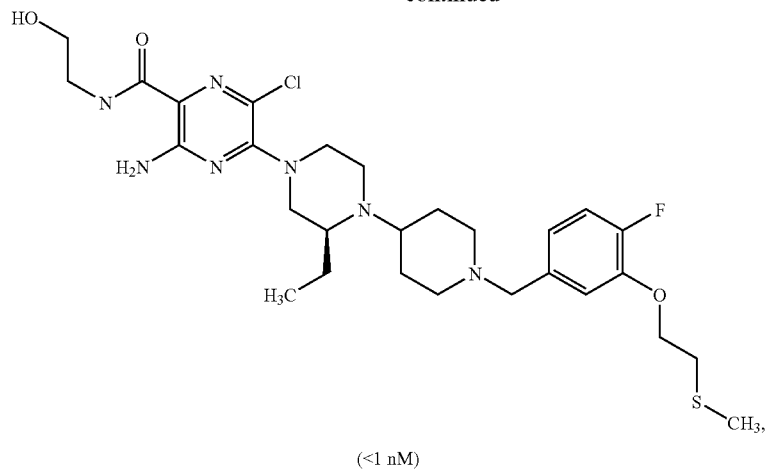
(<1 nM)
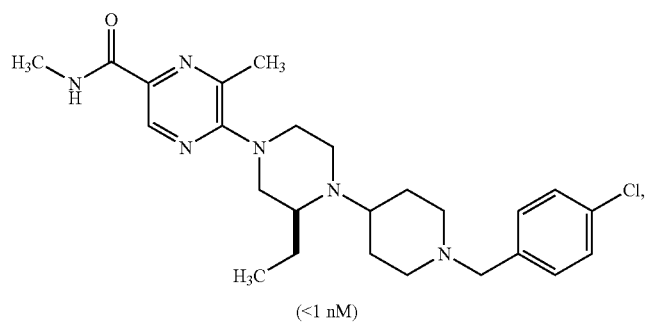
(<1 nM)
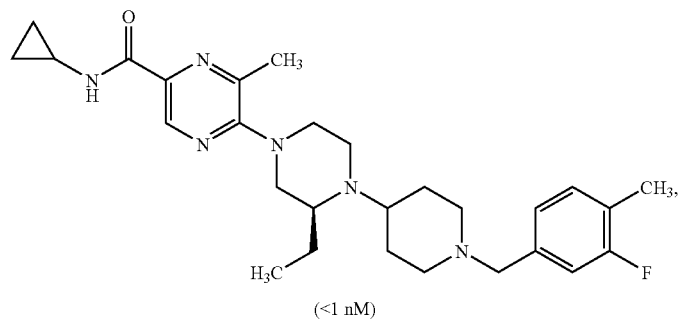
(<1 nM)
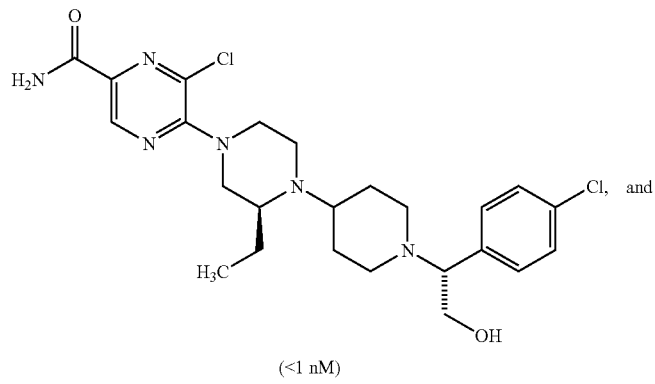
(<1 nM)

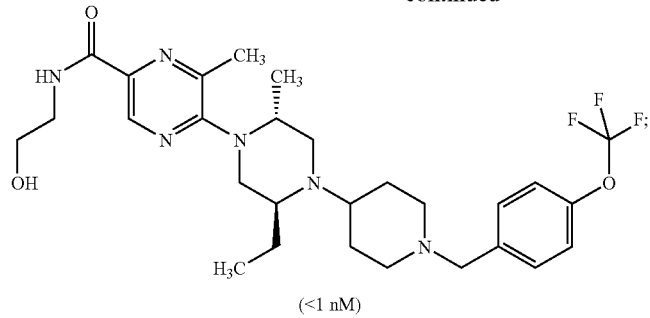
(<1 nM)
or pharmaceutically acceptable salts, solvates or esters thereof. The human IC$_{50}$ values (in nM) have been provided for each compound (underneath the structure) above.
In another aspect of the invention, the compound according to Formula 1 is selected from the group consisting of compounds of the formulae:
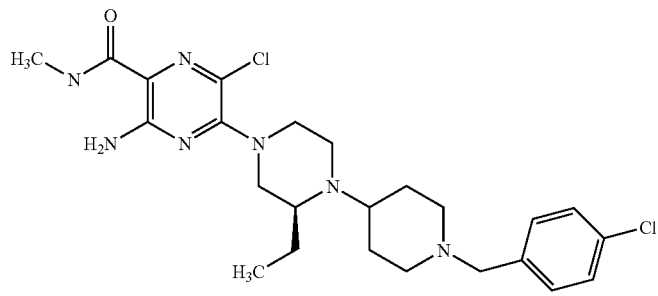
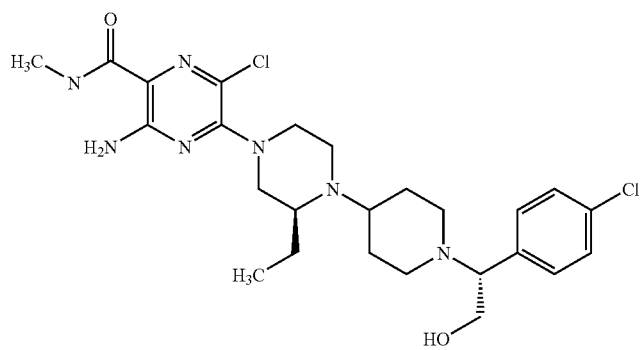
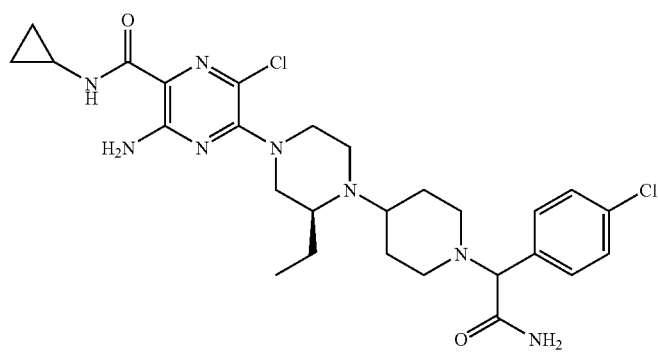

-continued
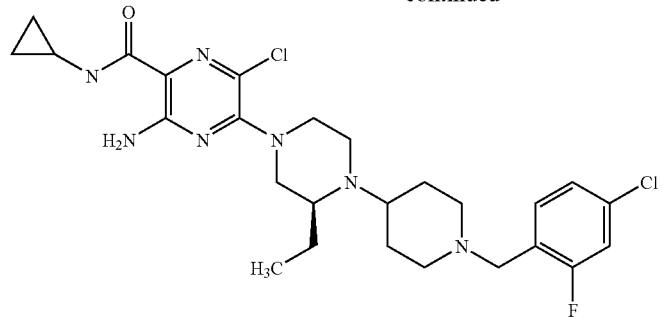
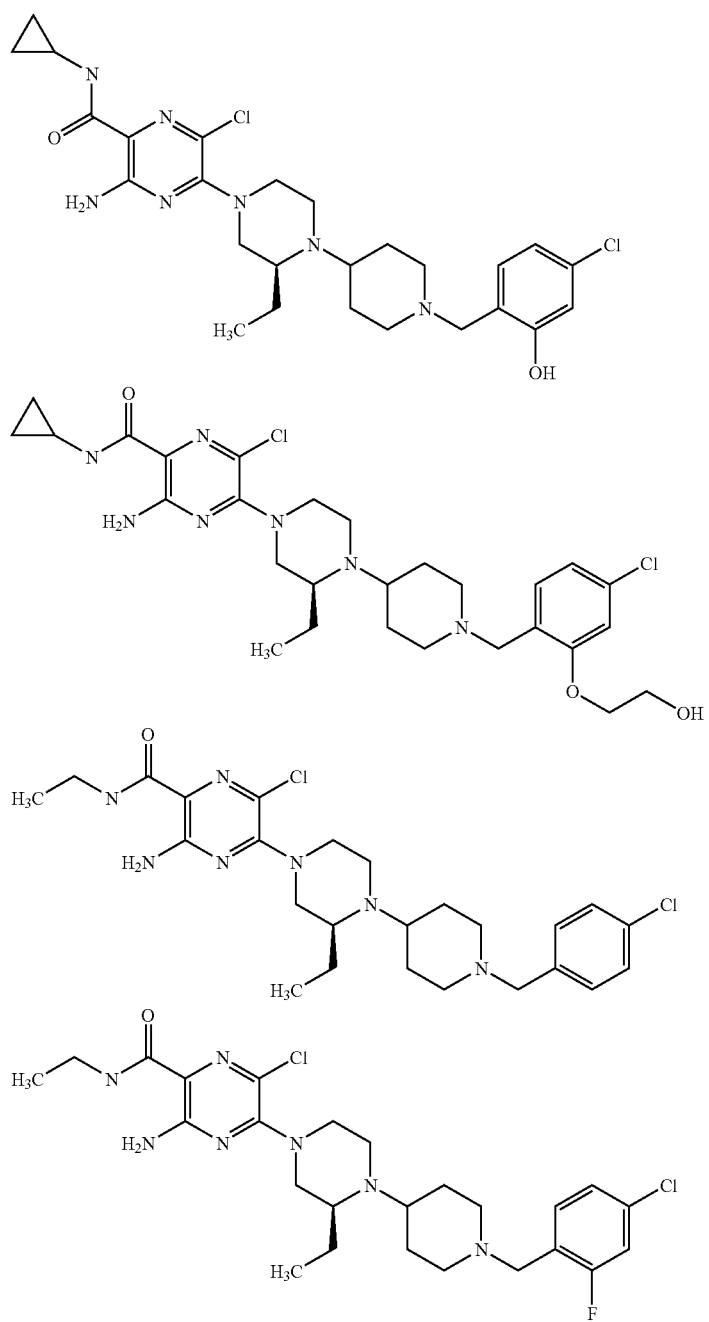

-continued
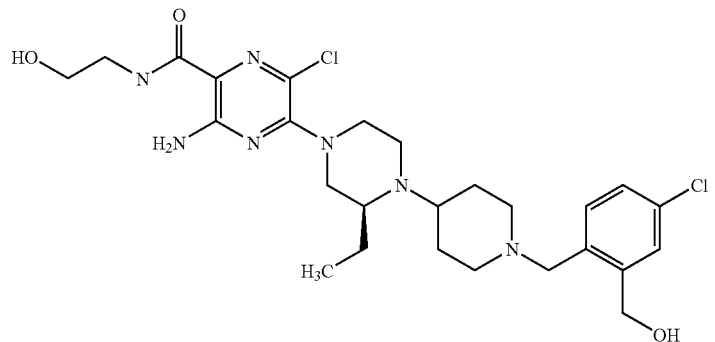
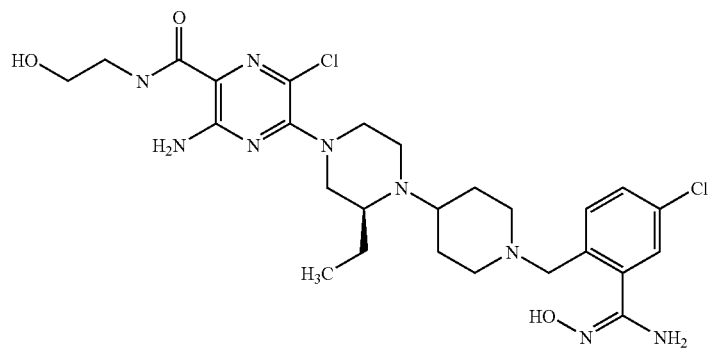
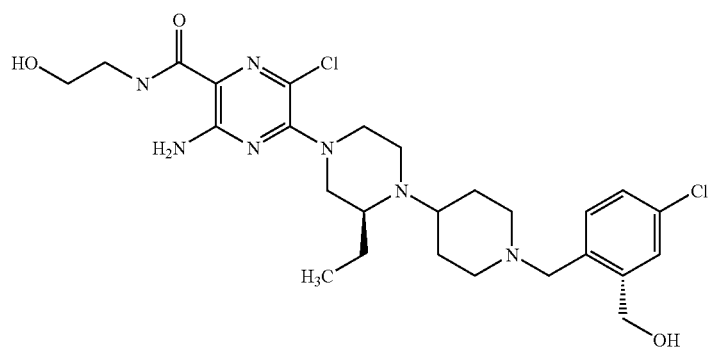
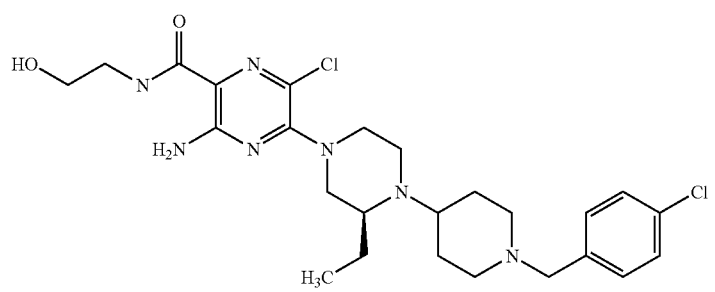
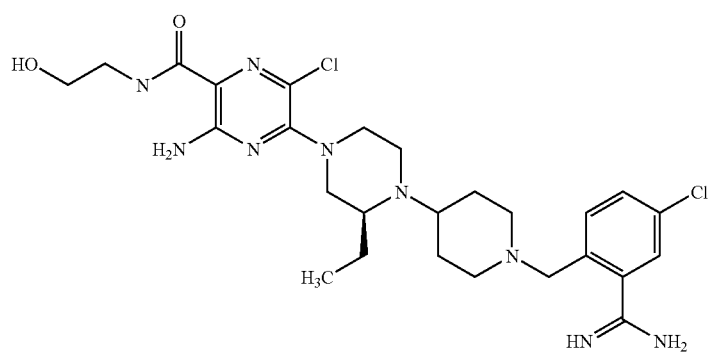

-continued
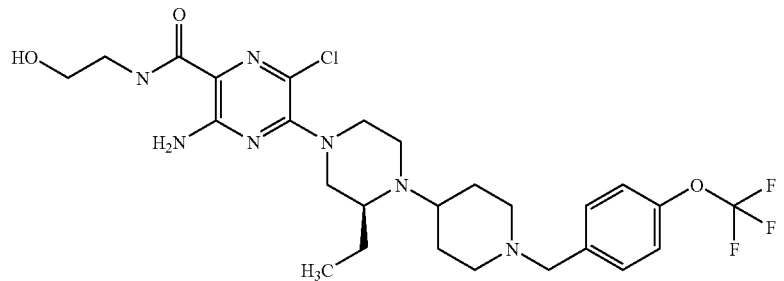
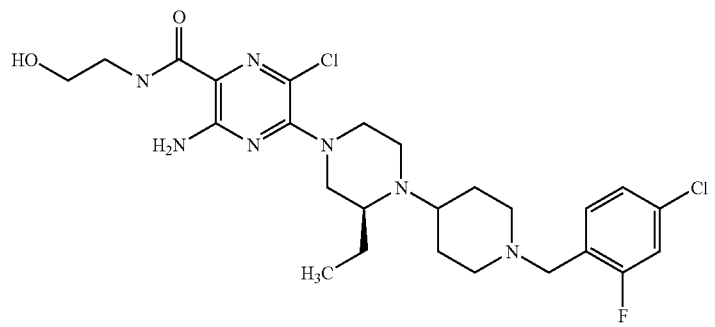
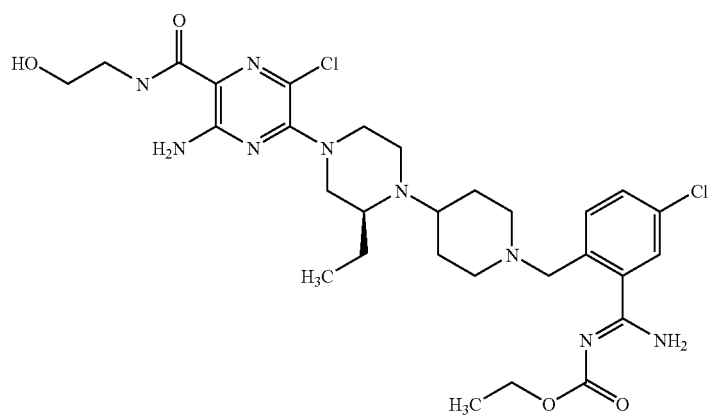
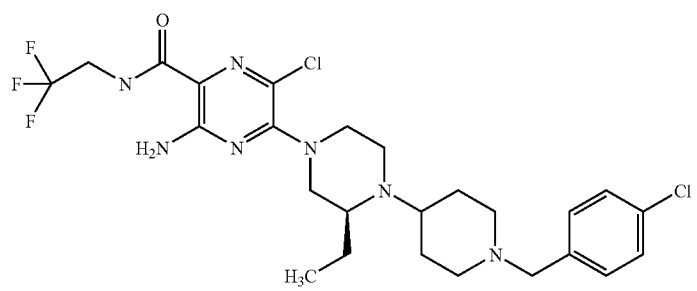
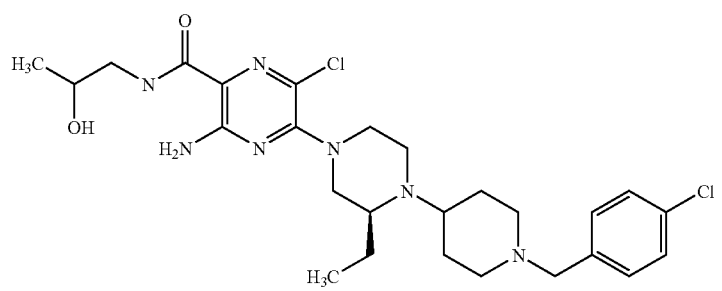

-continued
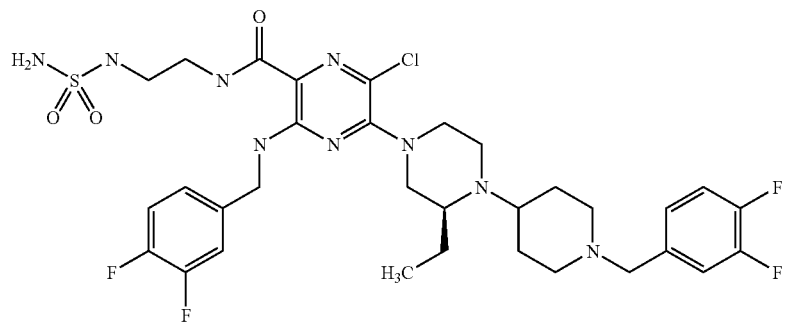
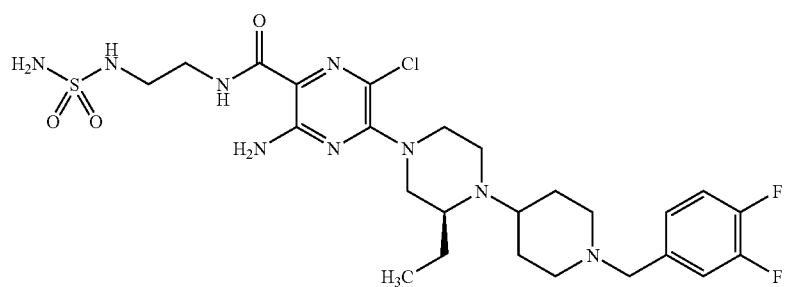
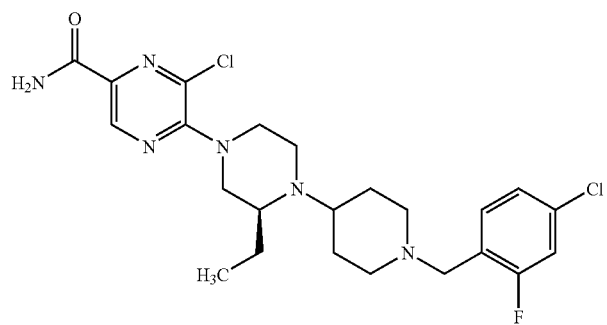
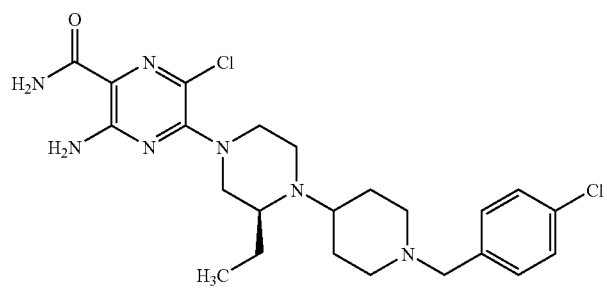
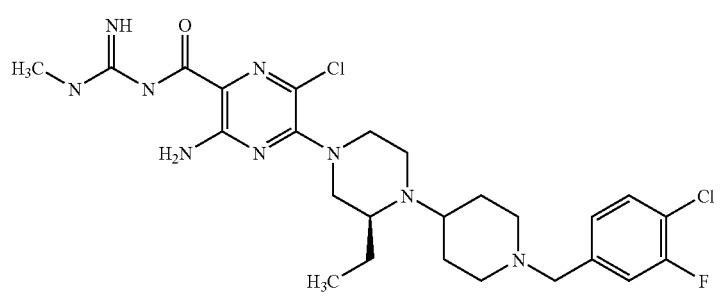

-continued
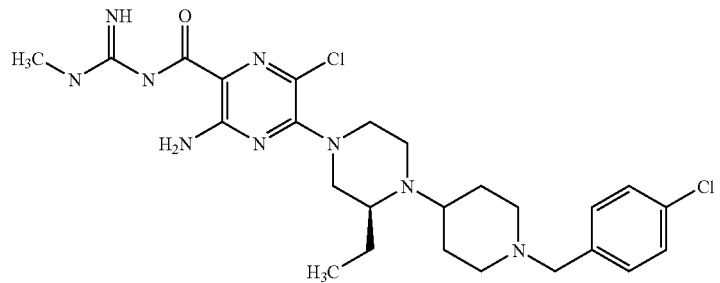
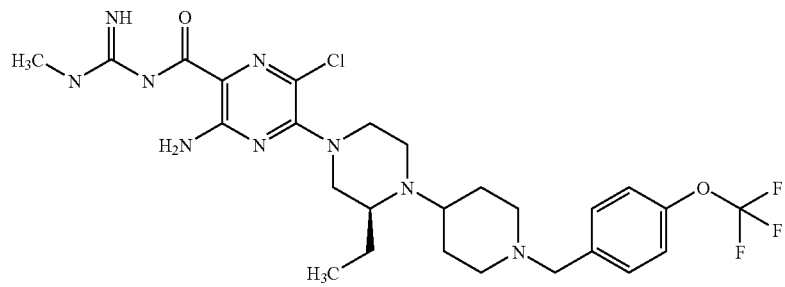
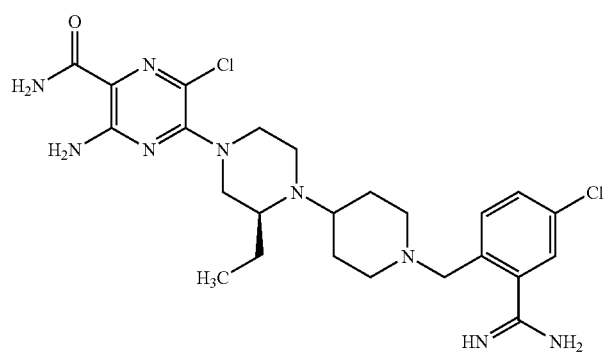
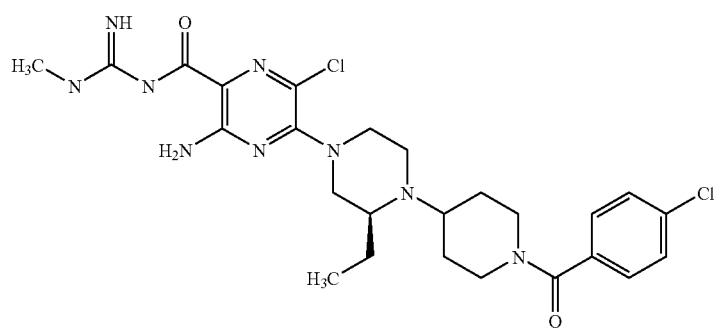
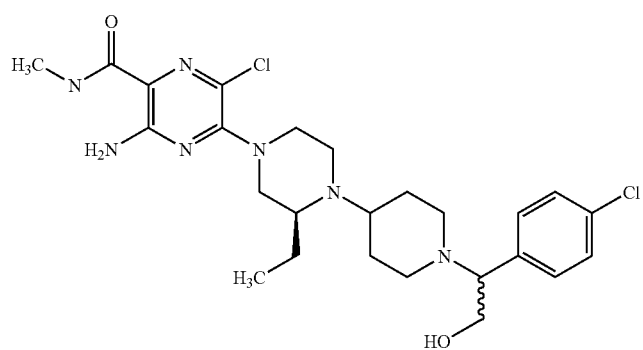

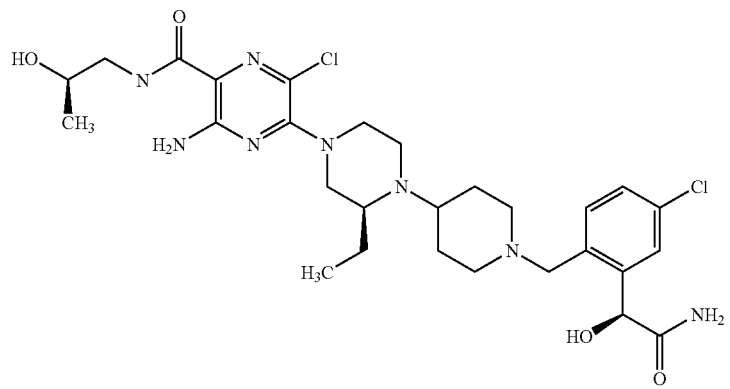
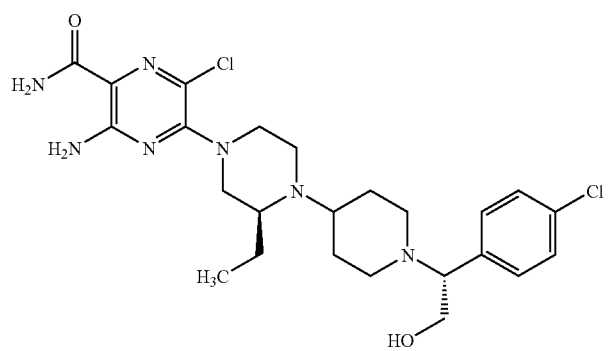
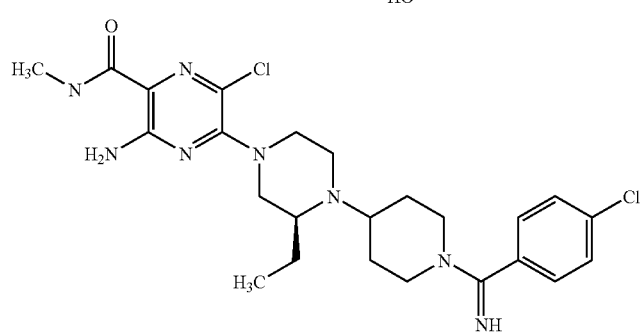
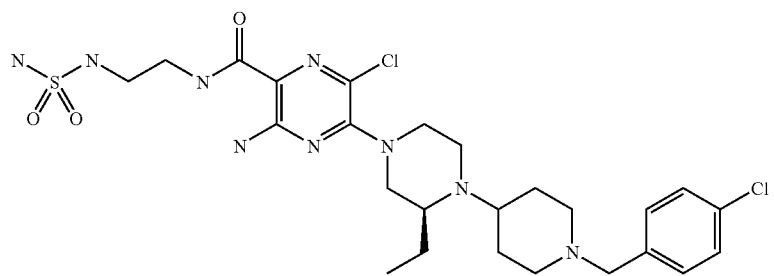
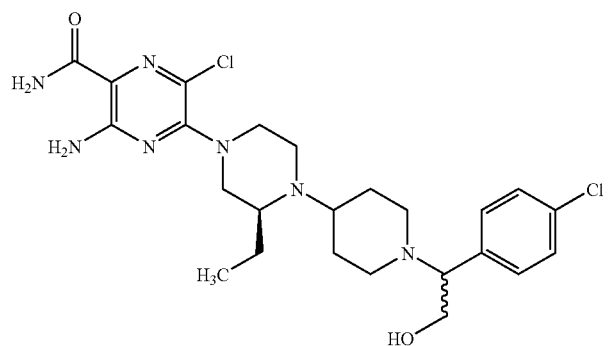

-continued
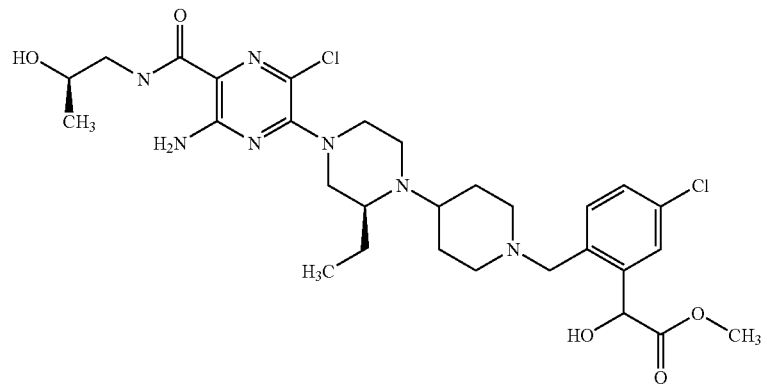
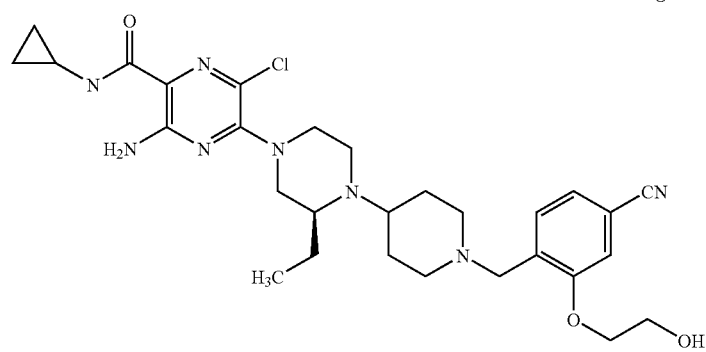
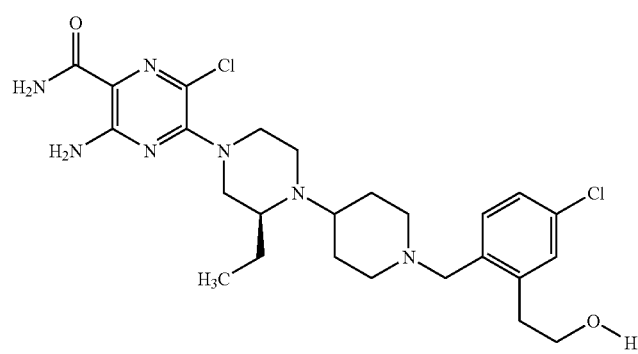
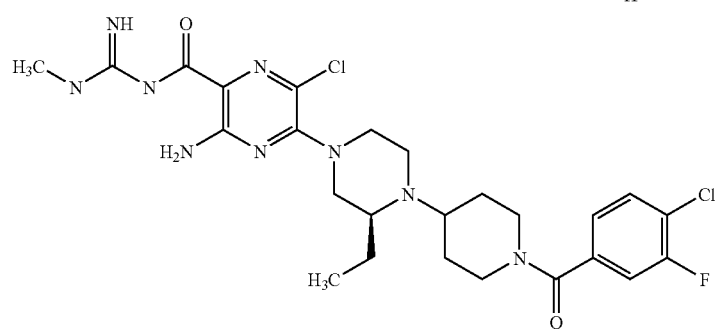
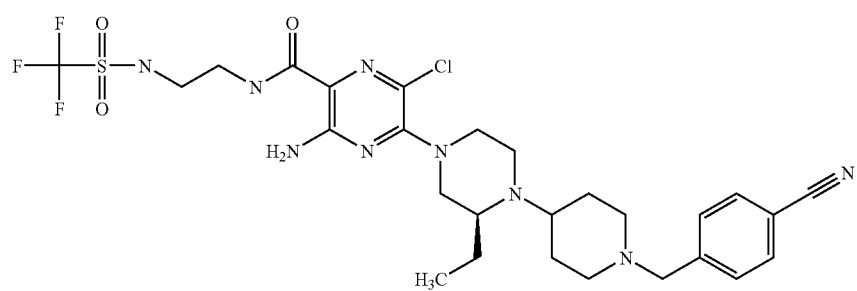

-continued
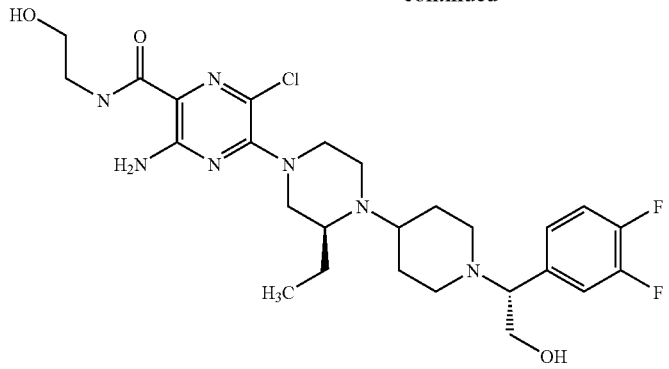
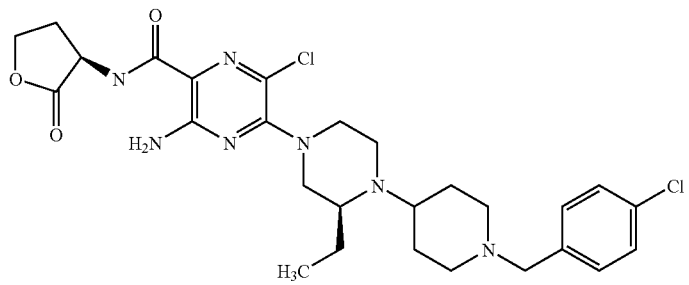
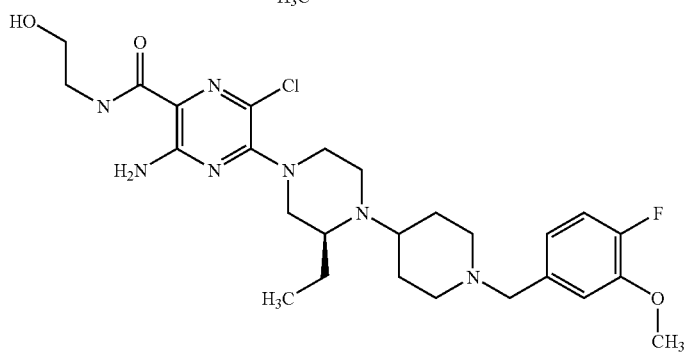
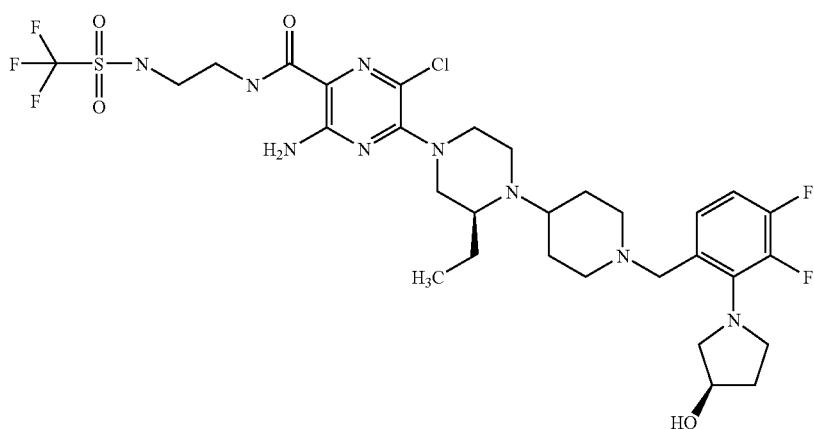
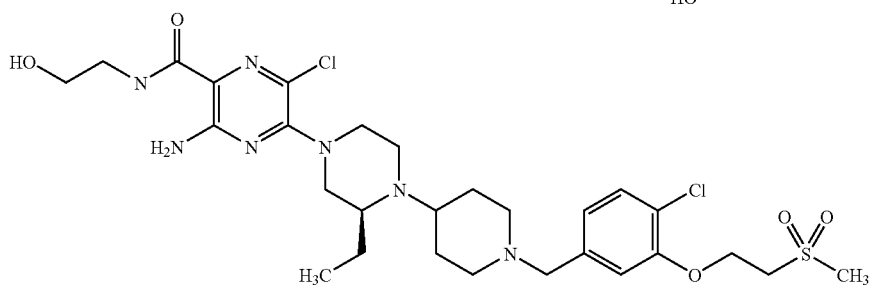

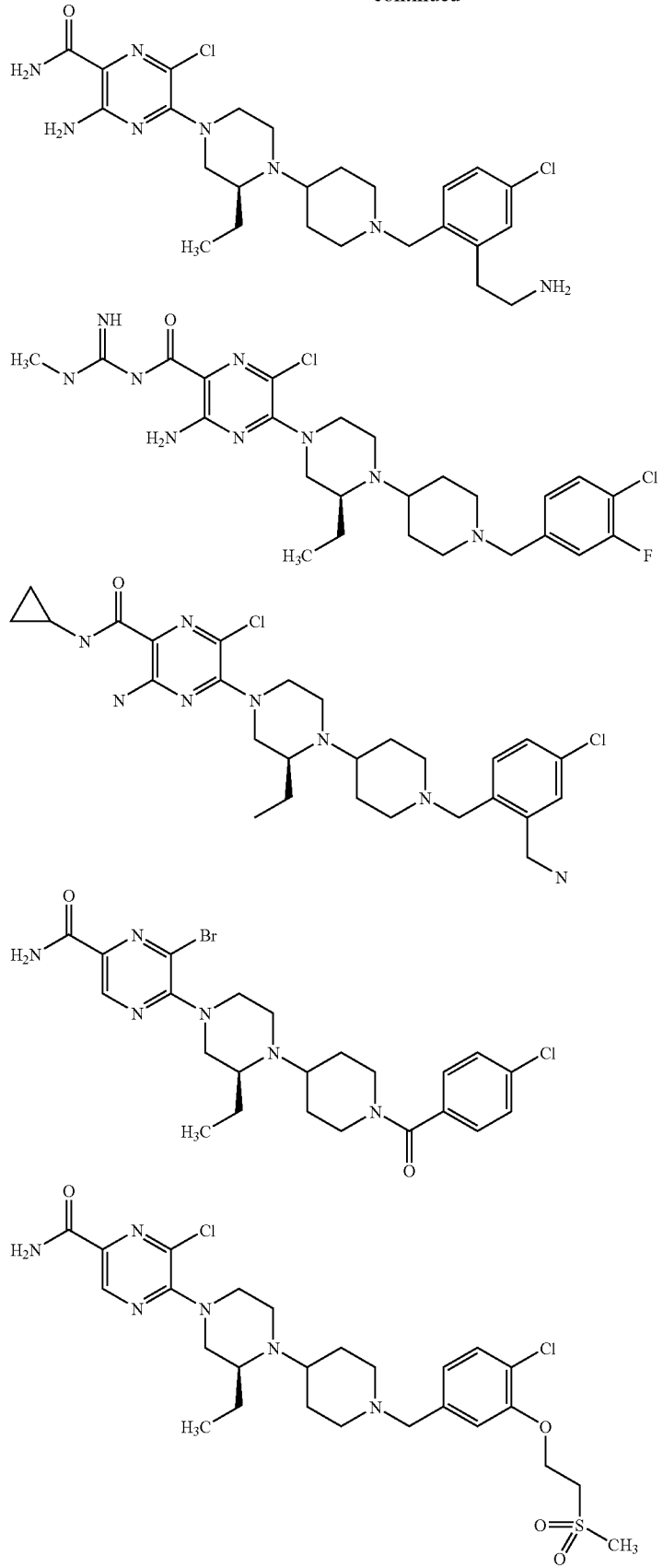

-continued
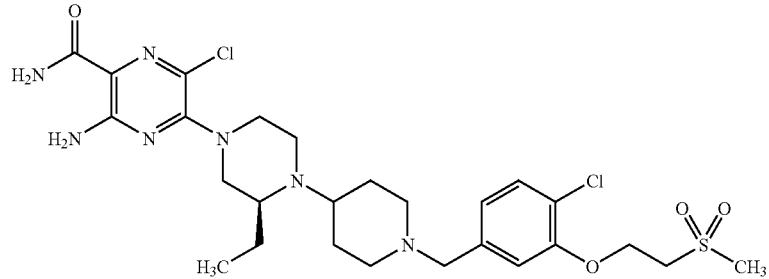
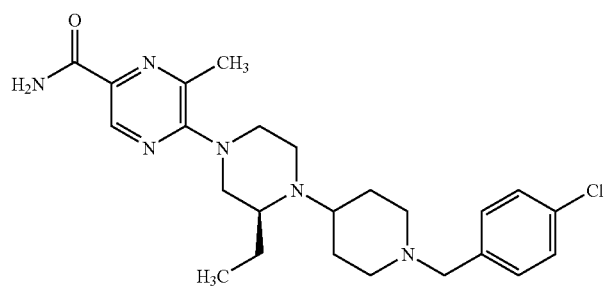
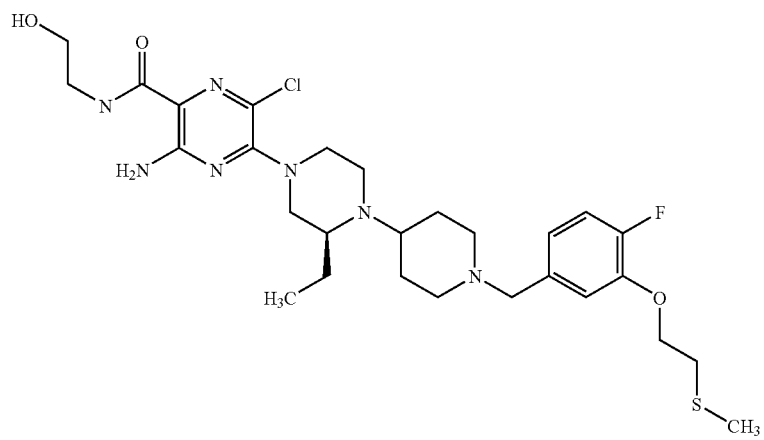
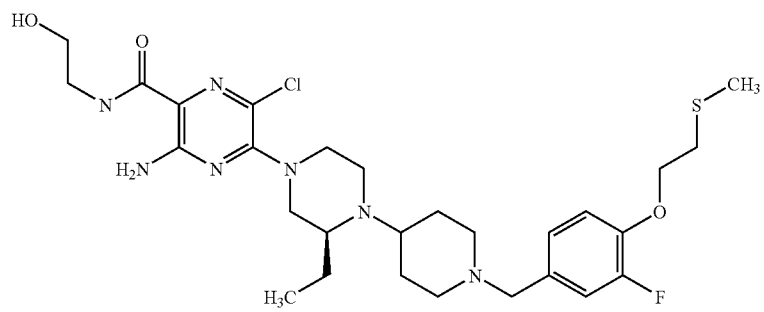

or pharmaceutically acceptable salts, solvates or esters thereof.

In another embodiment, a compound is selected from the group consisting of the following formulae:

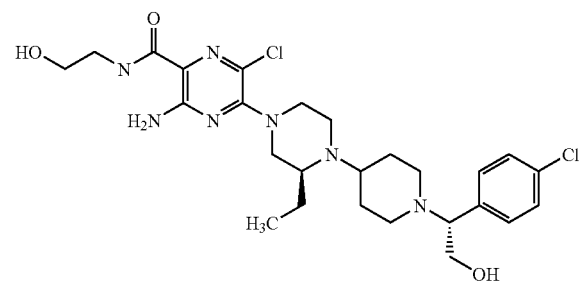

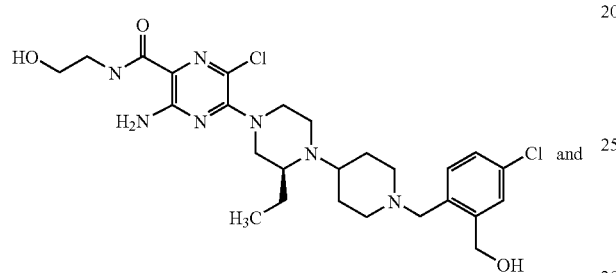

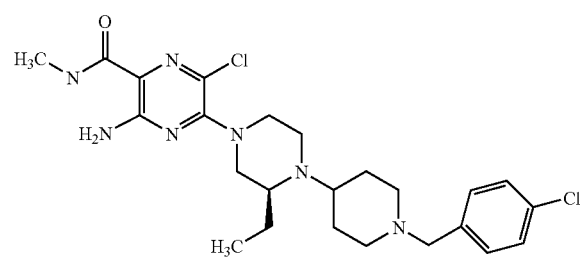

or pharmaceutically acceptable salts, solvates or esters thereof.

In another embodiment, the compound of Formula 1 is selected from the group consisting of In another embodiment, the compound of Formula 1 is selected from the group consisting of Formula 7, Formula 8, Formula 9, Formula 10, Formula 11, Formula 12 and Formula 13 (all of compounds of Formula 7-13 have human $IC_{50}$ values of less than 1 nM):

Formula 7

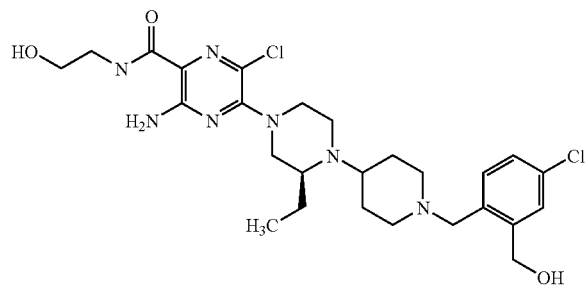

Formula 8

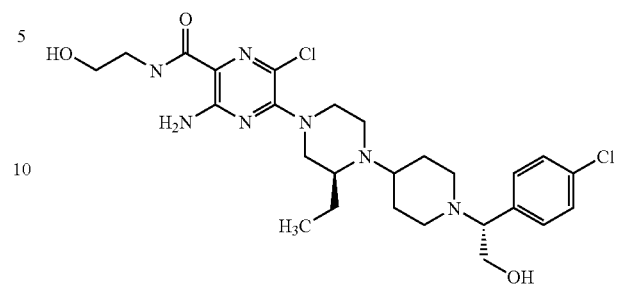

Formula 9

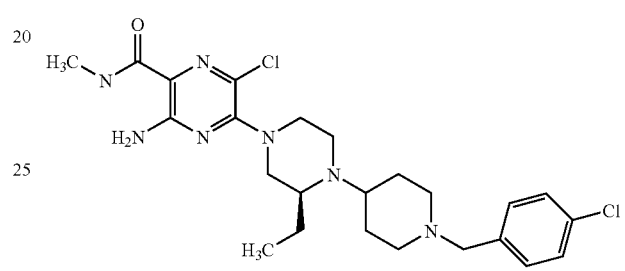

Formula 10

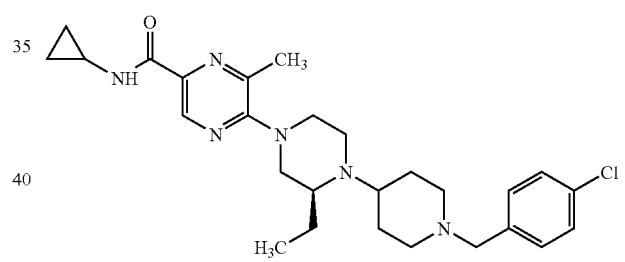

Formula 11

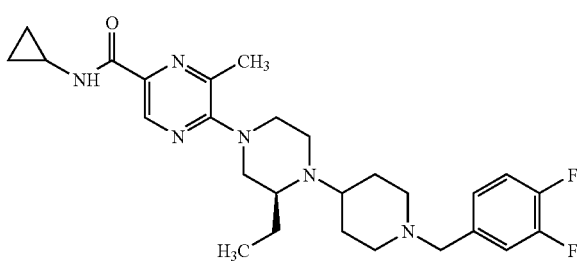

Formula 12

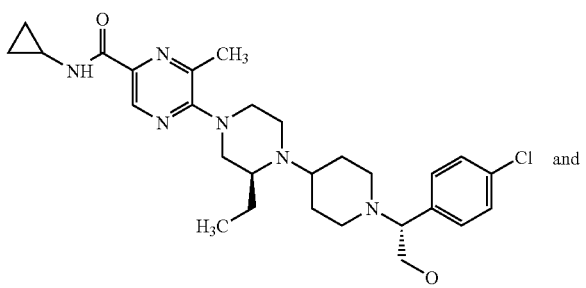

-continued

Formula 13

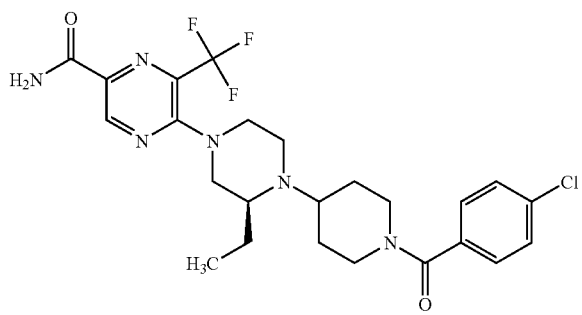

Formula 17

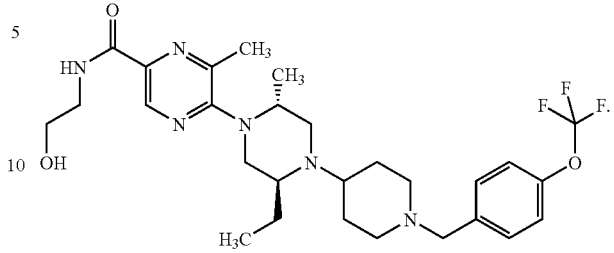

or pharmaceutically acceptable salts, solvates or esters thereof.

In another embodiment, the compound of Formula 1 is selected from the group consisting of Formula 7, Formula 8, Formula 9, Formula 10, Formula 11, Formula 12, Formula 13, Formula 14, Formula 15, Formula 16, or Formula 17, or pharmaceutically acceptable salts, solvate or hydrates thereof, wherein Formulae 7-13 are as set forth above, and Formulae 13-17 are set forth below:

Formula 14

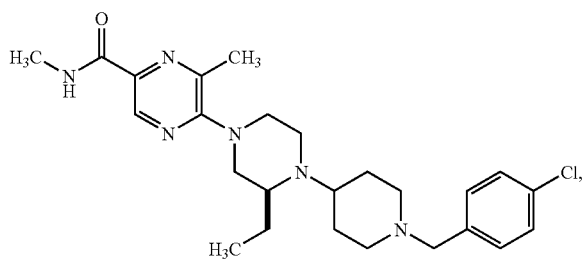

Formula 15

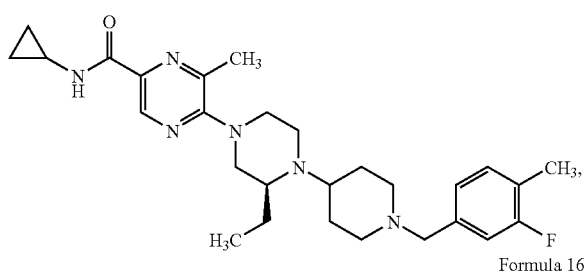

Formula 16

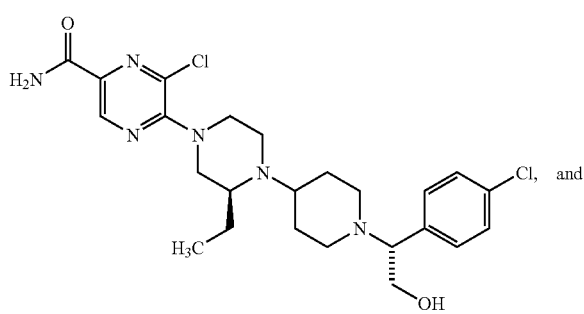

In yet another aspect, the compound according to Formula 1 is in purified form.

In another embodiment, this invention provides a pharmaceutical composition comprising at least one compound of Formula 1, or a pharmaceutically acceptable salt, solvate or ester thereof in combination with at least one pharmaceutically acceptable carrier.

In still another embodiment, the invention provides a pharmaceutical composition of Formula 1, further comprising at least one additional agent, drug, medicament, antibody and/or inhibitor for treating a CXCR3 chemokine receptor mediated disease.

When administering a combination therapy to a patient in need of such administration, the therapeutic agents in the combination, or a pharmaceutical composition or compositions comprising the therapeutic agents, may be administered in any order such as, for example, sequentially, concurrently, together, simultaneously and the like. The amounts of the various actives in such combination therapy may be different amounts (different dosage amounts) or same amounts (same dosage amounts). Thus, for non-limiting illustration purposes, a compound of Formula III and an additional therapeutic agent may be present in fixed amounts (dosage amounts) in a single dosage unit (e.g., a capsule, a tablet and the like). A commercial example of such single dosage unit containing fixed amounts of two different active compounds is VYTORIN® (available from Merck Schering-Plough Pharmaceuticals, Kenilworth, N.J.).

In yet another embodiment, the present invention discloses methods for preparing pharmaceutical compositions comprising the inventive heterocyclic substituted piperazine compounds of Formula 1 as an active ingredient. In the pharmaceutical compositions and methods of the present invention, the active ingredients will typically be administered in admixture with suitable carrier materials suitably selected with respect to the intended form of administration, i.e. oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Moreover, when desired or needed, suitable binders, lubricants, disintegrating agents and coloring agents may also be incorporated in the mixture. Powders and tablets may be comprised of from about 5 to about 95 percent inventive composition. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum and the like. Sweetening and flavoring agents and preservatives may also be included where appropriate. Some of the terms noted above, namely disintegrants, diluents, lubricants, binders and the like, are discussed in more detail below.

Additionally, the compositions of the present invention may be formulated in sustained release form to provide the rate controlled release of any one or more of the components or active ingredients to optimize the therapeutic effects, i.e. anti-inflammatory activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

Liquid form preparations include solutions, suspensions and emulsions. As an example may be mentioned water or water-propylene glycol solutions for parenteral injections or addition of sweeteners and pacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier such as inert compressed gas, e.g. nitrogen.

For preparing suppositories, a low melting wax such as a mixture of fatty acid glycerides such as cocoa butter is first melted, and the active ingredient is dispersed homogeneously therein by stirring or similar mixing. The molten homogeneous mixture is then poured into convenient sized molds, allowed to cool and thereby solidify.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions may take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in a unit dosage form. In such form, the preparation is subdivided into suitably sized unit doses containing appropriate quantities of the active components, e.g., an effective amount to achieve the desired purpose.

The quantity of the inventive active composition in a unit dose of preparation may be generally varied or adjusted from about 1.0 milligram to about 1,000 milligrams, preferably from about 1.0 to about 950 milligrams, more preferably from about 1.0 to about 500 milligrams, and typically from about 1 to about 250 milligrams, according to the particular application. The actual dosage employed may be varied depending upon the patient's age, sex, weight and severity of the condition being treated. Such techniques are well known to those skilled in the art.

Generally, the human oral dosage form containing the active ingredients can be administered 1 or 2 times per day. The amount and frequency of the administration will be regulated according to the judgment of the attending clinician. A generally recommended daily dosage regimen for oral administration may range from about 1.0 milligram to about 1,000 milligrams per day, in single or divided doses.

Some useful terms are described below:

Capsule—refers to a special container or enclosure made of methyl cellulose, polyvinyl alcohols, or denatured gelatins or starch for holding or containing compositions comprising the active ingredients. Hard shell capsules are typically made of blends of relatively high gel strength bone and pork skin gelatins. The capsule itself may contain small amounts of dyes, opaquing agents, plasticizers and preservatives.

Tablet—refers to a compressed or molded solid dosage form containing the active ingredients with suitable diluents. The tablet can be prepared by compression of mixtures or granulations obtained by wet granulation, dry granulation or by compaction.

Oral gels—refers to the active ingredients dispersed or solubilized in a hydrophillic semi-solid matrix.

Powders for constitution—refers to powder blends containing the active ingredients and suitable diluents which can be suspended in water or juices.

Diluent—refers to substances that usually make up the major portion of the composition or dosage form. Suitable diluents include sugars such as lactose, sucrose, mannitol and sorbitol; starches derived from wheat, corn, rice and potato; and celluloses such as microcrystalline cellulose. The amount of diluent in the composition can range from about 10 to about 90% by weight of the total composition, preferably from about 25 to about 75%, more preferably from about 30 to about 60% by weight, even more preferably from about 12 to about 60%.

Disintegrants—refers to materials added to the composition to help it break apart (disintegrate) and release the medicaments. Suitable disintegrants include starches; "cold water soluble" modified starches such as sodium carboxymethyl starch; natural and synthetic gums such as locust bean, karaya, guar, tragacanth and agar; cellulose derivatives such as methylcellulose and sodium carboxymethylcellulose; microcrystalline celluloses and cross-linked microcrystalline celluloses such as sodium croscarmellose; alginates such as alginic acid and sodium alginate; clays such as bentonites; and effervescent mixtures. The amount of disintegrant in the composition can range from about 2 to about 15% by weight of the composition, more preferably from about 4 to about 10% by weight.

Binders—refers to substances that bind or "glue" powders together and make them cohesive by forming granules, thus serving as the "adhesive" in the formulation. Binders add cohesive strength already available in the diluent or bulking agent. Suitable binders include sugars such as sucrose; starches derived from wheat, corn rice and potato; natural gums such as acacia, gelatin and tragacanth; derivatives of seaweed such as alginic acid, sodium alginate and ammonium calcium alginate; cellulosic materials such as methylcellulose and sodium carboxymethylcellulose and hydroxypropylmethylcellulose; polyvinylpyrrolidone; and inorganics such as magnesium aluminum silicate. The amount of binder in the composition can range from about 2 to about 20% by weight of the composition, more preferably from about 3 to about 10% by weight, even more preferably from about 3 to about 6% by weight.

Lubricant—refers to a substance added to the dosage form to enable the tablet, granules, etc. after it has been compressed, to release from the mold or die by reducing friction or wear. Suitable lubricants include metallic stearates such as magnesium stearate, calcium stearate or potassium stearate; stearic acid; high melting point waxes; and water soluble lubricants such as sodium chloride, sodium benzoate, sodium acetate, sodium oleate, polyethylene glycols and d'l-leucine. Lubricants are usually added at the very last step before compression, since they must be present on the surfaces of the granules and in between them and the parts of the tablet press. The amount of lubricant in the composition can range from about 0.2 to about 5% by weight of the composition, preferably from about 0.5 to about 2%, more preferably from about 0.3 to about 1.5% by weight.

Glidents—materials that prevent caking and improve the flow characteristics of granulations, so that flow is smooth and uniform. Suitable glidents include silicon dioxide and talc. The amount of glident in the composition can range from about 0.1% to about 5% by weight of the total composition, preferably from about 0.5 to about 2% by weight.

Coloring agents—excipients that provide coloration to the composition or the dosage form. Such excipients can include food grade dyes and food grade dyes adsorbed onto a suitable adsorbent such as clay or aluminum oxide. The amount of the coloring agent can vary from about 0.1 to about 5% by weight of the composition, preferably from about 0.1 to about 1%.

Bioavailability—refers to the rate and extent to which the active drug ingredient or therapeutic moiety is absorbed into the systemic circulation from an administered dosage form as compared to a standard or control. Conventional methods for preparing tablets are known. Such methods include dry methods such as direct compression and compression of granulation produced by compaction, or wet methods or other special procedures. Conventional methods for making other forms for administration such as, for example, capsules, suppositories and the like are also well known.

It will be apparent to those skilled in the art that many modifications, variations and alterations to the present disclosure, both to materials and methods, may be practiced. Such modifications, variations and alterations are intended to be within the spirit and scope of the present invention.

As stated earlier, the invention includes tautomers, enantiomers and other stereoisomers of the compounds also. Thus, as one skilled in the art knows, certain imidazole compounds may exist in tautomeric forms. Such variations are contemplated to be within the scope of the invention. Certain compounds of the present invention may exist in multiple crystalline forms or amorphous forms. All physical forms of the current invention are contemplated.

Compounds of this invention which contain unnatural proportions of atomic isotopes (i.e. "radiolabeled compounds") whether their use is therapeutic, diagnostic or as a research reagent are contemplated under this invention.

Another embodiment of the invention discloses the use of the pharmaceutical compositions disclosed above for treatment of diseases of a CXCR3 chemokine receptor mediated disease in a patient in need of such treatment comprising administering to the patient a therapeutically effective amount of at least one compound according to Formula 1, or a pharmaceutically acceptable salt, solvate or ester thereof.

In another embodiment, the method is directed to administering to the patient (a) an effective amount of at least one compound according to Formula 1, or a pharmaceutically acceptable salt, solvate or ester thereof concurrently or sequentially with (b) at least one additional agent, drug, medicament, antibody and/or inhibitor for treating a CXCR3 chemokine receptor mediated disease, in combination with a pharmaceutically acceptable carrier.

In another embodiment, at least one compound of Formula 1 binds to a CXCR3 receptor.

The method can further comprise administering: (a) a therapeutically effective amount of at least one compound according to Formula 1, or a pharmaceutically acceptable salt, solvate or ester thereof concurrently or sequentially with (b) at least one medicament selected from the group consisting of: disease modifying antirheumatic drugs; nonsteroidal anti-inflammatory drugs; COX-2 selective inhibitors; COX-1 inhibitors; immunosuppressives (such as cyclosporins and methotrexate); steroids (including corticosteroids such as glucorticoids); PDE IV inhibitors, anti-TNF-α compounds, TNF-α-convertase (TACE) inhibitors, MMP inhibitors, cytokine inhibitors, glucocorticoids, other chemokine inhibitors such as CCR2 and CCR5, CB2-selective inhibitors, p38 inhibitors, biological response modifiers; anti-inflammatory agents and therapeutics. The disease can be an inflammatory disease (e.g., psoriasis, inflammatory bowel disease)

Another embodiment of this invention is directed to a method of inhibiting or blocking T-cell mediated chemotaxis in a patient in need of such treatment the method comprising administering to the patient a therapeutically effective amount of at least one compound according to Formula 1 or a pharmaceutically acceptable salt, solvate or ester thereof.

Another embodiment of this invention is directed to a method of treating inflammatory bowel disease (such Crohn's disease, ulcerative colitis) in a patient in need of such treatment comprising administering to the patient a therapeutically effective amount of at least one compound according to Formula 1, or a pharmaceutically acceptable salt, solvate or ester thereof.

Another embodiment of this invention is directed to a method of treating inflammatory bowel disease in a patient in need of such treatment comprising administering to the patient a therapeutically effective amount of: (a) at least one compound of Formula 1, or a pharmaceutically acceptable salt, solvate or ester thereof concurrently or sequentially with (b) at least one compound selected from the group consisting of: sulfasalazine, 5-aminosalicylic acid, sulfapyridine, anti-TNF compounds, anti-IL-12 compounds, corticosteroids, glucocorticoids, T-cell receptor directed therapies (such as anti-CD3 antibodies), immunosuppresives, methotrexate, azathioprine, and 6-mercaptopurines.

Another embodiment of this invention is directed to a method of treating or preventing graft rejection in a patient in need of such treatment comprising administering to the patient a therapeutically effective amount of at least one compound according to Formula 1, or a pharmaceutically acceptable salt, solvate or ester thereof.

Another embodiment of this invention is directed to a method comprising administering to the patient a therapeutically effective amount of: (a) at least one compound according to Formula 1, or a pharmaceutically acceptable salt, solvate or ester thereof concurrently or sequentially with (b) at least one compound selected from the group consisting of: cyclosporine A, FK-506, FTY720, beta-interferon, rapamycin, mycophenolate, prednisolone, azathioprine, cyclophosphamide and an antilymphocyte globulin.

Another embodiment of this invention is directed to a method of treating multiple sclerosis in a patient in need of such treatment the method comprising administering to the patient a therapeutically effective amount of: (a) at least one compound according to Formula 1, or a pharmaceutically acceptable salt, solvate or ester thereof concurrently or sequentially with (b) at least one compound selected from the group consisting of: beta-interferon, glatiramer acetate, corticosteroids, glucocorticoids, methotrexate, azathioprine, mitoxantrone, VLA-4 inhibitors, FTY720, anti-IL-12 inhibitors, and CB2-selective inhibitors.

Another embodiment of this invention is directed to a method of treating multiple sclerosis in a patient in need of such treatment the method comprising administering to the patient a therapeutically effective amount of: a) at least one compound according to Formula 1, or a pharmaceutically acceptable salt, solvate or ester thereof concurrently or sequentially with (b) at least one compound selected from the group consisting of: methotrexate, cyclosporin, leflunomide, sulfasalazine, corticosteroids, β-methasone, β-interferon, glatiramer acetate, prednisone, etonercept, and infliximab.

Another embodiment of this invention is directed to a method of treating rheumatoid arthritis in a patient in need of such treatment the method comprising administering to the patient a therapeutically effective amount of: (a) at least one compound according to Formula 1, or a pharmaceutically acceptable salt, solvate or ester thereof concurrently or sequentially with (b) at least one compound selected from the group consisting of: non-steroidal anti-inflammatory agents, COX-2 inhibitors, COX-1 inhibitors, immunosuppressives, cyclosporine, methotrexate, steroids, PDE IV inhibitors, anti-TNF-α compounds, MMP inhibitors, corticosteroids, glucocorticoids, chemokine inhibitors, CB2-selective inhibitors, caspase (ICE) inhibitors and other classes of compounds indicated for the treatment of rheumatoid arthritis.

Another embodiment of this invention is directed to a method of treating psoriasis in a patient in need of such treatment the method comprising administering to the patient a therapeutically effective amount of: a) at least one compound according to Formula 1, or a pharmaceutically acceptable salt, solvate or ester thereof concurrently or sequentially with (b) at least one compound selected from the group consisting of: immunosuppressives, cyclosporins, methotrexate, steroids, corticosteroids, anti-TNF-α compounds, anti-IL compounds, anti-IL-23 compounds, vitamin A and D compounds and fumarates.

Another embodiment of this invention is directed to a method of treating ophthalmic inflammation (including, for e.g., uveitis, posterior segment intraocular inflammation, Sjogren's syndrome) or dry eye in a patient in need of such treatment the method comprising administering to the patient a therapeutically effective amount of: a) at least one compound according to Formula 1, or a pharmaceutically acceptable salt, solvate or ester thereof concurrently or sequentially with (b) at least one compound selected from the group consisting of: immunosuppressives, cyclosporins, methotrexate, FK506, steroids, corticosteroids, and anti-TNF-α compounds.

Another embodiment of this invention is directed to a method of treating a disease selected from the group consisting of: inflammatory disease, rheumatoid arthritis, multiple sclerosis, inflammatory bowel disease, graft rejection, psoriasis, fixed drug eruptions, cutaneous delayed-type hypersensitivity responses, ophthalmic inflammation (including e.g., uveitis, posterior segment intraocular inflammation, and Sjogren's syndrome), tuberculoid leprosy and cancer in a patient in need of such treatment, such method comprising administering to the patient an effective amount of at least one compound according to Formula 1, or a pharmaceutically acceptable salt, solvate or ester thereof.

Another embodiment of this invention is directed to a method of treating a disease selected from the group consisting of inflammatory disease, rheumatoid arthritis, multiple sclerosis, inflammatory bowel disease, graft rejection, psoriasis, fixed drug eruptions, cutaneous delayed-type hypersensitivity responses and tuberculoid leprosy, ophthalmic inflammation, type I diabetes, viral meningitis and cancer in a patient in need of such treatment, such method comprising administering to the patient an effective amount of (a) at least one compound according to Formula 1, or a pharmaceutically acceptable salt, solvate or ester thereof concurrently or sequentially with (b) at least one medicament selected from the group consisting of: disease modifying antirheumatic drugs; nonsteroidal antiinflammatory drugs; COX-2 selective inhibitors; COX-1 inhibitors; immunosuppressives; steroids; PDE IV inhibitors, anti-TNF-α compounds, MMP inhibitors, corticosteroids, glucocorticoids, chemokine inhibitors, CB2-selective inhibitors, biological response modifiers; anti-inflammatory agents and therapeutics.

Another embodiment of the invention discloses a method of making the inventive compounds disclosed above.

For the procedures described below, the following abbreviations are used:

Unless otherwise stated, the following abbreviations have the stated meanings in the Examples below:

DBU=1,8-diazabicyclo[5.4.0]undec-7-ene
DBN=1,5-diazabicyclo[4.3.0]non-5-ene
DIPEA=N,N'-diisopropylethylamine
EDCl=1-(3-dimethylaminopropyl)-3-ethylcarbodiimide
HOBT=1-hydroxybenzotriazole
DCC=dicyclohexylcarbodiimide
Dibal-H=diisobutylaluminum hydride
DMF=Dimethylformamide
LAH=lithium aluminum hydride
$NaBH(OAc)_3$=sodium triacetoxyborohydride
$NaBH_4$=sodium borohydride
$NaBH_3CN$=sodium cyanoborohydride
n-BOC=tert-butyloxycarbonyl
LDA=lithium diisopropylamide
p-TsOH=p-toluenesulfonic acid
m-CPBA=m-chloroperbenzoic acid
TMAD=N,N,N',N'-tetramethylazodicarboxamide
CSA=camphorsulfonic acid
NaHMDS=sodium hexamethyl disilylazide
HRMS=High Resolution Mass Spectrometry
HPLC=High Performance Liquid Chromatography
LRMS=Low Resolution Mass Spectrometry
nM=nanomolar
Ki=Dissociation Constant for substrate/receptor complex
pA2=–$logEC_{50}$, as defined by J. Hey, *Eur. J. Pharmacol.*, (1995), Vol. 294, 329-335.
Ci/mmol=Curie/mmol (a measure of specific activity)
TLC=Thin layer chromatography
Tr=Triphenylmethyl
Tris=Tris(hydroxymethyl)aminomethane General Preparative Schemes:

Compounds of the present invention can be prepared by a number of ways evident to one skilled in the art. Preferred methods include, but are not limited to, the general synthetic procedures described herein. One skilled in the art will recognize that one route will be optimal depending on the choice of appendage substituents. Additionally, one skilled in the art will recognize that in some cases the order of steps has to be controlled to avoid functional group incompatibilities. One skilled in the art will recognize that a more convergent route (non-limiting example(s) include non-linear or preassembly of certain portions of the molecule) is a more efficient method of assembly of the target compounds. Two such methods for the preparation of compounds of general Formula 1 with variables $R^1$, $R^2$, $R^3$, $R^6$, $R^7$, $R^8$, $R^{10}$, $R^{11}$, $R^{12}$, $R^{20}$, ring D, X, Y, m, n, and p, are as defined above, and are shown in Scheme 1 and Scheme 2. $Pr^1$, $Pr^2$ and $Pr^3$ are protecting groups exemplified below.

The following schemes describe the methods of synthesis of compounds of Formula 1. In Scheme 1, the $R^1R^2N$ group is introduced a late stage in the synthesis.

Scheme 1. Method A
Late Introduction of R¹R²N-
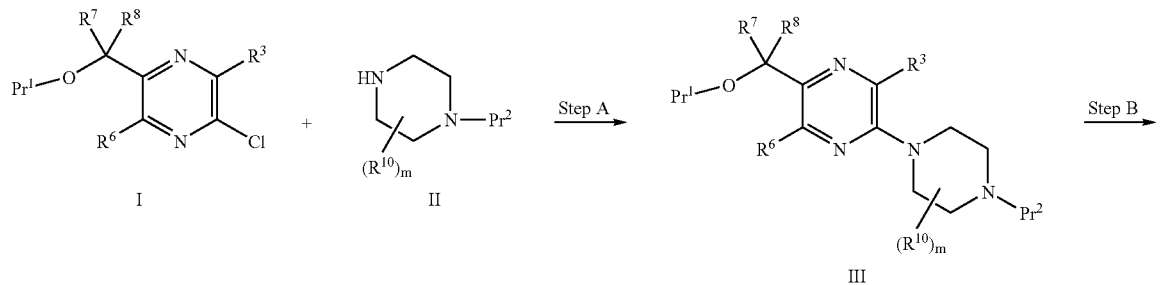
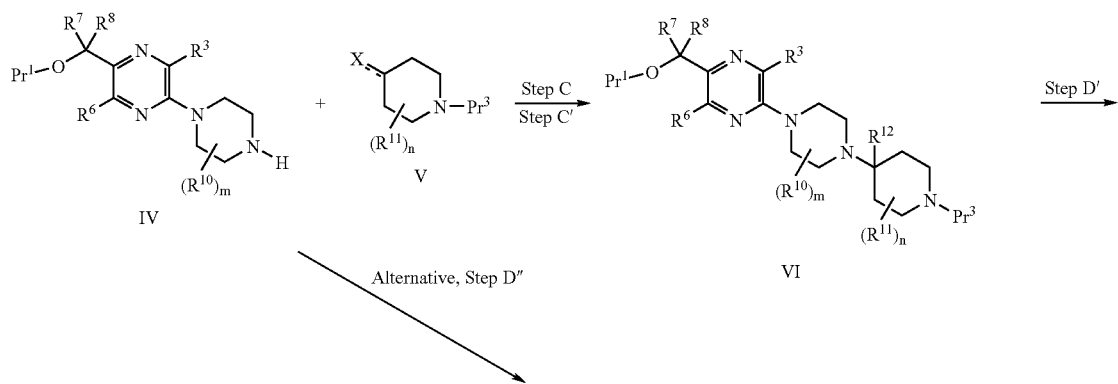
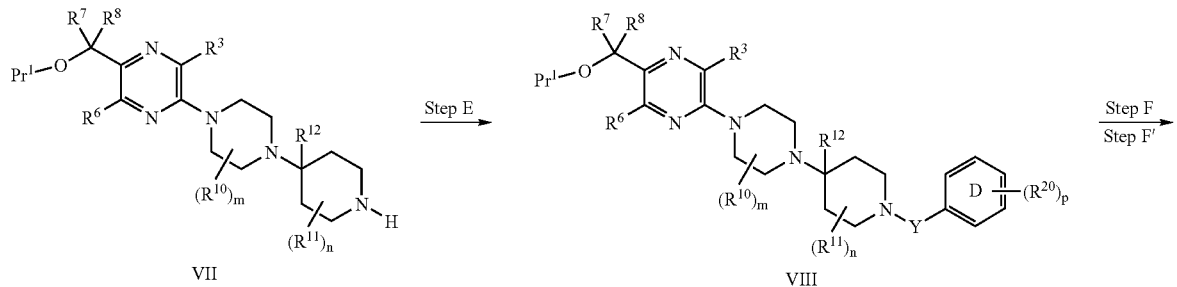
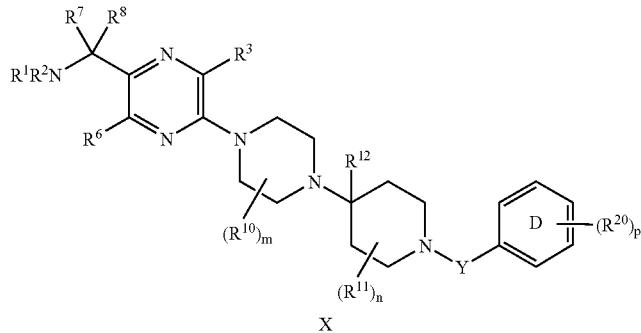

Alternatively, the R¹R²N group can be introduced earlier in the synthesis, as shown in Scheme 2.
Scheme 2. Method B.
Early Introduction of R¹R²N—
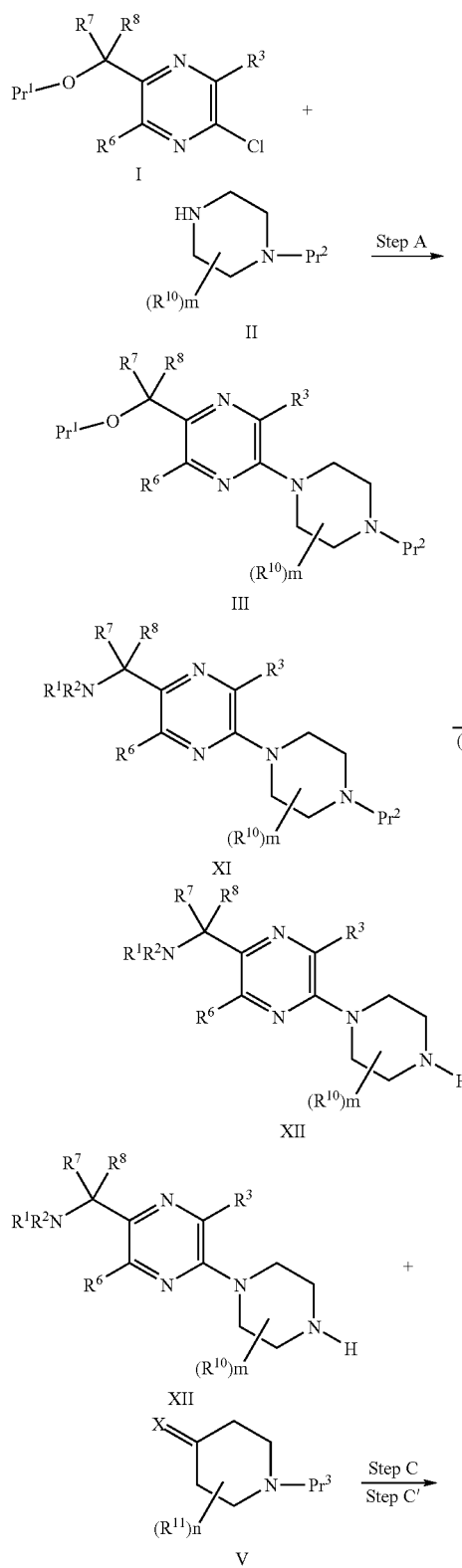
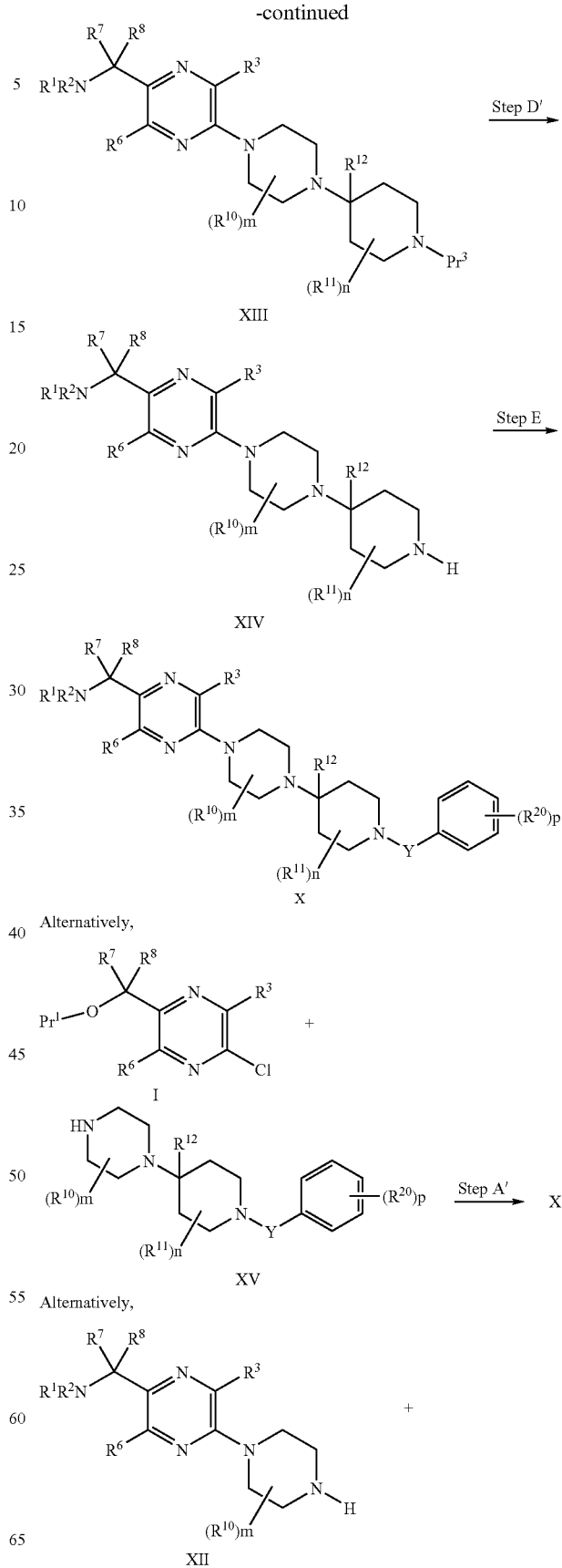

-continued

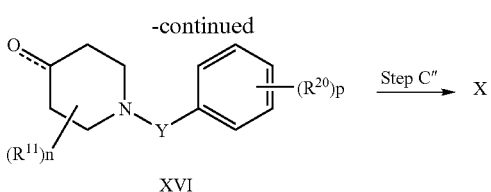

XVI

The starting material and reagents used in preparing compounds described are either available from commercial suppliers such as Aldrich Chemical Co. (Wisconsin, USA) and Acros Organics Co. (New Jersey, USA) or were prepared by literature methods known to those skilled in the art.

The preparation of arylpiperazine compounds related to structure III has been reported in WO-03037862 (Nippon Shinyaku).

One skilled in the art will recognize that the synthesis of compounds of Formula 1 may require the need for the protection of certain functional groups (non-limiting example(s) include derivatization for the purpose of chemical compatibility with a particular reaction condition). Suitable protecting groups for a carboxylic acid ($Pr^1$, when $R^7$ and $R^8$ taken together is =O) is the methyl, ethyl, isopropyl, or benzyl ester and the like. A suitable protecting group for an amine ($Pr^2$ and $Pr^3$) is methyl, benzyl, ethoxyethyl, t-butoxycarbonyl, phthaloyl and the like. All protecting groups can be appended to and removed by literature methods known to those skilled in the art.

One skilled in the art will recognize that the synthesis of compounds of Formula 1 may require the construction of an amide bond. Methods include but are not limited to the use of a reactive carboxy derivative (non-limiting example(s) include acid halide, or ester at elevated temperatures) or the use of an acid with a coupling reagent (non-limiting example(s) include EDCl, DCC) with an amine at 0° C. to 100° C. Suitable solvents for the reaction are halogenated hydrocarbons, ethereal solvents, dimethylformamide and the like. The reaction may be conducted under pressure or in a sealed vessel.

One skilled in the art will recognize that the synthesis of compounds of Formula 1 may require the construction of an amine bond. One such method is but not limited to the reaction of a primary or secondary amine with a reactive carbonyl (non-limiting example(s) include aldehyde or ketone) under reductive amination conditions. Suitable reducing reagents of the intermediate imine are sodium borohydride, sodium triacetoxyborohydride and the like at 0° C. to 100° C. Suitable solvents for the reaction are halogenated hydrocarbons, ethereal solvents, dimethylformamide and the like. Another such method is but not limited to the reaction of a primary or secondary amine with a reactive alkylating agent such as an alkyl halide, benzyl halide, mesylate, tosylate or the like. Suitable solvents for the reaction are halogenated hydrocarbons, ethereal solvents, dimethylformamide and the like. The reaction may be conducted under pressure or in a sealed vessel at 0° C. to 100° C.

One skilled in the art will recognize that the synthesis of compounds of Formula 1 may require the reduction of a reducible functional group. Suitable reducing reagents include sodium borohydride, lithium aluminum hydride, diborane and the like at −20° C. to 100° C. Suitable solvents for the reaction are halogenated hydrocarbons, ethereal solvents, dimethylformamide and the like.

One skilled in the art will recognize that the synthesis of compounds of Formula 1 may require the oxidation of a functional group. Suitable oxidizing reagents include oxygen, hydrogen peroxide, m-chloroperoxybenzoic acid and the like at −20° C. to 100° C. Suitable solvents for the reaction are halogenated hydrocarbons, ethereal solvents, water and the like.

The starting materials and the intermediates of a reaction may be isolated and purified if desired using conventional techniques, including but not limited to filtration, distillation, crystallization, chromatography and the like. Such materials can be characterized using conventional means, including physical constants and spectral data.

General Description of Methods A & B

Step A. Amination of a Pyrazine

A suitably protected 2-halo pyrazine of structure I is reacted with a piperazine of structure II to form a compound of structure III. Preferably the reaction is carried out in a solvent such as dioxane in the presence of a base such as potassium carbonate or cesium carbonate. Alternatively, other leaving groups may replace the chlorine (O-mesyl, Br etc.) or a group capable of activation under the reaction conditions (H, OH, etc.) may be used. Step A' (Method B)

A suitably protected 2-halo pyrazine of structure I is reacted with a piperazine of structure XV to form a compound of general structure X. Preferably the reaction is carried out in a solvent such as dioxane in the presence of a base such as potassium carbonate or cesium carbonate.

Step B.

A protected piperazine of structure III is deprotected to provide the secondary amine of structure IV. When $Pr^2$ is benzyl or substituted benzyl, deprotection can be effected by reaction under a pressure of hydrogen gas in the presence of a catalyst such as palladium. When $Pr^2$ is ethoxyethyl, deprotection can be effected by reaction with trimethylsilyl iodide. When $Pr^2$ is t-butoxycarbonyl, deprotection can be effected with a strong acid such as trifluoroacetic acid.

Step C.

A piperazine of structure IV or XII is reacted with a ketone of structure V in the presence of a reducing agent to form a compound of structure VI or XIII where $R^{12}$ is hydrogen. General conditions for the reductive amination reaction are described above.

Step C'

A piperazine of structure IV or XII is reacted with a ketone of structure V in the presence of a reducing agent to form a compound of structure VI or XIII where $R^{12}$ is a cyanide residue. Typical conditions are the reaction of an equi-molar quantity of a piperazine of structure IV or XII and a ketone of structure in the presence of titanium isopropoxide in a halogenated solvent, such as methylene chloride for 1-48 hours. Subsequent addition of a cyanide source such as dimethylaluminum cyanide affords a compound of structure VI or XIII where $R^{12}$ is a cyanide residue.

Step C" and Step D"

A piperazine of structure IV or XII is reacted with a ketone of structure V or XVI in the presence of a reducing agent to form a general compound of structure VIII or X respectively where $R^{12}$ is hydrogen. General conditions for the reductive amination reaction are described above.

Step D

Optionally, a compound of structure XI, when $R^3$ is Cl or Br is reacted with an organometallic alkylating agent, such as alkyl boronic acid, or an alkyl halide in the presence of a metal to promote heterocoupling, or a nucleophile to yield a different structure of general structure XII, where the halogen at the R³ position has been replaced by the appropriate group described for R³.

Step D'

A protected piperidine of structure VI (Method A) or XII (Method B) is deprotected to provide the secondary amine of structure VII (Method A) or XIV (Method B). When $Pr^2$ is benzyl or substituted benzyl, deprotection can be effected by reaction under a pressure of hydrogen gas in the presence of a catalyst such as palladium. When $Pr^2$ is ethoxyethyl, deprotection can be effected by reaction with trimethylsilyl iodide. When $Pr^2$ is t-butoxycarbonyl, deprotection can be effected with a strong acid such as trifluoroacetic acid.

Step E

A secondary piperidine of structure VII or XIV is either alkylated or acylated to provide compounds of structure VIII or X. General methods for such alkyations and acylations are described above and are well known to those skilled in the art.

Step F

A suitable protected ester of structure VIII (Method A) or structure III (Method B) where $R^7$ and $R^8$ taken together is =O and $Pr^1$ is alkyl is reacted with a primary or secondary amine to provide compounds of structure X or XI.

Optionally, functional group manipulation of a compound of structure X may be done to provide additional related compounds of structure X. Typical conditions include the reaction of the ester and the amine in a polar solvent such as methanol in a sealed tube at 25° C. to 100° C.

Step F'

Optionally, functional group manipulation of a compound of structure X may be done to provide additional related compounds of structure X.

Compounds of Formula 1 can be prepared by the general methods outlined in Schemes 1 and 2. Synthesis of the specifically exemplified compounds, were prepared as described in detailed below. The following EXAMPLES are being provided to further illustrate the present invention. They are for illustrative purposes only; the scope of the invention is not to be considered limited in any way thereby.

PREPARATIVE EXAMPLES

The following examples are intended to illustrate, but not to limit, the scope of the invention.

Preparative Example 1

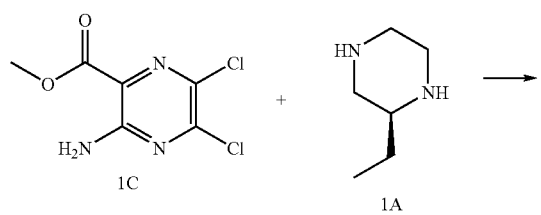

1C 1A

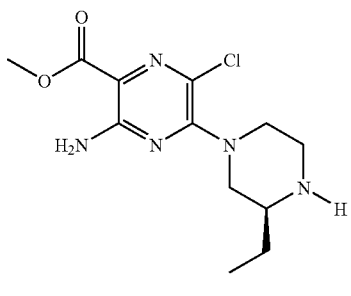

1B

A round bottomed flask was charged with methyl 6-amino 2,3-dichloro pyrazine 5-carboxylate (Aldrich, 25 g, 112.6 mmol), 2-S-Ethyl piperazine (prepared as per Williams et al. *J. Med. Chem* 1996, 39, 1345, 83% active, 15.7 g, 112.7 mmol), cesium carbonate (100 g, 300 mmol) and 1,4 dioxane (400 ml). The flask was equipped with a reflux condenser and heated to 80° C. After 12 hours, the reaction was cooled, diluted with methylene chloride (~200 ml), and filtered through celite. The filtrate was washed once with water and then concentrated to an oil. The crude product was purified by silica gel chromatography using a methanol/methylene chloride eluent (3% to 10% MeOH) to afford 30.8 g (91%) of the compound. MS, M+H=300.

Preparative Example 2

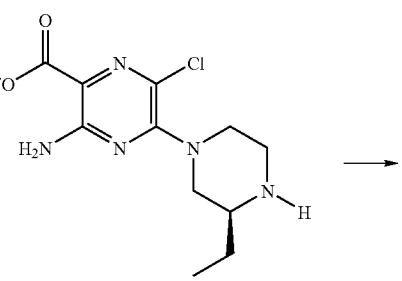

2A

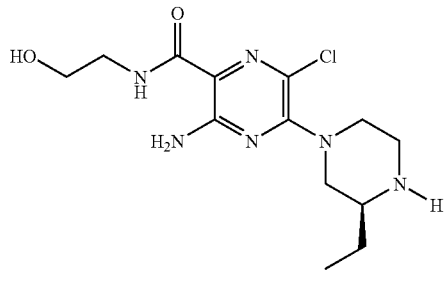

2B

A round bottomed flask was charged with the product of Preparative Example 1 (0.9 g, 3 mmol), 2-amino ethanol (1.5 ml, 25 mmol) and 1.4 dioxane (20 ml). The reaction was heated at 80° C. for 17 hours, and then concentrated to an oil under vacuum. The title compound was isolated by preparative TLC (10/90 MeOH/MC), which provided 0.8 g (2.4 mmol, 81% yield). M+H=330.

Preparative Example 3

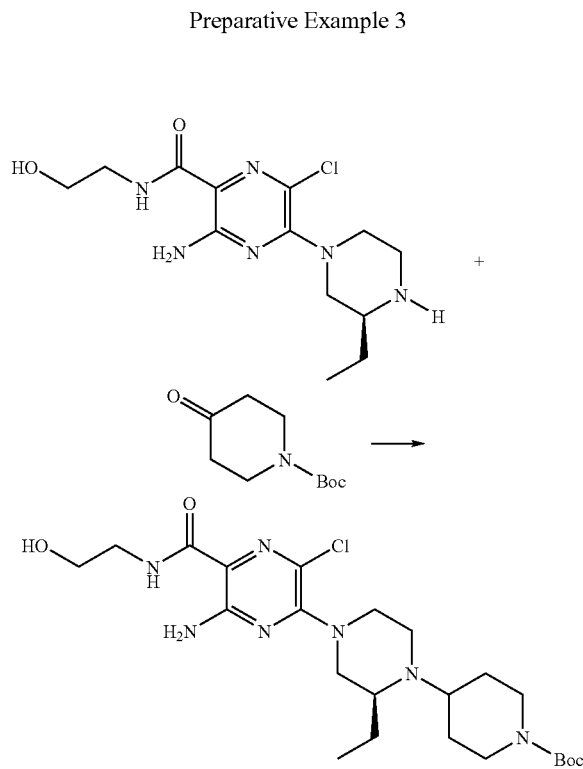

A round bottomed flask was charged with the product of Preparative Example 2 (0.79 g, 2.4 mmol), N—Boc piperidine-4-one (Lancaster, 1.4 g, 7.0 mmol), and methylene chloride (30 mL). NaB(OAc)$_3$H (1.5 g, 7.1 mmol) was added and the mixture stirred at room temperature for 12 hours. The reaction mixture was transferred to a separatory funnel and 1 N NaOH added. The crude product was extracted into methylene chloride (3×), the organic extracts concentrated and further purified by TLC to afford 0.83 g of the title compound (68% yield). M+H=513.

Preparative Example 4

Preparation of Table 1

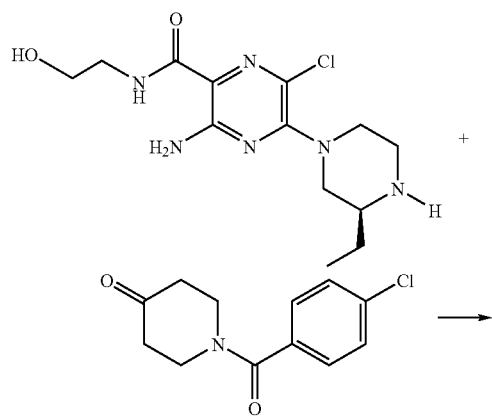

-continued

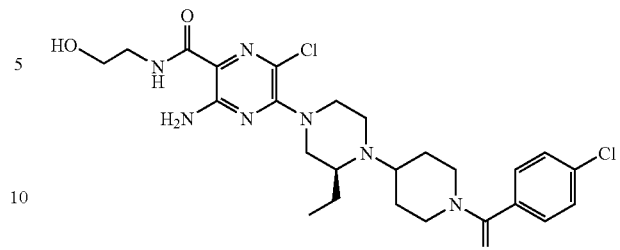

A round bottomed flask was charged with the product of Preparative Example 2 (0.08 g, 0.24 mmol), N-(4-ketopiperidyl) 4-chlorobenzamide (0.170 g, 0.71 mmol), and methylene chloride (0.5 mL). NaB(OAc)$_3$H (0.15 g, 0.71 mmol) was added and the mixture stirred at room temperature for 12 hours. The reaction mixture was transferred to a separatory funnel and 1 N NaOH added. The crude product was extracted into methylene chloride (3×), the organic extracts concentrated and further purified by TLC to afford 0.06 g of the title compound (43% yield). S M+H=550

Preparative Example 5

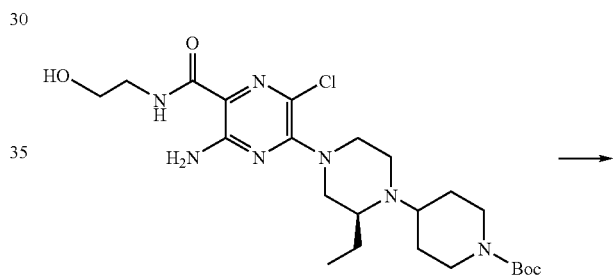

A round bottomed flask was charged with the product of Preparative Example 3 (6.67 g, 13 mmol), trifluoroacetic acid (60 ml, 778 mmol), methylene chloride (60 ml) and stirred at room temperature. After 4 hours, the reaction was concentrated in vacuo, and water (200 ml) and potassium carbonate (15 g, 108 mmol) were added to the residue. The product (4.85 g, 12 mmol, 91% yield) was isolated by extraction of the aqueous phase with methylene chloride (3×) and used without further purification. M+H=413.

Preparative Example 6

Preparation of Table 1, Compound No. 110

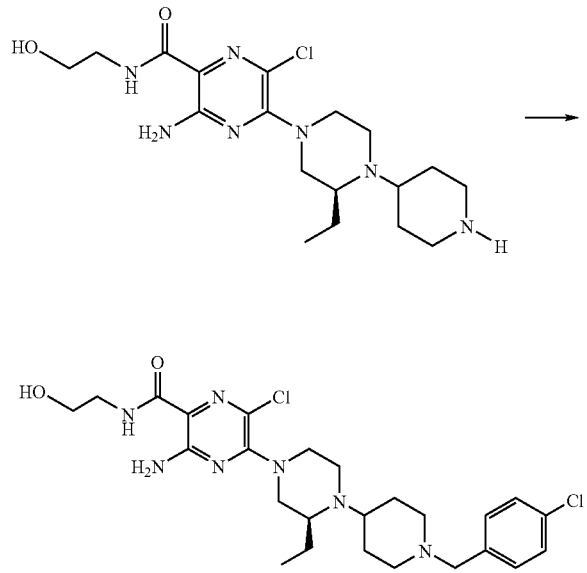

A round bottomed flask was charged with the product of Preparative Example 5 (0.05 g, 0.12 mmol), 4-chlorobenzaldehyde (0.05 g, 0.36 mmol), and methylene chloride (10 ml) and stirred at room temperature. After 2 hours NaB(OAc)₃H (75 mg, 0.35 mmol) was added and the reaction stirred an additional 15 hours. Additional methylene chloride (20 ml) was added, the organic phase washed with 1 N NaOH, dried over Na₂SO₄ and concentrated to an oil. The title compound was purified by TLC, which yielded 0.049 g (76% yield). Compound No. 110: M+H=536.

Reaction of the staring material of Preparative Example 6 with the appropriately substituted aldehyde afforded the following Compound Numbers: 112, 113, 115, 117, 118, 120, 121, 123, 126, 133, 136, 140, 144, 154, 158, 161 and 162.

Preparative Example 7

Preparation of Table 1 Compound No. 185

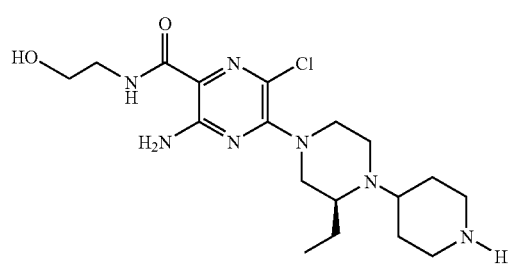

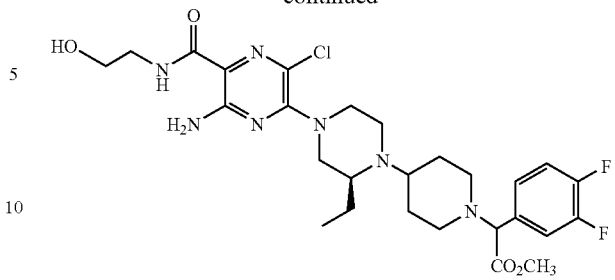

A round bottomed flask was charged with the product of Preparative Example 5 (0.262 g, 0.635 mmol) and dimethylformamide (1.8 ml).

2-chloro-2-(3,4-difluorophenyl) acetic acid, methyl ester (0.14 g, 0.635 mmol) and triethylamine (0.27 ml, 1.9 mmol) were added and the reaction allowed to stir at room temperature. After 12 hours, ethyl acetate (10 ml) and water (10 ml) were added, the organic layer was separated and dried over MgSO₄. The crude product was further purified by preparative TLC (10/90, MeOH/methylene chloride), which yielded isomer A (0.055 g, 15% yield) and isomer B (0.065 g 17% yield). Isomer A MS M+H=596; Isomer B MS M+H=596.

Reaction of the product of Preparative Example 7 with an appropriately substituted alpha-chloro ester afforded the following Compound Numbers: 150, 175 192, 200, and 206.

Preparative Example 8

Preparation of Table 1 Compound No. 395

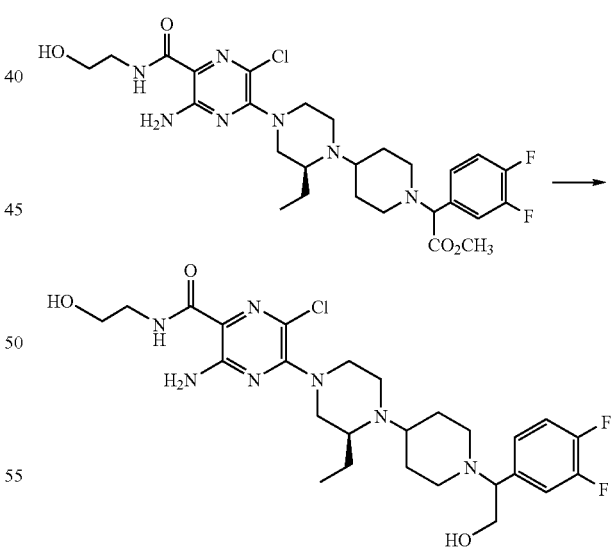

A round bottomed flask was charged with the product of Preparative Example 7 (Isomer A, 0.053 g, 0.089 mmol) and dry tetrahydrofuran (0.9 ml). Lithium borohydride (0.133 mL) of a 2 M solution in THF was added and the reaction was allowed to stir at room temperature. After 12 hours the reaction was diluted with methylene chloride (5 ml) and 1 N NaOH added (2 ml). The organic layer separated and dried over MgSO₄. The crude product was further purified by preparative TLC (10/90, MeOH/methylene chloride) to afford the title compound, Isomer A (0.030 g, 60% yield). Isomer A MS M+H=568.

Preparative Example 9

Preparation of Example No. 67

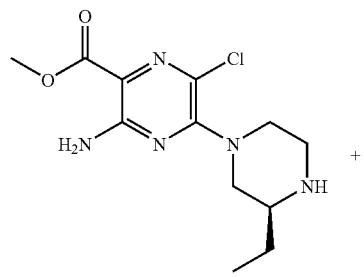

+

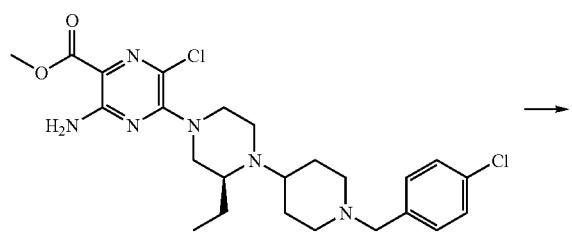

→

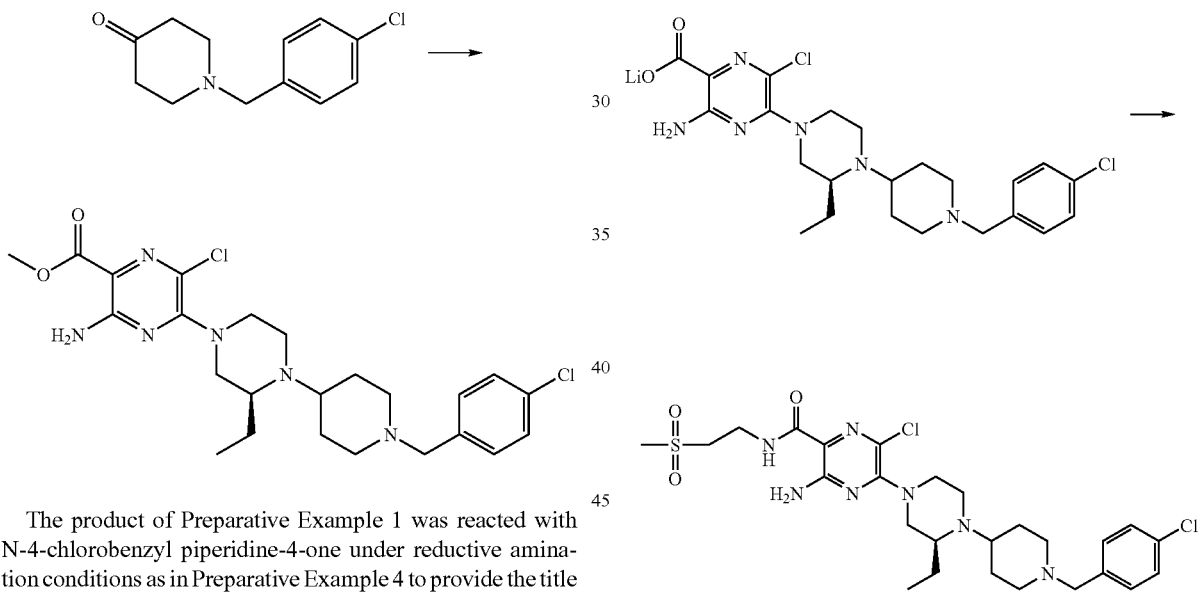

The product of Preparative Example 1 was reacted with N-4-chlorobenzyl piperidine-4-one under reductive amination conditions as in Preparative Example 4 to provide the title compound.

Preparative Example 10

Preparation of Example No. 301—Lithium Salt

-continued

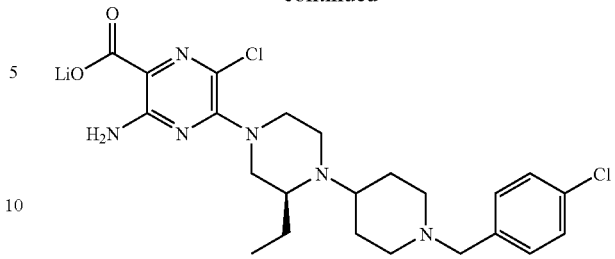

A round bottomed flask was charged with the product of Preparative Example 9 (0.85 g, 1.68 mmol), lithium hydroxide (2 ml of a 2 M LiOH in water) and methanol (10 ml). After stirring for 12 hours, the reaction mixture was concentrated to a pale solid and used as is in the step below. MS M+H=499.

Preparative Example 11

Preparation of Table 1 Compound No. 101

A round bottomed flask was charged with the product of Preparative Example 10 (0.060 g, 0.12 mmol), 2-methylsufonylethylamine (Array, 0.60 g, 0.38 mmol), EDCl (0.075 mg, 0.39 mmol), HOBT (0.53 mg, 0.39 mmol), DIPEA (0.5 ml) and dimethylformamide (5 mL). The reaction was heated to 80° C. for 5 hours, cooled and diluted with ethyl acetate. The reaction mixture was washed with water once, and the organic layer dried over Na₂SO₄. The crude product was purified by preparative TLC (10/90 MeOH/methylene chloride) to afford the title compound (0.049 g, 68% yield).

The dihydrochloride was prepared by treating the title compound, free base (49 mg, 0.08 mmol) dissolved in methanol (1 ml) with HCl (0.2 ml of a 0.81 M in dioxane). After stirring 20 minutes, the reaction mixture was concentrated in vacuo to afford the title compound, dihydrochloride salt (0.054 g, 100% yield).

Preparative Example 12

Preparation of Example No. 142

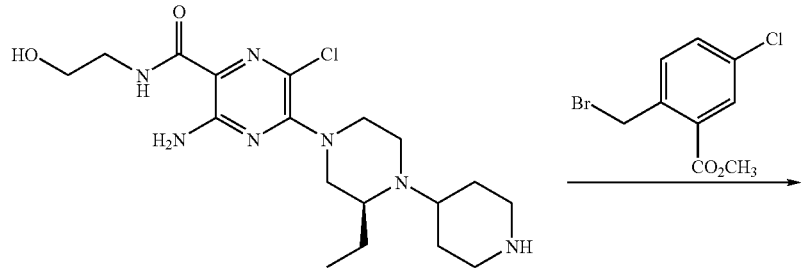

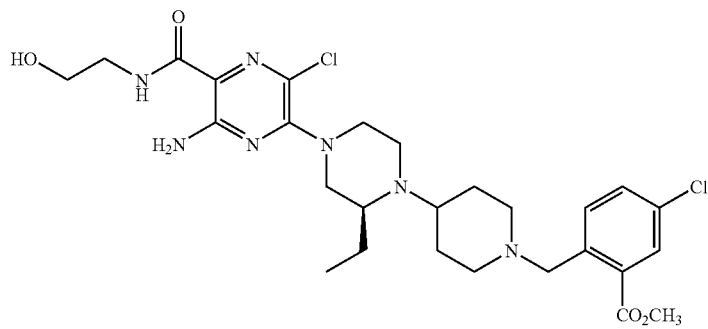

A round bottomed flask was charged with the product of Preparative Example 5 (0.140 g, 0.34 mmol), 2-Carboxy-4-Chloro Bromomethylbenzene methyl ester (0.11 g, 0.42 mmol), triethyl amine (0.5 ml) and methylene chloride (5 mL). The reaction mixture was stirred at room temperature overnight, and then transferred to a separatory funnel and washed with 1 N NaOH.

The organic extract was dried over $MgSO_4$ and then concentrated in vacuo to an oil. Purification by Prep TLC using 94:6 Methylene chloride: MeOH eluent afforded the title compound (0.095 g, 47% yield). MS M+H=594.53.

Preparative Example 13

Preparation of Table 1 Compound No. 107

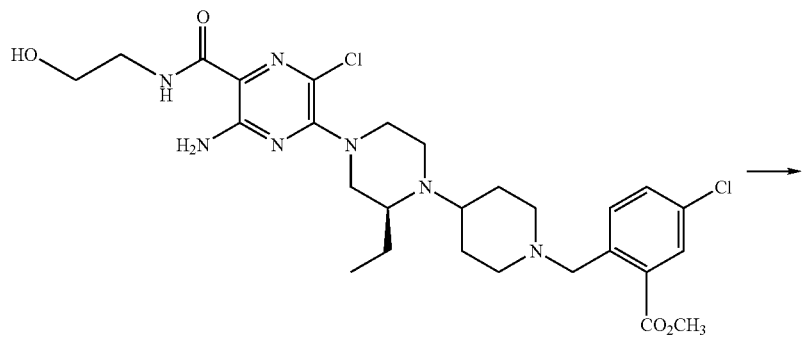

-continued

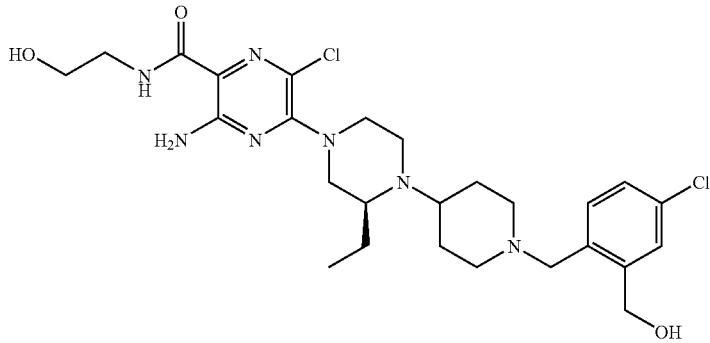

The product of Preparative Example 12 (0.090 g, 0.15 mmol) and dry THF (5 ml) were charged in a nitrogen flushed flask. Lithium Borohydride (0.25 ml of a 2 M THF solution) was added slowly at room temperature and allowed to stir overnight. After 16 hours, the reaction mixture was transferred to a separatory funnel and 1 N NaOH added. The crude product was extracted into methylene chloride (3×), the organic extracts concentrated and further purified by prep TLC using 90:10 Methylene chloride: MeOH eluent to afford 0.081 g of the title compound (95% yield). MS M+H=566.

Preparative Example 14

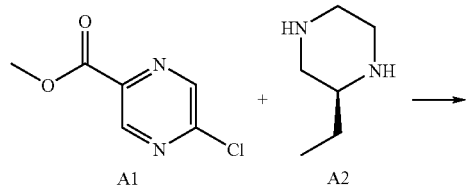

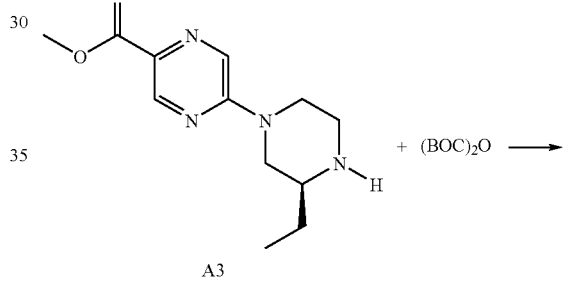

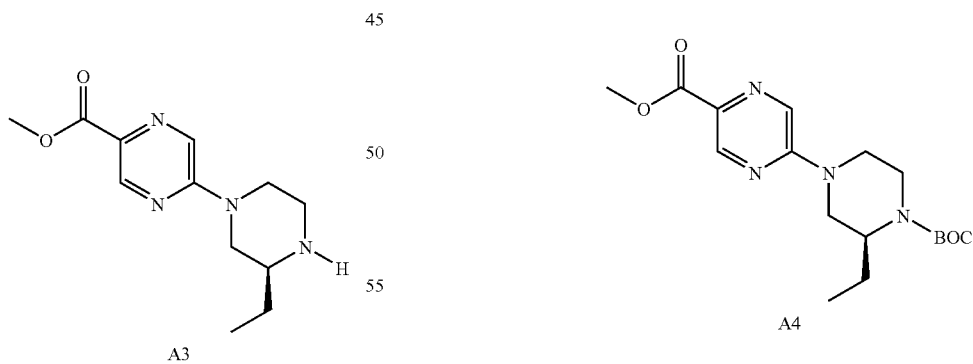

A round bottomed flask was charged with methyl 2-chloropyrazine-5-carboxylate (Lonza, 25.9 g, 145 mmol), 2-S-ethyl piperazine (prepared as per Williams et al J. Med. Chem 1996, 39, 1345, 85% active, 28.0 g, 208 mmol), cesium carbonate (Aldrich, 110 g, 338 mmol) and 1,4 dioxane (400 ml). The resulting suspension was stirred at room temperature for 18 hours and then filtered. The solid was washed with ethyl acetate (3×400 ml). The combined organic solutions were concentrated on a rotary evaporator to remove the solvent. The residue was purified by flash chromatography on silica gel using 5% to 10% methanol in dichloromethane as an eluent to provide A3 as a white solid (28.0 g, 77%).

Preparative Example 15

The starting materials A3 (28.0 g, 112 mmol), di-tert-butyl dicarbonate (24.5 g, 112 mmol), and dichloromethane (200 ml) were added to a 1000 ml flask. The resulting solution was stirred at room temperature for 20 hours, treated with 1.0 M aqueous NaOH solution (300 ml), and extracted with dichloromethane (3×200 ml). The combined dichloromethane solutions were dried over sodium sulfate, concentrated on a rotary evaporator to remove the solvent. The residue was dried on house vacuum to afford A4 as a gel (42 g) which was used for the next reaction without further purification.

Preparative Example 16

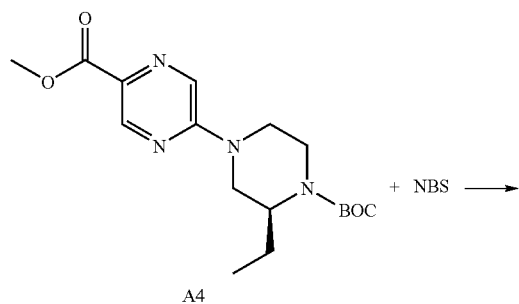

The compound A4 (crude, 42 g) and DMF (300 ml) were charged in a 1000 ml flask. To the stirring solution, NBS (32.0 g, 180 mmol) was added slowly at room temperature. The resulting solution was maintained at the same temperature with stirring for 17 hours, treated with saturated sodium sulfite (200 ml), diluted with ethyl acetate, and separated. The organic layer was washed with water (2×300 ml), dried over sodium sulfate, and concentrated under reduced pressure. Purification of the residue by flash chromatography on silica gel using 3% methanol in dichloromethane afforded A5 as an orange gel (47 g, 98% for 2 steps).

Preparative Example 17

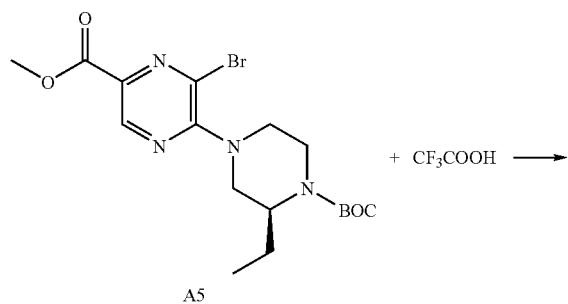

-continued

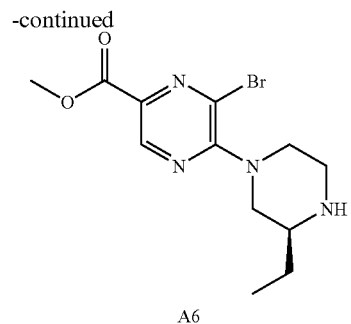

A round bottomed flask was charged with A5 (49.8 g, 116 mmol), trifluoroacetic acid (Acros, 100 ml), and dichloromethane (Aldrich, 100 ml). The resulting solution was stirred at room temperature for 4.5 hours and concentrated to remove the acid. The residue was treated with solid potassium carbonate (35 g), water (100 ml) and 1.0 M NaOH solution at 0° C. The mixture was extracted with dichloromethane (4×300 ml) and the combined organic layers were dried over sodium sulfate and concentrated under reduced pressure. The residue was dried on house vacuum to provide A6 as a brown oil (36.20 g) which was used for the next reaction without purification.

Preparative Example 18

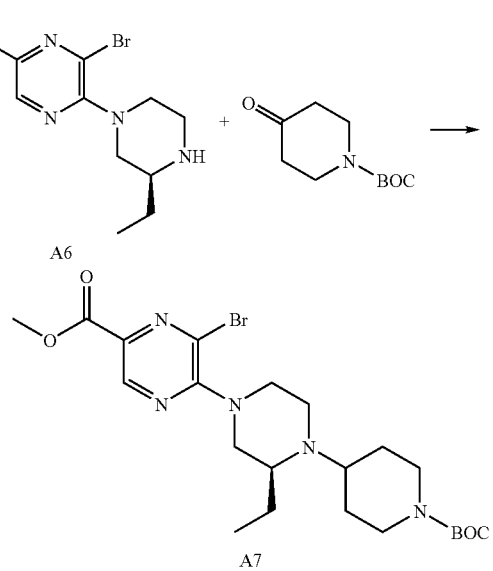

A round-bottomed flask was charged with A6 (36.0 g, 110 mmol), N—Boc piperidine-4-one (70.0 g, 351 mmol), and 1,2-dichloroethane (600 ml). The reducing reagent NaB (OAc)$_3$H (70.0 g, 330 mmol) was added slowly with stirring. The resulting suspension was stirred at room temperature for 3 days before it was treated with 1.0 M sodium hydroxide (800 ml) solution. The mixture was separated and the aqueous solution was extracted with dichloromethane (2×500 ml). The combined organic solutions were dried on sodium sulfate and concentrated on a rotary evaporator. The residue was purified by flash chromatography on silica gel using 20% ethyl acetate in hexanes and 2% methanol in dichloromethane as an eluent to provide A7 as a red gel (38.0 g, 68%).

Preparative Example 19

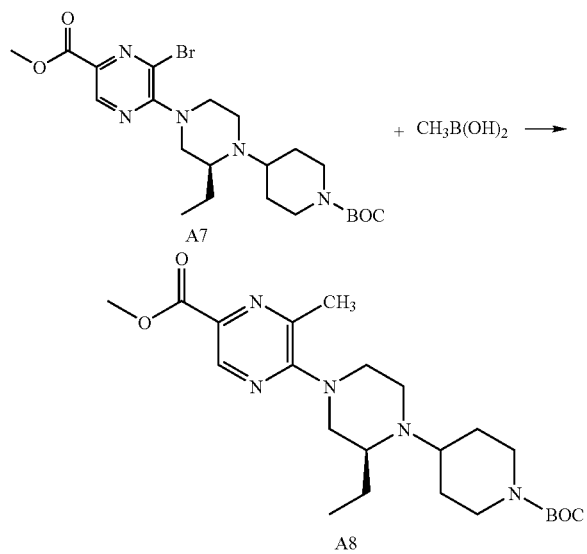

A round-bottomed flask was charged with A7 (10.87 g, 21.21 mmol), methylboronic acid (Aldrich, 3.82 g, 63.82 mmol), potassium carbonate (Aldrich, 15.0 g, 109 mmol), and DMF (100 ml). The resulting suspension was degassed for 30 min via bubbling nitrogen prior to the addition of dichlorobis(triphenylphosphine)palladium (II) (Aldrich, 1.5 g, 2.1 mmol). The reaction mixture was maintained at 85° C. for 20 hours with stirring, cooled to room temperature, and filtered. The filtrate was diluted with ethyl acetate (800 ml), washed with water (4×300 ml), dried on sodium sulfate, and concentrated on rotary evaporator. The residue was purified by flash chromatography on silica gel using 2% methanol in dichloromethane as an eluent to afford A8 as a red gel (5.95 g, 62%).

Preparative Example 20

Step A

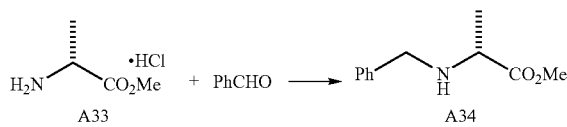

Benzaldehyde (19 mL, 19 g, 0.18 mol) was added to a solution of D-alanine methyl ester hydrochloride (25 g, 0.18 mol) in dry $CH_2Cl_2$ (300 mL). The solution was stirred at 22° C. for 19 h. The reaction mixture was cooled with an ice-water bath and solid sodium triacetoxyborohydride (46 g, 0.22 mol) was added in portions over ~15 min. The cooling bath was removed and the milky white solution was stirred at 22° C. for 7 h. The solvent was removed by rotary evaporation under reduced pressure and the resulting slush was partitioned between EtOAc (~100 mL) and 1 N HCl (~400 mL). The aqueous layer was extracted with EtOAc (~50 mL). The aqueous layer was adjusted to pH ~10 with 1 N NaOH (450 mL) and the milky aqueous layer was extracted immediately with EtOAc (3×250 mL). The combined organic layers were washed with brine (~250 mL), dried over anhydrous $MgSO_4$, filtered and concentrated under reduced pressure to afford N-benzyl-D-alanine methyl ester (28 g, 80%) as a colorless semi-solid.

Step B.

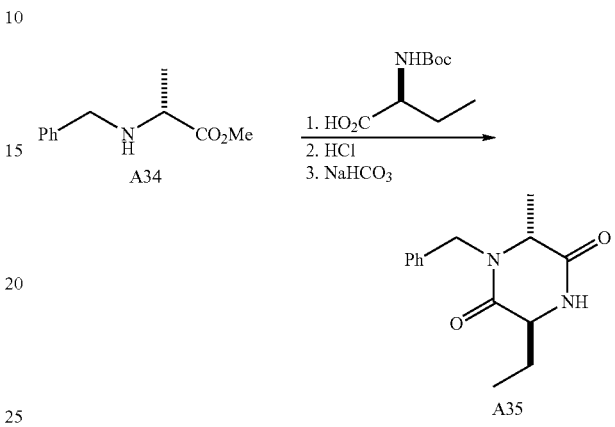

To a solution of N-benzyl-D-alanine methyl ester (28 g, 0.15 mol) and EDCl.HCl (30.6 g, 0.160 mmol) in $CH_2Cl_2$ (250 mL) was added a solution of N—Boc-2(S)-aminobutyric acid (29.5 g, 0.145 mol; Anaspec, Inc.) in $CH_2Cl_2$ (100 mL). The reaction mixture was stirred at 22° C. for 16 h. Additional N—Boc-2(S)-aminobutyric acid (5.9 g, 29 mmol) and EDCl.HCl (11.1 g, 58 mmol) and DMF (20 mL) were added. After 1 day, the solvents were removed under reduced pressure, and the residue was dissolved in EtOAc. The organic solution was washed with 0.5 N aqueous HCl, saturated aq. sodium carbonate, brine, and was then dried over anhydrous sodium sulfate. Subsequent filtration and concentration gave a colorless oil The oil was dissolved in $CH_2Cl_2$ (200 mL) and HCl gas was bubbled into the stirred solution for 1.5 h. After removal of solvent under reduced pressure, the resulting white solid was suspended in EtOAc (500 mL) and aqueous $NaHCO_3$ solution (150 mL). The mixture was stirred at rt for 18 h. The organic layer was separated, washed with brine, dried over anhydrous $MgSO_4$, filtered, and concentrated to give Compound A35 (21.9 g, 61% over 2 steps).

Step C.

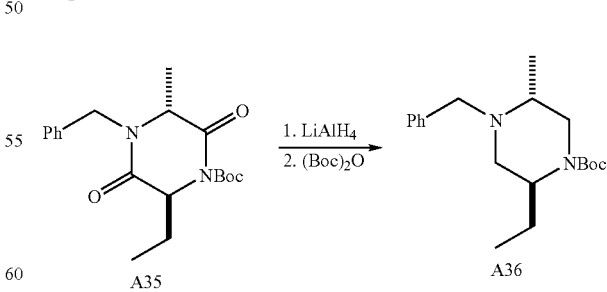

The diketopiperazine A35 (21.9 g, 89 mmol) was dissolved in dry THF (500 mL). Powdered $LiAlH_4$ (10.1 g, 267 mmol) was added cautiously and in portions over ~30 min. The reaction mixture was stirred at 22° C. for 1 h, at 65° C. for 1 d, and then at 22° C. for a further 24 h. The reaction was quenched by cautious dropwise addition of water (10 mL) over 1 h. 1 N aqueous NaOH solution (20 mL) and water (30 mL) were added sequentially and the milky white reaction mixture was stirred at rt for 1 h. The white gelatinous precipitate that formed was removed by filtration through Celite®. The filter cake was washed copiously with EtOAc (~500 mL). The combined filtrates were evaporated. The residue was dissolved in Et₂O (~500 mL) and then taken to dryness to afford 2(S)-ethyl-4-benzyl-5(R)-methylpiperazine (18.4 g, 93%) as a pale golden yellow oil.

The piperazine above (18.3 g, 84 mmol) was dissolved in CH₂Cl₂ (40 mL) and solid di-t-butyl dicarbonate (18.3 g, 84 mmol) was added. After stirring for 30 min at rt, the solvent was removed and the resulting yellow liquid was purified by flash column chromatography, eluting with 3:1 hexanes-Et₂O, to afford 1-Boc-2(S)-ethyl-4-benzyl-5(R)-methylpiperazine (A36) as a clear, colorless liquid (24.9 g, 93%).

Step D.

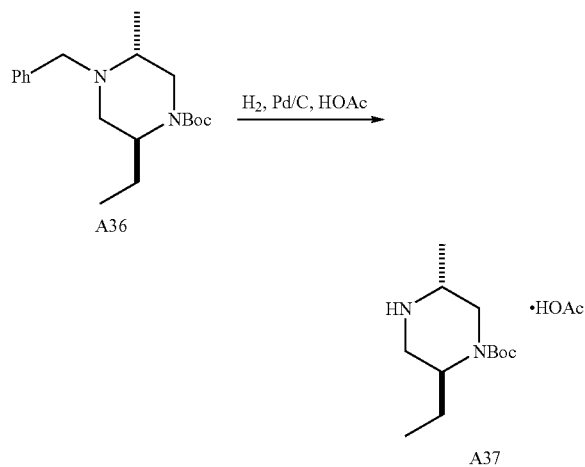

A mixture of 1-Boc-2(S)-ethyl-4-benzyl-5(R)-methylpiperazine (A36; 13.6 g, 43 mmol), glacial acetic acid (2.5 mL) and 10% Pd/C (4.5 g) in methanol (150 mL) was shaken under H₂ atmosphere (50 psi) for 24 h. The mixture was filtered through Celite® and the filter cake was washed copiously with EtOAc (~500 mL). The combined filtrates were dried over anhydrous MgSO₄, filtered, and concentrated under reduced pressure to afford a clear colorless oil. Further co-evaporation with CH₂Cl₂ (200 mL) and Et₂O (2×200 mL) gave the desired 1-Boc-2(S)-ethyl-5(R)-methylpiperazine acetic acid salt (A37, 9.7 g) as a viscous oil.

Preparative Example 21

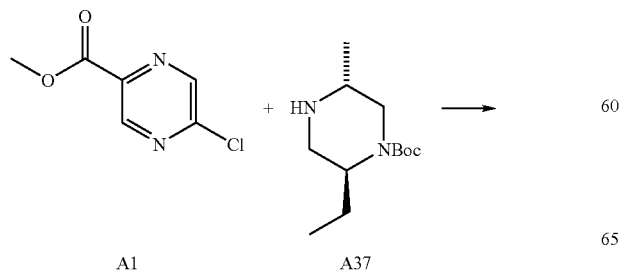

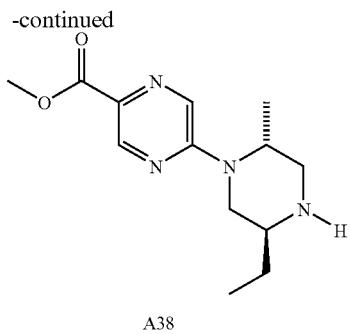

1-Boc-2(S)-ethyl-5(R)-methylpiperazine acetic acid salt (10 g) was dissolved in dichloromethane (100 mL) and treated with triethylamine (4 mL, 3 g). Solvent was evaporated and the residue was passed through a silica gel column, eluting with 3% methanol (containing ammonia) in dichloromethane, to give 1-Boc-2(S)-ethyl-5(R)-methylpiperazine free base (7.2 g).

A round bottomed flask was charged with methyl 2-chloropyrazine-5-carboxylate (Lonza, 4.83 g, 28 mmol), 1-Boc-2(S)-ethyl-5(R)-methylpiperazine free base (6.4 g, 28 mmol), cesium carbonate (Aldrich, 14 g, 42 mmol) and 1,4 dioxane (100 ml). The resulting suspension was stirred at 100° C. for 2 d and then filtered. The solid was washed with ethyl acetate (3×400 ml). The combined organic solutions were concentrated on a rotary evaporator to remove the solvent. The residue was purified by flash chromatography on silica gel using 1% methanol (containing 10% ammonium hydroxide) in dichloromethane as an eluent to provide A38 (9.0 g, 90%), as a beige solid Preparative Example 22

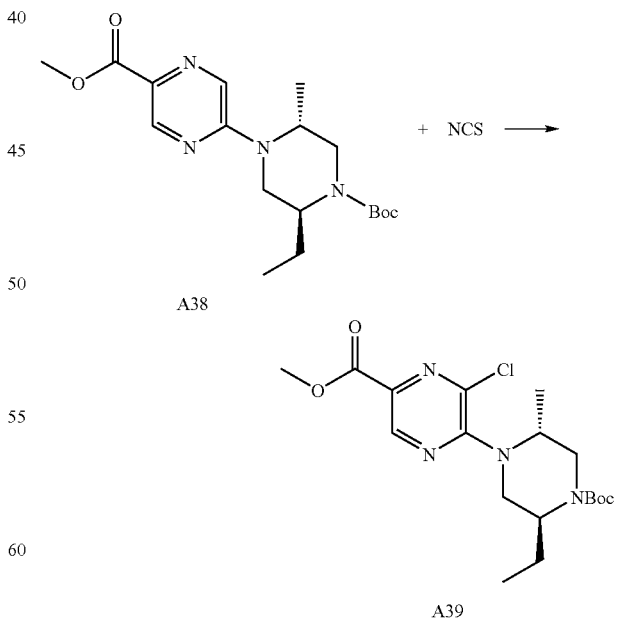

The compound A38 (9.0 g, 25 mmol) was dissolved in DMF (60 mL) and N-chlorosuccinimide (4.2 g, 32 mmol) was added. The reaction was stirred at rt for 18 h. The reaction mixture was diluted with ethyl acetate (500 mL) and washed sequentially with water (2×250 mL) and brine (250 mL). The organic phase was dried over anhydrous magnesium sulfate, filtered, and concentrated under reduced pressure to afford A39 (7.95 g, 81%) as a pale yellow solid.

Preparative Example 23

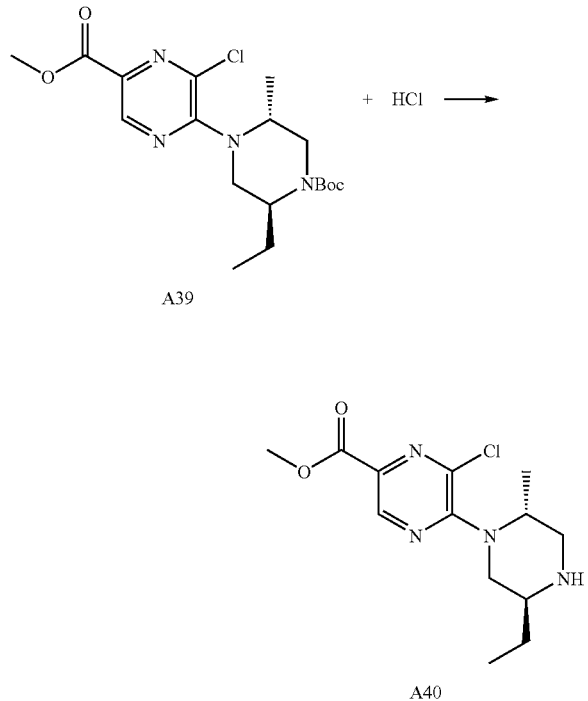

The compound A39 (7.95 g, 20 mmol) was dissolved in methanol (15 mL) and was treated with HCl (25 mL, 4 M in dioxane, 100 mmol). After stirring for 3 h at rt, solvent was removed to afford a yellow crude product. The crude product was taken up in methanol (100 mL), treated with triethylamine (10 mL), the solution concentrated under reduced pressure, and the residue purified by flash column chromatography, eluting with 4.5% methanol (containing ammonia) in dichloromethane. The desired product A40 (4.8 g, 81%).

Reaction of the Example No. 301-Lithium salt with an appropriately substituted amine as in example 11 above afforded the following Compound Numbers: 61, 65, 102, 105, 110, 209, 212, 213, 214, 215, 216, 217, 227, 229, 230, 233, 238, 245, 264, 273, 274, 277, 278, 279, 313, and 314.

Isolation of the compound at various stages of the reaction may be achieved by standard techniques such as, for example, filtration, evaporation of solvent and the like. Purification of the product, an intermediate and the like, may also be performed by standard techniques such as recrystallization, distillation, sublimation, chromatography, conversion to a suitable derivative which may be recrystallized and converted back to the starting compound, and the like. Such techniques are well known to those skilled in the art.

The prepared compounds may be analyzed for their composition and purity as well as characterized by standard analytical techniques such as, for example, elemental analysis, NMR, mass spectroscopy, and IR spectroscopy.

BIOLOGICAL EXAMPLES

The inventive compounds can readily be evaluated to determine activity at the CXCR3 receptors by known methods, such as, for example, development of a human CXCR3 (N-delta 4) Binding Assay.

Cloning and Expression of Human CXCR3 (N-delta 4):

The DNA encoding human CXCR3 was cloned by PCR using human genomic DNA (Promega, Madison, Wis.) as a template. The PCR primers were designed based on the published sequence of human orphan receptor GPR9 (1) with incorporated restriction sites, a Kozak consensus sequence, CD8 leader and Flag tag. The PCR product was subcloned into the mammalian expression vector pME18Sneo, a derivative of the SR-alpha expression vector (designated as pME18Sneo-hCXCR3 (N-delta 4).

IL-3-dependent mouse pro-B cells Ba/F3 were transfected by electroporation in 0.4 ml Dulbecco's PBS containing $4 \times 10^6$ cells with 20 µg of pME18Sneo-hCXCR3 (N-delta 4) plasmid DNA. Cells were pulsed at 400 Volts, 100 OHMs, 960 µFd. The transfected cells were under selection with 1 mg/ml G418 (Life Technologies, Gaithersburg, Md.). G418-resistant Ba/F3 clones were screened for CXCR3 expression by specific binding of [$^{125}$I] IP-10 (NEN Life Science Products, Boston, Mass.).

Preparation of Ba/F3-hCXCR3 (N-delta 4) Membranes:

Ba/F3 cells expressing human CXCR3 (N-delta 4) were pelleted and resuspended in the lysis buffer containing 10 mM HEPES, pH 7.5 and Complete® protease inhibitors (1 tablet per 100 ml) (Boehringer Mannheim, Indianapolis, Ind.) at a cell density of $20 \times 10^6$ cells per ml. After 5 minute incubation on ice, cells were transferred to 4639 cell disruption bomb (Parr Instrument, Moline, Ill.) and applied with 1,500 psi of nitrogen for 30 minutes on ice. Large cellular debris was removed by centrifugation at 1,000×g. Cell membrane in the supernatant was sedimented at 100,000×g. The membrane was resuspended in the lysis buffer supplemented with 10% sucrose and stored at −80° C. Total protein concentration of the membrane was determined by BCA method from Pierce (Rockford, Ill.).

Human CXCR3 (N-delta 4) Scintillation Proximity Assay (SPA):

For each assay point, 2 µg of membrane was preincubated for 1 hr with 300 µg wheat germ agglutinin (WGA) coated SPA beads (Amersham, Arlington Heights, Ill.) in the binding buffer (50 mM HEPES, 1 mM $CaCl_2$, 5 mM $MgCl_2$, 125 mM NaCl, 0.002% $NaN_3$, 1.0% BSA) at room temperature. The beads were spun down, washed once, resuspended in the binding buffer and transferred to a 96-well Isoplate (Wallac, Gaithersburg, Md.). 25 pM of [$^{125}$I] IP-10 with tested compounds in a series of titration were added to start the reaction. After 3 hr reaction at room temperature, the amount of [$^{125}$I] IP-10 bound to the SPA beads was determined with a Wallac 1450 Microbeta counter.

The Ki ratings for the various compounds of the present invention are given in the afore-mentioned Table 1. From these ratings and value ranges, it would be apparent to the skilled artisan that the compounds of the invention have excellent utility as CXCR3 receptor antagonists.

While the present invention has been describe in conjunction with the specific embodiments set forth above, many alternatives, modifications and variations thereof will be apparent to those of ordinary skill in the art. All such alternatives, medications and variations are intended to fall within the spirit and scope of the present invention.

What is claimed is:
1. A compound having the structure shown in Formula 1:

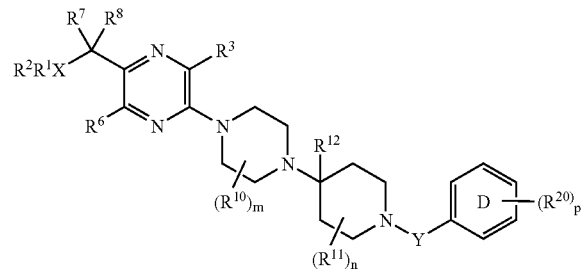

Formula 1 or a pharmaceutically acceptable salt thereof wherein:
X is N, O, alkyl, or heteroaryl;
ring D is a phenyl ring unsubstituted or optionally substituted with independently selected $R^{20}$ moieties as stated below;
$R^1$ and $R^2$ are independently absent or present, and if present each is independently selected from the group consisting of H, alkyl, alkoxy, alkenyl, carbonyl, cycloalkyl, alkyl-cycloalkyl-, cycloalkenyl, alkylaryl, arylalkyl, aryl, amino, alkylamino, amidinyl, carboxamido, cyano, hydroxyl, urea, —N≡CH, ═NCN, $(CH_2)_q$ CH, —$(CH_2)_qOR^{31}$, —$(CH_2)_qCF_3$, —$(CH_2)_q$ $NH_2$, —$(CH_2)_qNHR^{31}$, —$(CH_2)_qN(R^{31})_2$, —$(CH_2)_q$-amidinyl, cyclopropylhydroxy, cyclobutylhydroxy, cyclopentylhydroxy, —$(CH_2)_qC(═O)NHR^{31}$, —$(CH_2)_q$ $SO_2R^{31}$, —$(CH_2)_qNHSO_2R^{31}$, —$(CH_2)_q$ $SO_2NHR^{31}$, —C(═S)N(H)alkyl, —N(H)—S(O)$_2$-alkyl, —N(H)C(═O)N(H)-alkyl, —S(O)$_2$alkyl, —S(O)$_2$N(H)alkyl, —S(O)$_2$N(alkyl)$_2$, —S(O)$_2$aryl, —C(═S)N(H)cycloalkyl, —C(═O)N(H)NH$_2$, —C(═O))alkyl, —CH$_2$CH$_2$Ophenyl, —CH$_2$CH (OCH$_2$CH$_3$)$_2$, —C(═O)NHcyclopropyl, —C(═O)N (H)CH$_2$CF$_3$, —S(O)$_2$CH$_2$CF$_3$, —S(O)$_2$CF$_3$, -heteroaryl, heterocyclyl, heterocyclenyl, difluorophenyl, aminooxadiazolyl, fluorophenylmethylene, trifluoromethylphenylmethylene, cyanophenylmethylene, difluorophenylmethylene, bromophenylmethylene, chlorophenylmethylene, bromochlorophenylmethylene, fluorochlorophenylmethylene, dichlorophenylmethylene, methoxylphenylmethylene, —CH$_2$-cyclopropyl, cyclohexylmethylene, 5-methyl-isoxazolyl, chloropyridyl, pyridylmethylene,

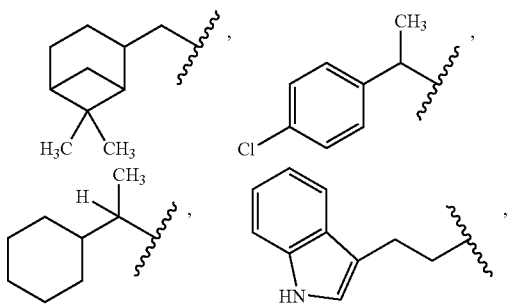

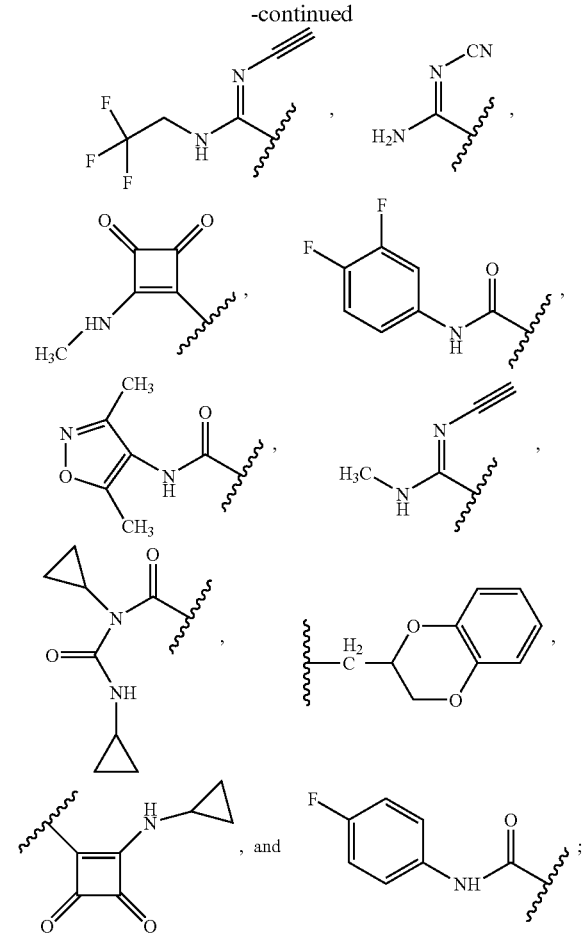

or alternatively when X is N, the N taken together with the $R^1$ and $R^2$ forms a heterocycyl, heteroaryl or —N═C(NH$_2$)$_2$;
$R^3$ is selected from the group consisting of H, alkyl, haloalkyl, halogen, —N(R$^{30}$)$_2$, and —OR$^{30}$;
$R^6$ is selected from the group consisting of H and —N(R$^{30}$)$_2$;
$R^7$ and $R^8$ taken together are ═O;
the $R^{10}$ moieties can be the same or different, each being independently selected from the group consisting of H, alkyl, —$(CH_2)_q$OH, —$(CH_2)_qOR^{31}$, and —OR$^{30}$;
the $R^{11}$ moieties can be the same or different, each being independently selected from the group consisting of H, alkyl, carboxamide, and —OR$^{30}$;
$R^{12}$ is selected from the group consisting of H and alkyl;
the $R^{20}$ moieties can be the same or different, each being independently selected from the group consisting of H, alkyl, alkenyl, alkylaryl, alkynyl, alkoxy, alkylamino, alkylthiocarboxy, alkylheteroaryl, alkylthio, alkylsulfinyl, alkylsulfonyl, alkoxycarbonyl, aminoalkyl, amidinyl, aralkyl, aralkenyl, aralkoxy, aralkoxycarbonyl, aralkylthio, aryl, aroyl, aryloxy, cyano, cycloalkyl, cycloalkenyl, formyl, guanidinyl, halogen, haloalkyl, heteroalkyl, heteroaryl, heterocyclyl, heterocyclenyl, hydroxyalkyl, haloalkoxy, hydroxamate, nitro, trifluoromethyl, trifluoromethoxy, —$(CH_2)_q$OH, —$(CH_2)_q$OR$^{31}$, —$(CH_2)_q$NH$_2$, —$(CH_2)_q$NHR$^{31}$, —$(CH_2)_q$N (R$^{31}$)$_2$, —$(CH_2)_q$C(═O)NHR$^{31}$, —$(CH_2)_q$SO$_2$R$^{31}$, —$(CH_2)_q$NHSO$_2$R$^{31}$, —$(CH_2)_q$SO$_2$NHR$^{31}$, -alkynylC (R$^{31}$)$_2$OR$^{31}$, —C(═O)R$^{30}$, —C(═O)N(R$^{30}$)$_2$, —C(=NR³⁰)NHR³⁰, —C(=NOH)N(R³⁰)₂, —C(=NOR³¹)N(R³⁰)₂, —C(=O)OR³⁰, —N(R³⁰)₂, —N(R³⁰)C(=O)R³¹, —NHC(=O)N(R³⁰)₂, —N(R³⁰)C(=O)OR³¹, —N(R³⁰)C(=NCN)N(R³⁰)₂, —N(R³⁰)C(=O)N(R³⁰)SO₂(R³¹), —N(R³⁰)C(=O)N(R³⁰)₂, —N(R³⁰)SO₂(R³¹), —N(R³⁰)S(O)₂N(R³⁰)₂, —OR³⁰, —OC(=O)N(R³⁰)₂, —SR³⁰, —SO₂N(R³⁰)₂, —SO₂(R³¹), —OSO₂(R³¹), —O(CH₂)$_q$SO₂R³¹, and —OSi(R³⁰)₃; or alternatively two R²⁰ moieties are linked together to form a five or six membered aryl, cycloalkyl, heterocyclyl, heterocyclenyl, or heteroaryl ring wherein said five or six membered aryl, cycloalkyl, heterocyclyl, heterocyclenyl, or heteroaryl ring is fused to ring D and the fused ring is optionally substituted with 0-4 R²¹ moieties;

the R²¹ moieties can be the same or different, each being independently selected from the group consisting of H, alkyl, alkenyl, alkylaryl, alkynyl, alkoxy, alkylamino, alkylthiocarboxy, alkylheteroaryl, alkylthio, alkylsulfinyl, alkylsulfonyl, alkoxycarbonyl, aminoalkyl, amidinyl, aralkyl, aralkenyl, aralkoxy, aralkoxycarbonyl, aralkylthio, aryl, aroyl, aryloxy, carboxamido, cyano, cycloalkyl, cycloalkenyl, formyl, guanidinyl, halogen, haloalkyl, heteroalkyl, heteroaryl, heterocyclyl, heterocyclenyl, hydroxyalkyl, hydroxamate, nitro, trifluoromethoxy, —(CH₂)$_q$OH, —(CH₂)$_q$OR³¹, —(CH₂)$_q$NH₂, —(CH₂)$_q$NHR³¹, —(CH₂)$_q$N(R³¹)₂, —(CH₂)$_q$C(=O)NHR³¹, —(CH₂)$_q$SO₂R³¹, —(CH₂)$_q$NHSO₂R³¹, —(CH₂)$_q$SO₂NHR³¹, -alkynylC(R³¹)₂OR³¹, —C(=O)R³⁰, —C(=O)N(R³⁰)₂, —C(=NR³⁰)NHR³⁰, —C(=NOH)N(R³⁰)₂, —C(=NOR³¹)N(R³⁰)₂, —C(=O)OR³⁰, —N(R³⁰)₂, —N(R³⁰)C(=O)R³¹, —NHC(=O)N(R³⁰)₂, —N(R³⁰)C(=O)OR³¹, —N(R³⁰)C(=NCN)N(R³⁰)₂, —N(R³⁰)C(=O)N(R³⁰)SO₂(R³¹), —N(R³⁰)C(=O)N(R³⁰)₂, —N(R³⁰)SO₂(R³¹), —N(R³⁰)S(O)₂N(R³⁰)₂, —OR³⁰, —OC(=O)N(R³⁰)₂, —SR³⁰, —SO₂N(R³⁰)₂, —SO₂(R³¹), —OSO₂(R³¹), and —OSi(R³⁰)₃;

Y is selected from the group consisting of —(CR¹³R¹³)$_r$—, —(CHR¹³)$_r$O—, —C(=O)—, —C(=NR³⁰)—, —(C(H)(heteroaryl))—, —(CHR¹³)$_r$C(=O)— and —(CHR¹³)$_r$N(H)C(=O)—;

the R¹³ moieties can be the same or different, each being independently selected from the group consisting of H, alkyl, —CO₂H, —C(=O)OR³¹, —C(=O)N(R³⁰)₂, —(CHR³⁰)$_q$OH, —(CHR³⁰)$_q$OR³¹, —(CHR³⁰)$_q$NH₂, and —(CH₂)$_q$NHSO₂R³¹;

the R³⁰ moieties can be the same or different, each being independently selected from the group consisting of H, alkyl, aralkyl, cycloalkyl, —(CH₂)$_q$OH, —(CH₂)$_q$Oalkyl, —(CH₂)$_q$NH₂, —(CH₂)$_q$NHalkyl, —(CH₂)$_q$N(alkyl)₂, —(CH₂)$_q$NHaralkyl, —(CH₂)$_q$C(=O)NHalkyl, —(CH₂)$_q$C(=O)N(alkyl)₂, —(CH₂)$_q$C(=O)NHaralkyl, —(CH₂)$_q$SO₂alkyl, and —(CH₂)$_q$SO₂NHalkyl;

the R³¹ moieties can be the same or different, each being independently selected from the group consisting of alkyl, aralkyl, cycloalkyl, —(CH₂)$_q$OH, —(CH₂)$_q$Oalkyl, —(CH₂)$_q$NH₂, —(CH₂)$_q$NHalkyl, —(CH₂)$_q$N(alkyl)₂, —(CH₂)$_q$NHaralkyl, —(CH₂)$_q$C(=O)NHalkyl, —(CH₂)$_q$C(=O)N(alkyl)₂, —(CH₂)$_q$C(=O)NHaralkyl, —(CH₂)$_q$SO₂alkyl, and —(CH₂)$_q$SO₂NHalkyl;

m is 0 to 4;
n is 0 to 4;
p is 0 to 5;

each q can be the same or different, each being independently selected from 1 to 5; and r is 1 to 4;

with the proviso that there are no two adjacent double bonds in any ring, and that when a nitrogen is substituted by two alkyl groups, said two alkyl groups may be optionally joined to each other to form a ring.

2. The compound according to claim 1, wherein R¹ and R² are independently absent or present, and if present each is independently selected from the group consisting of H, alkyl, aryl, amino, alkoxy, hydroxy, cycloalkyl, alkyl-cycloalkyl-, cycloalkenyl, arylalkyl, amidinyl, carboxamido, heteroaryl, heterocyclyl, heterocyclenyl, urea, —S(O)₂alkyl, —S(O)₂N(H)alkyl, —S(O)₂N(alkyl)₂, and —C(=S)N(H)cycloalkyl.

3. The compound according to claim 1, wherein R¹ and R² are independently absent or present, and if present each is independently selected from the group consisting of H, alkylaryl, alkyl-cycloalkyl-, aryl, heteroaryl, —(CH₂)$_q$CF₃, —(CH₂)$_q$OH, —(CH₂)$_q$OR³¹, —(CH₂)$_q$NH₂, —(CH₂)$_q$NHR³¹, —(CH₂)$_q$N(R³¹)₂, —(CH₂)$_q$C(=O)NHR³¹, —(CH₂)$_q$SO₂R³¹, —(CH₂)$_q$NHSO₂R³¹, —(CH₂)$_q$SO₂NHR³¹, —(CH₂)$_q$-amidinyl, cyclopropyl, cyclopropylhydroxyl, cyclobutyl, cyclobutylhydroxy, cyclopentyl, and cyclopentylhydroxy; and q is an integer from 1 to 5.

4. The compound according to claim 1, wherein R¹ and R² are independently absent or present, and if present each is independently selected from the group consisting of H, —CH₃, fluorophenylmethylene, trifluoromethylphenylmethylene, indanyl, cyanophenylmethylene, difluorophenylmethylene, bromophenylmethylene, chlorophenylmethylene, —CH₂CH₂Ophenyl, cyclopentyl, bromochlorophenylmethylene, fluorochlorophenylmethylene, dichlorophenylmethylene, phenylmethylene, —(CH₂)₃phenyl, —CH₂CF₃, methoxylphenylmethylene, —CH(CH₃)₂, —C₂H₅, —CH₂-cyclopropyl, —(CH₂)₂CH₃, cyclohexylmethylene, cyclohexyl, —CH₂CH₂SO₂CH₃, —CH₂—CH₂—NH₂, —CH₂CH₂OCH₃, cyclopropyl, CH₃-cyclopropyl, isoxazolyl, —CH₂CH₂OH, —CH₂CH₂CH₃, —NH₂, pyrazolyl, 5-methyl-isoxazolyl, —CH₂CH(OCH₂CH₃)₂, —OCH₃, —NHC(=O)NH₂, chloropyridyl, pyridylmethylene, —C(=O)NHcyclopropyl, —C(=O)N(H)C₂H₅, —C(=O)N(H)CH₂CF₃, —C(=O)N(H)C(CH₃)₃, —C(=S)N(H)cyclopropyl, —C(=O)NH₂, —C(=O)N(H)CH₃, —S(O)₂CH₃, —S(O)₂N(CH₃)₂, —S(O)₂CH₂CH₃, —C(=O)CH₃, —S(O)₂(CH₂)₂CH₃, —C(=O)N(H)cyclohexyl, —C(=NH)NH₂, —C(=O)N(H)NH₂, —C(=O)N(H)CH(CH₃)₂, thiazolyl, —C(=O)N(CH₃)₂, —S(O)₂CH₂CF₃, —S(O)₂CF₃,

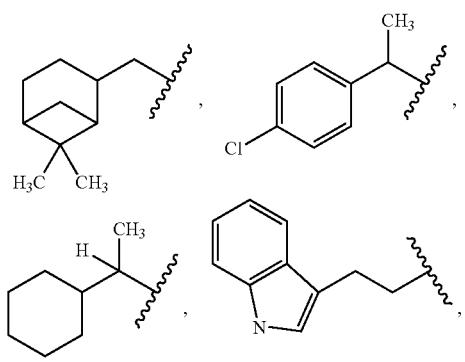

-continued

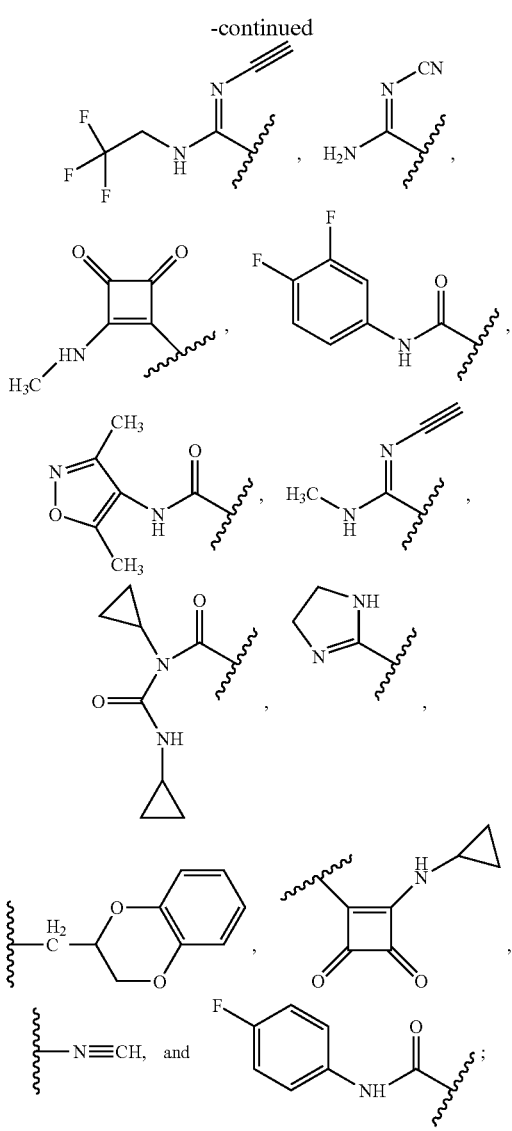

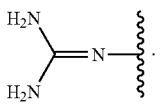

or when X is N, the N taken together with the R¹ and R² to which X is shown attached, forms an aziridine, azetidine, piperidine or 5. The compound according to claim 1, wherein R¹ and R² are independently absent or present, and if present each is independently selected from the group consisting of H, —CH₃, —C₂H₅, difluorophenylmethylene, cyclopropyl, CH₃-cyclopropyl-, dichlorophenylmethylene, —CH(CH₃)₂, cyclohexylmethylene, cyclohexyl, isoxazolyl, oxadiazolyl, aminooxadiazoyl, difluorophenyl, —CH₂CH₂OH, —CH₂CH₂N(CH₃)₂, —C(=O)N(H)cyclopropyl, —C(=O)N(H)C₂H₅, —C(=O)N(H)CH₂CF₃, —C(=O)N(H)cyclopropyl, —C(=O)N(H)C(CH₃)₃, —C(=S)N(H)cyclopropyl, —C(=O)NH₂, —C(=O)N(H)CH₃, —S(O)₂CH₃, —S(O)₂N(CH₃)₂, —S(O)₂CH₂CH₃, —C(=O)CH₃, —S(O)₂(CH₂)₂CH₃, —C(=O)N(H)cyclohexyl, —C(=NH)NH₂, —C(=O)N(H)NH₂, thiazolyl,

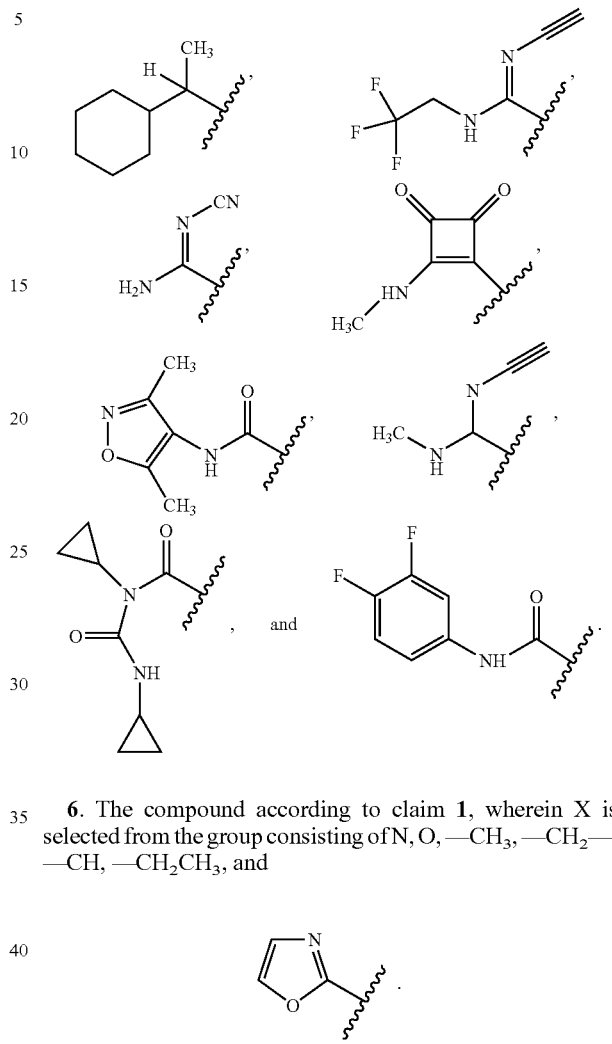

6. The compound according to claim 1, wherein X is selected from the group consisting of N, O, —CH₃, —CH₂—, —CH, —CH₂CH₃, and 7. The compound according to claim 1, wherein R³ is selected from the group consisting of H, alkyl, halogen, —N(R³⁰)₂, —OR³⁰ and —CF₃.

8. The compound according to claim 1, wherein R³ is selected from the group consisting of H, —CH₃, —CH₂CH₃, —F, —Cl, OCH₃, and CF₃.

9. The compound according to claim 1, wherein R⁶ is selected from the group consisting of H and —NH₂.

10. The compound according to claim 1, wherein R¹⁰ is selected from the group consisting of —CH₃, —CH₂CH₃ and —CH₂CH₂CH₃, and m is 0-2.

11. The compound according to claim 1, wherein R¹² is selected from the group consisting of H, —CH₃, and —CH₂CH₃.

12. The compound according to claim 1, wherein the phenyl ring D is substituted by independently selected 1-4 R²⁰ moieties.

13. The compound according to claim 1, wherein the R²⁰ moieties can be the same or different, each being independently selected from the group consisting of H, alkyl, alkylaryl, alkynyl, alkoxy, alkylamino, alkylheteroaryl, alkylsulfinyl, alkoxycarbonyl, aminoalkyl, amidinyl, aralkyl, aralkoxy, aryl, aryloxy, cyano, cycloalkyl, cycloalkenyl, halogen, haloalkyl, heteroalkyl, heteroaryl, heterocyclyl, hydroxyalkyl, trifluoromethyl, trifluoromethoxy, —$(CH_2)_q OR^{31}$, —$(CH_2)_q NHR^{31}$, —$(CH_2)_q C(=O)NHR^{31}$, —$(CH_2)_q SO_2R^{31}$, —$(CH_2)_q NHSO_2R^{31}$, —$(CH_2)_q SO_2NHR^{31}$, -alkynylC$(R^{31})_2 R^{31}$, —$C(=O)R^{30}$, —$C(=O)N(R^{30})_2$, —$O(=O)OR^{30}$, —$N(R^{30})_2$, —$N(R^{30})C(=O)R^{31}$, —$NHC(=O)N(R^{30})_2$, —$N(R^{30})C(=O)OR^{31}$, —$N(R^{30})C(=NCN)N(R^{30})_2$, —$N(R^{30})C(=O)N(R^{30})_2$, —$N(R^{30})SO_2(R^{31})$, —$N(R^{30})SO_2N(R^{30})_2$, —$OR^{30}$, —$OC(=O)N(R^{30})_2$, —$SR^{30}$, —$SO_2N(R^{30})_2$, —$SO_2(R^{31})$, —$OSO_2(R^{31})$, —$O(CH_2)_q SO_2R^{31}$, and —$OSi(R^{30})_3$.

14. The compound according to claim 1, wherein the $R^{20}$ moieties can be the same or different, each being independently selected from the group consisting of H, alkyl, alkoxy, amino, halogen, CN, $CH_3$, $CF_3$, $OCH_3$, $OCF_3$, —$(CH_2)_q OR^{31}$, —$(CH_2)_q NHR^{31}$, —$(CH_2)_q C(=O)NHR^{31}$, —$(CH_2)_q SO_2R^{31}$, —$(CH_2)_q NHSO_2R^{31}$, —$(CH_2)_q SO_2NHR^{31}$, -alkynylC$(R^{31})_2 R^{31}$, —$C(=O)R^{30}$, —$C(=O)OR^{30}$, —$N(R^{30})_2$, —$N(R^{30})C(=O)R^{31}$, —$NHC(=O)N(R^{30})_2$, —$N(R^{30})C(=O)OR^{31}$, —$N(R^{30})C(=NCN)N(R^{30})_2$, —$N(R^{30})C(=O)N(R^{30})_2$, —$OR^{30}$, —$OC(=O)N(R^{30})_2$, —$O(CH_2)_q SO_2R^{31}$ and —$OSO_2(R^{31})$.

15. The compound according to claim 1, wherein two $R^{20}$ moieties are linked together to form a five or six membered aryl, cycloalkyl, heterocyclenyl, heterocyclyl or heteroaryl ring wherein said five or six membered aryl, cycloalkyl, heterocyclenyl, heterocyclyl, and heteroaryl ring is fused to ring D and the fused ring is optionally substituted with 0 to 4 $R^{21}$ moieties.

16. The compound according to claim 1, wherein the $R^{20}$ moieties can be the same or different, each being independently selected from the group consisting of H, —CN, —$CH_3$, —$CF_3$, —$CH_2OH$, —$CO_2H$, —$CO_2CH_3$, —$NH_2$, —$NHCH_3$, —$OCF_3$, —OH, F, Cl, Br, —$C(=NOH)NH_2$, —$OCH_2CH_2S(O_2)CH_3$, —$C(=O)NH_2$,

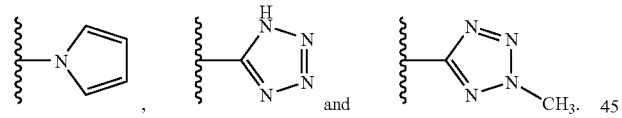
,

17. The compound according to claim 1, wherein Y is selected from the group consisting of: —$(CHR^{13})_r$—, —$(CR^{13}R^{13})_r$—, —$C(=O)$— and —$CHR^{13}C(=O)$—.

18. The compound according to claim 1, wherein Y is selected from the group consisting of: —$CH_2$—, —$CH(CH_3)$—, —$CH(CH_2OH)$—, —$C(=O)$— and —$CH(CO_2alkyl)$-.

19. The compound according to claim 1, wherein m is 0-3.

20. The compound according to claim 1, wherein n is 0-2.

21. The compound according to claim 1, wherein q is 1, 2 or 3.

22. The compound according to claim 1, wherein r is 1 or 2.

23. The compound according to claim 1, wherein X is N; $R^1$ and $R^2$ are independently selected from the group consisting of H, alkylaryl, aryl, heteroaryl, —$(CH_2)_q CF_3$, —$(CH_2)_q OH$, —$(CH_2)_q OR^{31}$, —$(CH_2)_q NH_2$, —$(CH_2)_q NHR^{31}$, —$(CH_2)_q N(R^{31})_2$, —$(CH_2)_q C(=O)NHR^{31}$, —$(CH_2)_q SO_2R^{31}$, —$(CH_2)_q NHSO_2R^{31}$, —$(CH_2)_q SO_2NHR^{31}$, —$(CH_2)_q$-amidinyl, cyclopropyl, alkyl-cyclopropyl-, cyclopropylhydroxyl, cyclobutyl, cyclobutylhydroxy, cyclopentyl, and cyclopentylhydroxy;

$R^3$ is selected from the group consisting of H, alkyl, haloalkyl, halogen, —$N(R^{30})_2$, —$OR^{30}$ and —$CF_3$;

$R^6$ is selected from the group consisting of H and —$N(R^{30})$;

$R^7$ and $R^8$ taken together are =O;

$R^{10}$ is selected from the group consisting of H and alkyl;

$R^{11}$ is H;

$R^{12}$ is selected from the group consisting of H and alkyl;

the $R^{20}$ moieties can be the same or different, each being independently selected from the group consisting of H, alkyl, alkoxy, amino, halogen, CN, $CH_3$, $CF_3$, $OCH_3$, $OCF_3$, —$(CH_2)_q OR^{31}$, —$(CH_2)_q NHR^{31}$, —$(CH_2)_q C(=O)NHR^{31}$, —$(CH_2)_q SO_2R^{31}$, —$(CH_2)_q NHSO_2R^{31}$, —$(CH_2)_q SO_2NHR^{31}$, -alkynylC$(R^{31})_2 OR^{31}$, —$C(=O)R^{30}$, —$C(=O)OR^{30}$, —$N(R^{30})_2$, —$N(R^{30})C(=O)R^{31}$, —$NHC(=O)N(R^{30})_2$, —$N(R^{30})C(=O)OR^{31}$, —$N(R^{30})C(=NCN)N(R^{30})_2$, —$N(R^{30})C(=O)N(R^{30})_2$, —$OR^{30}$, —$OC(=O)N(R^{30})_2$,

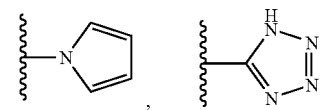

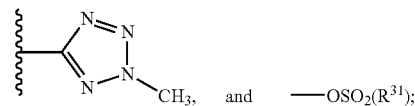
and —$OSO_2(R^{31})$;

Y is selected from the group consisting of: —$CH_2$—, —$CH(CH_2OH)$—, —$C(=O)$— and —$CH(CO_2alkyl)$-;

m is 0-2;

n is 0-2; and q is 1 or 2.

24. The compound according to claim 1, represented by the following structural Formula:

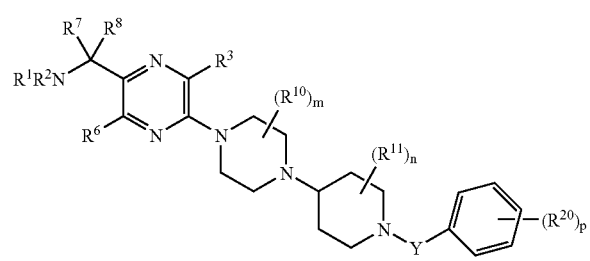

or a pharmaceutically acceptable salt thereof, wherein the various terms are as defined in claim 1.

25. A compound selected from the group consisting of:

-continued
| Compound No. | Compound Structure |
|---|---|
| 12 | 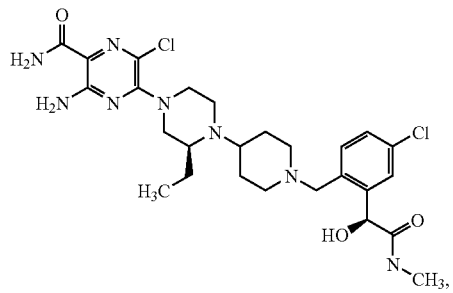 |
| 13 | 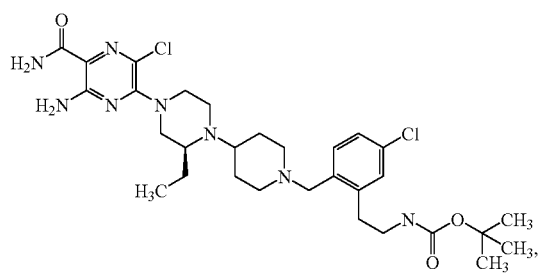 |
| 14 | 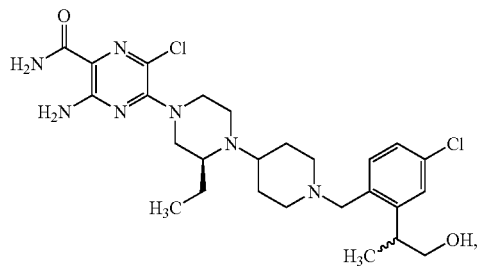 |
| 15 | 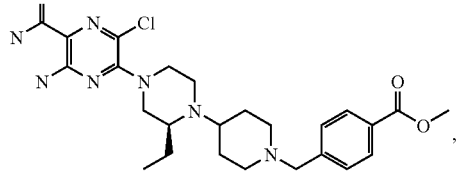 |
| 16 | 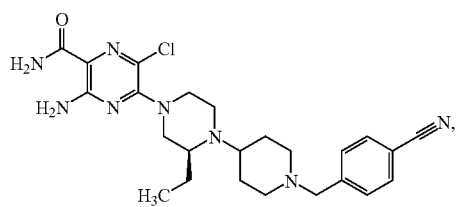 |
-continued
| Compound No. | Compound Structure |
|---|---|
| 17 | 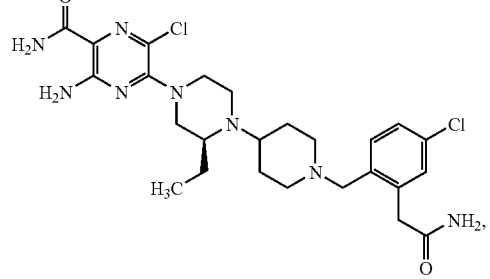 |
| 18 | 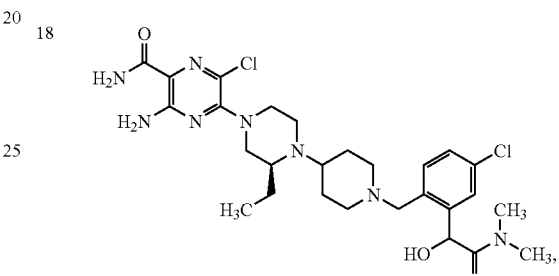 |
| 19 | 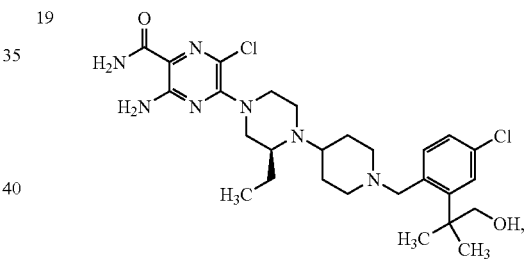 |
| 20 | 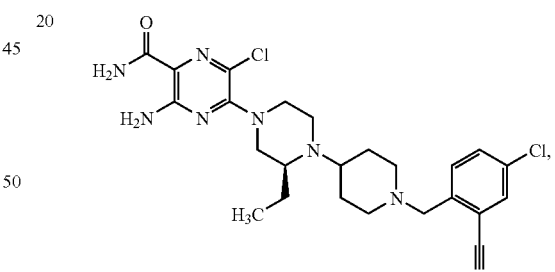 |
| 21 | 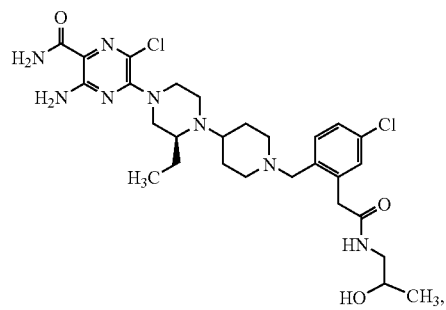 |

| Compound No. | Compound Structure |
|---|---|
| 22 | 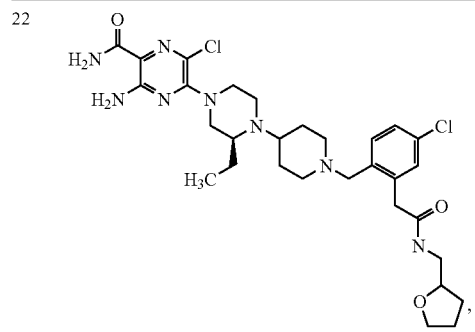 |
| 23 | 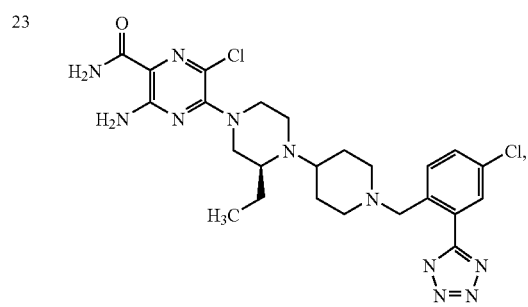 |
| 24 | 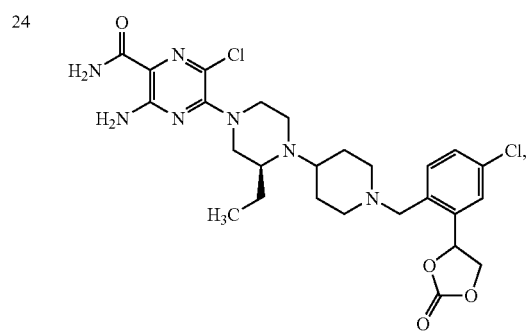 |
| 25 | 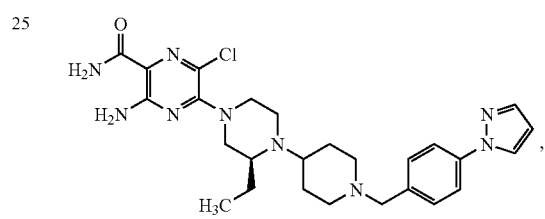 |
| 26 | 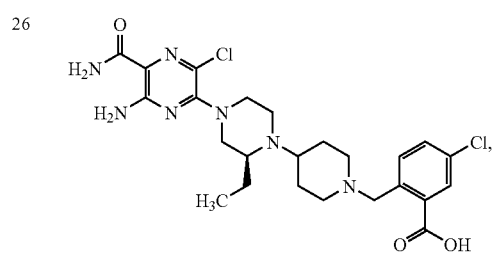 |
| 27 | 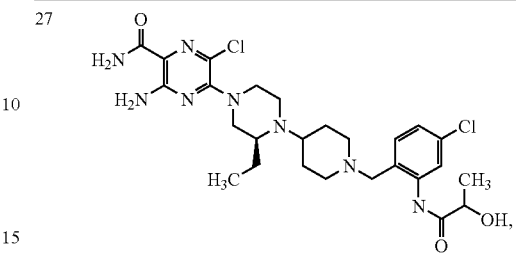 |
| 28 | 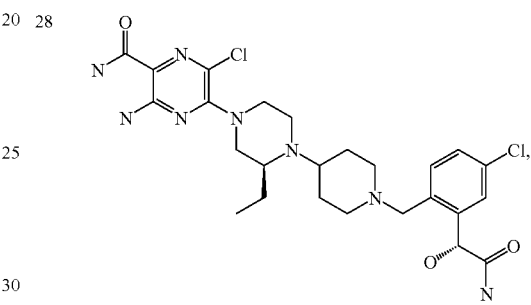 |
| 29 | 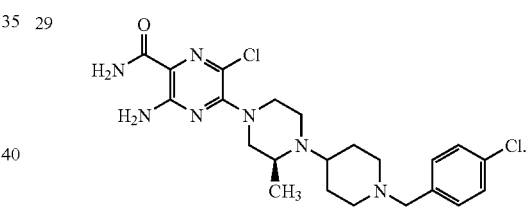 |
| 30 | 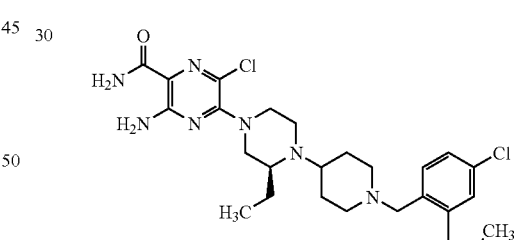 |
| 31 | 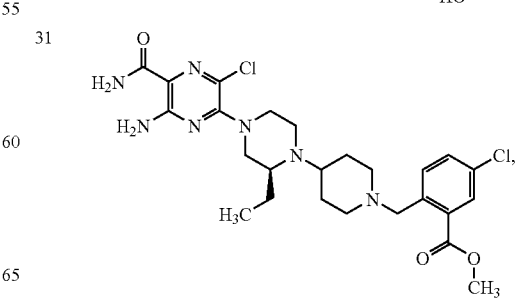 |

-continued
| Compound No. | Compound Structure |
|---|---|
| 32 | 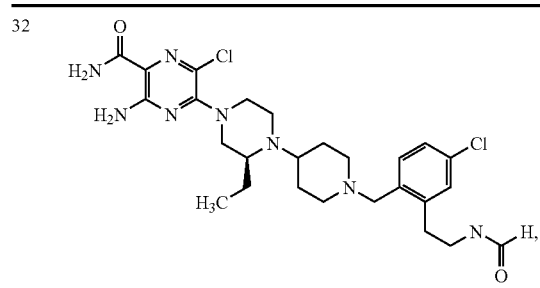 |
| 33 | 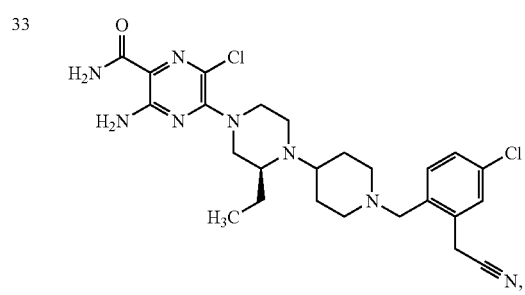 |
| 34 | 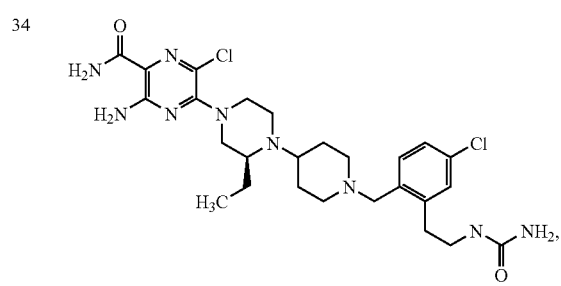 |
| 35 | 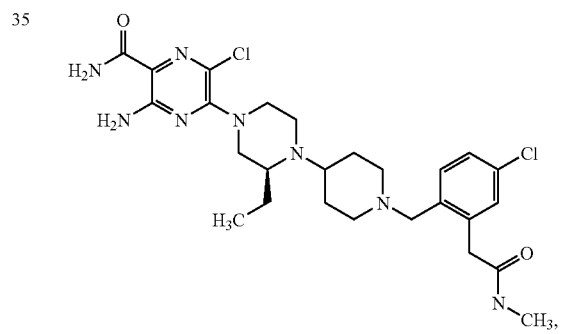 |
| 36 | 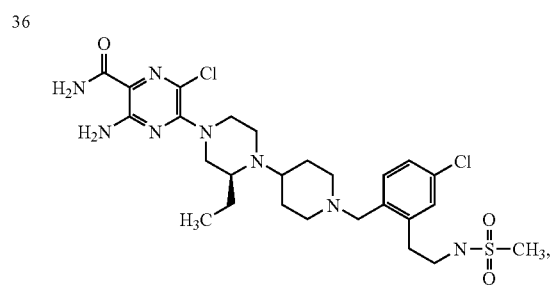 |
-continued
| Compound No. | Compound Structure |
|---|---|
| 37 | 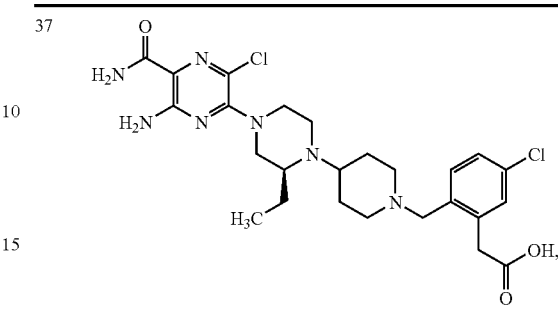 |
| 38 | 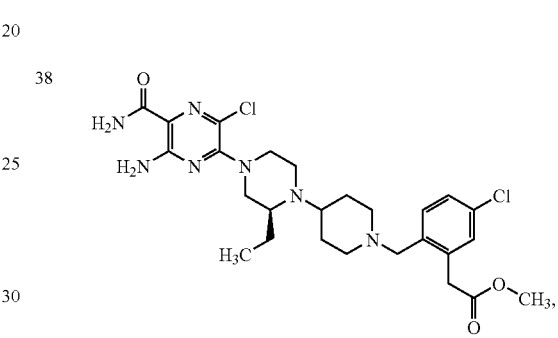 |
| 39 | 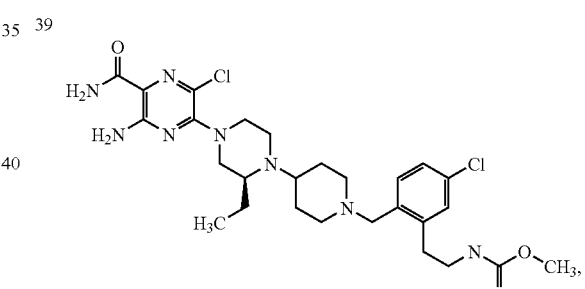 |
| 40 | 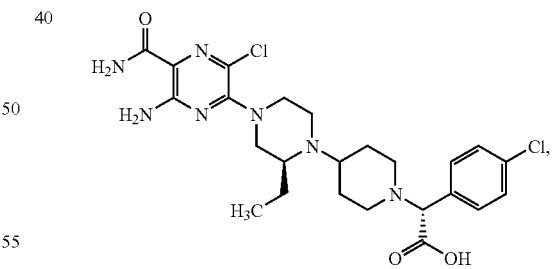 |
| 41 | 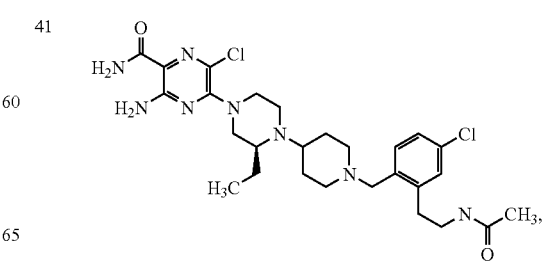 |

-continued
| Compound No. | Compound Structure |
|---|---|
| 42 | 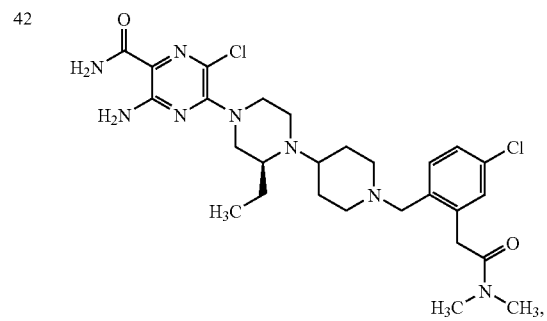 |
| 43 | 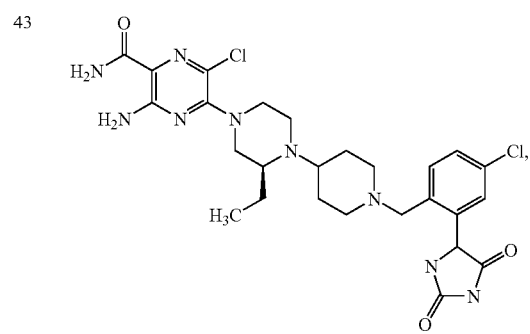 |
| 44 | 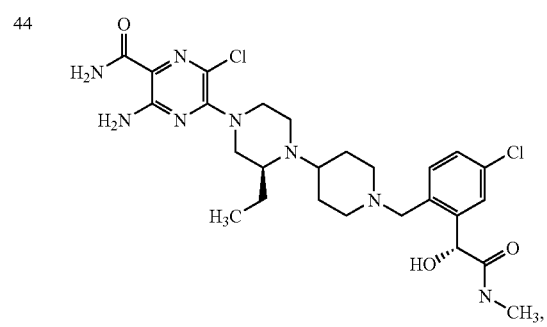 |
| 45 | 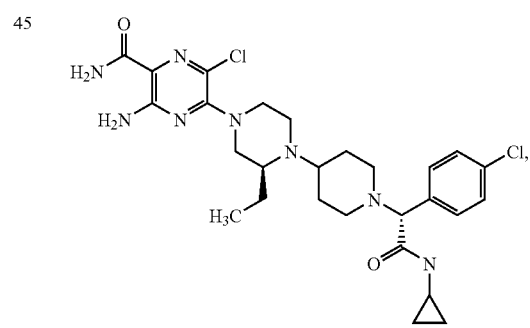 |
-continued
| Compound No. | Compound Structure |
|---|---|
| 46 | 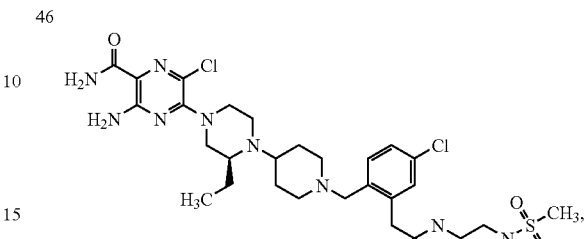 |
| 47 | 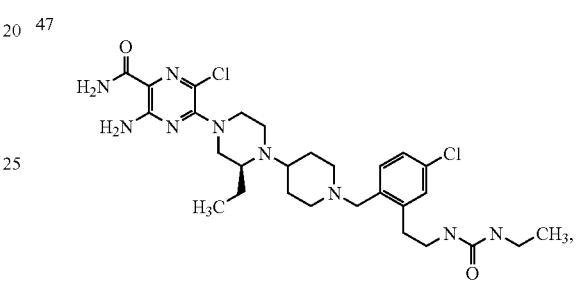 |
| 48 | 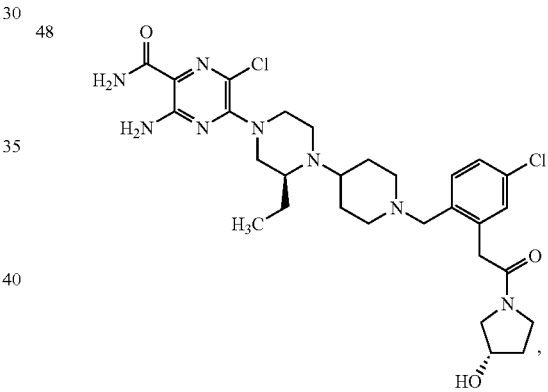 |
| 49 | 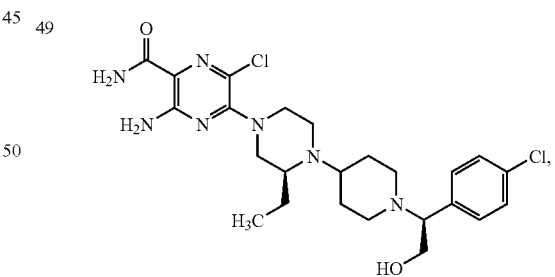 |
| 50 | 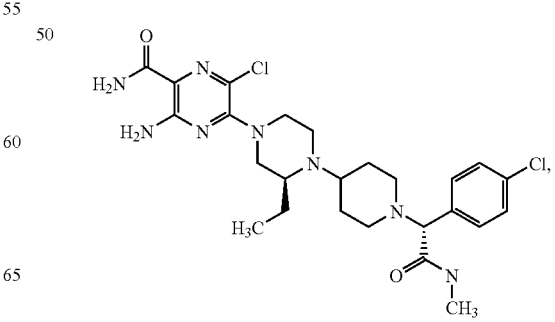 |

-continued
| Compound No. | Compound Structure |
|---|---|
| 51 | 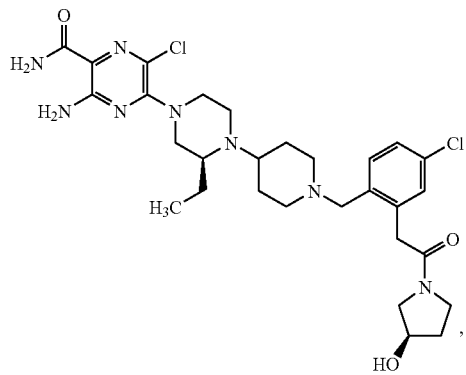 |
| 52 | 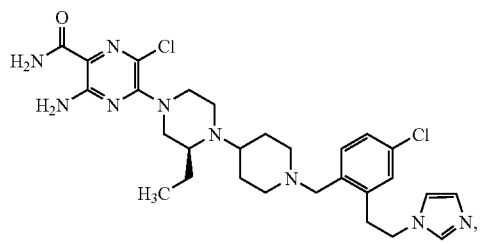 |
| 53 | 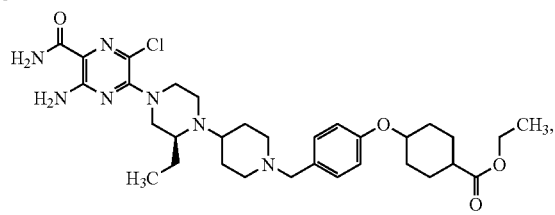 |
| 54 | 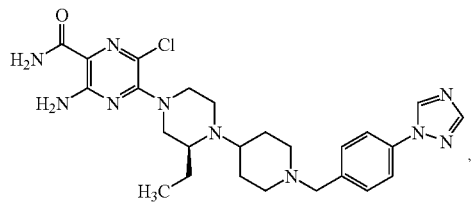 |
| 55 | 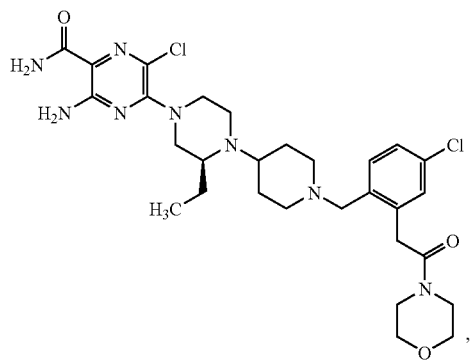 |
-continued
| Compound No. | Compound Structure |
|---|---|
| 56 | 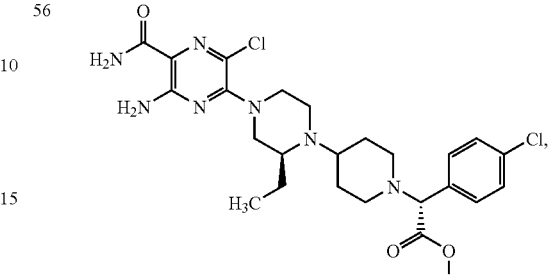 |
| 57 | 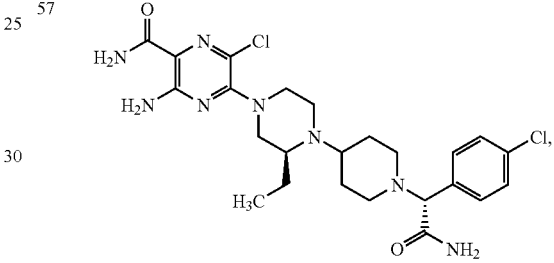 |
| 58 | 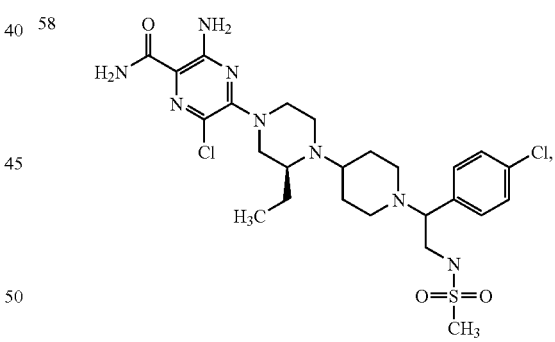 |
| 59 | 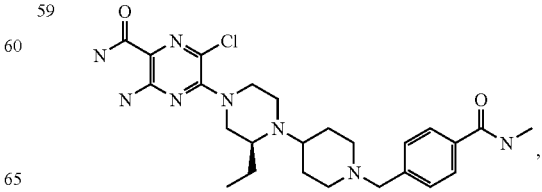 |

-continued
| Compound No. | Compound Structure |
|---|---|
| 60 | 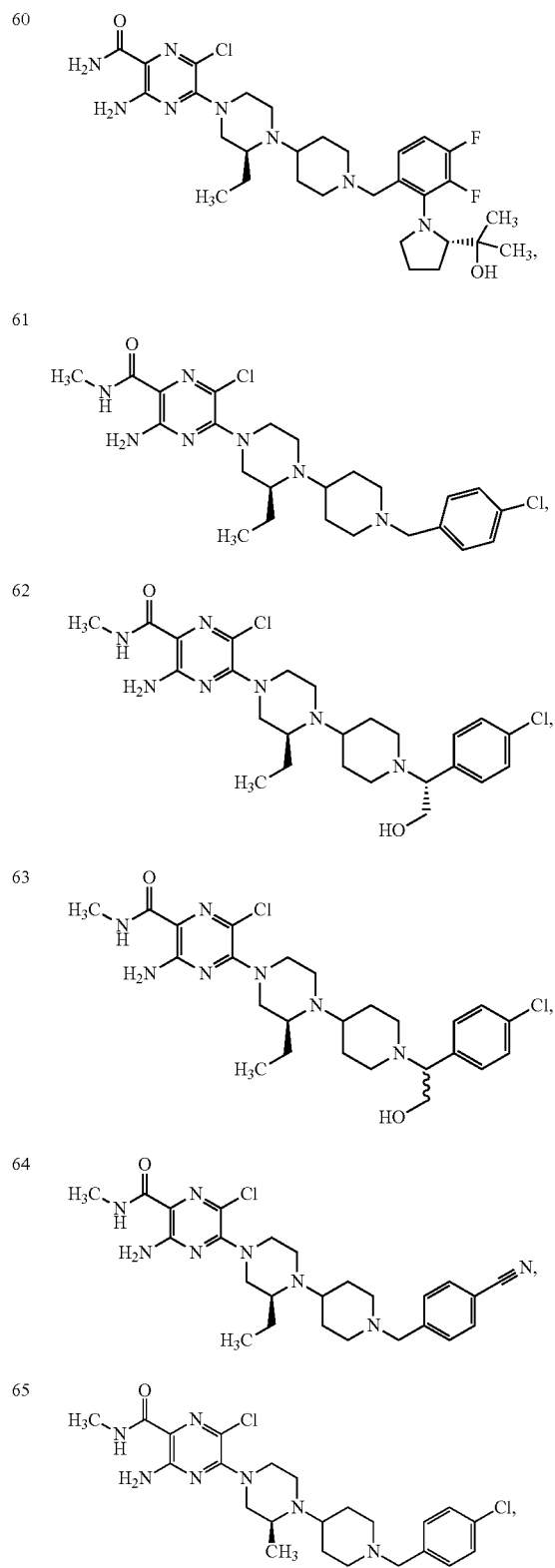 |
| 61 | 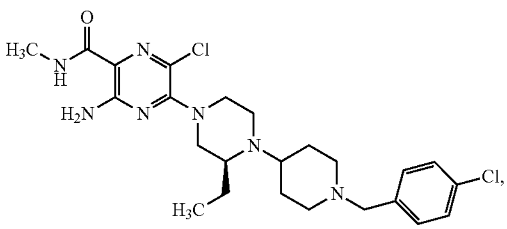 |
| 62 | 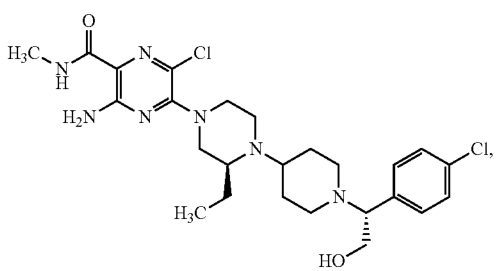 |
| 63 | 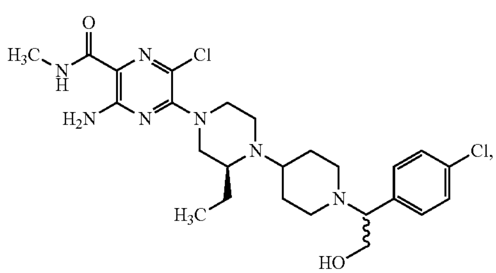 |
| 64 | 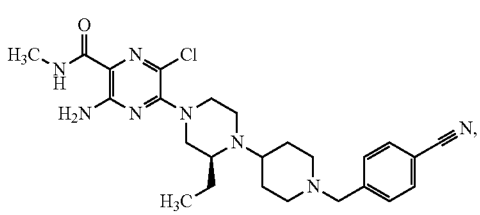 |
| 65 | 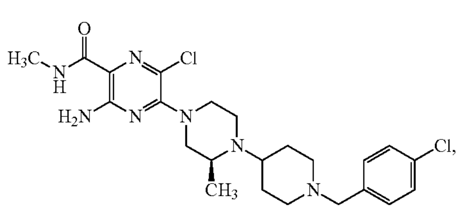 |
-continued
| Compound No. | Compound Structure |
|---|---|
| 66 | 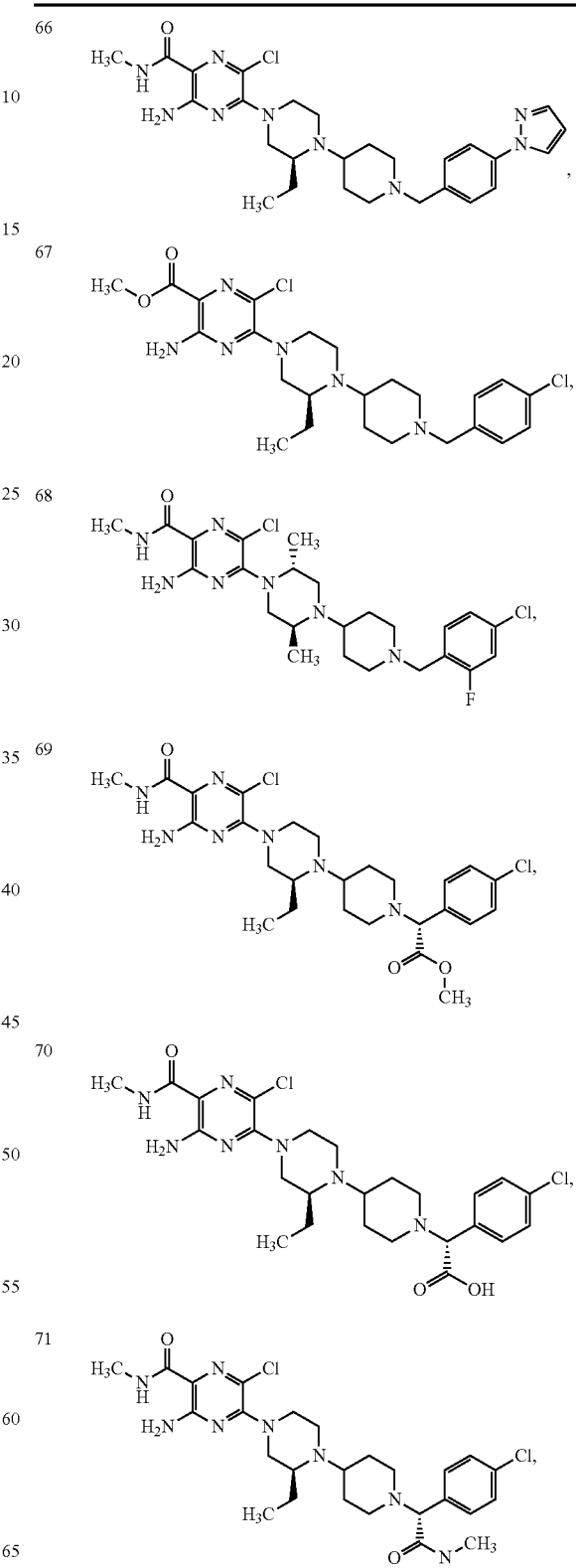 |
| 67 | 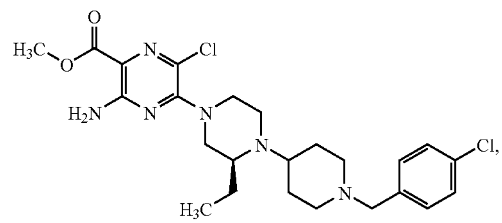 |
| 68 | 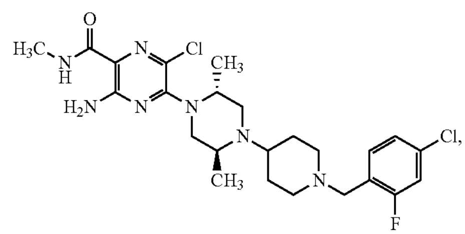 |
| 69 | 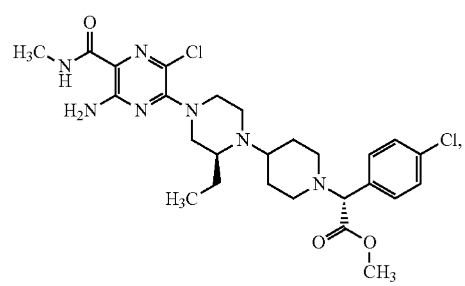 |
| 70 | 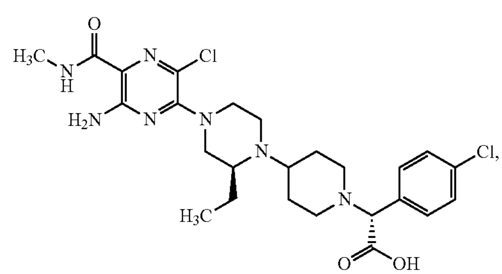 |
| 71 | 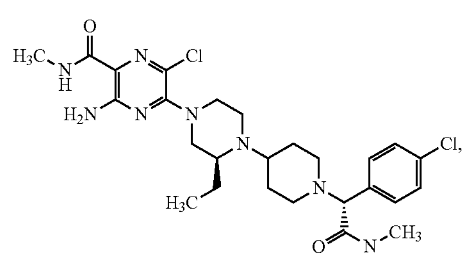 |

-continued

| Compound No. | Compound Structure |
|---|---|
| 72 | 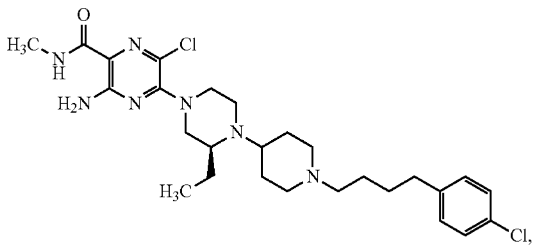 |
| 73 | 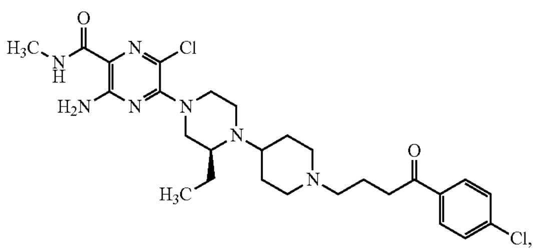 |
| 74 | 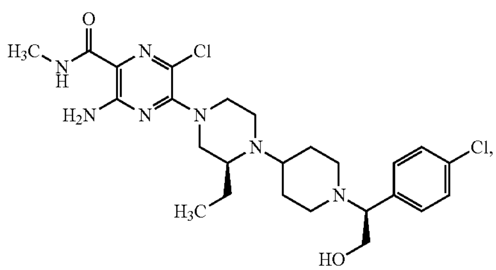 |
| 75 | 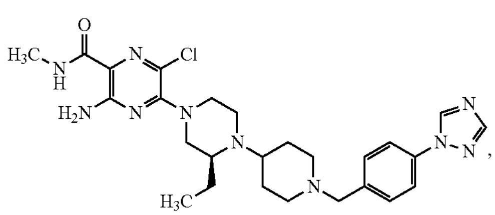 |
| 76 | 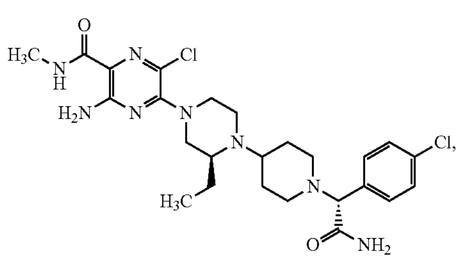 |

-continued

| Compound No. | Compound Structure |
|---|---|
| 77 | 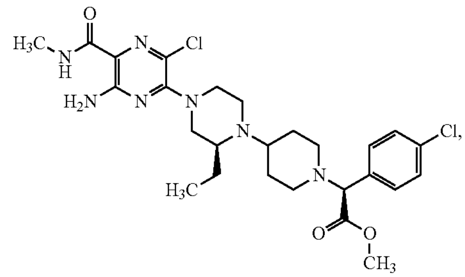 |
| 78 | 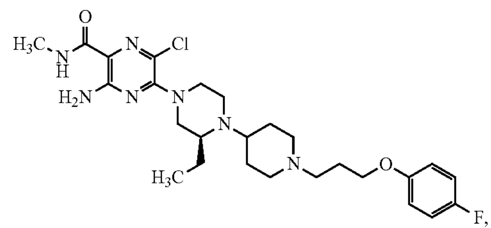 |
| 79 | 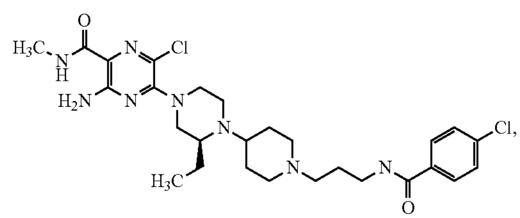 |
| 80 | 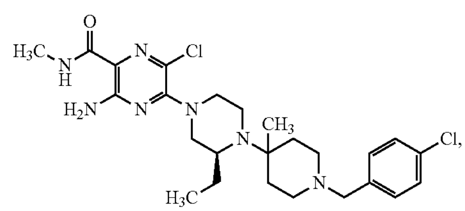 |
| 81 | 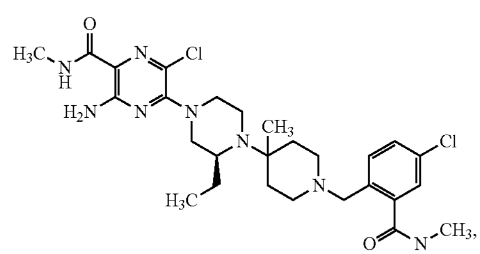 |
| 82 | 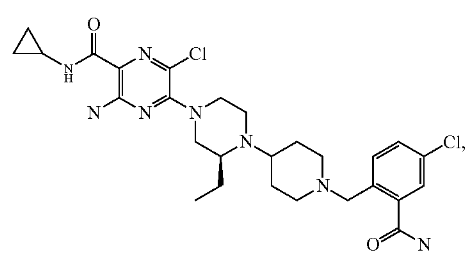 |

-continued
| Compound No. | Compound Structure |
|---|---|
| 83 | 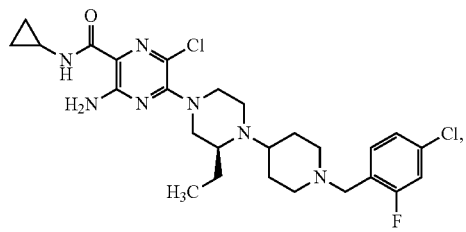 |
| 84 | 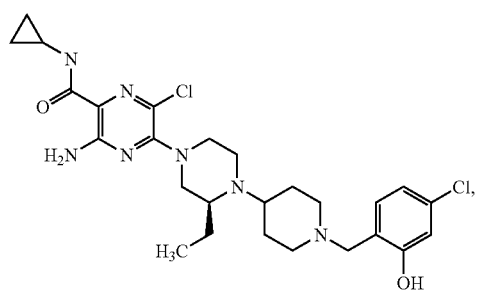 |
| 85 | 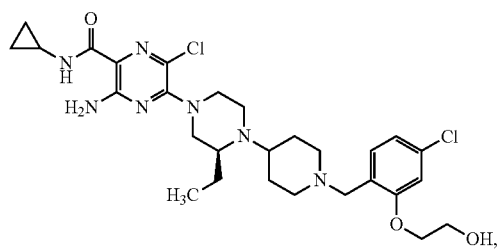 |
| 86 | 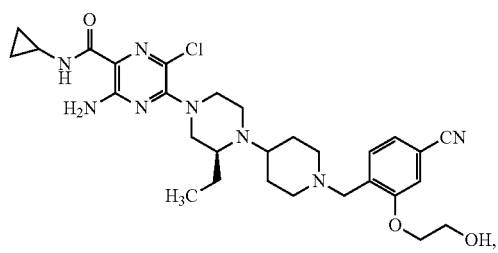 |
| 87 | 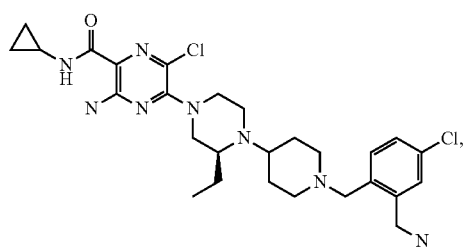 |
-continued
| Compound No. | Compound Structure |
|---|---|
| 88 | 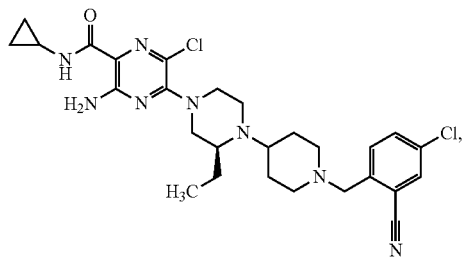 |
| 89 | 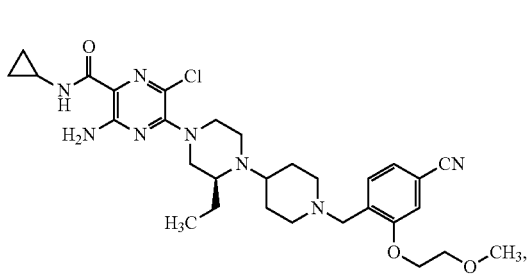 |
| 90 | 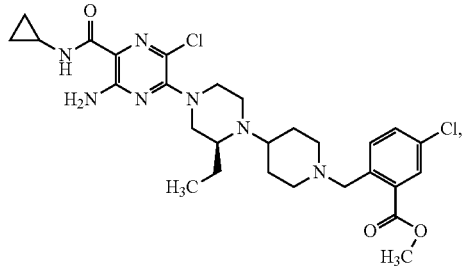 |
| 91 | 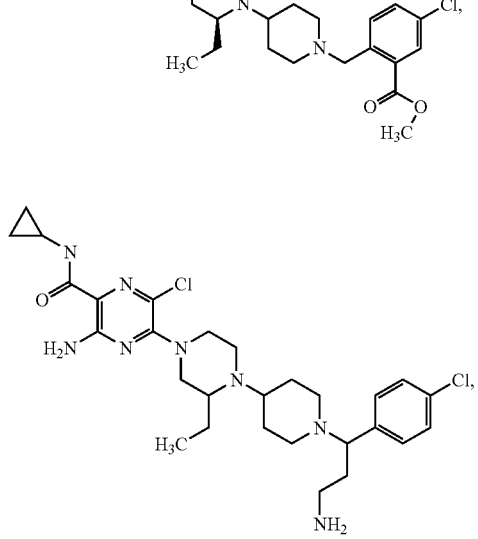 |
| 92 | 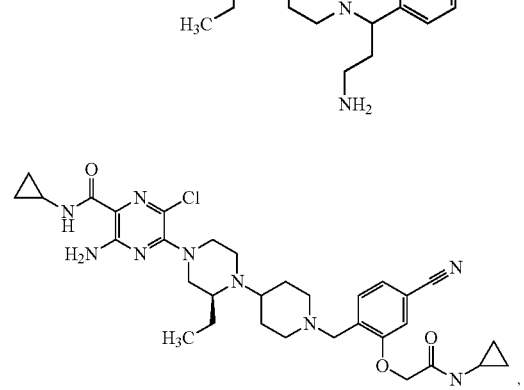 |

-continued

| Compound No. | Compound Structure |
|---|---|
| 93 | (structure) |
| 94 | (structure) |
| 95 | (structure) |
| 96 | (structure) |
| 97 | (structure) |
| 98 | (structure) |

-continued

| Compound No. | Compound Structure |
|---|---|
| 99 | (structure) |
| 100 | (structure) |
| 101 | (structure) |
| 102 | (structure) |
| 103 | (structure) |
| 104 | (structure) |
| 105 | (structure) |

| Compound No. | Compound Structure |
|---|---|
| 106 | (structure) |
| 107 | (structure) |
| 108 | (structure) |
| 109 | (structure) |
| 110 | (structure) |
| 111 | (structure) |
| 112 | (structure) |
| 113 | (structure) |
| 114 | (structure) |
| 115 | (structure) |
| 116 | (structure) |

-continued
| Compound No. | Compound Structure |
|---|---|
| 117 | 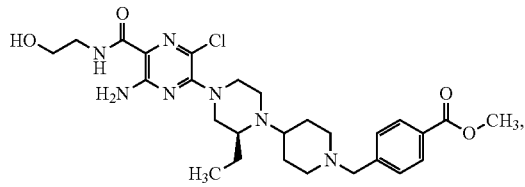 |
| 118 | 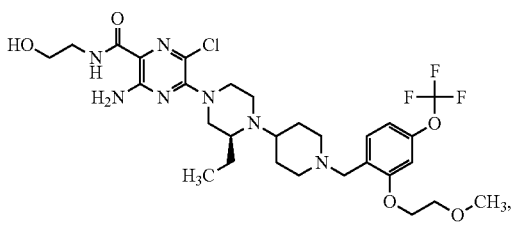 |
| 119 | 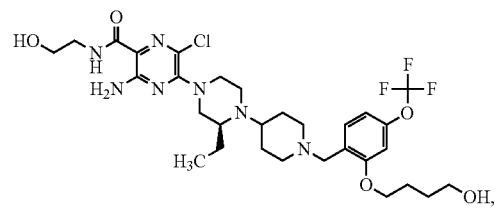 |
| 120 | 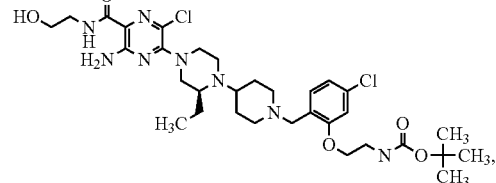 |
| 121 | 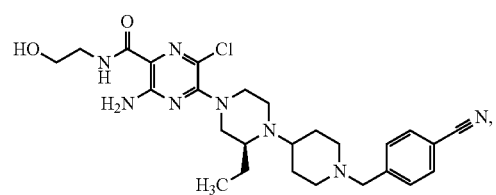 |
| 122 | 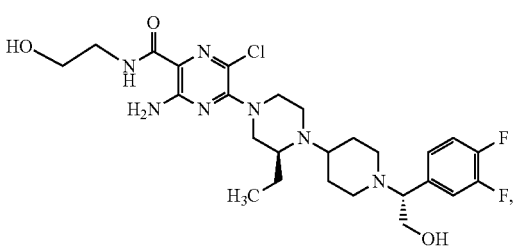 |
-continued
| Compound No. | Compound Structure |
|---|---|
| 123 | 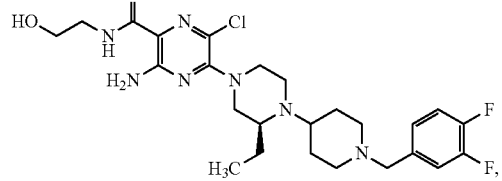 |
| 124 | 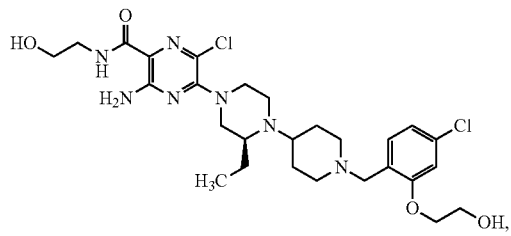 |
| 125 | 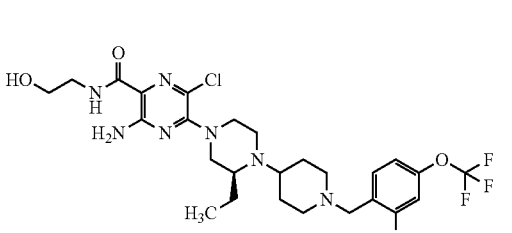 |
| 126 | 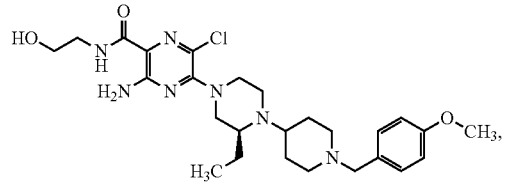 |
| 127 | 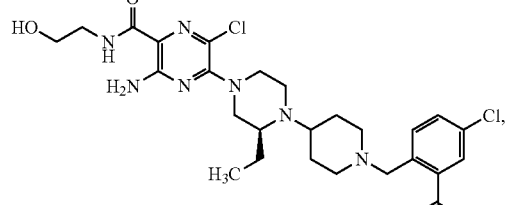 |
| 128 | 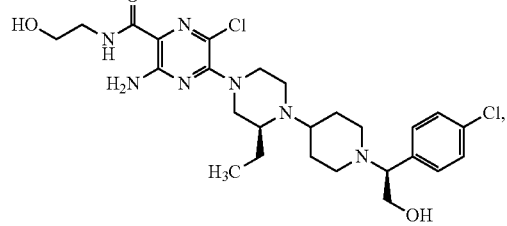 |

US 7,868,005 B2
407 408
-continued
| Compound No. | Compound Structure |
|---|---|
| 129 | 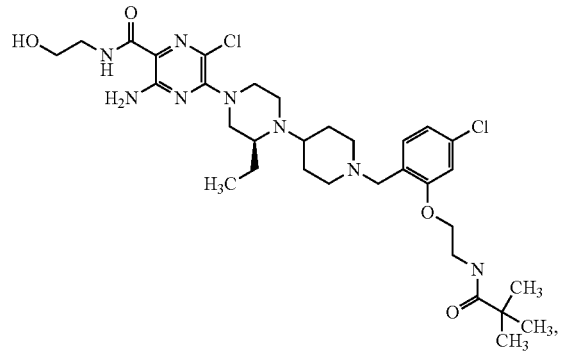 |
| 130 | 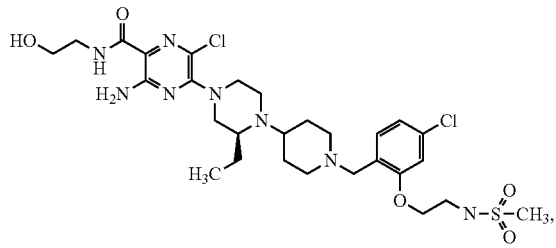 |
| 131 | 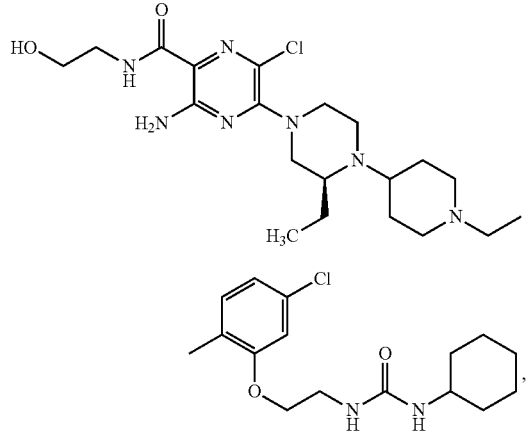 |
| 132 | 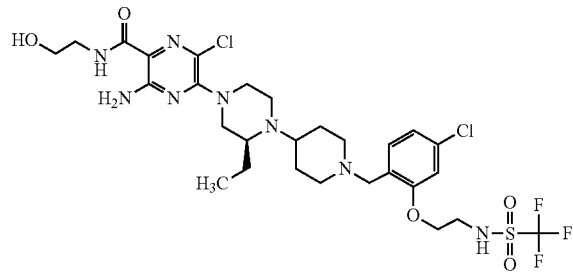 |
-continued
| Compound No. | Compound Structure |
|---|---|
| 133 | 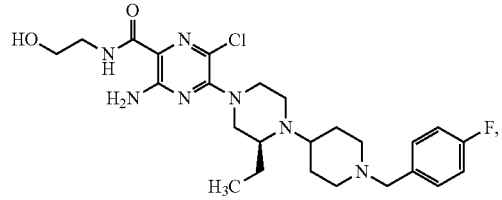 |
| 134 | 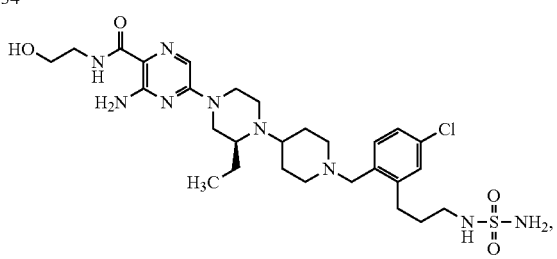 |
| 135 | 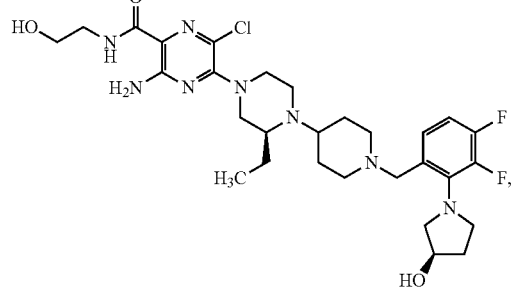 |
| 136 | 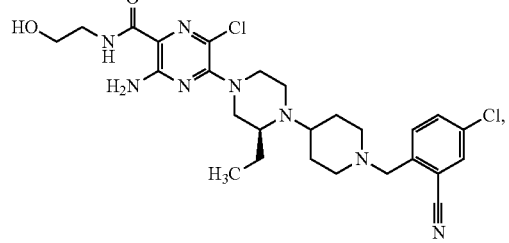 |
| 137 | 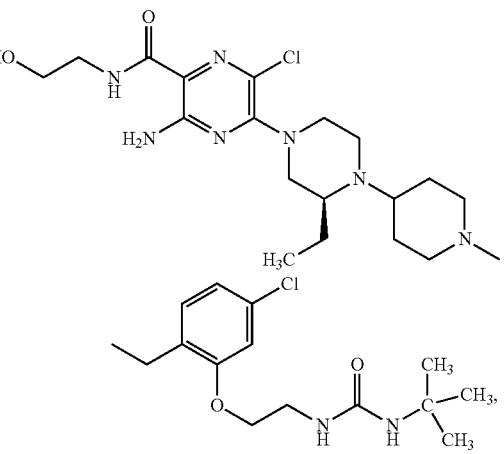 |

-continued
| Compound No. | Compound Structure |
|---|---|
| 138 | 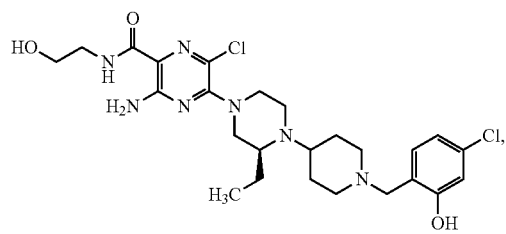 |
| 139 | 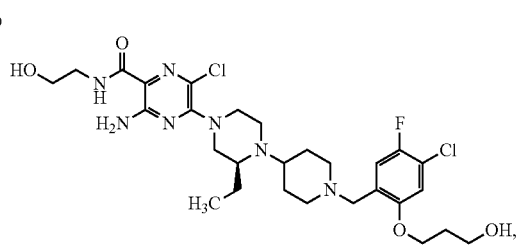 |
| 140 | 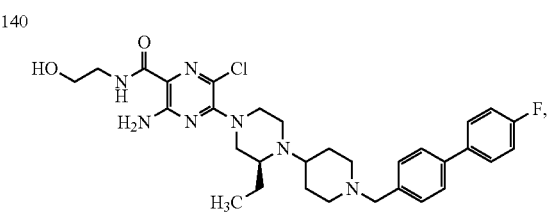 |
| 141 | 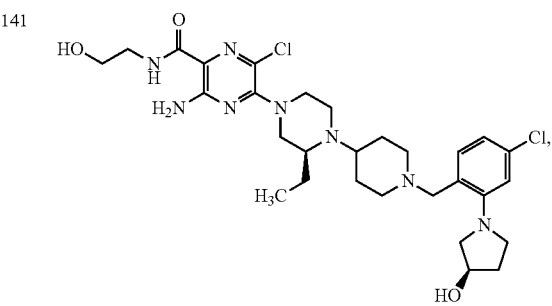 |
| 142 | 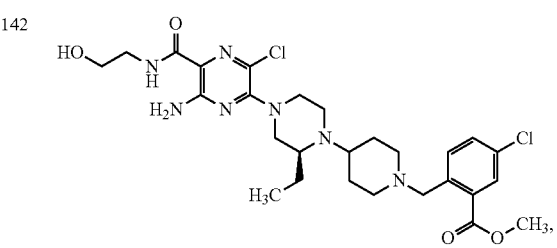 |
-continued
| Compound No. | Compound Structure |
|---|---|
| 143 | 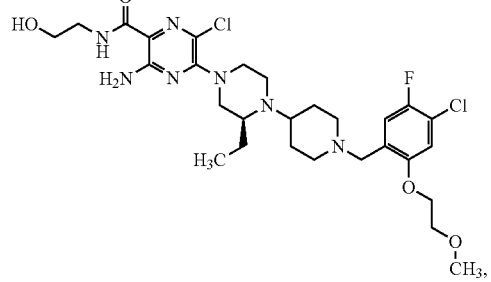 |
| 144 | 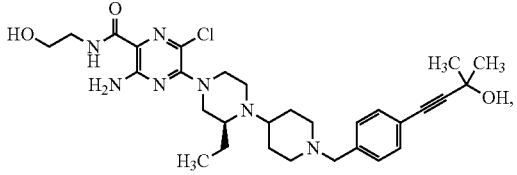 |
| 145 | 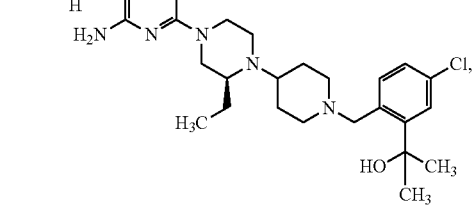 |
| 146 | 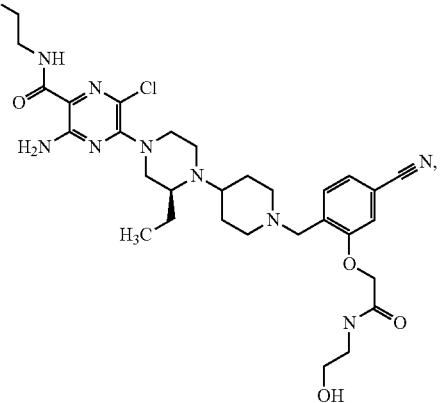 |
| 147 | 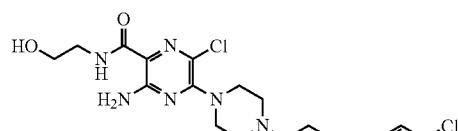 |

-continued
| Compound No. | Compound Structure |
|---|---|
| 148 | 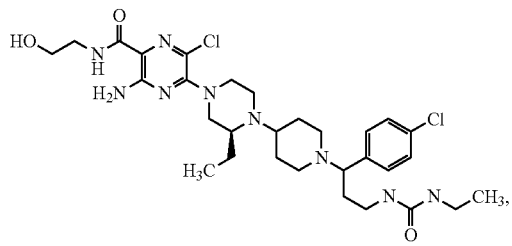 |
| 149 | 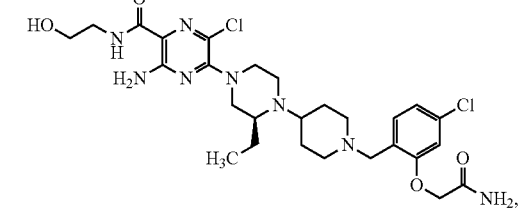 |
| 150 | 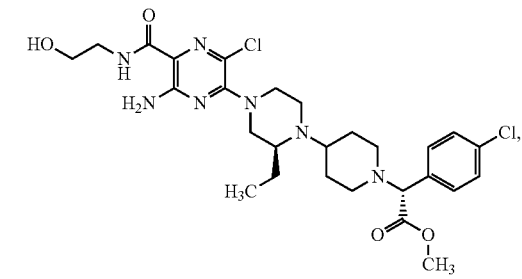 |
| 151 | 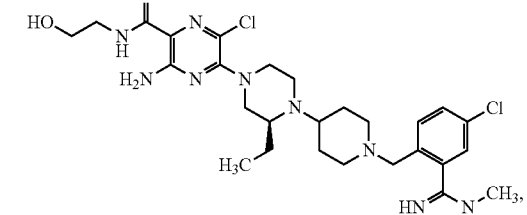 |
| 152 | 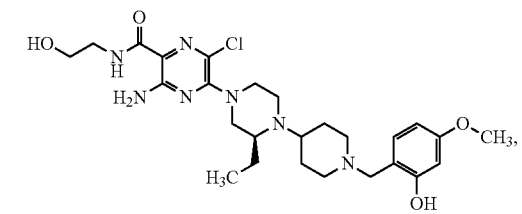 |
| 153 | 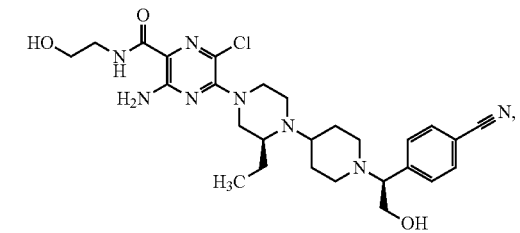 |
-continued
| Compound No. | Compound Structure |
|---|---|
| 154 | 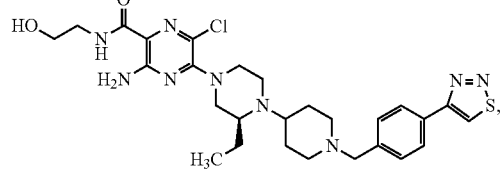 |
| 155 | 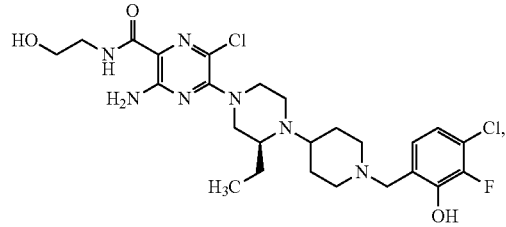 |
| 156 | 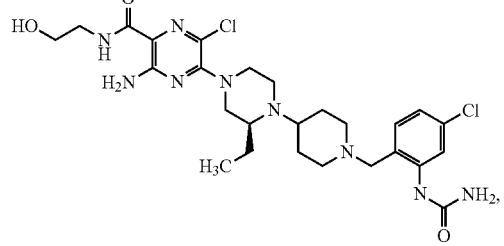 |
| 157 | 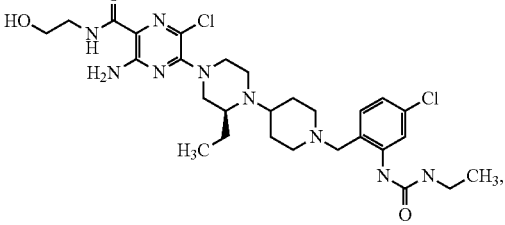 |
| 158 | 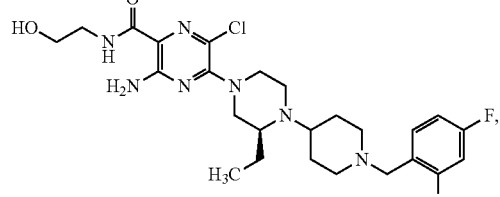 |
| 159 | 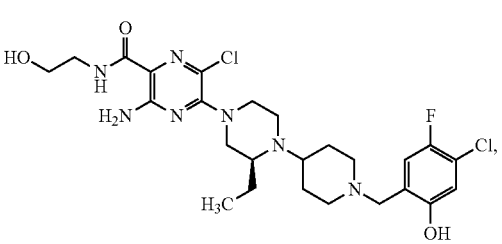 |

| Compound No. | Compound Structure |
|---|---|
| 160 | 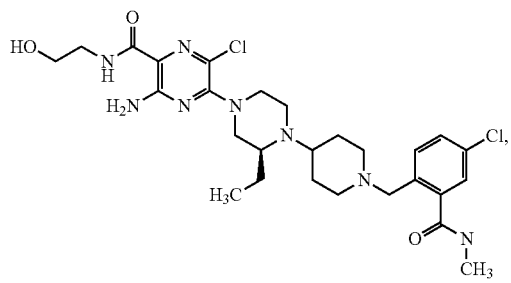 |
| 161 | 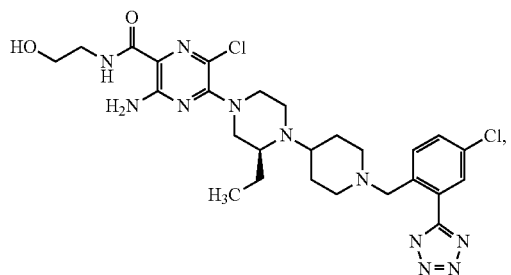 |
| 162 | 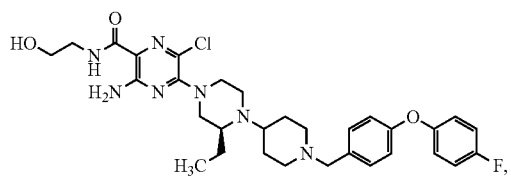 |
| 163 | 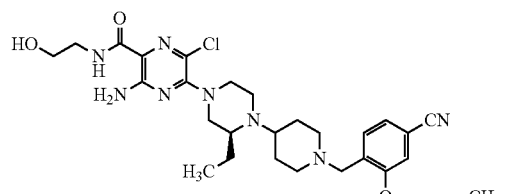 |
| 164 | 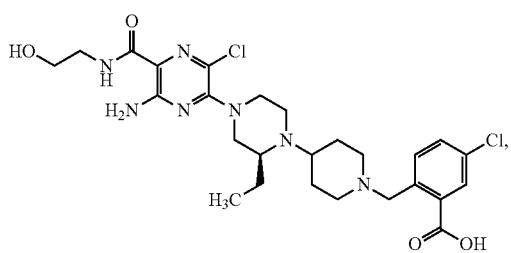 |
| Compound No. | Compound Structure |
|---|---|
| 165 | 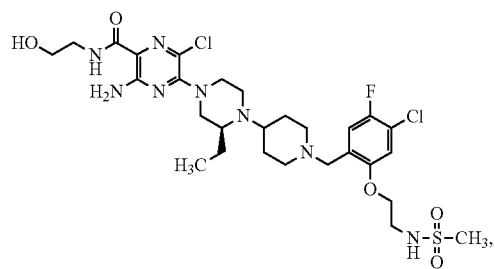 |
| 166 | 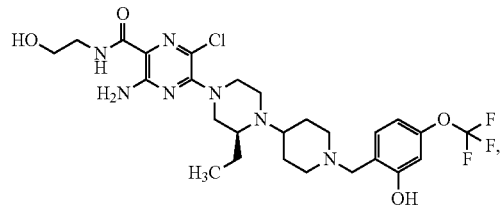 |
| 167 | 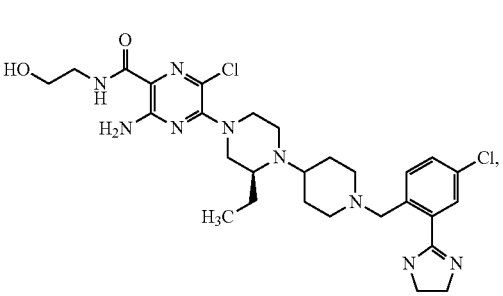 |
| 168 | 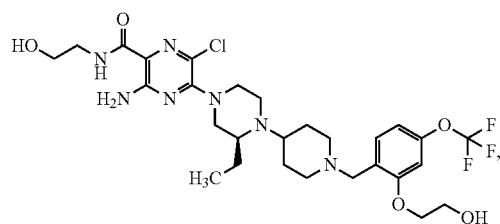 |
| 169 | 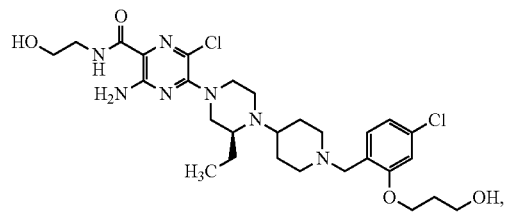 |
| 170 | 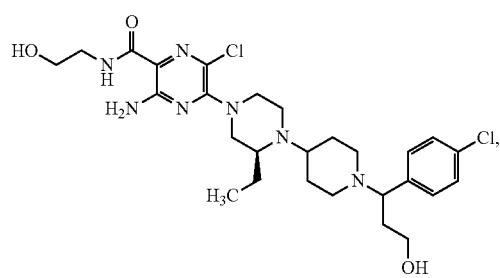 |

| Compound No. | Compound Structure |
|---|---|
| 171 | 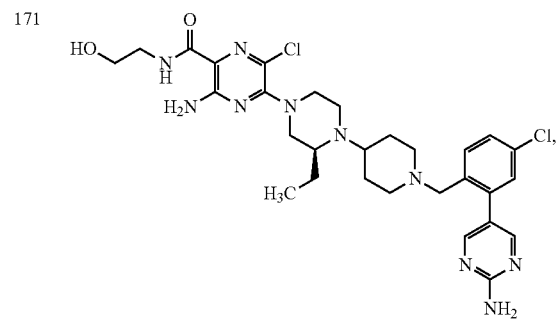 |
| 172 | 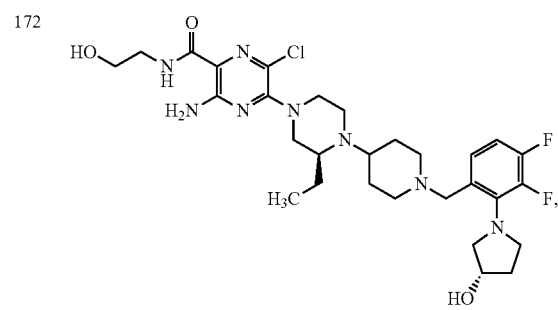 |
| 173 | 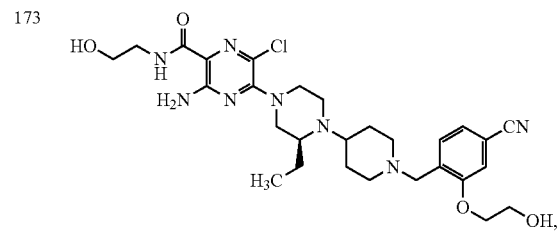 |
| 174 | 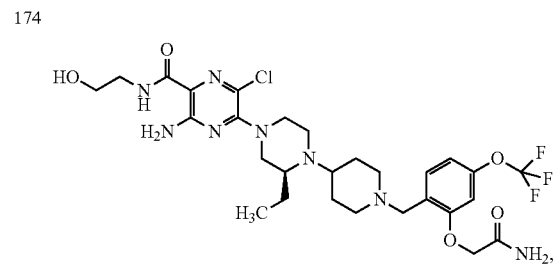 |
| 175 | 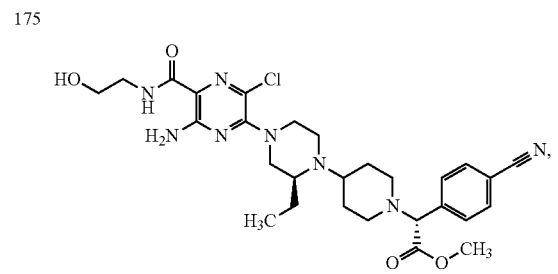 |
| 176 | 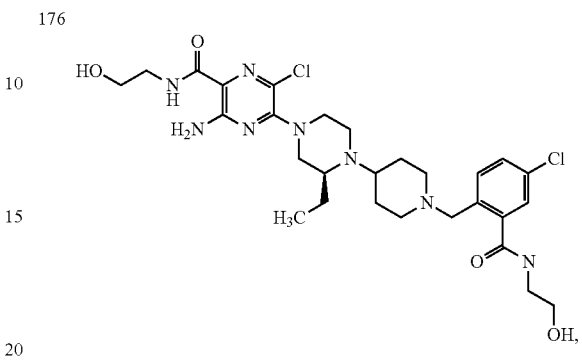 |
| 177 | 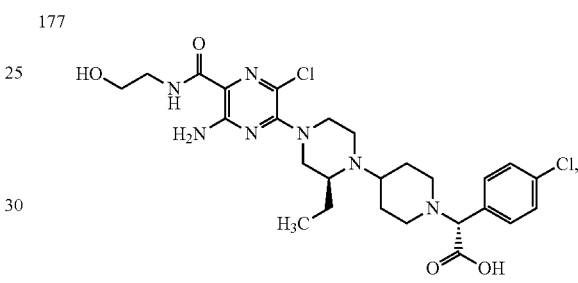 |
| 178 | 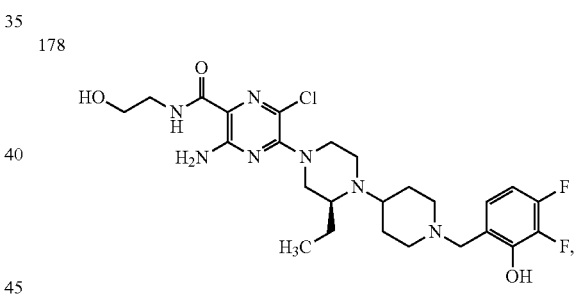 |
| 179 | 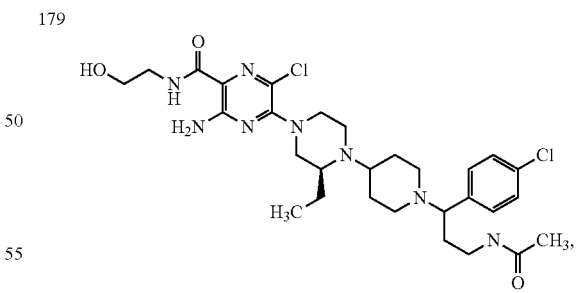 |
| 180 | 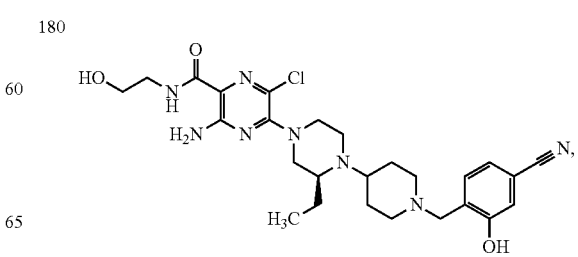 |

-continued
| Compound No. | Compound Structure |
|---|---|
| 181 | 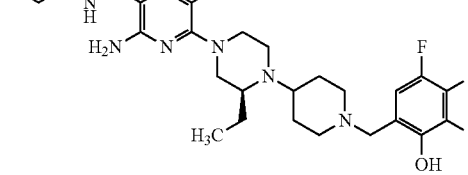 |
| 182 | 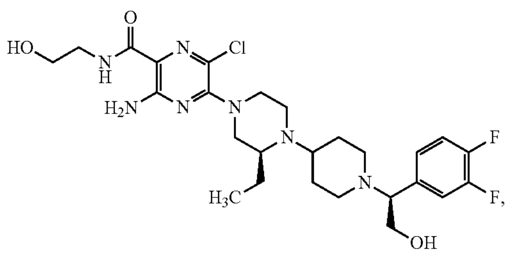 |
| 183 | 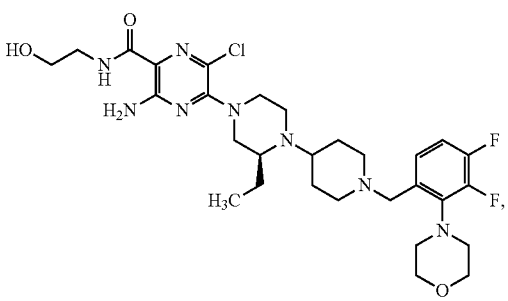 |
| 184 | 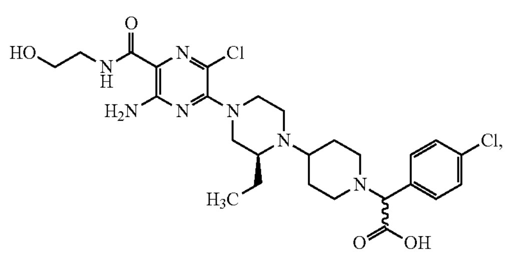 |
| 185 | 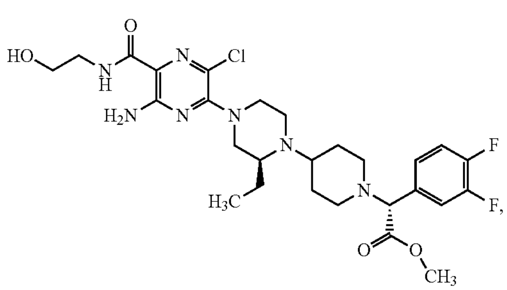 |
-continued
| Compound No. | Compound Structure |
|---|---|
| 186 | 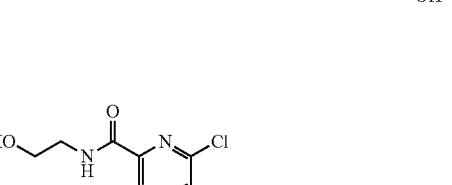 |
| 187 | 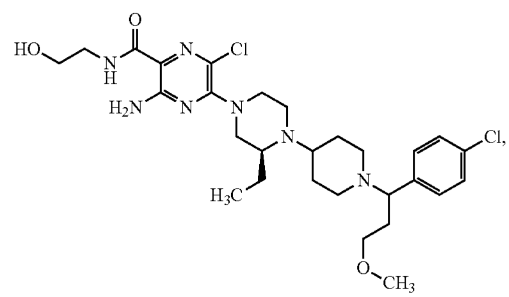 |
| 188 | 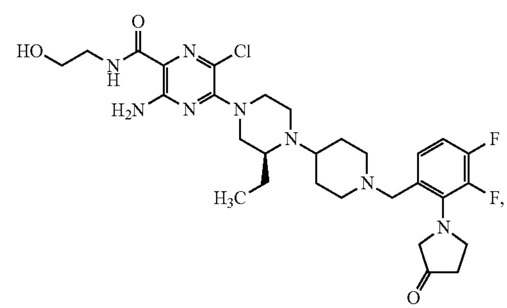 |
| 189 | 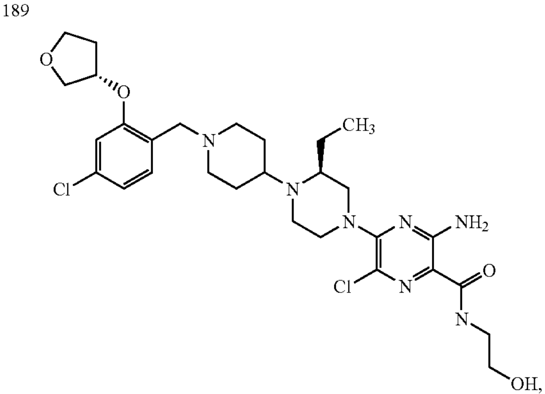 |

| Compound No. | Compound Structure |
|---|---|
| 190 | 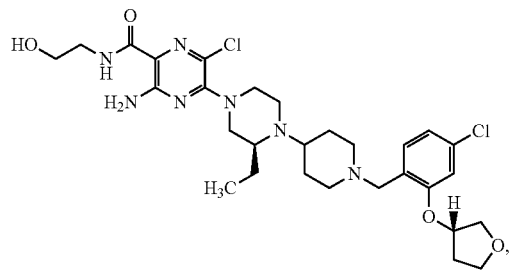 |
| 191 | 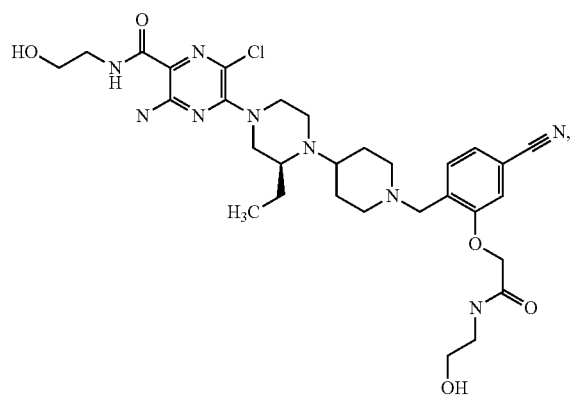 |
| 192 | 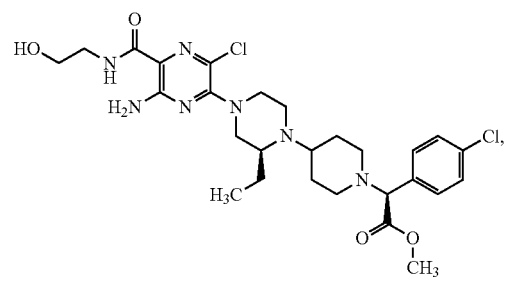 |
| 193 | 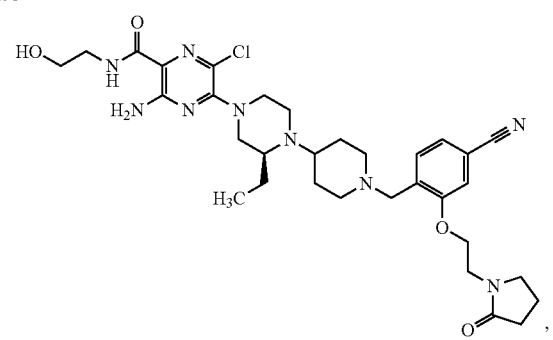 |
| Compound No. | Compound Structure |
|---|---|
| 194 | 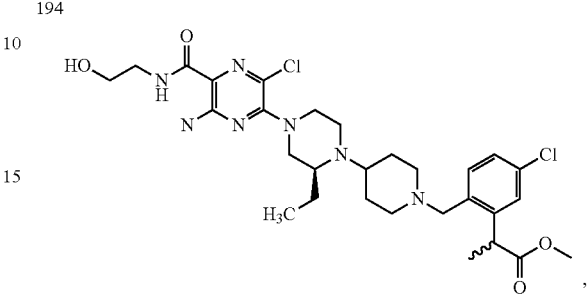 |
| 195 | 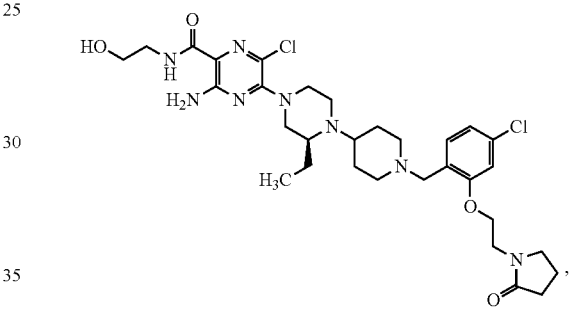 |
| 196 | 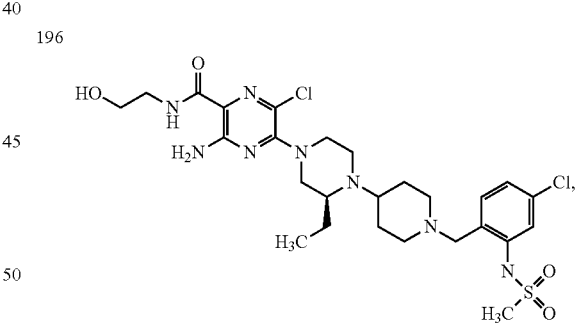 |
| 197 | 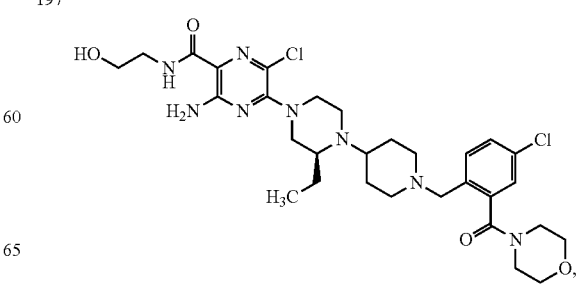 |

| Compound No. | Compound Structure |
|---|---|
| 198 | 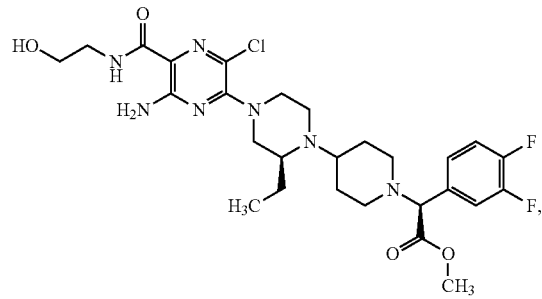 |
| 199 | 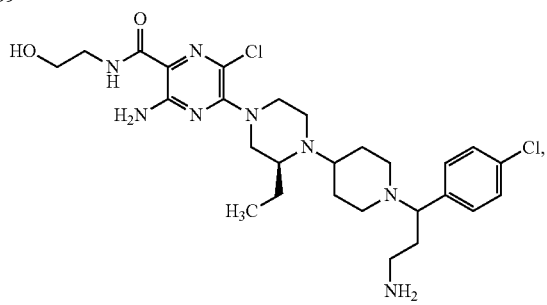 |
| 200 | 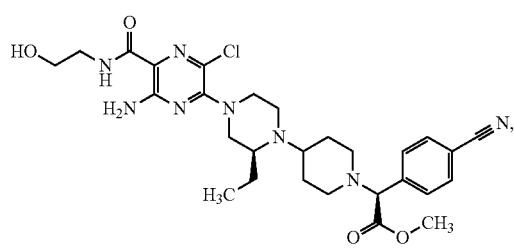 |
| 201 | 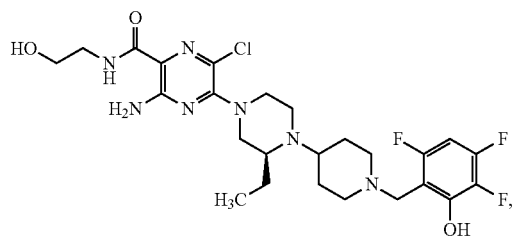 |
| 202 | 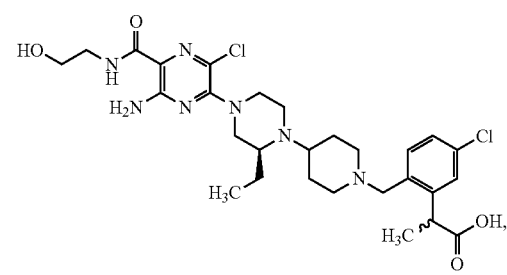 |
| Compound No. | Compound Structure |
|---|---|
| 203 | 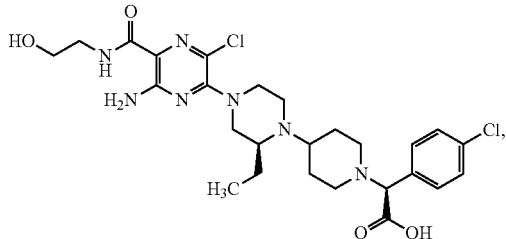 |
| 204 | 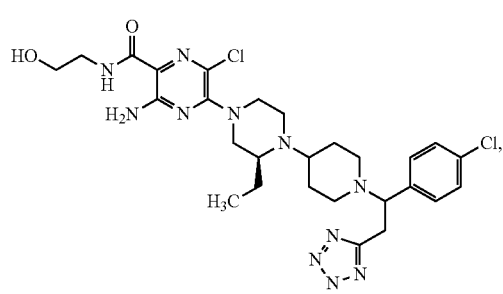 |
| 205 | 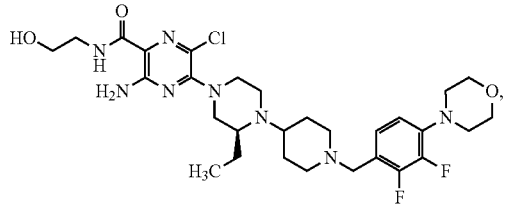 |
| 206 | 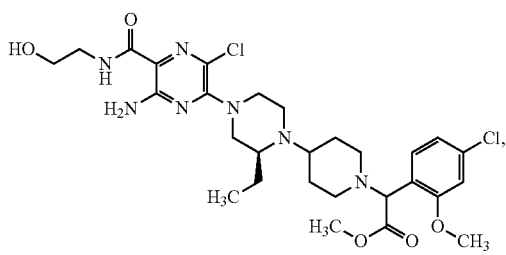 |
| 207 | 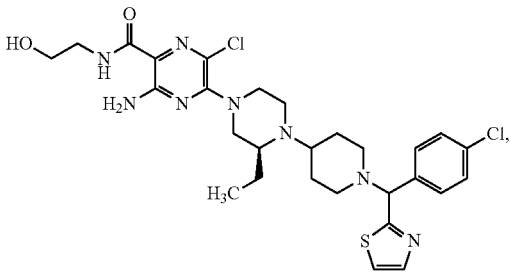 |

-continued
| Compound No. | Compound Structure |
|---|---|
| 208 | 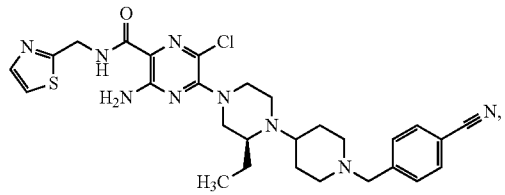 |
| 209 | 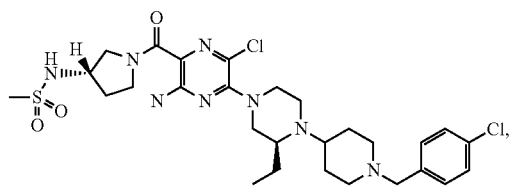 |
| 210 | 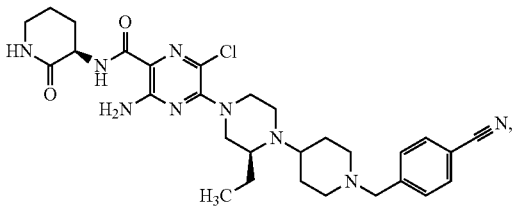 |
| 211 | 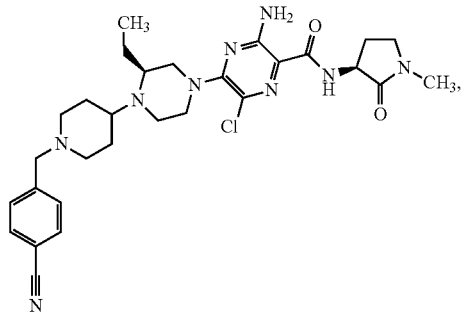 |
| 212 | 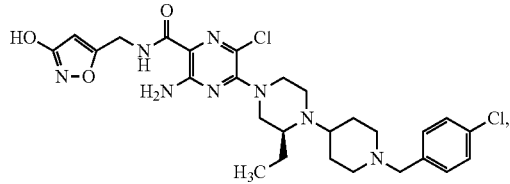 |
| 213 | 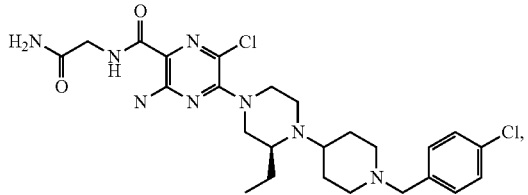 |
-continued
| Compound No. | Compound Structure |
|---|---|
| 214 | 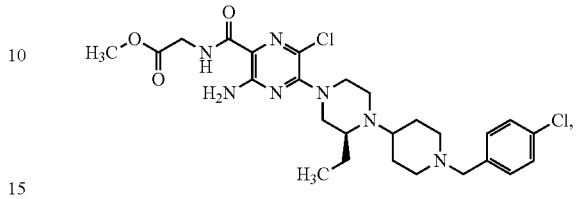 |
| 215 | 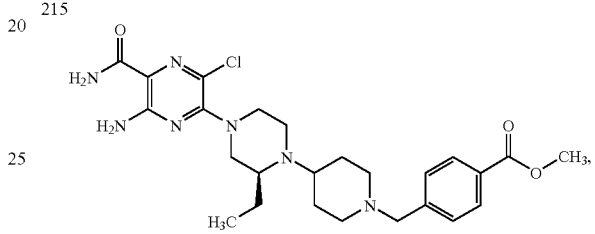 |
| 215A | 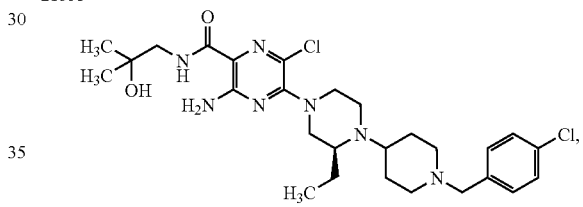 |
| 216 | 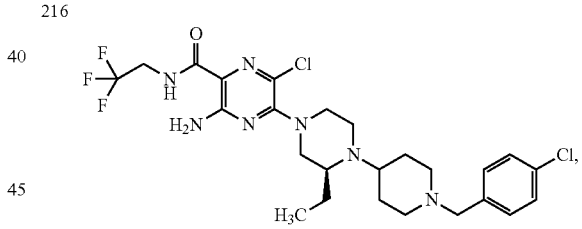 |
| 217 | 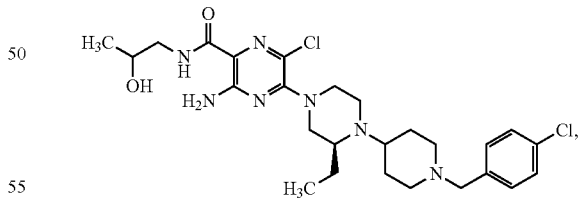 |
| 218 | 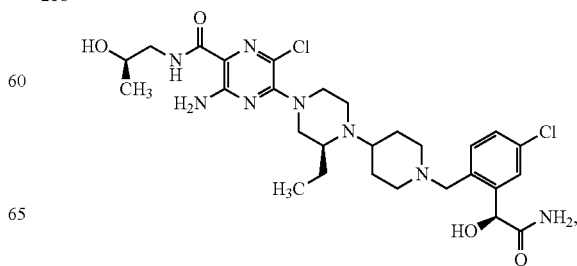 |

| Compound No. | Compound Structure |
|---|---|
| 219 | 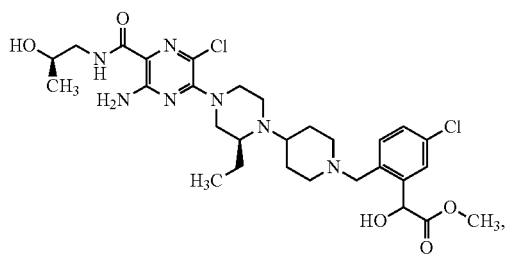 |
| 220 | 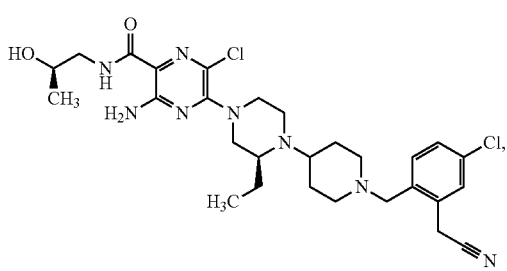 |
| 221 | 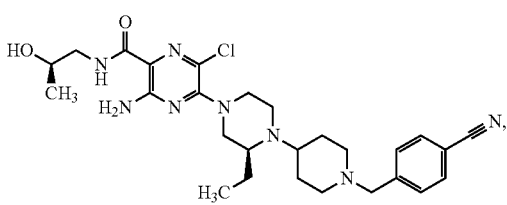 |
| 222 | 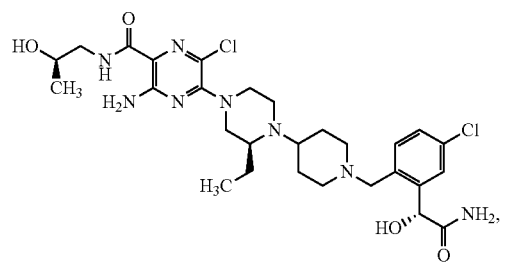 |
| 223 | 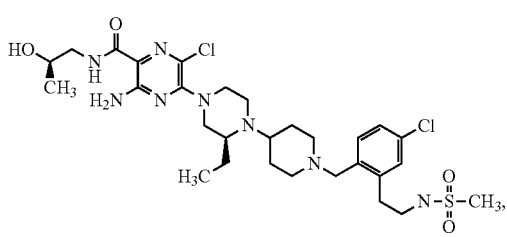 |
| Compound No. | Compound Structure |
|---|---|
| 224 | 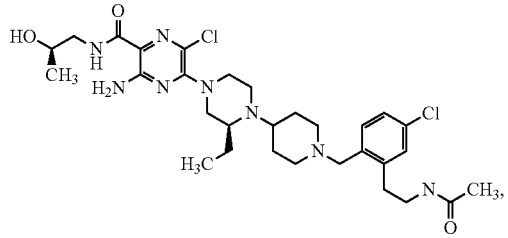 |
| 225 | 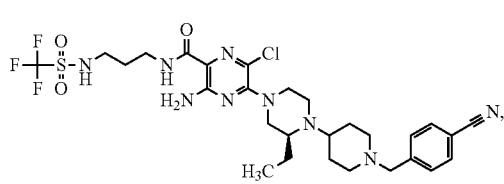 |
| 226 | 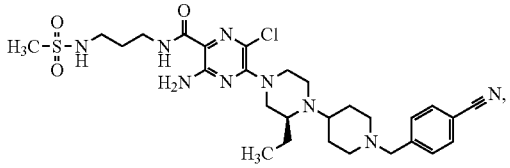 |
| 227 | 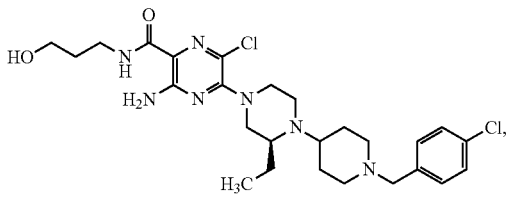 |
| 228 | 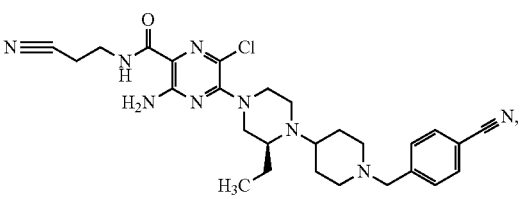 |
| 229 | 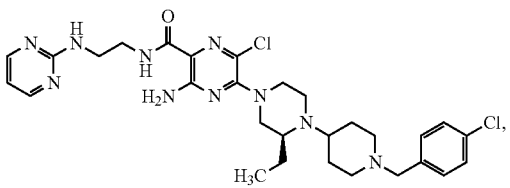 |

| Compound No. | Compound Structure |
|---|---|
| 230 | 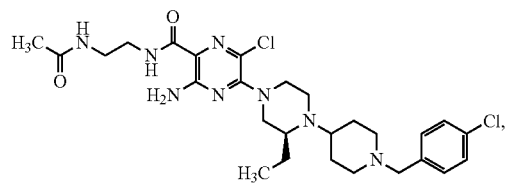 |
| 231 | 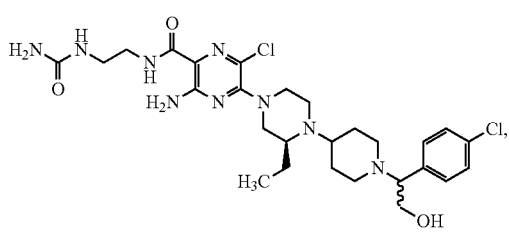 |
| 232 | 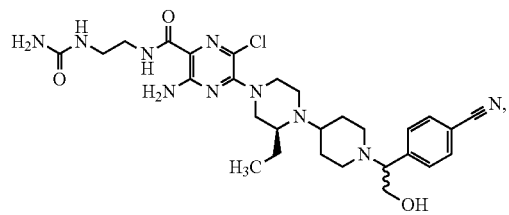 |
| 233 | 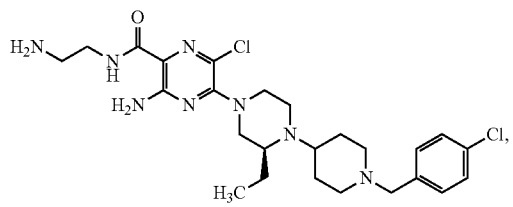 |
| 234 | 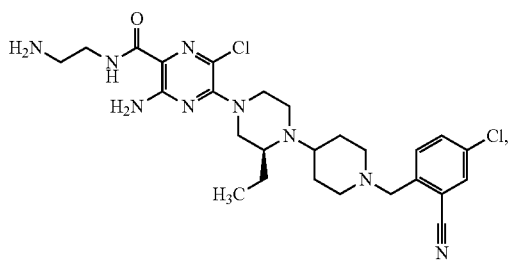 |
| 235 | 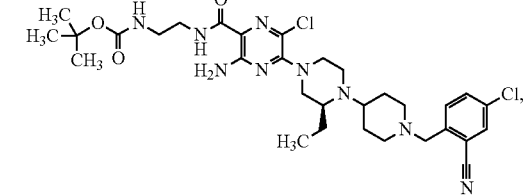 |
| Compound No. | Compound Structure |
|---|---|
| 236 | 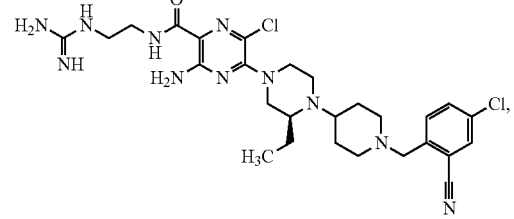 |
| 237 | 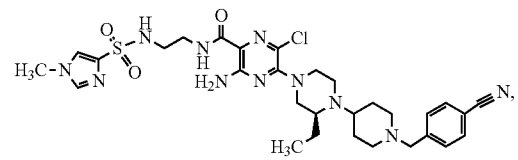 |
| 238 | 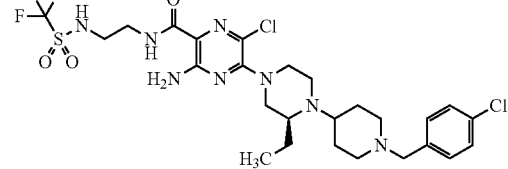 |
| 239 | 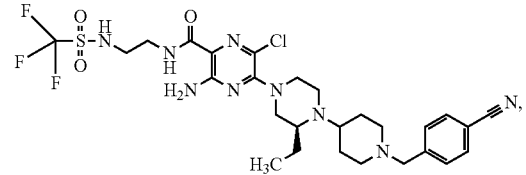 |
| 240 | 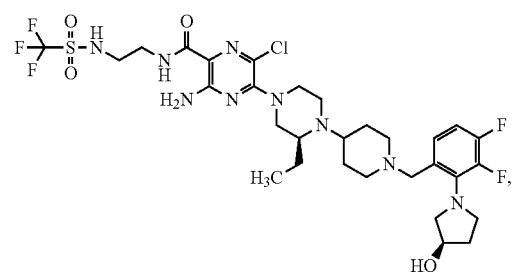 |
| 241 | 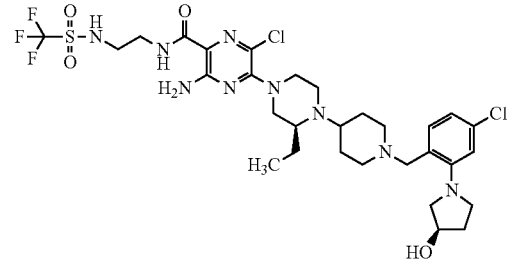 |

| Compound No. | Compound Structure |
|---|---|
| 242 | 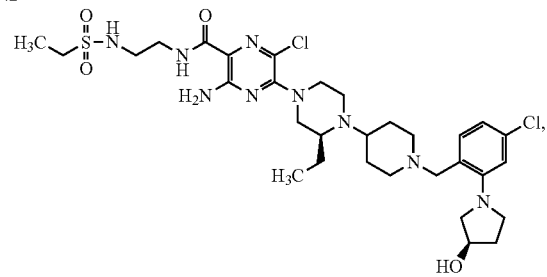 |
| 243 | 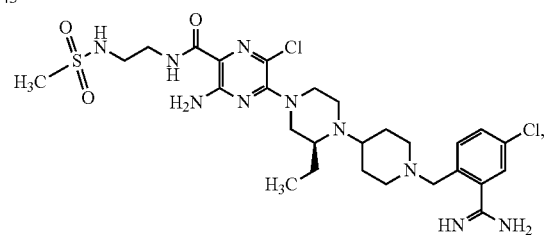 |
| 244 | 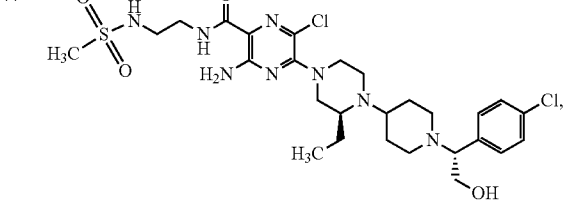 |
| 245 | 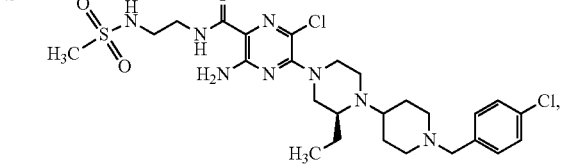 |
| 246 | 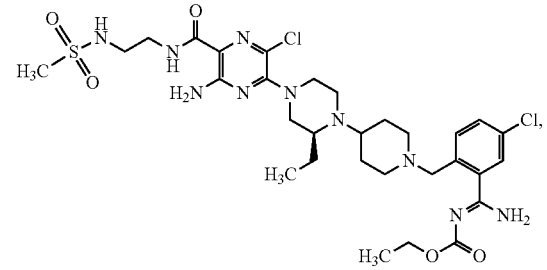 |
| 247 | 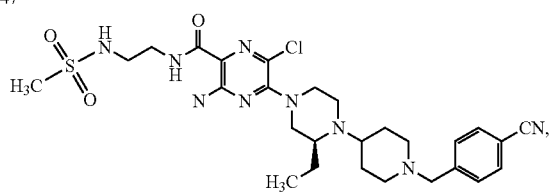 |
| Compound No. | Compound Structure |
|---|---|
| 248 | 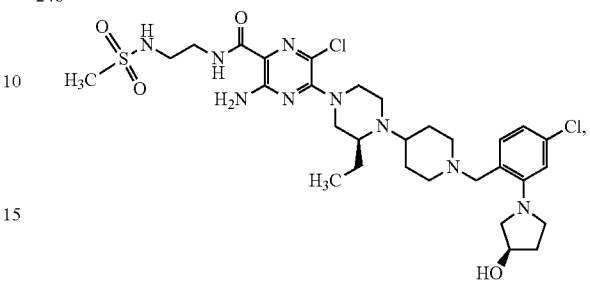 |
| 249 | 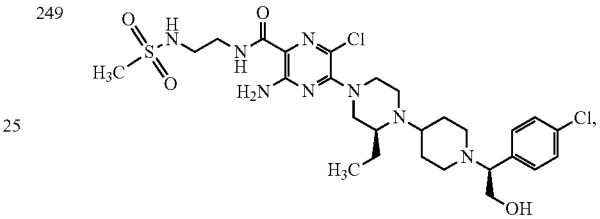 |
| 250 | 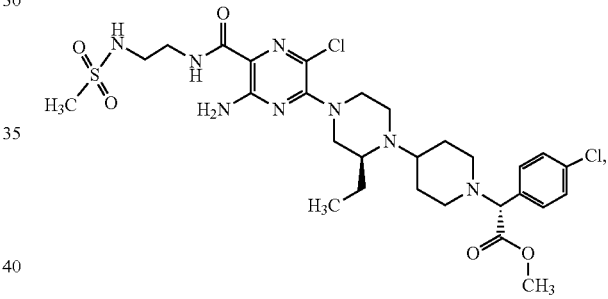 |
| 251 | 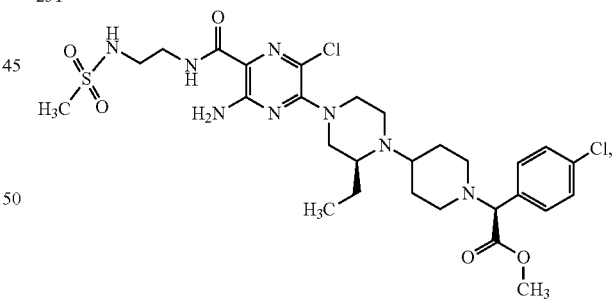 |
| 252 | 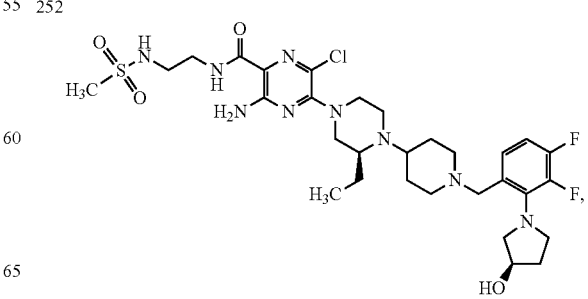 |

-continued

| Compound No. | Compound Structure |
|---|---|
| 253 | 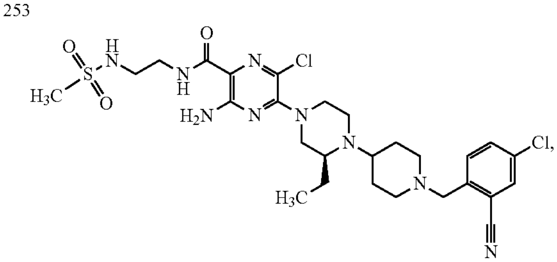 |
| 254 | 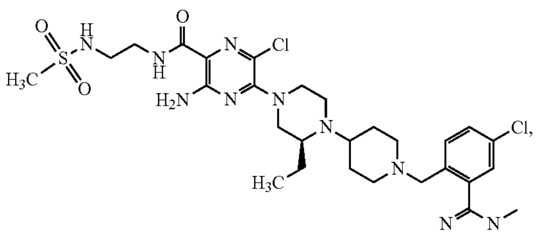 |
| 255 | 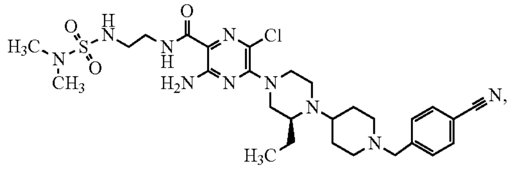 |
| 256 | 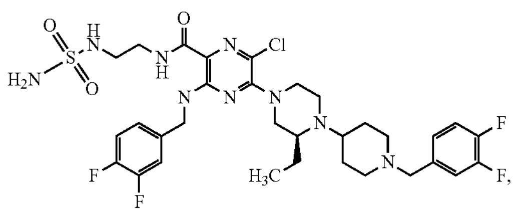 |
| 257 | 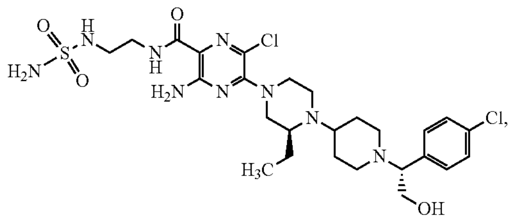 |
| 258 | 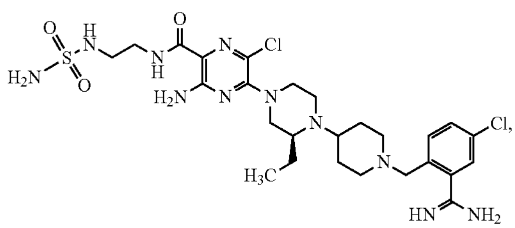 |

-continued

| Compound No. | Compound Structure |
|---|---|
| 259 | 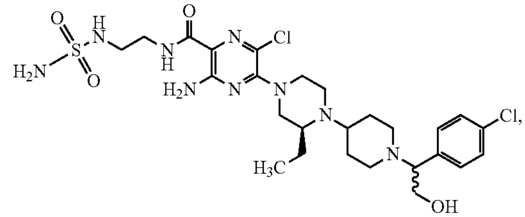 |
| 260 | 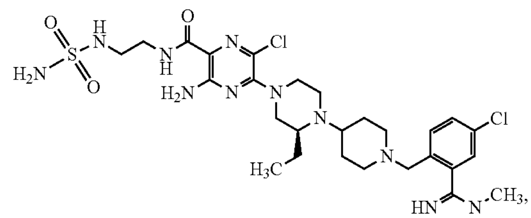 |
| 261 | 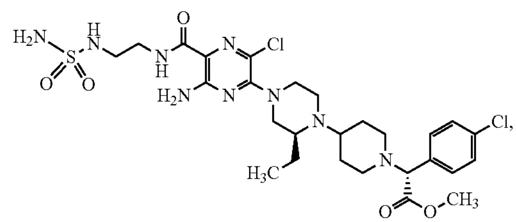 |
| 262 | 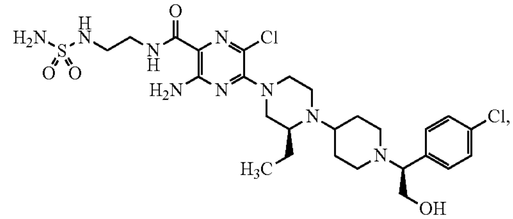 |
| 263 | 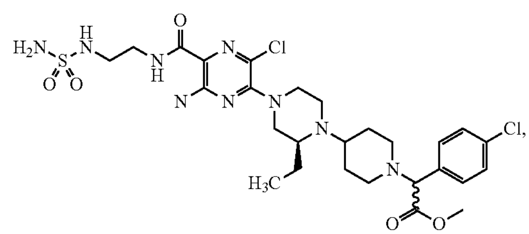 |
| 264 | 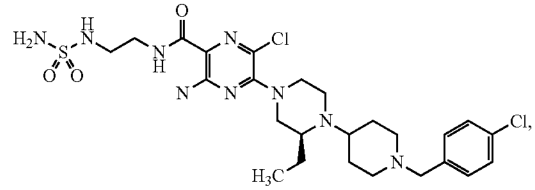 |
| 265 | 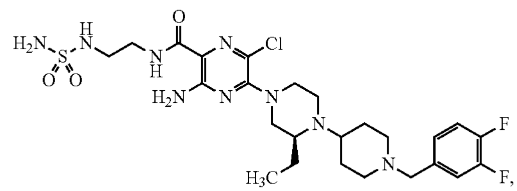 |

-continued

| Compound No. | Compound Structure |
|---|---|
| 266 | 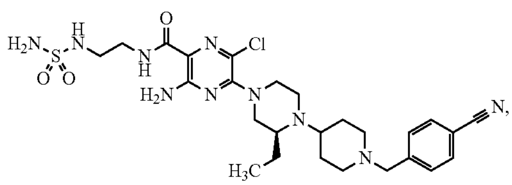 |
| 267 | 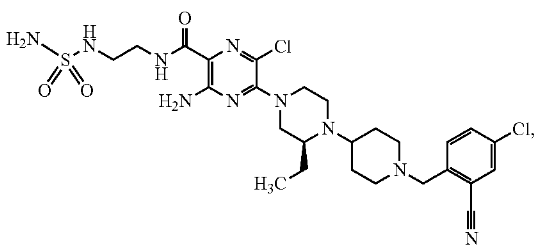 |
| 268 | 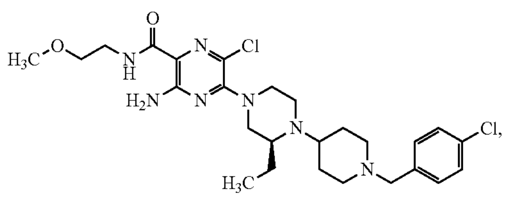 |
| 269 | 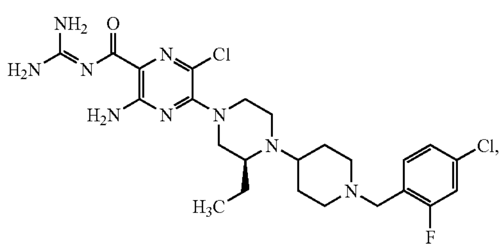 |
| 270 | 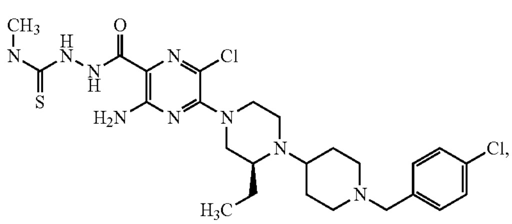 |
| 271 | 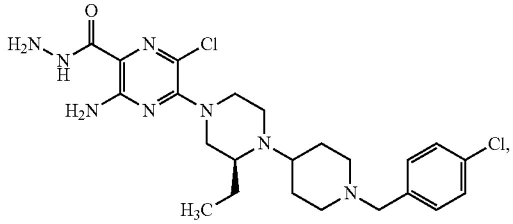 |

-continued

| Compound No. | Compound Structure |
|---|---|
| 272 | 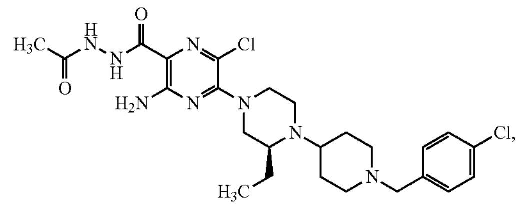 |
| 273 | 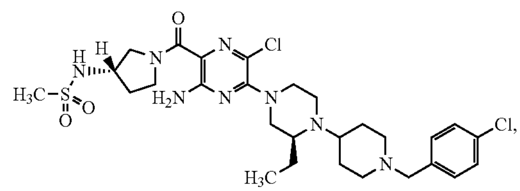 |
| 274 | 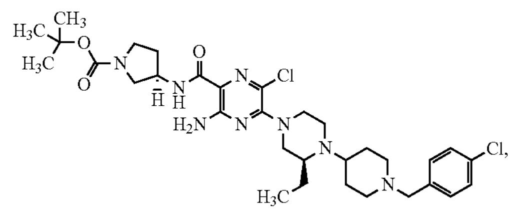 |
| 275 | 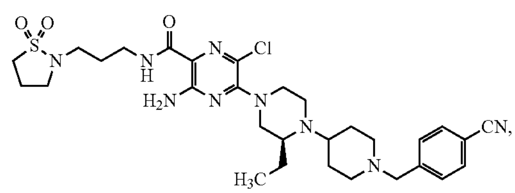 |
| 276 | 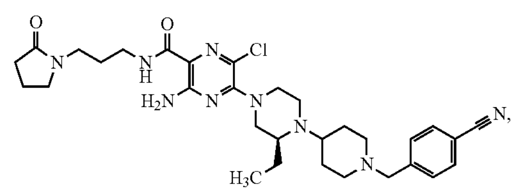 |
| 277 | 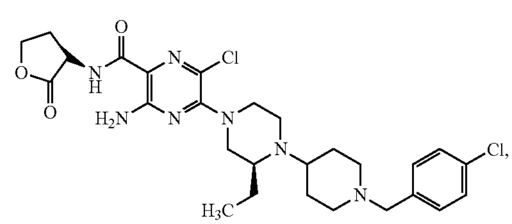 |
| 278 | 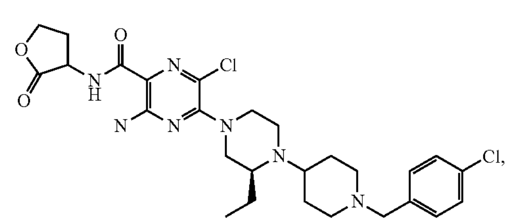 |

-continued
| Compound No. | Compound Structure |
|---|---|
| 279 | 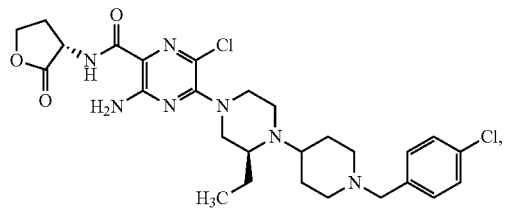 |
| 280 | 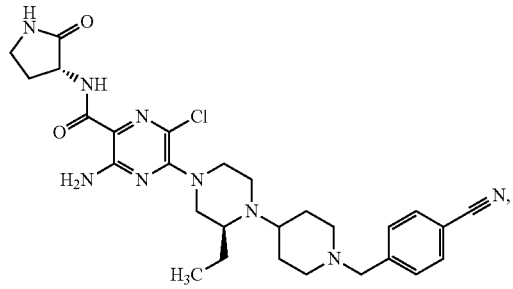 |
| 281 | 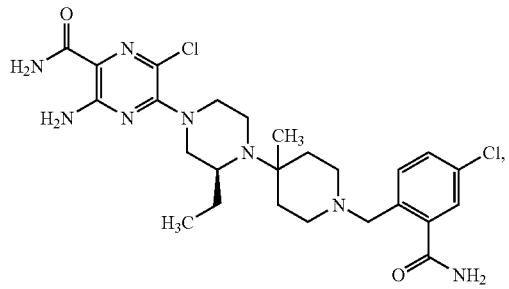 |
| 282 | 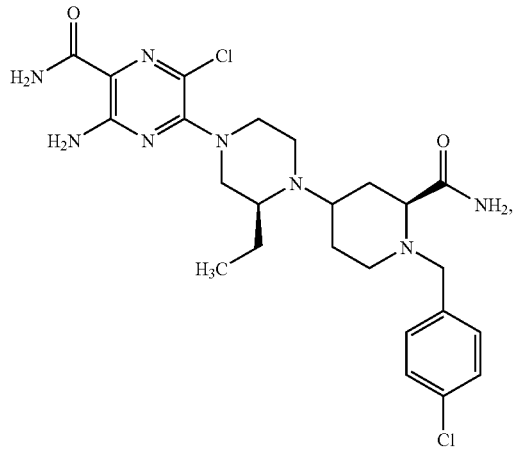 |
| 283 | 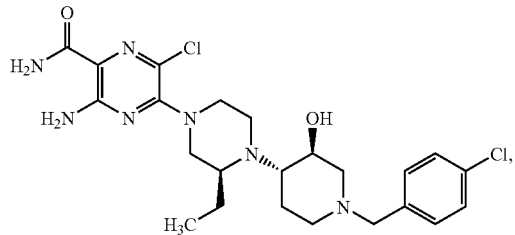 |
-continued
| Compound No. | Compound Structure |
|---|---|
| 284 | 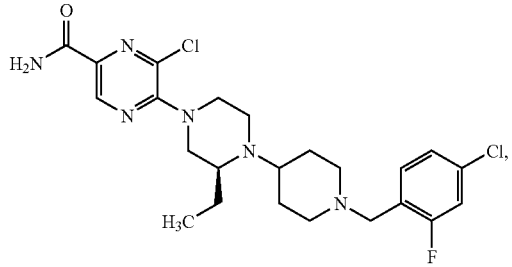 |
| 285 | 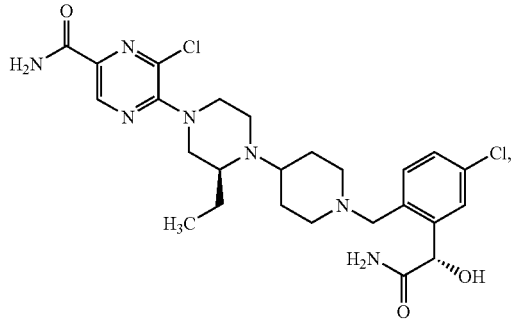 |
| 286 | 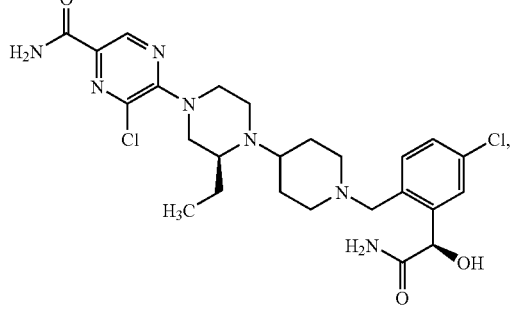 |
| 287 | 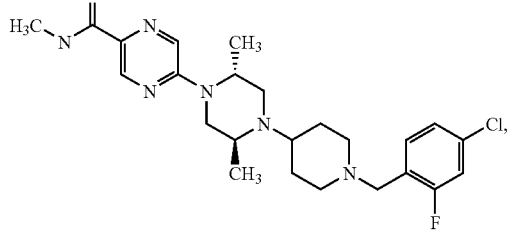 |
| 288 | 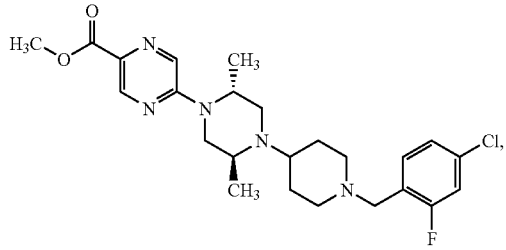 |

-continued
| Compound No. | Compound Structure |
|---|---|
| 289 | 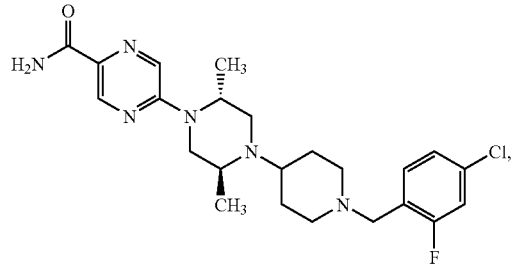 |
| 290 | 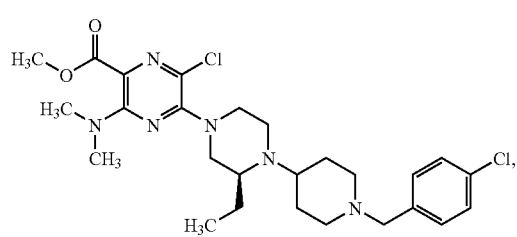 |
| 291 | 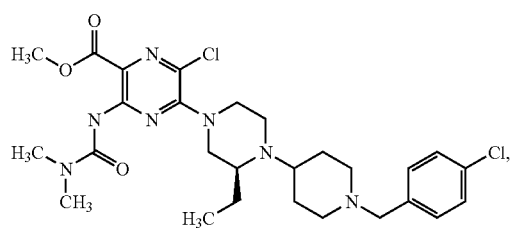 |
| 292 | 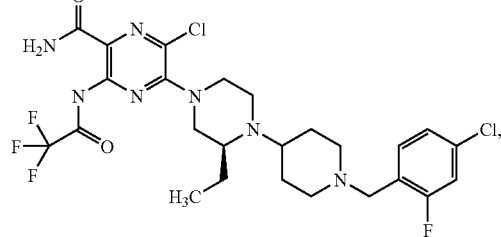 |
| 293 | 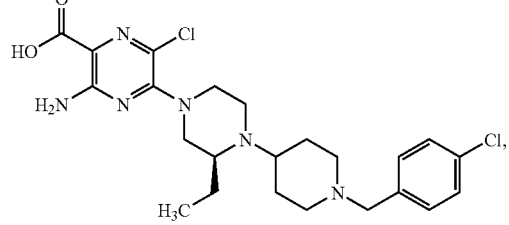 |
| 294 | 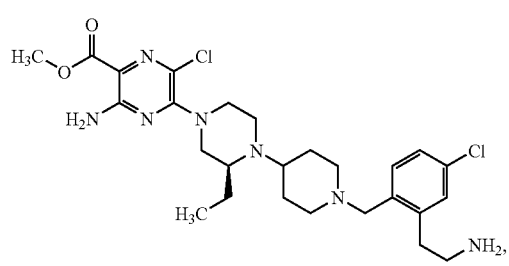 |
-continued
| Compound No. | Compound Structure |
|---|---|
| 295 | 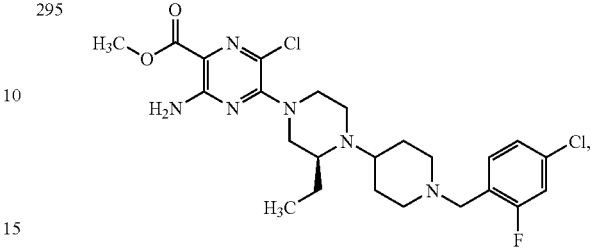 |
| 296 | 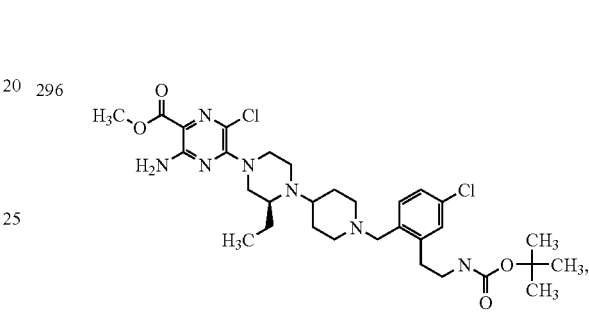 |
| 297 | 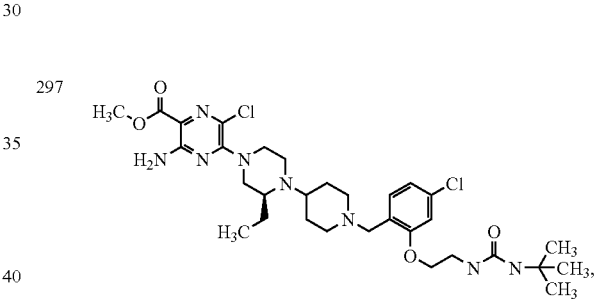 |
| 298 | 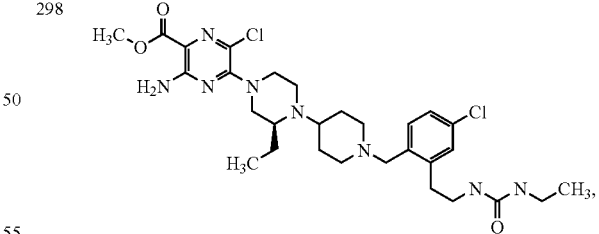 |
| 299 | 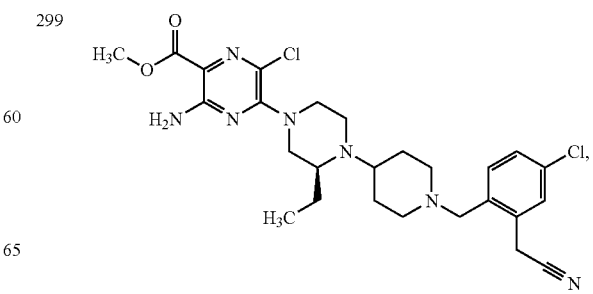 |

-continued

| Compound No. | Compound Structure |
|---|---|
| 300 | (methyl 3-amino-6-chloro-5-{4-[1-(4-chloro-2-cyanobenzyl)piperidin-4-yl]-3-ethylpiperazin-1-yl}pyrazine-2-carboxylate) |
| 301 | (methyl 3-amino-6-chloro-5-{4-[1-(4-chloro-2-fluorobenzyl)piperidin-4-yl]-2,5-dimethylpiperazin-1-yl}pyrazine-2-carboxylate) |
| 302 | (methyl 3-amino-6-chloro-5-{4-[1-(4-chlorobenzyl)piperidin-4-yl]-2-methylpiperazin-1-yl}pyrazine-2-carboxylate) |
| 303 | (methyl 3-amino-6-chloro-5-(4-{1-[4-chloro-2-(2-methanesulfonylaminoethyl)benzyl]piperidin-4-yl}-3-ethylpiperazin-1-yl)pyrazine-2-carboxylate) |
| 304 | (3-amino-6-chloro-5-{4-[1-(6-cyano-2-hydroxy-1,2,3,4-tetrahydronaphthalen-1-yl)piperidin-4-yl]-3-ethylpiperazin-1-yl}-N-(2-hydroxyethyl)pyrazine-2-carboxamide) |
| 305 | (methyl 3-amino-6-chloro-5-{4-[1-(6-cyano-2-hydroxy-1,2,3,4-tetrahydronaphthalen-1-yl)piperidin-4-yl]-3-ethylpiperazin-1-yl}pyrazine-2-carboxylate) |

-continued

| Compound No. | Compound Structure |
|---|---|
| 306 | (methyl 3-amino-6-chloro-5-{4-[1-(4-cyano-2-hydroxybenzyl)piperidin-4-yl]-3-ethylpiperazin-1-yl}pyrazine-2-carboxylate) |
| 307 | (methyl 3-amino-6-chloro-5-(4-{1-[4-cyano-2-(2-hydroxyethoxy)benzyl]piperidin-4-yl}-3-ethylpiperazin-1-yl)pyrazine-2-carboxylate) |
| 308 | (methyl 3-amino-6-chloro-5-(4-{1-[4-cyano-2-(2-methoxyethoxy)benzyl]piperidin-4-yl}-3-ethylpiperazin-1-yl)pyrazine-2-carboxylate) |
| 309 | (methyl 3-amino-5-(4-{1-[2-(2-acetylaminoethyl)-4-chlorobenzyl]piperidin-4-yl}-3-ethylpiperazin-1-yl)-6-chloropyrazine-2-carboxylate) |
| 310 | (methyl 3-amino-6-chloro-5-{4-[1-(4-chlorobenzyl)-4-methylpiperidin-4-yl]-3-ethylpiperazin-1-yl}pyrazine-2-carboxylate) |
| 311 | (isopropyl 3-amino-5-{4-[1-(4-chlorobenzyl)piperidin-4-yl]-3-ethylpiperazin-1-yl}pyrazine-2-carboxylate) |

| Compound No. | Compound Structure |
|---|---|
| 312 | 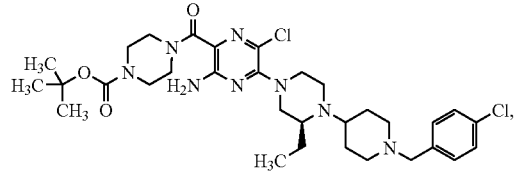 |
| 313 | 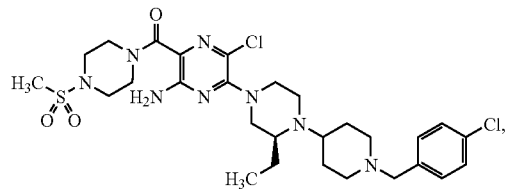 |
| 314 | 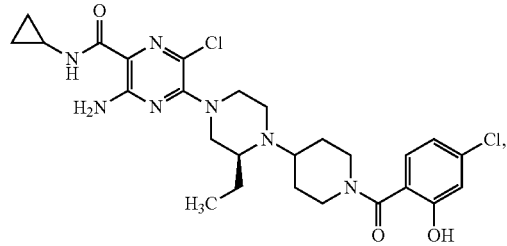 |
| 315 | 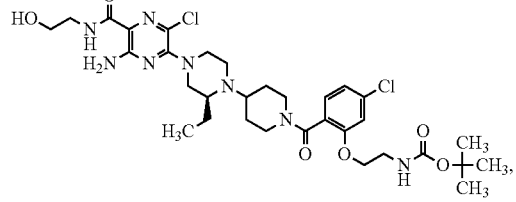 |
| 316 | 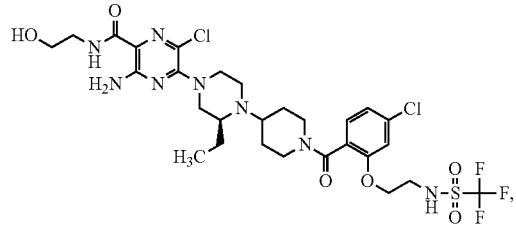 |
| 317 | 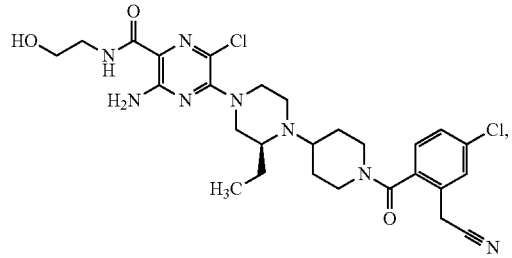 |
| Compound No. | Compound Structure |
|---|---|
| 318 | 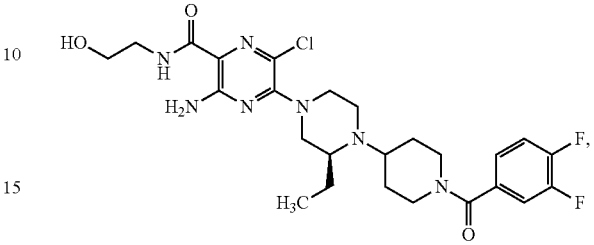 |
| 319 | 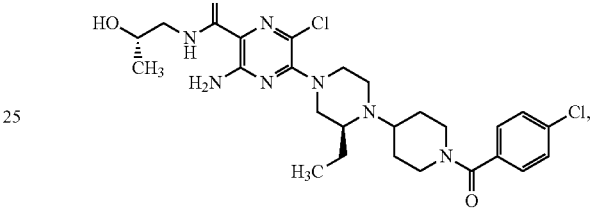 |
| 320 | 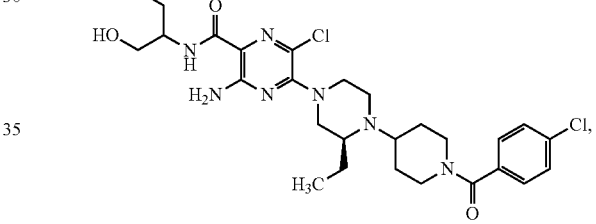 |
| 321 | 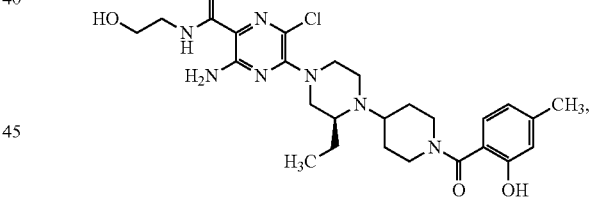 |
| 322 | 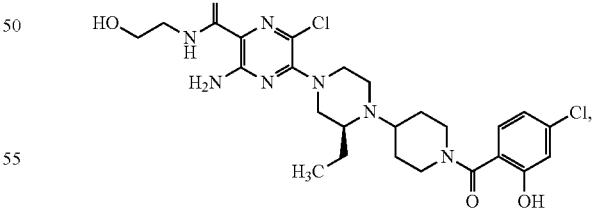 |
| 323 | 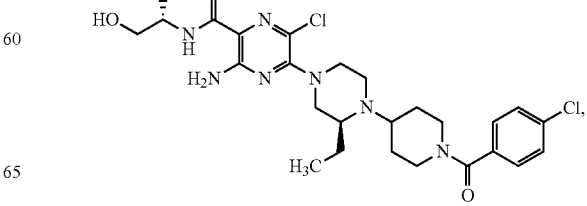 |

-continued

| Compound No. | Compound Structure |
|---|---|
| 324 | 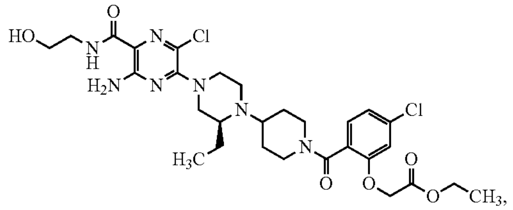 |
| 325 | 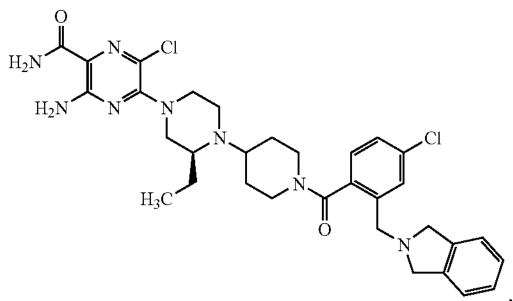 |
| 326 | 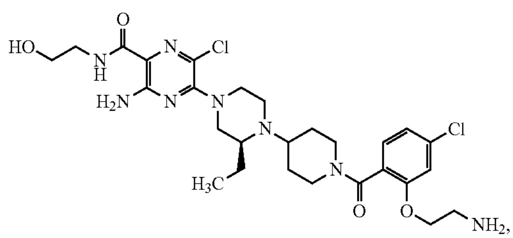 |
| 327 | 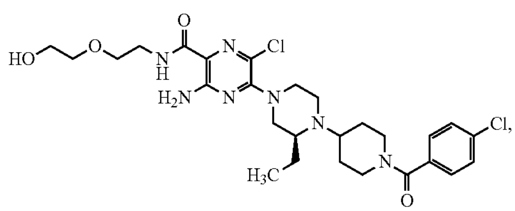 |
| 328 | 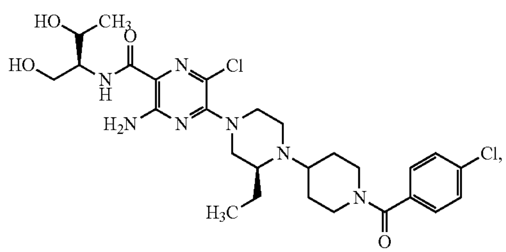 |
| 329 | 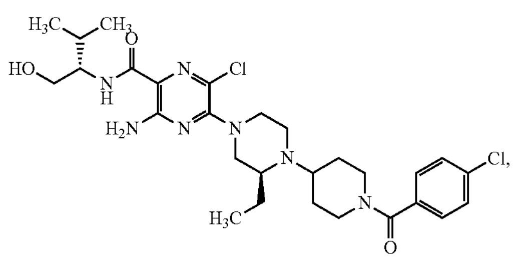 |

-continued

| Compound No. | Compound Structure |
|---|---|
| 330 | 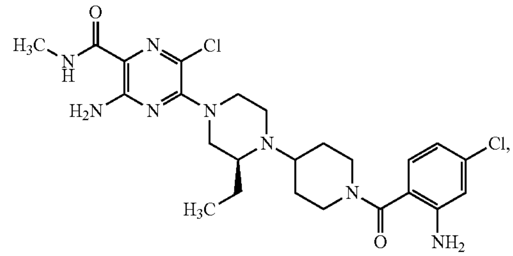 |
| 331 | 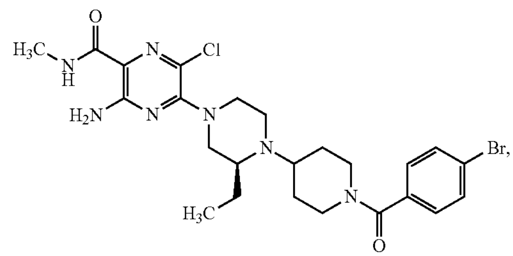 |
| 332 | 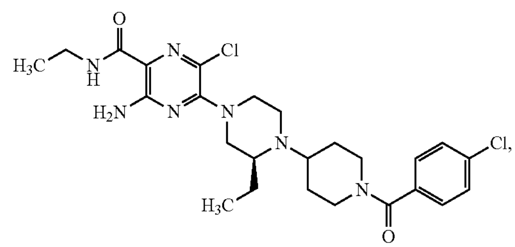 |
| 333 | 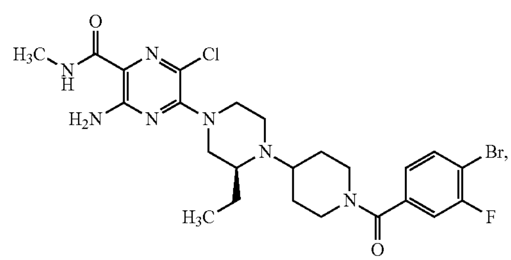 |
| 334 | 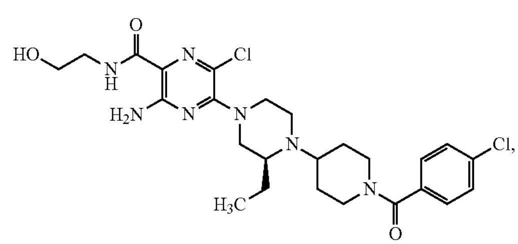 |
| 335 | 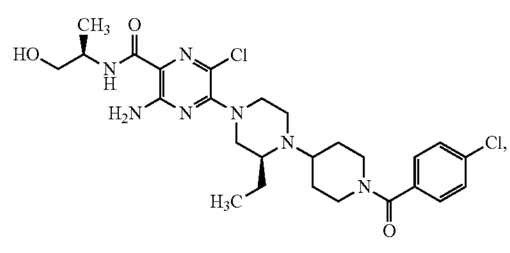 |

-continued
| Compound No. | Compound Structure |
|---|---|
| 336 | 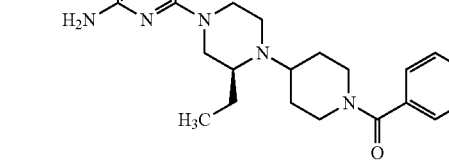 |
| 337 | 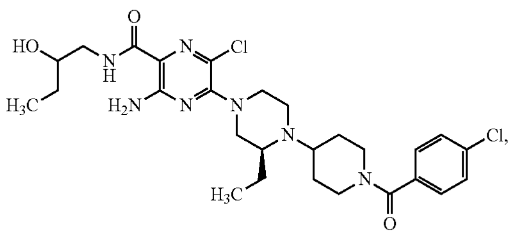 |
| 338 | 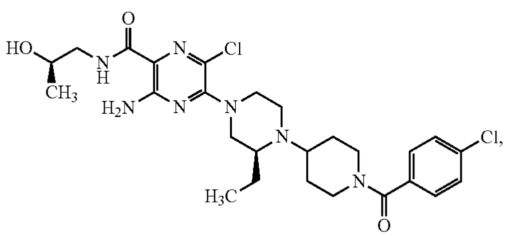 |
| 339 | 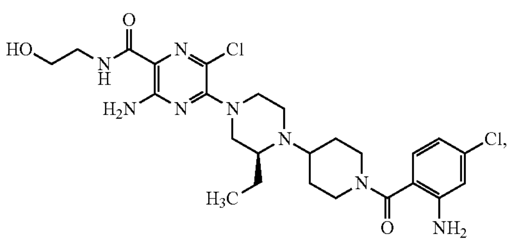 |
| 340 | 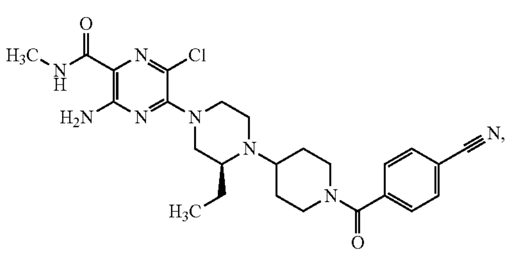 |
| 341 | 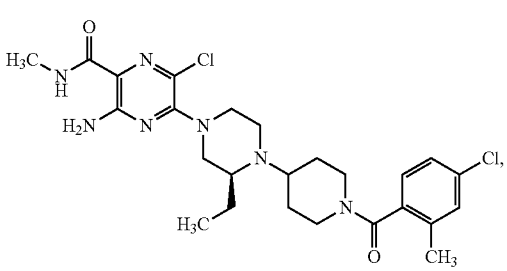 |
-continued
| Compound No. | Compound Structure |
|---|---|
| 342 | 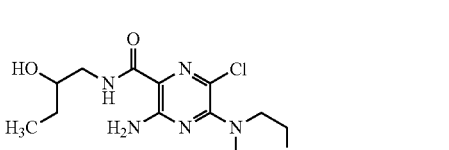 |
| 343 | 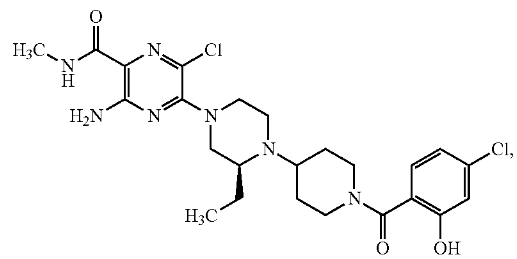 |
| 344 | 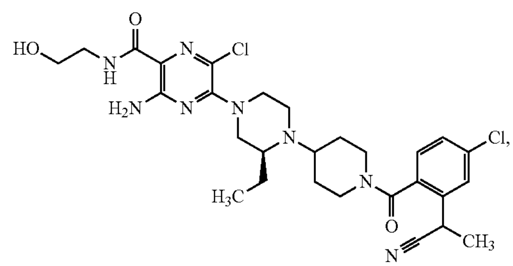 |
| 345 | 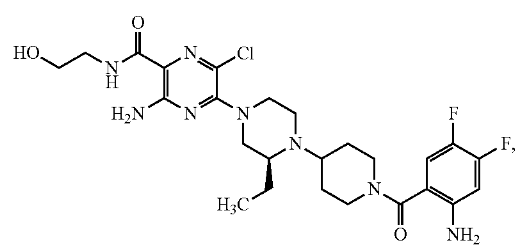 |
| 346 | 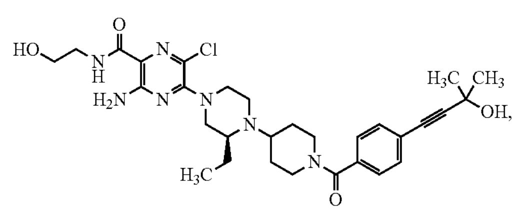 |
| 347 | 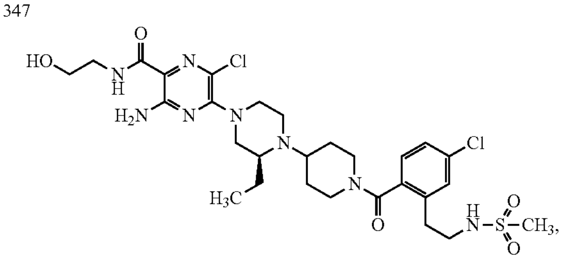 |

| Compound No. | Compound Structure |
|---|---|
| 348 | 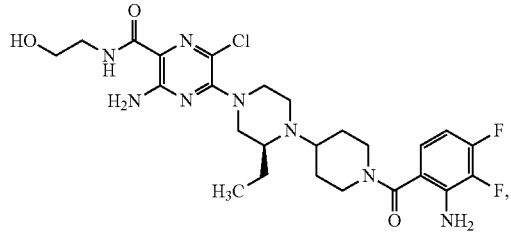 |
| 349 | 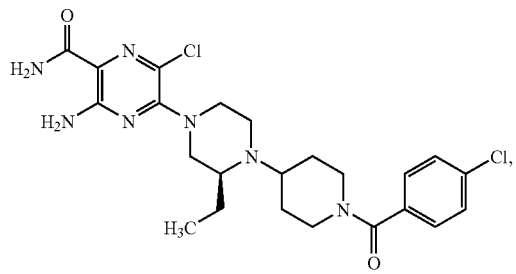 |
| 350 | 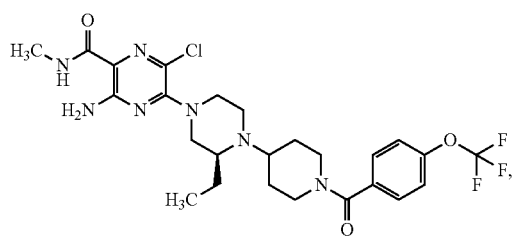 |
| 351 | 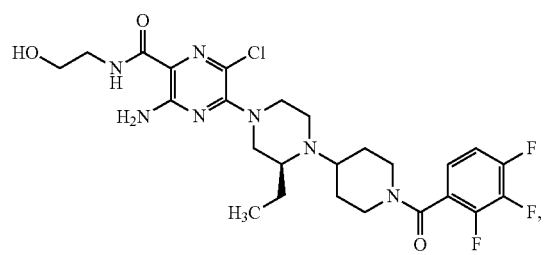 |
| 352 | 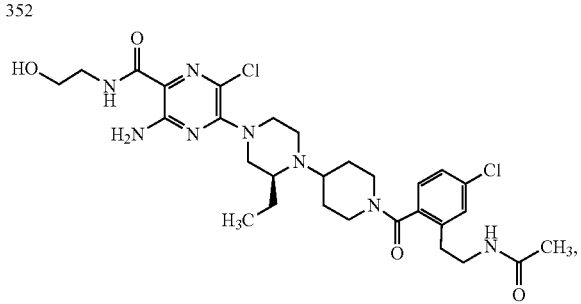 |
| Compound No. | Compound Structure |
|---|---|
| 353 | 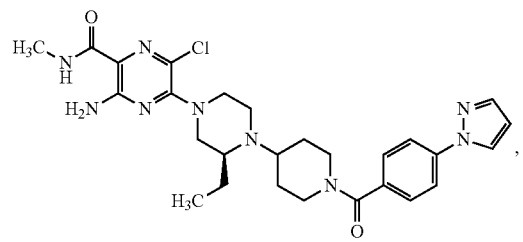 |
| 354 | 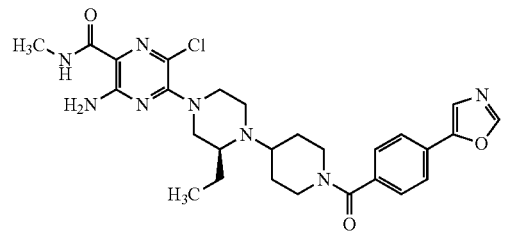 |
| 355 | 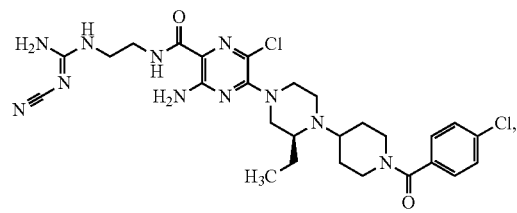 |
| 356 | 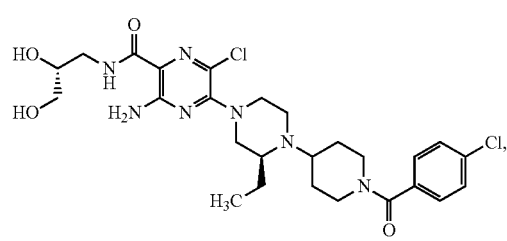 |
| 357 | 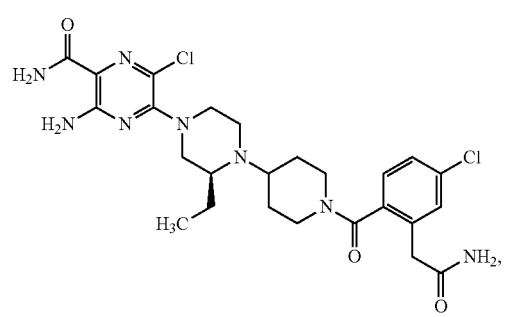 |
| 358 | 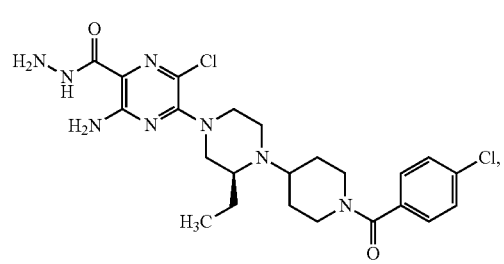 |

-continued
| Compound No. | Compound Structure |
|---|---|
| 359 | 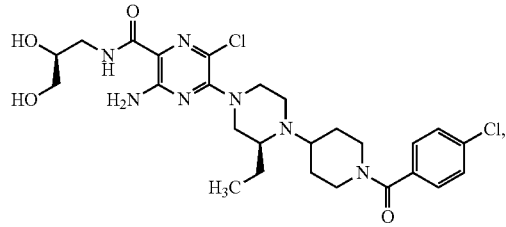 |
| 360 | 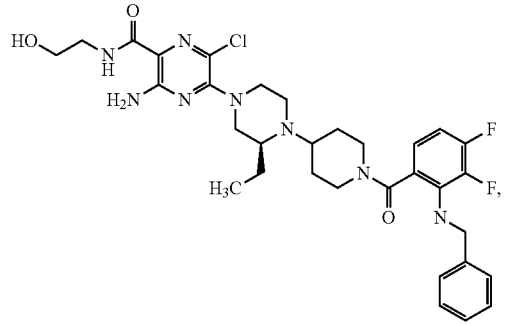 |
| 361 | 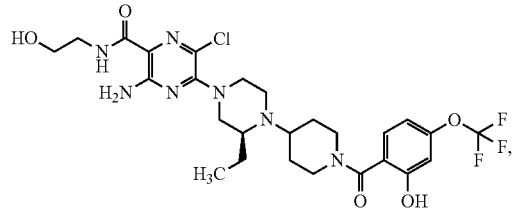 |
| 362 | 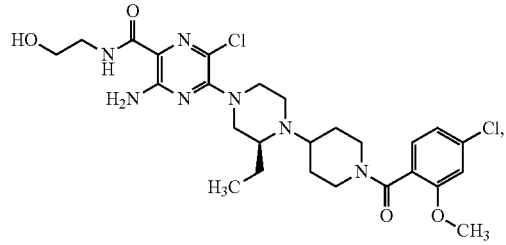 |
| 363 | 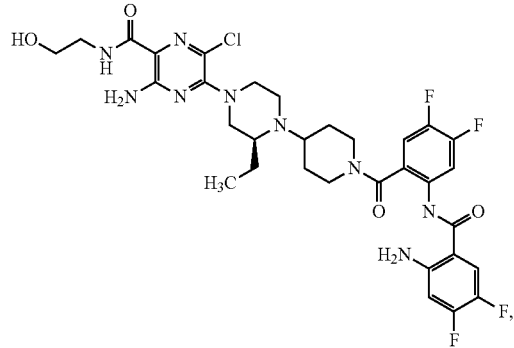 |
-continued
| Compound No. | Compound Structure |
|---|---|
| 364 | 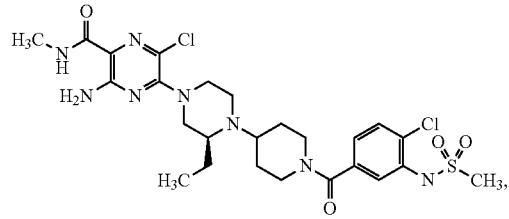 |
| 365 | 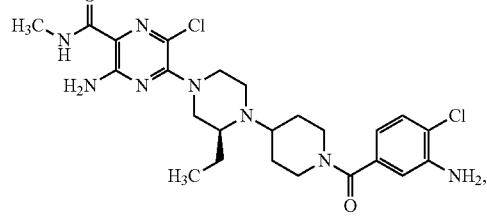 |
| 366 | 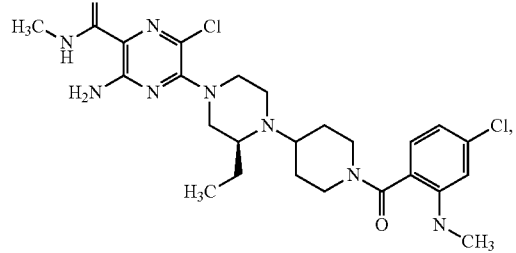 |
| 367 | 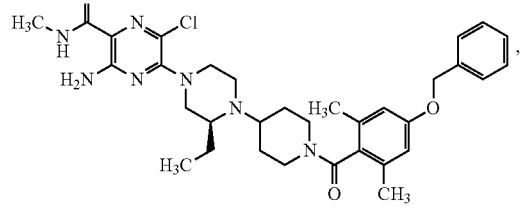 |
| 368 | 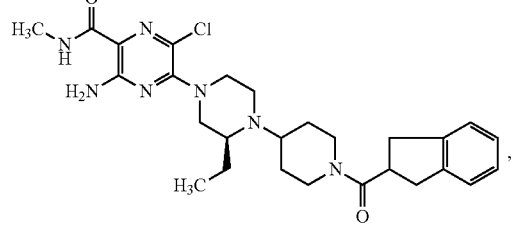 |
| 369 | 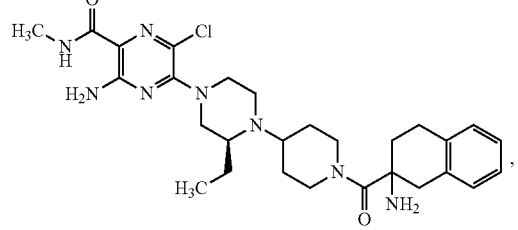 |

-continued
| Compound No. | Compound Structure |
|---|---|
| 370 | 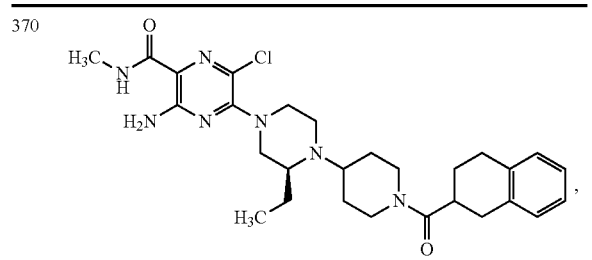 |
| 371 | 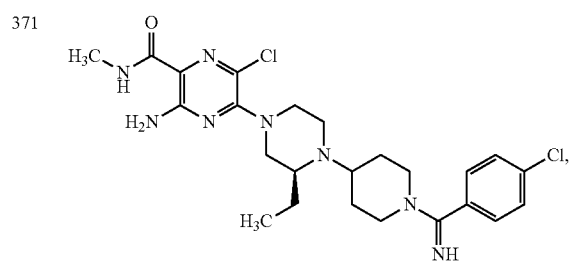 |
| 372 | 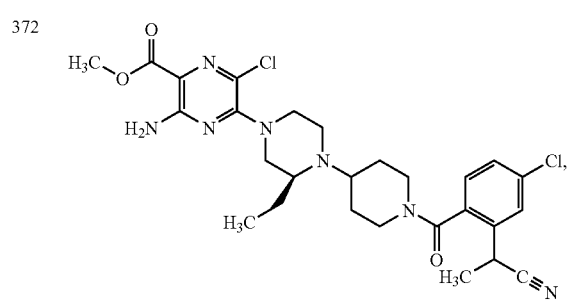 |
| 373 | 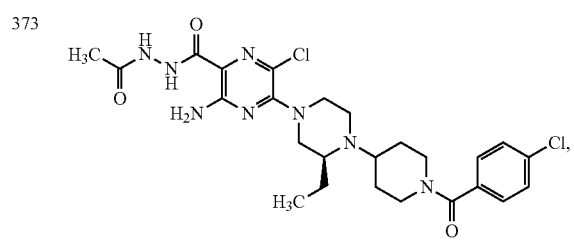 |
| 374 | 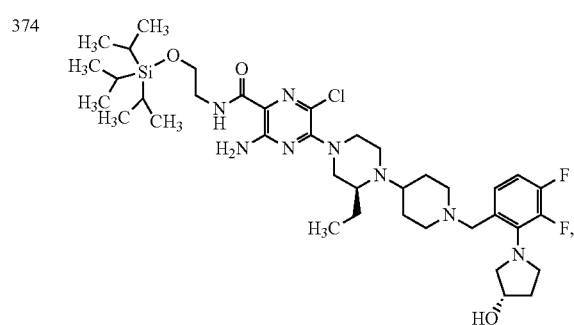 |
-continued
| Compound No. | Compound Structure |
|---|---|
| 375 | 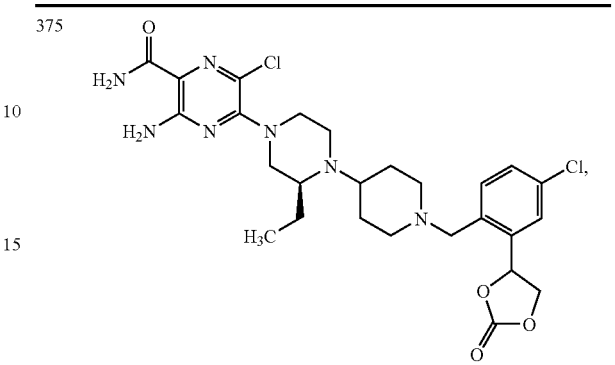 |
| 376 | 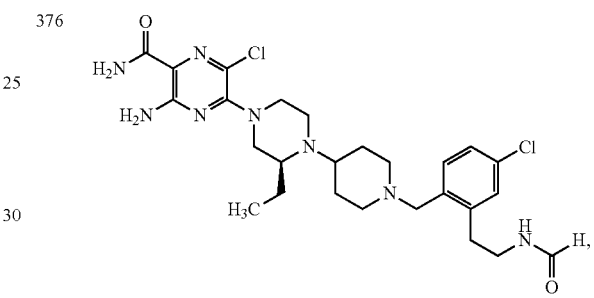 |
| 377 | 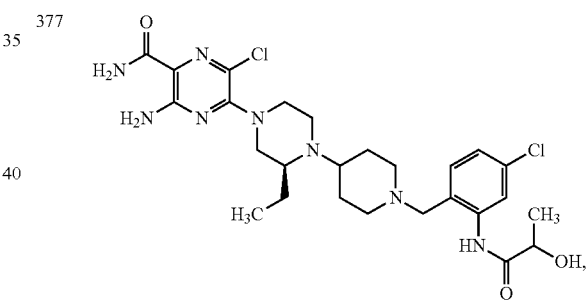 |
| 378 | 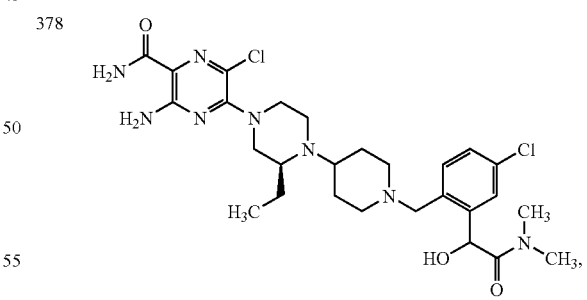 |
| 379 | 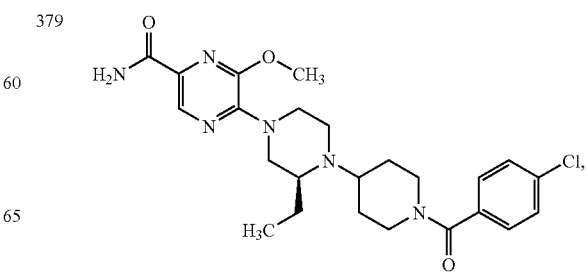 |

-continued
| Compound No. | Compound Structure |
|---|---|
| 380 | 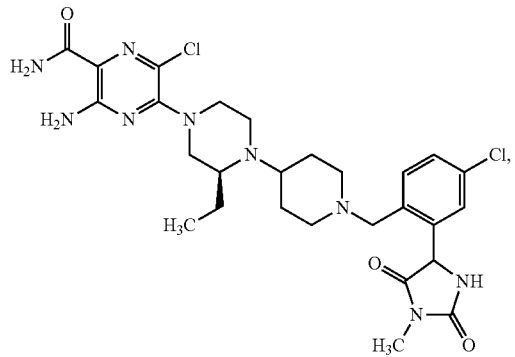 |
| 381 | 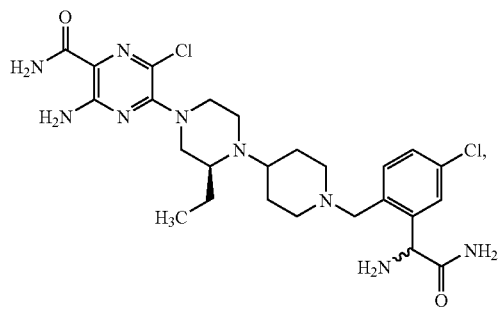 |
| 382 | 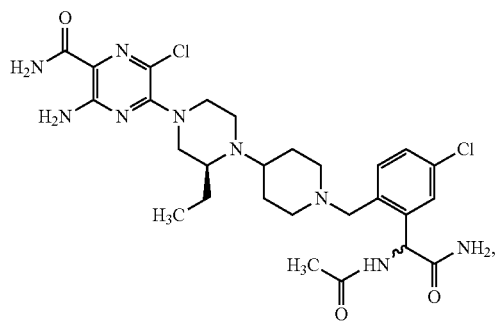 |
| 383 | 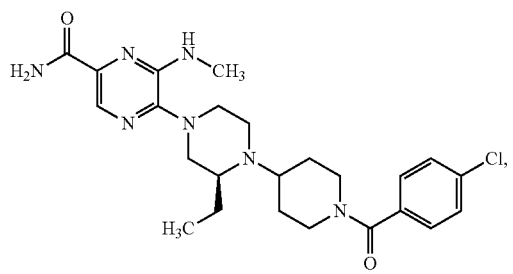 |
| 384 | 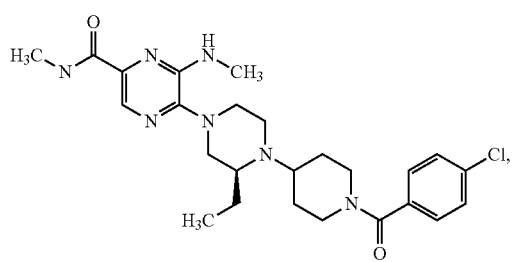 |
-continued
| Compound No. | Compound Structure |
|---|---|
| 385 | 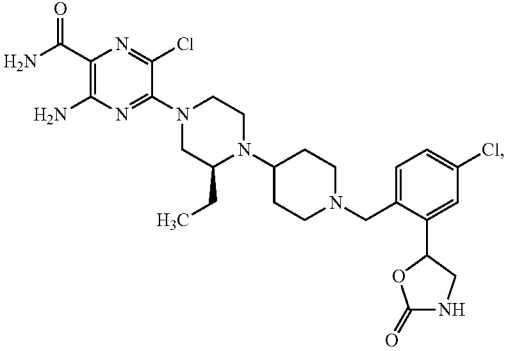 |
| 386 | 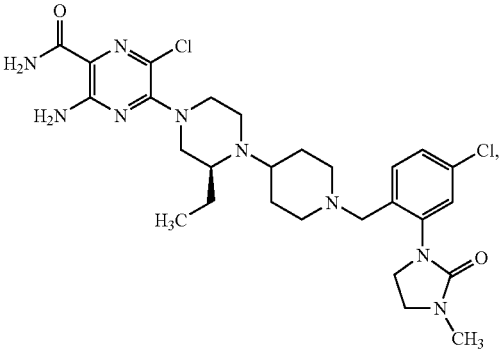 |
| 387 | 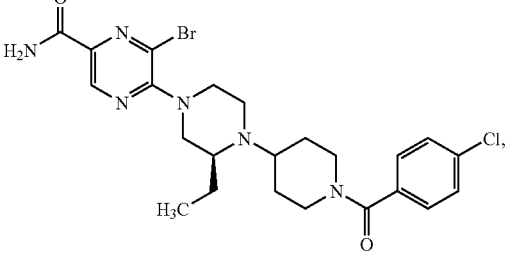 |
| 388 | 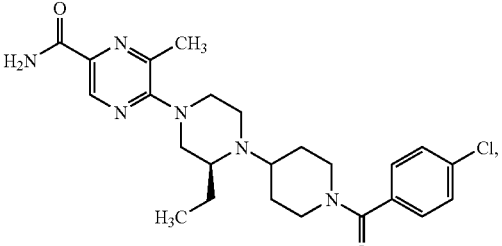 |
| 389 | 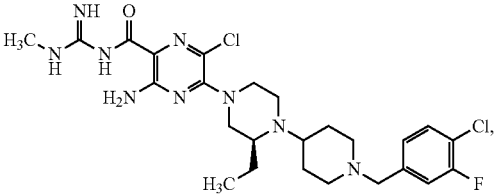 |

-continued

| Compound No. | Compound Structure |
|---|---|
| 390 | (structure) |
| 391 | (structure) |
| 392 | (structure) |
| 393 | (structure) |
| 394 | (structure) |
| 395 | (structure) |
| 396 | (structure) |
| 397 | (structure) |
| 398 | (structure) |
| 399 | (structure) |
| 400 | (structure) |

-continued
| Compound No. | Compound Structure |
|---|---|
| 401 | 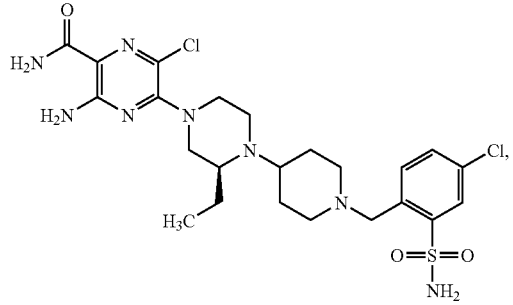 |
| 402 | 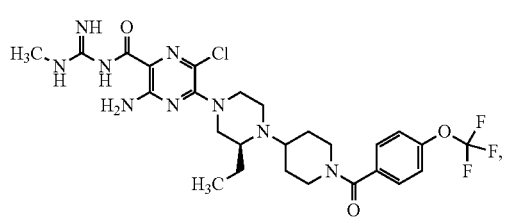 |
| 403 | 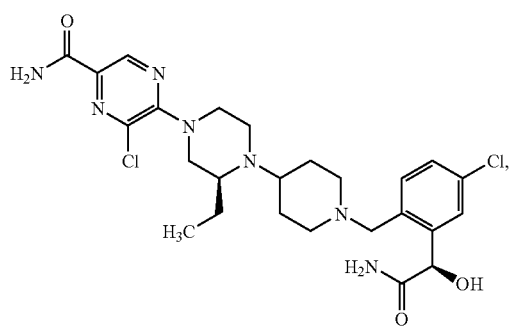 |
| 404 | 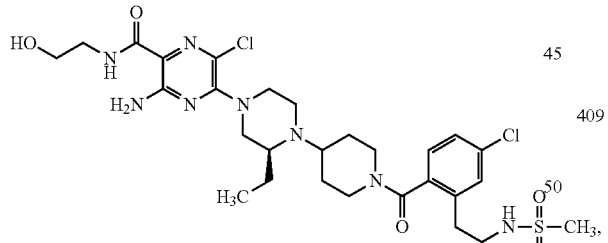 |
| 405 | 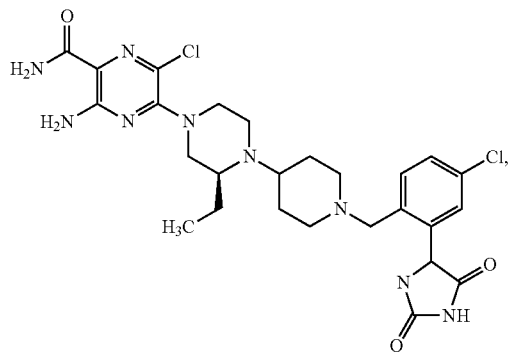 |
-continued
| Compound No. | Compound Structure |
|---|---|
| 406 | 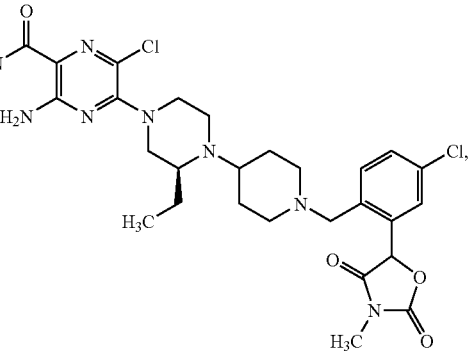 |
| 407 | 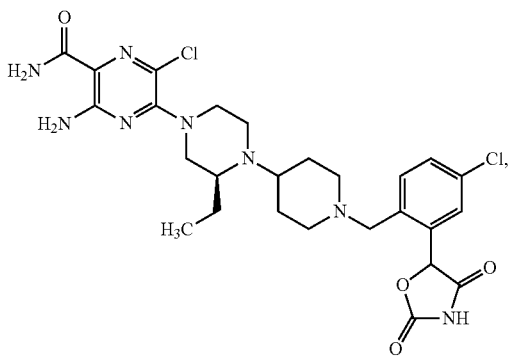 |
| 408 | 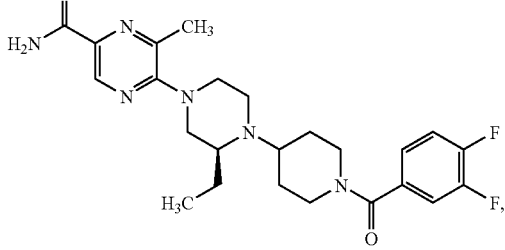 |
| 409 | 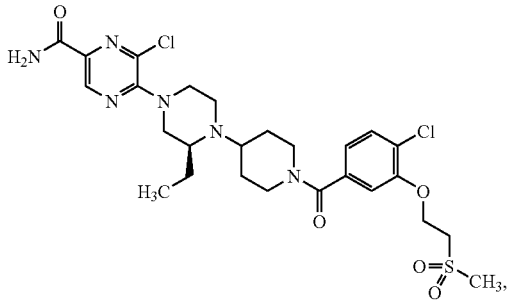 |
| 410 | 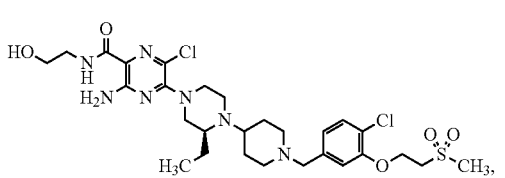 |

| Compound No. | Compound Structure |
|---|---|
| 411 | 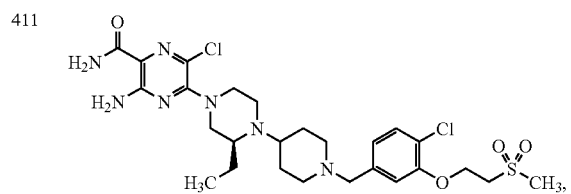 |
| 412 | 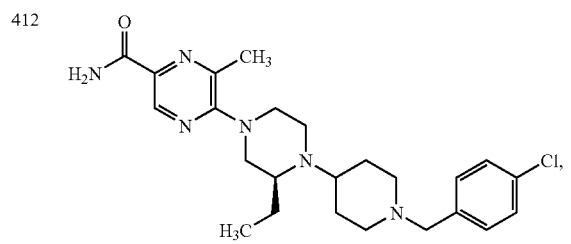 |
| 413 | 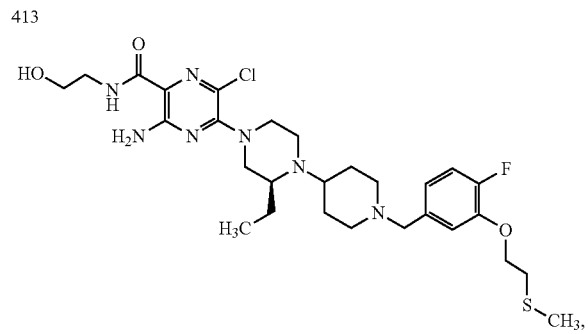 |
| 414 | 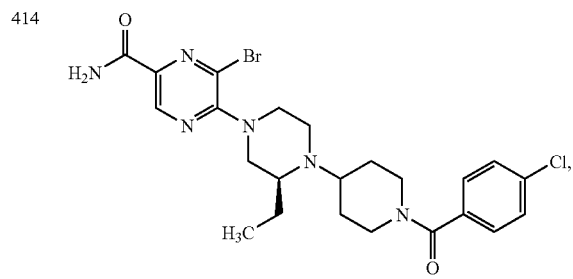 |
| 415 | 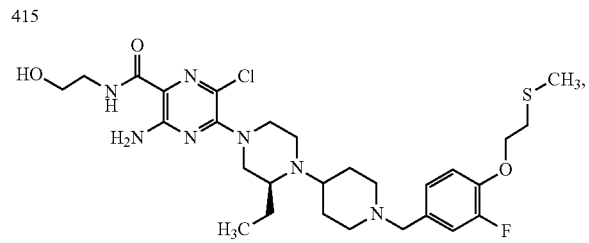 |
| 416 | 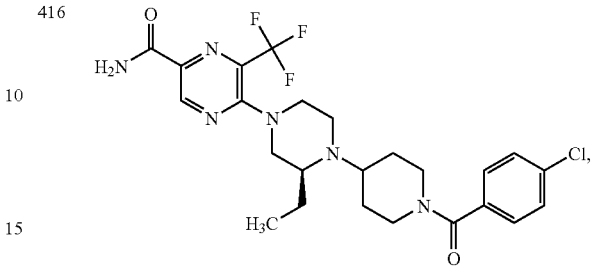 |
| 417 | 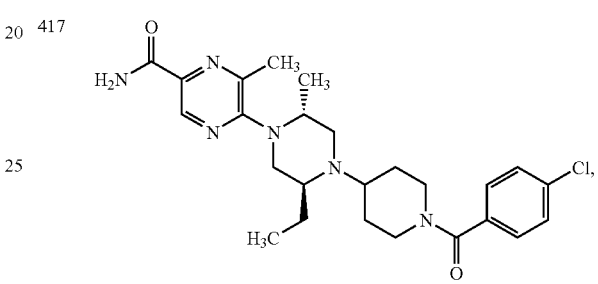 |
| 418 | 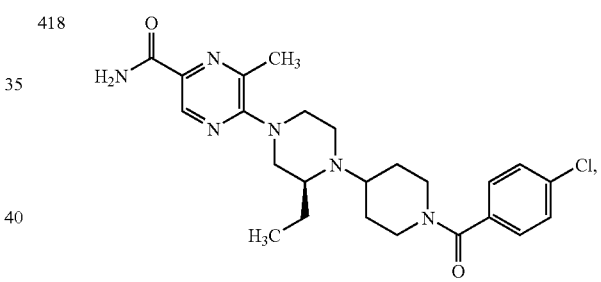 |
| 419 | 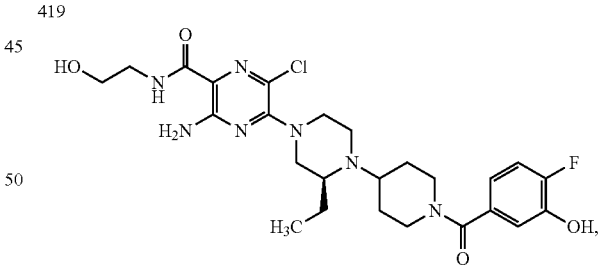 |
| 420 | 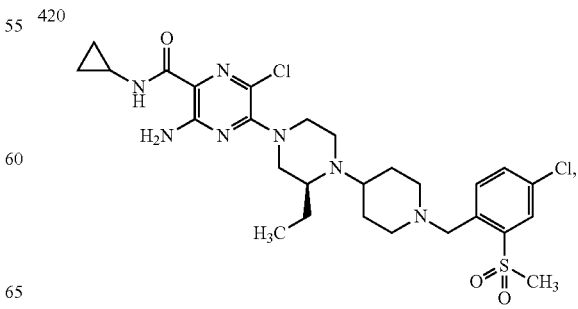 |

-continued
| Compound No. | Compound Structure |
|---|---|
| 421 | 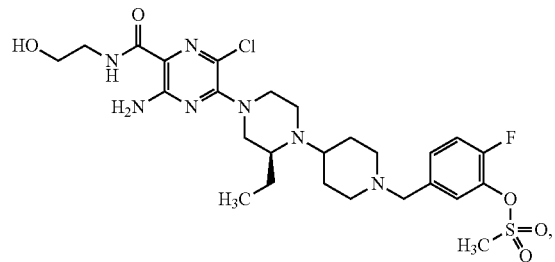 |
| 422 | 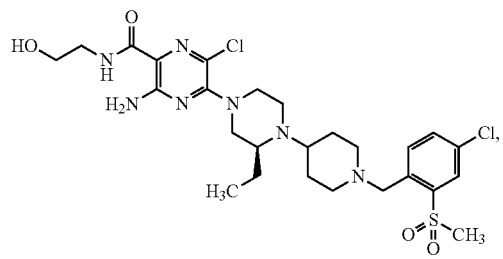 |
| 423 | 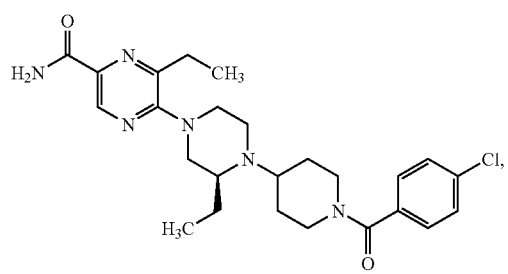 |
| 424 | 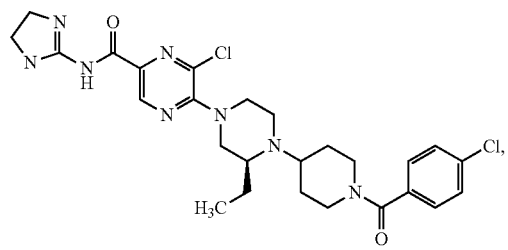 |
| 425 | 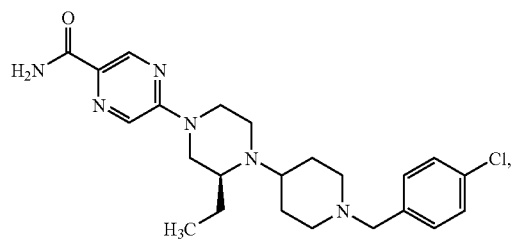 |
-continued
| Compound No. | Compound Structure |
|---|---|
| 426 | 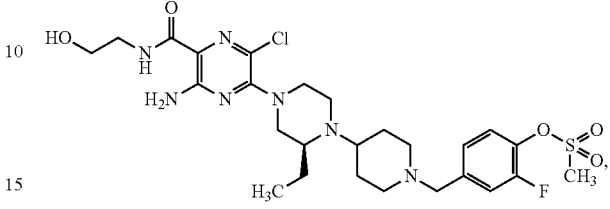 |
| 427 | 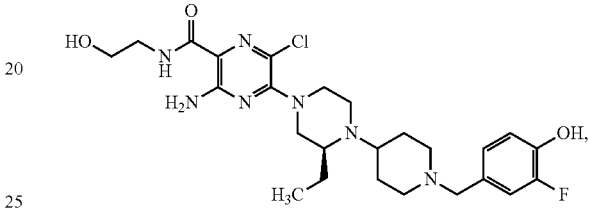 |
| 428 | 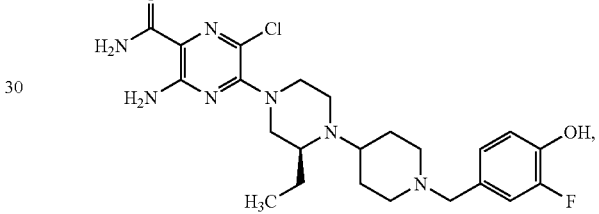 |
| 429 | 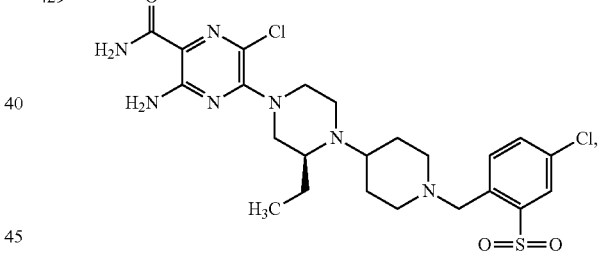 |
| 430 | 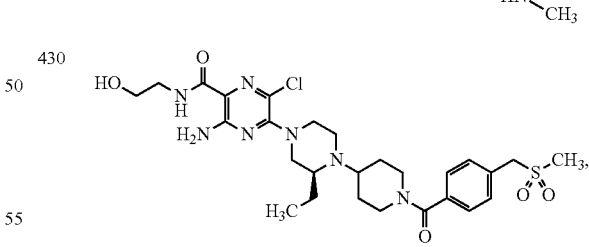 |
| 431 | 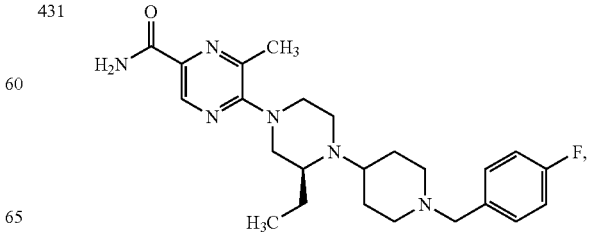 |

-continued
| Compound No. | Compound Structure |
|---|---|
| 432 | 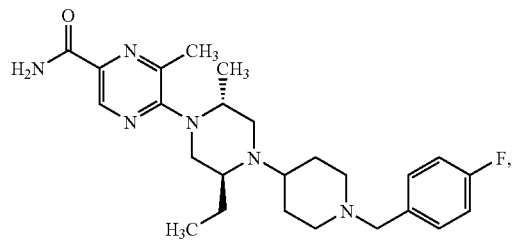 |
| 433 | 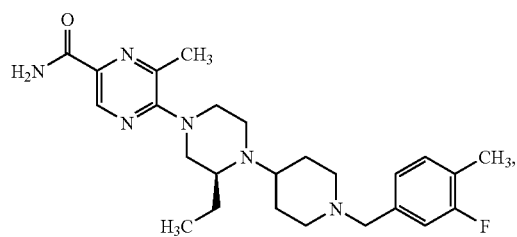 |
| 434 | 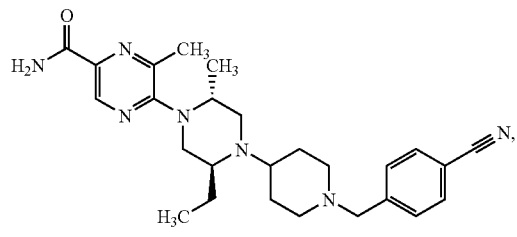 |
| 435 | 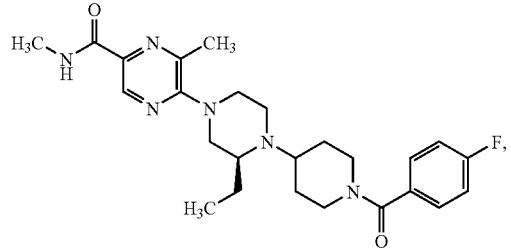 |
| 436 | 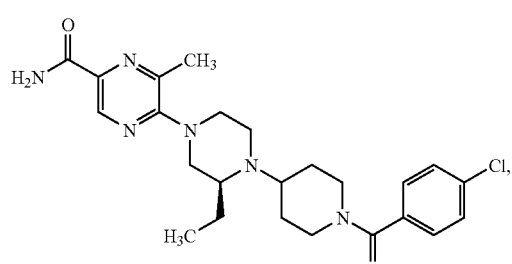 |
| 437 | 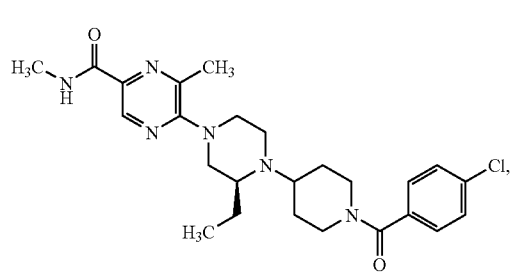 |
-continued
| Compound No. | Compound Structure |
|---|---|
| 438 | 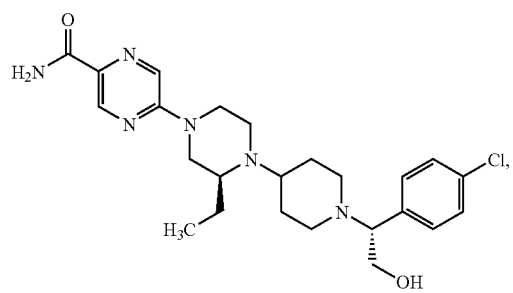 |
| 439 | 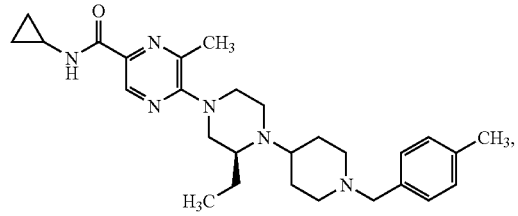 |
| 440 | 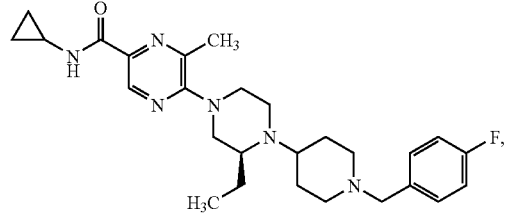 |
| 441 | 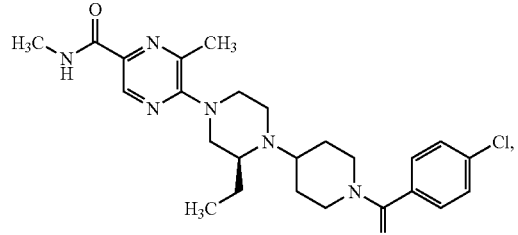 |
| 442 | 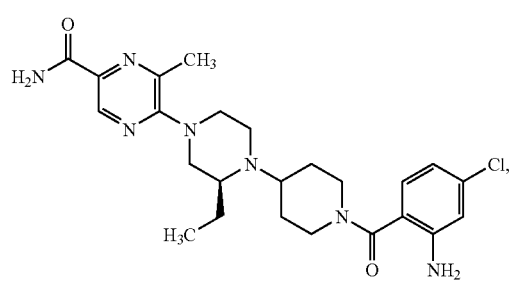 |

-continued
| Compound No. | Compound Structure |
|---|---|
| 443 | 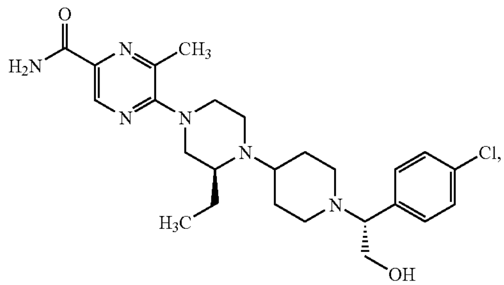 |
| 444 | 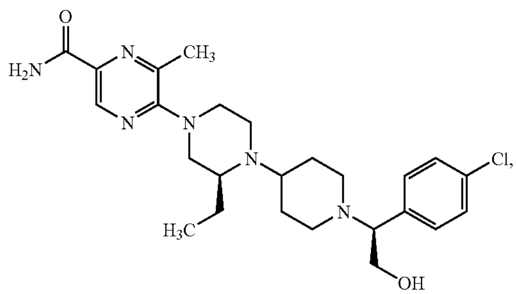 |
| 445 | 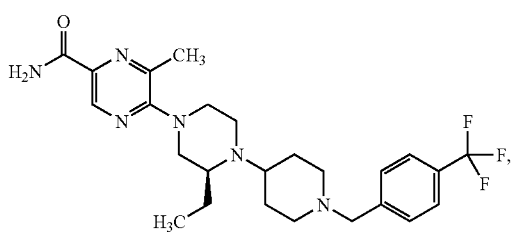 |
| 446 | 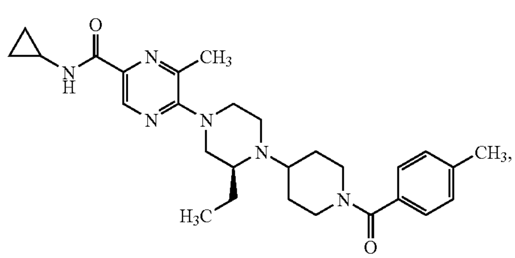 |
| 447 | 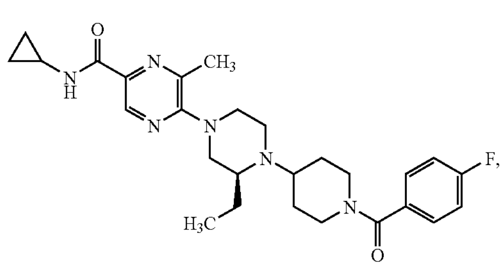 |
-continued
| Compound No. | Compound Structure |
|---|---|
| 448 | 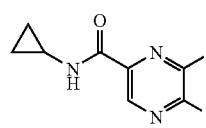 |
| 449 | 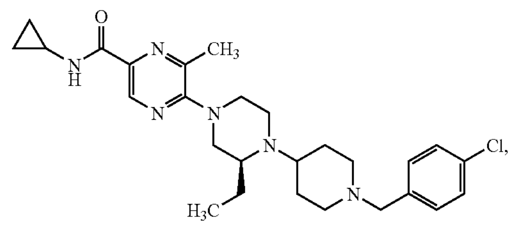 |
| 450 | 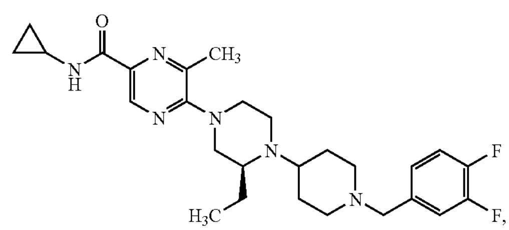 |
| 451 | 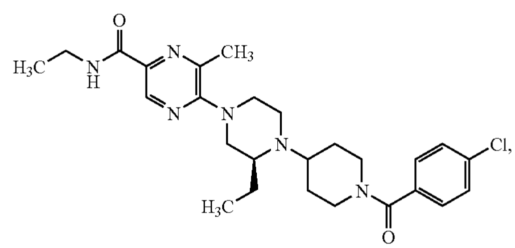 |
| 452 | 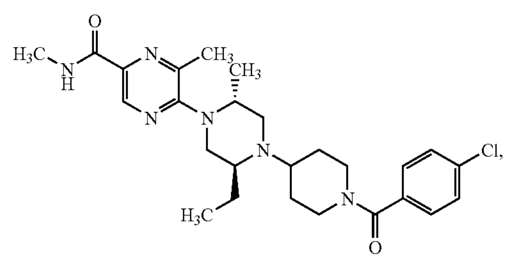 |
| 453 | 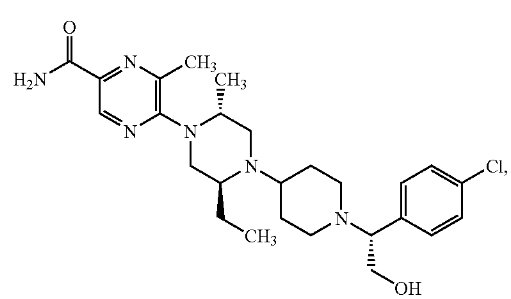 |

-continued
| Compound No. | Compound Structure |
|---|---|
| 454 | 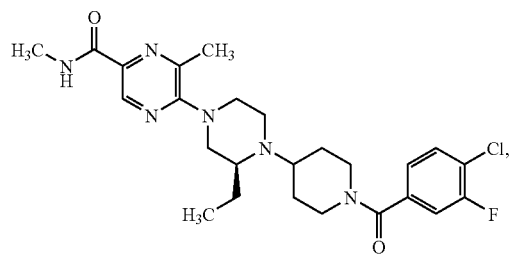 |
| 455 | 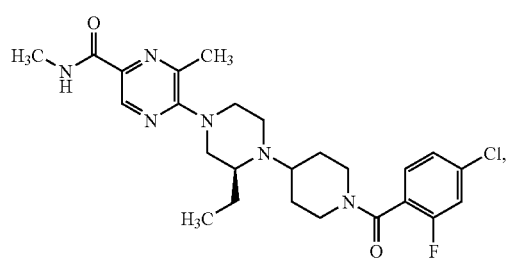 |
| 456 | 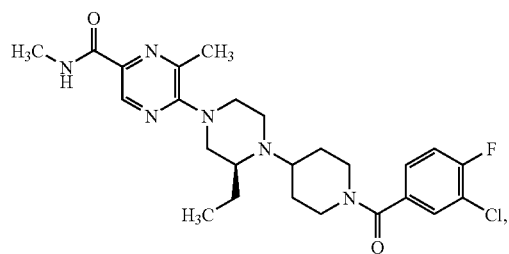 |
| 457 | 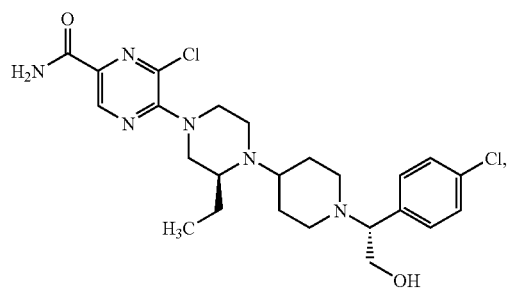 |
| 458 | 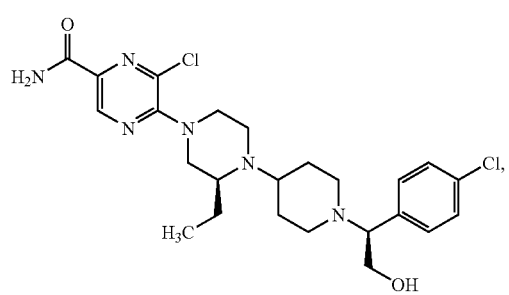 |
-continued
| Compound No. | Compound Structure |
|---|---|
| 459 | 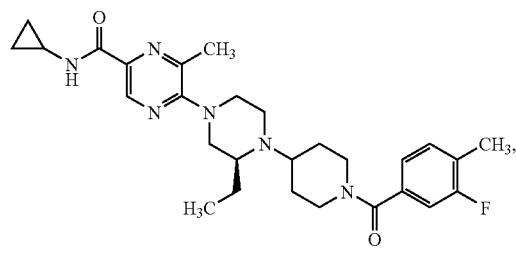 |
| 460 | 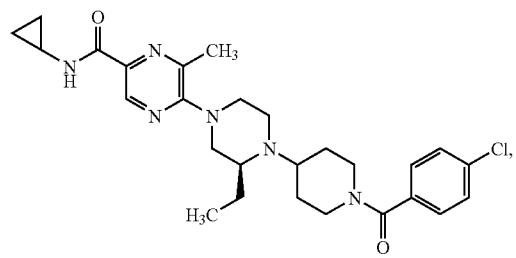 |
| 461 | 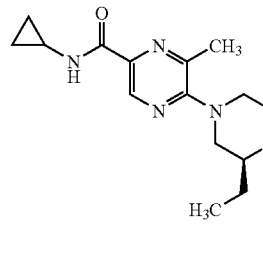 |
| 462 | 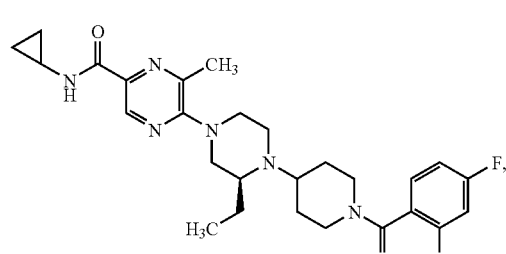 |
| 463 | 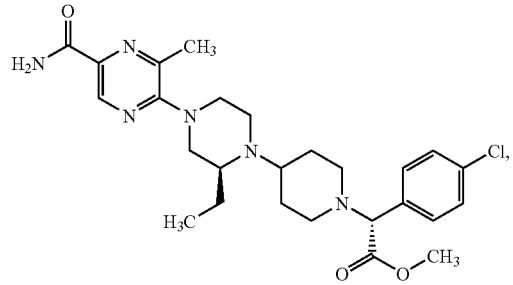 |

| Compound No. | Compound Structure |
|---|---|
| 464 | 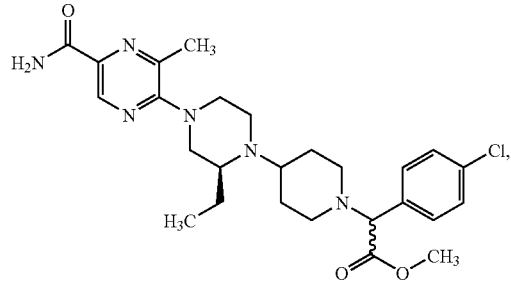 |
| 465 | 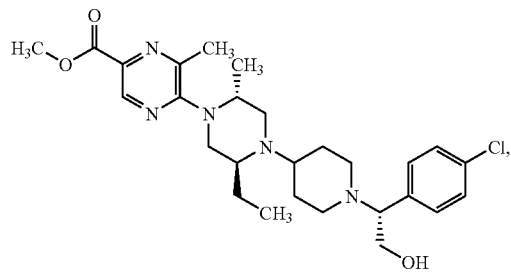 |
| 466 | 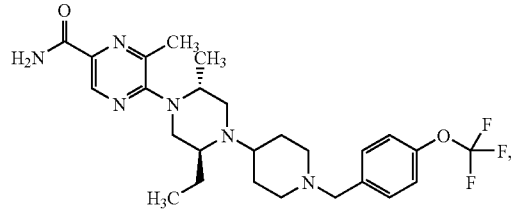 |
| 467 | 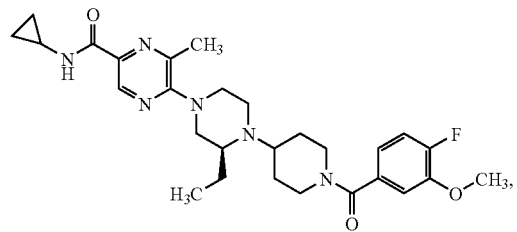 |
| 468 | 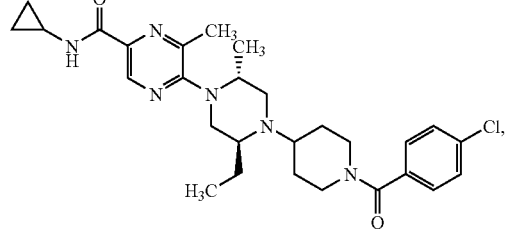 |
| Compound No. | Compound Structure |
|---|---|
| 469 | 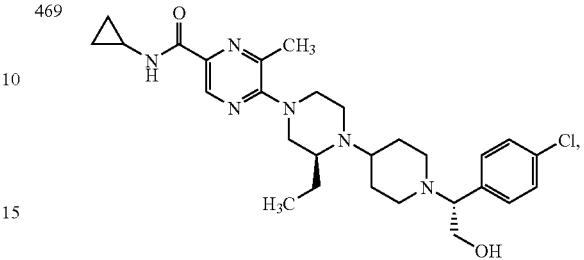 |
| 470 | 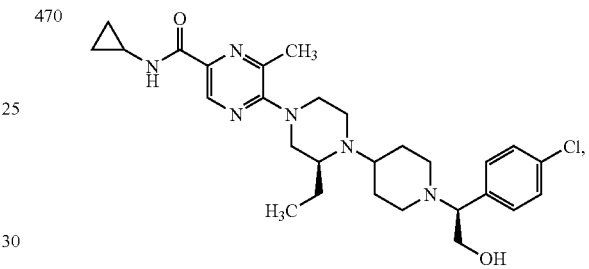 |
| 471 | 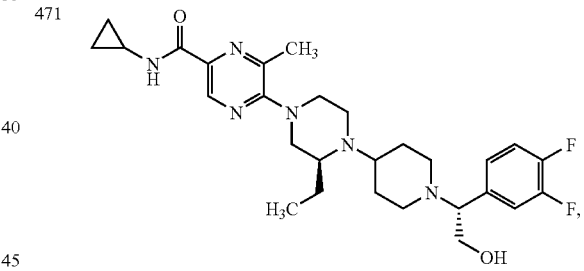 |
| 472 | 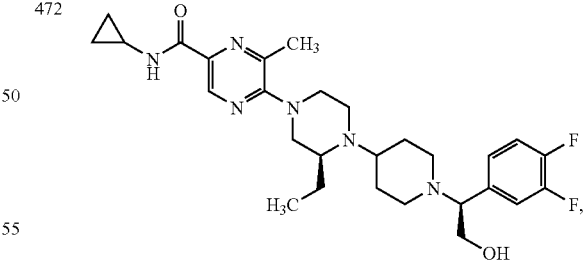 |
| 473 | 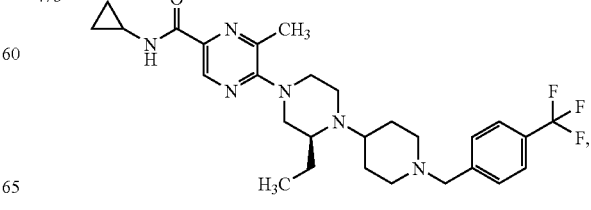 |

-continued
| Compound No. | Compound Structure |
|---|---|
| 474 | 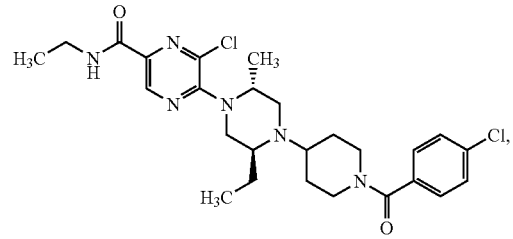 |
| 475 | 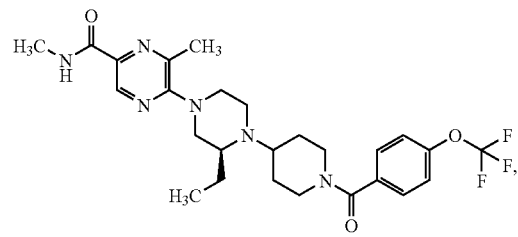 |
| 476 | 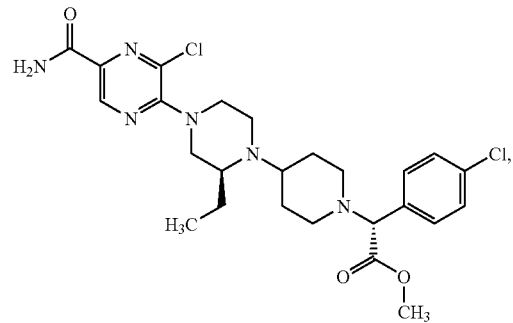 |
| 477 | 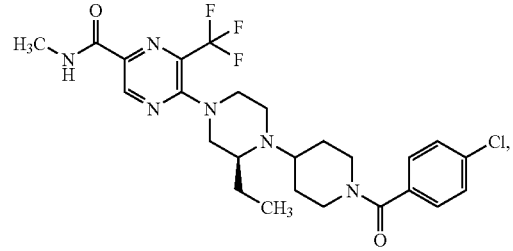 |
| 478 | 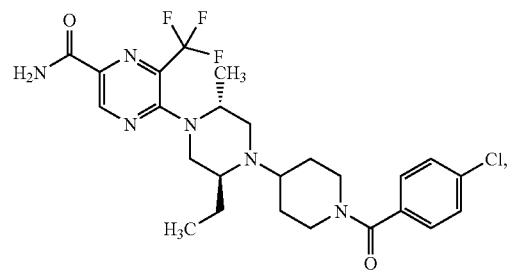 |
-continued
| Compound No. | Compound Structure |
|---|---|
| 479 | 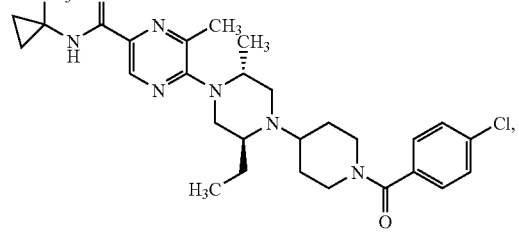 |
| 480 | 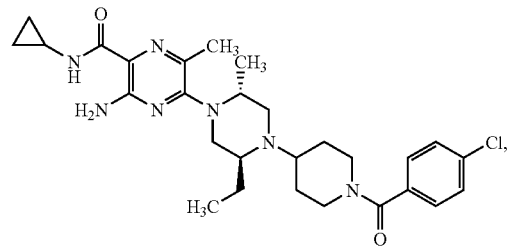 |
| 481 | 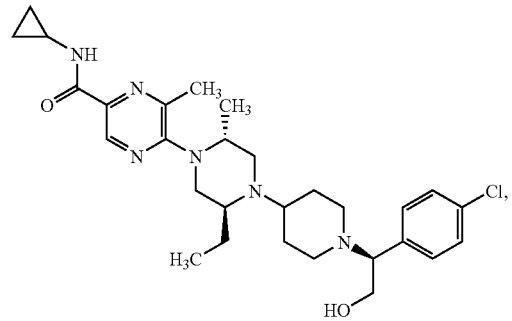 |
| 482 | 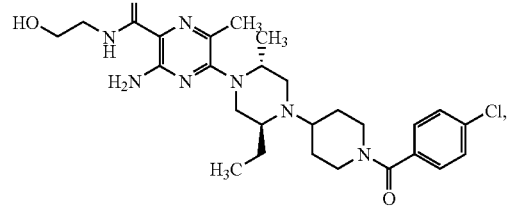 |
| 483 | 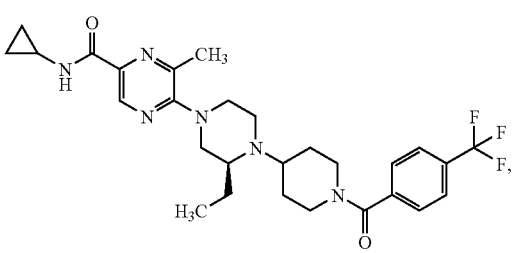 |

-continued
| Compound No. | Compound Structure |
|---|---|
| 484 | 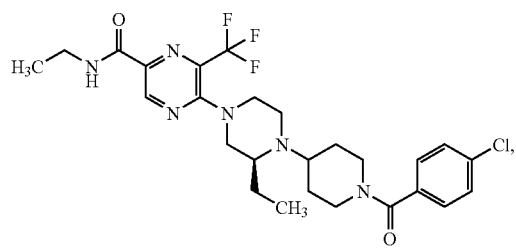 |
| 485 | 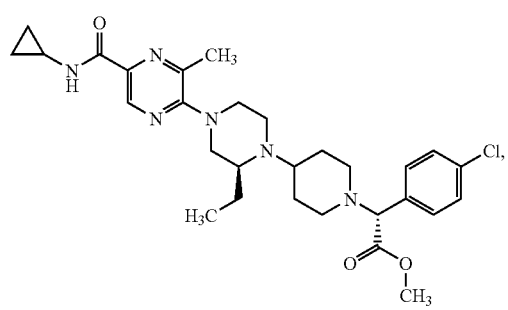 |
| 486 | 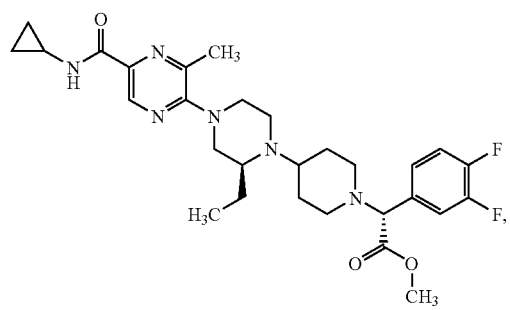 |
| 487 | 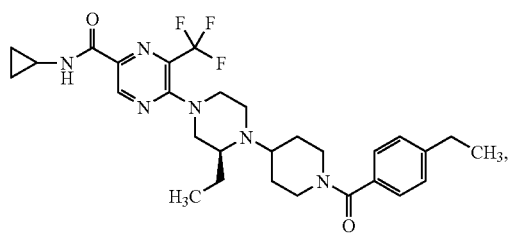 |
| 488 | 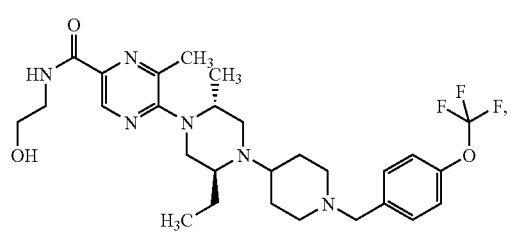 |
-continued
| Compound No. | Compound Structure |
|---|---|
| 489 | 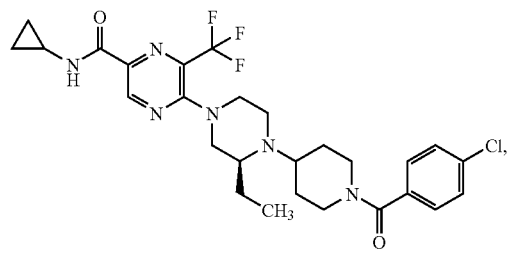 |
| 490 | 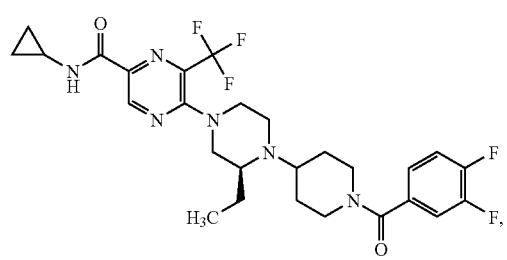 |
| 491 | 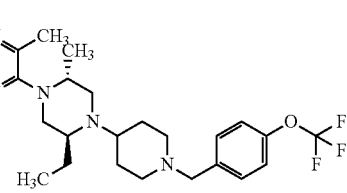 |
| | and |
| 492 | 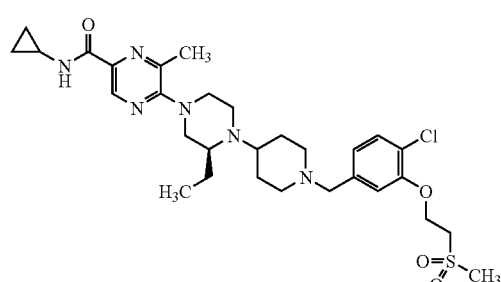 |
or a pharmaceutically acceptable salt thereof.

26. The compound according to claim 25, selected from the group consisting of:
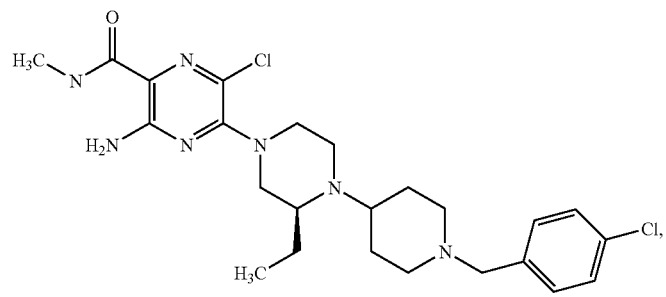
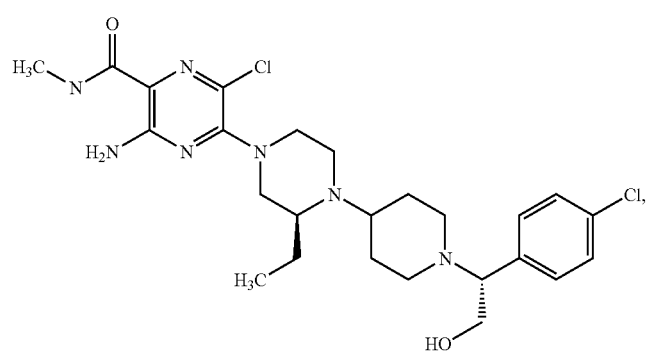
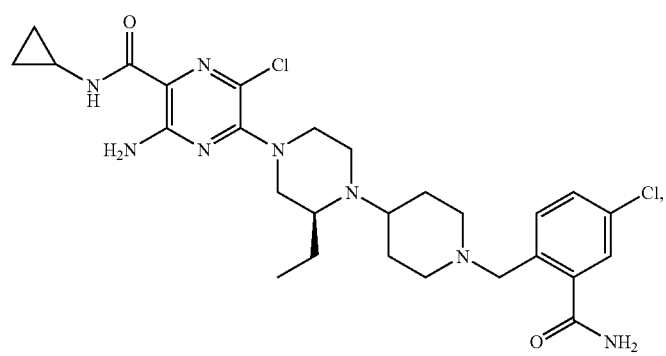
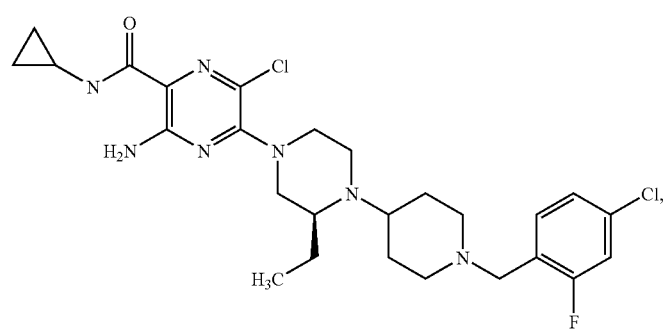

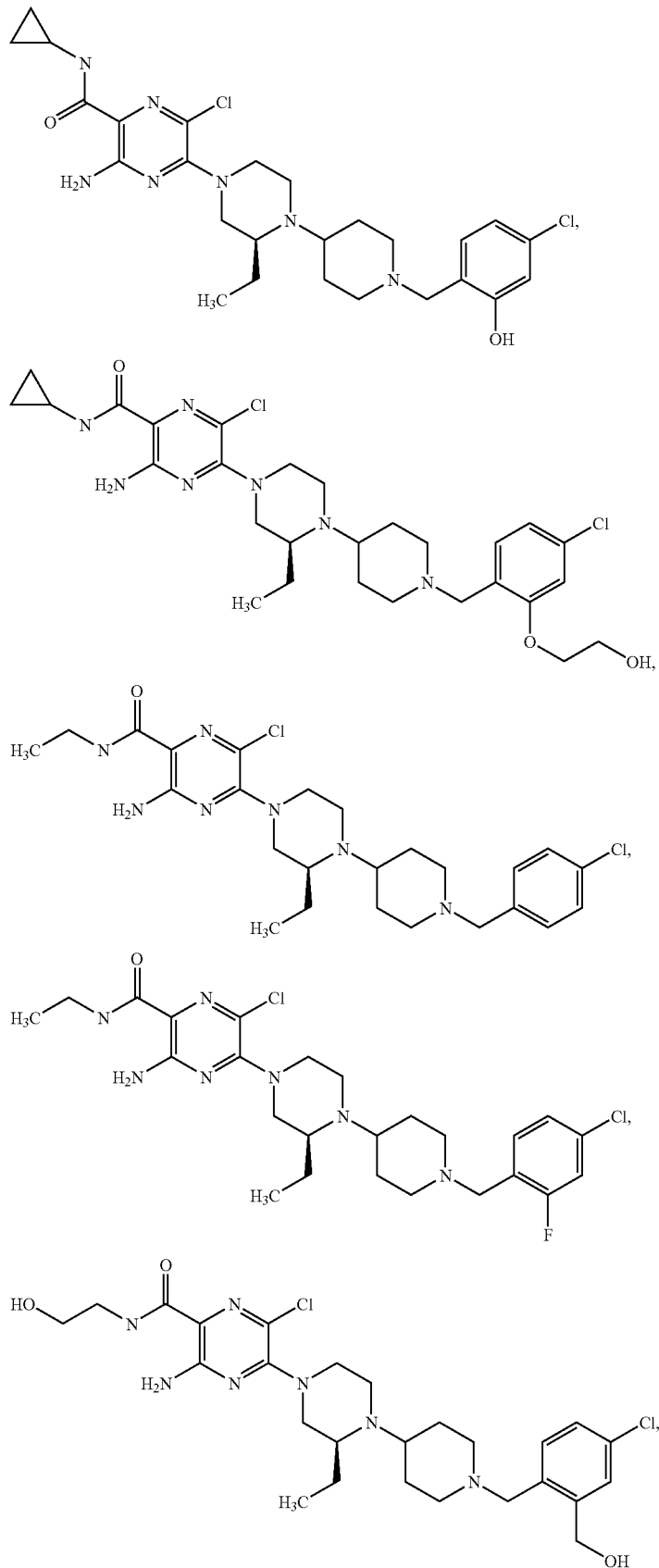

-continued
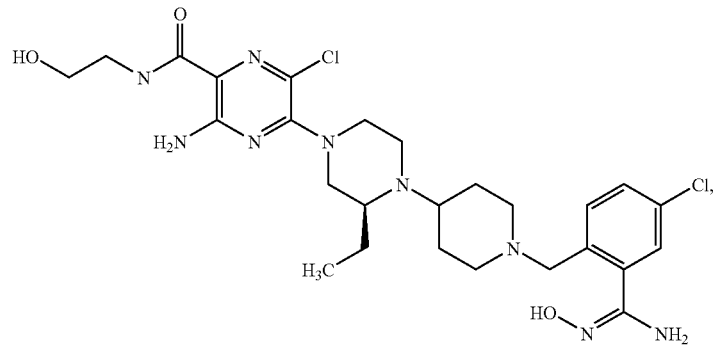
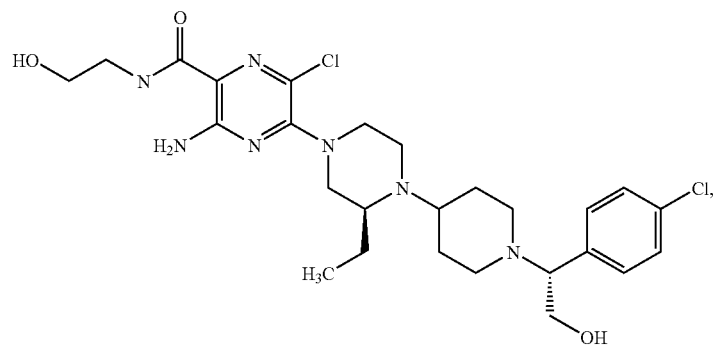
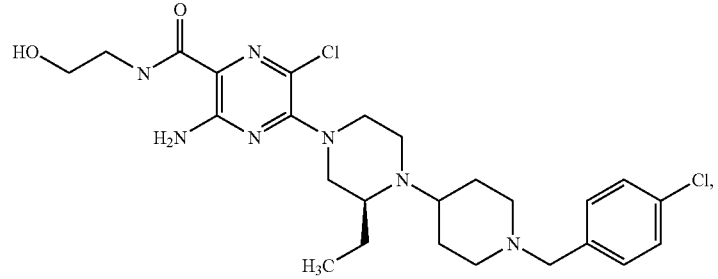
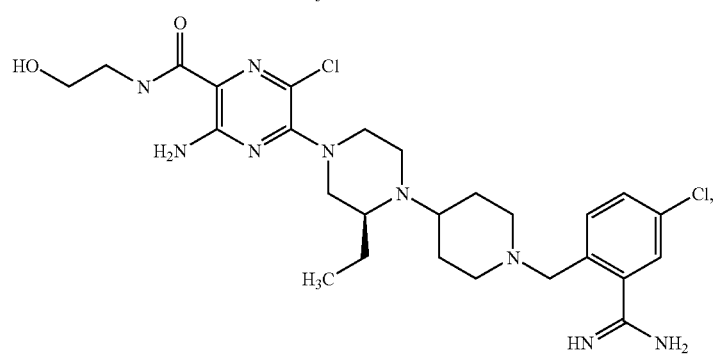
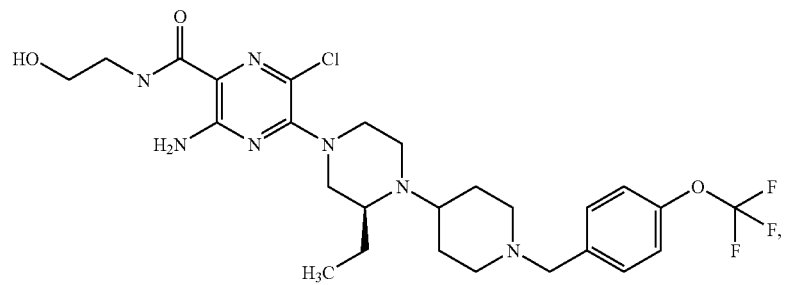

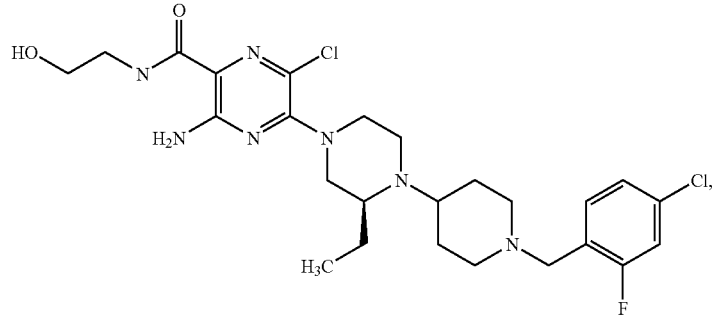
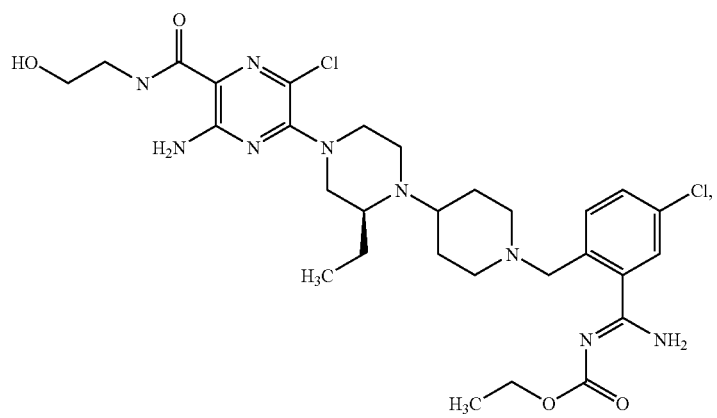
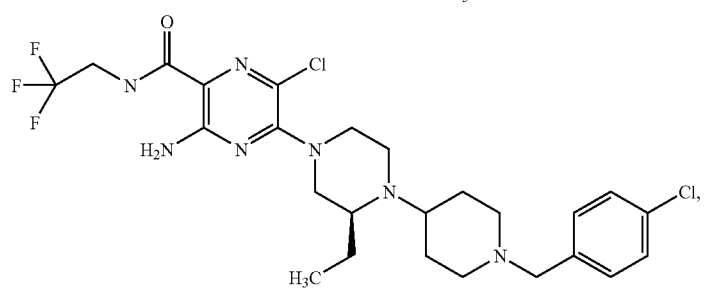
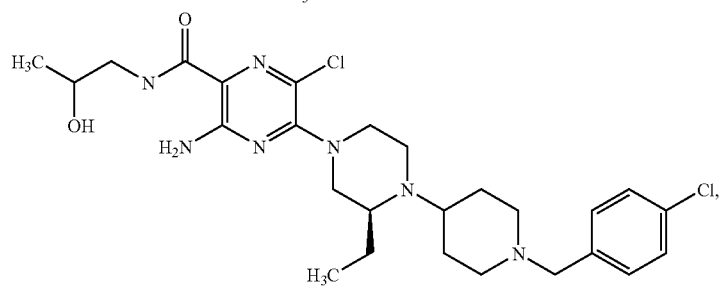
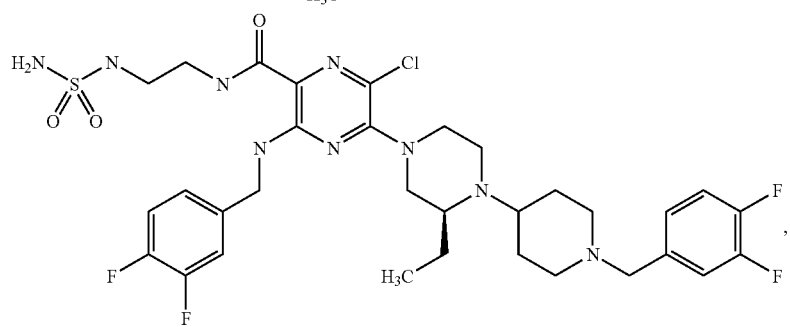

-continued
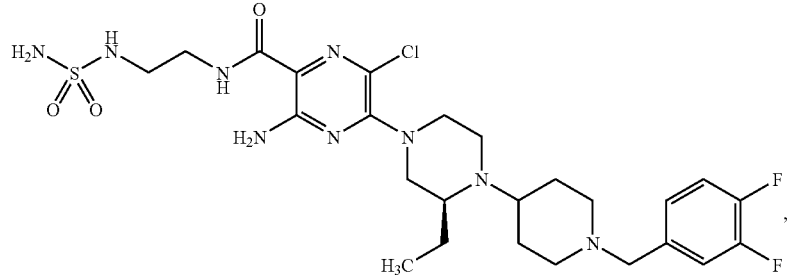
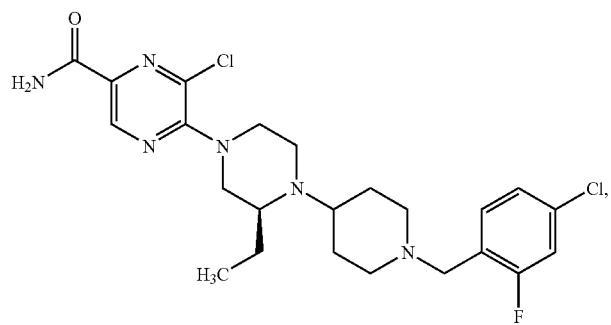
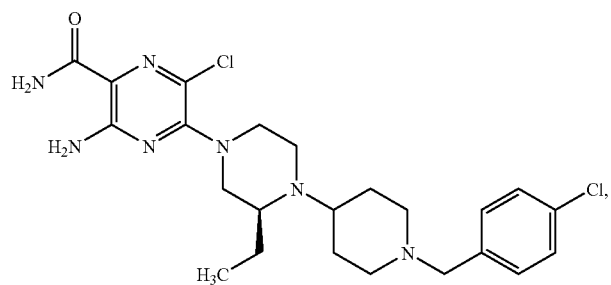
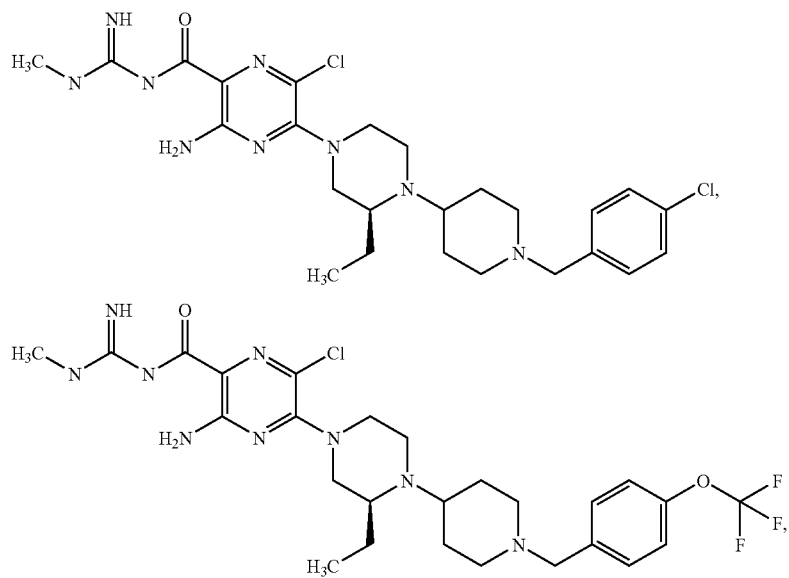

-continued
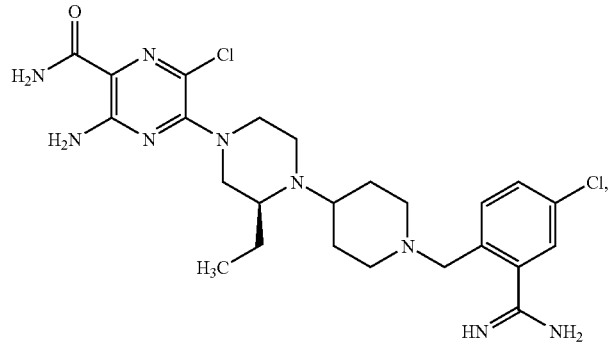
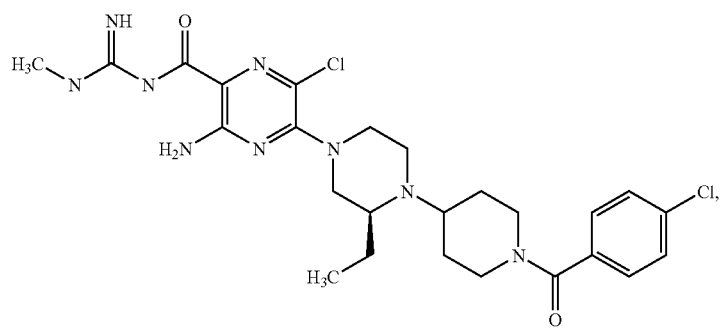
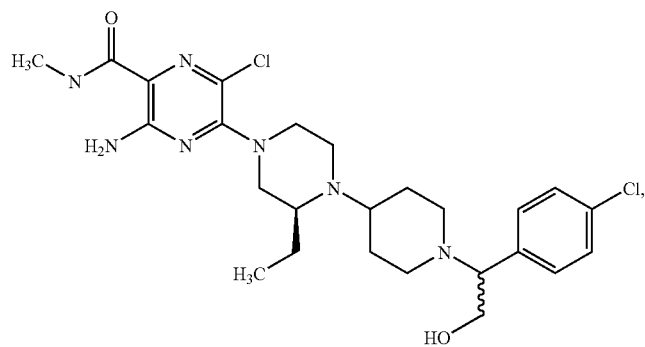
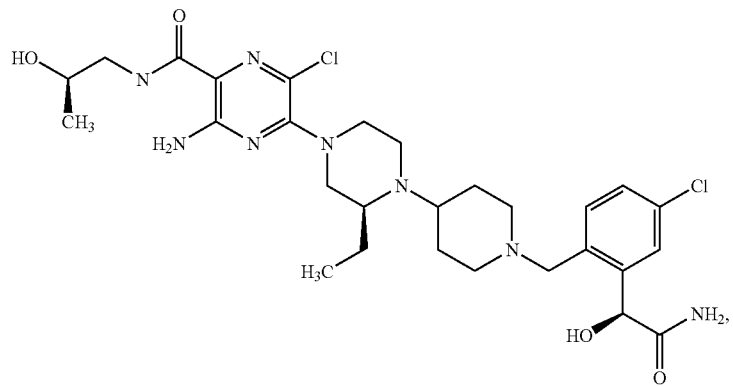

-continued
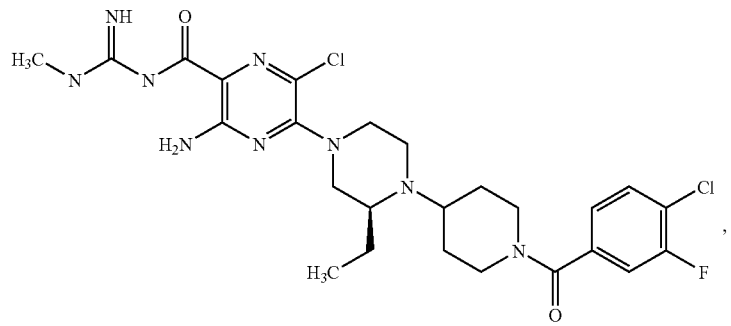
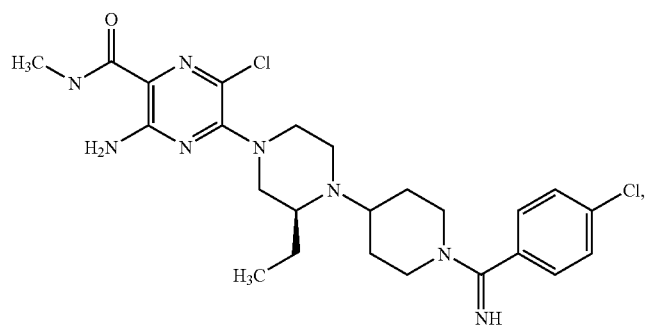
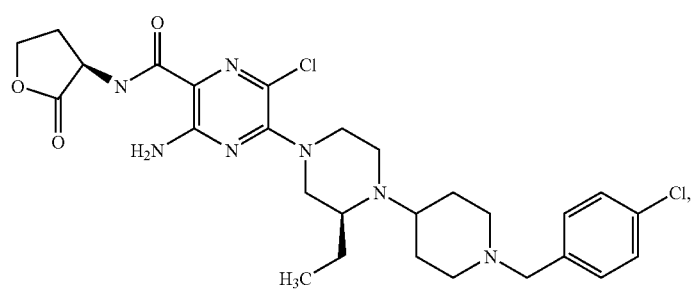
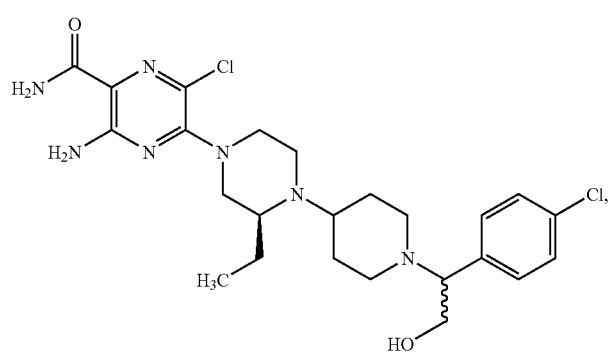
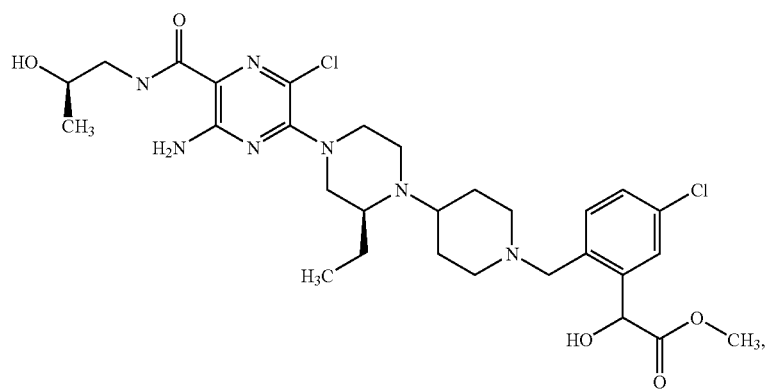

-continued
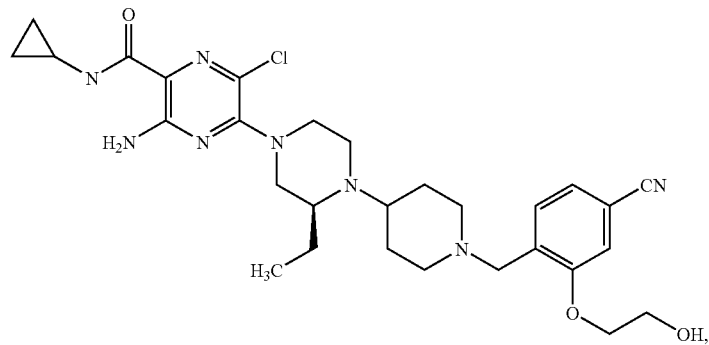
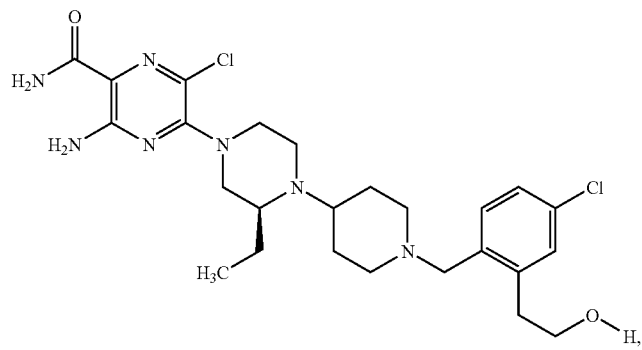
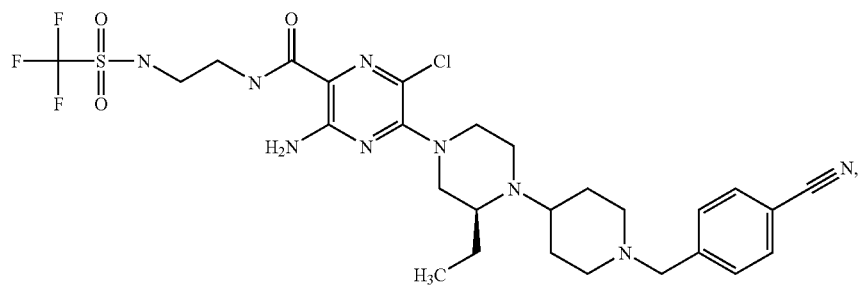
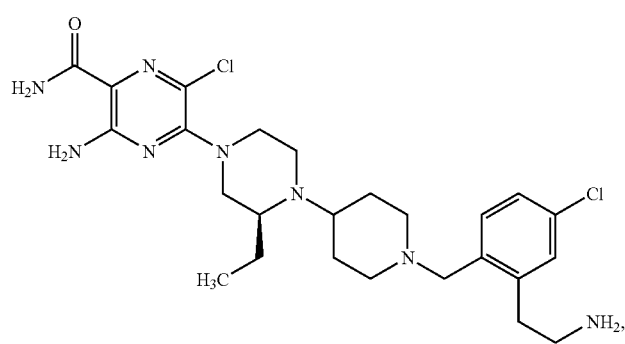
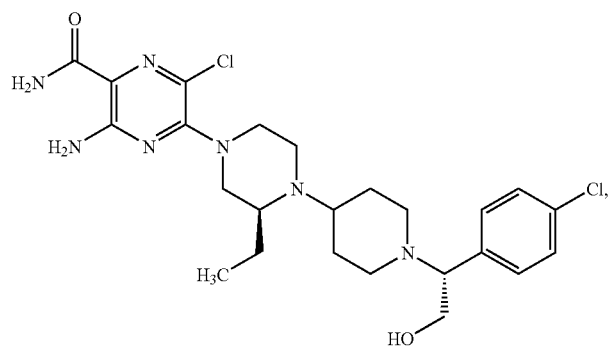

-continued
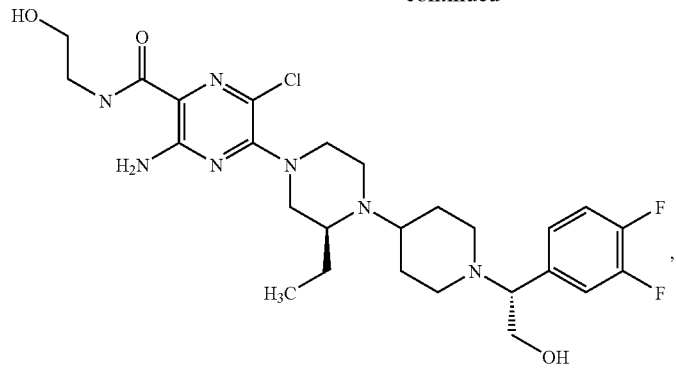
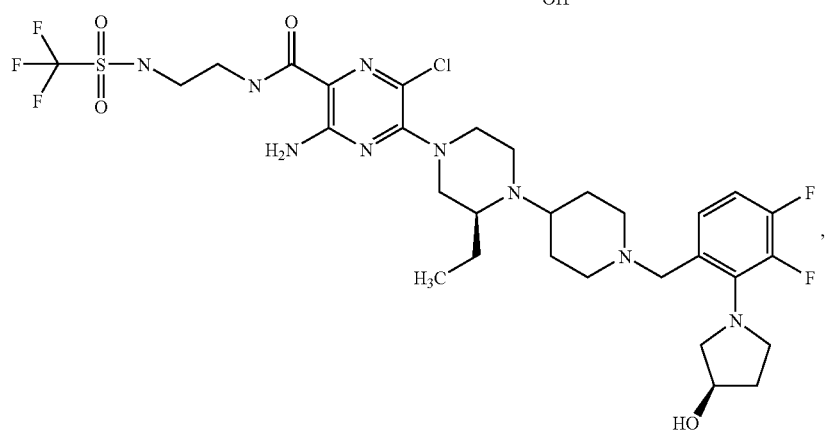
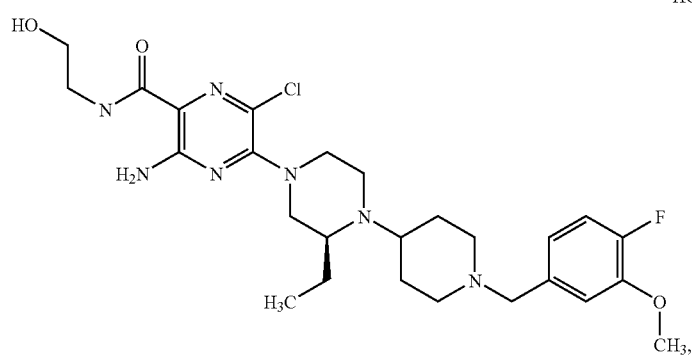
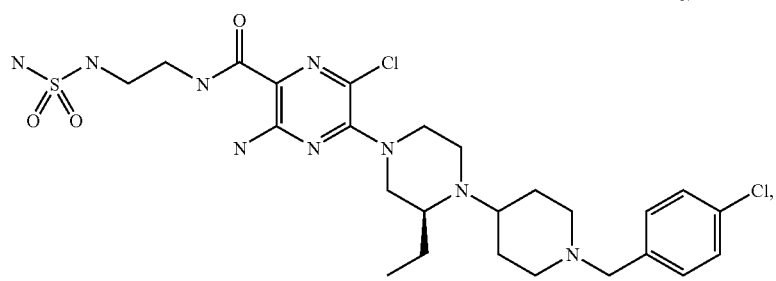
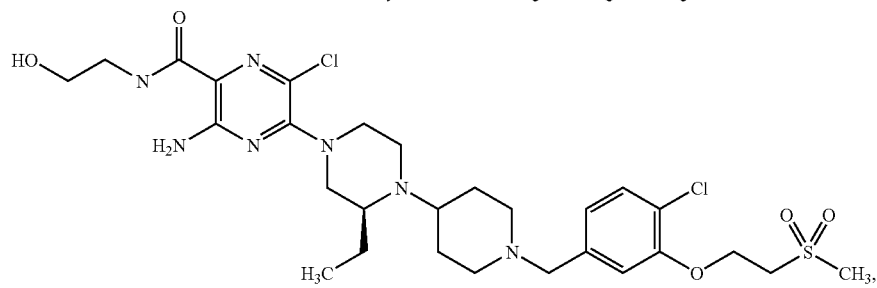

-continued
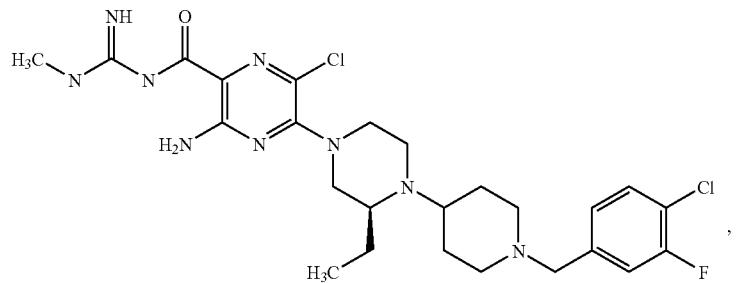
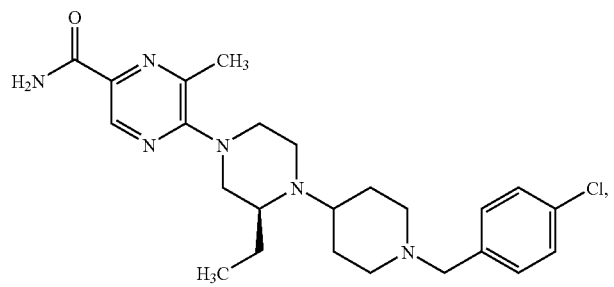
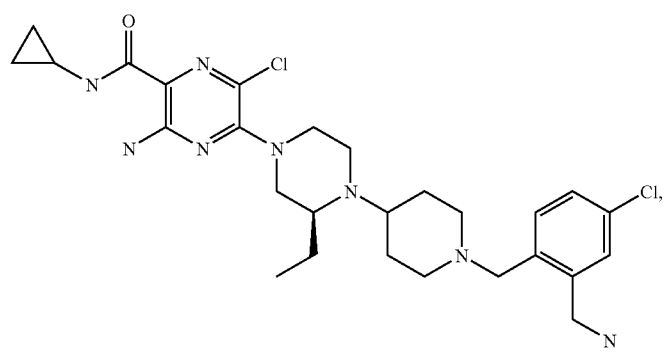
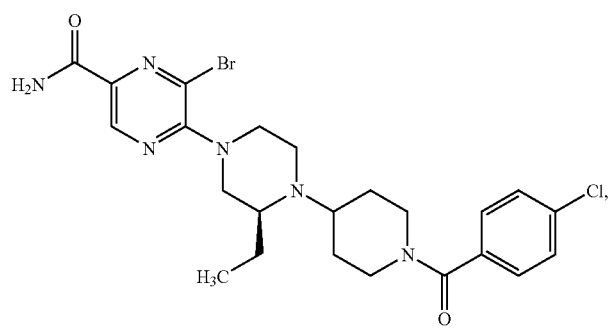
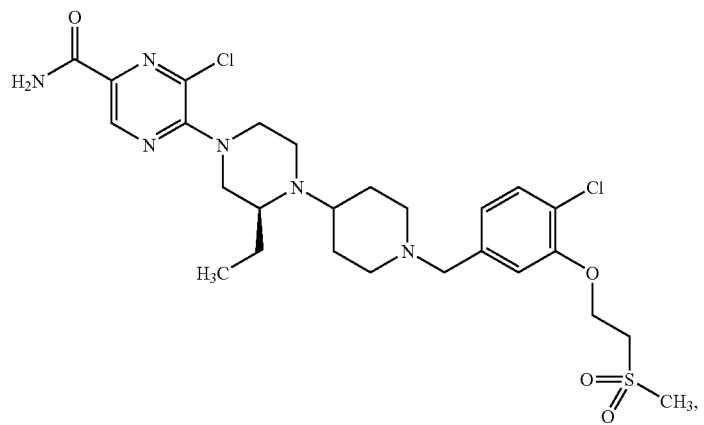

-continued
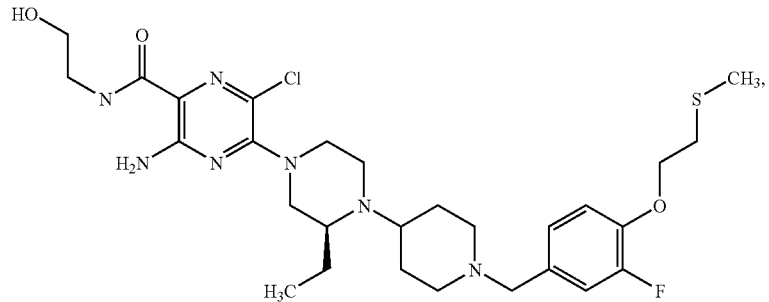
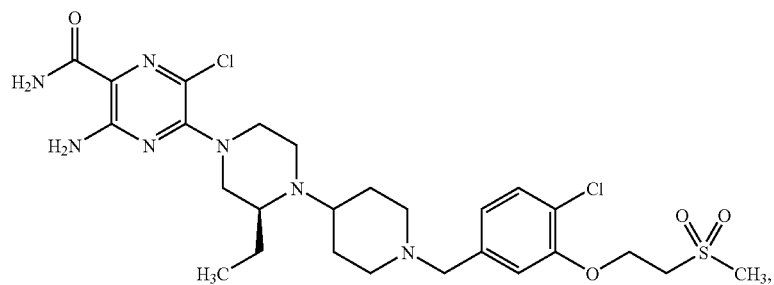
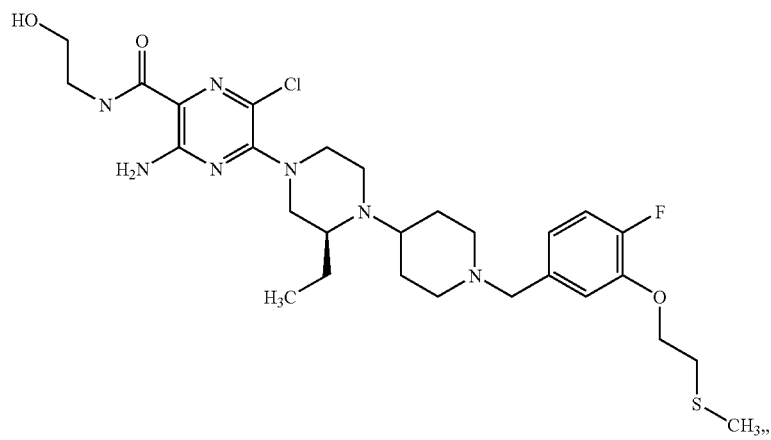
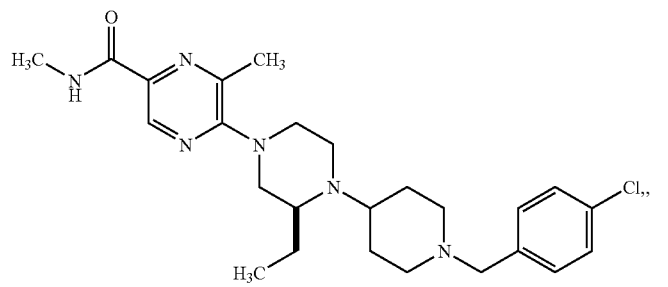
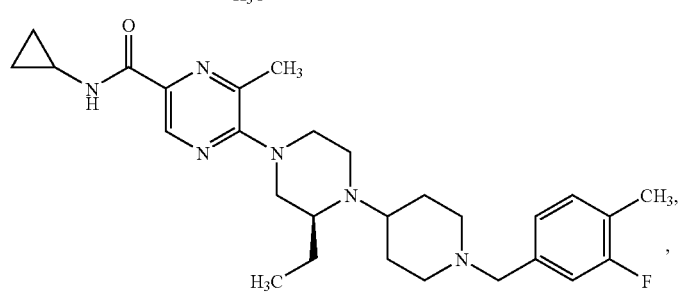

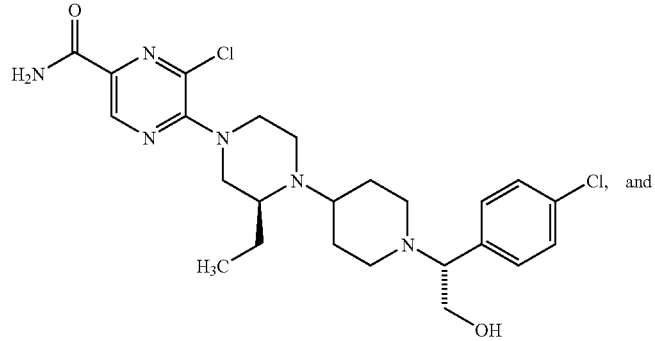
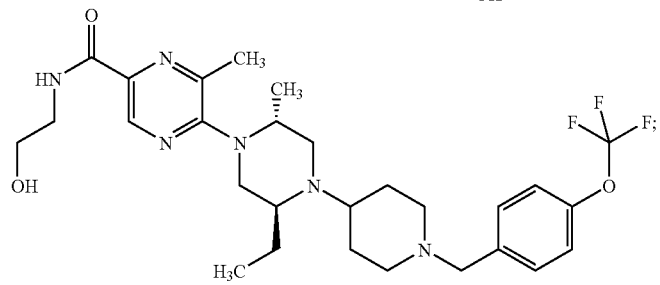
or a pharmaceutically acceptable salt thereof.
27. A compound of Formula 7, Formula 8, Formula 9, Formula 10, Formula 11, Formula 12, Formula 13, Formula 14, Formula 15, Formula 16, or Formula 17:
Formula 7
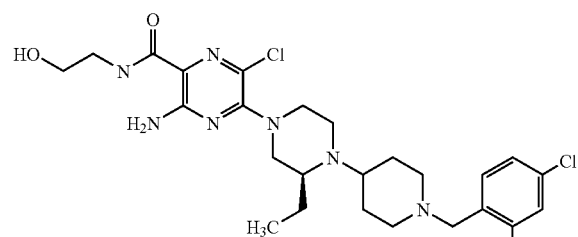
Formula 8
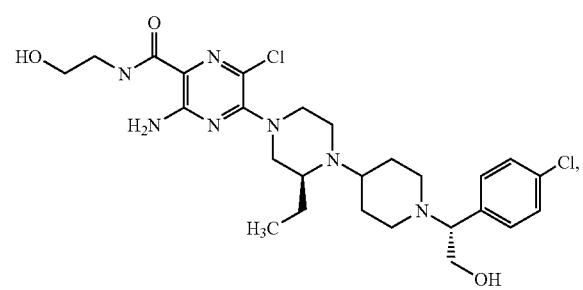
-continued
Formula 9
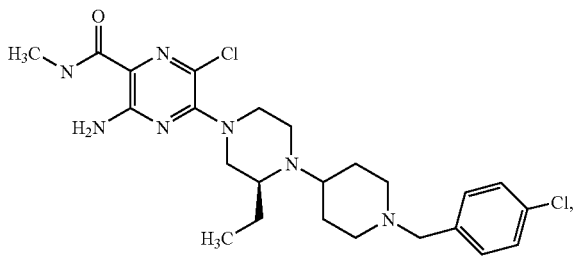
Formula 10
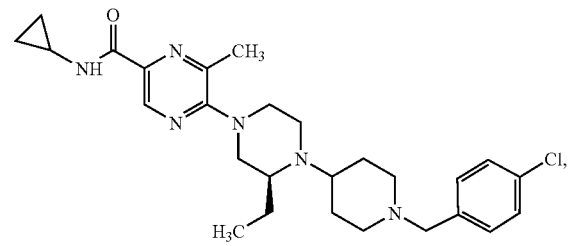
Formula 11
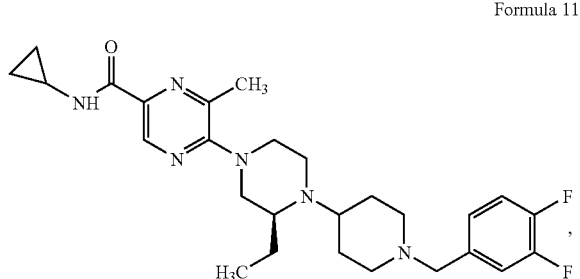

Formula 12

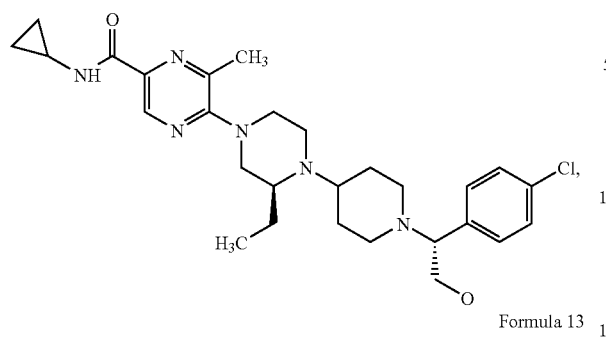

Formula 13

Formula 14

Formula 15

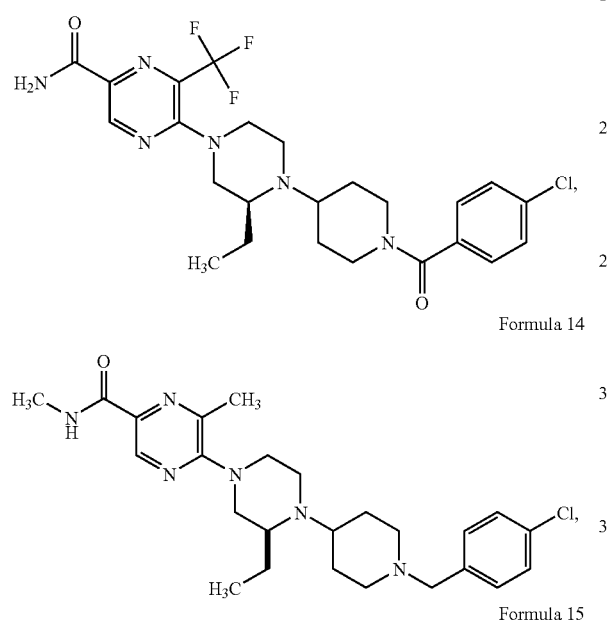

Formula 16

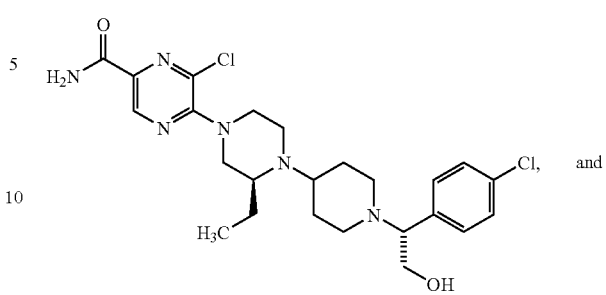

and

Formula 17

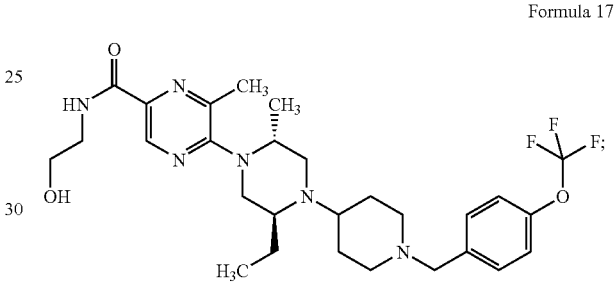

or a pharmaceutically acceptable salt thereof.

28. A pharmaceutical composition comprising at least one compound of claim 1 or a pharmaceutically acceptable salt thereof, in combination with at least one pharmaceutically acceptable carrier.

29. A pharmaceutical composition comprising at least one compound of claim 25 or a pharmaceutically acceptable salt thereof, in combination with at least one pharmaceutically acceptable carrier.

* * * * *